US012741031B2

(12) United States Patent
Lei et al.

(10) Patent No.: US 12,741,031 B2

(45) Date of Patent: Sep. 22, 2026

(54) GLUTARIMIDE COMPOUND AND USE THEREOF

(71) Applicant: MEDSHINE DISCOVERY INC., Jiangsu (CN)

(72) Inventors: Maoyi Lei, Shanghai (CN); Shaohui Wang, Shanghai (CN); Yu Xu, Shanghai (CN); Yunfu Luo, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 355 days.

(21) Appl. No.: 18/689,074

(22) PCT Filed: Sep. 7, 2022

(86) PCT No.: PCT/CN2022/117524

§ 371 (c)(1),
(2) Date: Apr. 11, 2024

(87) PCT Pub. No.: WO2023/036175

PCT Pub. Date: Mar. 16, 2023

(65) Prior Publication Data

US 2025/0127905 A1 Apr. 24, 2025

(30) Foreign Application Priority Data

| | | |
|---|---|---|
| Sep. 8, 2021 | (CN) | 202111050400.X |
| Nov. 12, 2021 | (CN) | 202111342997.5 |
| Nov. 15, 2021 | (CN) | 202111350840.7 |
| Nov. 23, 2021 | (CN) | 202111395625.9 |
| Dec. 16, 2021 | (CN) | 202111545015.2 |
| Dec. 24, 2021 | (CN) | 202111602536.7 |
| Aug. 26, 2022 | (CN) | 202211034817.1 |

(51) Int. Cl.

| | |
|---|---|
| ***A61K 47/55*** | (2017.01) |
| ***A61K 47/54*** | (2017.01) |
| ***A61P 17/06*** | (2006.01) |
| ***A61P 19/02*** | (2006.01) |

(52) U.S. Cl.

CPC ............ *A61K 47/55* (2017.08); *A61K 47/545* (2017.08); *A61P 17/06* (2018.01); *A61P 19/02* (2018.01)

(58) Field of Classification Search

CPC .............................. A61K 45/55; A61K 47/545

See application file for complete search history.

(56) References Cited

U.S. PATENT DOCUMENTS

| | | | |
|---|---|---|---|
| 10,874,743 | B2 | 12/2020 | Mainolfi et al. |
| 2022/0324848 | A1 | 10/2022 | Luo et al. |

FOREIGN PATENT DOCUMENTS

| | | | |
|---|---|---|---|
| CN | 112105385 | A | 12/2020 |
| WO | 2020113233 | A1 | 6/2020 |
| WO | 2021047627 | A1 | 3/2021 |
| WO | 2021127278 | A1 | 6/2021 |
| WO | 2021158634 | A1 | 8/2021 |
| WO | 2021170109 | A1 | 9/2021 |
| WO | 2022161414 | A1 | 8/2022 |

OTHER PUBLICATIONS

Aug. 6, 2025 The extended European Search Report issued in European Patent Application No. 22866638.4.
Apr. 22, 2025 First Office Action issued in Japanese Patent Application No. 2024515406.
Oct. 28, 2025 Second Office Action issued in Japanese Patent Application No. 2024515406.
Oct. 18, 2022 International Search Report issued in International Patent Application No. PCT/CN2022/117524.
Oct. 18, 2022 Written Opinion of the International Searching Authority issued in International Patent Application No. PCT/CN2022/117524.
English translation of priority document No. CN202111050400.X.
English translation of priority document No. CN202111342997.5.
English translation of priority document No. CN202111350840.7.
English translation of priority document No. CN202111395625.9.
English translation of priority document No. CN202111545015.2.
English translation of priority document No. CN202111602536.7.
English translation of priority document No. CN202211034817.1.

*Primary Examiner* — Andrew D Kosar

(74) *Attorney, Agent, or Firm* — Houston Beshining Law Office PLLC; Liangang Ye

(57) ABSTRACT

Disclosed in the present invention are a glutarimide compound, and the use thereof. Specifically disclosed are a compound as represented by formula (VII-0) and a pharmaceutically acceptable salt thereof.

(VII-0)

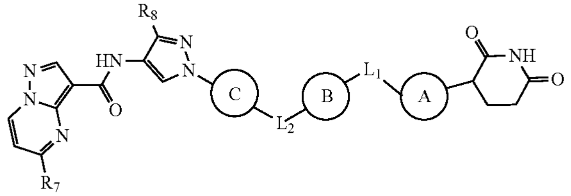

19 Claims, No Drawings

GLUTARIMIDE COMPOUND AND USE THEREOF

The present application is a National Stage of International Application No. PCT/CN2022/117524, filed on Sep. 7, 2022, which claims priority of the Chinese Patent Application No. CN202111050400X, filed on Sep. 8, 2021; the Chinese Patent Application No. CN2021113429975, filed on Nov. 12, 2021; the Chinese Patent Application No. CN2021113508407, filed on Nov. 15, 2021; the Chinese Patent Application No. CN2021113956259, filed on Nov. 23, 2021; the Chinese Patent Application No. CN2021115450152, filed on Dec. 16, 2021; the Chinese Patent Application No. CN2021116025367, filed on Dec. 24, 2021; the Chinese Patent Application No. CN2022110348171, filed on Aug. 26, 2022.

TECHNICAL FIELD

The present disclosure relates to a class of glutarimide compounds and a use thereof. It specifically relates to a compound of formula (VII) and a pharmaceutically acceptable salt thereof.

BACKGROUND

Interleukin-1 receptor-associated kinase 4 (IRAK4) is a member of the IRAK family of intracellular serine/threonine kinases, which plays an important role in protein phosphorylation as well as cellular signaling. IRAK4 is a key protein in inflammatory and immune responses mediated by activation of toll-like receptor (TLR) and interleukin-1 receptor (IL-1R). As a key protein downstream of the signaling pathway of TLR and IL-1R, IRAK4 receives upstream signals and thus activates its downstream NF-κB and JNK signaling pathways. Therefore, IRAK4 is considered to play an important role in inflammatory response and immune regulation, making it an important therapeutic target that has attracted extensive research and development interest.

The IRAK4 protein folds to form a "pocket-like" structure that can bind to ATP, thereby achieving its protein phosphorylation function. Most of the current IRAK4 small molecule inhibitors competitively bind to this "pocket" region, thereby inhibiting its phosphorylation function for drug development. However, IRAK4 functions not only by phosphorylating proteins, but also by forming a complex with myeloid differentiation factor (MyD88). IRAK4 requires its phosphorylation function for the activation of the JNK signaling pathway, but not for the activation of the NF-κB signaling pathway, indicating that IRAK4 not only functions as a kinase, but also functions as a scaffold protein playing a role in the signaling pathway. Therefore, conventional small molecule kinase inhibitors targeting IRAK4 cannot completely block all biological functions of IRAK4.

The brand new research approach is to degrade IRAK4 and more completely block all biological functions of IRAK4. Proteolysis targeting chimera (PROTAC) is a technique that applies the ubiquitin-proteasome system to target specific proteins and induce their intracellular degradation. The ubiquitin-proteasome system is the main pathway for intracellular protein degradation, mainly responsible for the removal of denatured, mutated, or harmful proteins from the cell as its normal physiological functions. 80% more of intracellular protein degradation is dependent on the ubiquitin-proteasome system. PROTAC utilizes the cell's own protein destruction mechanism to remove specific targeted proteins from the cell. To date, PROTAC technology has become increasingly mature and can be used to target a variety of proteins, including scaffold proteins, transcription factors, enzymes, and regulatory proteins.

Therefore, the development of PROTAC molecules targeting IRAK4 can more completely block all functions of IRAK4 by degrading IRAK4 and removing IRAK4, and thus comprehensively inhibit the IRAK4 signaling pathway, thereby better exerting anti-inflammatory and immunomodulatory effects.

CONTENT OF THE PRESENT INVENTION

The present disclosure also provides a compound of formula (VII-0) or a pharmaceutically acceptable salt thereof, (VII-0)

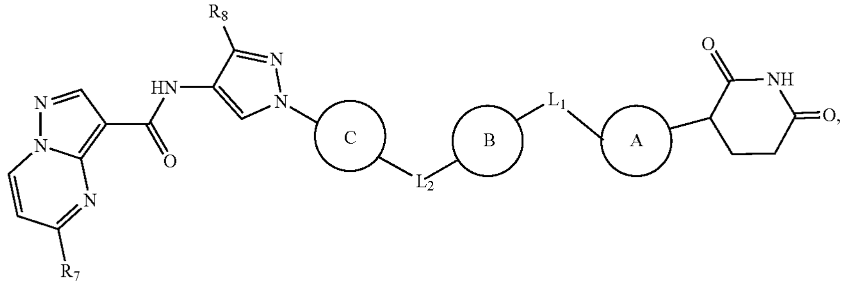

wherein $L_1$ is selected from

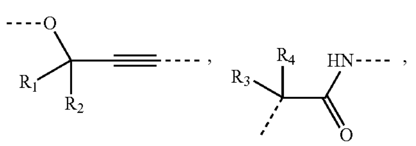

$-(CH_2)_3-$, and $-O(CH_2)_3-$;

$L_2$ is selected from $-CR_5R_6-$ and O;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$R_7$ is selected from

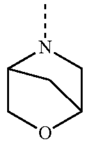,
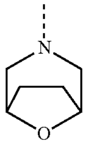, and
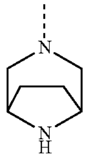;

$R_8$ is selected from $C_{1-4}$ alkyl, $C_{1-4}$ haloalkyl, cyclopropyl, and halocyclopropyl;

ring A is selected from

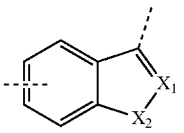 or
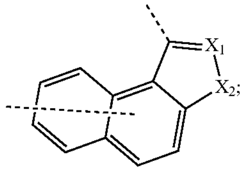

$X_1$ is selected from CH and N;

$X_2$ is selected from NH, O, S, and Se;

ring B is selected from $C_{5-8}$ cycloalkyl and 5- to 8-membered heterocycloalkyl, and the $C_{5-8}$ cycloalkyl and 5- to 8-membered heterocycloalkyl are each independently and optionally substituted by 1, 2, 3, or 4 $R_a$;

$R_a$ is selected from halogen, OH, $NH_2$, $C_{1-3}$ alkyl, $C_{1-3}$ alkoxy, $C_{1-3}$ haloalkyl, and $C_{1-3}$ haloalkoxy;

ring C is selected from $C_{5-8}$ cycloalkyl and 5- to 8-membered heterocycloalkyl, and the $C_{5-8}$ cycloalkyl and 5- to 8-membered heterocycloalkyl are each independently and optionally substituted by 1, 2, 3, or 4 $R_b$;

$R_b$ is selected from halogen, OH, $NH_2$, $C_{1-3}$ alkyl, $C_{1-3}$ alkoxy, $C_{1-3}$ haloalkyl, and $C_{1-3}$ haloalkoxy.

The present disclosure also provides a compound of formula (VII) or a pharmaceutically acceptable salt thereof, (VII)

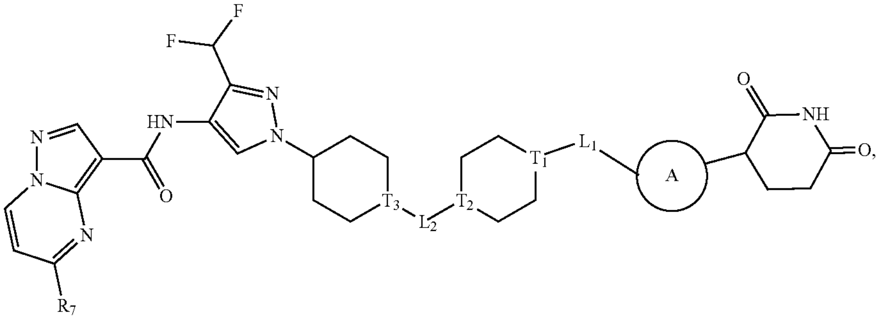

wherein $L_1$ is selected from

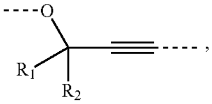,
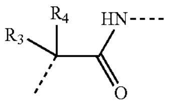, $-(CH_2)_3-$, and $-O(CH_2)_3-$;

$L_2$ is selected from $-CR_5R_6-$ and O;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$R_7$ is selected from

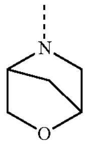,
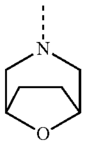, and
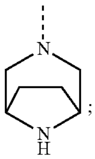;

$T_1$ is selected from CH and N;

$T_2$ is selected from CH and N;

$T_3$ is selected from CH and N;

ring A is selected from

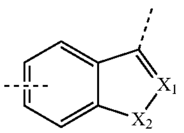 or
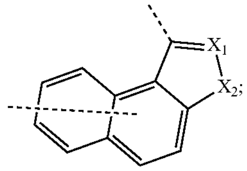

$X_1$ is selected from CH and N;

$X_2$ is selected from NH, O, S, and Se.

In some embodiments of the present disclosure, the $R_1$, $R_2$, $R_3$, $R_4$, $R_5$, and $R_6$ are each independently selected from H and F, and other variables are as defined in the present disclosure.

In some embodiments of the present disclosure, the $L_1$ is selected from

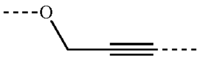,
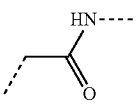,
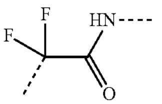,

-continued

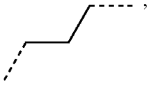

, and

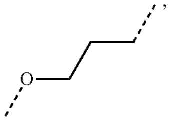

and other variables are as defined in the present disclosure.

In some embodiments of the present disclosure, the $L_2$ is selected from $-CH_2-$ and O, and other variables are as defined in the present disclosure.

In some embodiments of the present disclosure, the

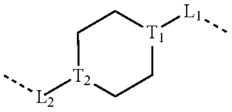

is selected from

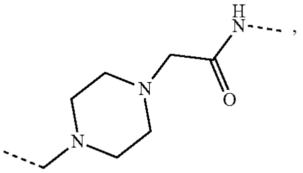

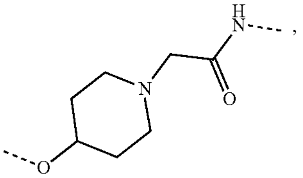

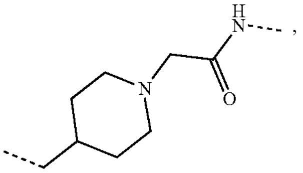

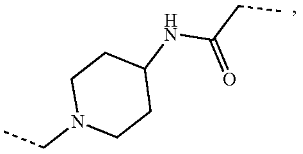

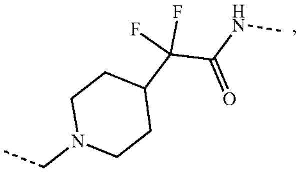

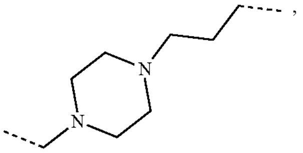

-continued

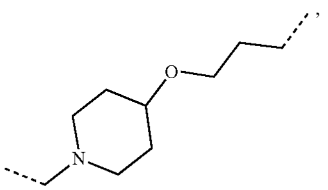

and

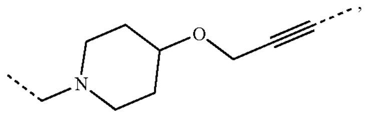

and other variables are as defined in the present disclosure.

In some embodiments of the present disclosure, the structural moiety

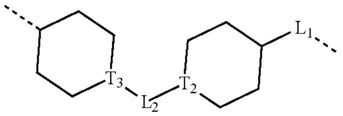

is selected from N P

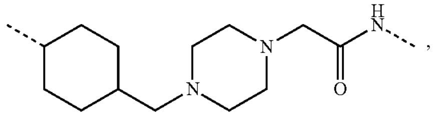

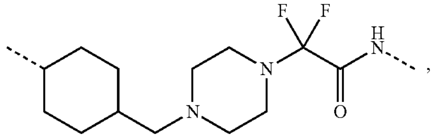

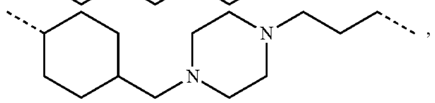

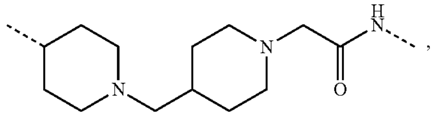

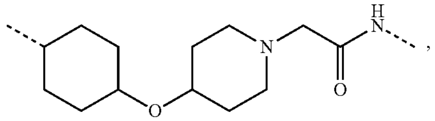

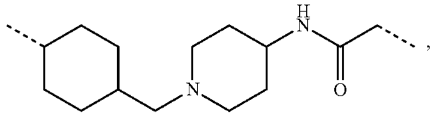

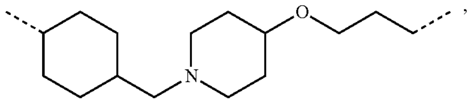

and

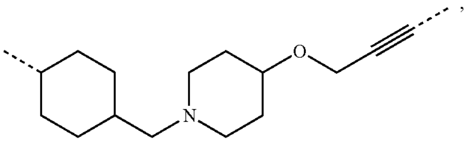

and other variables are as defined in the present disclosure.

In some embodiments of the present disclosure, the $R_7$ is selected from

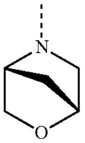
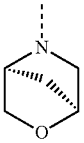
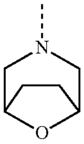
and
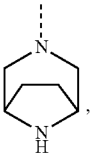

and other variables are as defined in the present disclosure.

In some embodiments of the present disclosure, the ring A is selected from

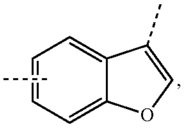
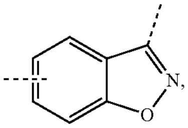
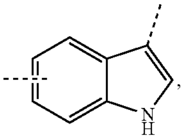
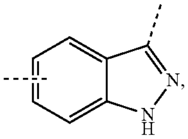
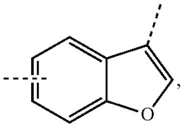
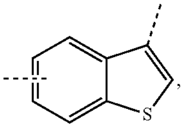
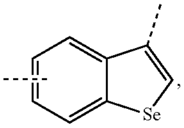
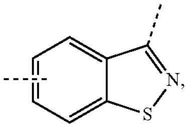
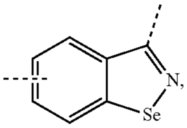
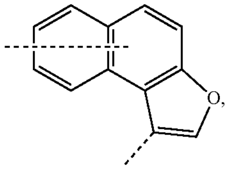
and
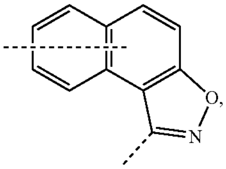

and other variables are as defined in the present disclosure.

In some embodiments of the present disclosure, the ring A is selected from

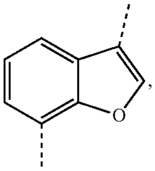
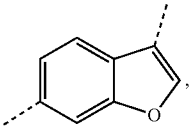
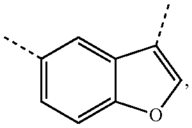
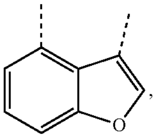

-continued

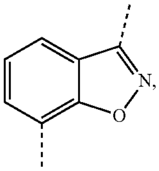
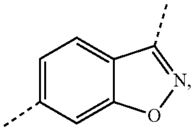
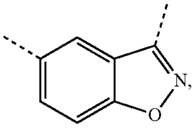
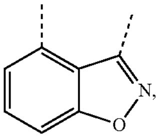
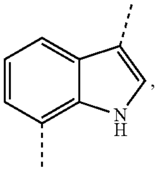
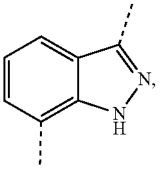
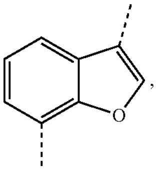
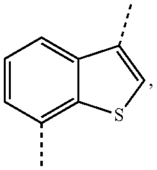
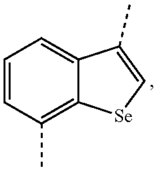
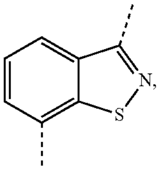
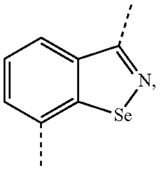
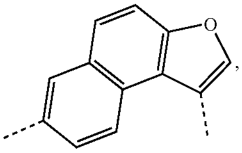
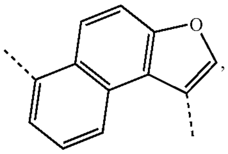
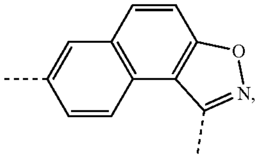
and
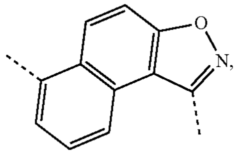

and other variables are as defined in the present disclosure.

The present disclosure also provides a compound of formulas (VII-1), (VII-2), (VII-3), (VII-4), (VII-5), and (VII-6) or a pharmaceutically acceptable salt thereof, (VII-1)
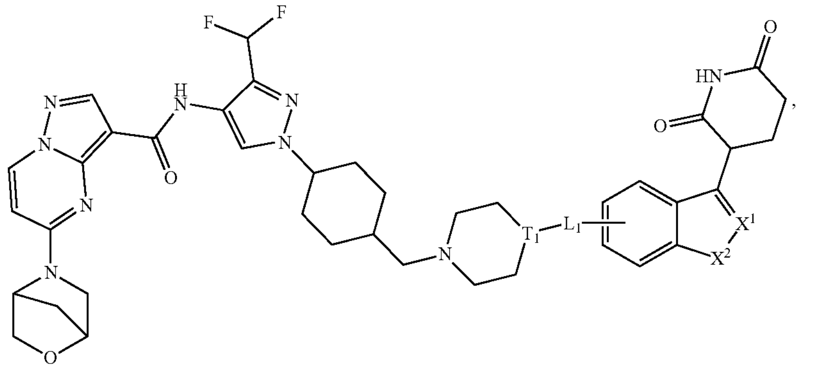
(VII-2)
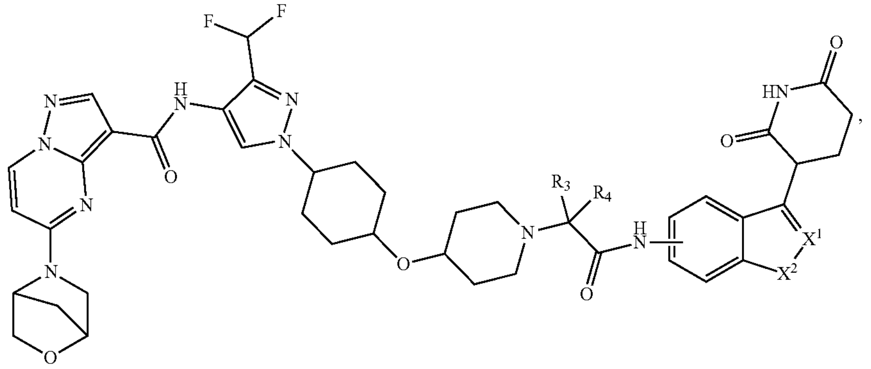
(VII-3)
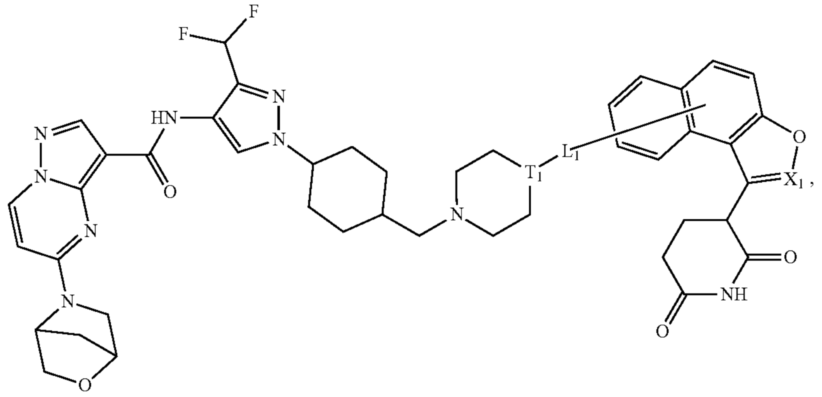
(VII-4)
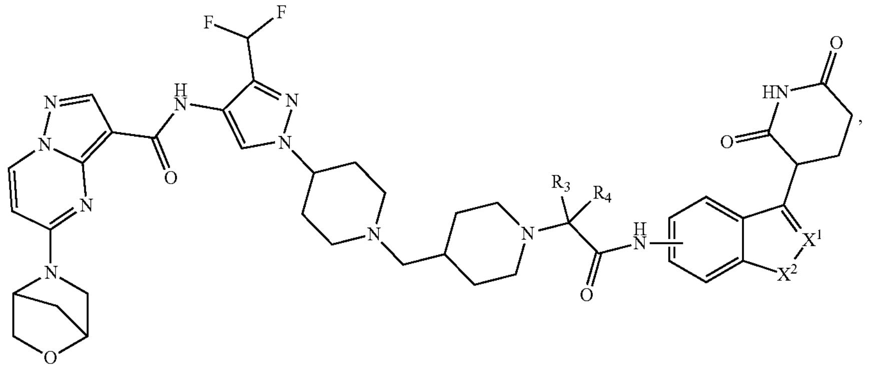

-continued
(VII-5)
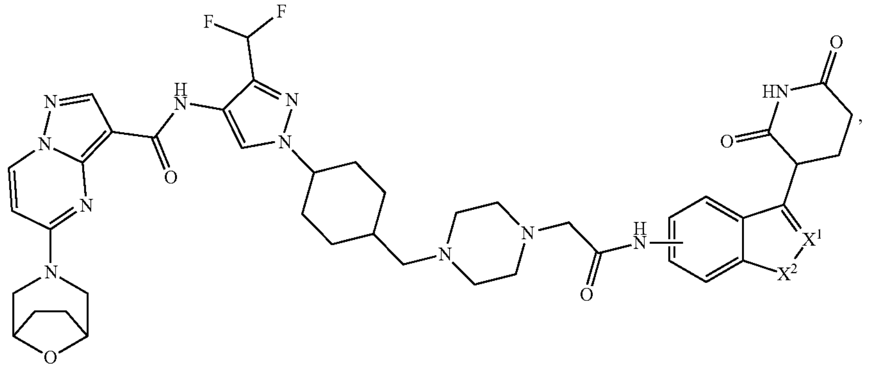
(VII-6)
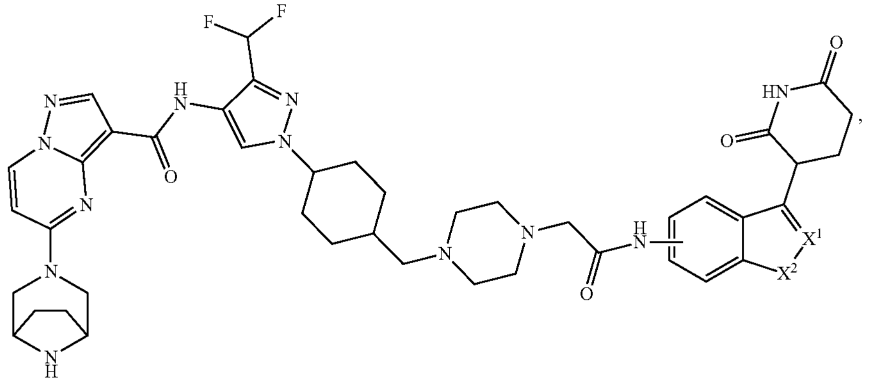
wherein $X_1$, $X_2$, $R_3$, $R_4$, $T_1$, and $L_1$ are as defined in the present disclosure.
The present disclosure also provides a compound of formulas (VII-1R), (VII-1S), (VII-2R), (VII-2S), (VII-3R), (VII-3S), (VII-4R), and (VII-4S) or a pharmaceutically acceptable salt thereof,
(VII-1R)
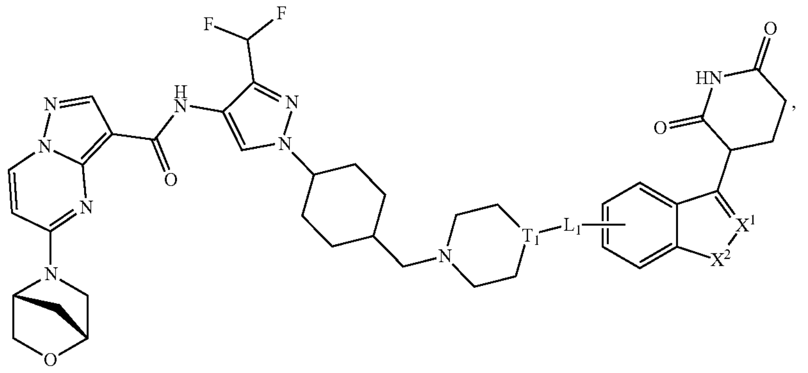

-continued
(VII-1S)
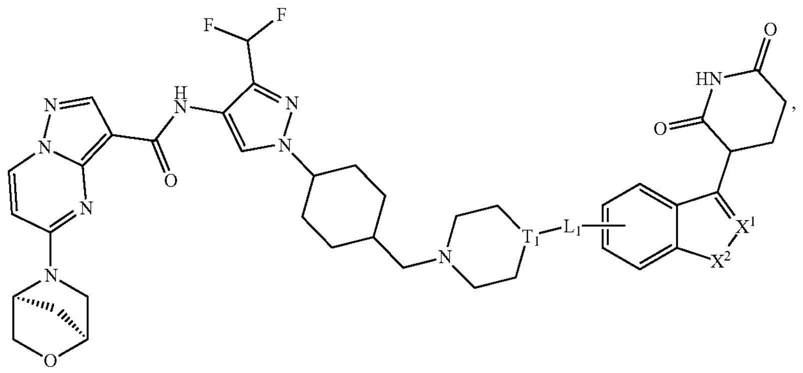
(VII-2R)
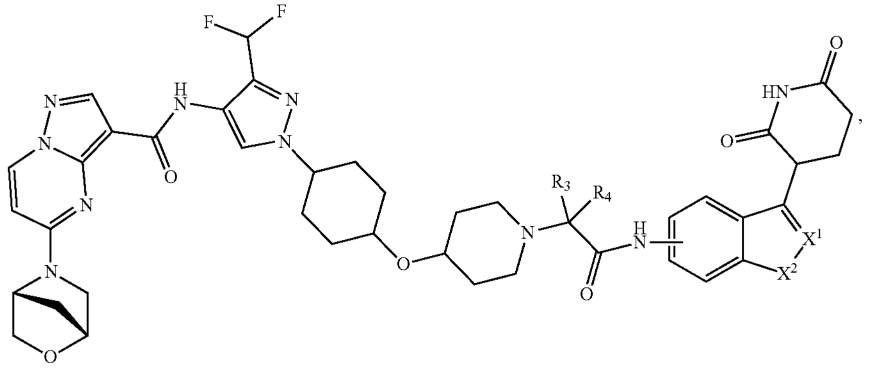
(VII-2S)
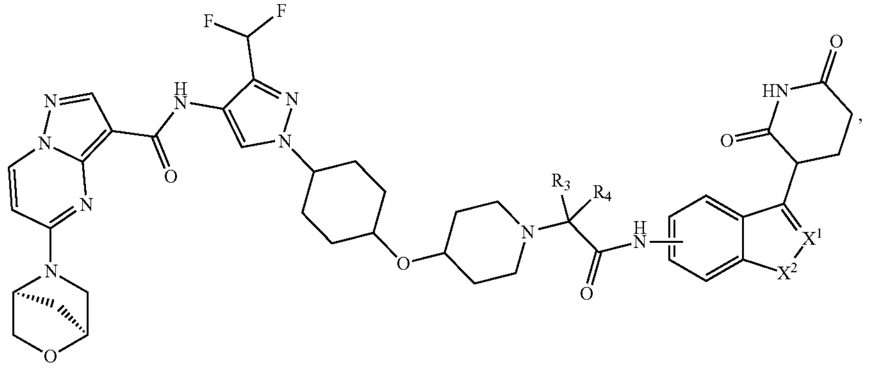
(VII-3R)
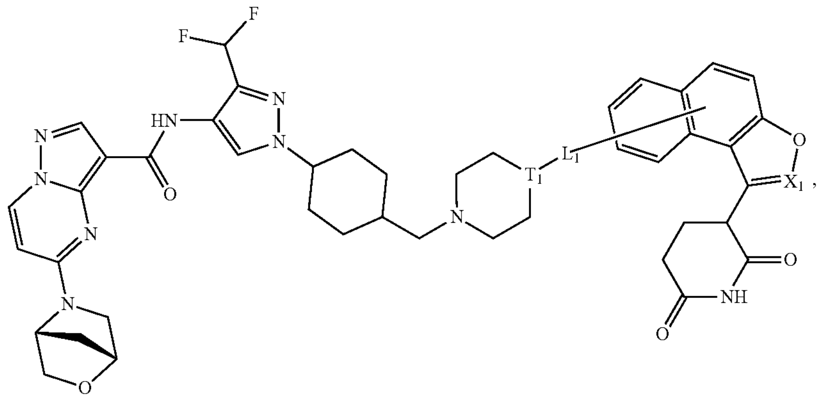

-continued
(VII-3S)
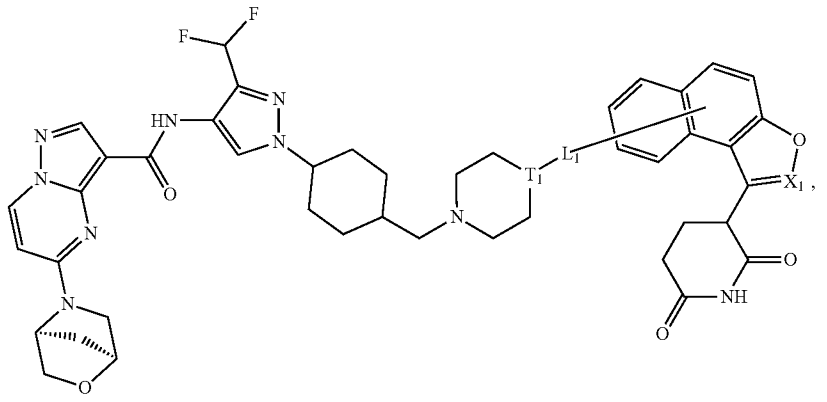
(VII-4R)
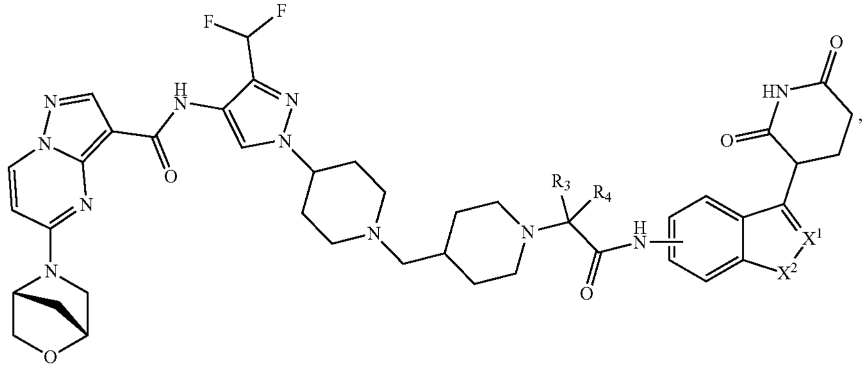
(VII-4S)
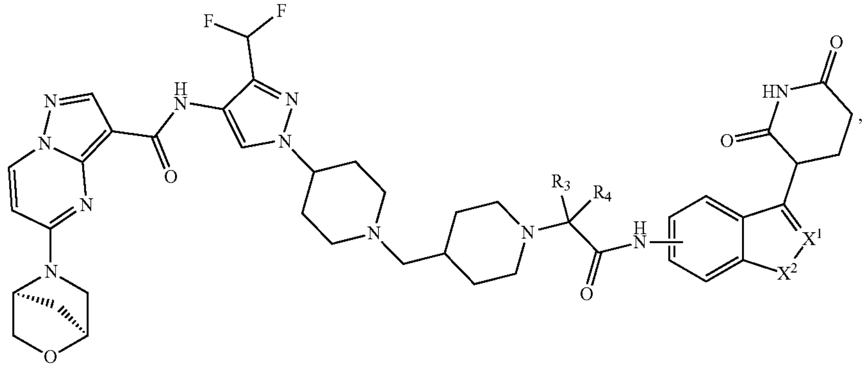
wherein $X_1$, $X_2$, $R_3$, $R_4$, $T_1$, and $L_1$ are as defined in the present disclosure.
The present disclosure also provides a compound of formulas (VII-1RT), (VII-1ST), (VII-2RT), (VII-2ST), (VII-3RT), (VII-3ST), (VII-5T), and (VII-6T) or a pharmaceutically acceptable salt thereof, (VII-1RT)
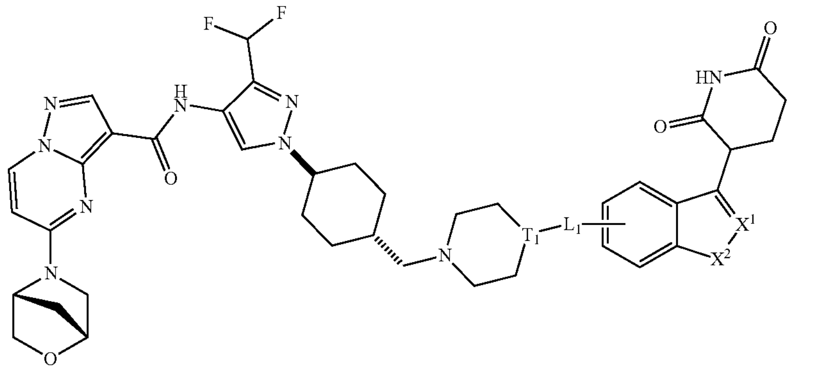
(VII-1ST)
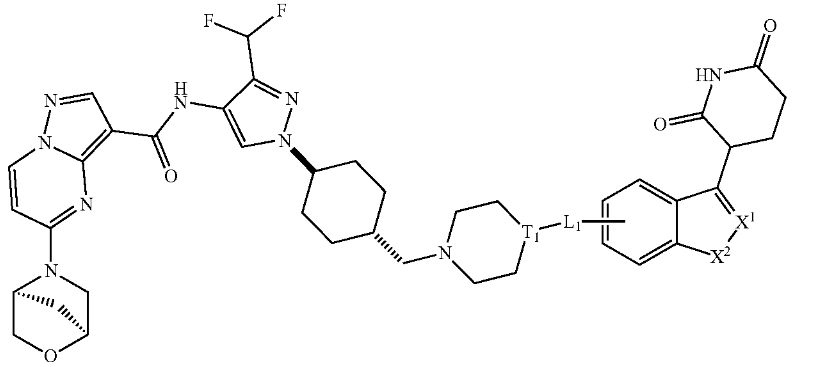
(VII-2RT)
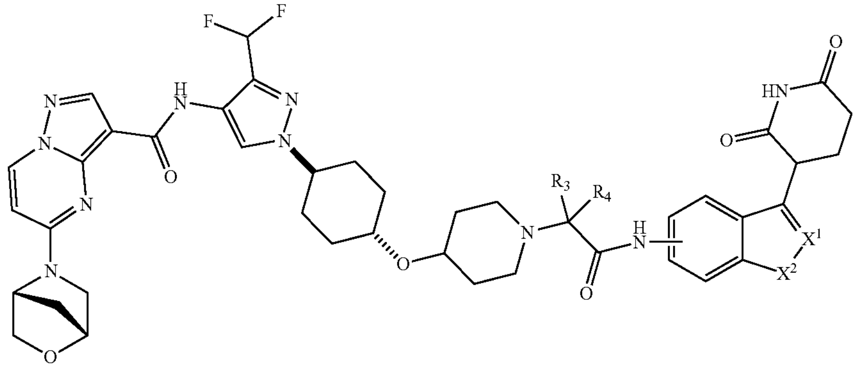
(VII-2ST)
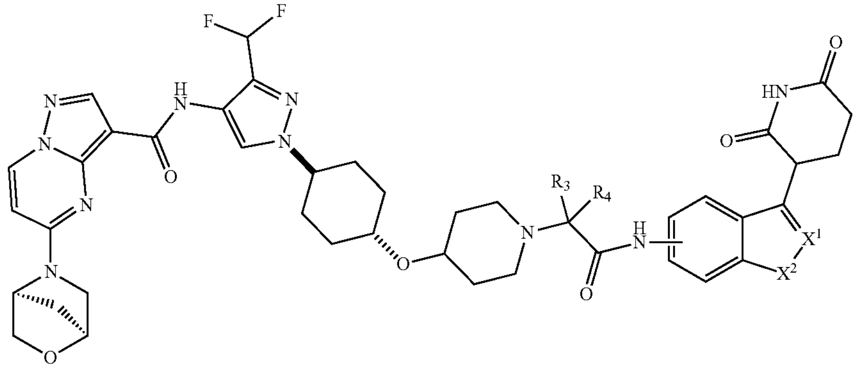

-continued
(VII-3RT)
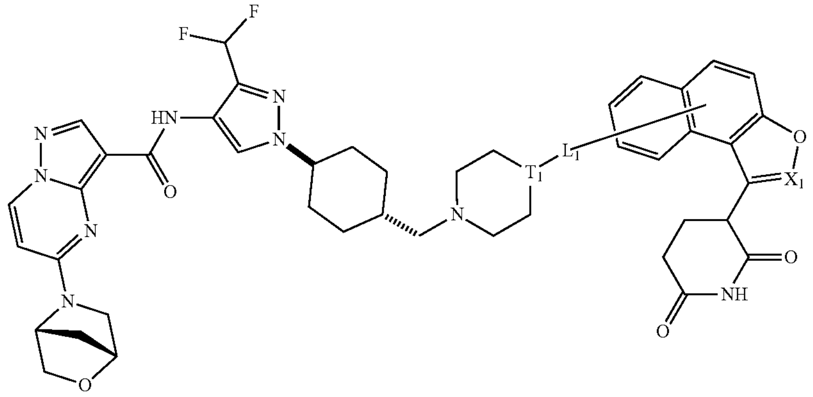
(VII-3ST)
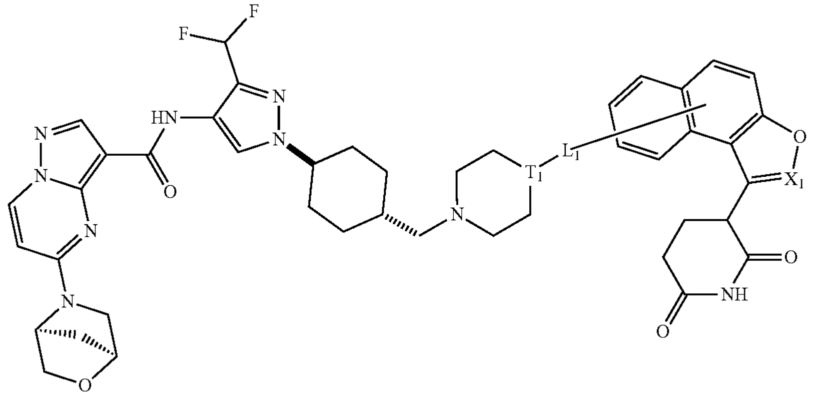
(VII-5T)
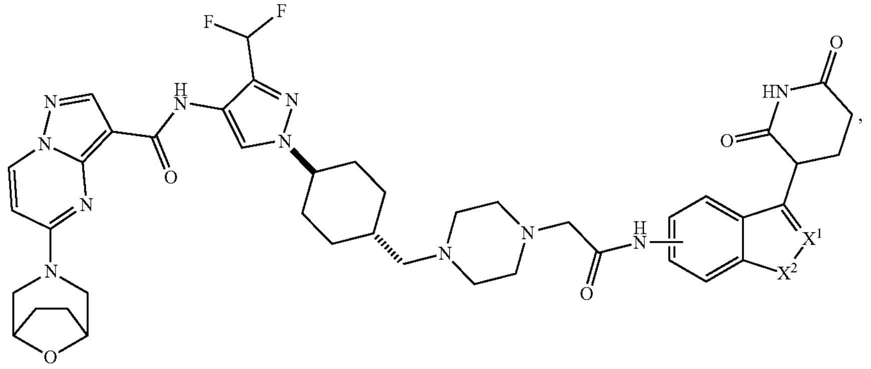
(VII-6T)
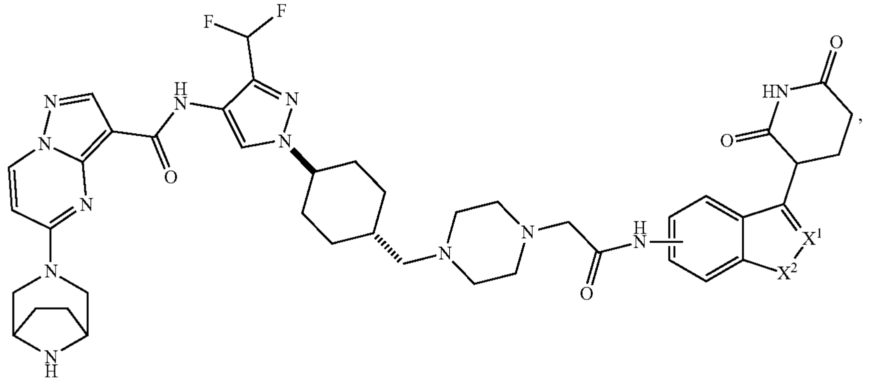
wherein $X_1$, $X_2$, $R_3$, $R_4$, $T_1$, and $L_1$ are as defined in the present disclosure.

The present disclosure also provides a compound of the following formula or a pharmaceutically acceptable salt thereof,
(VII-1RTS)
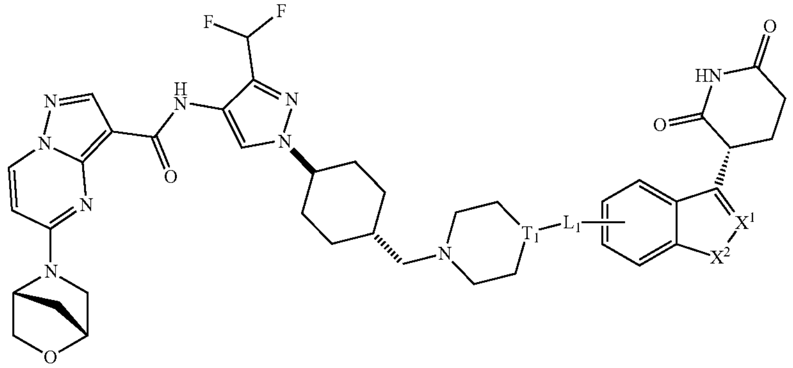
(VII-1RTT)
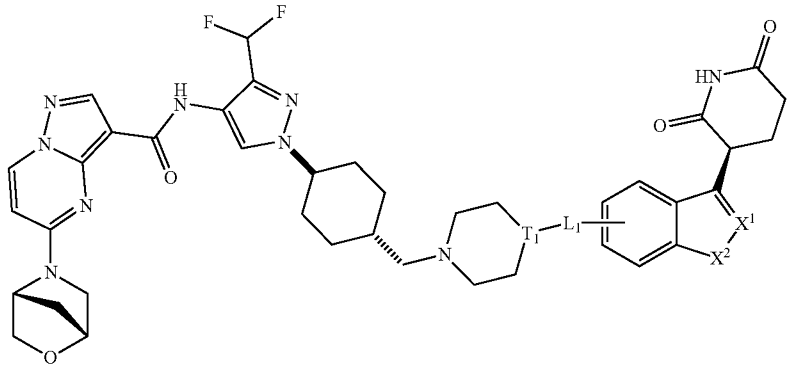
(VII-1STS)
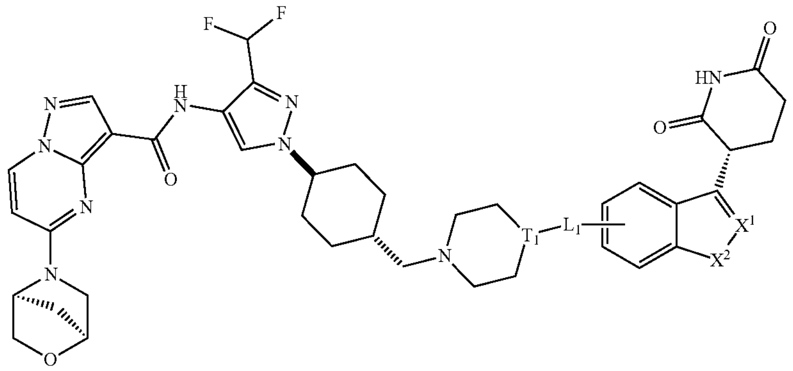
(VII-1STT)
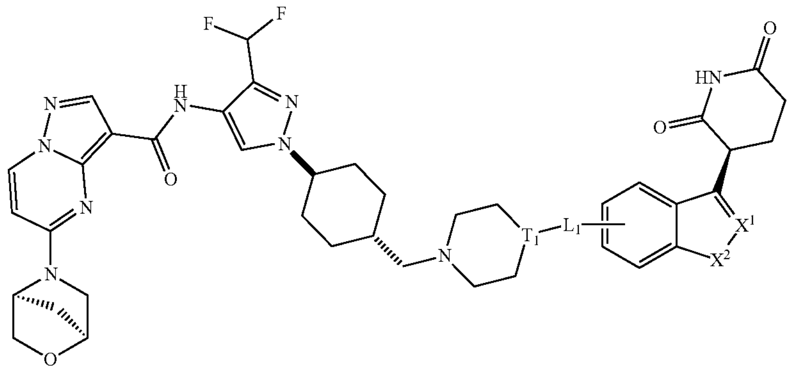

-continued
(VII-2RTS)
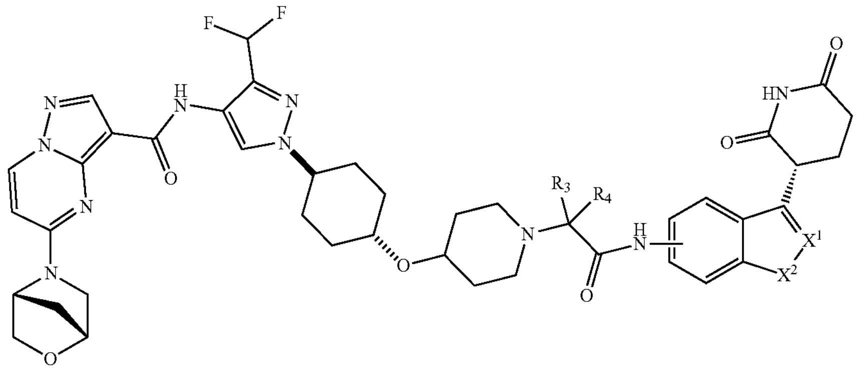
(VII-2RTT)
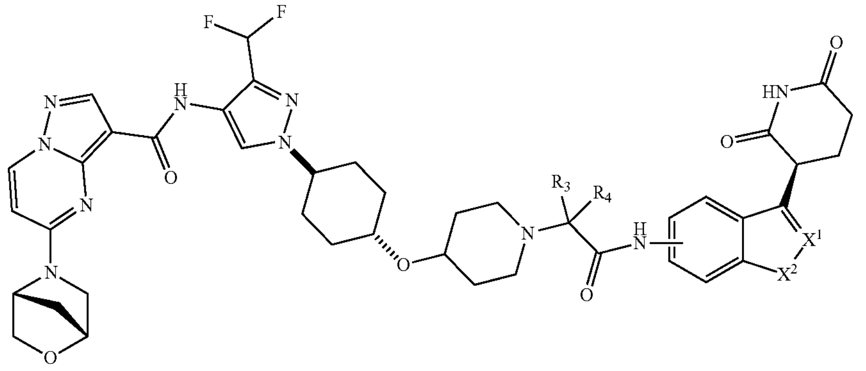
(VII-2STS)
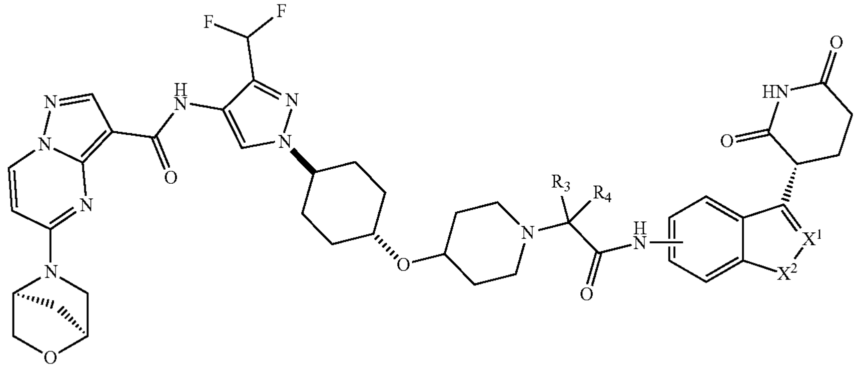
(VII-2STT)
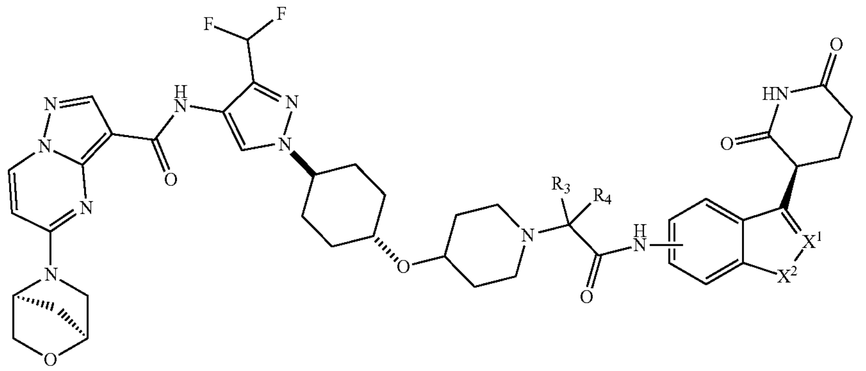

-continued
(VII-3RTS)
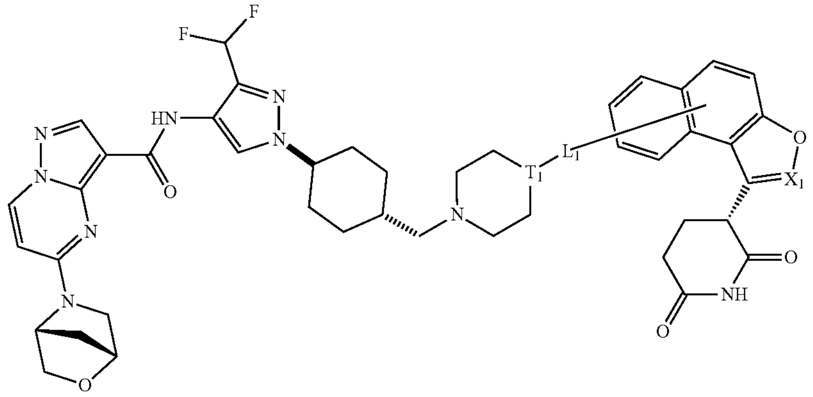
(VII-3RTT)
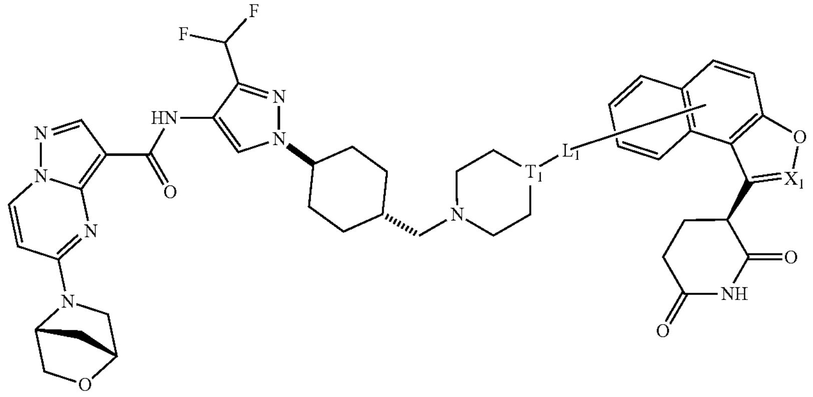
(VII-3STS)
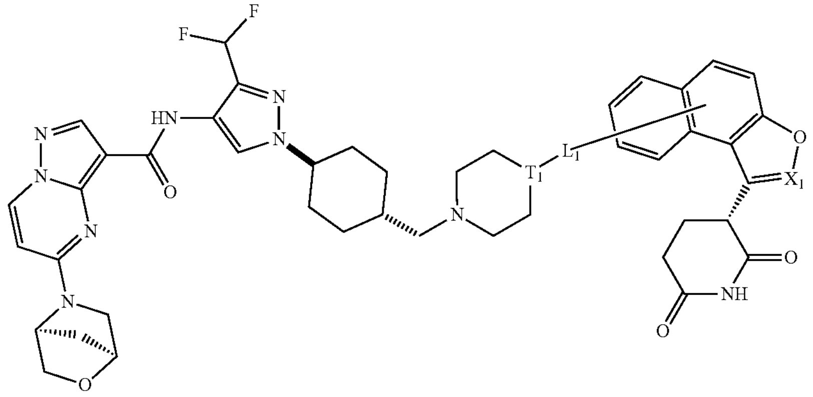
(VII-3STT)
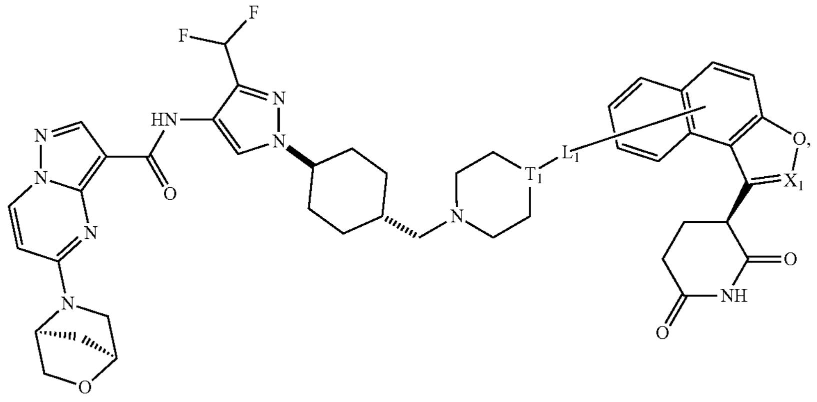

-continued
(VII-4RS)
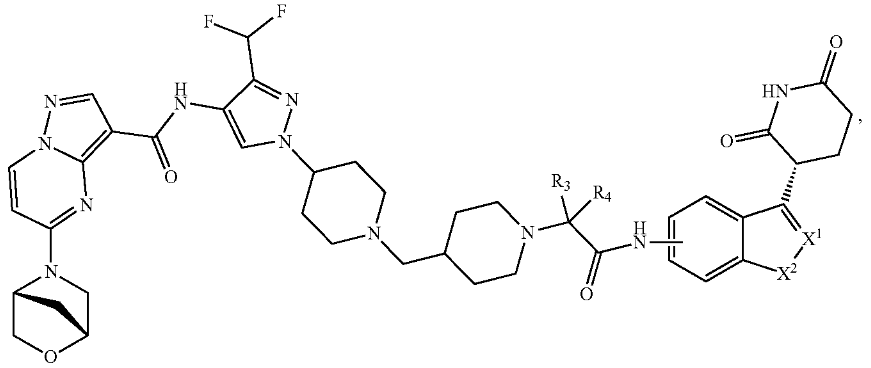
(VII-4RT)
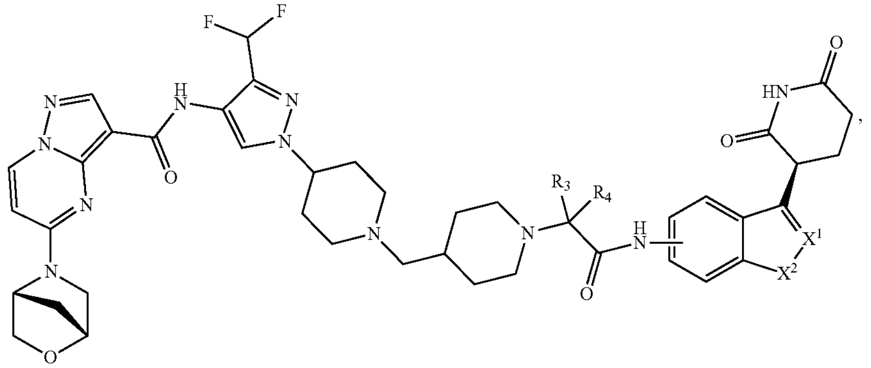
(VII-5TS)
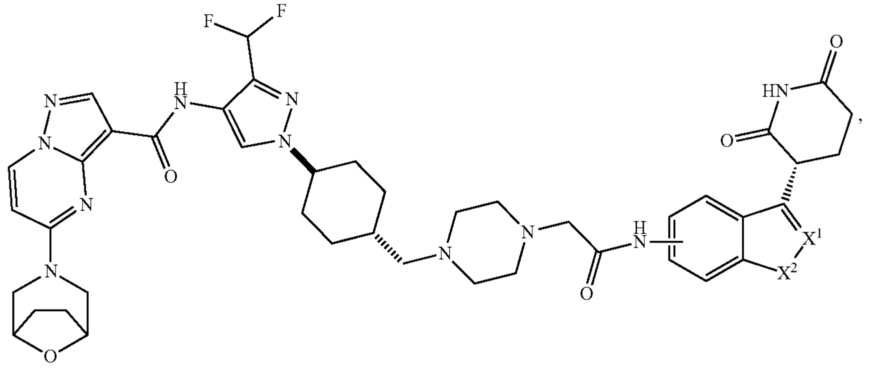
(VII-5TT)
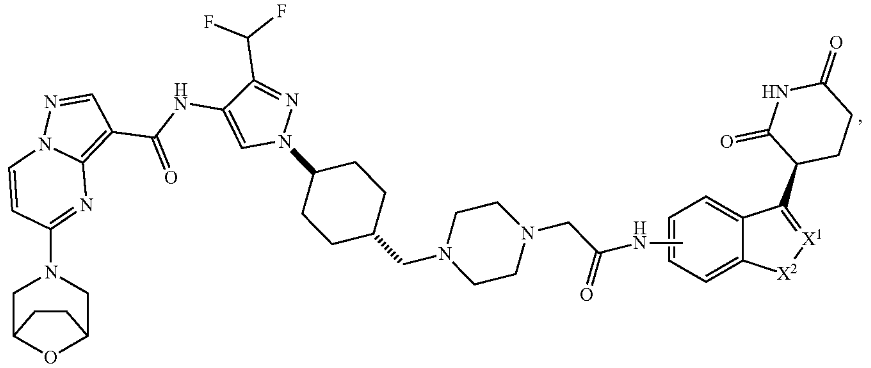

-continued
(VII-6TS)
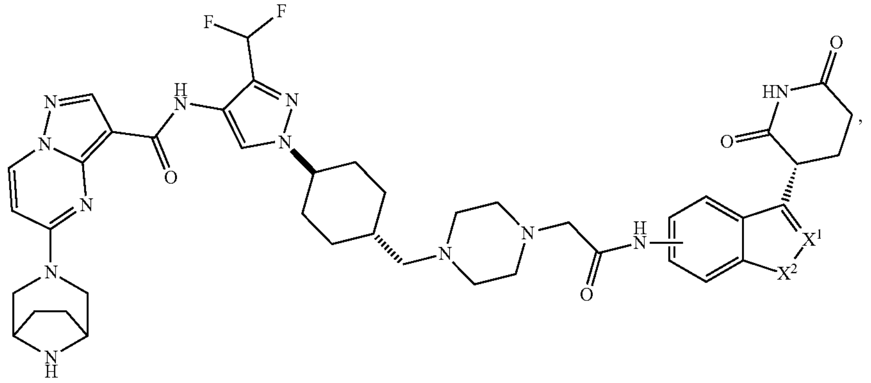
(VII-6TT)
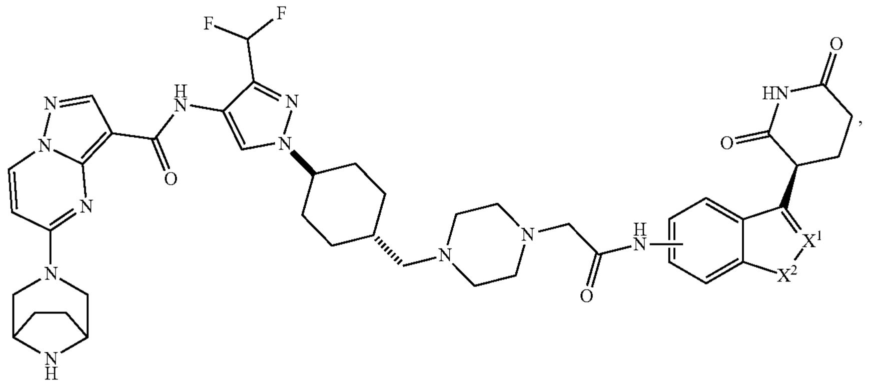
wherein $X_1$, $X_2$, $R_3$, $R_4$, $T_1$, and $L_1$ are as defined in the present disclosure.
The present disclosure provides a compound of formula (IV) or a pharmaceutically acceptable salt thereof,
(IV)
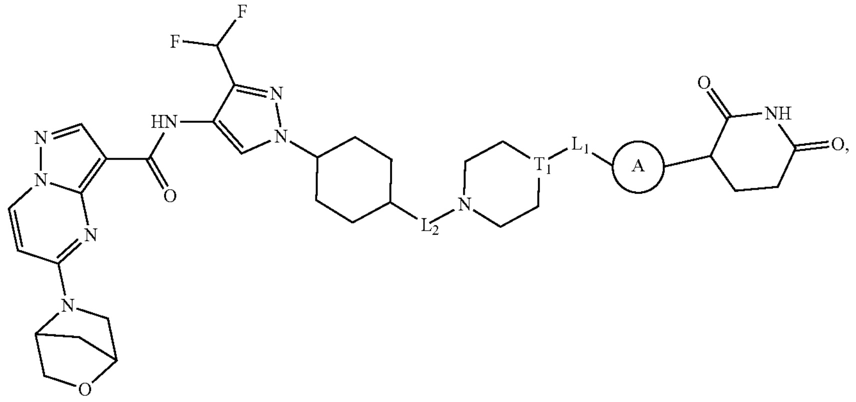

wherein $L_1$ is selected from $R_2$ and

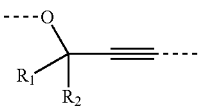

and

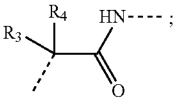

;

$L_2$ is selected from $-CR_5R_6-$;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$T_1$ is selected from CH and N;

ring A is selected from

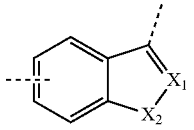

and

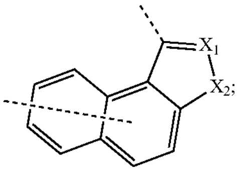

;

$X_1$ is selected from CH and N;

$X_2$ is selected from NH, O, S, and Se.

In some embodiments of the present disclosure, the $R_1$, $R_2$, $R_3$, $R_4$, $R_5$, and $R_6$ in formula (IV) are each independently selected from H and F, and other variables are as defined in the present disclosure.

In some embodiments of the present disclosure, the $L_1$ in formula (IV) is selected from

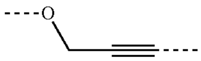

and

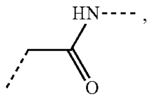

, and other variables are as defined in the present disclosure.

In some embodiments of the present disclosure, the $L_2$ in formula (IV) is selected from $-CH_2-$, and other variables are as defined in the present disclosure.

In some embodiments of the present disclosure, the structural moiety

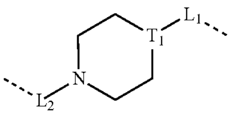

in formula (IV) is selected from

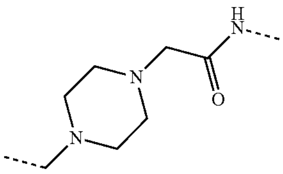

and

-continued

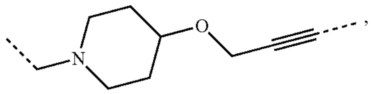

, and other variables are as defined in the present disclosure.

In some embodiments of the present disclosure, the ring Ain formula (IV) is selected from

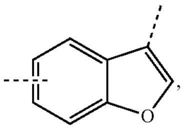

,

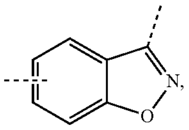

,

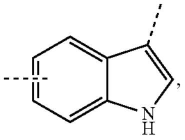

,

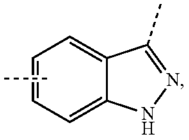

,

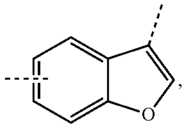

,

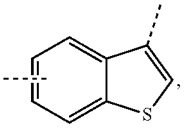

,

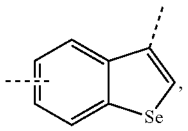

,

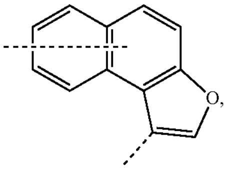

, and

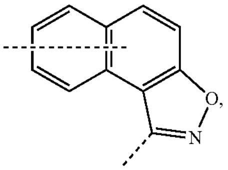

, and other variables are as defined in the present disclosure.

In some embodiments of the present disclosure, the ring Ain formula (IV) is selected from

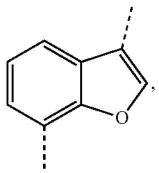

,

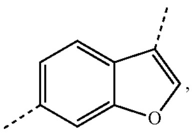

,

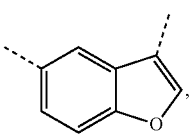

,

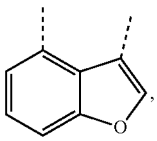

,

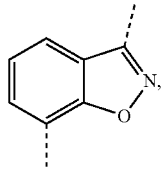

,

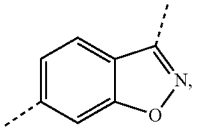

,

-continued

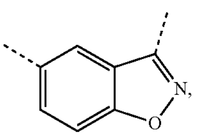
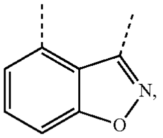
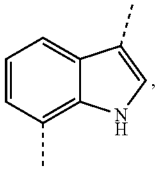
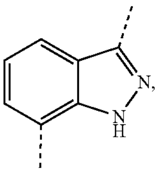
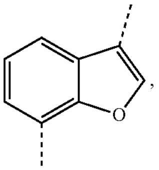
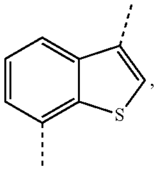

-continued

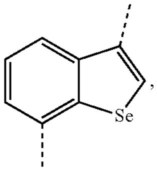
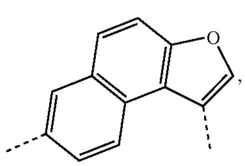
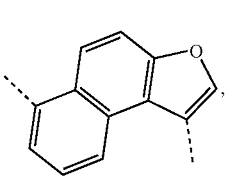
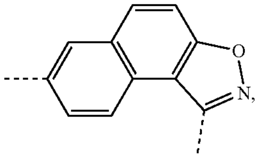
and
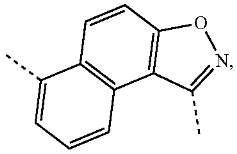

and other variables are as defined in the present disclosure.

The present disclosure also provides a compound of formula (IV-1) or a pharmaceutically acceptable salt thereof, (IV-1)

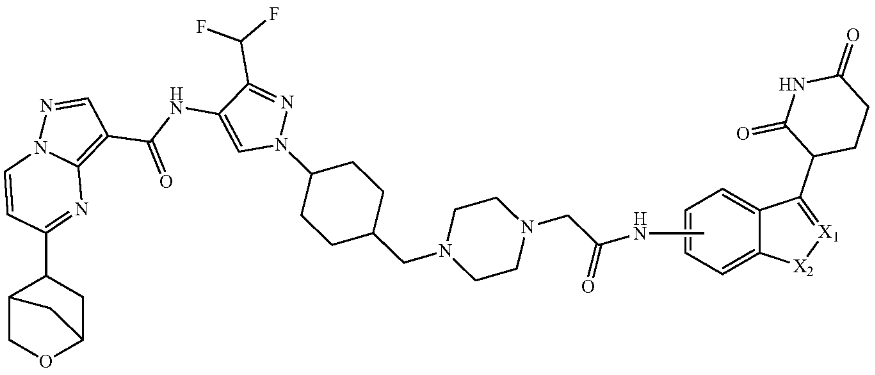

wherein $X_1$ is selected from CH and N;

$X_2$ is selected from NH, O, S, and Se.

The present disclosure also provides a compound of formulas (III-2) and (IV-2) or a pharmaceutically acceptable salt thereof, (III-2)

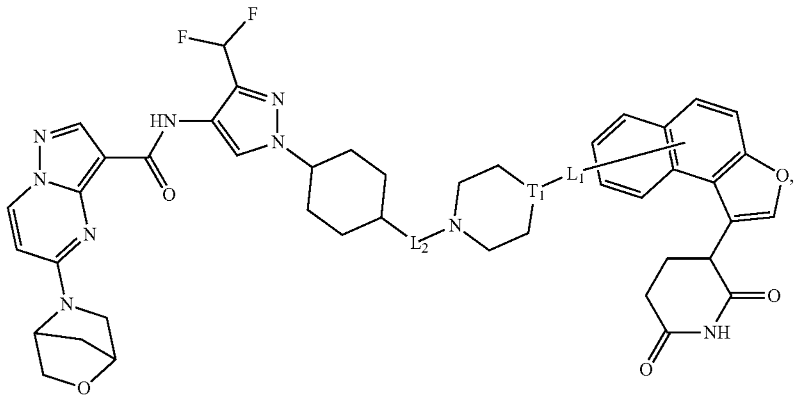

-continued (IV-2)

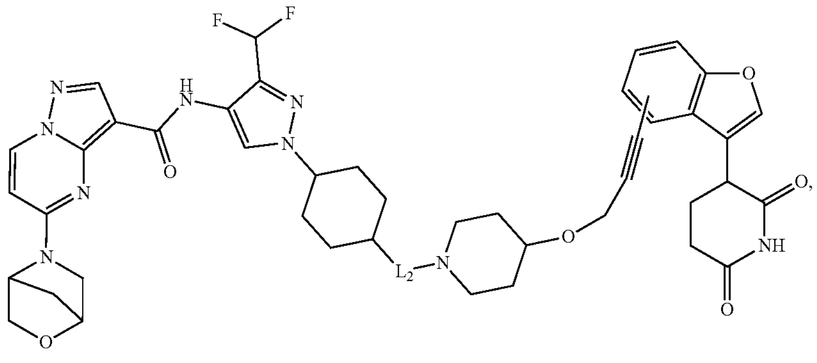

wherein $X_1$ is selected from CH and N;

$L_1$, $L_2$, and $T_1$ are as defined in the present disclosure.

The present disclosure also provides a compound of formula (I-2) or (IV-2a) or a pharmaceutically acceptable salt thereof, (I-2)

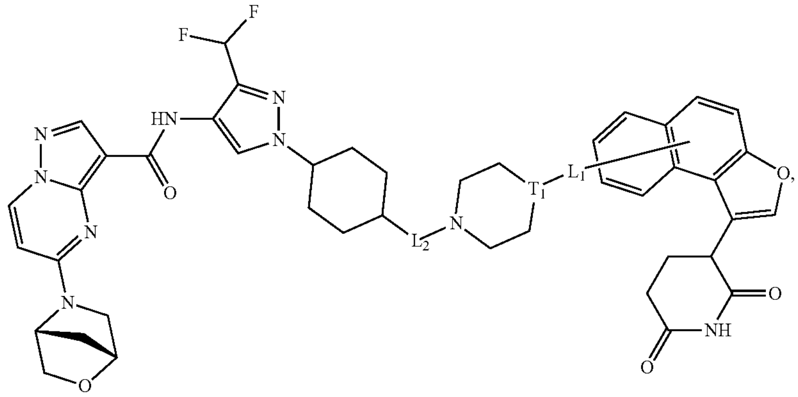

(IV-2a)

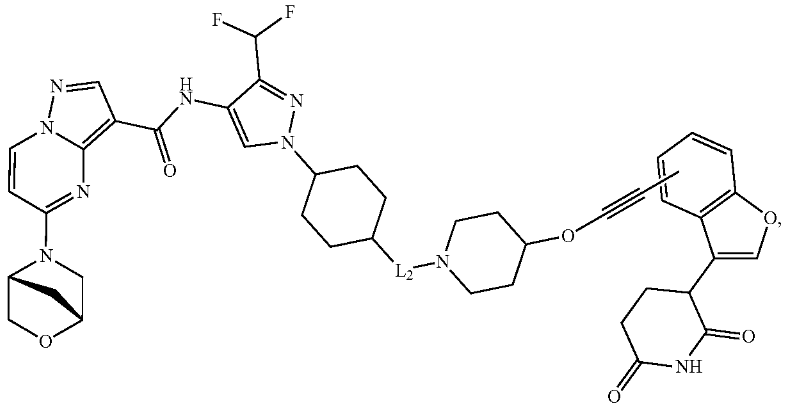

wherein $T_2$ is selected from CH and N;

$L_1$, $L_2$, and $T_1$ are as defined in the present disclosure.

The present disclosure provides a compound of formula (I) or a pharmaceutically acceptable salt thereof, (I)

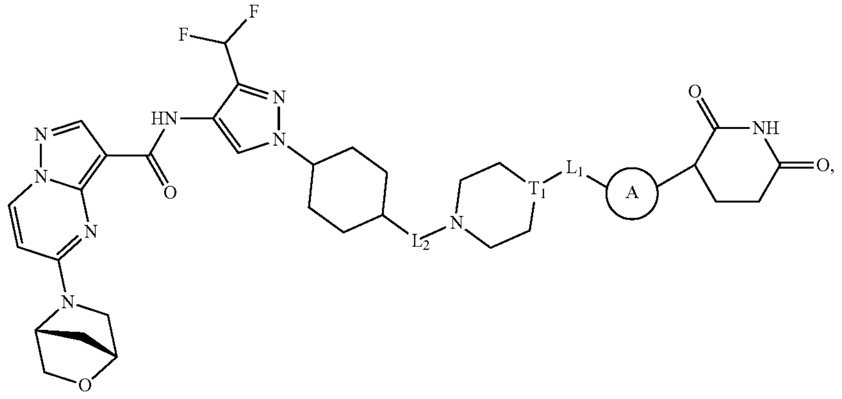

wherein
$L_1$ is selected from

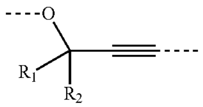
and
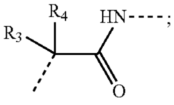
;

$L_2$ is selected from $-CR_5R_6-$;
$R_1$, $R_2$, $R_3$, $R_4$, $R_5$, and $R_6$ are each independently selected from H and halogen;
or, $R_1$ and $R_2$, $R_3$ and $R_4$, $R_5$ and $R_6$, optionally together with the carbon atom to which they are attached form a cyclopropyl ring;
$T_1$ is selected from CH and N;
ring A is selected from

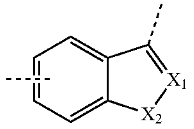
and
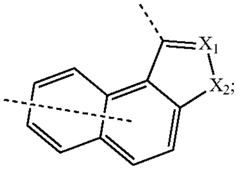
;

$X_1$ is selected from CH and N;
$X_2$ is selected from $CH_2$, NH, O, S, and Se.

In some embodiments of the present disclosure, the $R_1$, $R_2$, $R_3$, $R_4$, $R_5$, and $R_6$ in formula (I) are each independently selected from H and F, and other variables are as defined in the present disclosure.

In some embodiments of the present disclosure, the $L_1$ in formula (I) is selected from

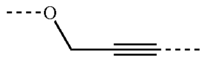
and
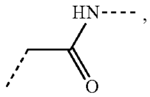
, and other variables are as defined in the present disclosure.

In some embodiments of the present disclosure, the $L_2$ in formula (I) is selected from $-CH_2-$, and other variables are as defined in the present disclosure.

In some embodiments of the present disclosure, the structural moiety

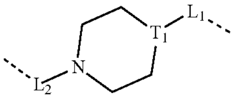

in formula (I) is selected from

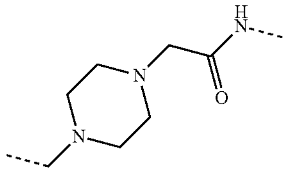
and
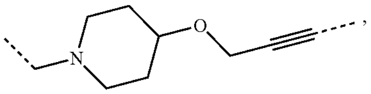
, and other variables are as defined in the present disclosure.

In some embodiments of the present disclosure, the ring A in formula (I) is selected from

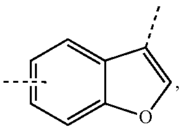
,
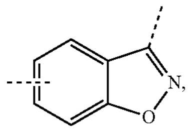
,
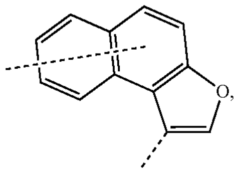
, or
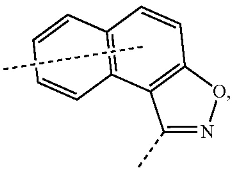
, and other variables are as defined in the present disclosure.

In some embodiments of the present disclosure, the ring A in formula (I) is selected from

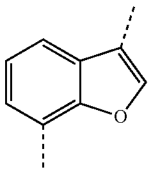,
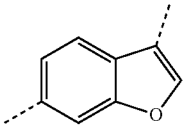,
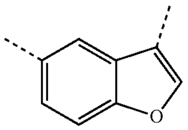,
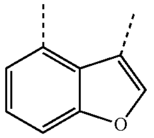,
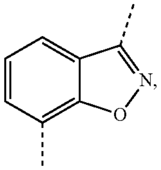
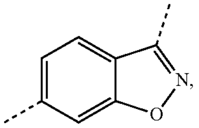
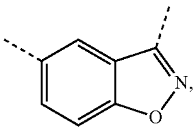
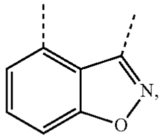

-continued

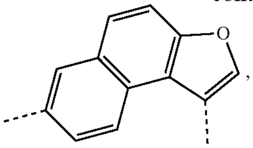,
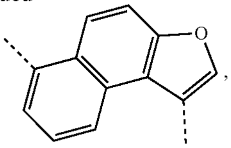,
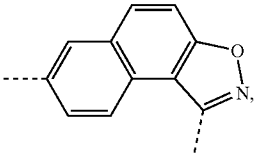 and 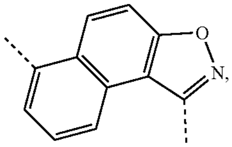

and other variables are as defined in the present disclosure.

The present disclosure also provides a compound of formulas (I-1) and (I-2) or a pharmaceutically acceptable salt thereof, (I-1)

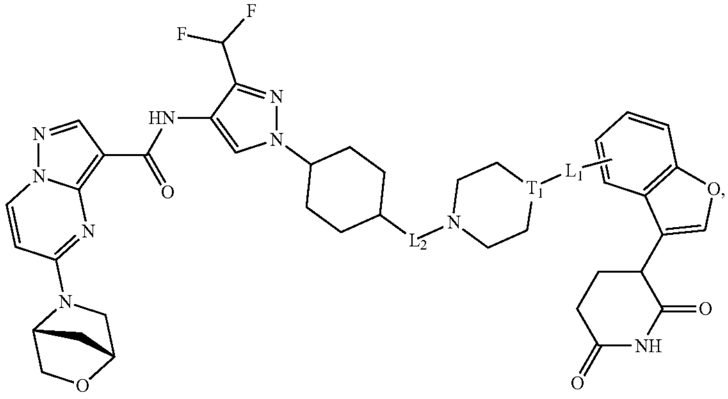

(I-2)

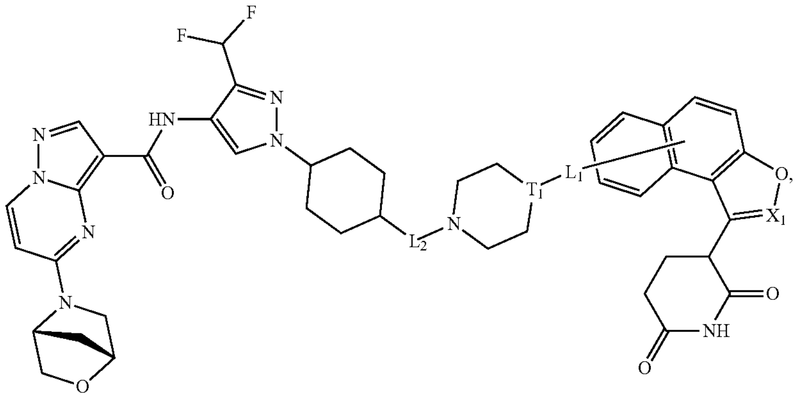

wherein $X_1$ is selected from CH and N;

$L_1$, $L_2$, and $T_1$ are as defined in the present disclosure.

The present disclosure provides a compound of formula (II) or a pharmaceutically acceptable salt thereof, (II)

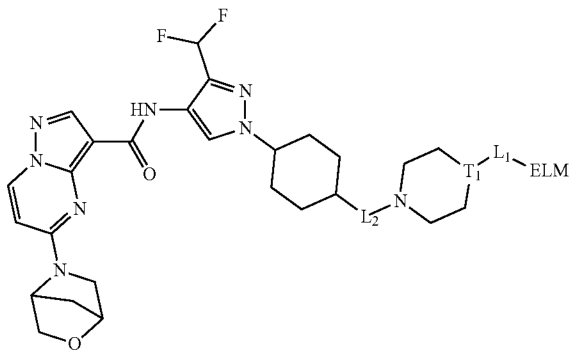

wherein $L_1$ is selected from $R_2$ and

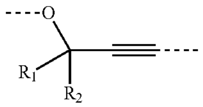

and

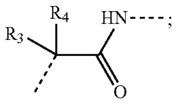

$L_2$ is selected from $—CR_5R_6—$;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$T_1$ is selected from CH and N;

ELM is selected from

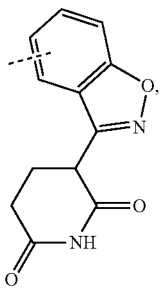

In some embodiments of the present disclosure, the $R_1$, $R_2$, $R_3$, $R_4$, $R_5$, and $R_6$ in formula (II) are each independently selected from H and F, and other variables are as defined in the present disclosure.

In some embodiments of the present disclosure, the $L_1$ in formula (II) is selected from

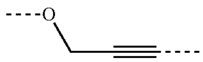

and

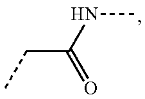

and other variables are as defined in the present disclosure.

In some embodiments of the present disclosure, the $L_2$ in formula (II) is selected from $—CH_2—$, and other variables are as defined in the present disclosure.

In some embodiments of the present disclosure, the structural moiety

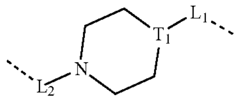

in formula (II) is selected from

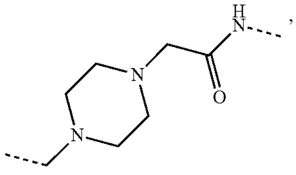

and other variables are as defined in the present disclosure.

The present disclosure provides a compound of formula (I) or a pharmaceutically acceptable salt thereof, (I)

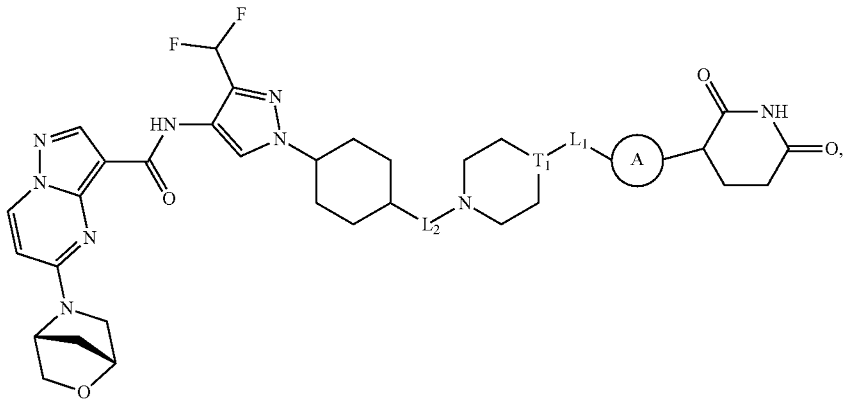

wherein $L_1$ is selected from $R_2$ and

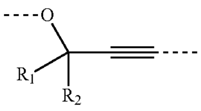

and

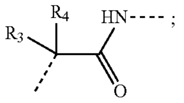

$L_2$ is selected from —$CR_5R_6$—;

$R_1$, $R_2$, $R_3$, $R_4$, $R_5$, and $R_6$ are each independently selected from H or halogen;

or, $R_1$ and $R_2$, $R_3$ and $R_4$, $R_5$ and $R_6$, optionally together with the carbon atom to which they are attached form a cyclopropyl ring;

$T_1$ is selected from CH and N;

ring A is selected from

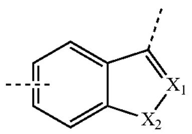

or

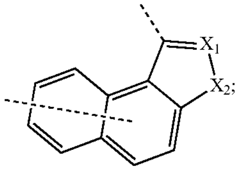

$X_1$ is selected from CH or N;

$X_2$ is selected from $CH_2$, NH, O, S, or Se.

In some embodiments of the present disclosure, the $R_1$, $R_2$, $R_3$, $R_4$, $R_5$, and $R_6$ in formula (I) are each independently selected from H and F, and other variables are as defined in the present disclosure.

In some embodiments of the present disclosure, the $L_1$ in formula (I) is selected from

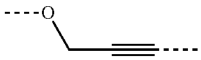

and

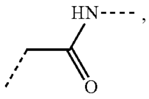

and other variables are as defined in the present disclosure.

In some embodiments of the present disclosure, the $L_2$ in formula (I) is selected from —$CH_2$—, and other variables are as defined in the present disclosure.

In some embodiments of the present disclosure, the structural moiety

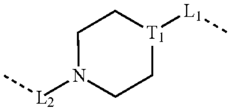

in formula (I) is selected from

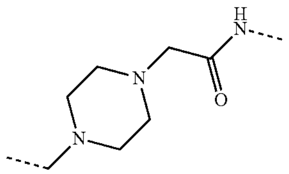

or

-continued

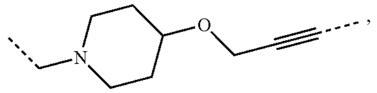

and other variables are as defined in the present disclosure.

In some embodiments of the present disclosure, the ring A in formula (I) is selected from

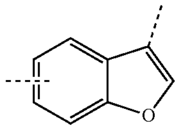

,

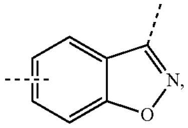

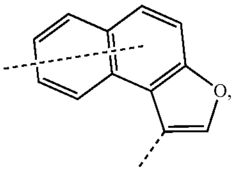

or

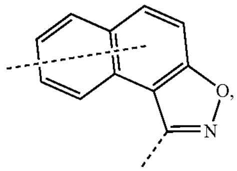

and other variables are as defined in the present disclosure.

In some embodiments of the present disclosure, the ring A in formula (I) is selected from

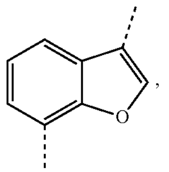

,

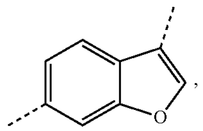

,

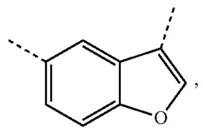

,

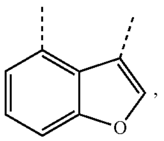

,

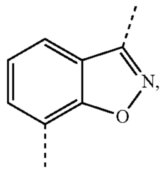

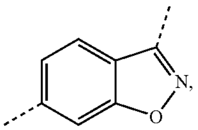

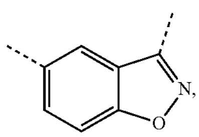

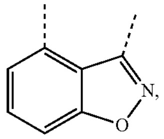

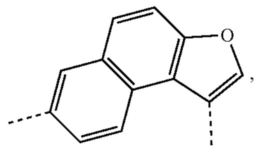

,

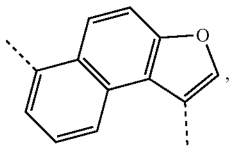

,

-continued
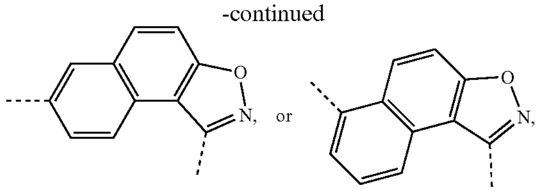
and other variables are as defined in the present disclosure.
The present disclosure also provides a compound of formula (III-1), (III-2), or (III-3) or a pharmaceutically acceptable salt thereof,
(III-1)
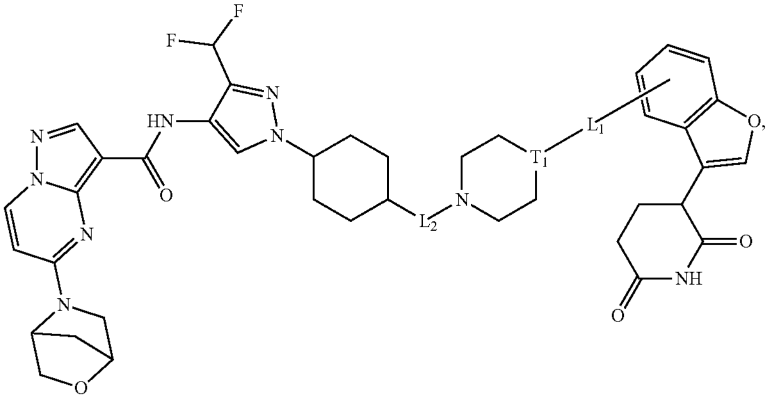
(III-2)
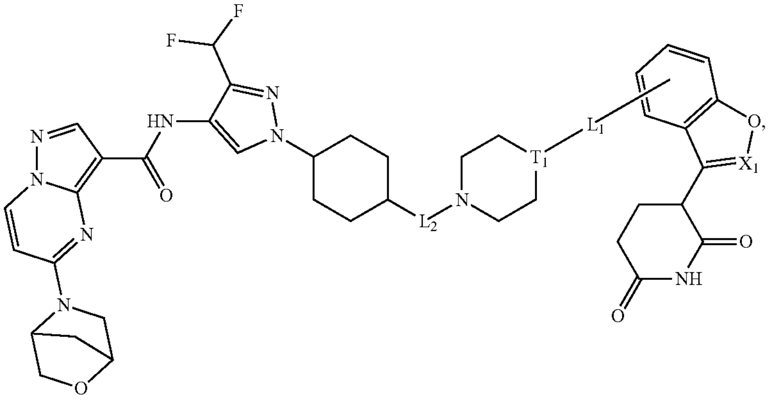
(III-3)
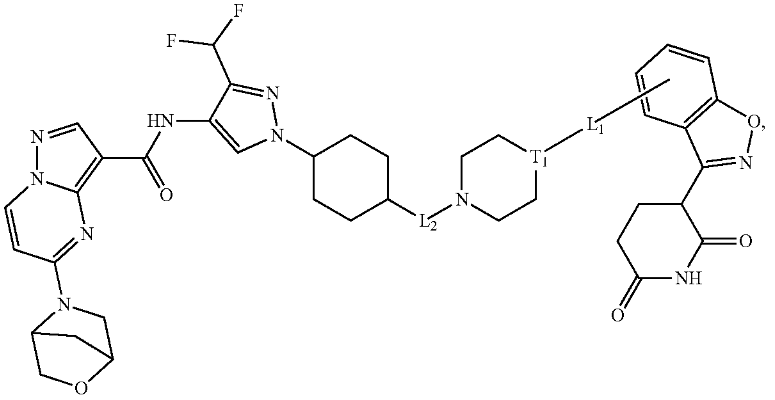
wherein $X_1$ is selected from CH and N;
$L_1$, $L_2$, and $T_1$ are as defined in the present disclosure.

The present disclosure also provides a compound of formula (I-1), (I-2), or (III-3a) or a pharmaceutically acceptable salt thereof, (I-1)

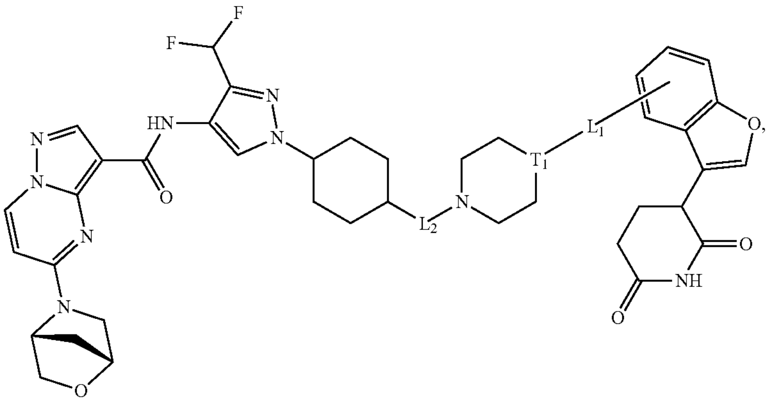

(I-2)

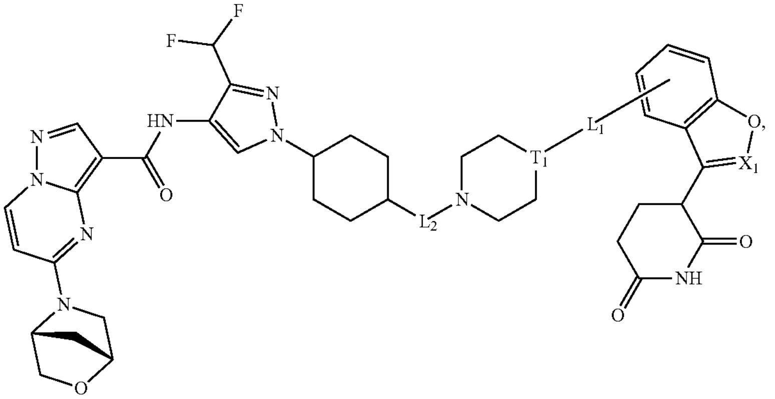

(I-3)

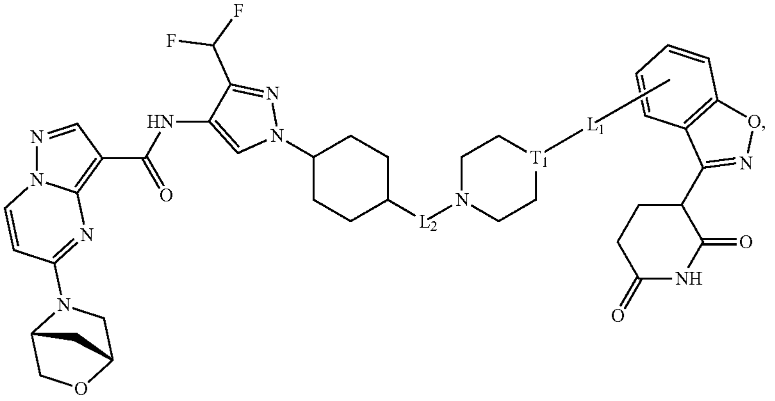

wherein $X_1$ is selected from CH and N;

$L_1$, $L_2$, and $T_1$ are as defined in the present disclosure.

There are still some embodiments of the present disclosure which are obtained by any combination of the above variables.

The present disclosure also provides the following compounds or pharmaceutically acceptable salts thereof:

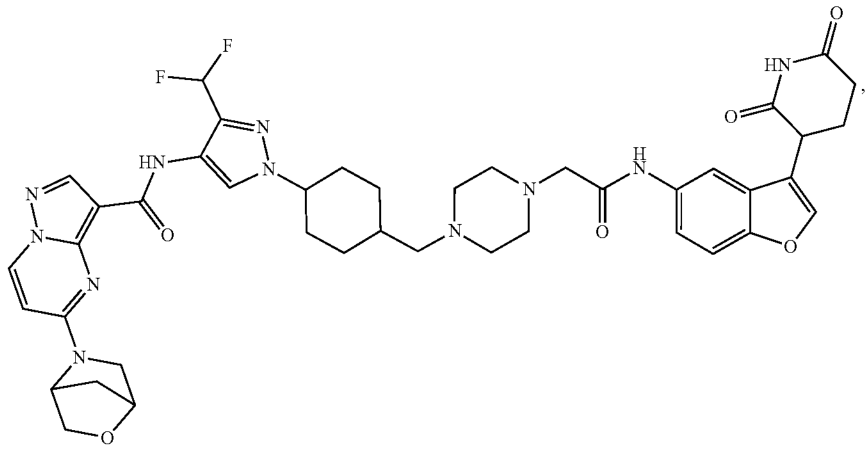
,
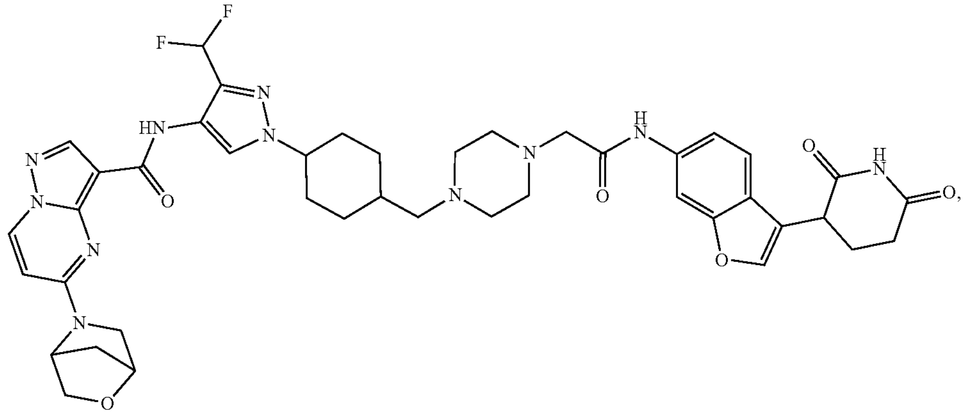
,
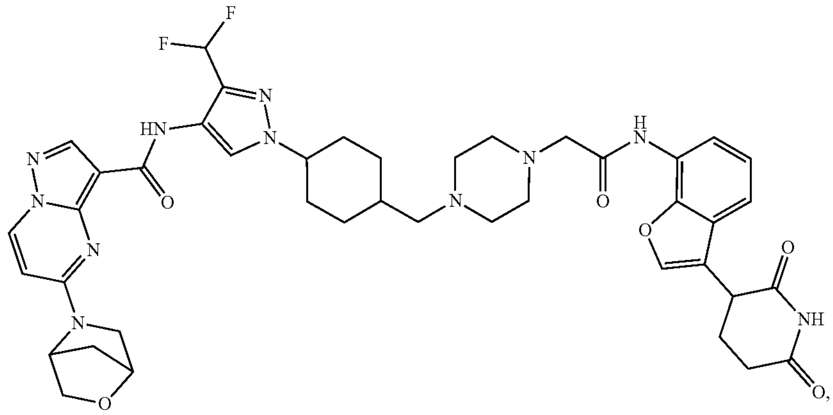
,
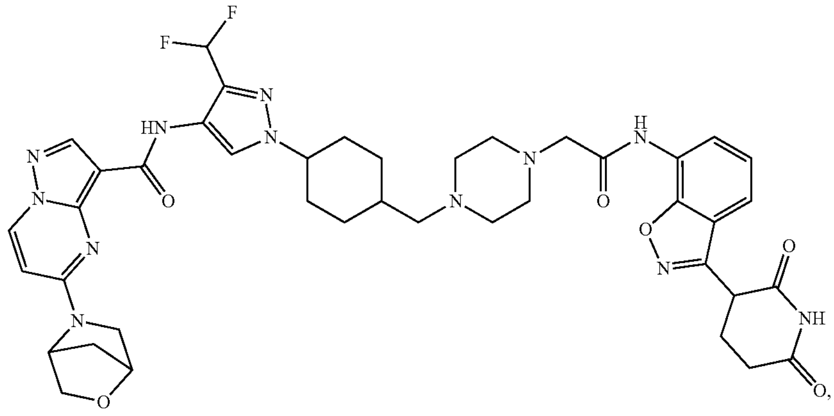
,

-continued
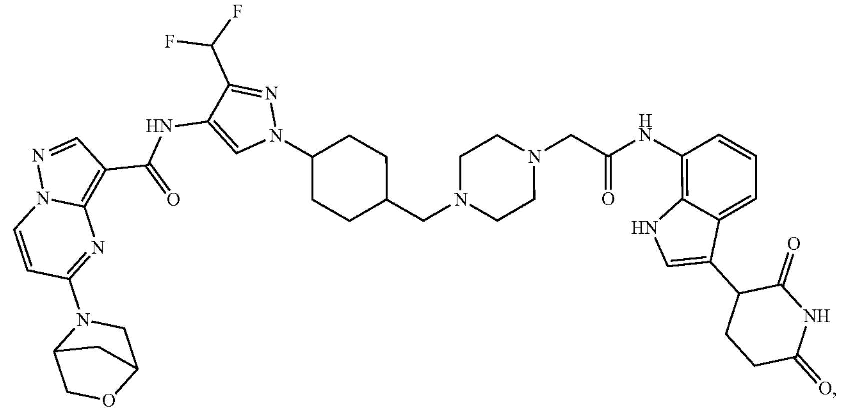
,
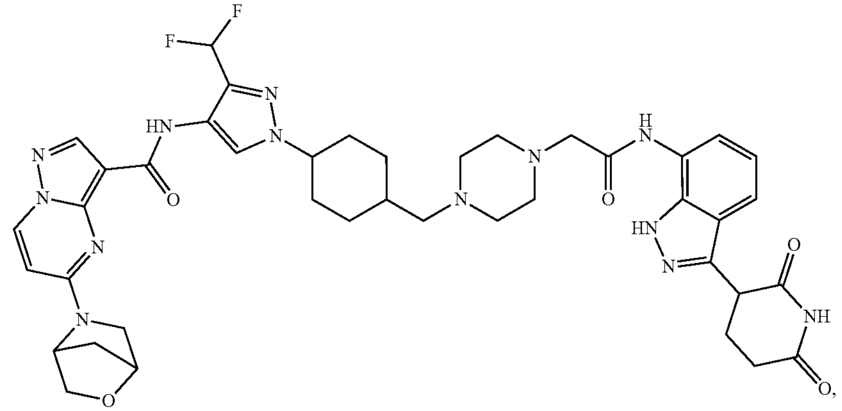
,
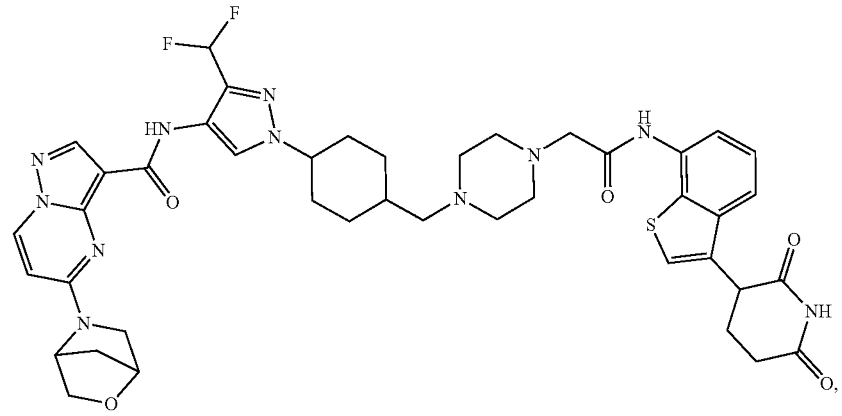
,
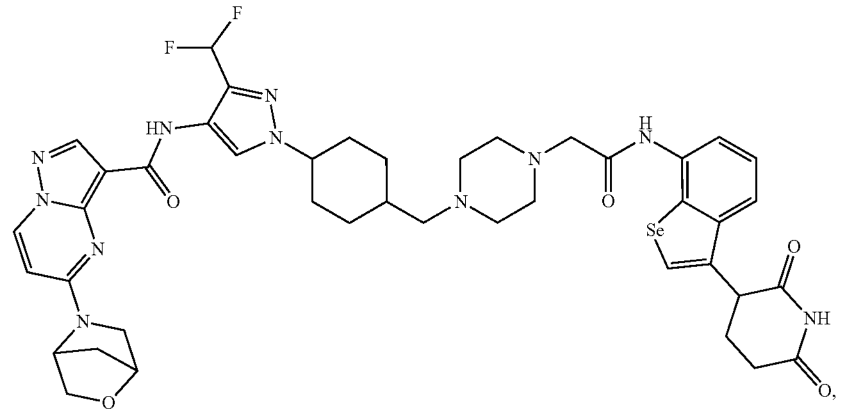
,

-continued
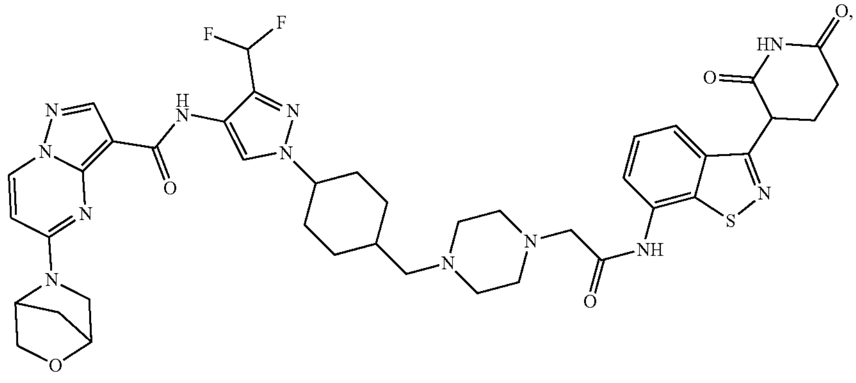
,
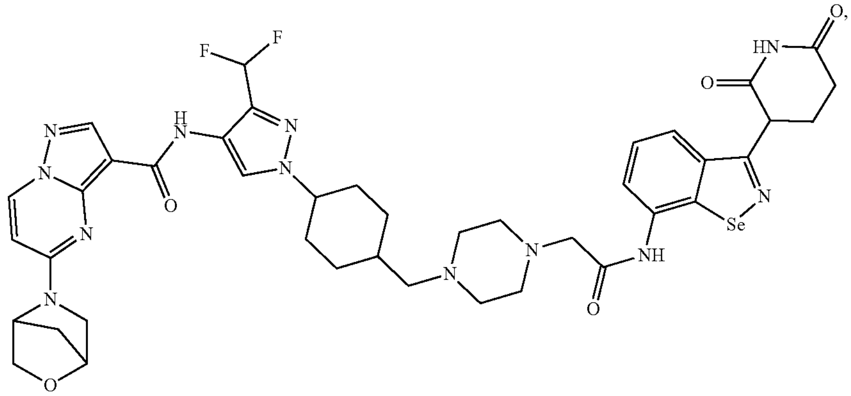
,
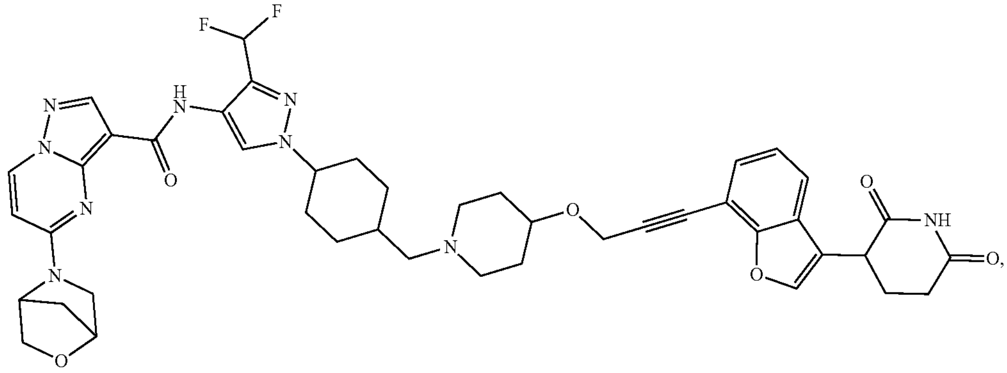
,
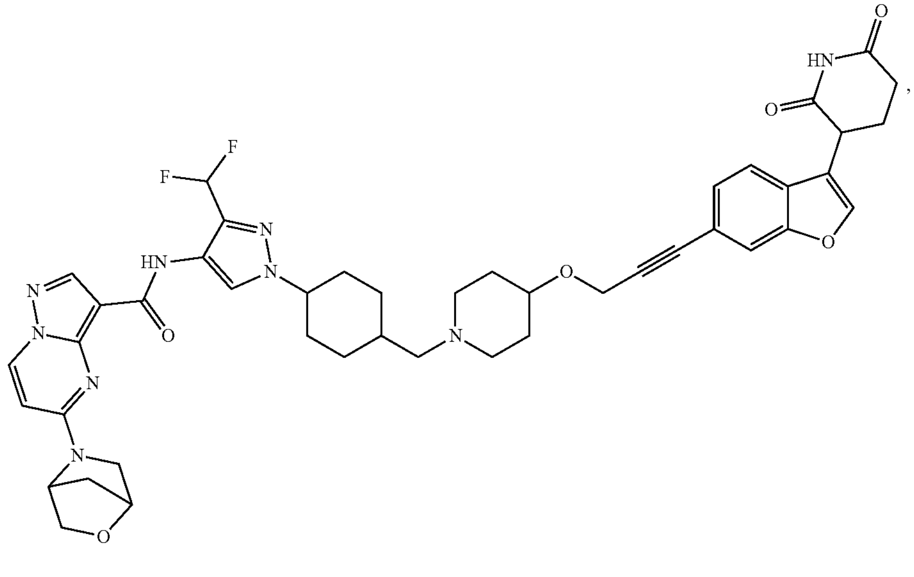
,

-continued
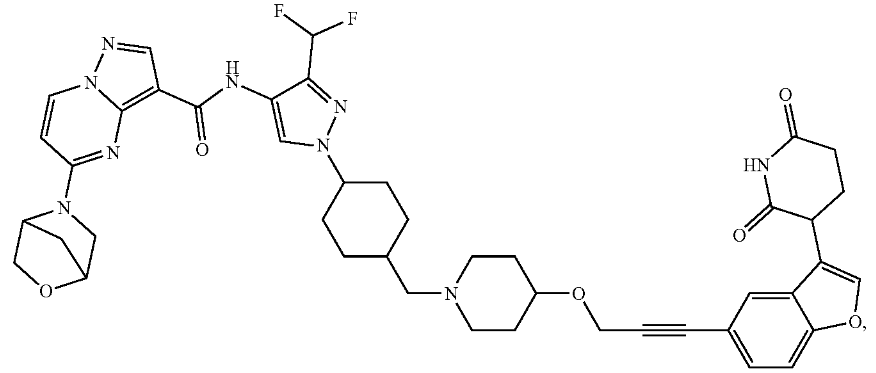
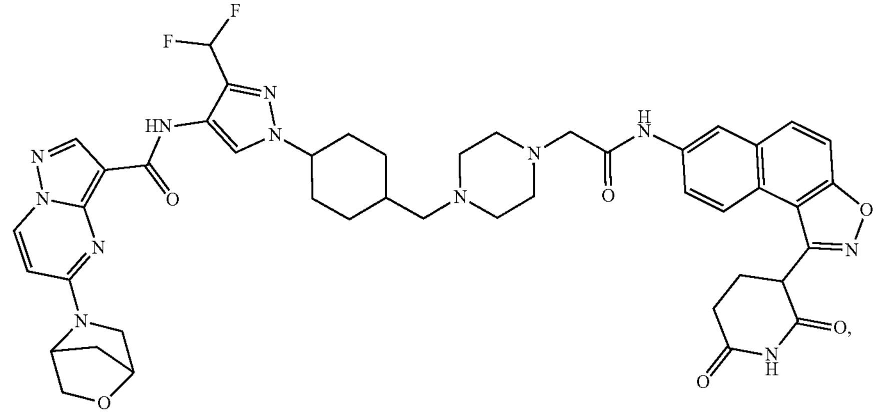
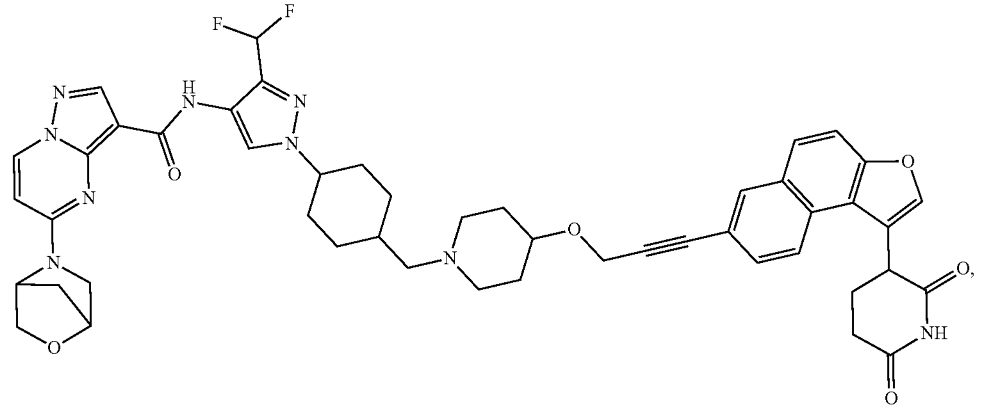
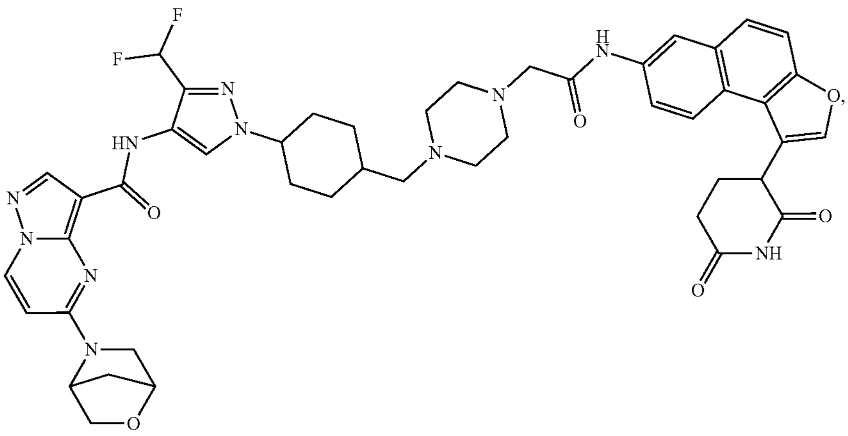

-continued
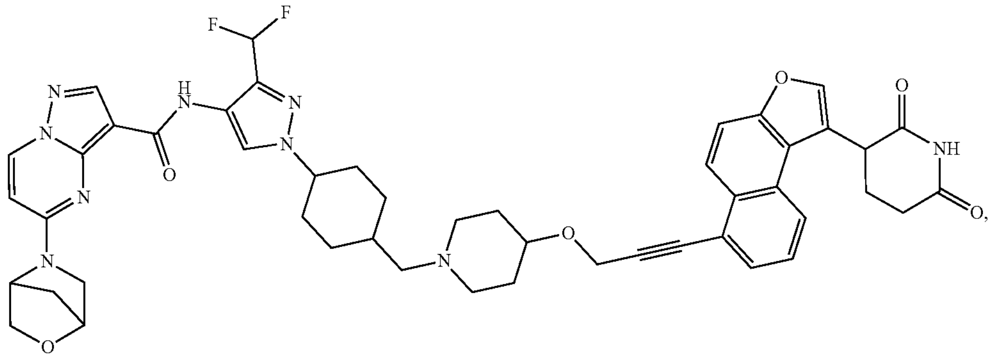
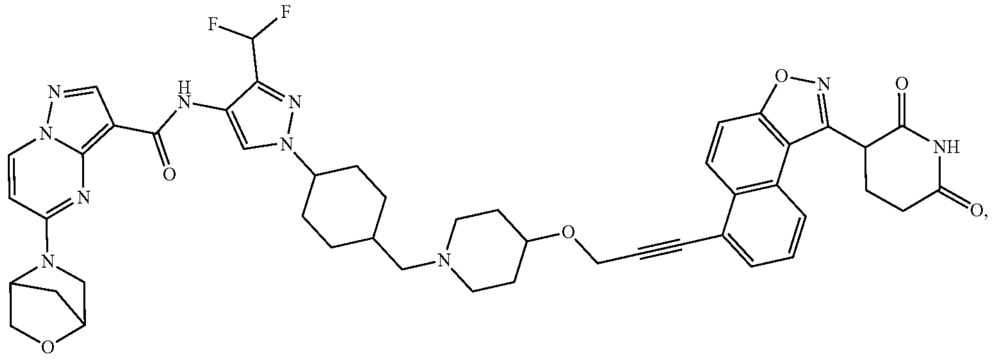
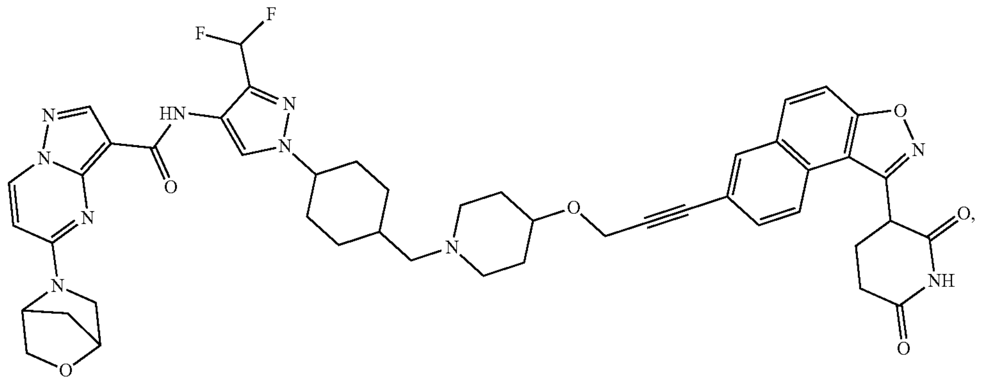
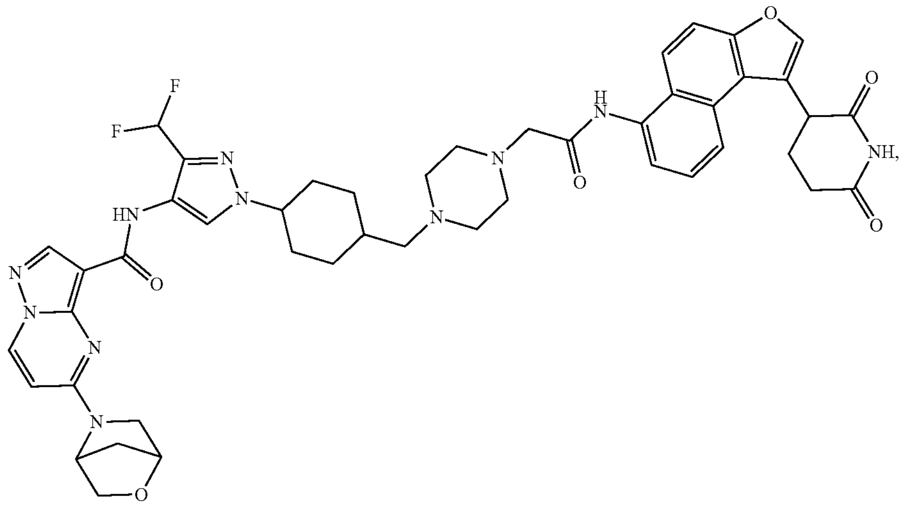

-continued
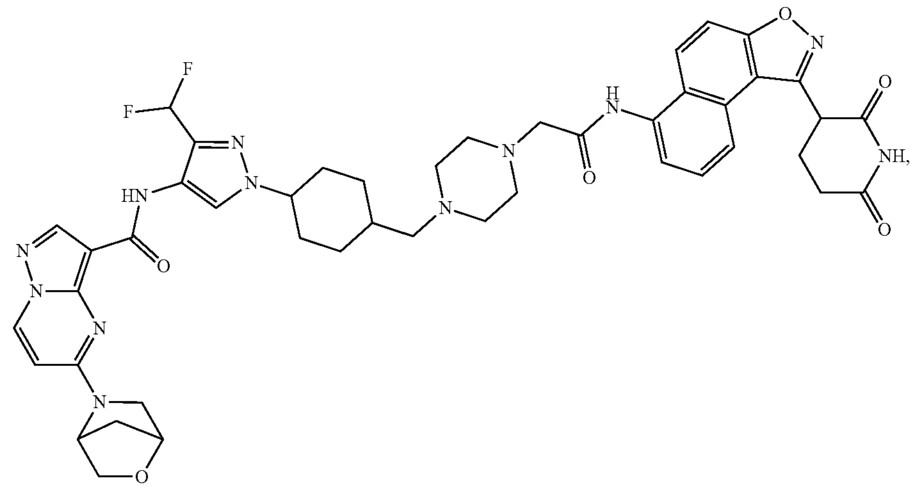
,
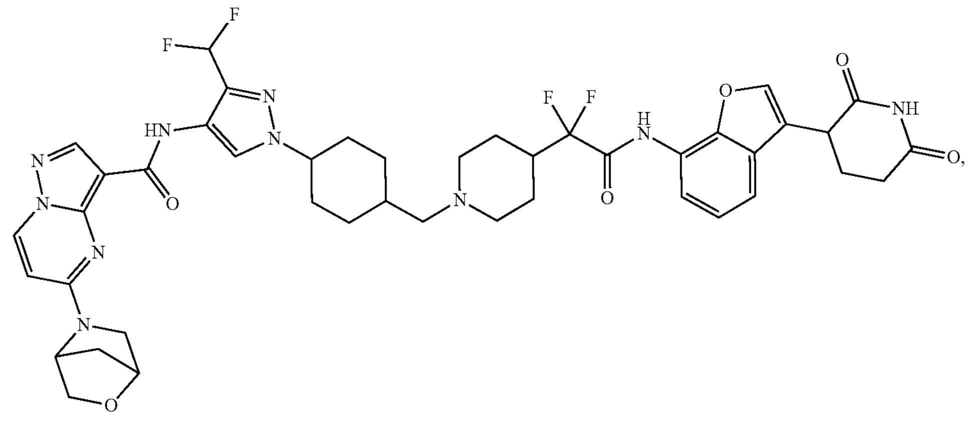
,
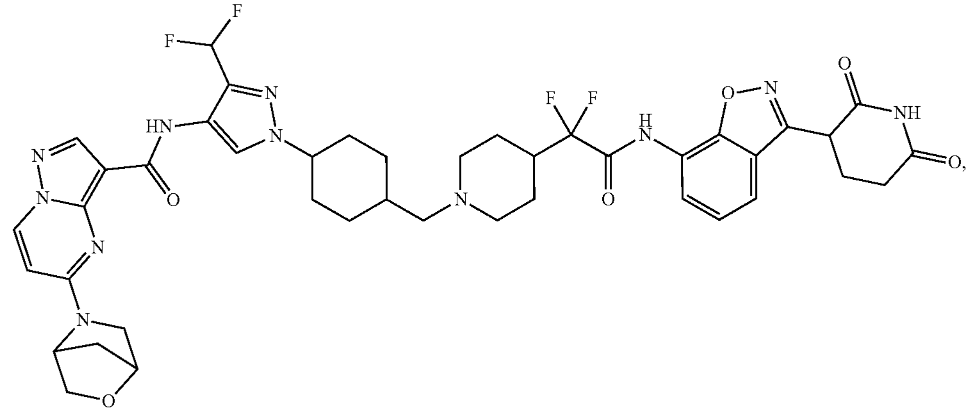
,

-continued
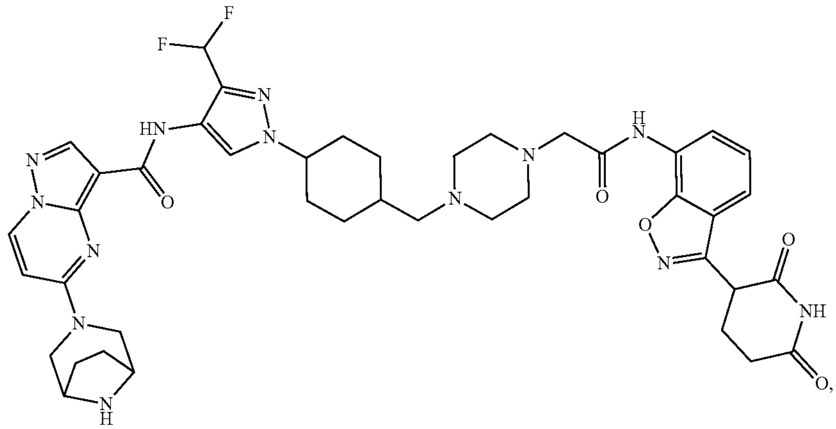
,
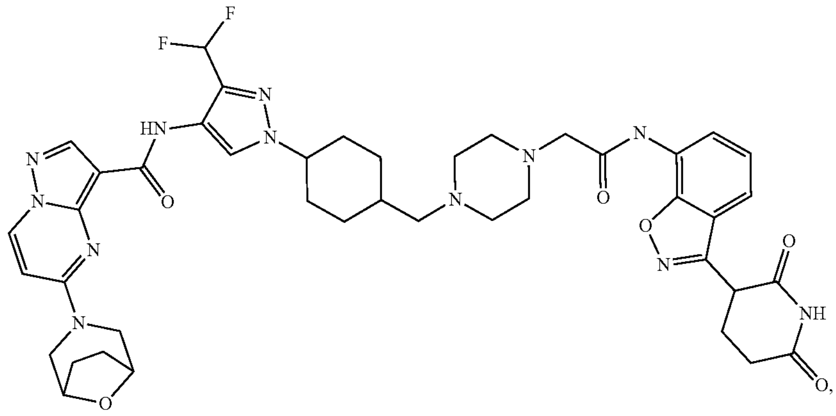
,
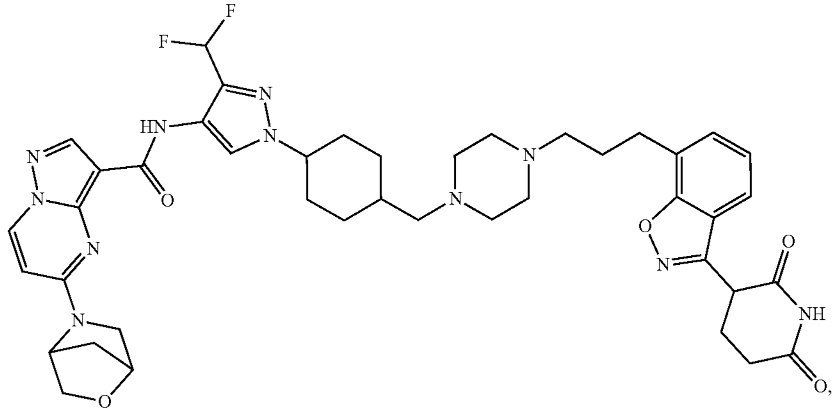
,
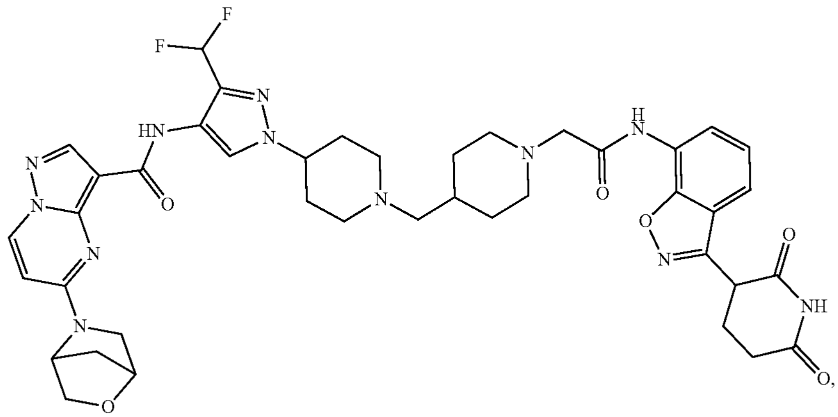
,

-continued
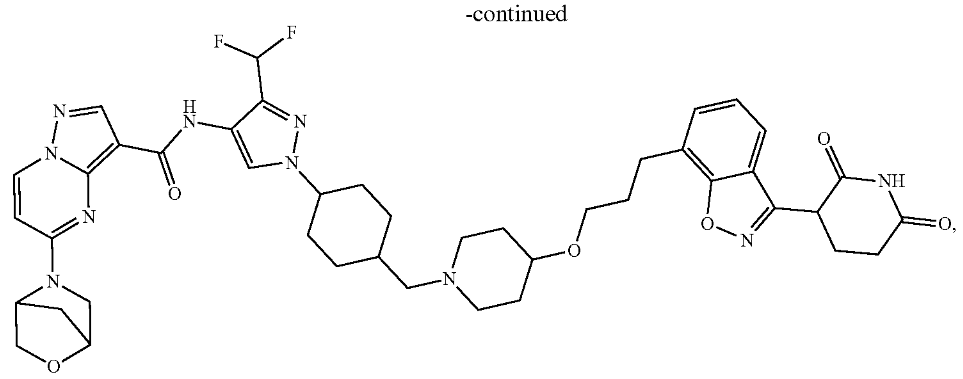
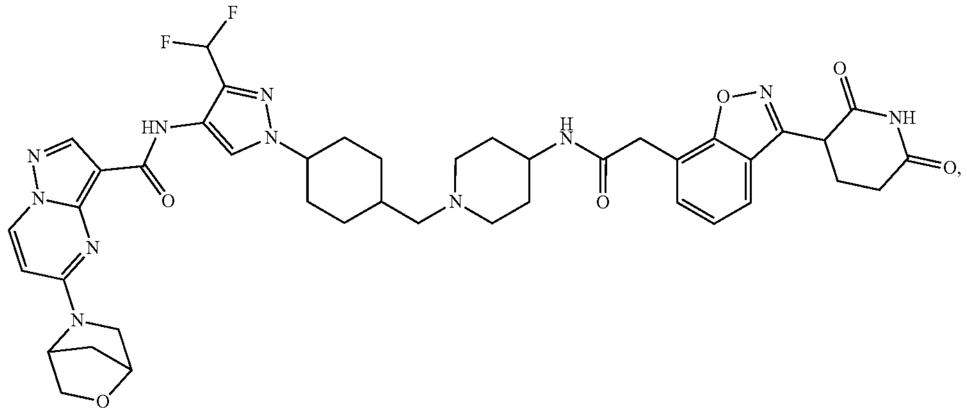
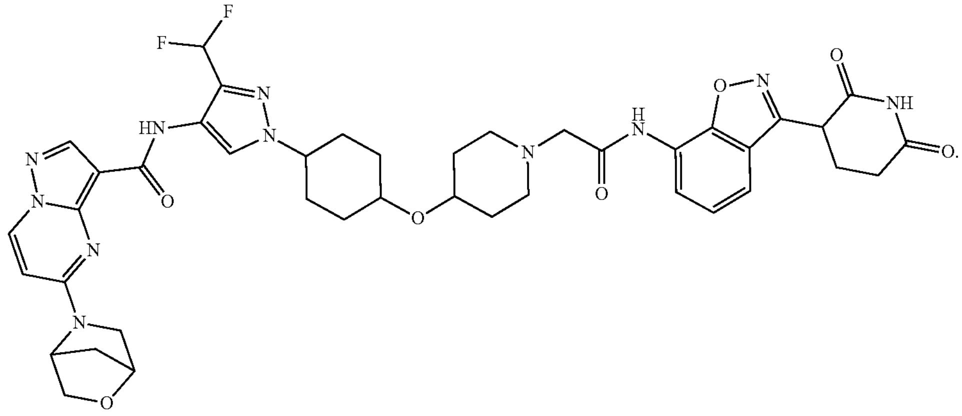
In some embodiments of the present disclosure, the compound is selected from:

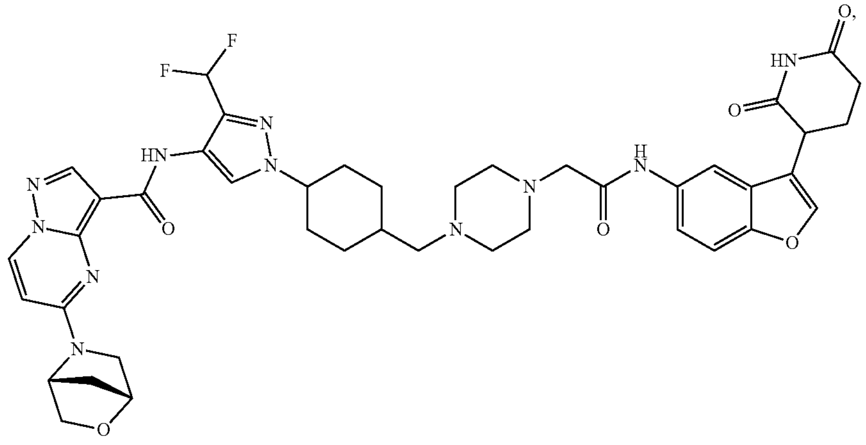
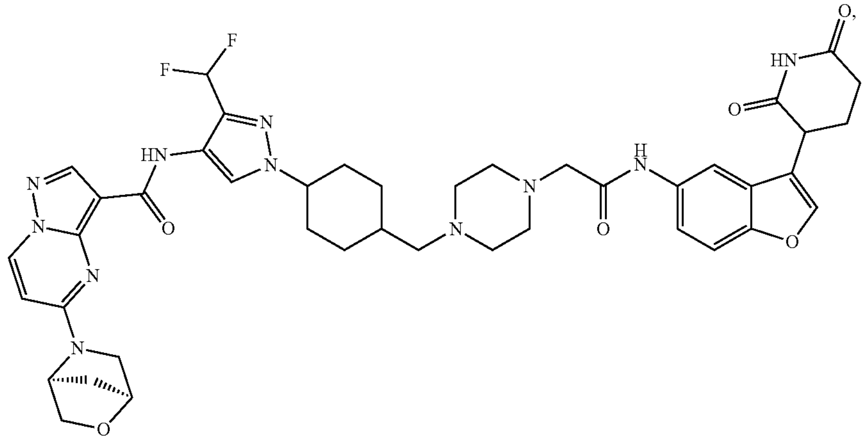
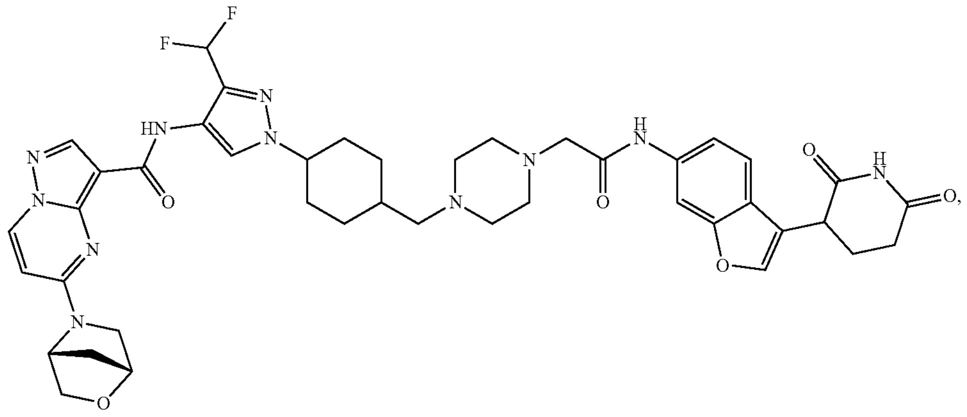
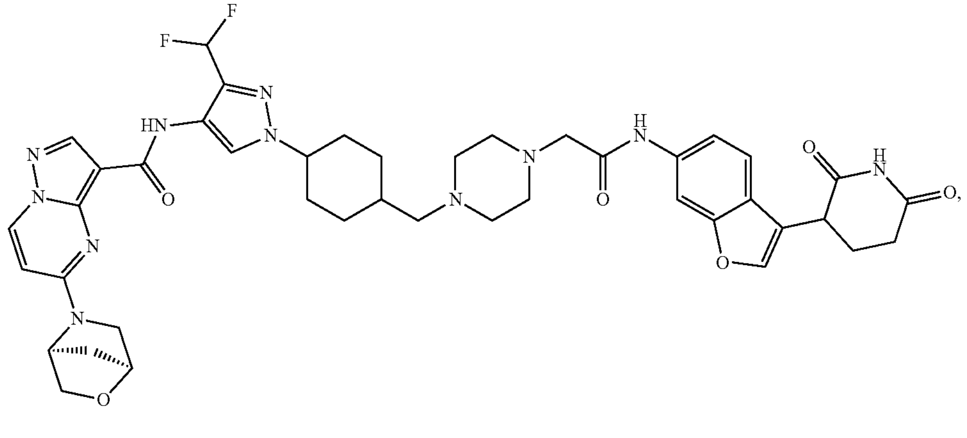

-continued
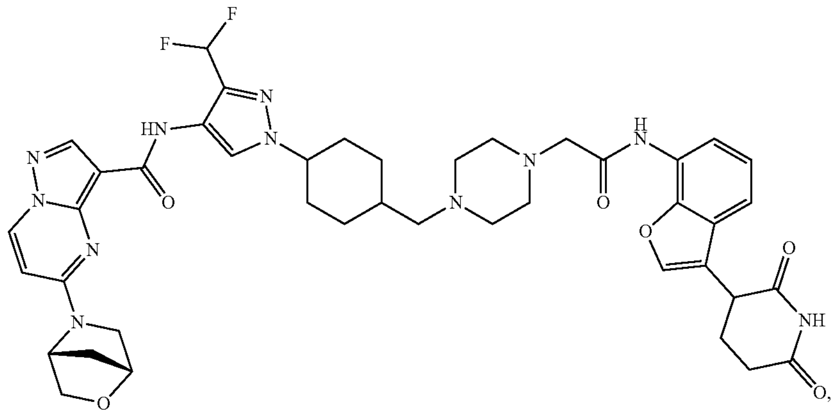
,
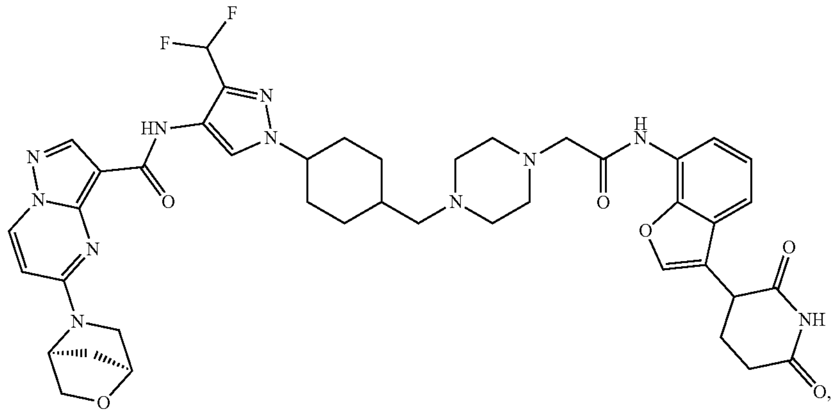
,
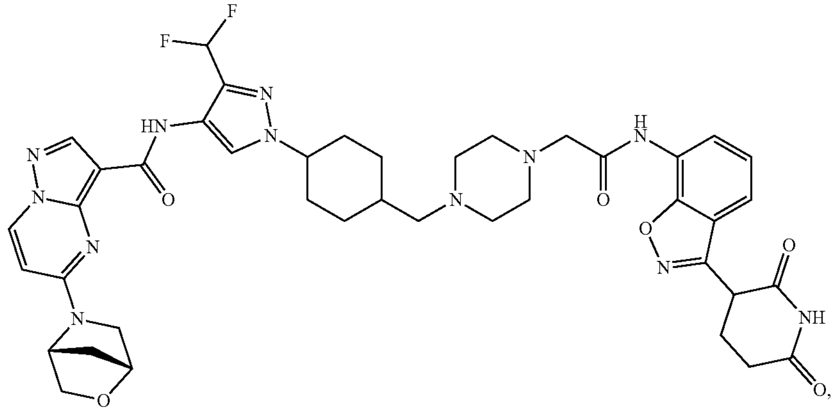
,
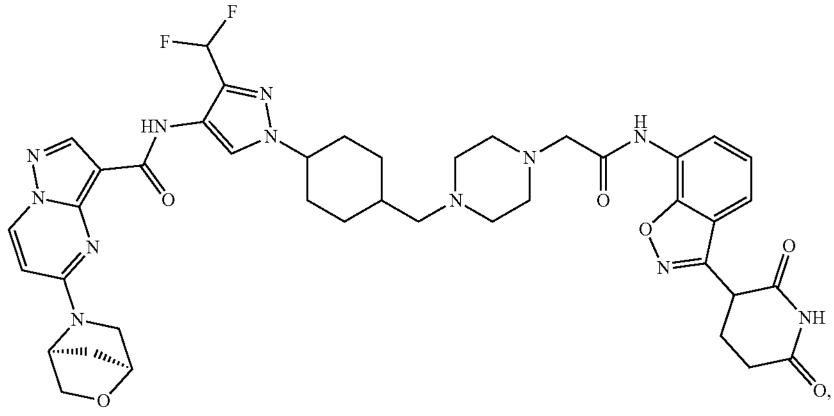
,

-continued
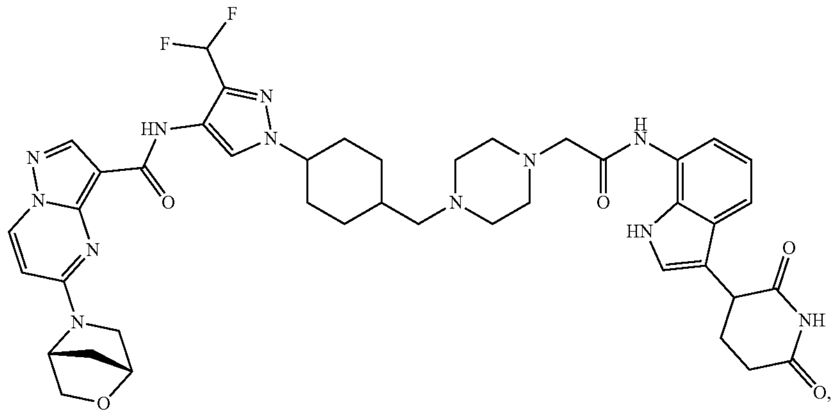
,
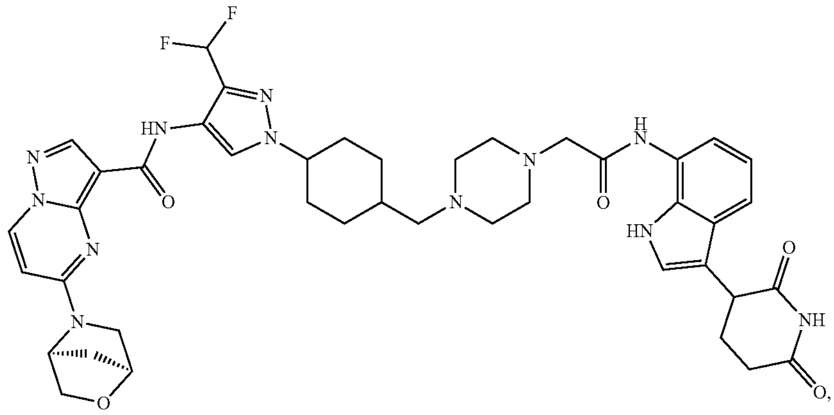
,
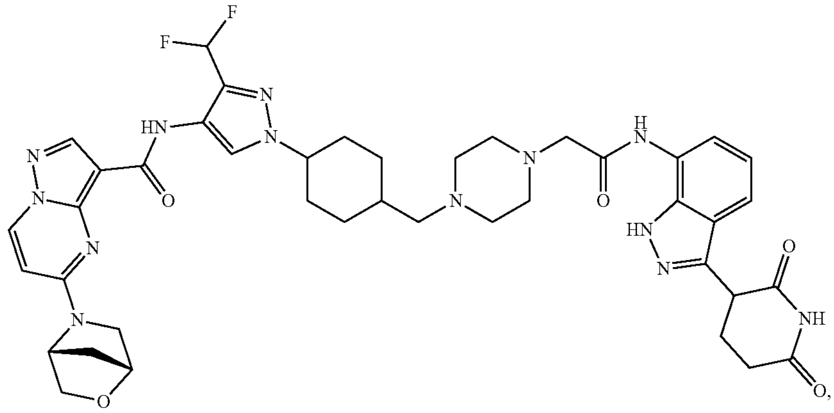
,
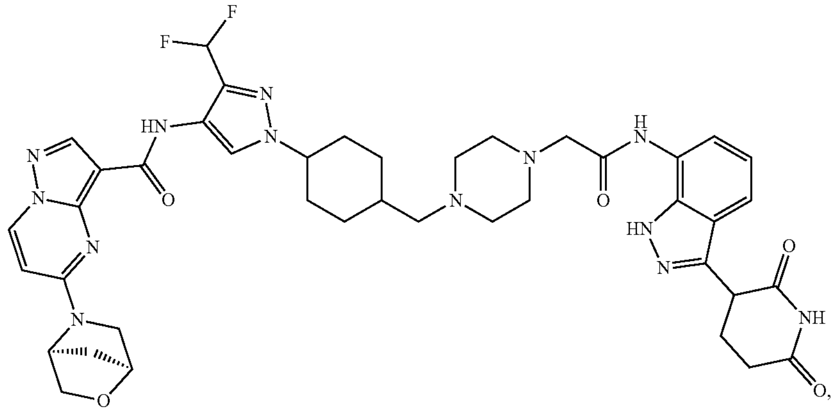
,

-continued
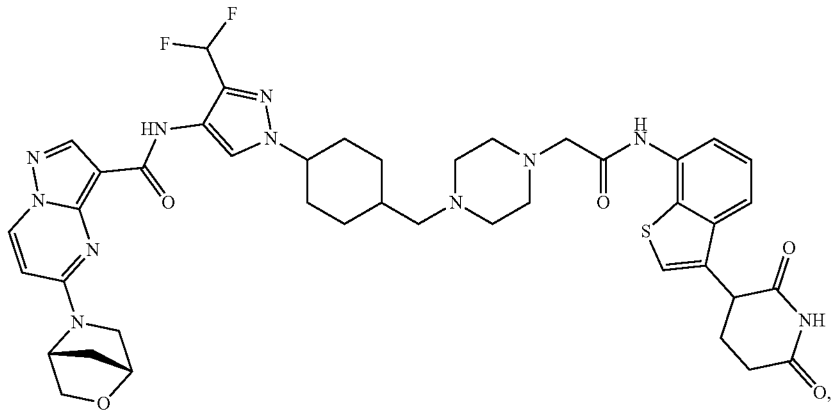
,
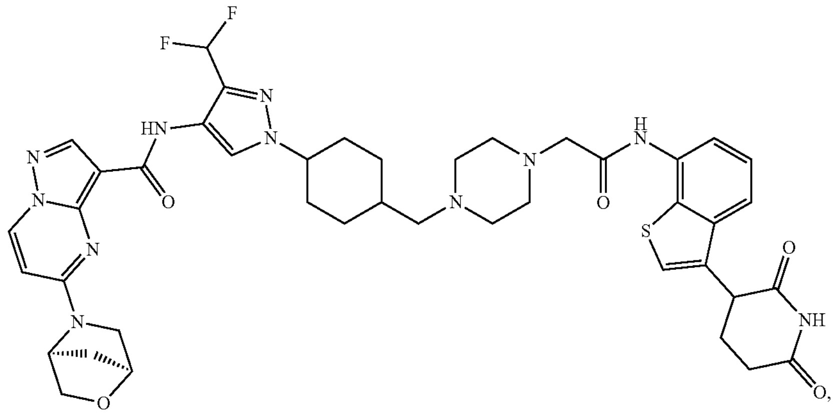
,
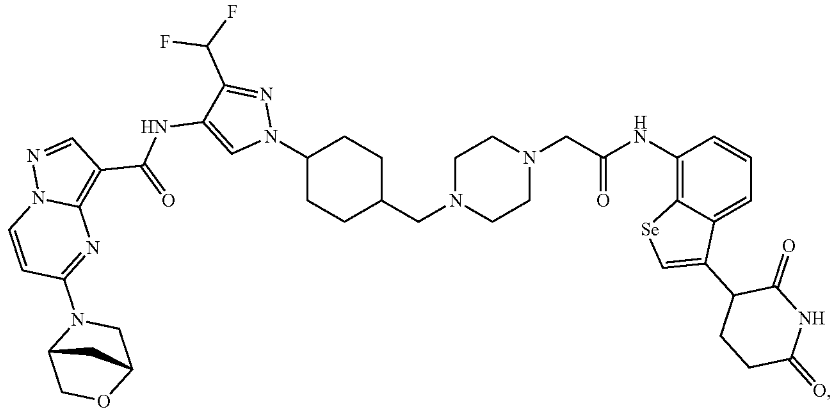
,
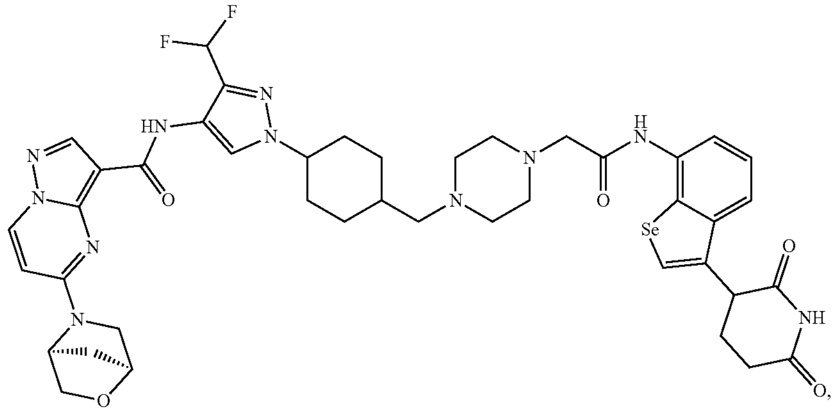
,

-continued
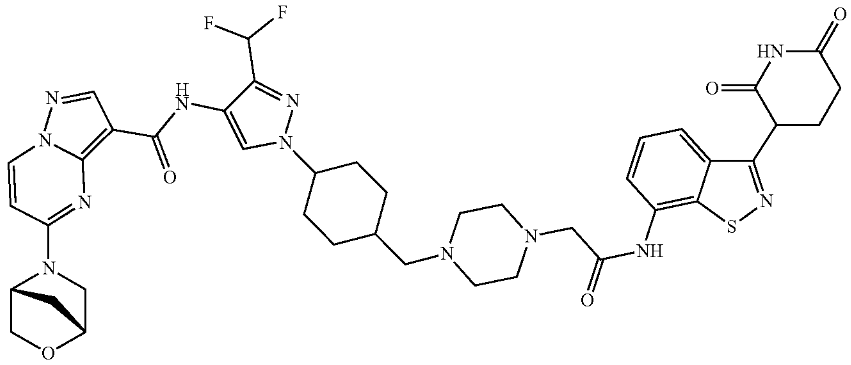
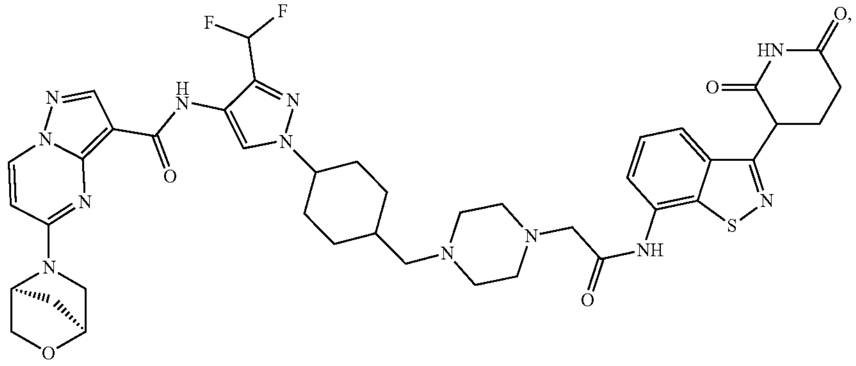
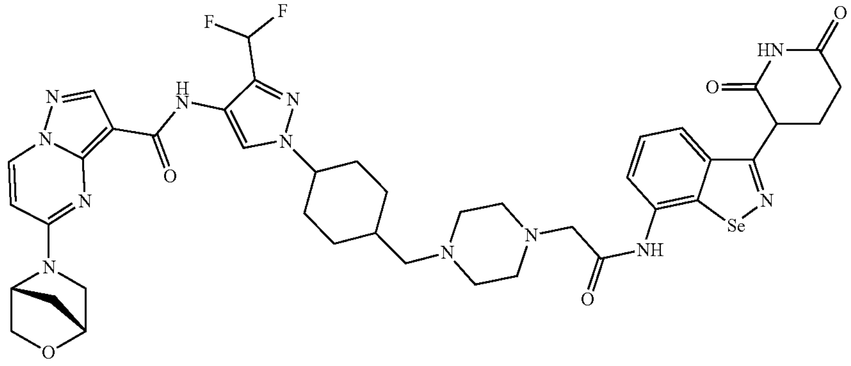
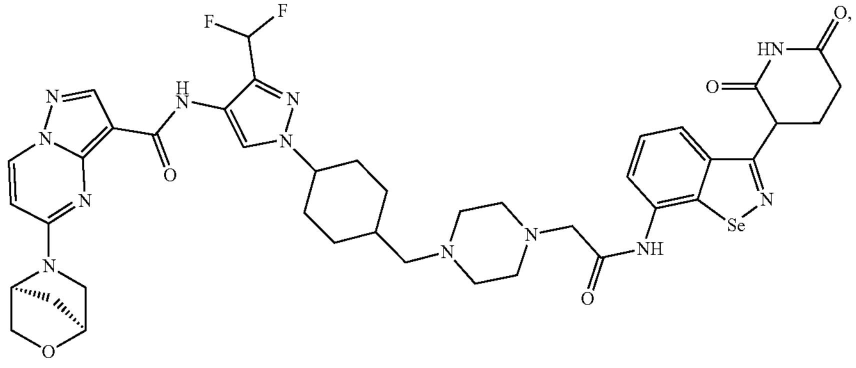

-continued
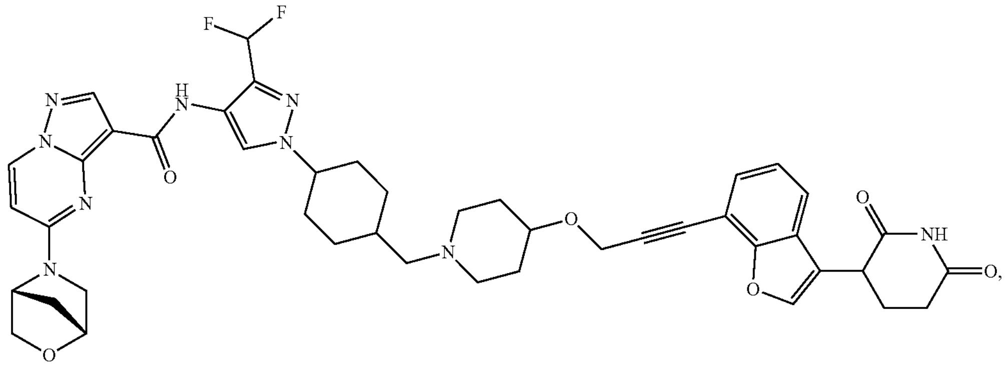
,
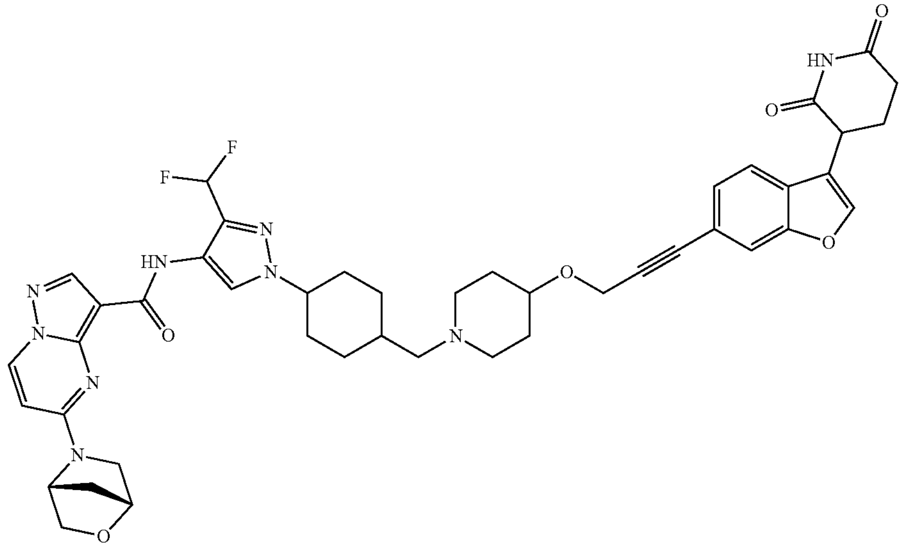
,
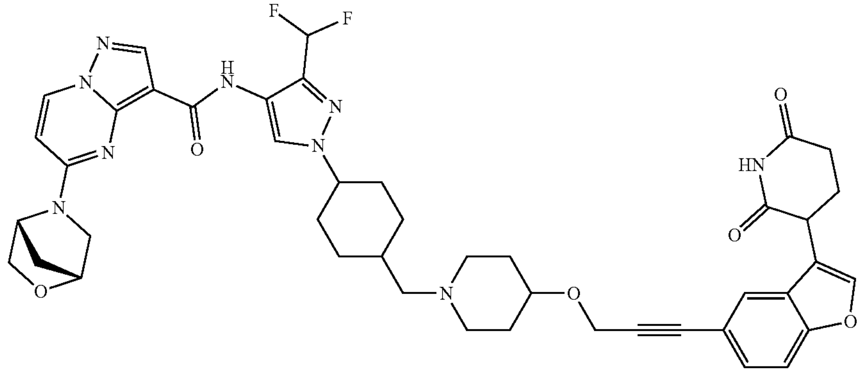
,
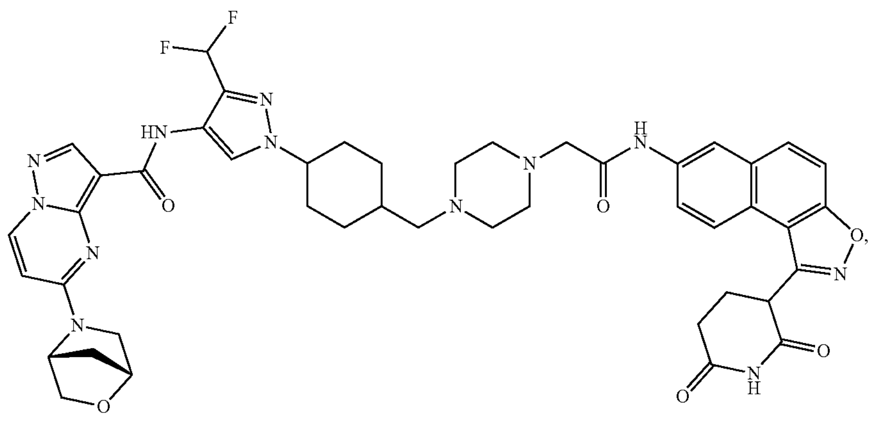
,

-continued
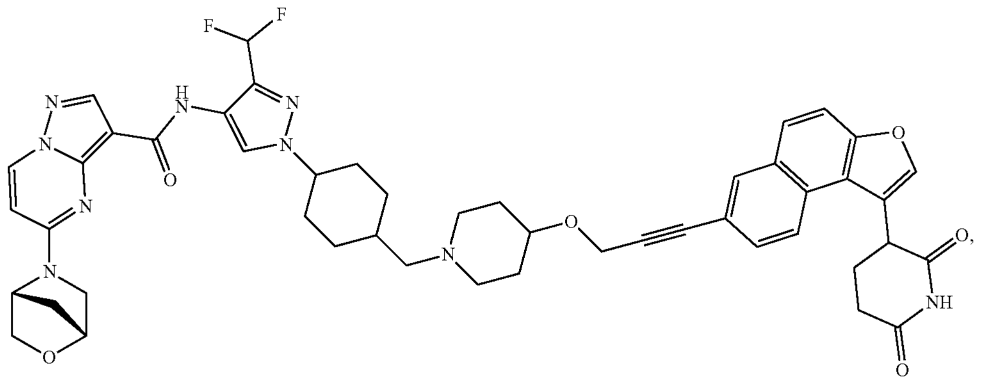
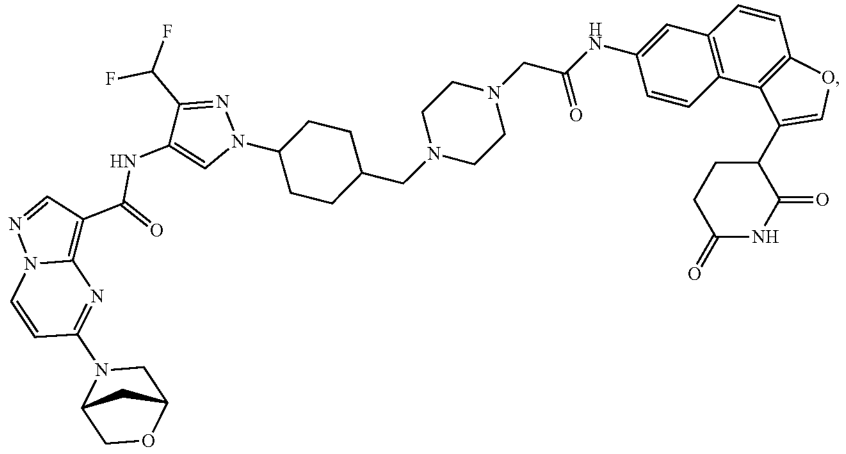
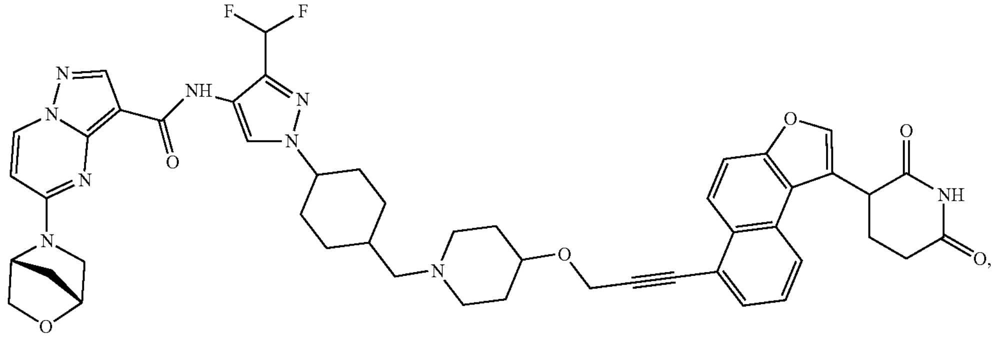
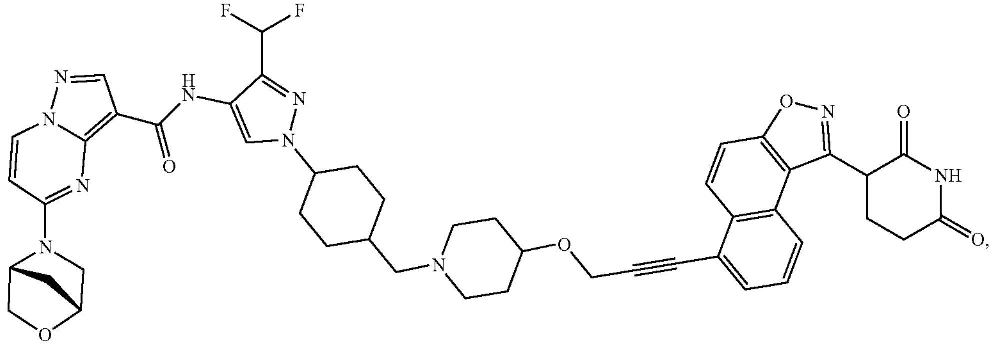

-continued
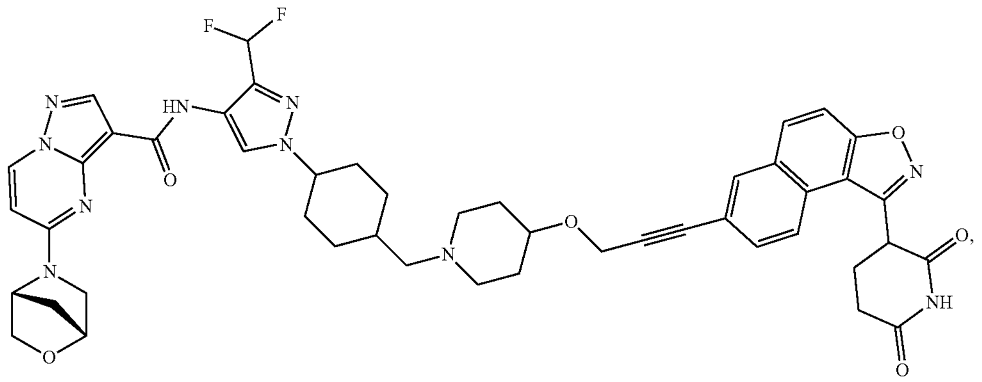
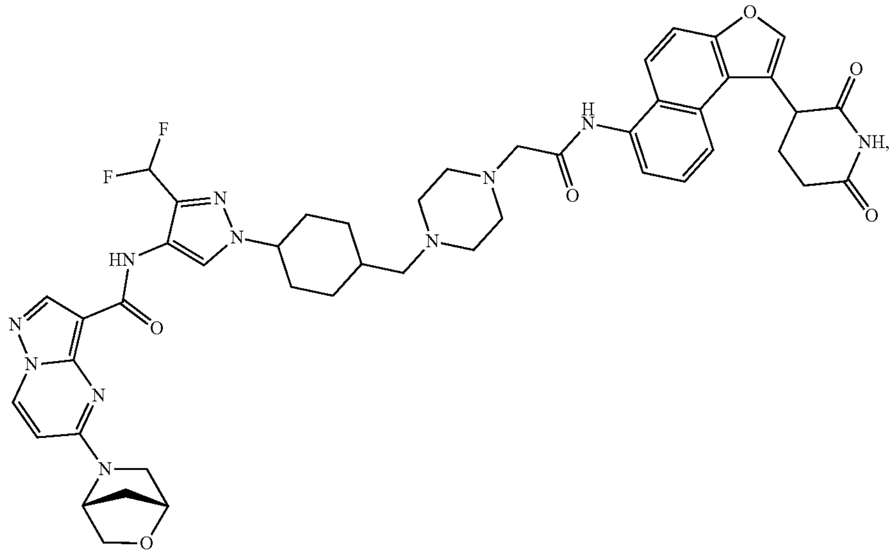
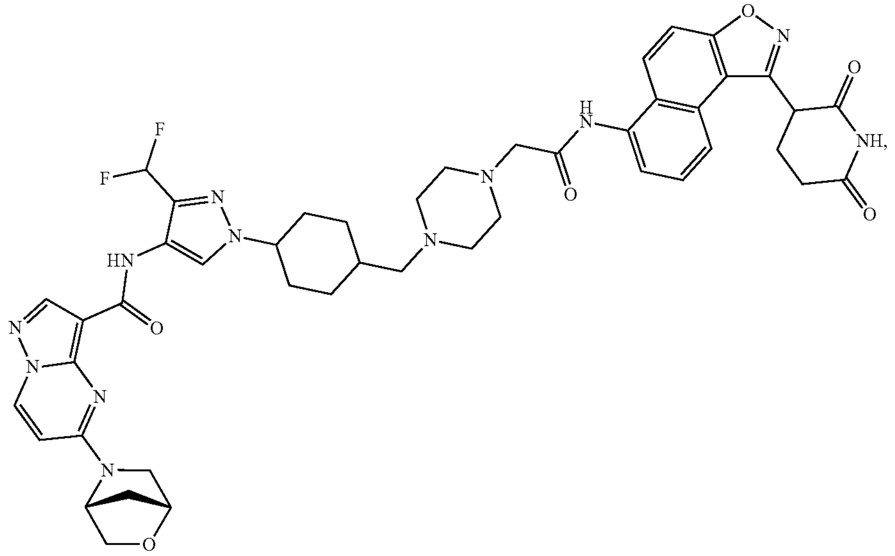

-continued
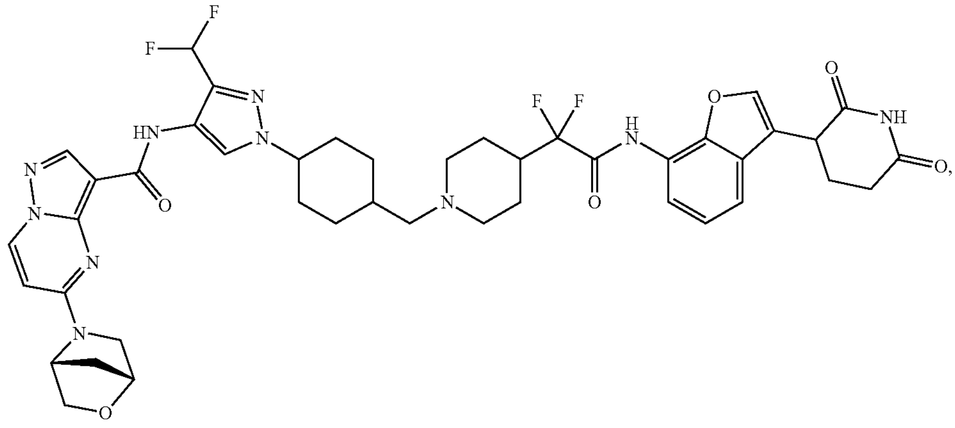
,
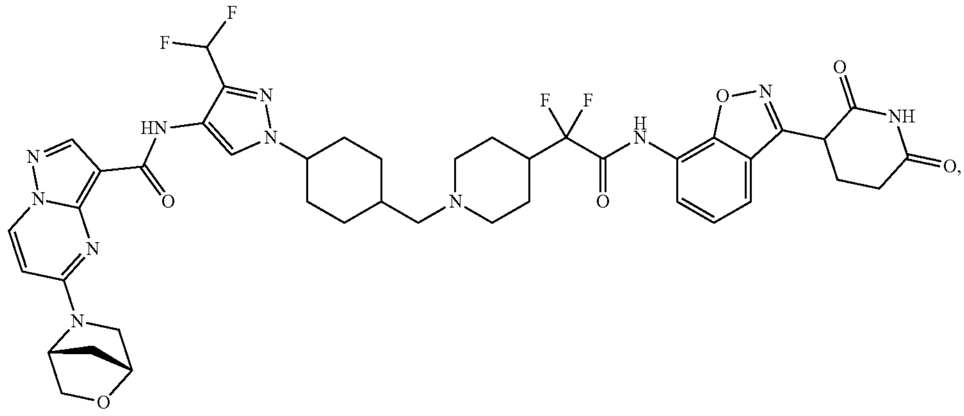
,
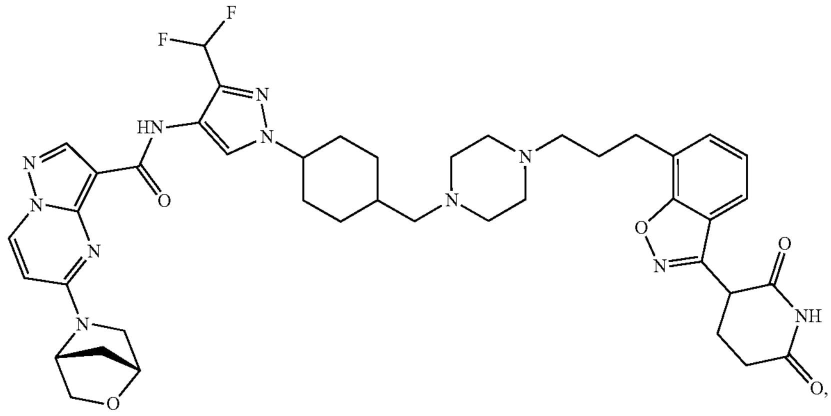
,
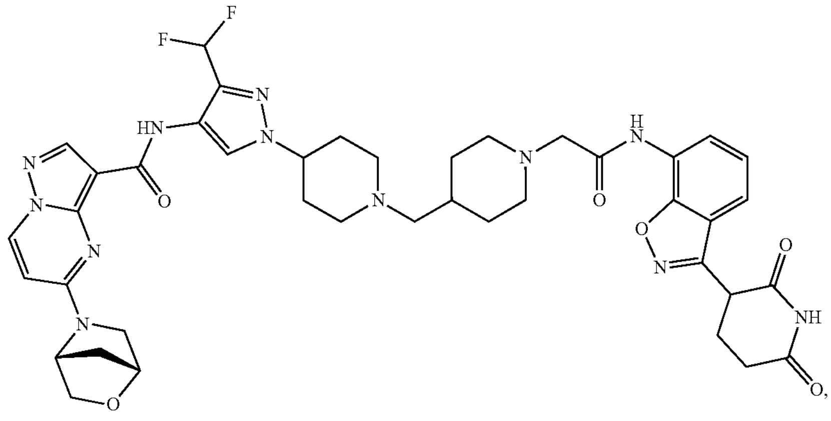
,

-continued
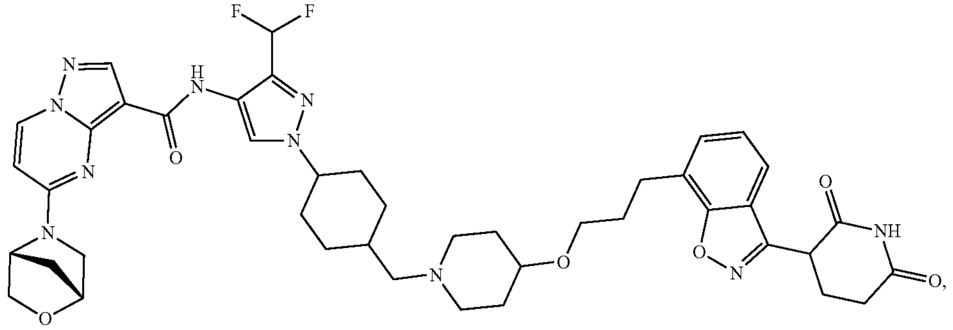
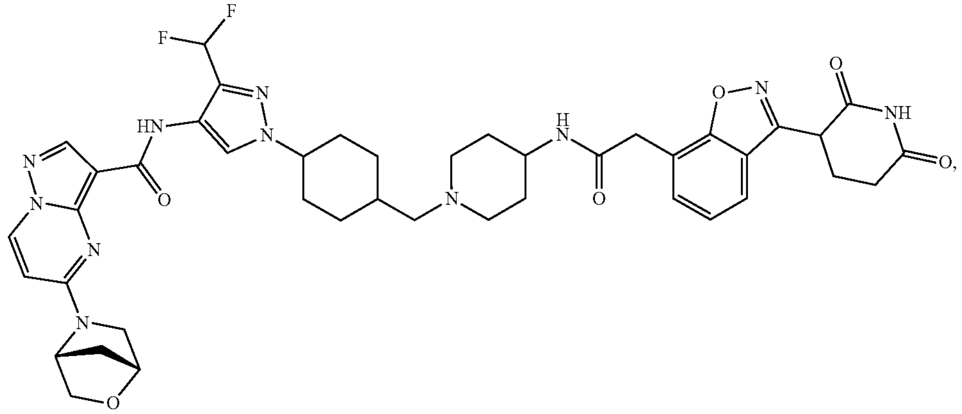
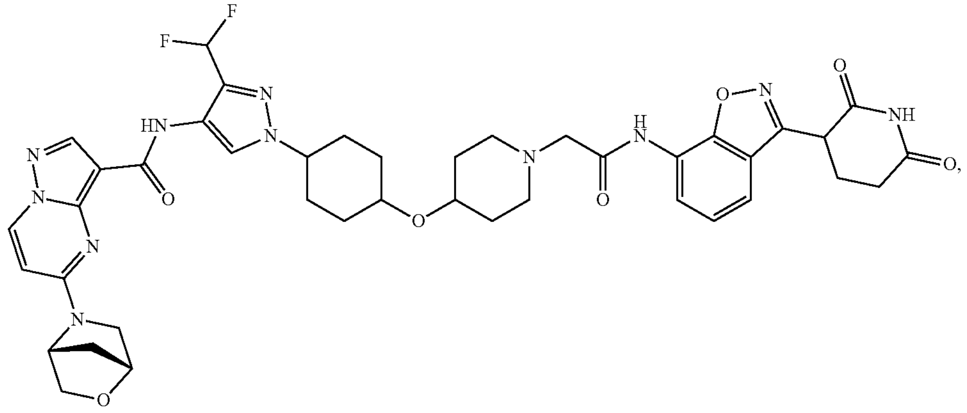
In some embodiments of the present disclosure, the compound is selected from:
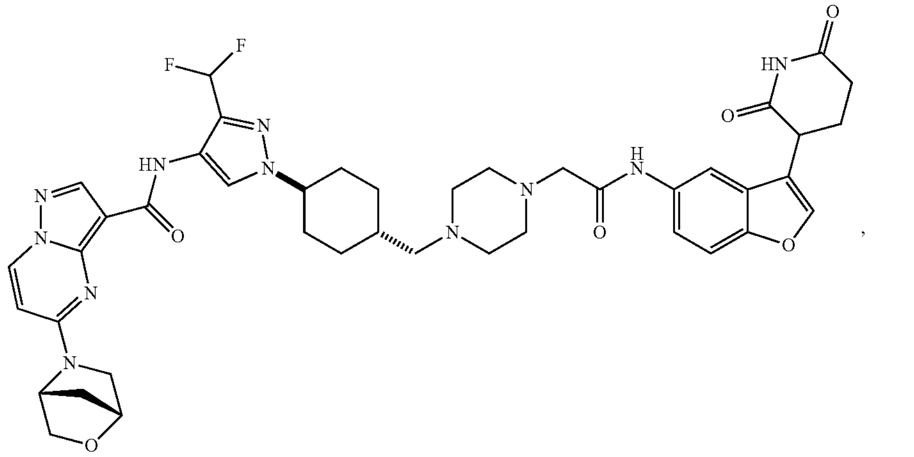
, -continued
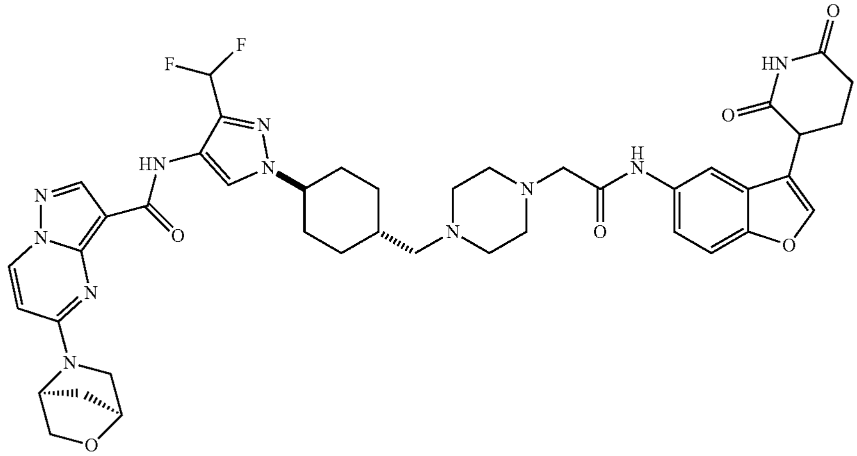
,
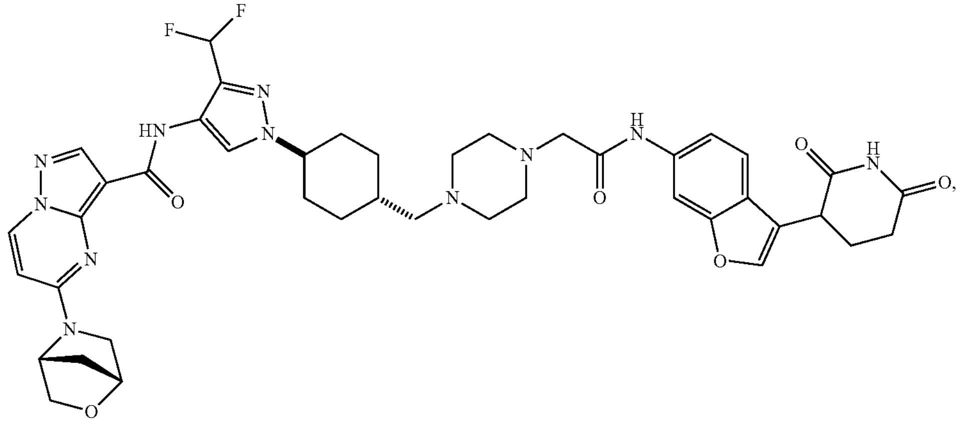
,
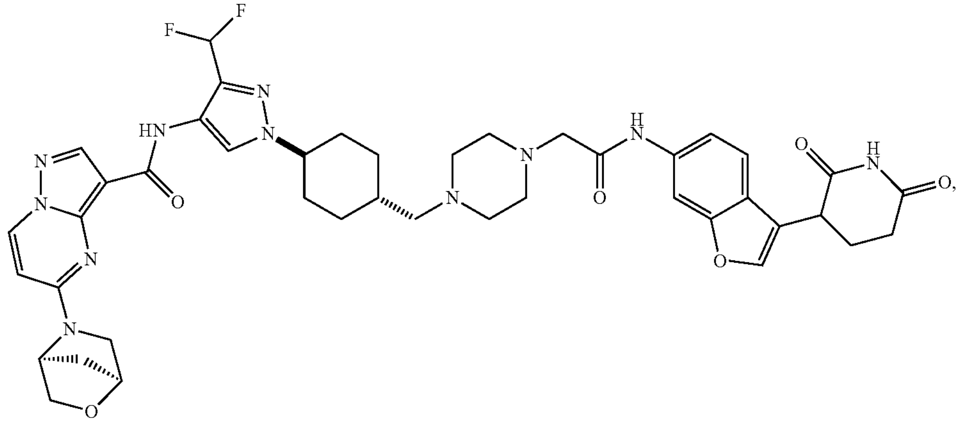
,
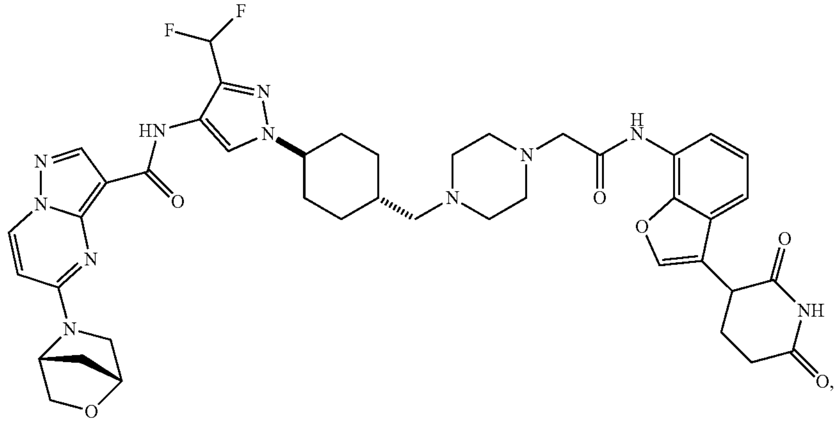
, -continued
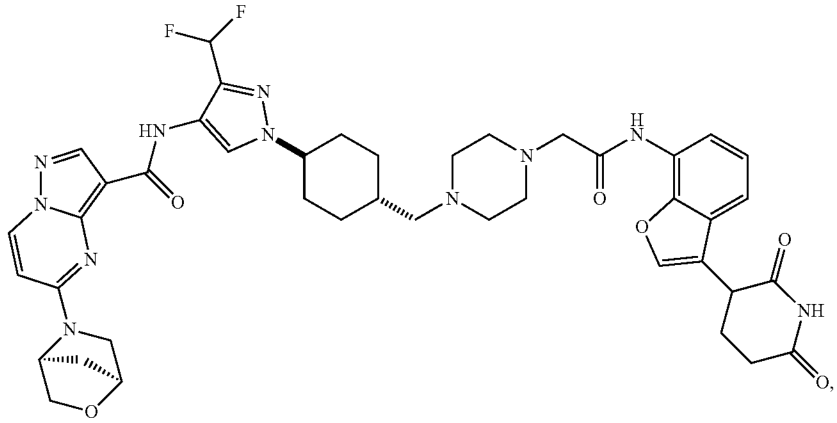
,
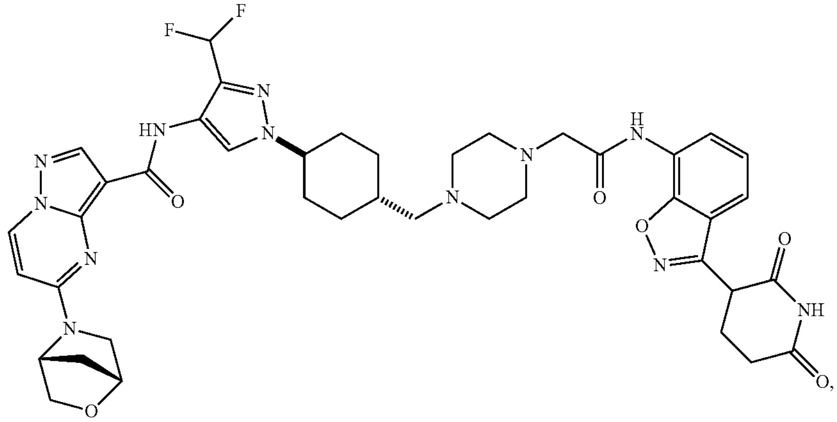
,
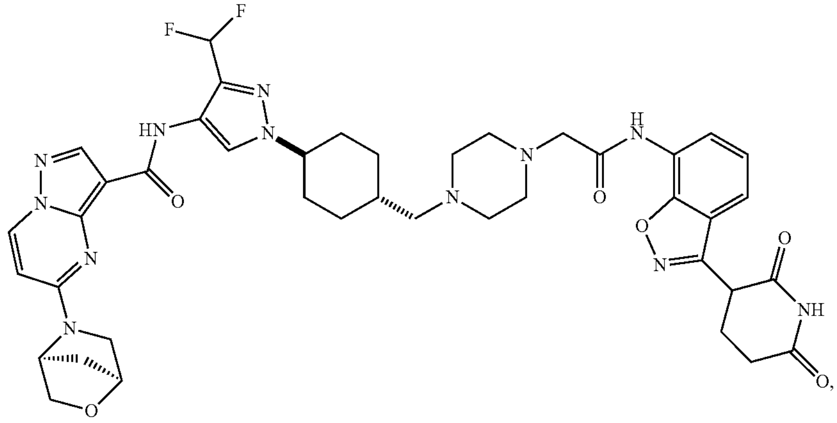
,
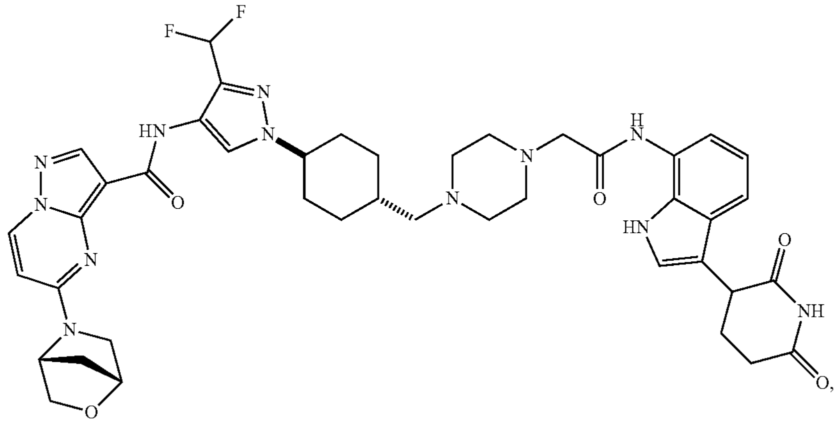
, -continued
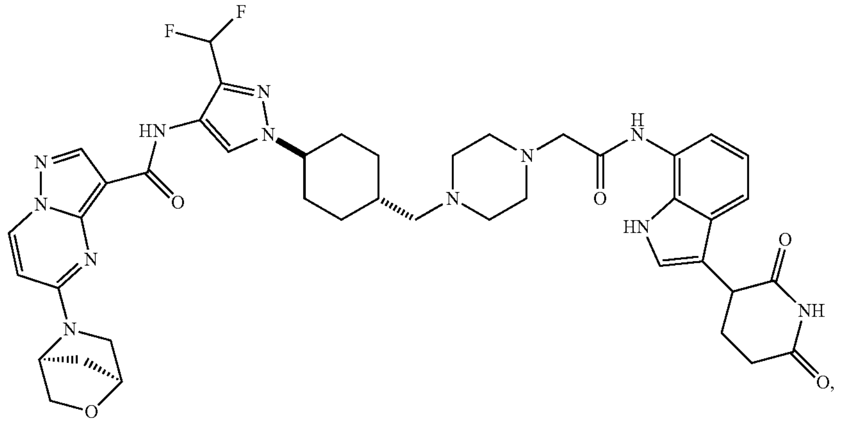
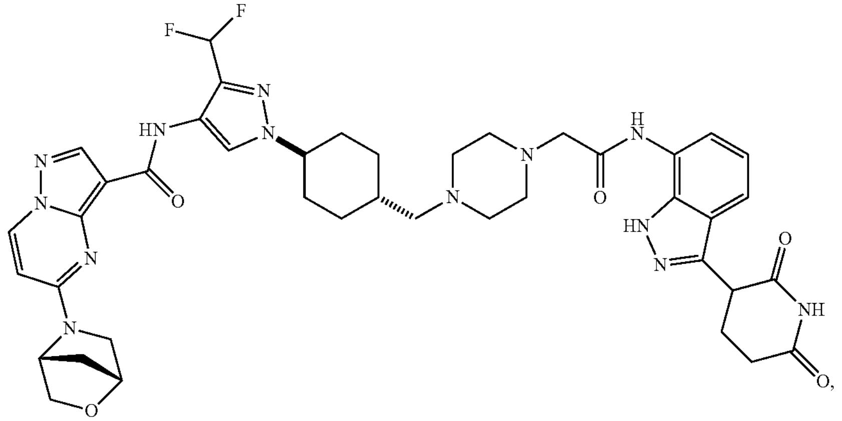
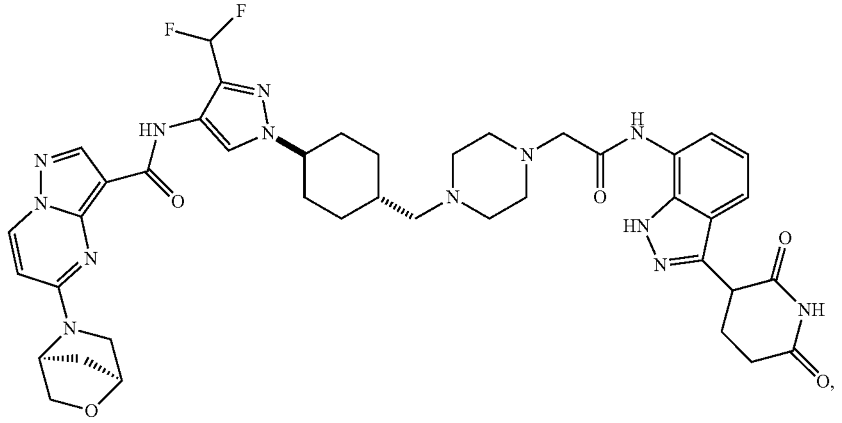
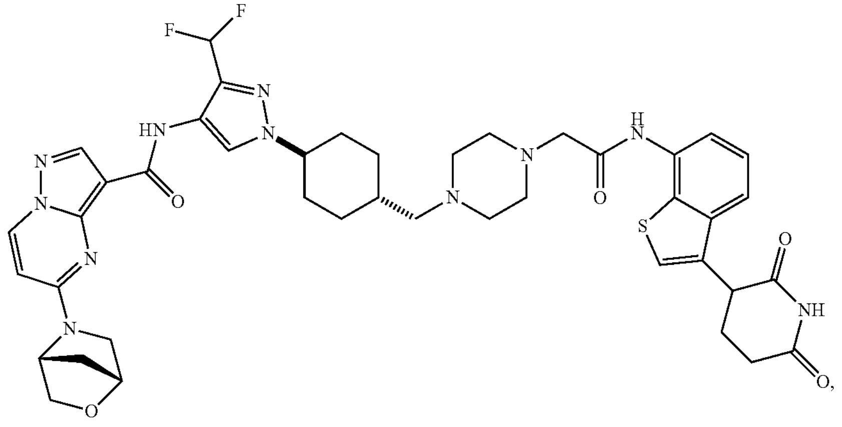

-continued
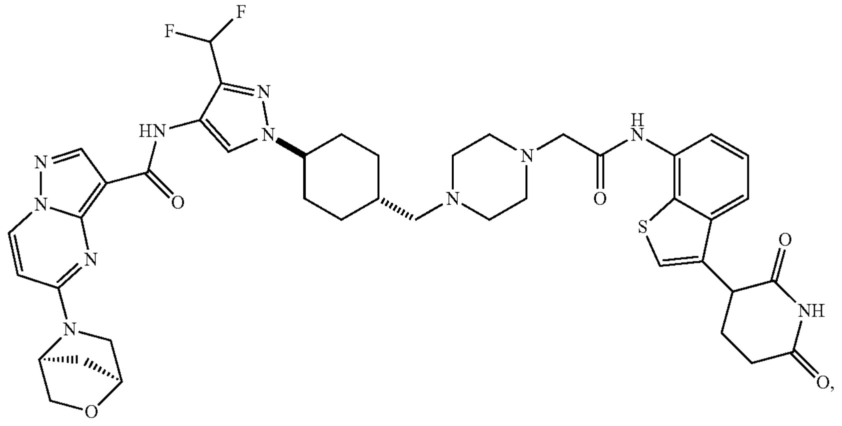
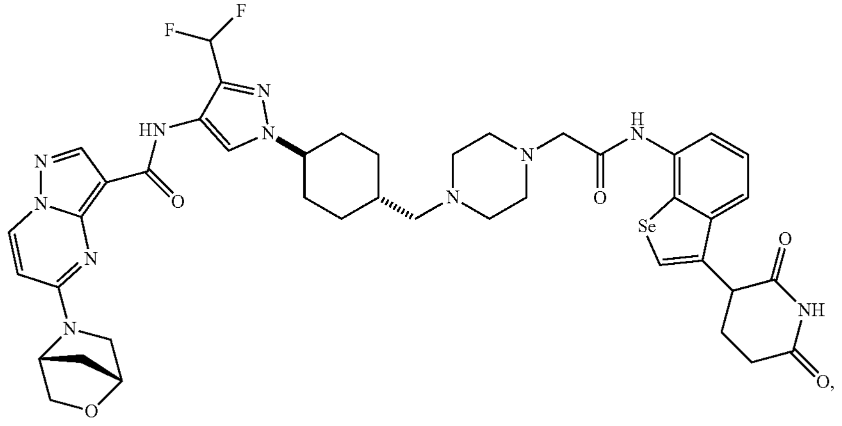
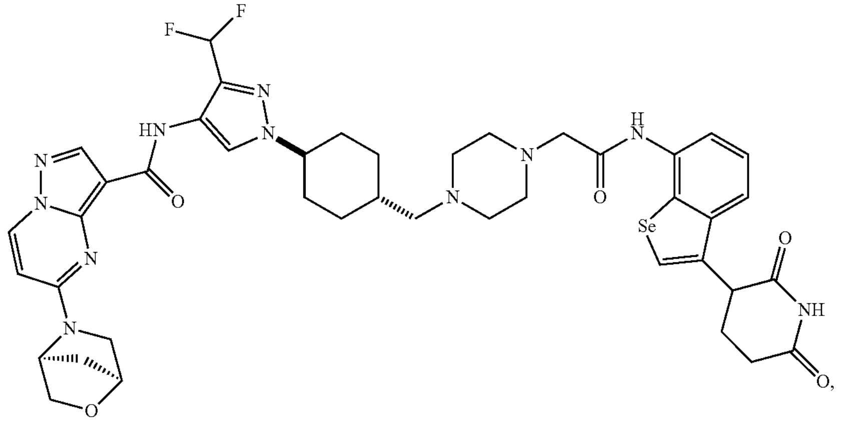
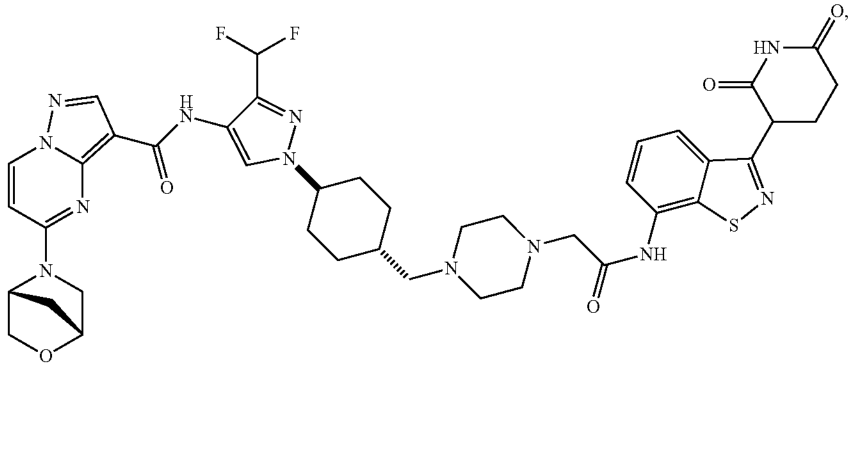

-continued
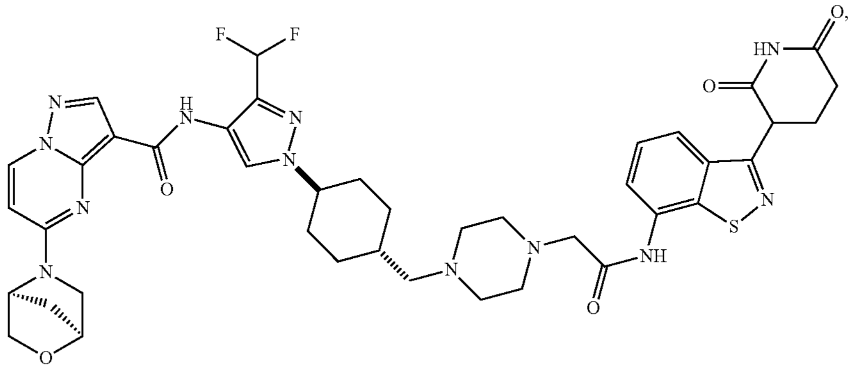
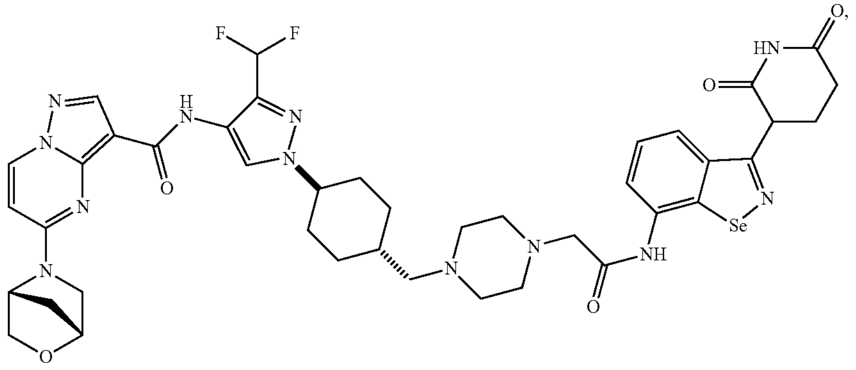
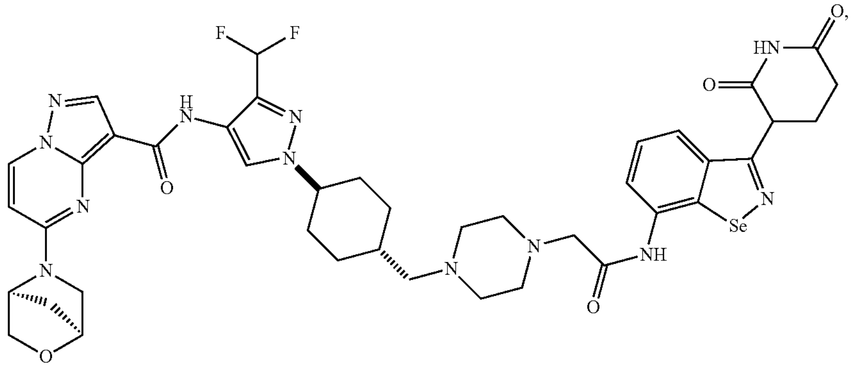
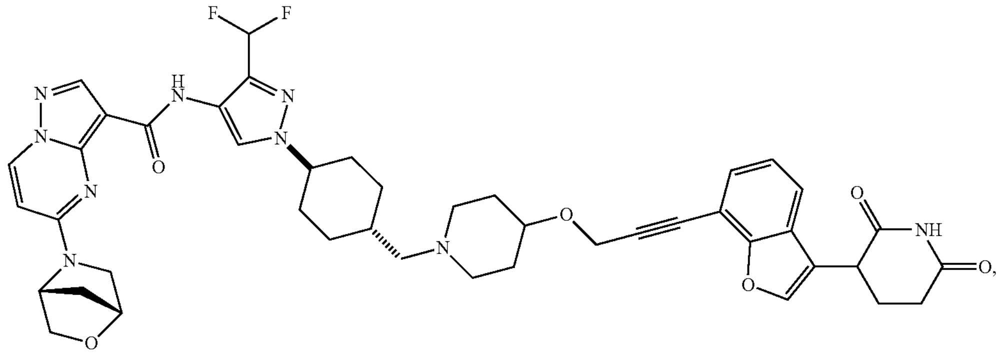

-continued
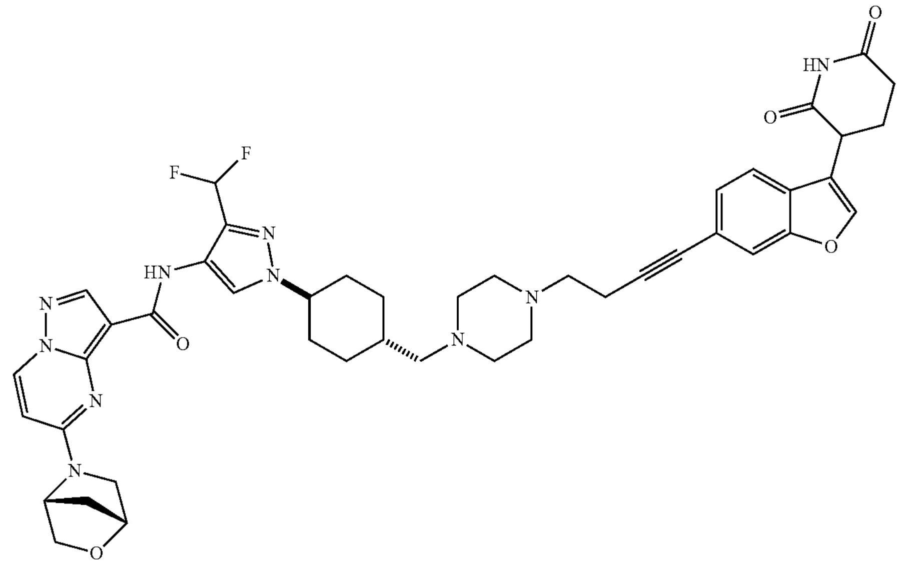
,
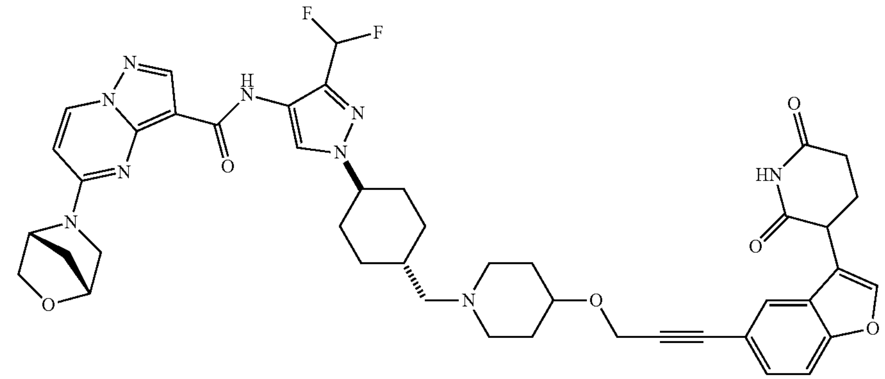
,
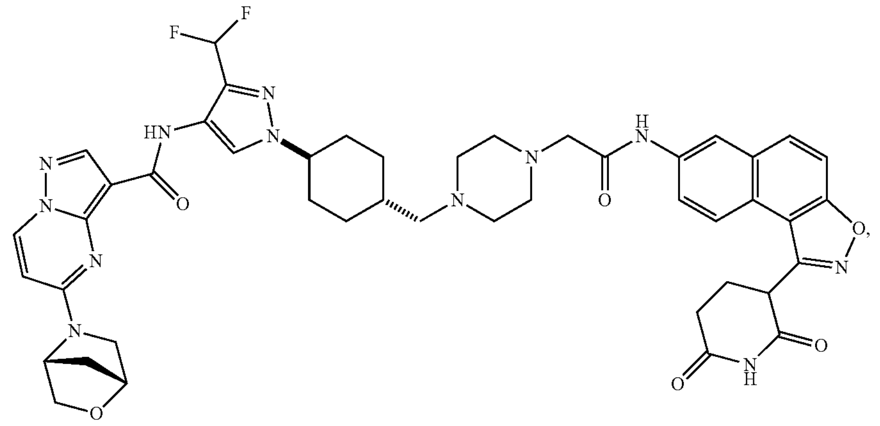
,

-continued
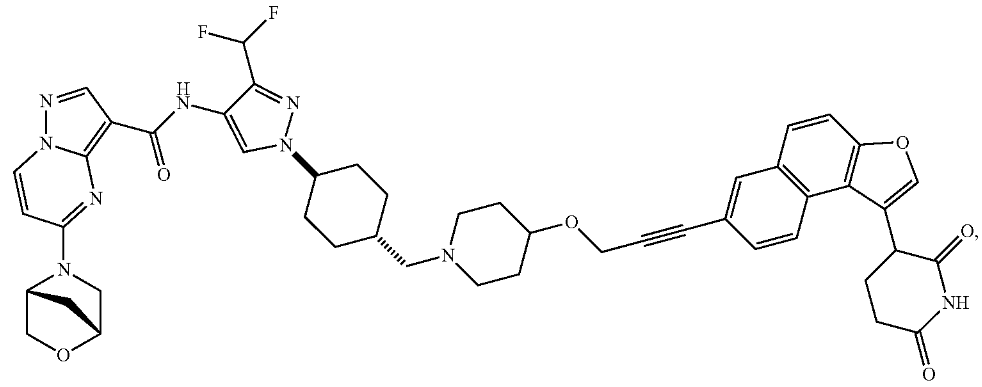
,
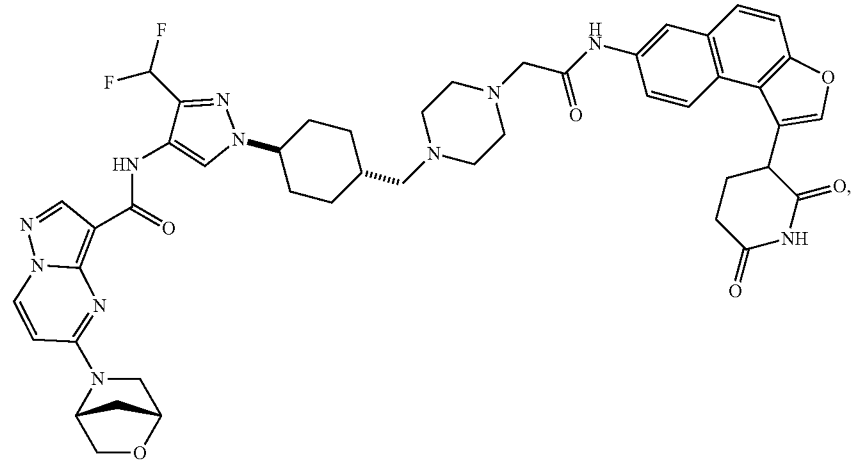
,
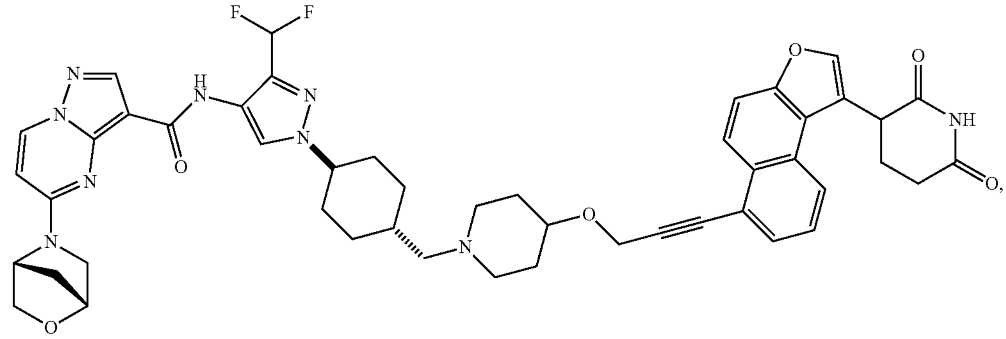
,
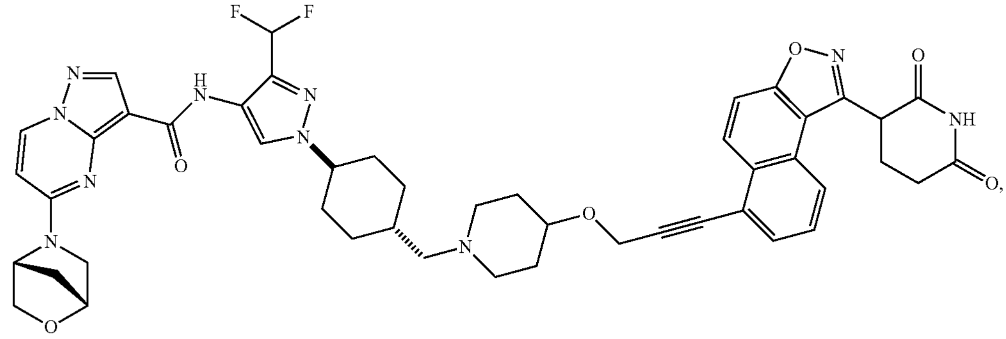
,

-continued
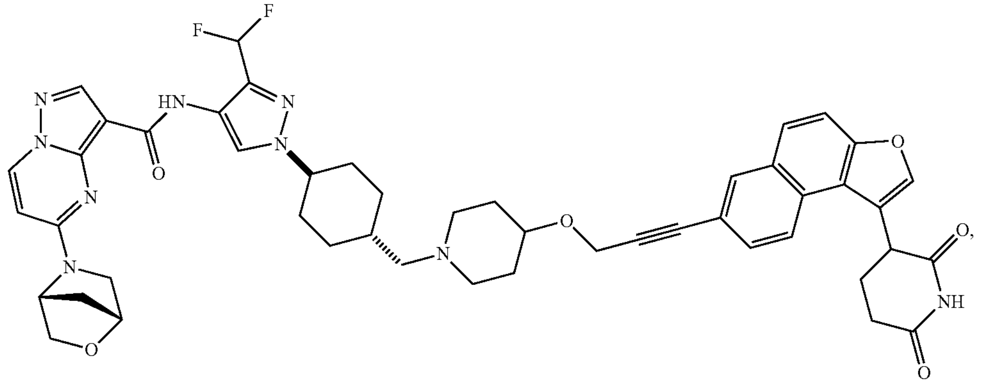
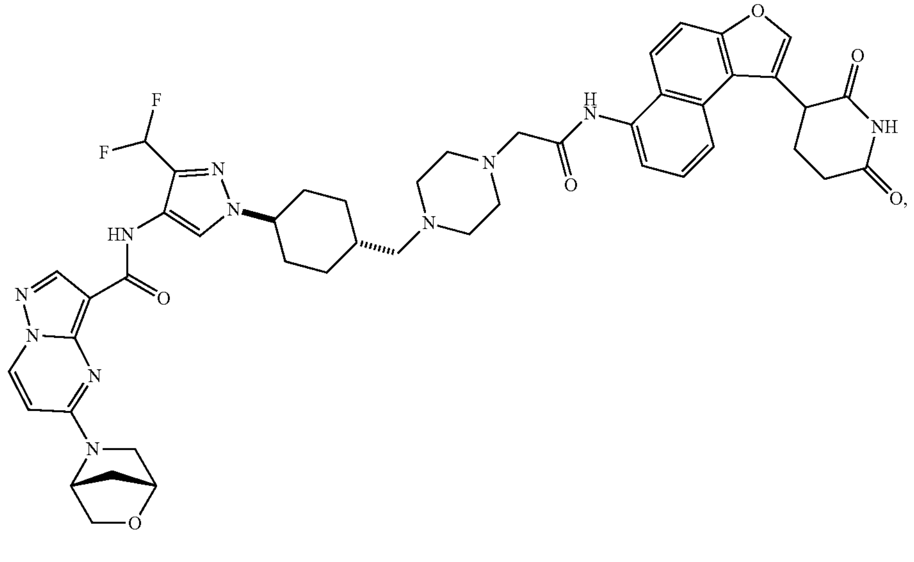
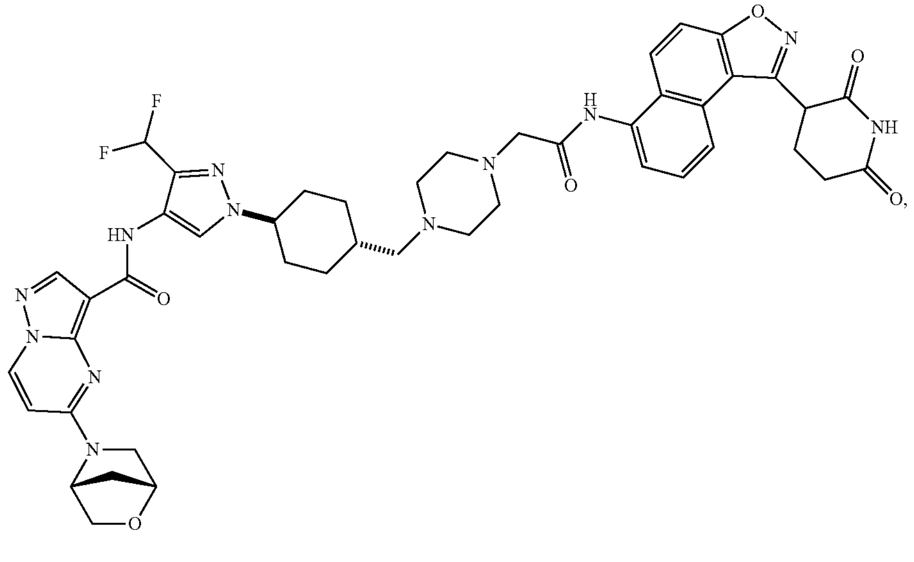

-continued
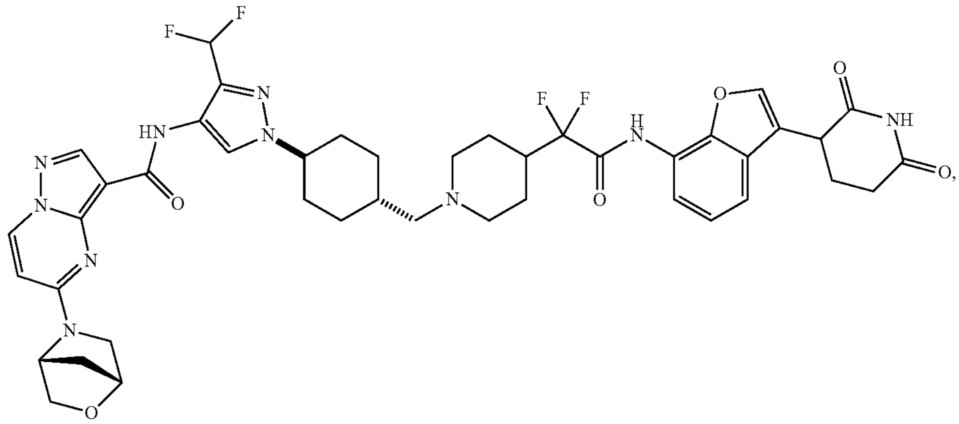
,
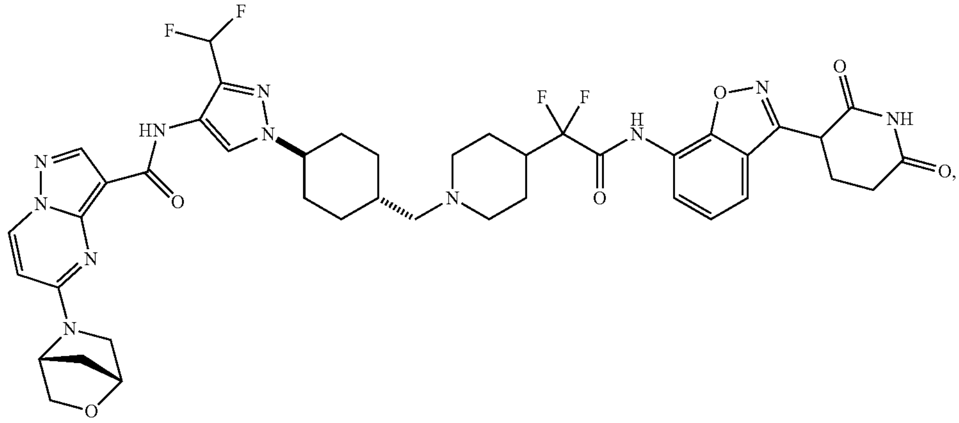
,
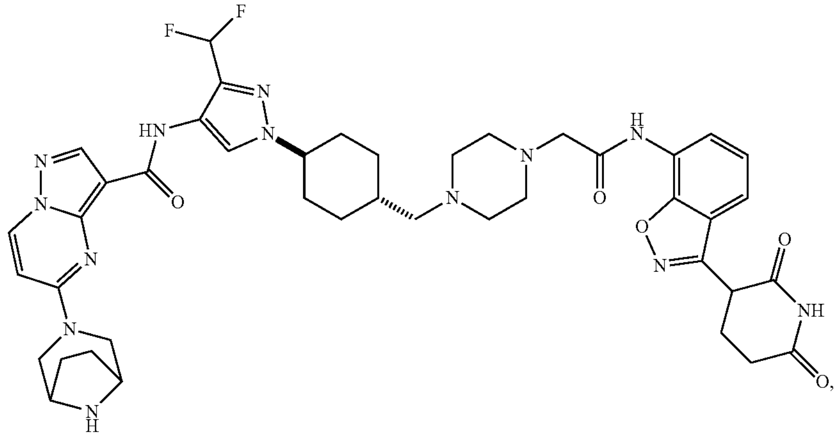
,
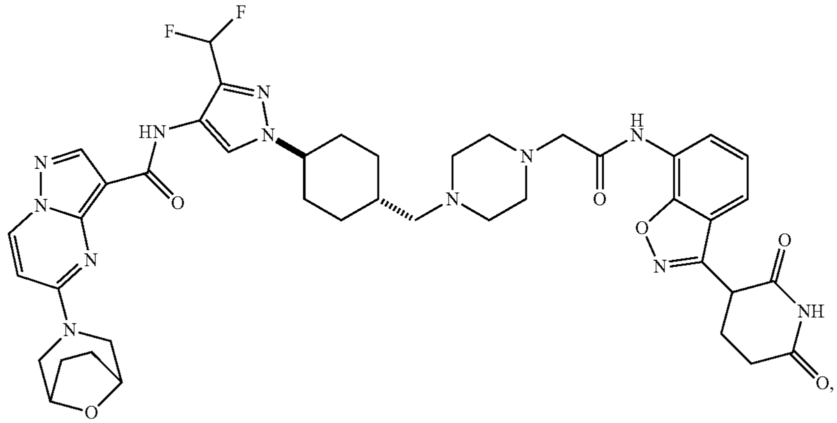
,

-continued
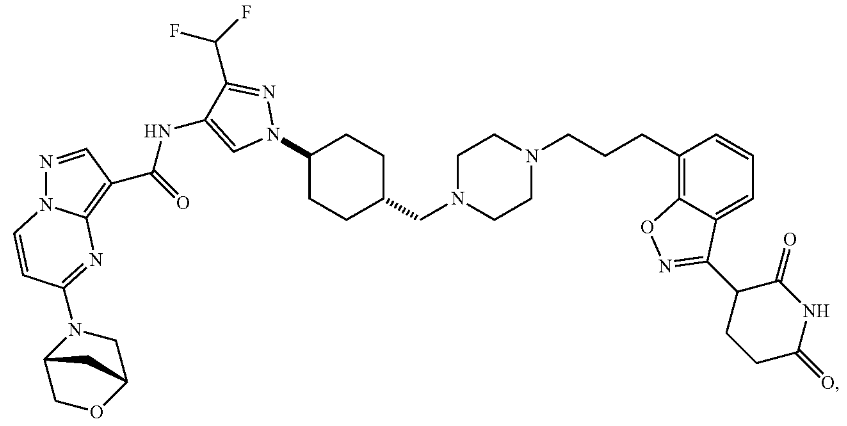
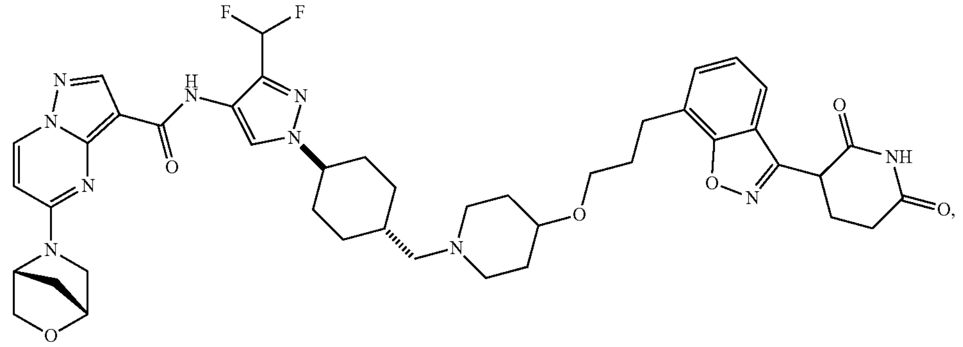
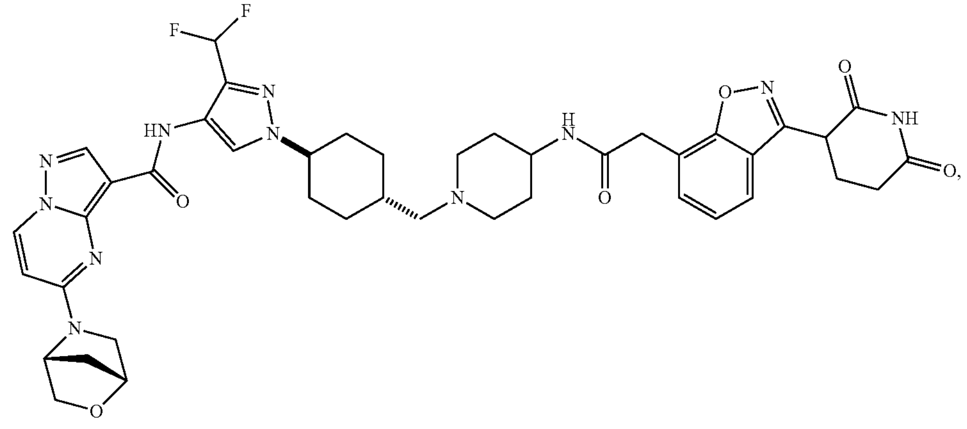
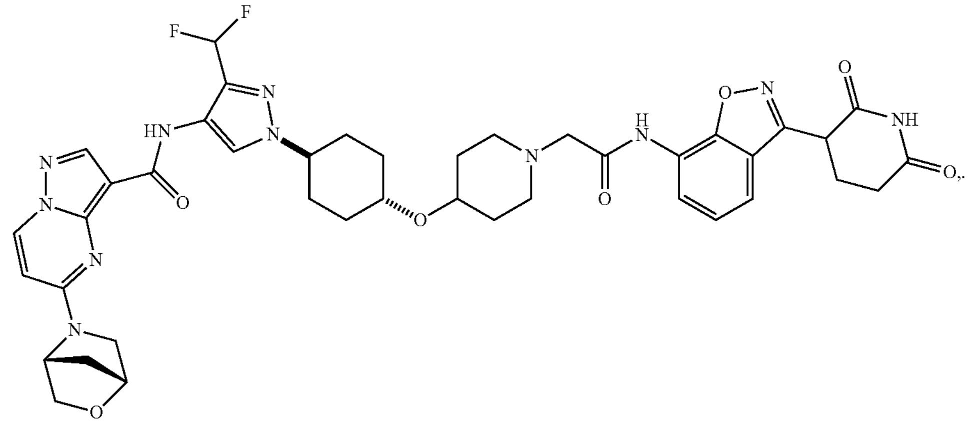 [SMILES: O=C1CCC(c2noc3c(NC(=O)CN4CCC(O[C@H]5CC[C@H](n6cc(NC(=O)c7cnn8ccc(N9C[C@H]%10C[C@@H]9CO%10)nc78)c(C(F)F)n6)CC5)CC4)cccc23)C(=O)N1]

In some embodiments of the present disclosure, the compound is selected from:
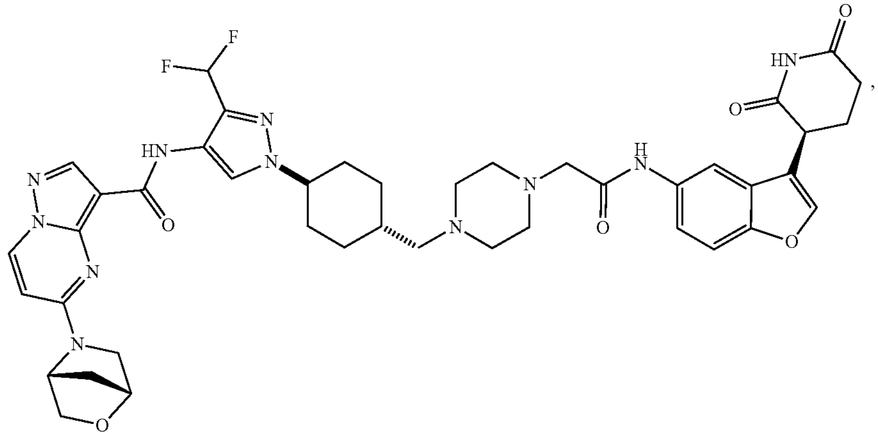
,
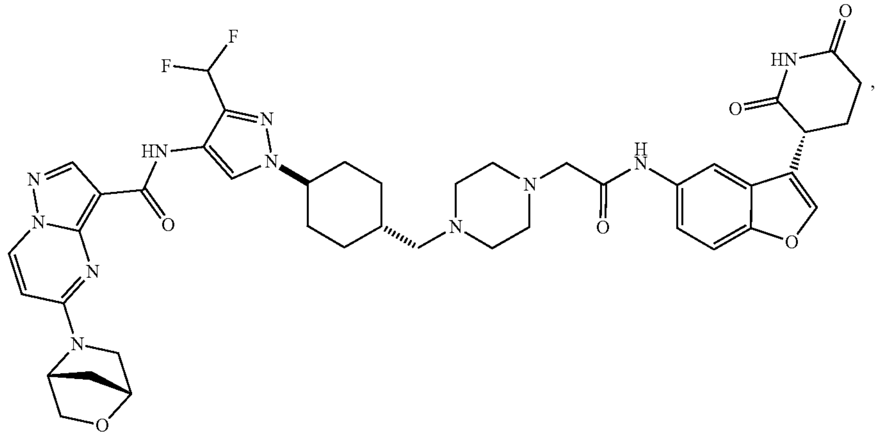
,
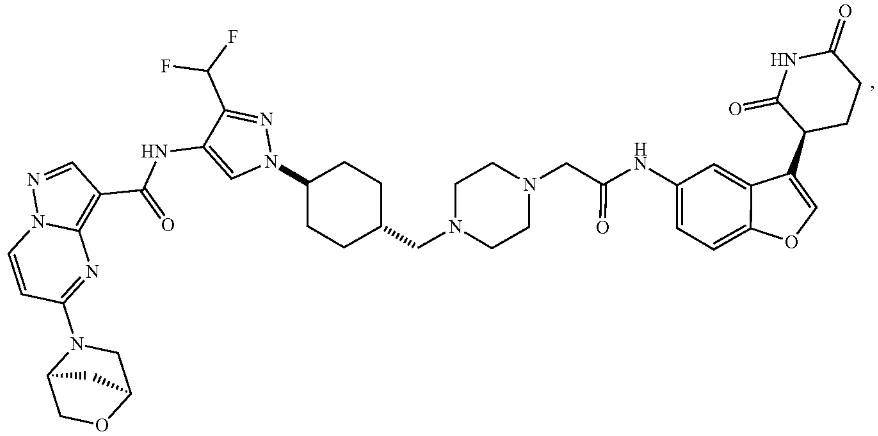
, -continued
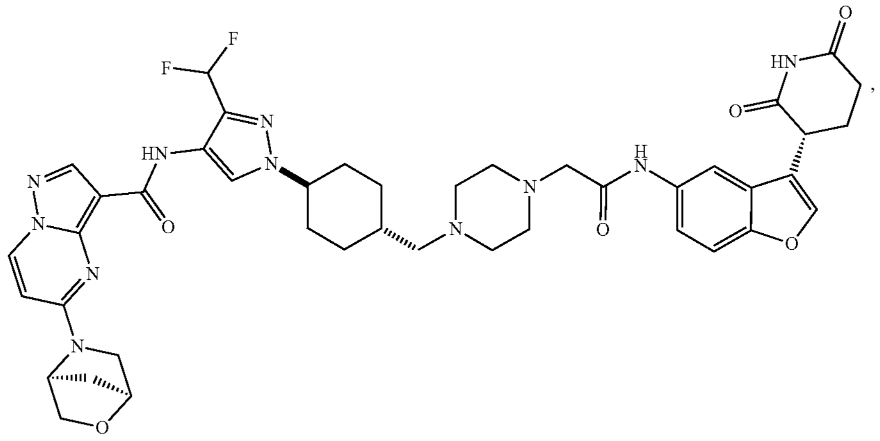
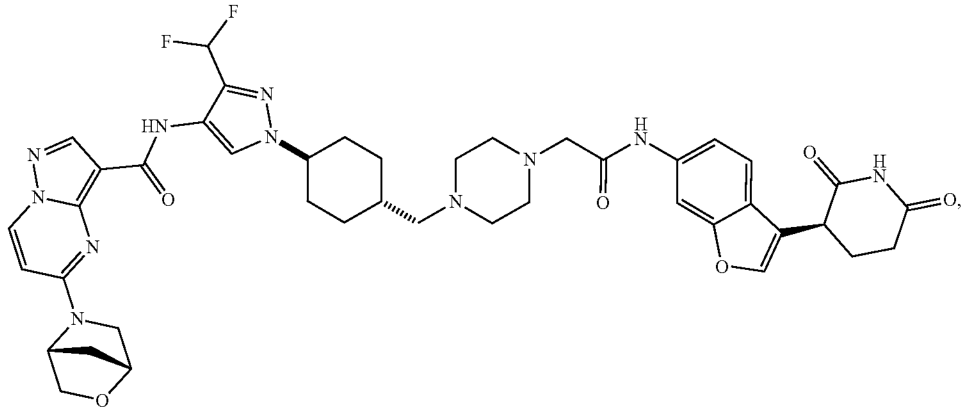
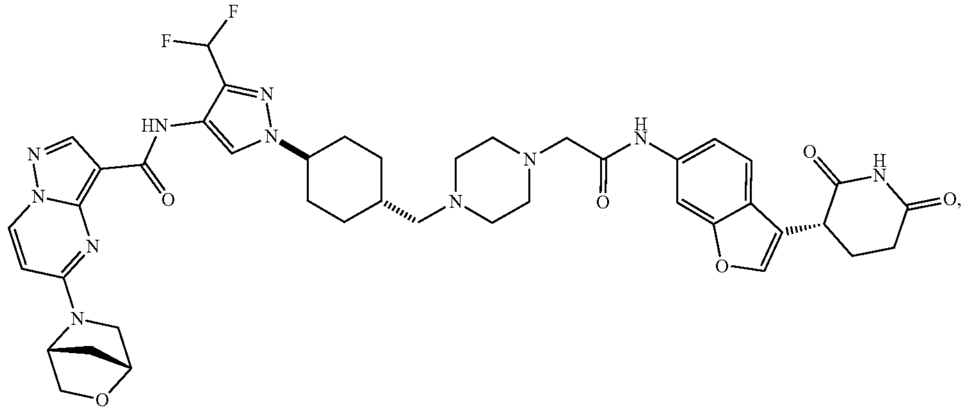
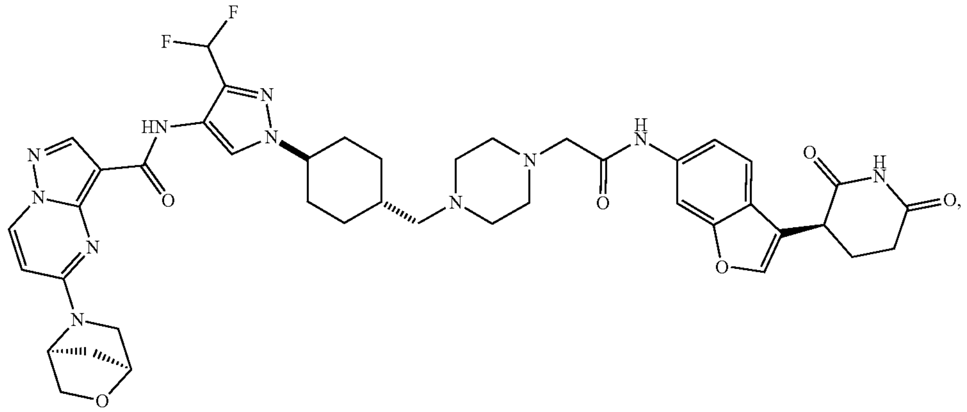

-continued
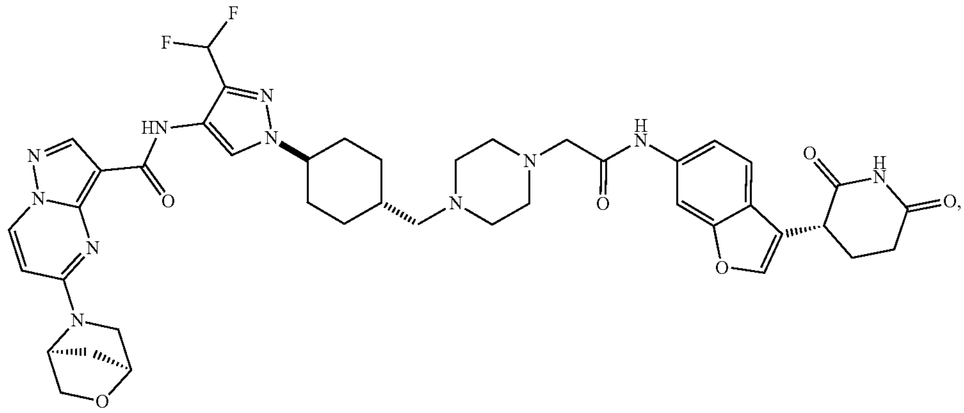
,
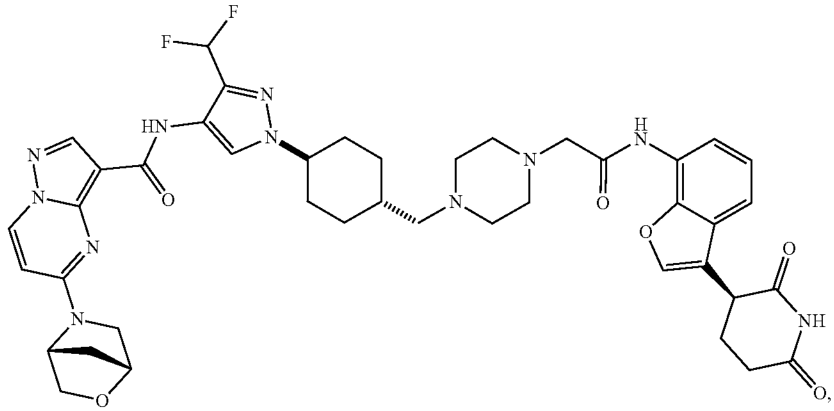
,
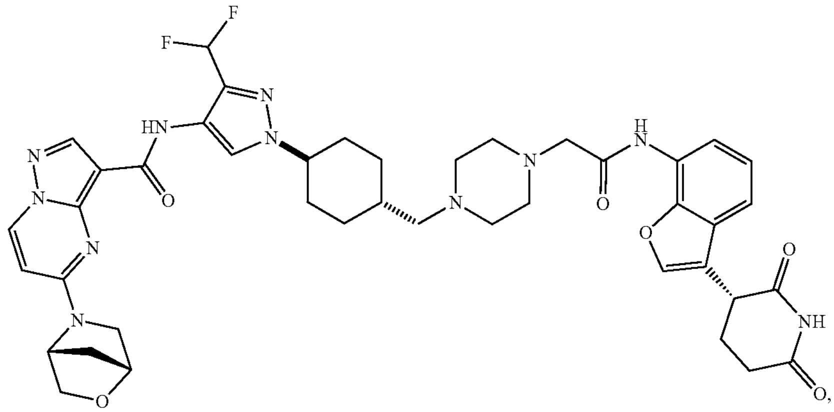
,
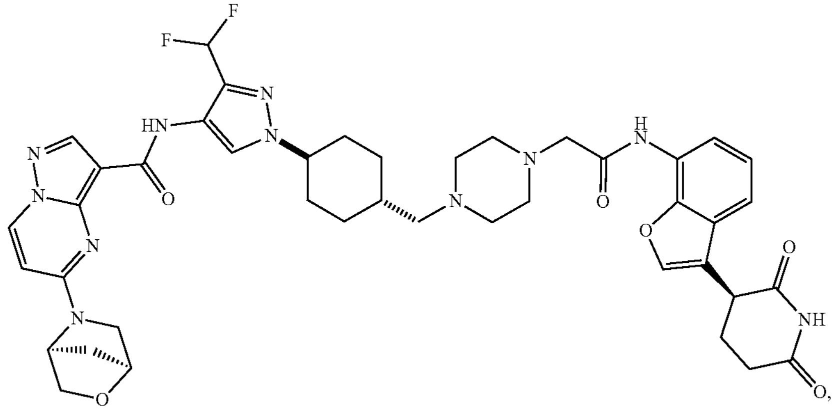
,

-continued
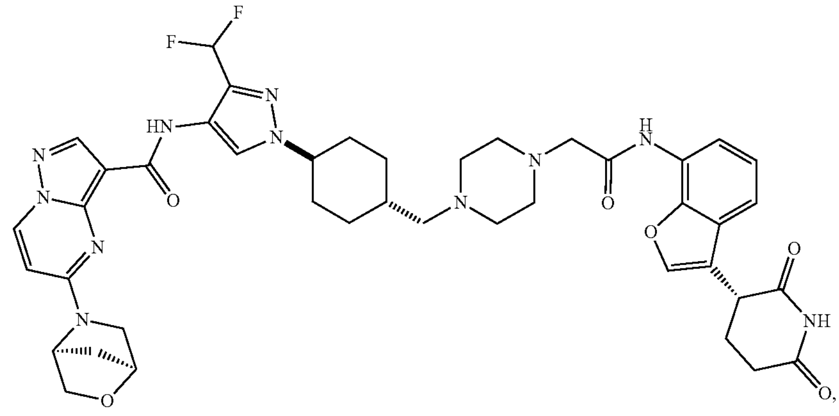
,
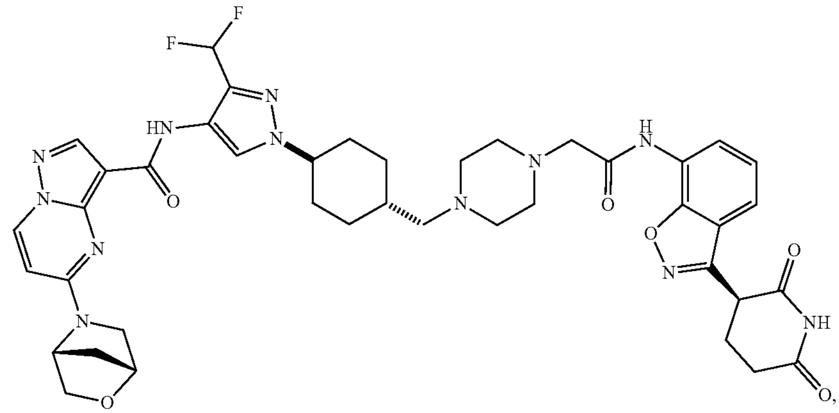
,
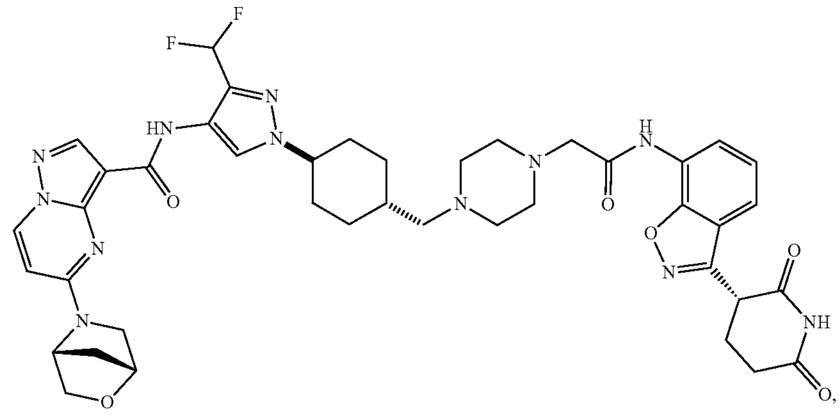
,
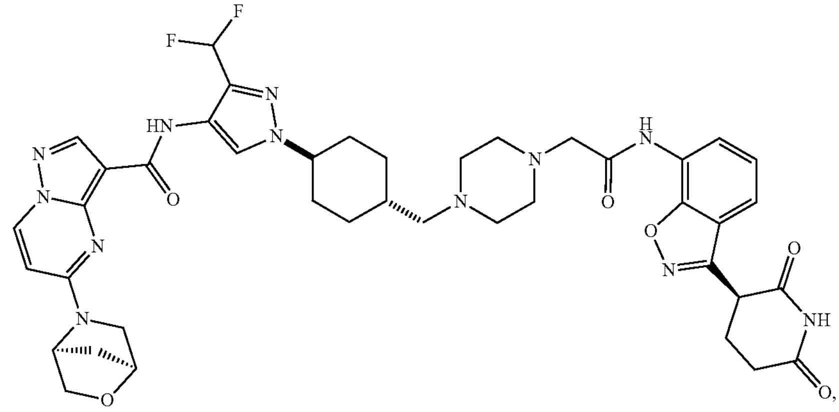
,

-continued
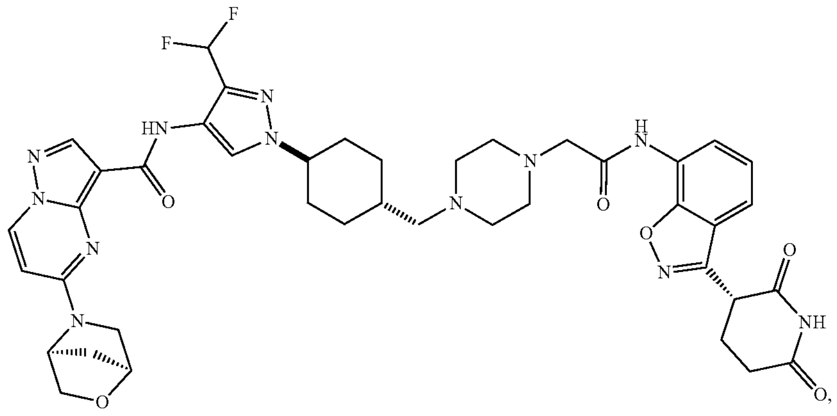
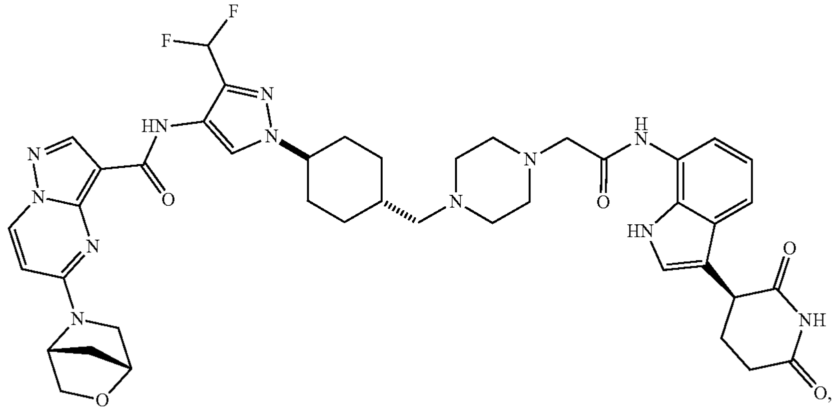
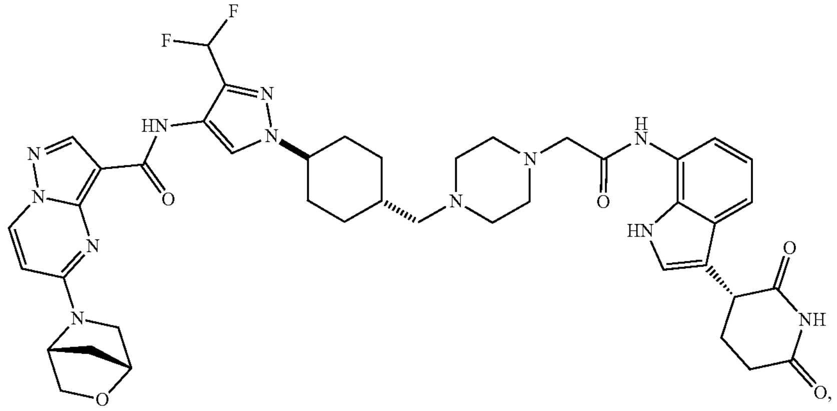
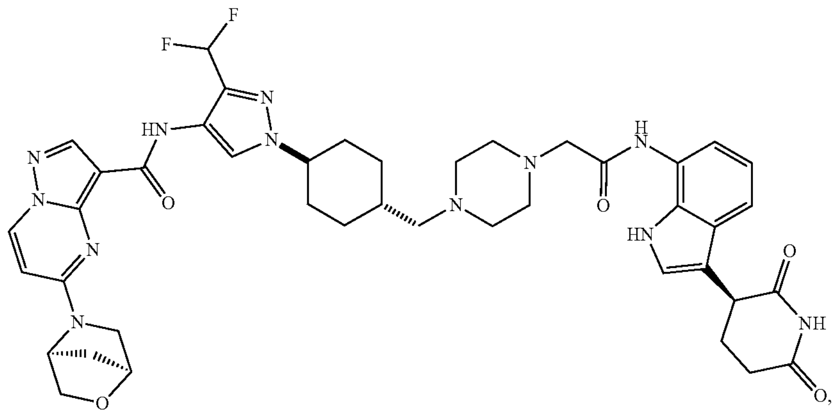

-continued
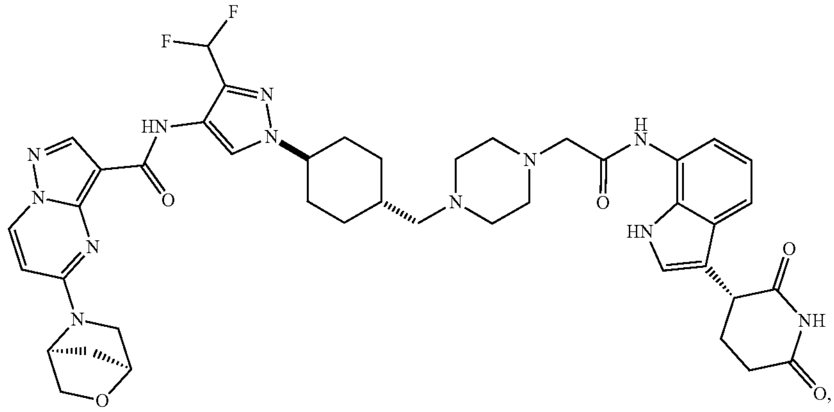
,
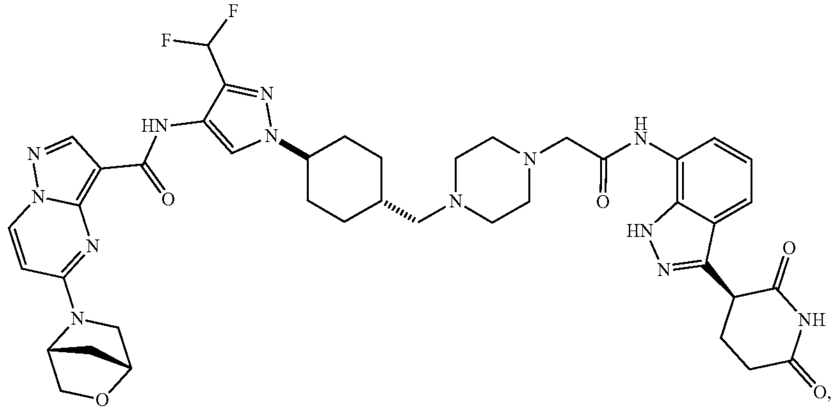
,
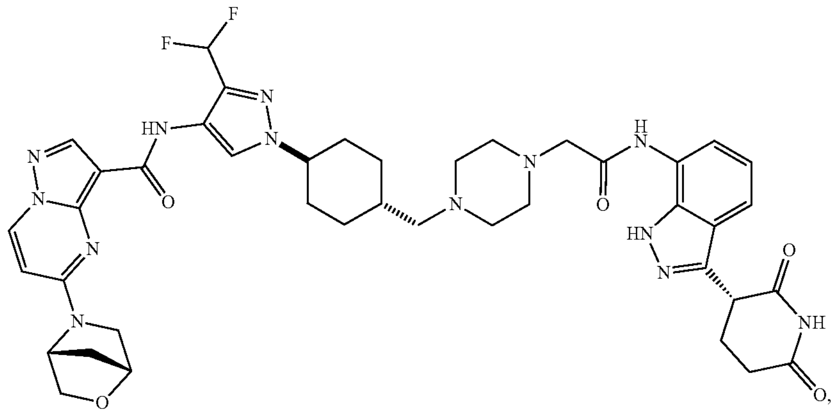
,
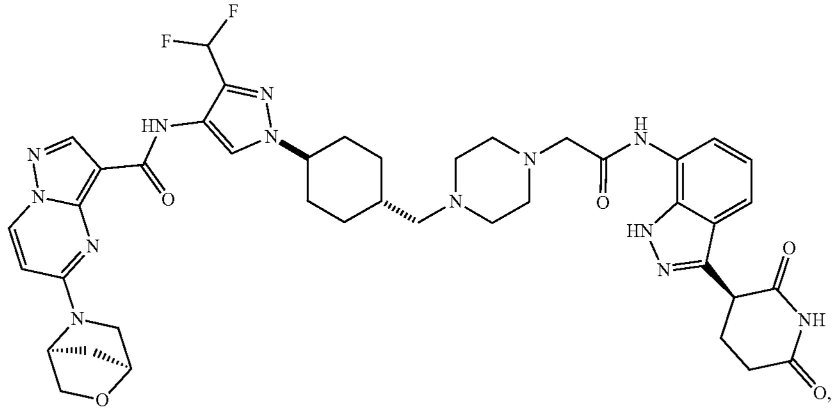
,

-continued
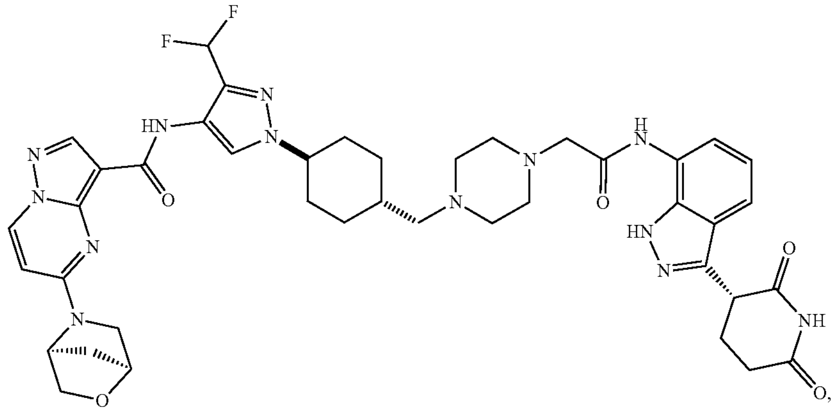
,
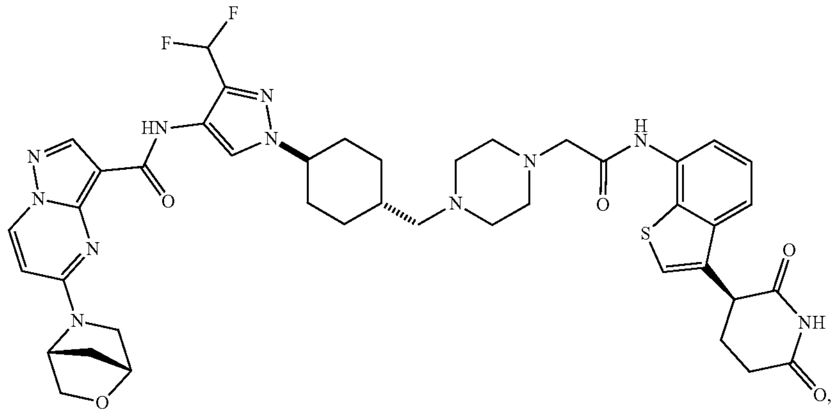
,
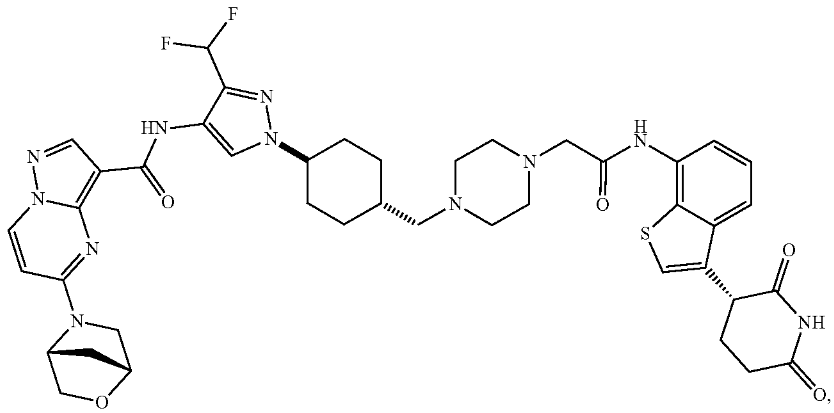
,
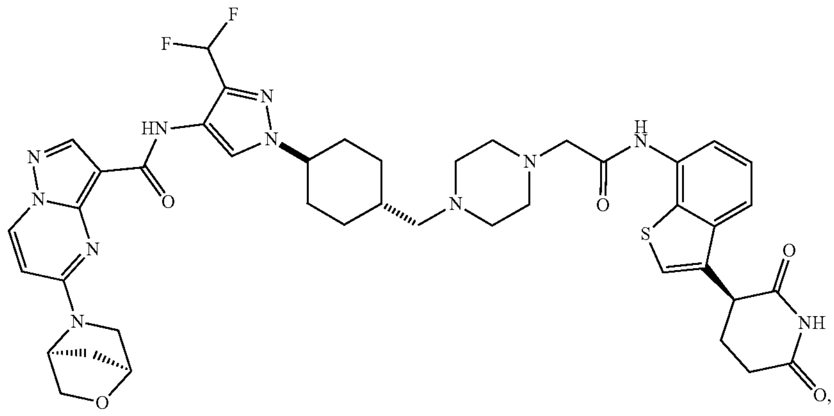
,

-continued
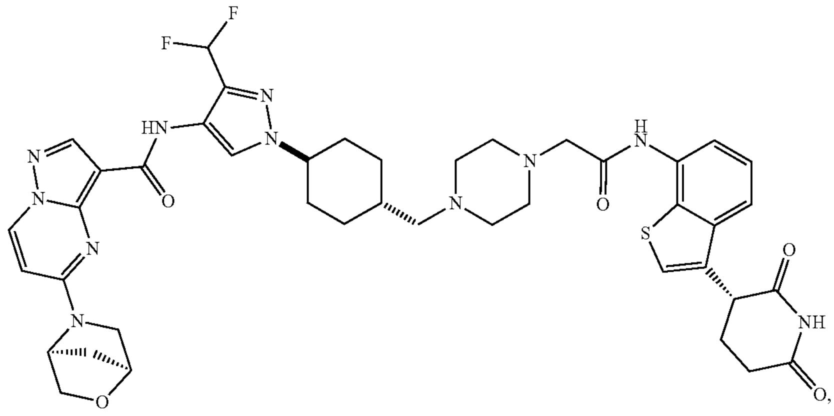
,
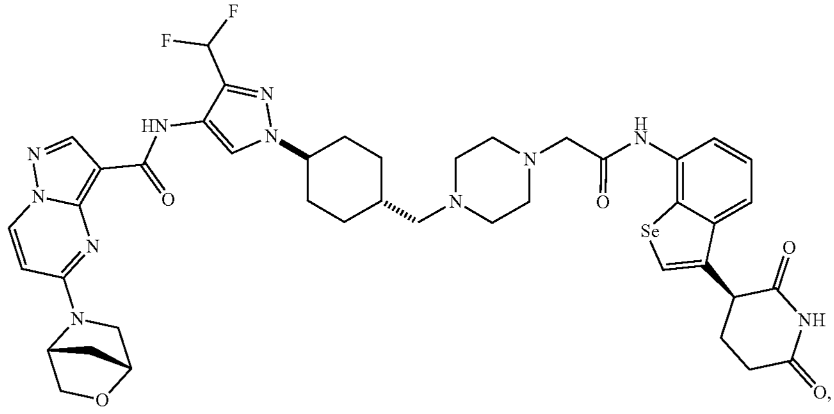
,
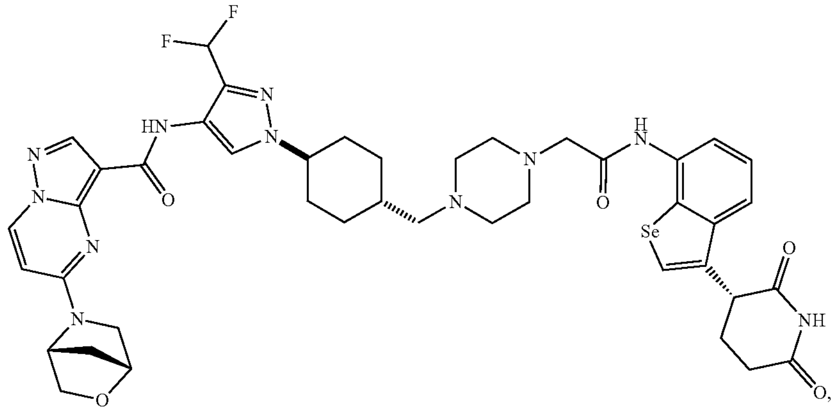
,
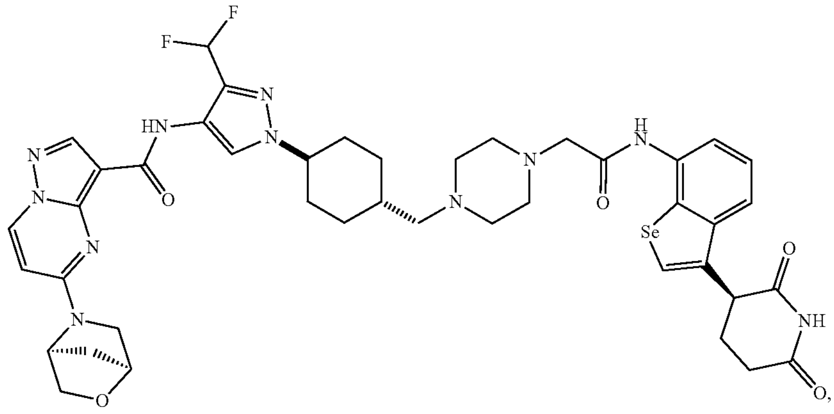
,

-continued
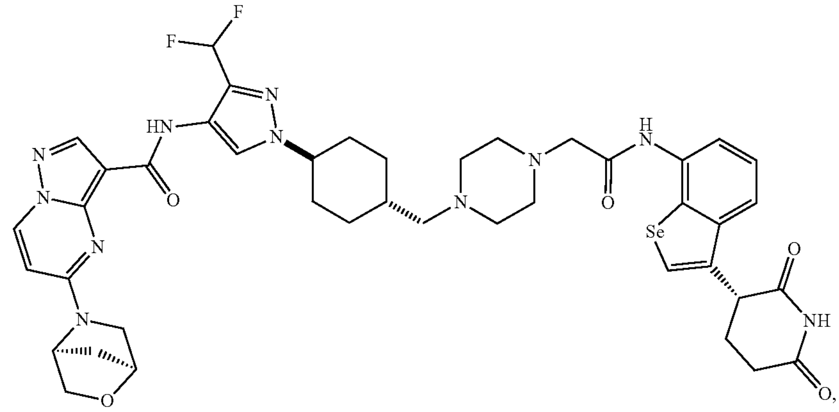
,
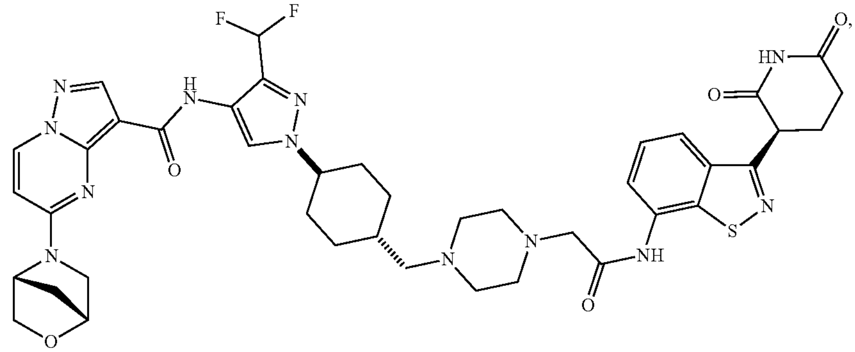
,
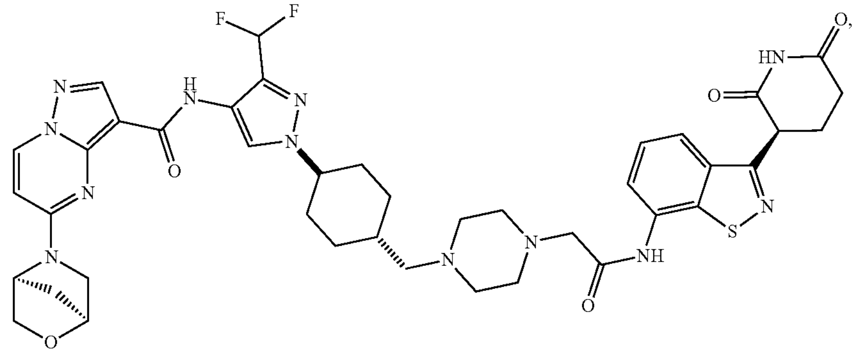
,
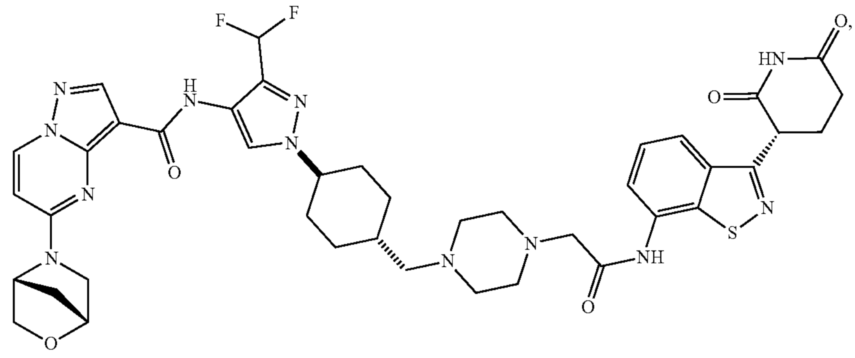
,

-continued
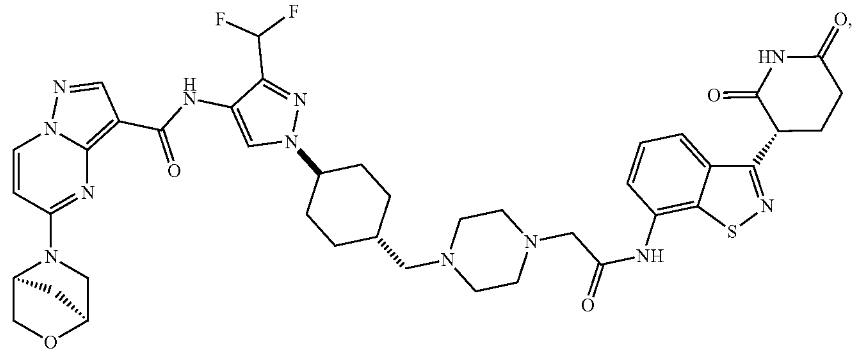
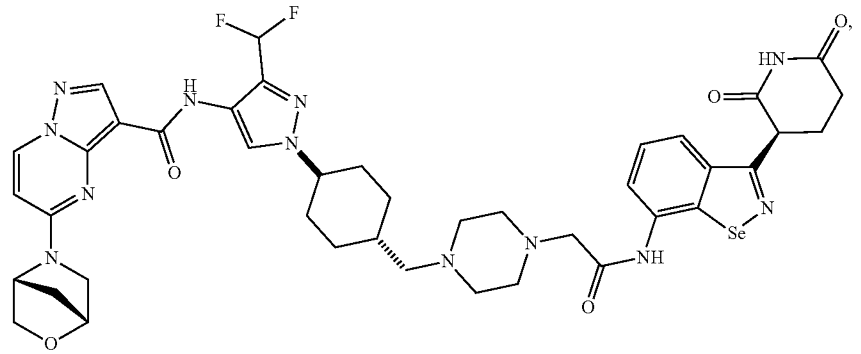
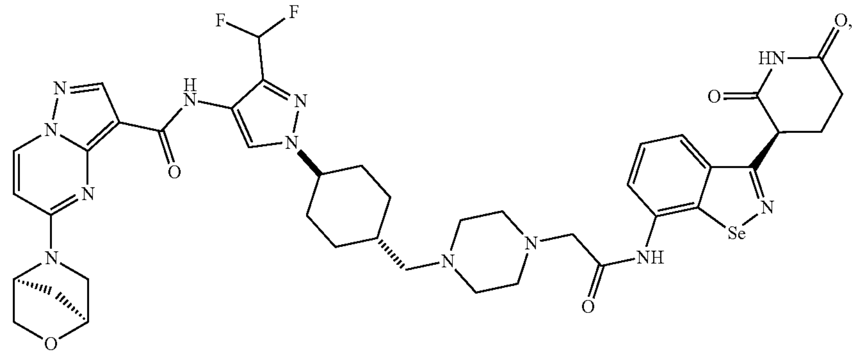
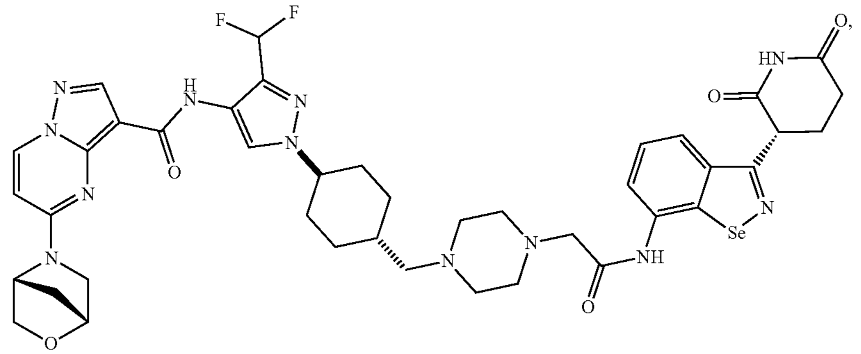

-continued
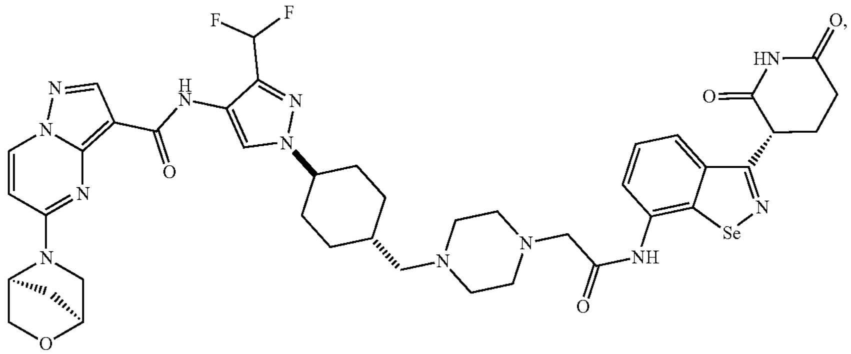
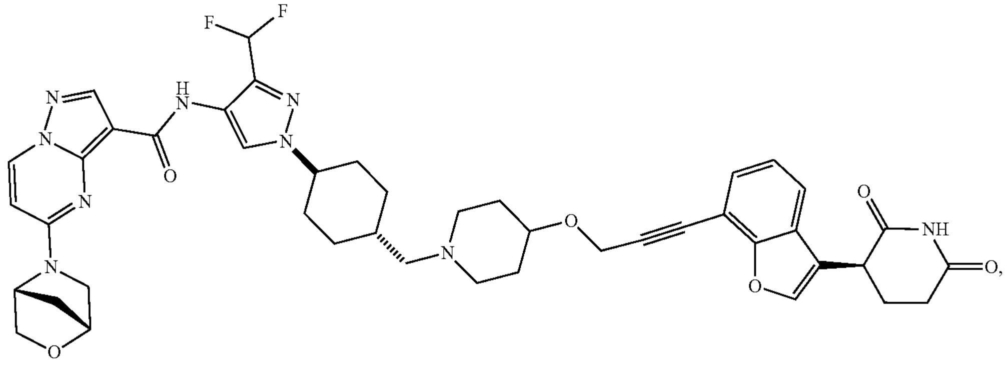
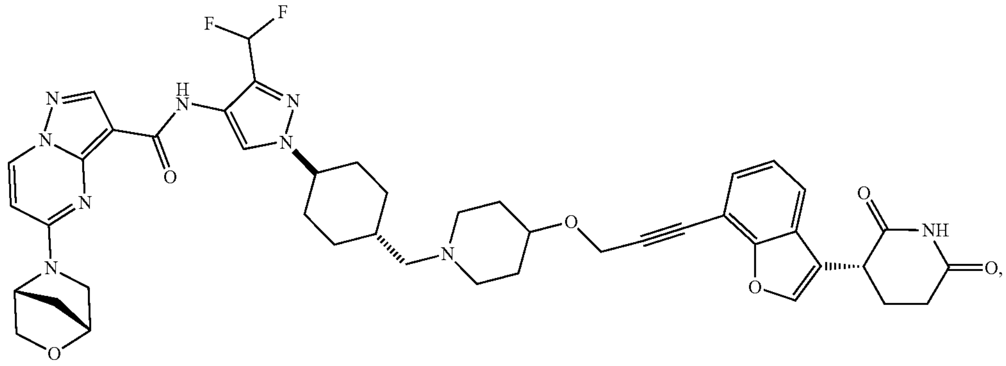
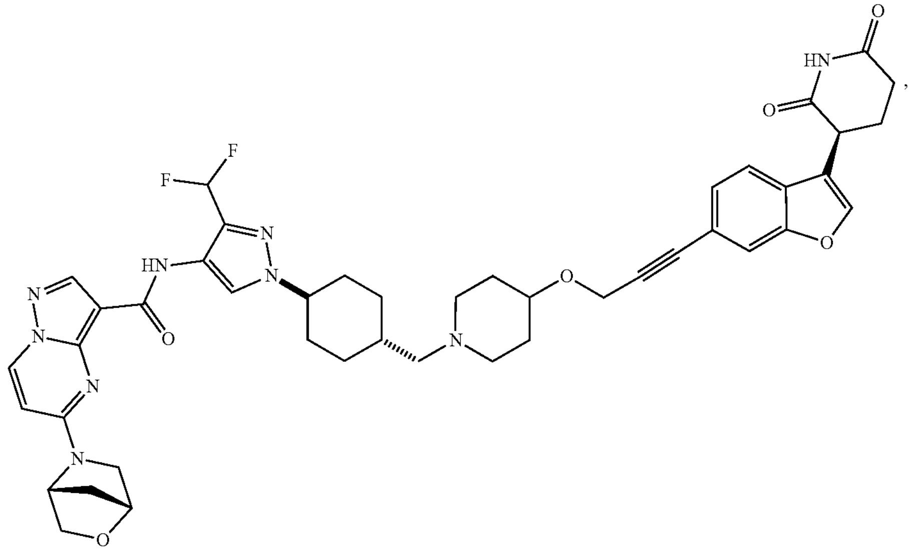

-continued
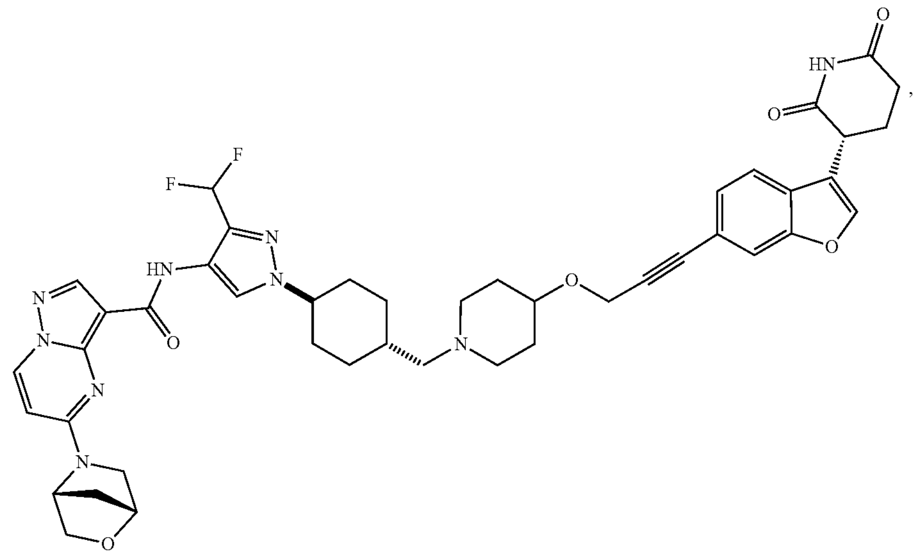
,
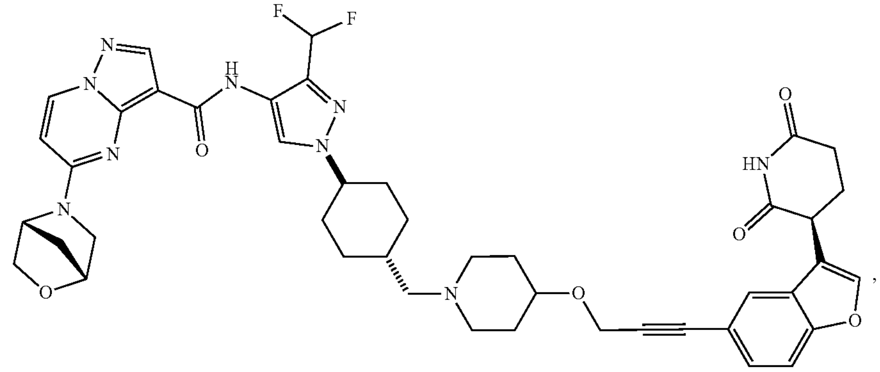
,
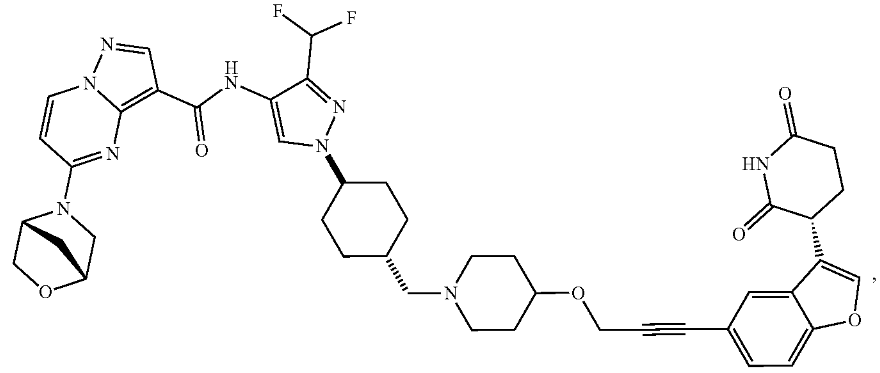
,
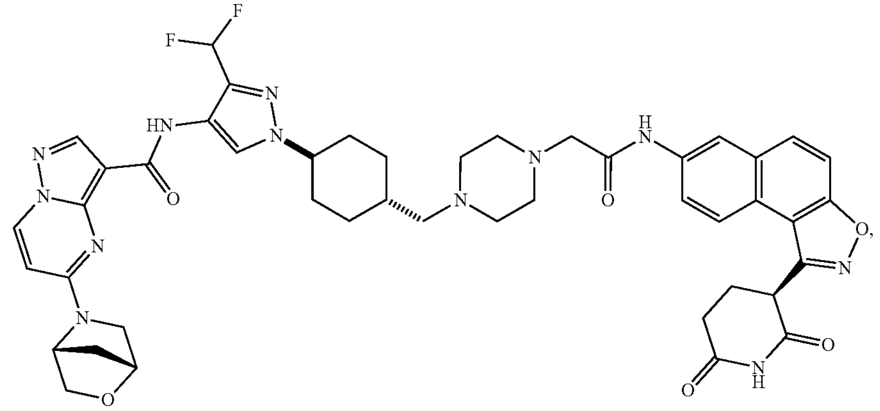
,

-continued
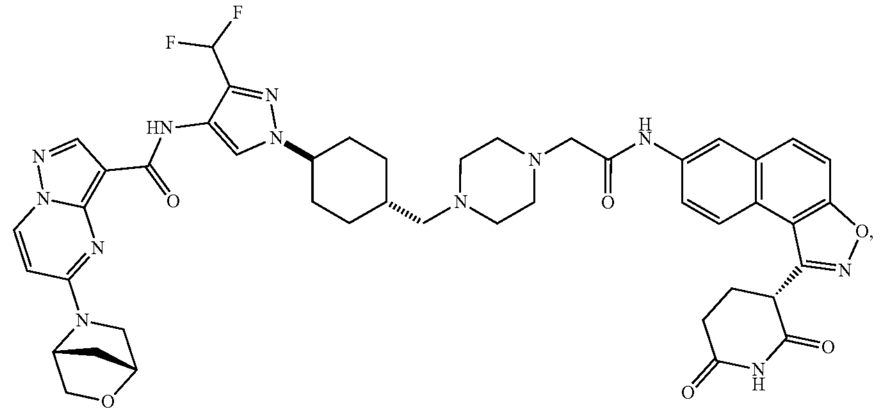
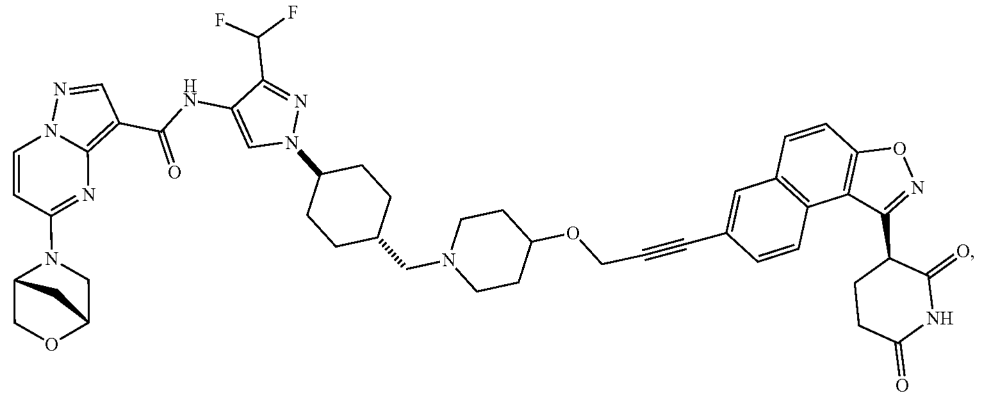
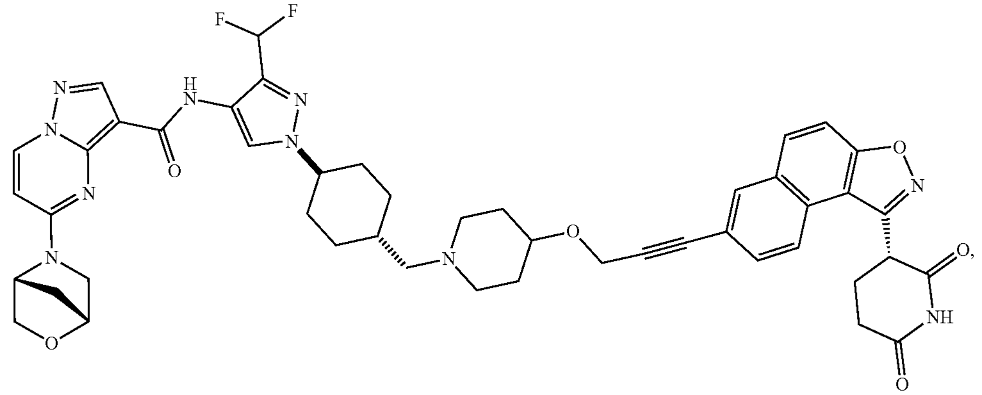
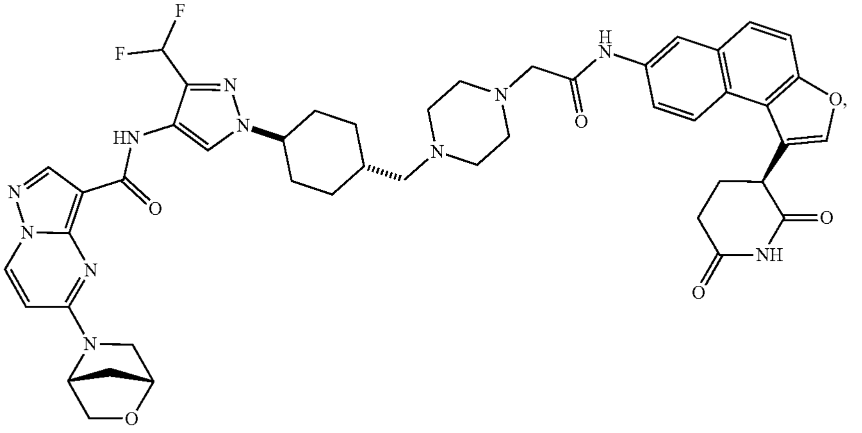

-continued
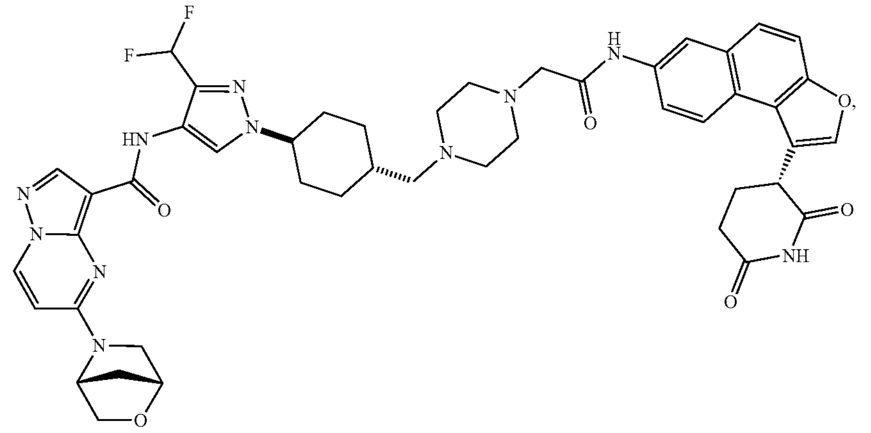
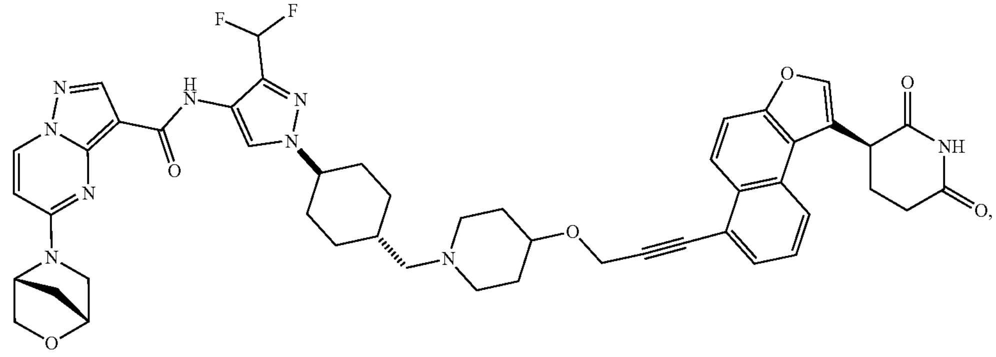
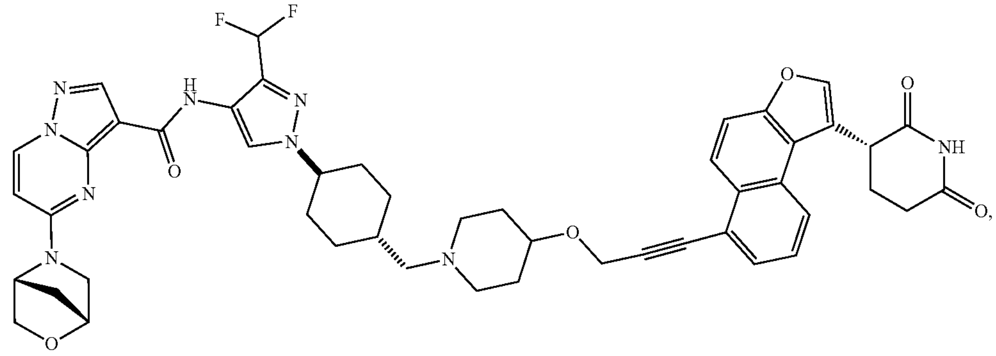
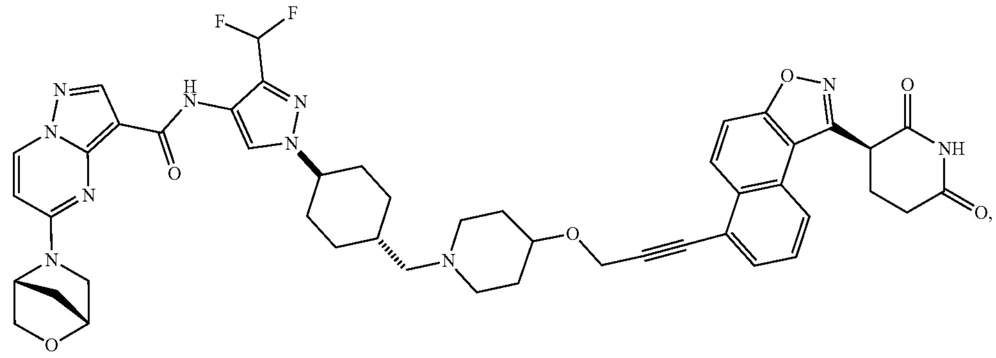

-continued
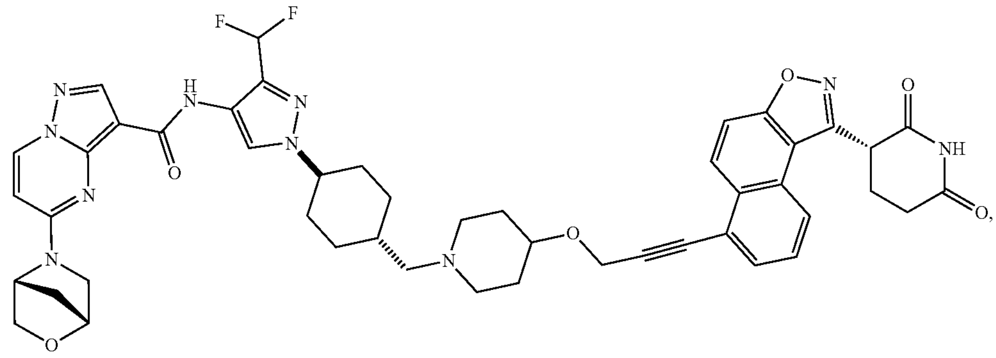
,
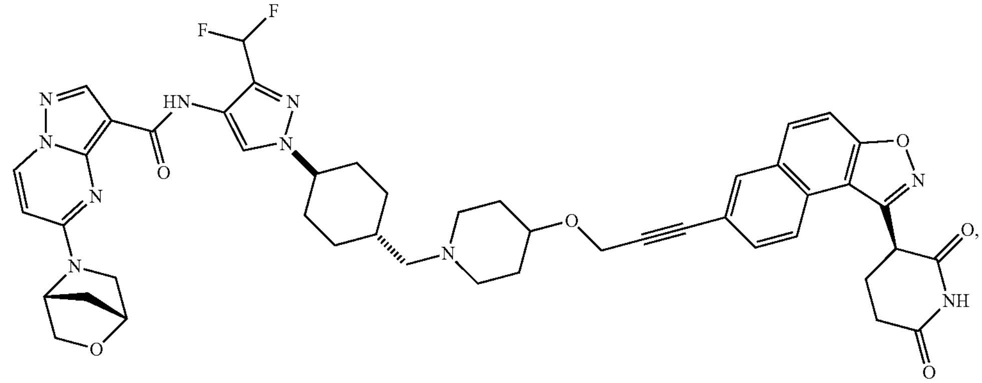
,
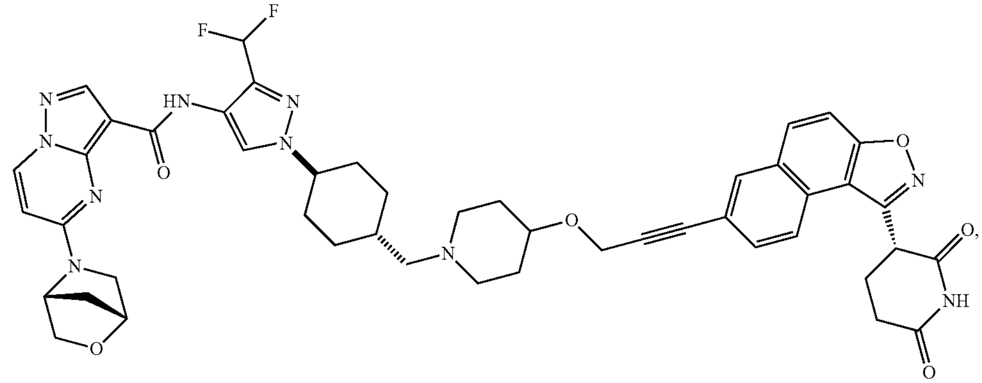
,

-continued
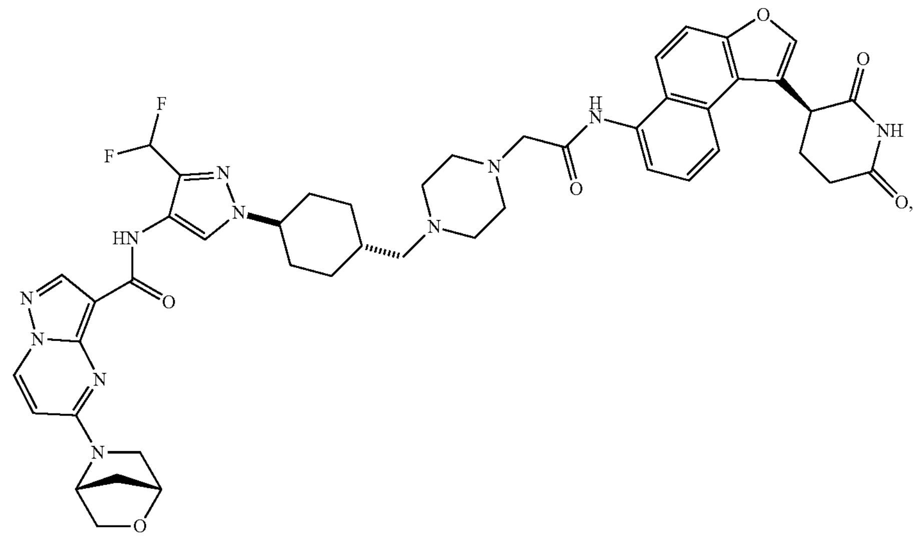
,
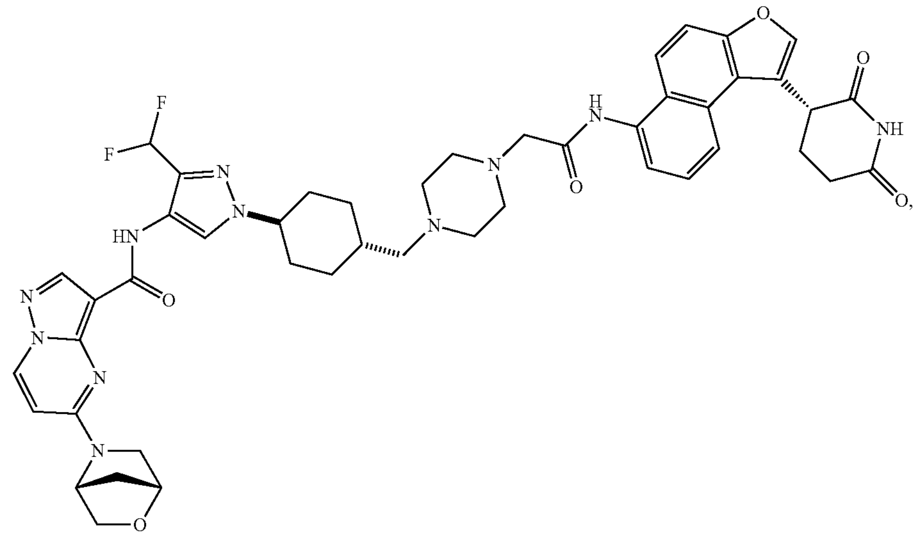
,
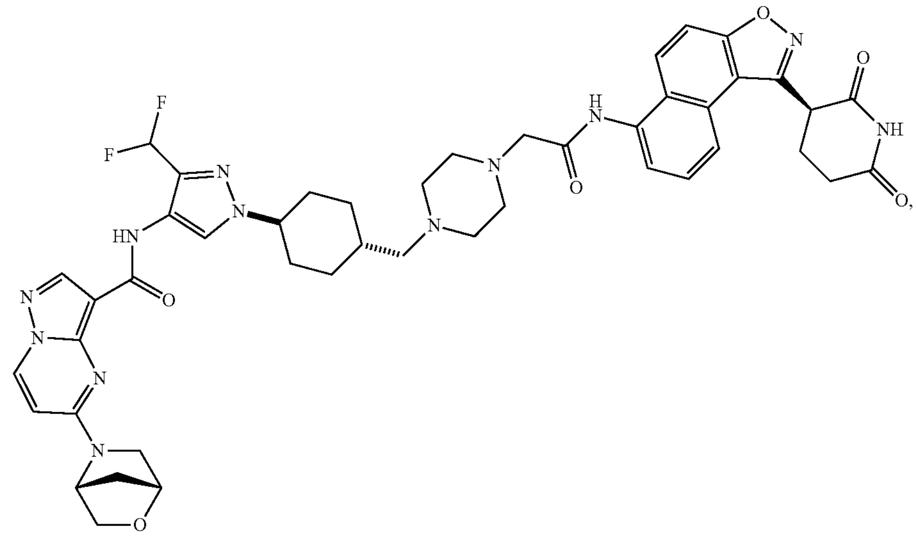
,

-continued
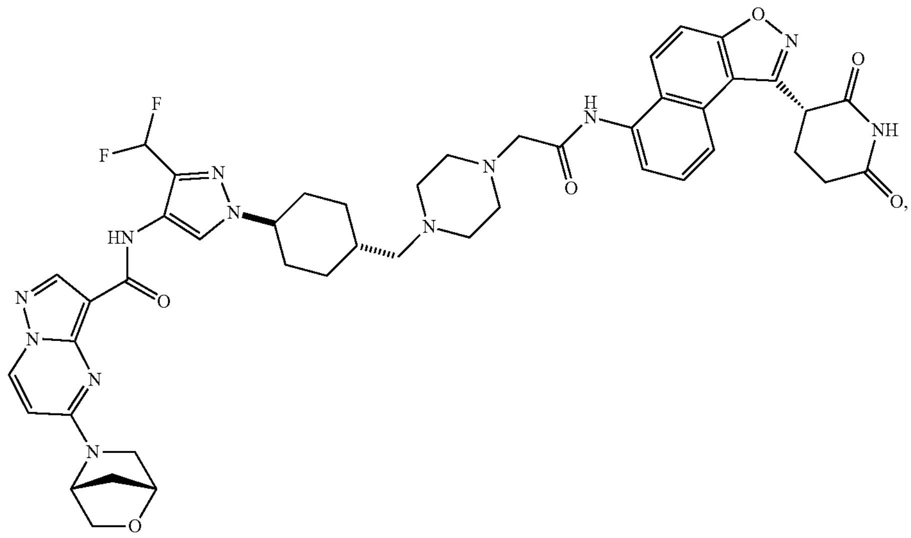
,
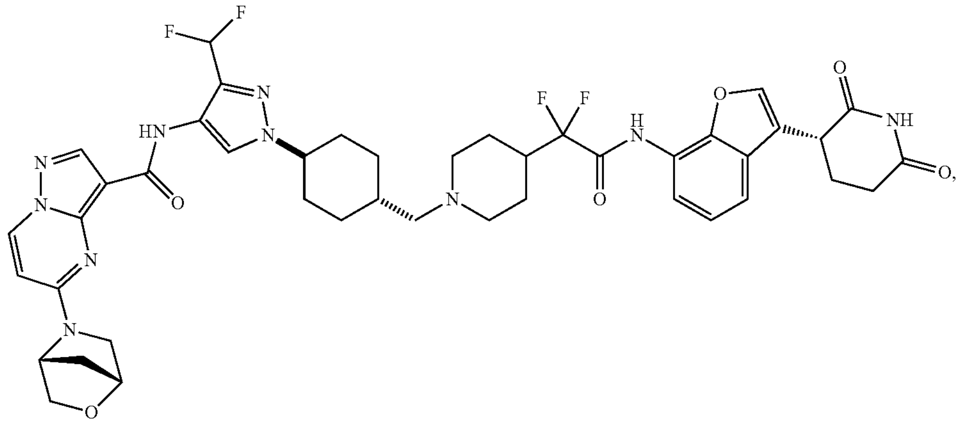
,
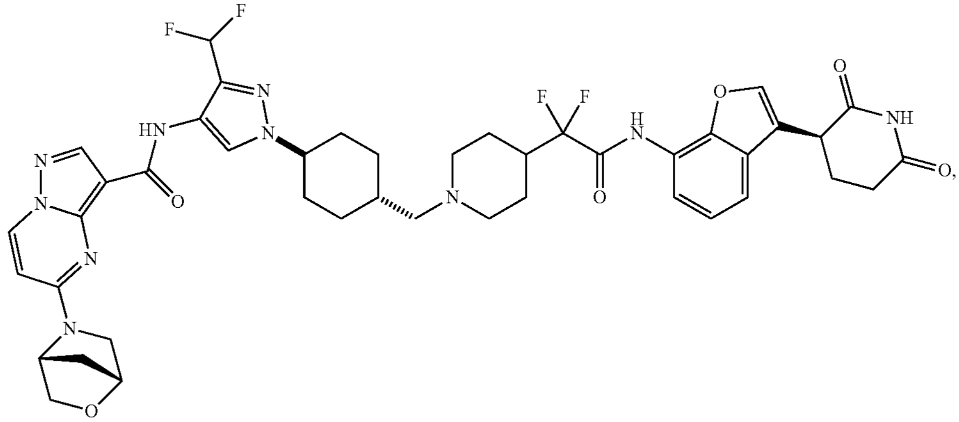
,

-continued
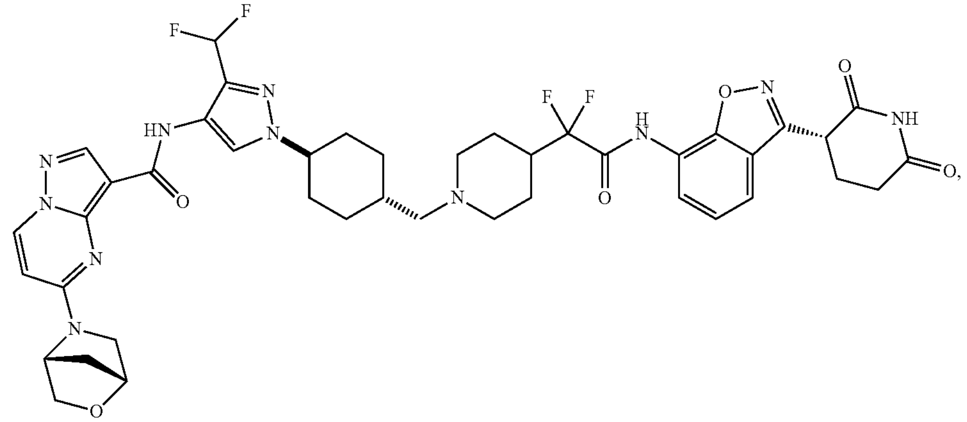
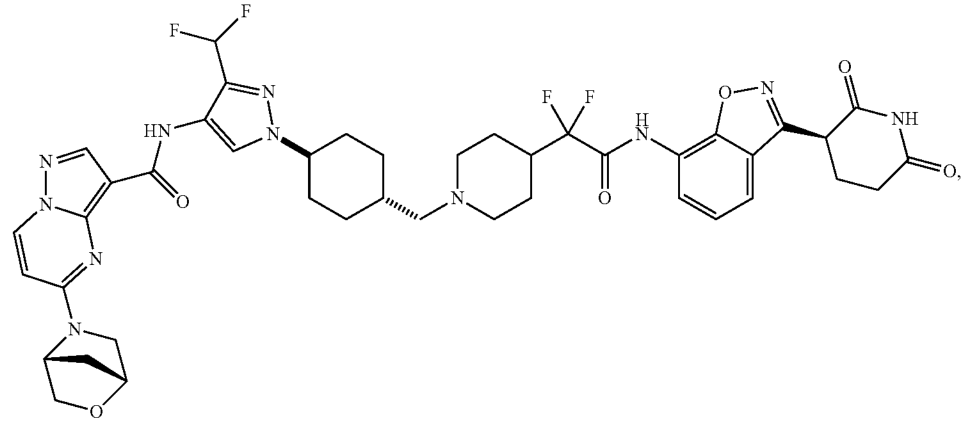
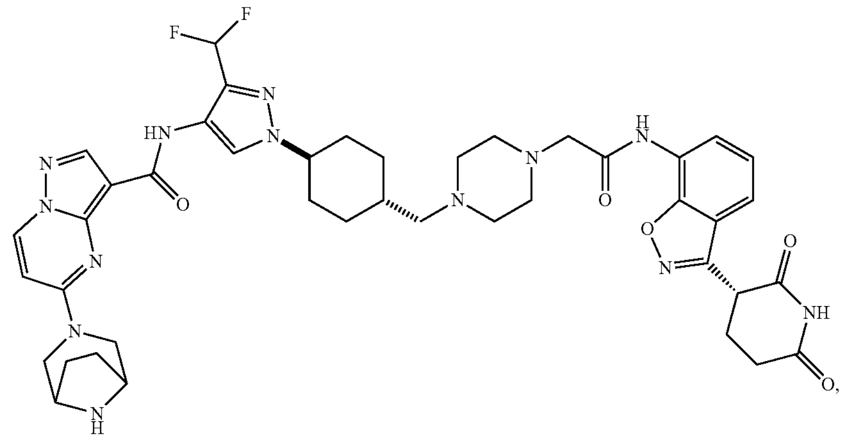
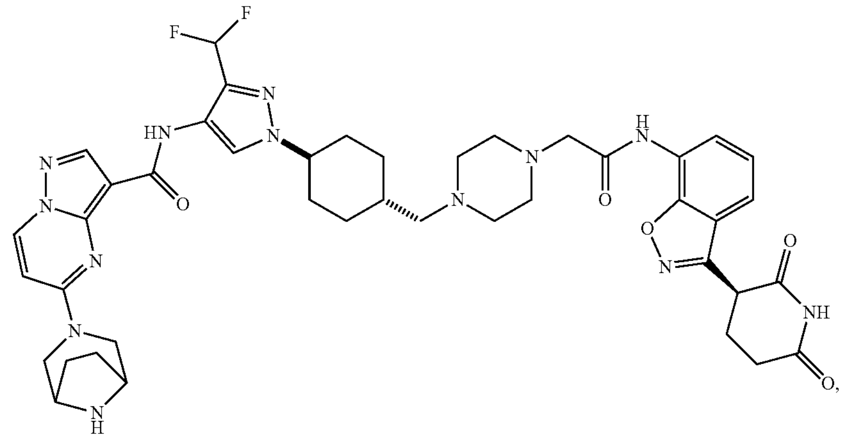

-continued
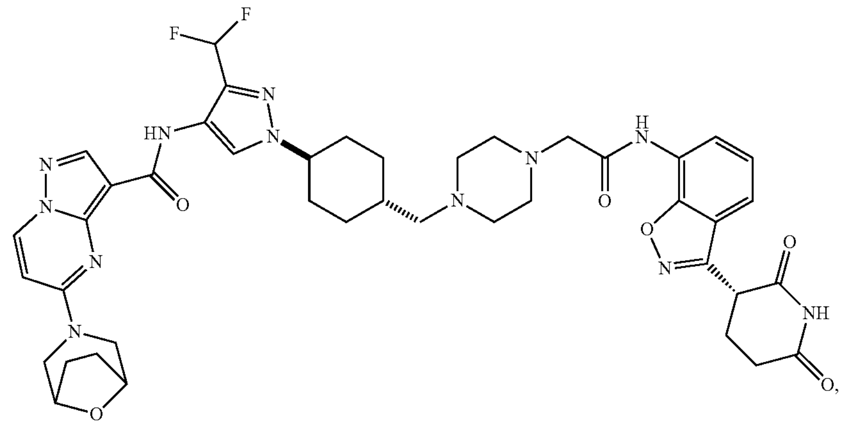
,
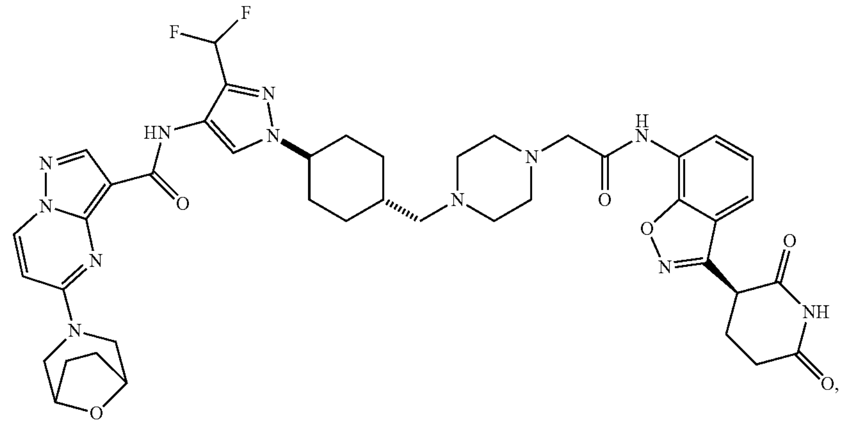
,
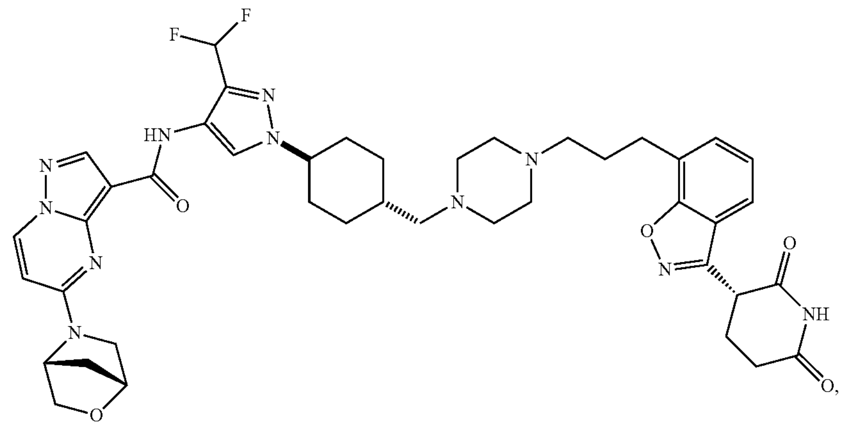
,
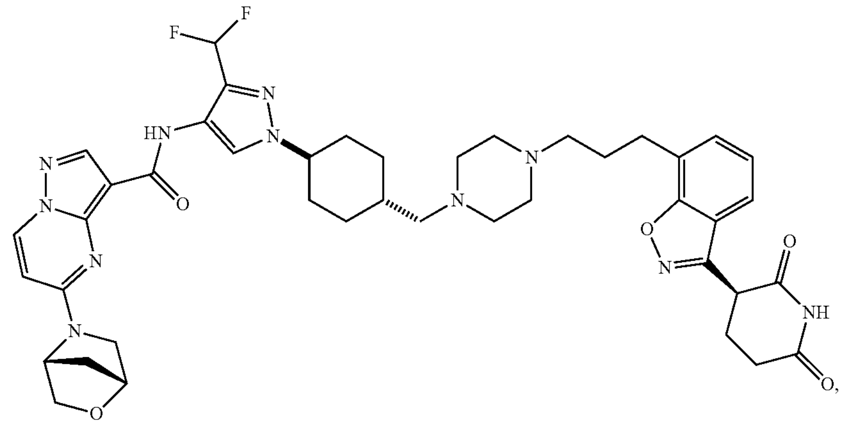
,

-continued
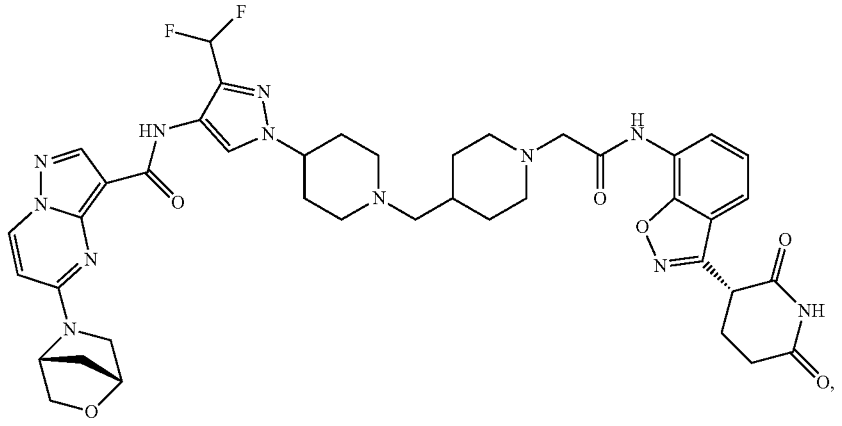
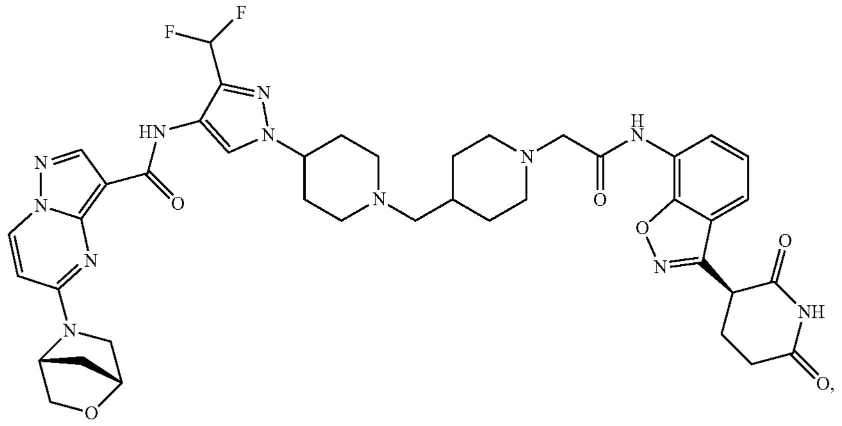
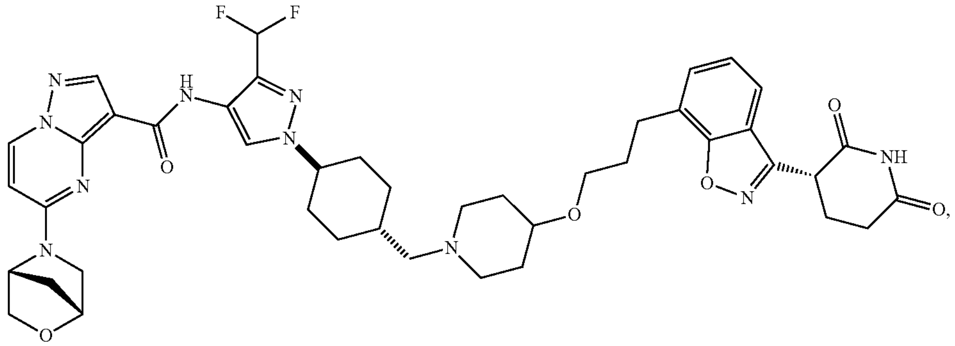
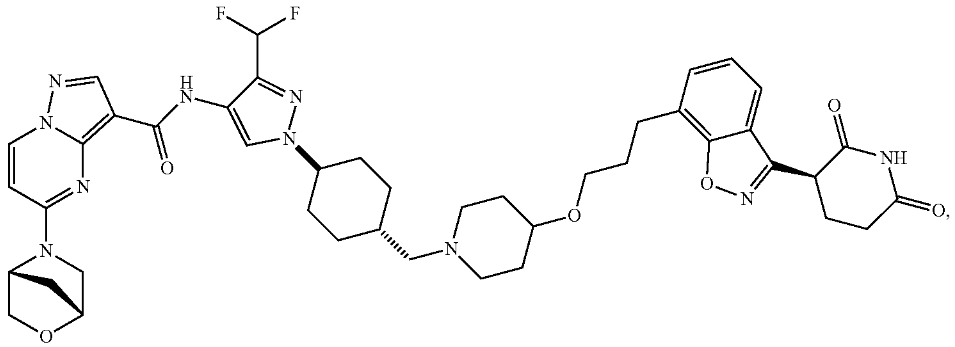

-continued
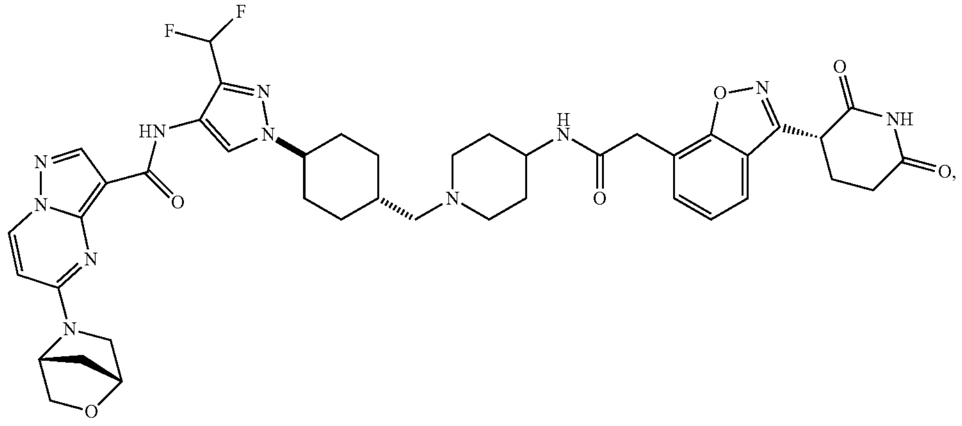
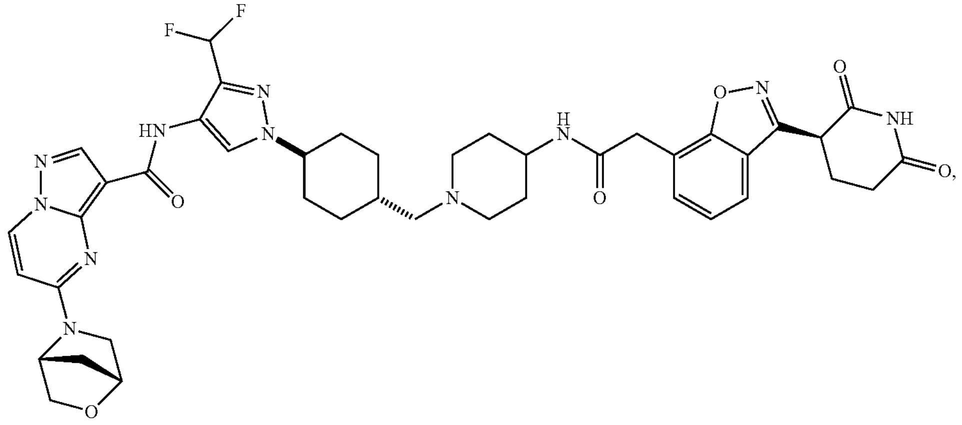
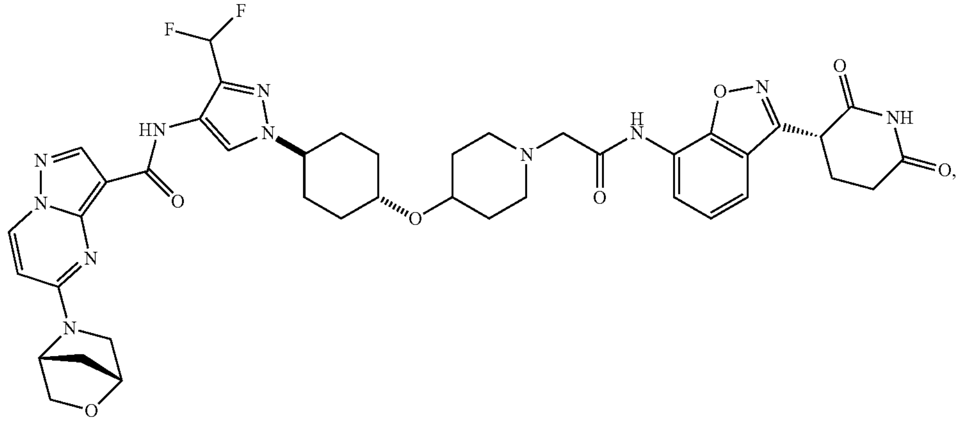
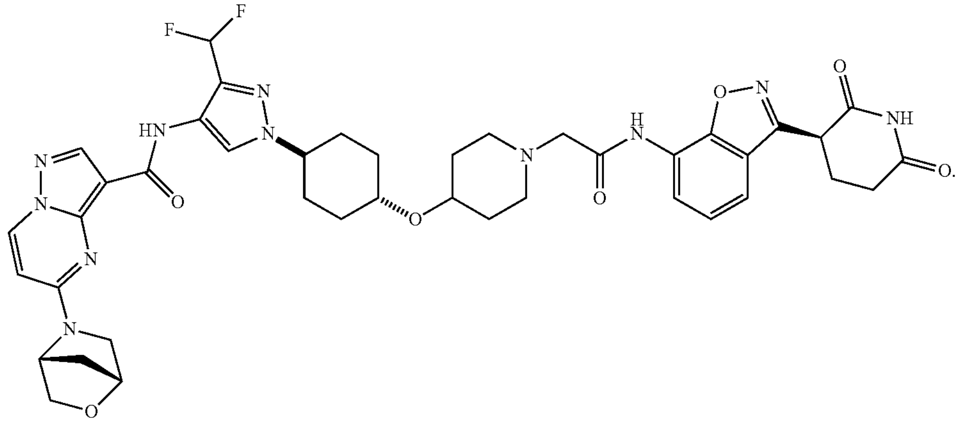

The present disclosure also provides a use of the compound or the pharmaceutically acceptable salt thereof of the present disclosure in the manufacture of a medicament for treating a disease related to interleukin-1 receptor-associated kinase 4 proteolysis targeting chimera.

The present disclosure also provides a method for treating a disease related to interleukin-1 receptor-associated kinase 4 proteolysis targeting chimera, comprising administering a therapeutically effective amount of the compound or the pharmaceutically acceptable salt thereof of the present disclosure to a mammal (preferably a human) in need of the treatment.

In some embodiments of the present disclosure, the disease related to interleukin-1 receptor-associated kinase 4 proteolysis targeting chimera is selected from inflammatory or immune diseases.

The present disclosure also provides the following synthesis routes:

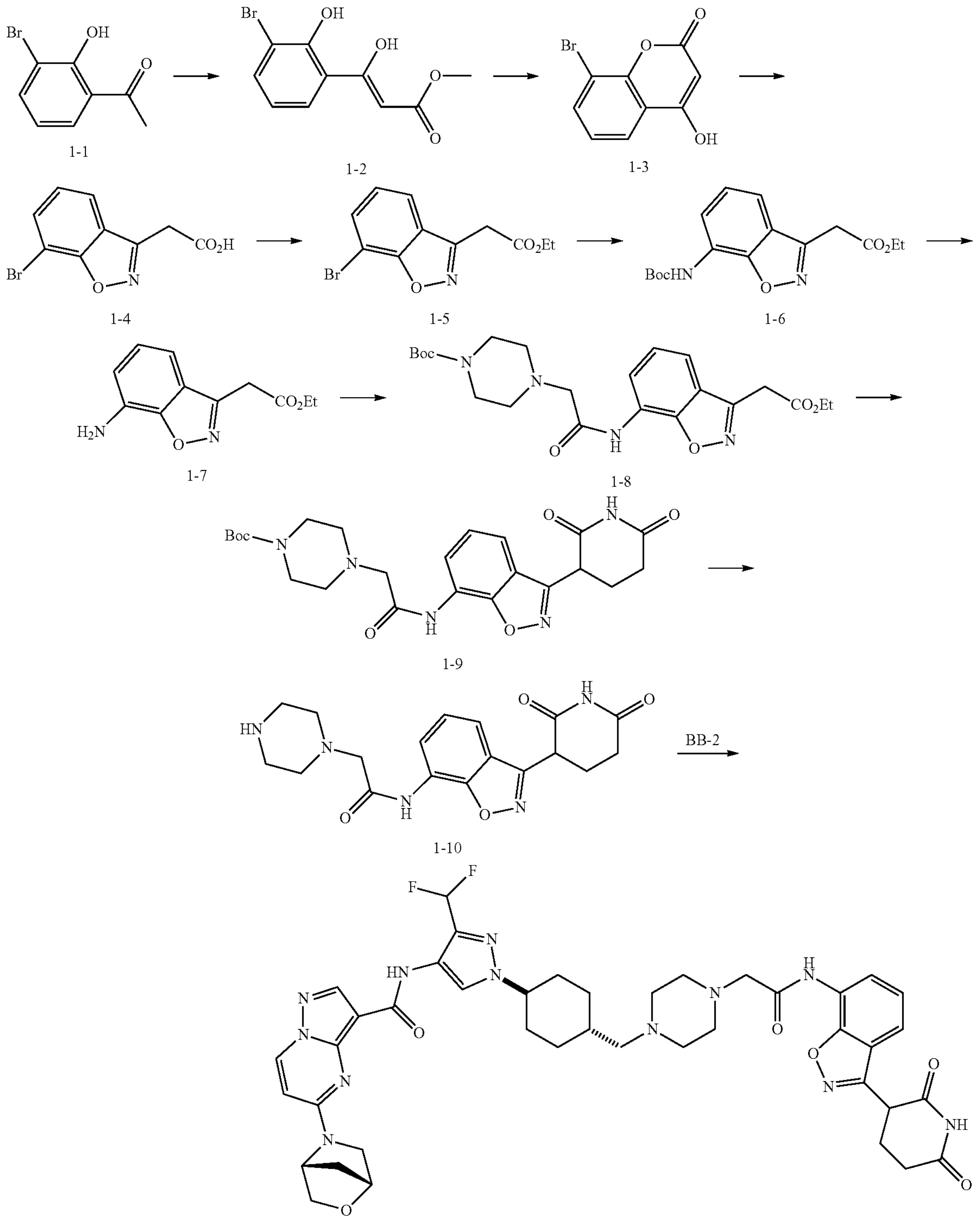

1-1 1-2 1-3 1-4 1-5 1-6 1-7 1-8 1-9 1-10

1

-continued

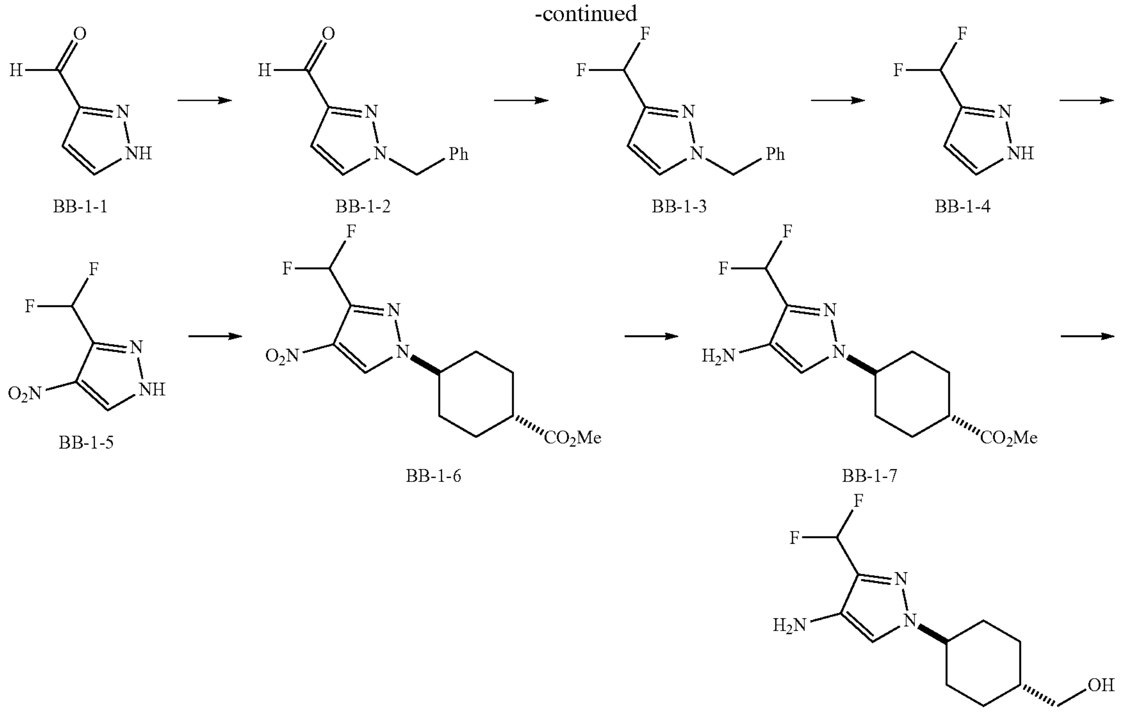

BB-1-1 BB-1-2 BB-1-3 BB-1-4 BB-1-5 BB-1-6 BB-1-7 BB-1

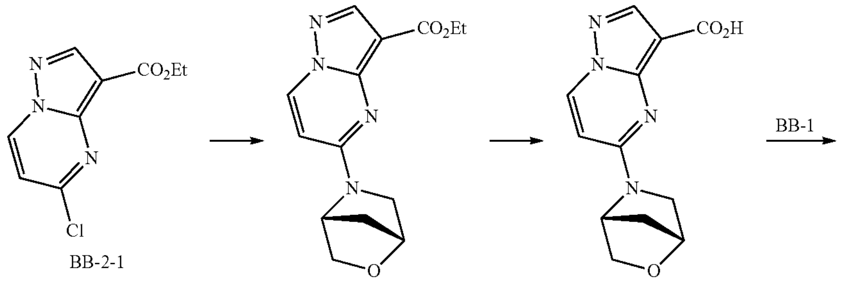

BB-2-1 BB-2-2 BB-2-3

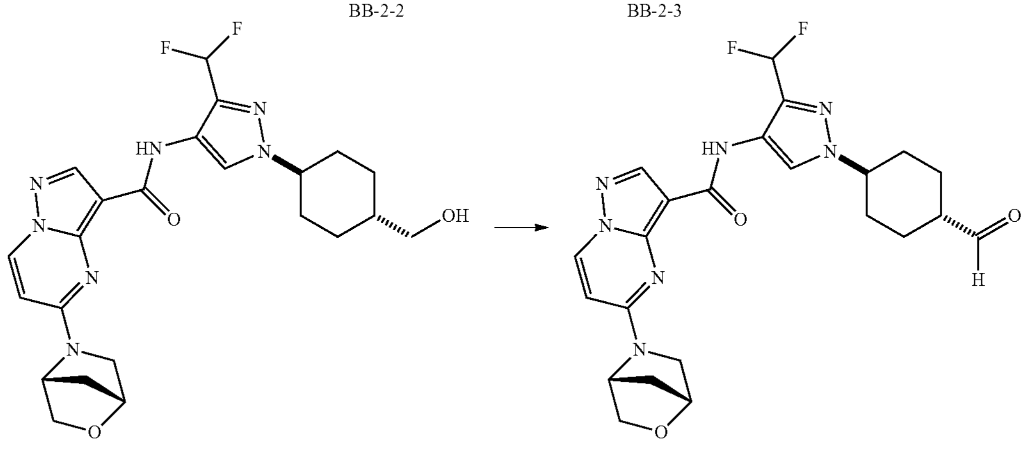

BB-2-4 BB-2

Technical Effect

The compound of the present disclosure exhibits excellent target protein degradation effect in K562 IRAK4-HiBiT cells. The compound of the present disclosure has high oral systemic plasma exposure. The compound of the present disclosure has superior pharmacokinetic properties in rodents such as mice and non-rodent animals such as Beagles and cynomolgus monkeys. The compound of the present disclosure has a therapeutic effect on hindfoot volume, hindfoot arthritis index score, and hindfoot weight-bearing difference in sodium urate-induced acute gouty arthritis in rats in a dose-dependent manner. The compound of the present disclosure has an ameliorating effect on pathological scores, increased ear thickness, and spleen weight of imiquimod-induced psoriasis model in mice, as well as an inhibitory effect on inflammatory factors in the skin at the lesion site, suggesting that it has a therapeutic effect in the psoriasis model in animals, and that the therapeutic effect of high dose (300 mpk) is superior to that of medium and low doses (100 mpk and 30 mpk).

Definition and Description

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction, or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The term "ubiquitin ligase" refers to a family of proteins that facilitate the transfer of ubiquitin to a specific substrate protein, targeting the substrate protein for degradation. For example, IAP, an E3 ubiquitin ligase protein, which alone or in combination with an E2 ubiquitin-conjugating enzyme causes the attachment of ubiquitin to a lysine on a target protein, and subsequently targets the specific protein substrate for degradation by the proteasome. Thus, E3 ubiquitin ligase alone or in complex with an E2 ubiquitin-conjugating enzyme is responsible for the transfer of ubiquitin to a target protein. In general, the ubiquitin ligase is involved in polyubiquitination such that a second ubiquitin is attached to a first ubiquitin; a third ubiquitin is attached to a second ubiquitin, and so forth. Polyubiquitination marks proteins for degradation by the proteasome. However, there are some ubiquitination events that are limited to mono-ubiquitination, in which only a single ubiquitin is added to a substrate molecule via a ubiquitin ligase. Mono-ubiquitinated proteins are not targeted to the proteasome for degradation, but can be altered in their cellular location or function, for example, via binding to other proteins with domains capable of binding ubiquitin. To complicate matters further, different lysines of ubiquitin can be targeted by E3 to make chains. The most common lysine is Lys48 on the ubiquitin chain. It is the lysine used to make polyubiquitin, which is recognized by the proteasome.

The term "targeting chimera" refers to a bifunctional molecule comprising two small molecule ligands, the first with high affinity for the target protein of interest, and the second for the recruitment of an E3 ligase, which ubiquitinates and targets the protein for proteolysis by the 26S proteasome.

The therapeutic dosage of the compound of the present disclosure may be determined based on, for example, the specific use of the treatment, the mode of administration of the compound, the health and condition of the patient, and the judgment of the prescribing physician. The proportion or concentration of the compound of the present disclosure in the pharmaceutical composition may not be fixed and depends on a variety of factors including dosage, chemical properties (e.g., hydrophobicity), and route of administration.

The term "treatment" refers to the administration of the compound or formulation of the present disclosure to ameliorate or eliminate a disease or one or more than one symptom associated with the disease, and includes:

(i) inhibiting a disease or disease state, i.e., arresting its development;

(ii) alleviating a disease or disease state, i.e., causing its regression.

The term "therapeutically effective amount" refers to an amount of the compound of the present disclosure for (i) treating a specific disease, condition, or disorder; (ii) alleviating, ameliorating, or eliminating one or more than one symptom of a specific disease, condition, or disorder, or (iii) preventing or delaying the onset of one or more than one symptom of a specific disease, condition, or disorder described herein. The amount of the compound of the present disclosure composing the "therapeutically effective amount" varies depending on the compound, the disease state and its severity, the mode of administration, and the age of the mammal to be treated, but can be routinely determined by those skilled in the art based on their knowledge and the present disclosure.

Unless the context requires otherwise, throughout the specification and claims thereafter, the term "comprise" and English variations thereof, such as "comprises" and "comprising", are to be construed in an open and inclusive sense, i.e., "including, but not limited to".

Reference throughout the specification to "one embodiment" or "an embodiment" or "another embodiment" or "some embodiments" means that at least one embodiment includes specific reference elements, structures, or characteristics described in connection with the embodiment. Accordingly, the phase "in one embodiment" or "in an embodiment" or "in another embodiment" or "in some embodiments" appearing in various places throughout the specification are not necessarily all referring to the same embodiment. In addition, the specific elements, structures, or characteristics may be combined in any suitable manner in one or more than one embodiment.

Unless otherwise specified, the term "isomer" is intended to include a geometric isomer, a cis-trans isomer, a stereoisomer, an enantiomer, an optical isomer, a diastereoisomer, and a tautomeric isomer.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, racemic, and other mixtures thereof, such as enantiomer or diastereomer enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term “enantiomer” or “optical isomer” refers to stereoisomers that are mirror images of each other.

Unless otherwise specified, the term “cis-trans isomer” or “geometric isomer” is caused by the inability to rotate freely of double bonds or single bonds of ring-forming carbon atoms.

Unless otherwise specified, the term “diastereomer” refers to a stereoisomer in which a molecule has two or more chiral centers and the relationship between the molecules is not mirror images.

Unless otherwise specified, “(+)” refers to dextrorotation, “(−)” refers to levorotation, and “(±)” refers to racemic.

Unless otherwise specified, the absolute configuration of a stereogenic center is represented by a wedged solid bond () and a wedged dashed bond (), and the relative configuration is represented by a straight solid bond () and a straight dashed bond (), for example, trans-1,4-disubstituted cyclohexane is represented by

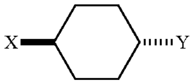

or

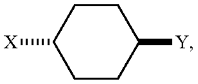

and cis-1,4-disubstituted cyclohexane is represented by

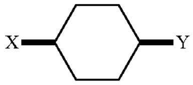

or

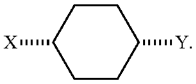

Unless otherwise specified, the terms “enriched in one isomer”, “enriched in isomers”, “enriched in one enantiomer”, or “enriched in enantiomers” refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term “isomer excess” or “enantiomeric excess” refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers, or D and L isomers can be prepared using chiral synthesis, chiral reagents, or other conventional techniques. If one kind of enantiomer of certain compound of the present disclosure is to be obtained, it can be obtained by asymmetric synthesis or derivative action of chiral auxiliary, wherein the resulting diastereomeric mixture is separated and the auxiliary group is cleaved to provide the pure desired enantiomer. Alternatively, when the molecule contains a basic functional group (such as amino) or an acidic functional group (such as carboxyl), a salt of a diastereoisomer is formed with an appropriate optically active acid or base, and then diastereomeric resolution is performed by conventional methods known in the art, and then the pure enantiomer is recovered. In addition, the enantiomer and the diastereoisomer are generally separated through chromatography which uses a chiral stationary phase and optionally combines with a chemical derivative method (such as carbamate generated from amine).

The compound of the present disclosure may contain an unnatural proportion of atomic isotope at one or more than one atom that constitutes the compound. For example, the compound can be radiolabeled with a radioactive isotope, such as tritium ($^3H$), iodine-125 ($^{125}I$), or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

When the enumerative linking group does not indicate the direction for linking, the direction for linking is arbitrary, for example, the linking group L contained in

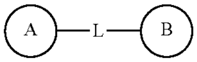

is -M-W—, then -M-W— can link ring A and ring B to form

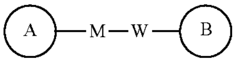

in the direction same as left-to-right reading order, and form

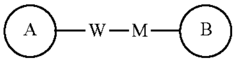

in the direction contrary to left-to-right reading order. A combination of the linking groups, substituents and/or variables thereof is allowed only when such combination can result in a stable compound.

Unless otherwise specified, when a group has one or more than one linkable site, any one or more than one site of the group can be linked to other groups through chemical bonds. When the linking site of the chemical bond is not positioned, and there is an H atom at the linkable site, then the number of H atoms at the site will decrease correspondingly with the number of the chemical bonds linking thereto so as to meet the corresponding valence. The chemical bond between the site and other groups can be represented by a straight solid bond (), a straight dashed bond (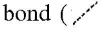), or a wavy line (). For example, the straight solid bond in $—OCH_3$ means that it is linked to other groups through the oxygen atom in the group; the straight dashed bond in

means that it is linked to other groups through the two ends of nitrogen atom in the group; the wave line in

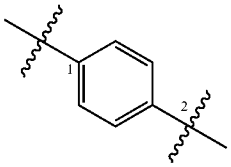 [SMILES: *c1ccc(*)cc1]

means that the phenyl group is linked to other groups through carbon atoms at position 1 and position 2;

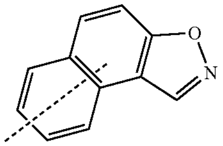

means that it can be linked to other groups through any linkable sites on the naphthalene ring by one chemical bond, including at least six types of linkage, including

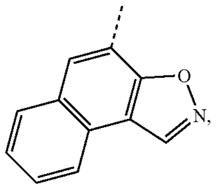
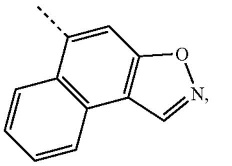
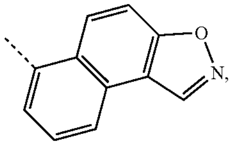
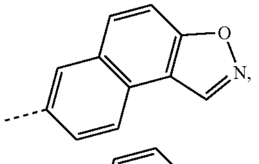
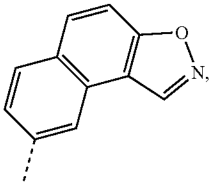
and
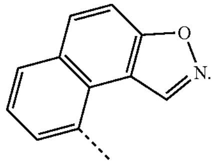

"Optional" or "optionally" means that the subsequent event or condition may occur but not requisite, that the term includes the instance in which the event or condition occurs and the instance in which the event or condition does not occur.

The term "substituted" means one or more than one hydrogen atom on a specific atom is substituted by the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted with up to two R, wherein the definition of R at each occurrence is independent. Moreover, a combination of the substituent and/or the variant thereof is allowed only when the combination results in a stable compound.

Unless otherwise specified, the term "halo" or "halogen" by itself or as part of another substituent refers to fluorine, chlorine, bromine, or iodine atom.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$, $C_{1-3}$, $C_{2-3}$ alkyl, etc.; it can be monovalent (such as methyl), divalent (such as methylene), or multivalent (such as methine). Examples of $C_{1-4}$ alkyl include, but are not limited to, methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene), or multivalent (such as methine).

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$, $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "haloalkyl" refers to an alkyl group in which one or more than one hydrogen is substituted by halogen, and specifically includes monohaloalkyl, dihaloalkyl, and polyhaloalkyl. For example, "$C_{1-3}$ haloalkyl" refers to monohaloalkyl and polyhaloalkyl containing 1 to 3 carbon atoms. The $C_{1-3}$ haloalkyl includes $C_{1-2}$, $C_{2-3}$, $C_3$, $C_2$, $C_1$ haloalkyl, etc. Examples of $C_{1-3}$ haloalkyl include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, etc.

Unless otherwise specified, the term "haloalkyl" refers to an alkoxy group in which one or more than one hydrogen is substituted by halogen, and specifically includes monohaloalkoxy, dihaloalkoxy, and polyhaloalkoxy. For example, "$C_{1-3}$ haloalkoxy" refers to monohaloalkoxy and polyhaloalkoxy containing 1 to 3 carbon atoms. The $C_{1-3}$ haloalkoxy includes $C_{1-2}$, $C_{2-3}$, $C_3$, $C_2$, $C_1$ haloalkoxy, etc. Examples of $C_{1-3}$ haloalkoxy include, but are not limited to, trifluoromethoxy, trichloromethoxy, 2,2,2-trifluoroethoxy, pentafluoroethoxy, pentachloroethoxy, 3-bromopropoxy, etc.

Unless otherwise specified, "ring" refers to substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic system as well as a bicyclic or polycyclic system such as a spiro ring, fused ring, and a bridged ring. The number of atoms in a ring is usually defined as the number of ring members, for example, "5- to 7-membered ring" means that 5 to 7 atoms are arranged around. Unless otherwise specified, the ring optionally contains 1 to 3 heteroatoms. Thus, "5- to 7-membered ring" includes, for example, phenyl, pyridyl, and piperidinyl; on the other hand, the term "5- to 7-membered heterocycloalkyl" includes pyridyl and piperidinyl, but does not include phenyl. The term "ring" also includes a ring system containing at least one ring, where each "ring" independently conforms to the definition provided above.

Unless otherwise specified, "$C_{5-8}$ cycloalkyl" refers to a saturated cyclic hydrocarbon group consisting of 5 to 8 carbon atoms, including monocyclic and bicyclic systems, wherein the bicyclic system includes a spiro ring, a fused ring, and a bridged ring. The $C_{5-8}$ cycloalkyl includes $C_{5-6}$, $C_{5-7}$, $C_{6-7}$, $C_5$, $C_6$, $C_7$, $C_8$ cycloalkyl, etc.; it can be monovalent, divalent, or multivalent. Examples of $C_{5-7}$ cycloalkyl include, but are not limited to, cyclopentyl, cyclohexyl, cycloheptyl,

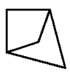, 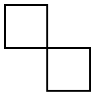, 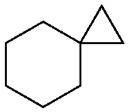, 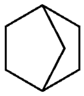, 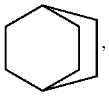, etc.

Unless otherwise specified, the term "5- to 8-membered heterocycloalkyl" by itself or in combination with other terms refers to a saturated cyclic group consisting of 5 to 8 ring atoms, wherein 1, 2, 3, or 4 ring atoms are heteroatoms independently selected from O, S, N, Si, or Se, and the rest are carbon atoms, wherein carbon atoms can be oxidized (i.e., C(O)), nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic system includes a spiro ring, a fused ring, and a bridged ring. In addition, in the case of the "5- to 8-membered heterocycloalkyl", the heteroatom may occupy the position where the heterocycloalkyl is linked to the rest of the molecule. Examples of 5- to 8-membered heterocycloalkyl include, but are not limited to, pyrrolidinyl, pyrazolidinyl, imidazolidinyl, tetrahydrothiophenyl (including tetrahydrothiophen-2-yl, tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxinyl, dithianyl, isoxazolidinyl, isothiazolidinyl, 1,2-oxazinyl, 1,2-thiazinyl, hexahydropyridazinyl,

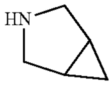, 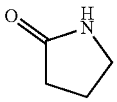, 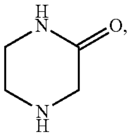, 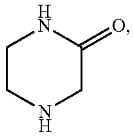,

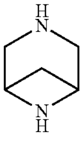, 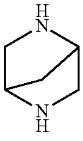, 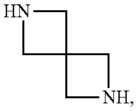, 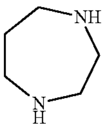,

-continued

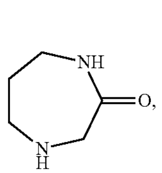, 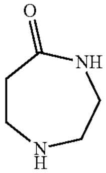, 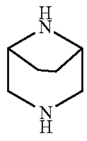, 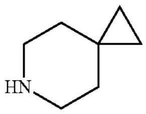, etc.

The structure of the compounds of the present disclosure can be confirmed by conventional methods known to those skilled in the art, and if the present disclosure involves an absolute configuration of a compound, then the absolute configuration can be confirmed by means of conventional techniques in the art. For example, in the case of single crystal X-ray diffraction (SXRD), diffraction intensity data are collected from the cultured single crystal using a Bruker D8 venture diffractometer with CuKα radiation as the light source and scanning mode: φ/ω scan, and after collecting the relevant data, the crystal structure is further analyzed by direct method (Shelxs97), so that the absolute configuration can be confirmed.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, and preferred embodiments include, but are not limited to, the examples of the present disclosure.

The compounds of the present disclosure are named according to the conventional naming principles in the art or by ChemDraw® software, and the commercially available compounds use the supplier catalog names.

The solvents used in the present disclosure are commercially available.

The following abbreviations are used in the present disclosure: Ph stands for phenyl; Me stands for methyl; Et stands for ethyl; M stands for moles per liter; Boc stands for tert-butoxycarbonyl, which is an amino protecting group; room temperature stands for 20 to 25° C.

DETAILED DESCRIPTION OF THE PREFERRED EMBODIMENT

The present disclosure is described in detail by the examples below, but it does not mean that there are any adverse restrictions on the present disclosure. The present disclosure has been described in detail herein, and its specific examples have also been disclosed; for one skilled in the art, it is obvious to make various modifications and improvements to the examples of the present disclosure without departing from the spirit and scope of the present disclosure.

Reference Example 1

BB-1

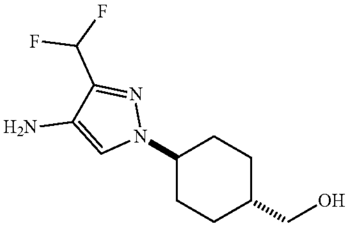

Synthetic Route

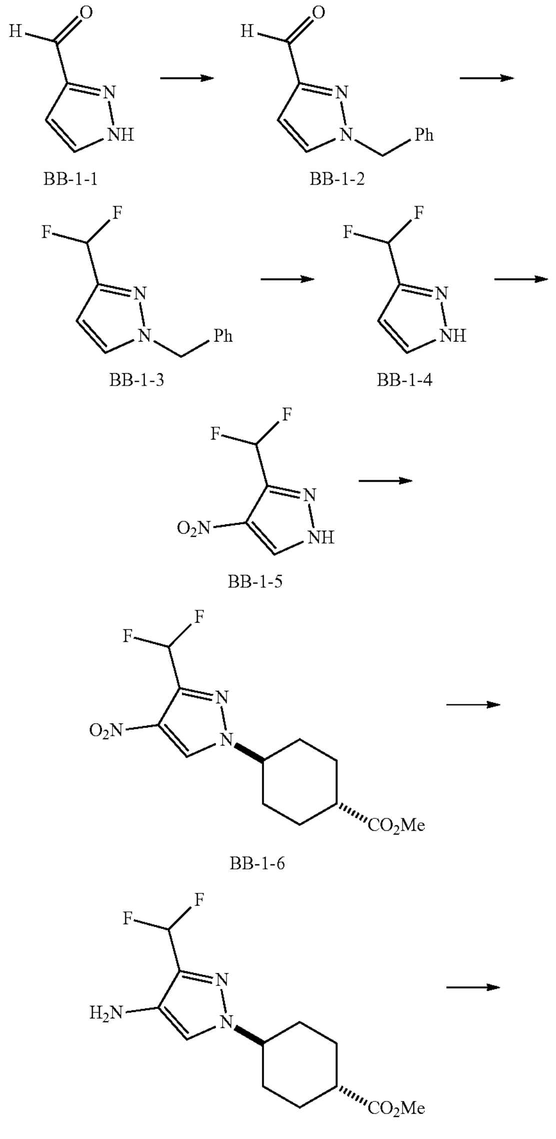

BB-1-1 BB-1-2 BB-1-3 BB-1-4 BB-1-5 BB-1-6 BB-1-7

-continued

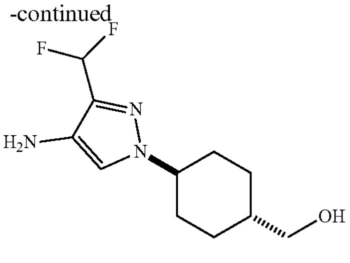

BB-1

Step 1: Synthesis of Intermediate BB-1-2

Compound BB-1-1 (40 g, 416.29 mmol) was dissolved in N,N-dimethylformamide (400 mL) at room temperature under nitrogen atmosphere, then benzyl bromide (74.76 g, 437.10 mmol, 51.92 mL) and cesium carbonate (339.09 g, 1.04 mol) were sequentially added thereto, and the reaction mixture was stirred and reacted at room temperature for 2 hours. After the reaction was completed, the reaction mixture was added with water (1500 mL) and extracted with ethyl acetate (1000 mL×5). The organic phases were combined, washed with 10% saline (1000 mL×3), dried over anhydrous sodium sulfate, filtered, and the filtrate was concentrated under reduced pressure to remove the solvent. The resulting residue was separated by column chromatography (eluent: petroleum ether/ethyl acetate=1/0 to 20/1, v/v) to obtain intermediate BB-1-2. MS-ESI m/z: 187.2 $[M+H]^+$.

Step 2: Synthesis of Intermediate BB-1-3

Intermediate BB-1-2 (58 g, 311.48 mmol) was dissolved in dichloromethane (500 mL) at room temperature under nitrogen atmosphere, then the reaction mixture was cooled to 0° C., and diethylaminosulfur trifluoride (150.62 g, 934.43 mmol) was added thereto. The reaction mixture was slowly warmed to room temperature, and stirred and reacted at room temperature for 16 hours. After the reaction was completed, the reaction mixture was cooled to 0° C., slowly added dropwise with methanol (200 mL), then added with water (1000 mL), and extracted with ethyl acetate (1000 mL×3). The organic phases were combined, washed with saturated sodium bicarbonate solution (1000 mL) and saturated brine (1000 mL), dried over anhydrous sodium sulfate, filtered, and the filtrate was concentrated under reduced pressure to remove the solvent. The resulting residue was separated by column chromatography (eluent: petroleum ether/ethyl acetate=1/0 to 20/1, v/v) to obtain a crude product. The resulting crude product was added with petroleum ether (20 mL), stirred at room temperature for 2 hours, and filtered. The filter cake was rinsed with petroleum ether (10 mL), collected, and dried under vacuum to obtain intermediate BB-1-3. MS-ESI m/z: 209.1 $[M+H]^+$. $^1H$ NMR (400 MHz, $CDCl_3$) δ: 7.40-7.32 (m, 4H), 7.24-7.22 (m, 2H), 6.73 (t, J=55.2 Hz, 1H), 6.51 (t, J=1.0 Hz, 1H), 5.33 (s, 2H).

Step 3: Synthesis of Intermediate BB-1-4

Intermediate BB-1-3 (26.5 g, 127.28 mmol) was dissolved in methanol (300 mL) at room temperature, then Pd/C hydroxide (5 g, purity: 20%) and hydrochloric acid (2 M, 25 mL) were sequentially added thereto, and the reaction mixture was heated to 60° C. and stirred and reacted under hydrogen (50 psi) atmosphere for 30 hours. After the reaction was completed, the reaction mixture was cooled to room temperature, and filtered to remove insoluble material. The filter cake was rinsed with methanol (800 mL), and the filtrate was concentrated under reduced pressure to remove the solvent to obtain intermediate BB-1-4. $^1$H NMR (400 MHz, DMSO_d$_6$) δ: 11.41 (br s, 1H), 7.84 (d, J=2.0 Hz, 1H), 7.00 (t, J=54.8 Hz, 1H), 6.51 (J=1.2 Hz, 1H).

Step 4: Synthesis of Intermediate BB-1-5

Intermediate BB-1-4 (30 g, 254.06 mmol) was dissolved in concentrated sulfuric acid (300 mL, purity: 98%) at 0° C., and then concentrated nitric acid (68.950 g, 711.24 mmol, 49.25 mL, purity: 65 to 68%) was added dropwise thereto. The reaction mixture was stirred and reacted at 0° C. for 10 minutes, then heated to 115° C., and stirred and reacted for 16 hours. After the reaction was completed, the reaction mixture was cooled to room temperature, slowly poured into ice water (1000 mL), and extracted with ethyl acetate (500 mL×3). The organic phases were combined, washed with saturated sodium bicarbonate solution (500 mL) and saturated brine (500 mL), dried over anhydrous sodium sulfate, filtered, and the filtrate was concentrated under reduced pressure to remove the solvent to obtain intermediate BB-1-5. MS-ESI m/z: 164.1 [M+H]$^+$. $^1$H NMR (400 MHz, DMSO_d$_6$) δ: 14.39 (s, 1H), 9.00 (s, 1H), 7.31 (t, J=53.0 Hz, 1H).

Step 5: Synthesis of Intermediate BB-1-6

Methyl cis-4-hydroxycyclohexane carboxylate (35 g, 221.25 mmol) was dissolved in dichloromethane (350 mL) at room temperature under nitrogen atmosphere, and then triethylamine (22.39 g, 221.25 mmol, 30.79 mL) was added thereto. The reaction mixture was cooled to 0° C., and then methanesulfonyl chloride (31.99 g, 279.26 mmol, 21.61 mL) was slowly added dropwise thereto. After the dropwise addition was completed, the reaction mixture was stirred and reacted at 0° C. for 0.5 hours. After the reaction was completed, the reaction mixture was slowly added with water (300 mL) and extracted with dichloromethane (300 mL). The organic phase was washed with saturated brine (300 mL), dried over anhydrous sodium sulfate, filtered, and the filtrate was concentrated under reduced pressure to remove the solvent to obtain a crude product, which was directly used in the next step.

The resulting crude product and intermediate BB-1-5 (13.5 g, 82.78 mmol) were dissolved in N,N-dimethylformamide (300 mL) at room temperature, then potassium carbonate (24 g, 173.65 mmol) was added thereto, and the reaction mixture was heated to 80° C. and stirred and reacted for 16 hours. After the reaction was completed, the reaction mixture was cooled to room temperature, added with water (100 mL), and extracted with ethyl acetate (40 mL×2). The organic phases were combined, dried over anhydrous sodium sulfate, filtered, and the filtrate was concentrated under reduced pressure to remove the solvent. The resulting residue was separated by column chromatography (eluent: ethyl acetate/petroleum ether=1/3, v/v) to obtain intermediate BB-1-6. $^1$H NMR (400 MHz, CDCl$_3$) δ: 8.22 (s, 1H), 7.12 (t, J=53.6 Hz, 1H), 4.25-4.16 (m, 1H), 3.72 (s, 3H), 2.46-2.36 (m, 1H), 2.36-2.28 (m, 2H), 2.28-2.20 (m, 2H), 1.89-1.77 (m, 2H), 1.72-1.60 (m, 2H).

Step 6: Synthesis of Intermediate BB-1-7

To tetrahydrofuran (200 mL) was added wet Pd/C (1.5 g, purity: 10%) at room temperature, then added intermediate BB-1-6 (7.5 g, 24.73 mmol), and the reaction mixture was stirred and reacted at room temperature under hydrogen (15 psi) atmosphere for 15 hours. After the reaction was completed, the reaction mixture was filtered to remove insoluble material. The filter cake was rinsed with dichloromethane (50 mL×2), and the filtrate was concentrated under reduced pressure to remove the solvent. The resulting residue was separated by column chromatography (eluent: ethyl acetate/petroleum ether=1/2, v/v) to obtain intermediate BB-1-7. MS-ESI m/z: 274.1 [M+H]$^+$.

Step 7: Synthesis of Intermediate BB-1

Intermediate BB-1-7 (4 g, 14.64 mmol) was dissolved in a mixed solvent of tetrahydrofuran (40 mL) and methanol (5 mL) at room temperature under nitrogen atmosphere, and then a solution of lithium borohydride in tetrahydrofuran (2 M, 14.64 mL) was slowly added dropwise thereto. After the dropwise addition was completed, the reaction mixture was heated to 60° C. and stirred and reacted for 1 hour. After the reaction was completed, the reaction mixture was cooled to room temperature, slowly added with water (20 mL), and extracted with ethyl acetate (100 mL×5). The organic phases were combined, dried over anhydrous sodium sulfate, filtered, and the filtrate was concentrated under reduced pressure to remove the solvent to obtain intermediate BB-1. $^1$H NMR (400 MHz, CDCl$_3$) δ: 7.03 (s, 1H), 6.69 (t, J=54.8 Hz, 1H), 3.95 (tt, J=4.0 Hz, 12.0 Hz, 1H), 3.51 (d, J=6.4 Hz, 2H), 2.21-2.13 (m, 2H), 2.01-1.93 (m, 2H), 1.77-1.64 (m, 2H), 1.63-1.51 (m, 2H), 1.21-1.09 (m, 2H).

Reference Example 2

BB-2

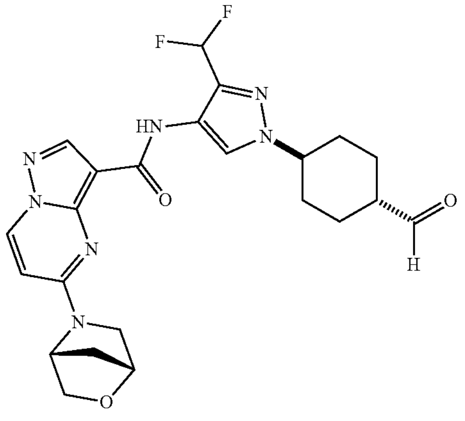

Synthetic Route

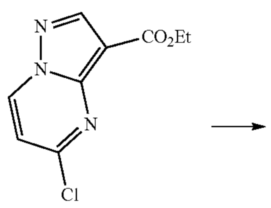

BB-2-1

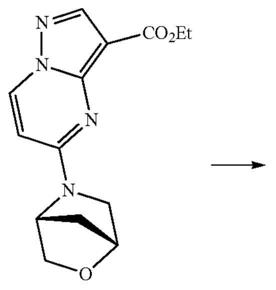

BB-2-2

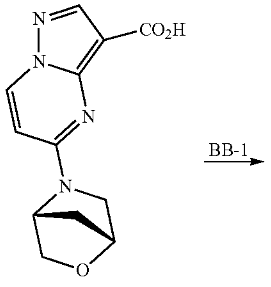

BB-2-3

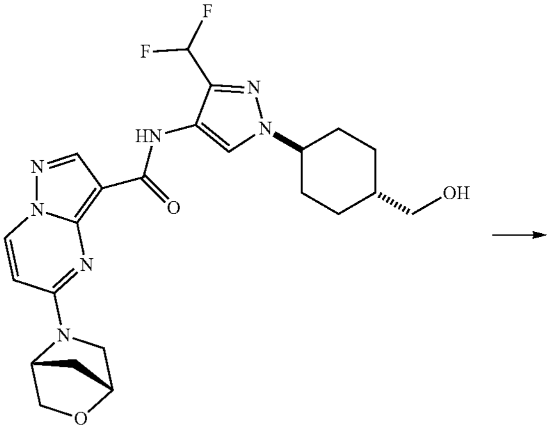

BB-2-4

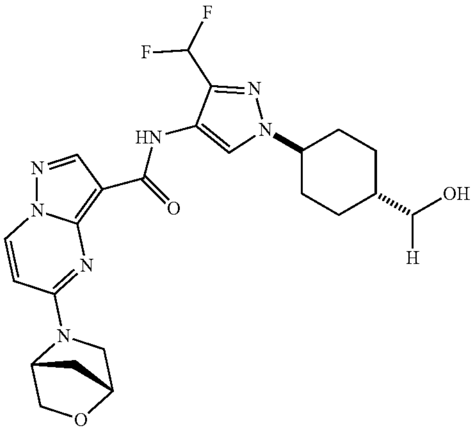

BB-2

Step 1: Synthesis of Intermediate BB-2-2

Intermediate BB-2-1 (5.5 g, 24.38 mmol) and (1R,4R)-2-oxa-5-azabicyclo[2.2.1]heptane hydrochloride (4.96 g, 36.56 mmol) were dissolved in acetonitrile (60 mL) at room temperature, then N,N-diisopropylethylamine (9.45 g, 73.13 mmol, 12.74 mL) was added thereto, and the reaction mixture was heated to 60° C. and stirred and reacted for 3 hours. After the reaction was completed, the reaction mixture was cooled to room temperature, directly concentrated under reduced pressure to remove the solvent, and the resulting residue was separated by column chromatography (eluent: first dichloromethane, then ethyl acetate) to obtain intermediate BB-2-2. MS-ESI m/z: 289.2 $[M+H]^+$.

Step 2: Synthesis of Intermediate BB-2-3

Intermediate BB-2-2 (7 g, 24.28 mmol) and lithium hydroxide monohydrate (5.09 g, 121.40 mmol) were dissolved in a mixed solvent of methanol (70 mL) and water (14 mL) at room temperature, and the reaction mixture was heated to 60° C. and stirred and reacted for 16 hours. After the reaction was completed, the reaction mixture was cooled to room temperature, and directly concentrated under reduced pressure to remove the solvent. The resulting residue was added with water (150 mL), then added with 1 M dilute hydrochloric acid to adjust the pH to 5 to 6, and extracted with ethyl acetate (150 mL×6). The organic phases were combined, dried over anhydrous sodium sulfate, filtered, and the filtrate was concentrated under reduced pressure to remove the solvent to obtain intermediate BB-2-3. $^1$H NMR (400 MHz, DMSO_$d_6$) δ: 11.62 (s, 1H), 8.70 (d, J=7.6 Hz, 1H), 8.16 (s, 1H), 6.85-6.30 (m, 1H), 5.09 (d, J=75.2 Hz, 1H), 4.73 (s, 1H), 3.76 (d, J=42.4 Hz, 2H), 3.60-3.40 (m, 2H), 1.99-1.90 (m, 2H).

Step 3: Synthesis of Intermediate BB-2-4

Intermediate BB-2-3 (3.5 g, 11.80 mmol) was dissolved in acetonitrile (40 mL) at room temperature, then N-methylimidazole (3.39 g, 41.29 mmol) and tetramethylchlorourea hexafluorophosphate (3.97 g, 14.16 mmol) were sequentially added thereto, and the reaction mixture was stirred and reacted at room temperature for 1 hour. Intermediate BB-1 (3.47 g, 14.16 mmol) was then added thereto, and the reaction mixture was stirred and reacted for another 16 hours. After the reaction was completed, the reaction mixture was filtered. The filter cake was rinsed with acetonitrile (3 mL), collected, and dried under vacuum to obtain intermediate BB-2-4. MS-ESI m/z: 488.3 $[M+H]^+$. $^1$H NMR (400 MHz, $CDCl_3$) δ: 9.61 (s, 1H), 8.43 (d, J=5.2 Hz, 2H), 8.32 (d, J=7.6 Hz, 1H), 6.78 (t, J=54.4 Hz, 1H), 6.13 (d, J=8.0 Hz, 1H), 5.46 (s, 1H), 4.80 (s, 1H), 4.07 (td, J=4.0 Hz, 12.0 Hz, 1H), 4.02-3.95 (m, 2H), 3.61-3.47 (m, 4H), 2.28-2.20 (m, 2H), 2.13-2.08 (m, 1H), 2.05-1.96 (m, 3H), 1.88-1.75 (m, 2H), 1.67-1.55 (m, 2H), 1.25-1.13 (m, 2H).

Step 4: Synthesis of Intermediate BB-2

Intermediate BB-2-4 (160 mg, 328.20 mol) was dissolved in dichloromethane (5 mL) at room temperature under nitrogen atmosphere, then Dess-Martin periodinane (167.05 mg, 393.85 mol) was added thereto, and the reaction mixture was stirred and reacted at room temperature for 3 hours. After the reaction was completed, the reaction mixture was filtered. The filter cake was rinsed with dichloromethane (2 mL), and the filtrate was dried with nitrogen flow to obtain intermediate BB-2, which was directly used in the next step. MS-ESI m/z: 486.3 $[M+H]^+$.

Reference Example 3

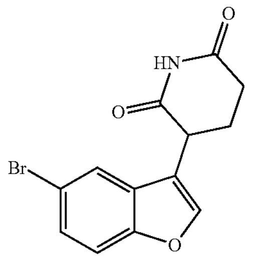

BB-3

Synthetic Route

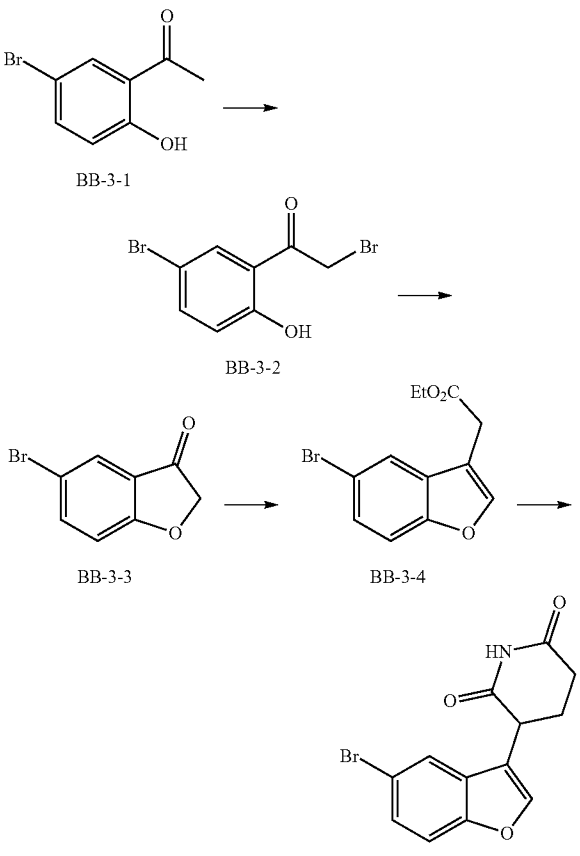

BB-3-1

BB-3-2

BB-3-3

BB-3-4

BB-3

Step 1: Synthesis of Intermediate BB-3-2

Compound BB-3-1 (200 g, 930.04 mmol) was dissolved in chloroform (1000 mL) and ethyl acetate (1000 mL) at room temperature under nitrogen atmosphere, then copper bromide (415.45 g, 1.86 mol) was added thereto, and the reaction mixture was heated to 90° C. and stirred and reacted for 16 hours. After the reaction was completed, the reaction mixture was cooled to room temperature, filtered, and the filter cake was rinsed with dichloromethane (1.5 L) to obtain a solution of intermediate BB-3-2, which was directly used in the next step.

Step 2: Synthesis of Intermediate BB-3-3

The resulting solution of intermediate BB-3-2 (3.5 L) was cooled to 0° C., and then triethylamine (141.17 g, 1.40 mol, 194.18 mL) was slowly added dropwise thereto. After the dropwise addition was completed, the reaction mixture was slowly warmed to room temperature and stirred and reacted for 2 hours. After the reaction was completed, the reaction mixture was added with water (2 L). The phases were separated, and the aqueous phase was extracted with dichloromethane (500 mL). The organic phases were combined, washed with saturated brine (1 L×2), dried over anhydrous sodium sulfate, filtered, and the filtrate was concentrated under reduced pressure to remove the solvent to obtain intermediate BB-3-3.

Step 3: Synthesis of Intermediate BB-3-4

Intermediate BB-3-3 (198.1 g, 929.93 mmol) was dissolved in toluene (1.5 L) at room temperature under nitrogen atmosphere, then (ethoxycarbonylmethylene)triphenylphosphorane (388.76 g, 1.12 mol) was added thereto, and the reaction mixture was heated to 130° C. and stirred and reacted for 36 hours. After the reaction was completed, the reaction mixture was cooled to room temperature and concentrated under reduced pressure to remove the solvent. The resulting residue was added with methyl tert-butyl ether (700 mL×3), stirred at room temperature for 20 minutes, and filtered. The filter cake was rinsed with methyl tert-butyl ether (100 mL), and the filtrate was collected. The filtrate was concentrated under reduced pressure to remove the solvent, and the resulting residue was separated by column chromatography (eluent: petroleum ether/ethyl acetate=1/0 to 70/1, v/v) to obtain intermediate BB-3-4. $^1H$ NMR (400 MHz, $CDCl_3$) δ: 7.72 (d, J=2.0 Hz, 1H), 7.64 (s, 1H), 7.41 (dd, J=2.0 Hz, 8.8 Hz, 1H), 7.36 (d, J=8.8 Hz, 1H), 4.21 (q, J=7.0 Hz, 2H), 3.66 (d, J=0.8 Hz, 2H), 1.30 (t, J=7.2 Hz, 3H).

Step 4: Synthesis of Intermediate BB-3

Intermediate BB-3-4 (5 g, 17.66 mmol) was dissolved in N,N-dimethylformamide (50 mL) at room temperature, then acrylamide (1.51 g, 21.19 mmol) and potassium tert-butoxide (2.97 g, 26.49 mmol) were sequentially added thereto, and the reaction mixture was stirred and reacted at room temperature for 1 hour. After the reaction was completed, the reaction mixture was poured into 1 M dilute hydrochloric acid (200 mL) and extracted with ethyl acetate (100 mL×2). The organic phases were combined, washed with 10% saline (150 mL×2), dried over anhydrous sodium sulfate, filtered, and the filtrate was concentrated under reduced pressure to remove the solvent. The resulting residue was added with ethyl acetate (30 mL), stirred for 10 minutes, filtered, and the filter cake was collected and dried under vacuum to obtain intermediate BB-3. MS-ESI m/z: 308.0 $[M+H]^+$, 310.1 $[M+H+2]^+$.

Reference Example 4

BB-4

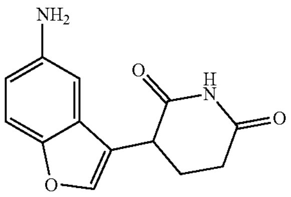

Synthetic Route

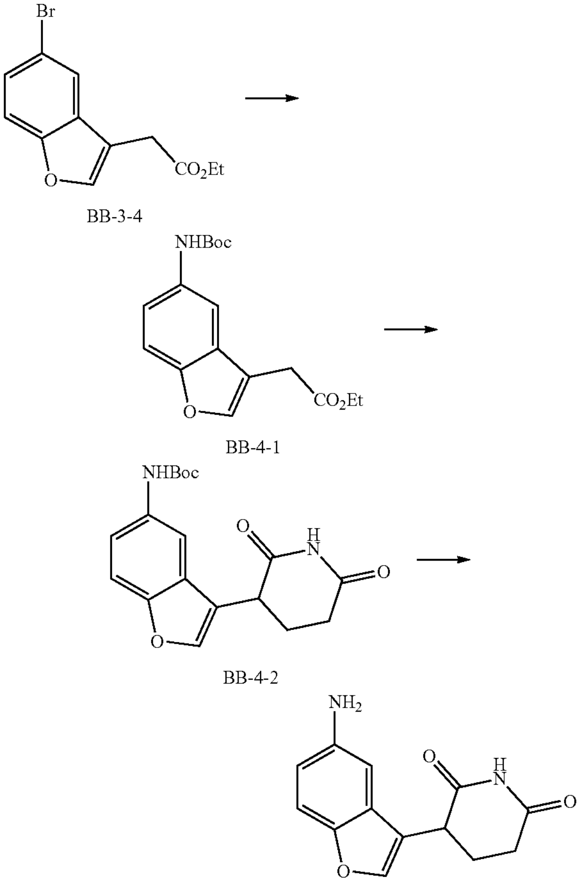

BB-3-4

BB-4-1

BB-4-2

BB-4

Step 1: Synthesis of Intermediate BB-4-1

To a mixed solvent of toluene (100 mL) and water (20 mL) were sequentially added intermediate BB-3-4 (5 g, 17.66 mmol), tert-butyl carbamate (2.48 g, 21.19 mmol), potassium phosphate (11.25 g, 52.98 mmol), tris(dibenzylideneacetone)dipalladium (323.44 mg, 353.21 mol), and 2-di-tert-butylphosphino-2',4',6'-triisopropylbiphenyl (299.98 mg, 706.42 mol) at room temperature under nitrogen atmosphere, and the reaction mixture was heated to 110° C. and stirred and reacted for 16 hours. After the reaction was completed, the reaction mixture was cooled to room temperature, added with water (100 mL), filtered, and the filter cake was rinsed with ethyl acetate (100 mL). The filtrates were combined, allowed for phase separation, and the organic phase was collected. The organic phase was dried over anhydrous sodium sulfate, filtered, and the filtrate was concentrated under reduced pressure to remove the solvent. The resulting residue was separated by column chromatography (eluent: ethyl acetate/petroleum ether=1/5, v/v) to obtain intermediate BB-4-1. $^1$H NMR (400 MHz, $CDCl_3$) δ: 7.71 (br s, 1H), 7.62 (s, 1H), 7.37 (d, J=8.8 Hz, 1H), 7.15 (dd, J=2.0 Hz, 8.8 Hz, 1H), 6.58 (s, 1H), 4.20 (q, J=7.2 Hz, 2H), 3.67 (q, J=1.2 Hz, 2H), 1.53 (s, 9H), 1.29 (t, J=7.2 Hz, 3H).

Step 2: Synthesis of Intermediate BB-4-2

Intermediate BB-4-1 (5.6 g, 17.54 mmol) and acrylamide (1.50 g, 21.05 mmol) were dissolved in N,N-dimethylformamide (100 mL) at room temperature, then potassium tert-butoxide (1.8 g, 16.04 mmol) was added thereto, and the reaction mixture was stirred and reacted at room temperature for 2 hours. Additional potassium tert-butoxide (0.6 g, 5.35 mmol) was then added thereto, and the reaction mixture was stirred and reacted at room temperature for another 0.5 hours. After the reaction was completed, the reaction mixture was poured into 1 M dilute hydrochloric acid (300 mL), stirred for 10 minutes, filtered, and the filter cake was rinsed with water (100 mL) and collected. The resulting filter cake was separated by column chromatography (eluent: ethyl acetate/petroleum ether=1/1, v/v) to obtain intermediate BB-4-2. $^1$H NMR (400 MHz, $CDCl_3$) δ: 8.32 (br s, 1H), 7.72 (br s, 1H), 7.53 (s, 1H), 7.39 (d, J=8.8 Hz, 1H), 7.12 (dd, J=2.0 Hz, 8.8 Hz, 1H), 6.71 (br s, 1H), 3.97 (t, J=7.6 Hz, 1H), 2.82-2.63 (m, 2H), 2.39-2.29 (m, 2H), 1.53 (s, 9H).

Step 3: Synthesis of Hydrochloride of Intermediate BB-4

Intermediate BB-4-2 (2.3 g, 6.68 mmol) was dissolved in ethyl acetate (20 mL) at room temperature, then a solution of hydrochloric acid in ethyl acetate (4 M, 40 mL) was added thereto, and the reaction mixture was stirred and reacted at room temperature for 16 hours. After the reaction was completed, the reaction mixture was filtered. The filter cake was rinsed with ethyl acetate (20 mL), collected, and dried under vacuum to obtain hydrochloride of intermediate BB-4. $^1$H NMR (400 MHz, $D_2O$) δ: 7.85 (s, 1H), 7.67 (d, J=8.8 Hz, 1H), 7.56 (d, J=1.6 Hz, 1H), 7.34 (dd, J=2.0 Hz, 8.8 Hz, 1H), 4.24 (dd, J=5.2 Hz, 12.4 Hz, 1H), 2.91-2.74 (m, 2H), 2.50-2.37 (m, 1H), 2.35-2.25 (m, 1H).

Reference Example 5

BB-5

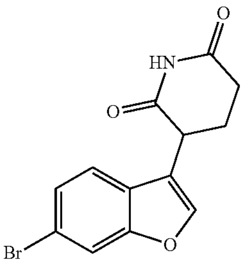

Synthetic Route

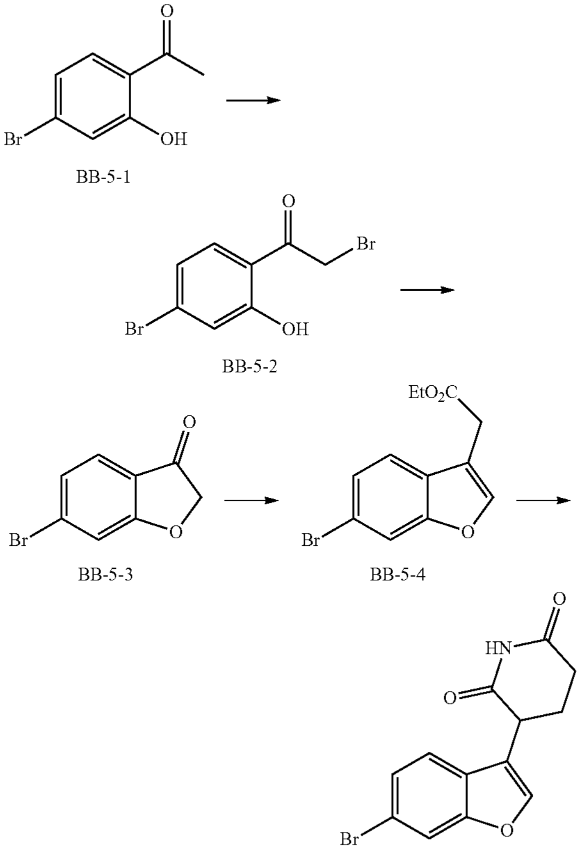

BB-5-1

BB-5-2

BB-5-3

BB-5-4

BB-5

Step 1: Synthesis of Intermediate BB-5-2

Compound BB-5-1 (200 g, 930.04 mmol) was dissolved in chloroform (1 L) and ethyl acetate (1 L) at room temperature under nitrogen atmosphere, then copper bromide (415.45 g, 1.86 mol) was added thereto, and the reaction mixture was heated to 90° C. and stirred and reacted for 12 hours. After the reaction was completed, the reaction mixture was cooled to room temperature, and filtered. The filter cake was rinsed with dichloromethane (300 mL×2), and the filtrate was collected to obtain a solution of intermediate BB-5-2, which was directly used in the next step.

Step 2: Synthesis of Intermediate BB-5-3

The resulting solution of intermediate BB-5-2 (273 g, 928.76 mmol) was cooled to 0° C., and then triethylamine (140.97 g, 1.39 mol, 193.91 mL) was slowly added dropwise thereto. After the dropwise addition was completed, the reaction mixture was slowly warmed to room temperature and stirred and reacted for 1 hour. After the reaction was completed, the reaction mixture was added with water (600 mL), extracted, and the phases were separated. The organic phase was washed with saturated brine (1 L), dried over anhydrous sodium sulfate, and filtered. The filtrate was concentrated under reduced pressure to remove half of the solvent, added with toluene (500 mL), and concentrated under reduced pressure to remove the residual low-boiling solvent to obtain a solution of intermediate BB-5-3 in toluene.

Step 3: Synthesis of Intermediate BB-5-4

To half of the solution of intermediate BB-5-3 in toluene was added toluene (2 L) at room temperature under nitrogen atmosphere, then added (ethoxycarbonylmethylene)triphenylphosphorane (161.90 g, 464.73 mmol), and the reaction mixture was heated to 130° C. and stirred and reacted for 20 hours. After the reaction was completed, the reaction mixture was cooled to room temperature, and 2 batches were combined for processing. The reaction mixture was concentrated under reduced pressure to remove the solvent. The resulting residue was added with methyl tert-butyl ether (800 mL), stirred at room temperature for 30 minutes, and filtered. The filter cake was rinsed with methyl tert-butyl ether (100 mL×2), and the filtrate was concentrated under reduced pressure to remove the solvent. The resulting residue was separated by column chromatography (eluent: petroleum ether/ethyl acetate=100/1 to 10/1, v/v) to obtain intermediate BB-5-4. $^1$H NMR (400 MHz, $CDCl_3$) δ: 7.94 (s, 1H), 7.88 (s, 1H), 7.56 (d, J=8.4 Hz, 1H), 7.44 (d, J=8.4 Hz, 1H), 4.11 (q, J=7.2 Hz, 2H), 3.79 (s, 2H), 1.19 (t, J=7.2 Hz, 3H).

Step 4: Synthesis of Intermediate BB-5

Intermediate BB-5-4 (5.00 g, 17.66 mmol) was dissolved in N,N-dimethylformamide (50 mL) at room temperature, then acrylamide (1.51 g, 21.19 mmol) and potassium tert-butoxide (2.97 g, 26.49 mmol) were sequentially added thereto, and the reaction mixture was stirred and reacted at room temperature for 2 hours. After the reaction was completed, the reaction mixture was poured into 1 M dilute hydrochloric acid (100 mL) and extracted with ethyl acetate (30 mL×2). The organic phases were combined, washed with 10% saline (100 mL×2), dried over anhydrous sodium sulfate, filtered, and the filtrate was concentrated under reduced pressure to remove the solvent. The resulting residue was separated by column chromatography (eluent: ethyl acetate/petroleum ether=1/1, v/v) to obtain intermediate BB-5. MS-ESI m/z: 308.0 $[M+H]^+$, 310.0 $[M+H+2]^+$. $^1$H NMR (400 MHz, DMSO_$d_6$) δ: 10.91 (s, 1H), 7.94 (s, 1H), 7.89 (d, J=1.6 Hz, 1H), 7.56 (d, J=8.4 Hz, 1H), 7.42 (dd, J=1.6 Hz, 8.0 Hz, 1H), 4.15 (dd, J=4.8 Hz, 12.0 Hz, 1H), 2.80-2.68 (m, 1H), 2.58 (dt, J=4.0 Hz, 17.2 Hz, 1H), 2.38-2.25 (m, 1H), 2.15-2.05 (m, 1H).

Reference Example 6

BB-6

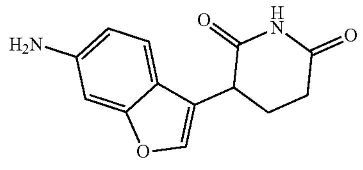

Synthetic Route

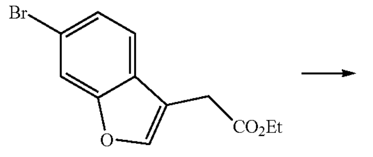

BB-5-4

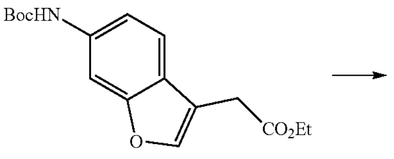

BB-6-1

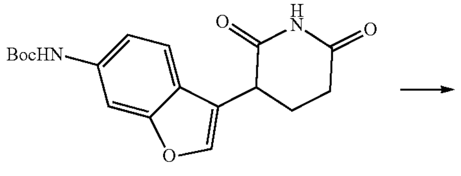

BB-6-2

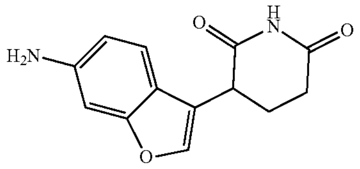

BB-6

Step 1: Synthesis of Intermediate BB-6-1

Intermediate BB-5-4 (10 g, 35.32 mmol), tert-butyl carbamate (4.97 g, 42.39 mmol), potassium phosphate (22.49 g, 105.96 mmol), tris(dibenzylideneacetone)dipalladium (646.88 mg, 706.42 mol), and 2-di-tert-butylphosphino-2',4',6'-triisopropylbiphenyl (599.95 mg, 1.41 mmol) were dissolved in toluene (100 mL) and water (20 mL) at room temperature under nitrogen atmosphere, and the reaction mixture was heated to 110° C. and stirred and reacted for 12 hours. After the reaction was completed, the reaction mixture was cooled to room temperature, added with water (100 mL), and extracted with ethyl acetate (70 mL×3). The organic phases were combined, washed with saturated brine (70 mL×2), dried over anhydrous sodium sulfate, filtered, and the filtrate was concentrated under reduced pressure to remove the solvent. The residue was added with n-heptane (70 mL), stirred at room temperature for 10 minutes, filtered, and the filter cake was collected. The filter cake was added with n-heptane (50 mL) again, stirred at room temperature for 10 minutes, and filtered. The filter cake was rinsed with n-heptane (10 mL×3), collected, and dried under vacuum to obtain intermediate BB-6-1. MS-ESI m/z: 264.2 $[M-55]^+$. $^1H$ NMR (400 MHz, $CDCl_3$) δ: 7.77 (s, 1H), 7.56 (s, 1H), 7.44 (d, J=8.4 Hz, 1H), 7.06 (dd, J=1.6 Hz, 8.4 Hz, 1H), 6.58 (s, 1H), 4.19 (q, J=7.0 Hz, 2H), 3.66 (s, 2H), 1.54 (s, 9H), 1.27 (t, J=7.2 Hz, 3H).

Step 2: Synthesis of Intermediate BB-6-2

Intermediate BB-6-1 (9.8 g, 30.69 mmol) and acrylamide (2.62 g, 36.83 mmol) were dissolved in N,N-dimethylformamide (100 mL) at room temperature, then potassium tert-butoxide (6.20 g, 55.24 mmol) was added thereto, and the reaction mixture was stirred and reacted at room temperature for 1 hour. After the reaction was completed, the reaction mixture was poured into 0.5 M hydrochloric acid (120 mL), added with water (300 mL), and extracted with ethyl acetate (150 mL×3). The organic phases were combined, washed with saturated brine (150 mL), dried over anhydrous sodium sulfate, filtered, and the filtrate was concentrated under reduced pressure to remove the solvent. The resulting residue was added with methyl tert-butyl ether (70 mL), stirred at room temperature for 0.5 hours, and filtered. The filter cake was rinsed with methyl tert-butyl ether (10 mL×3), collected, and dried under vacuum to obtain intermediate BB-6-2. $^1H$ NMR (400 MHz, DMSO_$d_6$) δ: 10.88 (s, 1H), 9.47 (s, 1H), 7.78 (s, 2H), 7.43 (d, J=8.8 Hz, 1H), 7.23 (dd, J=1.4 Hz, 8.6 Hz, 1H), 4.07 (dd, J=4.8 Hz, 12.0 Hz, 1H), 2.78-2.65 (m, 1H), 2.62-2.53 (m, 1H), 2.35-2.23 (m, 1H), 2.15-2.06 (m, 1H), 1.49 (s, 9H).

Step 3: Synthesis of Hydrochloride of Intermediate BB-6

Intermediate BB-6-2 (6.6 g, 19.17 mmol) was dissolved in dichloromethane (20 mL) at room temperature, then a solution of hydrochloric acid in ethyl acetate (4 M, 150 mL) was added thereto, and the reaction mixture was stirred and reacted at room temperature for 4 hours. After the reaction was completed, the reaction mixture was concentrated under reduced pressure to remove the solvent to obtain hydrochloride of intermediate BB-6. $^1H$ NMR (400 MHz, DMSO_$d_6$) δ: 10.92 (s, 1H), 10.06 (s, 2H), 7.98 (s, 1H), 7.66 (d, J=8.4 Hz, 1H), 7.57 (d, J=1.6 Hz, 1H), 7.21 (dd, J=1.8 Hz, 8.2 Hz, 1H), 4.16 (dd, J=4.8 Hz, 12.0 Hz, 1H), 2.81-2.69 (m, 1H), 2.63-2.54 (m, 1H), 2.39-2.26 (m, 1H), 2.16-2.07 (m, 1H).

Reference Example 7

BB-7

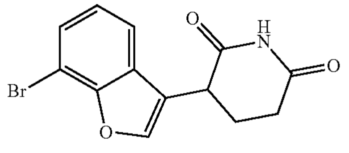

Synthetic Route

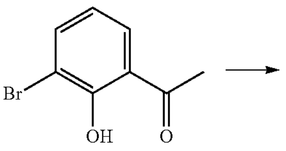

BB-7-1

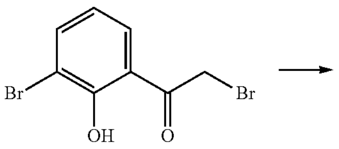

BB-7-2

-continued

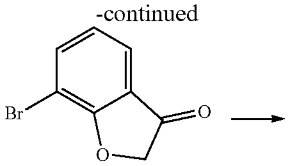

BB-7-3

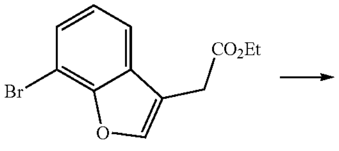

BB-7-4

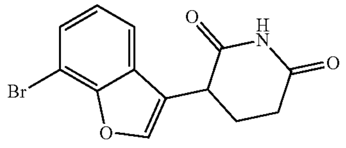

BB-7

Step 1: Synthesis of Intermediate BB-7-2

Intermediate BB-7-1 (11.39 g, 52.97 mmol) was dissolved in chloroform (100 mL) and ethyl acetate (100 mL) at room temperature under nitrogen atmosphere, then copper bromide (23.66 g, 105.93 mmol) was added thereto, and the reaction mixture was heated to 110° C. and stirred and reacted for 16 hours. After the reaction was completed, the reaction mixture was cooled to room temperature, filtered, and the filtrate was concentrated under reduced pressure to remove the solvent. The residue was then added with water (20 mL) and extracted with ethyl acetate (20 mL×3). The organic phases were combined, dried over anhydrous sodium sulfate, filtered, and the filtrate was concentrated under reduced pressure to remove the solvent. The resulting residue was separated by column chromatography (eluent: petroleum ether/ethyl acetate=1/0 to 100/1, v/v) to obtain intermediate BB-7-2. $^1$H NMR (400 MHz, $CDCl_3$) δ: 12.39 (s, 1H), 7.81 (dd, J=1.2 Hz, 8.0 Hz, 1H), 7.76 (dd, J=1.2 Hz, 8.0 Hz, 1H), 6.88 (t, J=8.0 Hz, 1H), 4.47 (s, 2H).

Step 2: Synthesis of Intermediate BB-7-3

Intermediate BB-7-2 (6.86 g, 18.44 mmol) was dissolved in dichloromethane (80 mL) at 0° C., then triethylamine (1.87 g, 18.44 mmol) was slowly added dropwise thereto, and the reaction mixture was slowly warmed to room temperature and stirred and reacted for 1 hour. After the reaction was completed, the reaction mixture was directly concentrated under reduced pressure to remove the solvent to obtain a crude product of intermediate BB-7-3, which was directly used in the next step.

Step 3: Synthesis of Intermediate BB-7-4

The crude product of intermediate BB-7-3 (3.93 g, 18.45 mmol) was dissolved in toluene (80 mL) at room temperature under nitrogen atmosphere, then (ethoxycarbonylmethylene)triphenylphosphorane (9.64 g, 27.67 mmol) was added thereto, and the reaction mixture was heated to 130° C. and stirred and reacted for 36 hours. After the reaction was completed, the reaction mixture was cooled to room temperature and concentrated under reduced pressure to remove the solvent. The residue was then added with water (100 mL) and extracted with ethyl acetate (50 mL×3). The organic phases were combined, washed with saturated brine (50 mL), dried over anhydrous sodium sulfate, and filtered. The filtrate was concentrated under reduced pressure to remove the solvent, and the resulting residue was separated by column chromatography (eluent: petroleum ether/ethyl acetate=1/0 to 100/1, v/v) to obtain intermediate BB-7-4. $^1$H NMR (400 MHz, $CDCl_3$) δ: 7.72 (s, 1H), 7.52 (dd, J=0.8 Hz, 7.6 Hz, 1H), 7.48 (dd, J=0.8 Hz, 7.6 Hz, 1H), 7.15 (t, J=7.6 Hz, 1H), 4.20 (q, J=7.2 Hz, 2H), 3.70 (d, J=0.8 Hz, 2H), 1.28 (t, J=7.2 Hz, 3H).

Step 4: Synthesis of Intermediate BB-7

Intermediate BB-7-4 (4.77 g, 16.85 mmol) was dissolved in N,N-dimethylformamide (30 mL) at 0° C. under nitrogen atmosphere, then acrylamide (1.20 g, 16.85 mmol) and potassium tert-butoxide (1.89 g, 16.85 mmol) were sequentially added thereto, and the reaction mixture was stirred and reacted at 0° C. for 1 hour. After the reaction was completed, the reaction mixture was pour into saturated ammonium chloride solution (50 mL) to precipitate a large amount of white solid, filtered, and the solid was collected. The solid was slurried with methanol (20 mL×2) at room temperature, filtered, and the filter cake was collected and dried under vacuum to obtain intermediate BB-7. $^1$H NMR (400 MHz, DMSO_$d_6$) δ: 10.92 (s, 1H), 8.04 (s, 1H), 7.62 (dd, J=0.8 Hz, 7.6 Hz, 1H), 7.56 (d, J=7.6 Hz, 1H), 7.21 (t, J=7.6 Hz, 1H), 4.17 (dd, J=4.8 Hz, 12.0 Hz, 1H), 2.79-2.70 (m, 1H), 2.63-2.55 (m, 1H), 2.40-2.27 (m, 1H), 2.16-2.08 (m, 1H).

Reference Example 8

BB-8

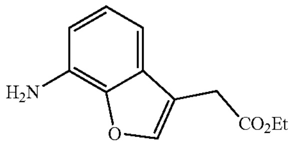

Synthetic Route

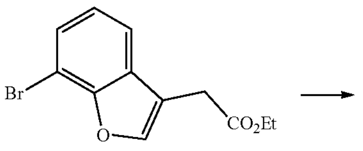

BB-7-4

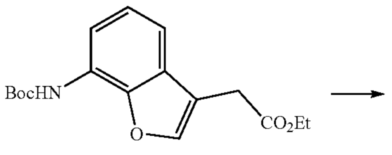

BB-8-1

-continued

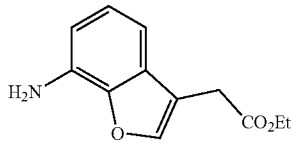

BB-8

Step 1: Synthesis of Intermediate BB-8-1

Intermediate BB-7-4 (2 g, 7.06 mmol) was dissolved in toluene (50 mL) and water (5 mL) at room temperature under nitrogen atmosphere, then tris(dibenzylideneacetone) dipalladium (647 mg, 706.42 mol), 2-di-tert-butylphosphino-2',4',6'-triisopropylbiphenyl (450 mg, 1.06 mmol), potassium phosphate (6 g, 28.26 mmol), and tert-butyl carbamate (1.66 g, 14.13 mmol) were sequentially added thereto, and the reaction mixture was heated to 100° C. and stirred and reacted for 16 hours. After the reaction was completed, the reaction mixture was cooled to room temperature, poured into water (20 mL), and extracted with ethyl acetate (10 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=10/0 to 10/1, v/v) to obtain intermediate BB-8-1. $^{1}H$ NMR (400 MHz, $CDCl_3$) δ: 7.93 (br s, 1H), 7.62 (s, 1H), 7.24-7.20 (m, 2H), 6.97 (s, 1H), 4.20 (q, J=6.8 Hz, 2H), 3.69 (d, J=0.8 Hz, 2H), 1.56 (s, 9H), 1.28 (t, J=7.2 Hz, 3H).

Step 2: Synthesis of Hydrochloride of Intermediate BB-8

Compound BB-8-1 (1.32 g, 4.13 mmol) was dissolved in ethyl acetate (3 mL) at room temperature, then a solution of hydrochloric acid in ethyl acetate (4 M, 15 mL) was added thereto, and the reaction mixture was stirred and reacted at room temperature for 2 hours. After the reaction was completed, the reaction mixture was directly concentrated under reduced pressure to remove the solvent to obtain hydrochloride of intermediate BB-8.

Reference Example 9

BB-9

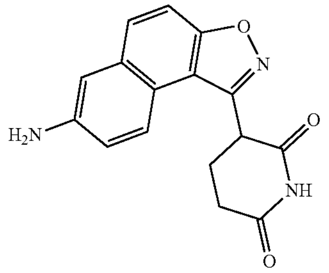

Synthetic Route

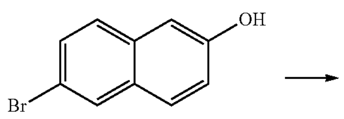

BB-9-1

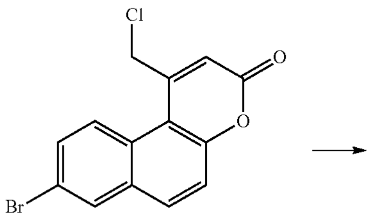

BB-9-2

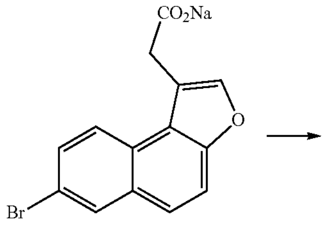

BB-9-3

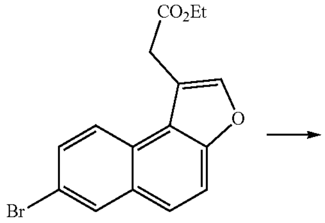

BB-9-4

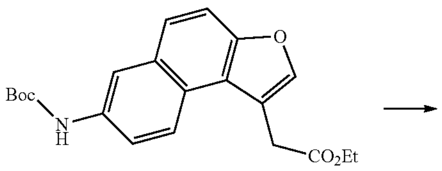

BB-9-5

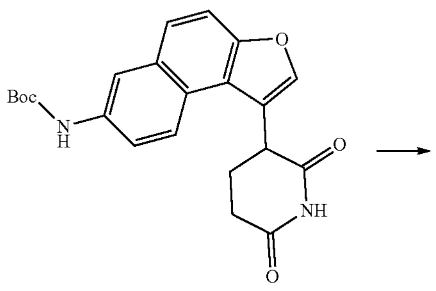

BB-9-6

-continued

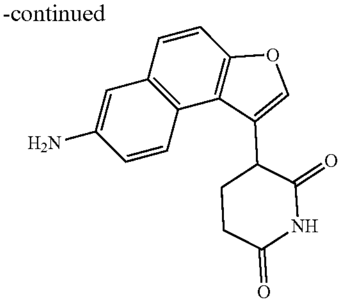

BB-9

Step 1: Synthesis of Intermediate BB-9-2

To a mixture of compound BB-9-1 (25 g, 112.07 mmol) and ethyl 4-chloroacetoacetate (18.45 g, 112.07 mmol) was slowly added dropwise concentrated sulfuric acid (103.08 g, 1.03 mol, 56.02 mL, purity: 98%) at 0° C., and the internal temperature was controlled at 0 to 5° C. After the dropwise addition was completed, the reaction mixture was warmed to room temperature and stirred and reacted for 12 hours. 4 batches were combined for processing. After the reaction was completed, the reaction mixture was slowly poured into ice water (3 L) with stirring, stirred at room temperature for 10 minutes, filtered, and the filter cake was collected and dried under vacuum to obtain intermediate BB-9-2. MS-ESI m/z: 323.0 $[M+H]^+$, 325.0 $[M+H+2]^+$.

Step 2: Synthesis of Intermediate BB-9-3

Sodium hydroxide (17.65 g, 441.36 mmol) was dissolved in water (700 mL) at room temperature, then intermediate BB-9-2 (54.40 g, 110.34 mmol, purity: 65.63%) was added thereto, and the reaction mixture was heated to 80° C. and stirred and reacted for 12 hours. 3 batches were combined for processing. After the reaction was completed, the reaction mixture was cooled to room temperature, filtered, and the filter cake was washed with water (500 mL), collected and dried under vacuum to obtain intermediate BB-9-3. $^1H$ NMR (400 MHz, DMSO_$d_6$) δ: 8.50 (d, J=9.2 Hz, 1H), 8.26 (d, J=2.4 Hz, 1H), 7.84 (s, 1H), 7.76 (d, J=1.6 Hz, 2H), 7.63 (dd, J=2.0 Hz, 8.8 Hz, 1H), 3.50 (s, 2H).

Step 3: Synthesis of Intermediate BB-9-4

Intermediate BB-9-3 (33.16 g, 101.37 mmol) was dissolved in ethanol (300 mL) at room temperature, then concentrated sulfuric acid (27.19 g, 271.68 mmol, 14.78 mL, purity: 98%) was slowly added dropwise thereto, and the reaction mixture was heated to 80° C. and stirred and reacted for 12 hours. 2 batches were combined for processing. After the reaction was completed, the reaction mixture was cooled to room temperature and concentrated under reduced pressure to remove the solvent. The resulting residue was added with water (600 mL) and extracted with ethyl acetate (200 mL×2). The organic phases were combined, sequentially washed with sodium hydroxide aqueous solution (2 M, 300 mL) and saturated brine (500 mL), dried over anhydrous sodium sulfate, filtered, and the filtrate was concentrated under reduced pressure to remove the solvent to obtain intermediate BB-9-4. $^1H$ NMR (400 MHz, $CDCl_3$) δ: 8.13-8.06 (m, 2H), 7.78 (s, 1H), 7.69-7.60 (m, 3H), 4.23 (q, J=7.2 Hz, 2H), 4.03 (s, 2H), 1.27 (t, J=7.2 Hz, 3H).

Step 4: Synthesis of Intermediate BB-9-5

Intermediate BB-9-4 (1 g, 3.00 mmol), tris(dibenzylideneacetone)dipalladium (275 mg, 300.14 mol), 2-di-tert-butylphosphino-2',4',6'-triisopropylbiphenyl (191.18 mg, 450.21 mmol), potassium phosphate (2.55 g, 12.01 mmol), and tert-butyl carbamate (527.41 mg, 4.50 mmol) were dissolved in a mixed solvent of toluene (50 mL) and water (5 mL) at room temperature under nitrogen atmosphere, and the reaction mixture was heated to 100° C. and stirred and reacted for 12 hours. After the reaction was completed, the reaction mixture was cooled to room temperature, poured into water (20 mL), and extracted with ethyl acetate (10 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=10/0 to 10/1, v/v) to obtain intermediate BB-9-5. MS-ESI m/z: 392.2 $[M+Na]^+$. $^1H$ NMR (400 MHz, $CDCl_3$) δ: 8.14 (d, J=9.2 Hz, 1H), 8.12 (br s, 1H), 7.74 (s, 1H), 7.67 (d, J=9.2 Hz, 1H), 7.62 (d, J=8.8 Hz, 1H), 7.45 (dd, J=2.2 Hz, 9.0 Hz, 1H), 6.64 (br s, 1H), 4.22 (q, J=7.0 Hz, 2H), 4.04 (s, 2H), 1.57 (s, 9H), 1.27 (t, J=7.2 Hz, 3H).

Step 5: Synthesis of Intermediate BB-9-6

Intermediate BB-9-5 (1.13 g, 2.74 mmol, purity: 89.57%) and acrylamide (234 mg, 3.29 mmol) were dissolved in N,N-dimethylformamide (10 mL) at 0° C. under nitrogen atmosphere, then potassium tert-butoxide (368.93 mg, 3.29 mmol) was added thereto, and the reaction mixture was stirred and reacted at 0° C. for 1 hour. After the reaction was completed, the reaction mixture was slowly poured into saturated ammonium chloride aqueous solution (30 mL) and extracted with ethyl acetate (15 mL×3). The organic phases were combined, washed with saturated brine (10 mL), dried over anhydrous sodium sulfate, filtered, and the filtrate was concentrated under reduced pressure to remove the solvent. The resulting residue was added with methanol (10 mL), stirred at room temperature for 0.5 hours, filtered, and the filter cake was collected and dried under vacuum to obtain intermediate BB-9-6. MS-ESI m/z: 417.0 $[M+Na-100]^+$. $^1H$ NMR (400 MHz, $CDCl_3$) δ: 8.13 (br s, 1H), 8.08 (br s, 1H), 7.90 (d, J=8.8 Hz, 1H), 7.71 (d, J=9.2 Hz, 1H), 7.67-7.62 (m, 2H), 7.48 (dd, J=2.4 Hz, 8.8 Hz, 1H), 6.67 (br s, 1H), 4.47 (dd, J=5.4 Hz, 8.6 Hz, 1H), 2.85-2.71 (m, 2H), 2.55-2.40 (m, 2H), 1.57 (s, 9H).

Step 6: Synthesis of Hydrochloride of Intermediate BB-9

Intermediate BB-9-6 (421 mg, 1.07 mmol) was dissolved in hydrochloric acid/dioxane solution (4 M, 20 mL) at room temperature, and the reaction mixture was stirred and reacted at room temperature for 12 hours. After the reaction was completed, the reaction mixture was cooled, then poured into saturated ammonium chloride solution (100 mL), and extracted with ethyl acetate (10 mL×3). The organic phases were combined, washed with saturated brine (10 mL), dried over anhydrous sodium sulfate, filtered, and subjected to rotary evaporation until dryness. The resulting residue was separated by column chromatography (eluent: petroleum ether/ethyl acetate=1/1, v/v) to obtain hydrochloride of intermediate BB-9. MS-ESI m/z: 294.9 $[M+H]^+$. $^1H$ NMR (400 MHz, DMSO_$d_6$) δ: 10.95 (br s, 1H), 8.23 (d, J=9.2 Hz, 1H), 8.04 (s, 1H), 7.88-7.81 (m, 3H), 7.48-7.42 (m, 1H), 4.66 (dd, J=4.4 Hz, 12.4 Hz, 1H), 2.92-2.81 (m, 1H), 2.69-2.60 (m, 1H), 2.46-2.38 (m, 1H), 2.31-2.23 (m, 1H).

Reference Example 10

BB-10

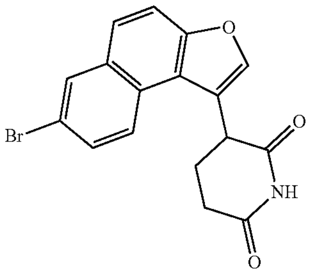

Synthetic Route

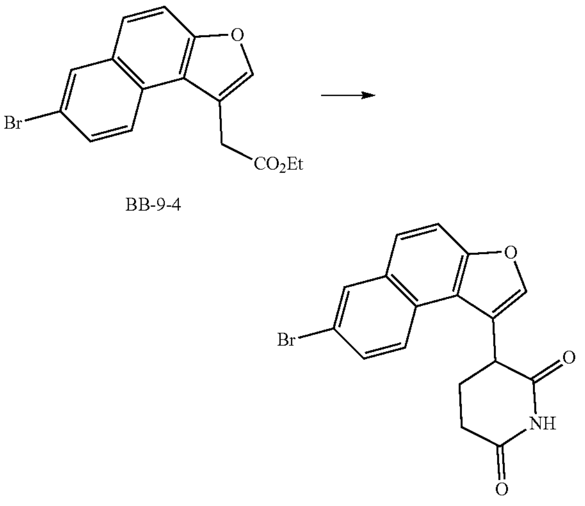

BB-9-4

BB-10

Synthesis of Intermediate BB-10

Intermediate BB-9-4 (1 g, 3.00 mmol) was dissolved in N,N-dimethylformamide (10 mL) at room temperature under nitrogen atmosphere, then acrylamide (256 mg, 3.60 mmol) and potassium tert-butoxide (404.15 mg, 3.60 mmol) were sequentially added thereto, and the reaction mixture was stirred and reacted at room temperature for 1 hour. After the reaction was completed, the reaction mixture was slowly poured into saturated ammonium chloride aqueous solution (100 mL), stirred at room temperature for 1 hour, filtered, and the filter cake was collected. The resulting filter cake was added with methanol (20 mL), stirred at room temperature for 0.5 hours, filtered, and the filter cake was collected and dried under vacuum to obtain intermediate BB-10. MS-ESI m/z: 357.7 $[M+H]^+$, 359.7 $[M+H^+2]^+$. $^1H$ NMR (400 MHz, $CDCl_3$) δ: 8.15 (d, J=2.0 Hz, 1H), 8.06 (br s, 1H), 7.87 (d, J=8.8 Hz, 1H), 7.72-7.65 (m, 4H), 4.47 (dd, J=5.2 Hz, 9.6 Hz, 1H), 2.89-2.74 (m, 2H), 2.58-2.41 (m, 2H).

Reference Example 11

BB-11

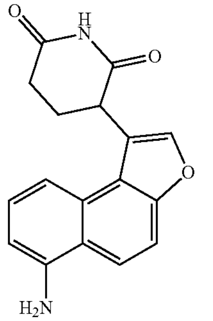

Synthetic Route

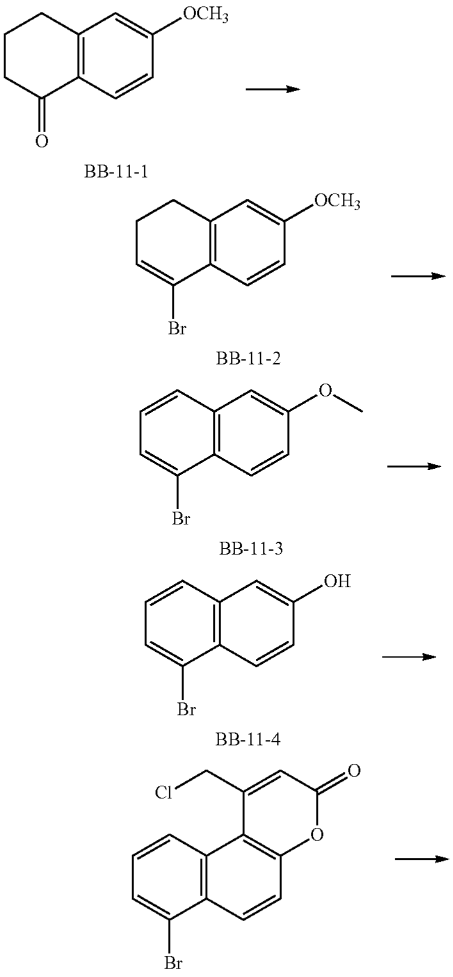

BB-11-1

BB-11-2

BB-11-3

BB-11-4

BB-11-5

-continued

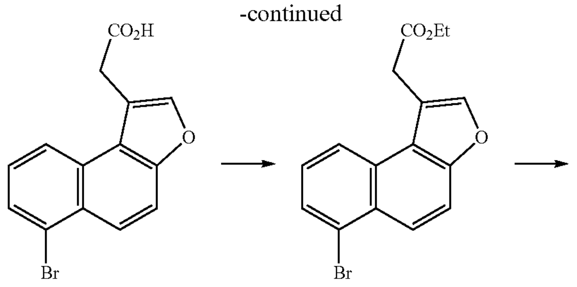

BB-11-6 BB-11-7

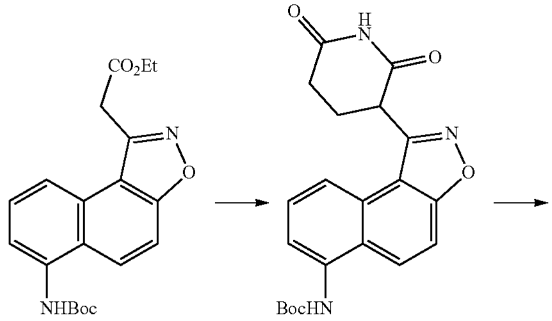

BB-11-8 BB-11-9

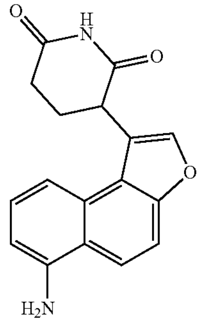

BB-11

Step 1: Synthesis of Intermediate BB-11-2

Triphenyl phosphite (149.14 g, 480.67 mmol) was dissolved in dichloromethane (1.3 L) at room temperature under nitrogen atmosphere, then the reaction mixture was cooled to −70° C., and liquid bromine (83.80 g, 524.37 mmol, 27.03 mL) was added dropwise thereto. After the dropwise addition was completed, triethylamine (57.48 g, 568.07 mmol, 79.07 mL) and a solution of compound BB-11-1 (77 g, 436.98 mmol) in dichloromethane (200 mL) were sequentially added dropwise thereto. After the dropwise addition was completed, the reaction mixture was slowly warmed to room temperature and stirred and reacted for 15 hours. After the reaction was completed, the reaction mixture was slowly poured into saturated sodium sulfite aqueous solution (1.5 L), stirred for 10 minutes, and extracted with dichloromethane (1 L). The organic phase was washed with saturated brine (1 L), dried over anhydrous sodium sulfate, filtered, and the filtrate was concentrated under reduced pressure to remove the solvent. The resulting residue was separated by column chromatography (eluent: petroleum ether) to obtain intermediate BB-11-2.

Step 2: Synthesis of Intermediate BB-11-3

Intermediate BB-11-2 (87 g, 363.85 mmol) was dissolved in toluene (1 L) at room temperature under nitrogen atmosphere, and the reaction mixture was cooled to 0° C. 2,3-Dichloro-5,6-dicyanobenzoquinone (90.86 g, 400.24 mmol) was slowly added thereto in batches, and the reaction mixture was slowly warmed to room temperature and stirred and reacted for 15 hours. After the reaction was completed, the reaction mixture was added dropwise with saturated sodium sulfite aqueous solution (2 L), stirred for 10 minutes, then added with 1 N sodium hydroxide aqueous solution (1 L), and extracted with ethyl acetate (500 mL×3). The organic phases were combined, washed with saturated brine (1 L), dried over anhydrous sodium sulfate, filtered, and the filtrate was concentrated under reduced pressure to remove the solvent. The resulting residue was added with petroleum ether (500 mL), stirred for 10 minutes, and filtered. The filter cake was rinsed with petroleum ether (50 mL×2), and the filtrate was collected and concentrated under reduced pressure to remove the solvent. The resulting residue was separated by column chromatography (eluent: petroleum ether) to obtain intermediate BB-11-3. $^1H$ NMR (400 MHz, $CDCl_3$) δ: 8.12 (d, J=9.2 Hz, 1H), 7.68 (d, J=8.4 Hz, 1H), 7.60 (d, J=7.6 Hz, 1H), 7.26-7.20 (m, 2H), 7.11 (d, J=2.4 Hz, 1H), 3.92 (s, 3H).

Step 3: Synthesis of Intermediate BB-11-4

Intermediate BB-11-3 (21.4 g, 90.26 mmol) was dissolved in dichloromethane (250 mL) at room temperature under nitrogen atmosphere, then the reaction mixture was cooled to 0° C., and boron tribromide (27.13 g, 108.31 mmol, 10.44 mL) was slowly added dropwise thereto. After the dropwise addition was completed, the reaction mixture was warmed to room temperature and stirred and reacted for 3 hours. After the reaction was completed, the reaction mixture was poured into ice water (500 mL) and extracted with dichloromethane (200 mL). The organic phase was washed with saturated brine (500 mL), dried over anhydrous sodium sulfate, filtered, and the filtrate was concentrated under reduced pressure to remove the solvent to obtain intermediate BB-11-4. $^1H$ NMR (400 MHz, $CDCl_3$) δ: 8.15 (d, J=98.8 Hz, 1H), 7.65-7.59 (m, 2H), 7.25 (t, J=7.8 Hz, 1H), 7.19 (dd, J=2.4 Hz, 9.2 Hz, 1H), 7.14 (d, J=2.4 Hz, 1H), 5.03 (s, 1H).

Step 4: Synthesis of Intermediate BB-11-5

Intermediate BB-11-4 (20 g, 89.66 mmol) was dissolved in methanesulfonic acid (200 mL) at room temperature, then ethyl 4-chloroacetoacetate (22.14 g, 134.49 mmol) was added dropwise thereto, and the reaction mixture was stirred and reacted at room temperature for 15 hours. After the reaction was completed, the reaction mixture was poured into ice water (1 L), stirred at room temperature for 10 minutes, and filtered. The filter cake was rinsed with water (200 mL×3), collected, and dried under vacuum to obtain intermediate BB-11-5. $^1H$ NMR (400 MHz, DMSO_$d_6$) δ: 8.58 (d, J=9.2 Hz, 1H), 8.49 (d, J=9.2 Hz, 1H), 8.02 (d, J=7.2 Hz, 1H), 7.74 (d, J=9.2 Hz, 1H), 7.65 (dd, J=7.6 Hz, 8.4 Hz, 1H), 6.93 (s, 1H), 5.41 (s, 2H).

Step 5: Synthesis of Intermediate BB-11-6

To sodium hydroxide aqueous solution (2 M, 300 mL) was added intermediate BB-11-5 (29 g, 89.63 mmol) at room temperature, and the reaction mixture was heated to 80° C. and stirred and reacted for 3 hours. After the reaction was completed, the reaction mixture was cooled to room temperature, added with water (200 mL), then added with 6 M hydrochloric acid to adjust the pH to 4, and extracted with ethyl acetate (300 mL×3). The organic phases were combined, washed with saturated brine (200 mL), dried over anhydrous sodium sulfate, filtered, and the filtrate was concentrated under reduced pressure to remove the solvent. The resulting residue was added with methyl tert-butyl ether (50 mL), stirred at room temperature for 10 minutes, and filtered. The filter cake was rinsed with methyl tert-butyl ether (10 mL×2), collected, and dried under vacuum to obtain intermediate BB-11-6. MS-ESI m/z: 305.0 $[M+H]^+$, 306.9 $[M+H+2]^+$. $^1H$ NMR (400 MHz, DMSO_$d_6$) δ: 12.68 (br s, 1H), 8.24 (d, J=8.4 Hz, 1H), 8.12 (t, J=4.6 Hz, 2H), 7.96 (d, J=9.2 Hz, 1H), 7.90 (d, J=7.6 Hz, 1H), 7.54 (t, J=7.8 Hz, 1H), 4.09 (s, 2H).

Step 6: Synthesis of Intermediate BB-11-7

Intermediate BB-11-6 (18 g, 58.99 mmol) was dissolved in ethanol (180 mL) at room temperature, then concentrated sulfuric acid (5.31 g, 53.09 mmol, 2.89 mL, purity: 98%) was added thereto, and the reaction mixture was heated to 80° C. and stirred and reacted for 15 hours.

After the reaction was completed, the reaction mixture was cooled to room temperature and concentrated under reduced pressure to remove the solvent. The residue was added with ethyl acetate (300 mL) and saturated sodium bicarbonate aqueous solution (500 mL), extracted, and the phases were separated. The organic phase was washed with saturated brine (300 mL), dried over anhydrous sodium sulfate, filtered, and the filtrate was concentrated under reduced pressure to remove the solvent. The residue was added with petroleum ether (50 mL), stirred at room temperature for 10 minutes, and filtered. The filter cake was rinsed with petroleum ether (20 mL×2), collected, and dried under vacuum to obtain intermediate BB-11-7. $^1H$ NMR (400 MHz, $CDCl_3$) δ: 8.22 (t, J=8.4 Hz, 2H), 7.84-7.78 (m, 2H), 7.75 (d, J=9.2 Hz, 1H), 7.41 (dd, J=7.6 Hz, 8.4 Hz, 1H), 4.23 (q, J=7.0 Hz, 2H), 4.06 (d, J=0.8 Hz, 2H), 1.26 (t, J=7.2 Hz, 3H).

Step 7: Synthesis of Intermediate BB-11-8

Intermediate BB-11-7 (5 g, 15.01 mmol), tris(dibenzylideneacetone)dipalladium (961.96 mg, 1.05 mmol), 2-di-tert-butylphosphino-2',4',6'-triisopropylbiphenyl (892.16 mg, 2.10 mmol), potassium phosphate (12.74 g, 60.03 mmol), and tert-butyl carbamate (2.64 g, 22.51 mmol) were dissolved in a mixed solvent of toluene (50 mL) and water (10 mL) at room temperature under nitrogen atmosphere, and the reaction mixture was heated to 100° C. and stirred and reacted for 15 hours. After the reaction was completed, the reaction mixture was cooled to room temperature, filtered, and the filter cake was rinsed with ethyl acetate (30 mL×3). The filtrate was washed with saturated brine (100 mL), dried over anhydrous sodium sulfate, filtered, and the filtrate was concentrated under reduced pressure to remove the solvent. The residue was added with methyl tert-butyl ether (50 mL), stirred at room temperature for 10 minutes, and filtered. The filter cake was rinsed with methyl tert-butyl ether (10 mL×2), collected, and dried under vacuum to obtain intermediate BB-11-8.

Step 8: Synthesis of Intermediate BB-11-9

Intermediate BB-11-8 (4.2 g, 11.37 mmol) and acrylamide (888.93 mg, 12.51 mmol) were dissolved in N,N-dimethylformamide (40 mL) at room temperature under nitrogen atmosphere, and the reaction mixture was cooled to 0° C. Potassium tert-butoxide (2.55 g, 22.74 mmol) dissolved in N,N-dimethylformamide (10 mL) was then added dropwise thereto, and the reaction mixture was warmed to room temperature and stirred and reacted for 2 hours. After the reaction was completed, the reaction mixture was poured into 0.2 M hydrochloric acid (200 mL) and extracted with ethyl acetate (100 mL×3). The organic phases were combined, washed with saturated brine (100 mL), dried over anhydrous sodium sulfate, filtered, and the filtrate was concentrated under reduced pressure to remove the solvent. The resulting residue was added with dichloromethane (20 mL), stirred at room temperature for 10 minutes, and filtered. The filter cake was rinsed with dichloromethane (10 mL), collected, and dried under vacuum to obtain intermediate BB-11-9. $^1H$ NMR (400 MHz, DMSO_$d_6$) δ: 10.94 (s, 1H), 9.28 (s, 1H), 8.05-7.92 (m, 3H), 7.79 (d, J=9.6 Hz, 1H), 7.58-7.47 (m, 2H), 4.68 (dd, J=4.4 Hz, 12.0 Hz, 1H), 2.95-2.81 (m, 1H), 2.70-2.56 (m, 1H), 2.47-2.34 (m, 1H), 2.33-2.22 (m, 1H), 1.49 (s, 9H).

Step 9: Synthesis of Hydrochloride of Intermediate BB-11

Intermediate BB-11-9 (1.3 g, 3.30 mmol) was dissolved in ethyl acetate (5 mL) at room temperature, then a solution of hydrochloric acid in ethyl acetate (4 M, 50 mL) was added thereto, and the reaction mixture was stirred and reacted at room temperature for 3 hours. After the reaction was completed, the reaction mixture was concentrated under reduced pressure to remove the solvent to obtain hydrochloride of intermediate BB-11.

Reference Example 12

BB-12

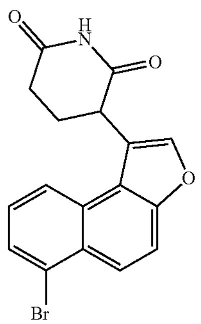

Synthetic Route

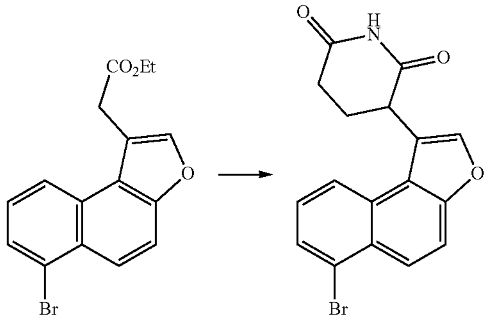

BB-11-7 BB-12

Synthesis of Intermediate BB-12

Acrylamide (234.67 mg, 3.30 mmol) and intermediate BB-11-7 (1 g, 3.00 mmol) were dissolved in N,N-dimethylformamide (15 mL) at room temperature under nitrogen atmosphere, then potassium tert-butoxide (370.47 mg, 3.30 mmol) was added thereto, and the reaction mixture was stirred and reacted at room temperature for 0.5 hours. After the reaction was completed, the reaction mixture was poured into 0.1 M hydrochloric acid (10 mL) and extracted with dichloromethane (5 mL×2). The organic phases were combined, washed with saturated brine (5 mL), dried over anhydrous sodium sulfate, filtered, and the filtrate was concentrated under reduced pressure to remove the solvent. The resulting residue was added with dichloromethane (5 mL), stirred at room temperature for 1 hour, filtered, and the filter cake was rinsed with dichloromethane (1 mL). The filter cake was collected and dried under vacuum to obtain intermediate BB-12. MS-ESI m/z: 358.1 $[M+H]^+$, 360.1 $[M+H+2]^+$.

Reference Example 13

BB-13

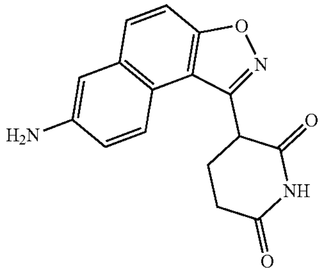

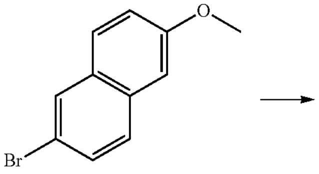

BB-13-1

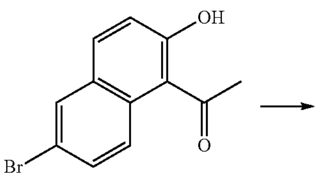

BB-13-2

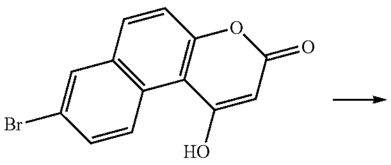

BB-13-3

-continued

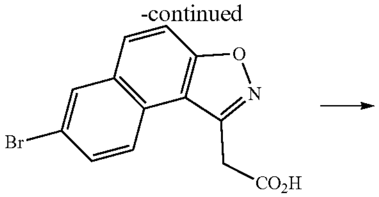

BB-13-4

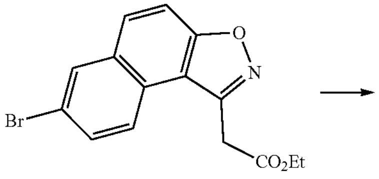

BB-13-5

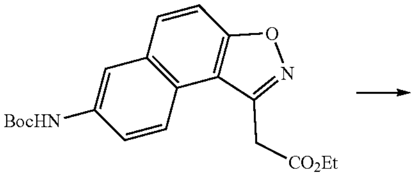

BB-13-6

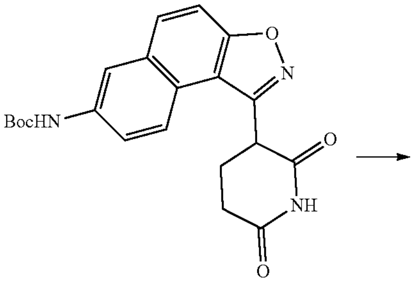

BB-13-7

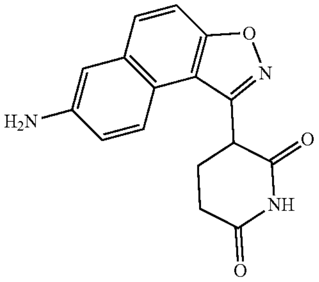

BB-13

Step 1: Synthesis of Intermediate BB-13-2

Compound BB-13-1 (150 g, 632.67 mmol) was dissolved in dichloromethane (3 L) at room temperature under nitrogen atmosphere, then acetyl chloride (49.66 g, 632.67 mmol, 45.15 mL) was added thereto, and the reaction mixture was cooled to 5 to 15° C. Aluminum trichloride (177.16 g, 1.33 mol) was added thereto in batches, and the reaction mixture was warmed to room temperature and stirred and reacted for 4 hours. Additional aluminum trichloride (29.53 g, 221.43 mmol) was added thereto, and the reaction mixture was stirred and reacted at room temperature for another 12 hours. After the reaction was completed, the reaction mixture was slowly poured into ice water (3 L), extracted, and the phases were separated. The aqueous phase was then extracted with dichloromethane (2 L×2). The organic phases were combined, washed with saturated brine (6 L×2), dried over anhydrous sodium sulfate, filtered, and the filtrate was concentrated under reduced pressure to remove the solvent to obtain intermediate BB-13-2. MS-ESI m/z: 265.1 $[M+H]^+$, 267.1 $[M+H+2]^+$.

Step 2: Synthesis of Intermediate BB-13-3

Intermediate BB-13-2 (200 g, 754.43 mmol) and dimethyl carbonate (271.83 g, 3.02 mol, 254.04 mL) were dissolved in tetrahydrofuran (2 L) at room temperature under nitrogen atmosphere, and the reaction mixture was cooled to 0° C. Potassium tert-butoxide (507.93 g, 4.53 mol) was slowly added thereto, and the reaction mixture was heated to 70° C. and stirred and reacted for 12 hours. After the reaction was completed, the reaction mixture was cooled to room temperature and concentrated under reduced pressure to remove the solvent. The residue was added with ice water (4 L), then added with 6 M hydrochloric acid to adjust the pH to 2 to 3 to precipitate a large amount of solid, and filtered. The filter cake was sequentially rinsed with water (1 L) and methyl tert-butyl ether (1 L), collected, and dried under vacuum to obtain intermediate BB-13-3. MS-ESI m/z: 291.0 $[M+H]^+$, 293.0 $[M+H+2]^+$. $^1H$ NMR (400 MHz, DMSO_$d_6$) δ: 9.18 (d, J=9.2 Hz, 1H), 8.30 (d, J=1.2 Hz, 1H), 8.16 (d, J=8.8 Hz, 1H), 7.79 (d, J=7.6 Hz, 1H), 7.56 (d, J=8.8 Hz, 1H), 5.83 (s, 1H).

Step 3: Synthesis of Intermediate BB-13-4

Intermediate BB-13-3 (200 g, 687.06 mmol), sodium acetate (309.99 g, 3.78 mol), and hydroxylamine hydrochloride (262.59 g, 3.78 mol) were dissolved in ethanol (2 L) at room temperature, and the reaction mixture was heated to 80° C. and stirred and reacted for 12 hours. After the reaction was completed, the reaction mixture was cooled to room temperature, poured into water (2 L), concentrated under reduced pressure to remove the solvent, added with 2 M hydrochloric acid to adjust the pH to 2 to 3, and extracted with ethyl acetate/tetrahydrofuran=1/1 (2 L×3, v/v). The organic phases were combined, dried over anhydrous sodium sulfate, filtered, and the filtrate was concentrated under reduced pressure to remove the solvent. The residue was added with methyl tert-butyl ether (600 mL), stirred at room temperature for 1 hour, filtered, and the filter cake was collected and dried under vacuum to obtain intermediate BB-13-4. MS-ESI m/z: 306.0 $[M+H]^+$, 308.0 $[M+H+2]^+$.

Step 4: Synthesis of Intermediate BB-13-5

Concentrated sulfuric acid (33.38 g, 333.49 mmol, 18.14 mL, purity: 98%) was dissolved in ethanol (1.3 L) at room temperature, then intermediate BB-13-4 (135 g, 373.32 mmol, purity: 84.65%) was added thereto, and the reaction mixture was heated to 75° C. and stirred and reacted for 16 hours. After the reaction was completed, the reaction mixture was cooled to room temperature and concentrated under reduced pressure to remove the solvent. The residue was added with ethanol (600 mL), stirred at room temperature for 5 minutes, and filtered. The filter cake was rinsed with ethanol (100 mL×2), collected, and dried under vacuum to obtain intermediate BB-13-5. MS-ESI m/z: 334.1 $[M+H]^+$, 336.0 $[M+H+2]^+$. $^1H$ NMR (400 MHz, DMSO_$d_6$) δ: 8.47 (d, J=1.6 Hz, 1H), 8.19 (d, J=9.2 Hz, 1H), 8.08 (d, J=8.8 Hz, 1H), 8.00 (d, J=9.2 Hz, 1H), 7.89 (dd, J=2.0 Hz, 8.8 Hz, 1H), 4.51 (s, 2H), 4.14 (q, J=7.2 Hz, 2H), 1.16 (t, J=7.2 Hz, 3H).

Step 5: Synthesis of Intermediate BB-13-6

To a mixed solvent of toluene (150 mL) and water (30 mL) were sequentially added intermediate BB-13-5 (15 g, 44.89 mmol), tris(dibenzylideneacetone)dipalladium (1.44 g, 1.57 mmol), 2-di-tert-butylphosphino-2',4',6'-triisopropylbiphenyl (1.33 g, 3.14 mmol), potassium phosphate (38.11 g, 179.55 mmol), and tert-butyl carbamate (7.89 g, 67.33 mmol) at room temperature under nitrogen atmosphere, and the reaction mixture was heated to 100° C. and stirred and reacted for 12 hours. After the reaction was completed, the reaction mixture was cooled to room temperature, added with water (100 mL) and ethyl acetate (150 mL), extracted, and the phases were separated. The aqueous phase was then extracted with ethyl acetate (200 mL×3). The organic phases were combined, washed with saturated brine (200 mL×3), dried over anhydrous sodium sulfate, filtered, and the filtrate was concentrated under reduced pressure to remove the solvent. The resulting residue was separated by column chromatography (eluent: petroleum ether/ethyl acetate=20/1 to 1/1, v/v) to obtain intermediate BB-13-6. MS-ESI m/z: 371.2 $[M+H]^+$. $^1H$ NMR (400 MHz, $CDCl_3$) δ: 8.20 (br s, 1H), 8.03 (d, J=8.8 Hz, 1H), 7.90 (d, J=9.2 Hz, 1H), 7.67 (d, J=9.2 Hz, 1H), 7.53 (dd, J=2.0 Hz, 8.8 Hz, 1H), 6.75 (s, 1H), 4.31 (s, 2H), 4.21 (q, J=7.2 Hz, 2H), 1.57 (s, 9H), 1.20 (t, J=7.2 Hz, 3H).

Step 6: Synthesis of Intermediate BB-13-7

Intermediate BB-13-6 (7.3 g, 19.71 mmol) and acrylamide (1.54 g, 21.68 mmol) were dissolved in tetrahydrofuran (70 mL) at room temperature under nitrogen atmosphere, and the reaction mixture was cooled to 0° C. Potassium tert-butoxide (2.43 g, 21.68 mmol) was added thereto, and the reaction mixture was warmed to room temperature and stirred and reacted for 1 hour. After the reaction was completed, the reaction mixture was poured into 0.1 M hydrochloric acid (30 mL) and extracted with ethyl acetate (80 mL×3). The organic phases were combined, washed with saturated brine (50 mL×2), dried over anhydrous sodium sulfate, filtered, and the filtrate was concentrated under reduced pressure to remove the solvent. The resulting residue was added with dichloromethane (5 mL), stirred at room temperature for 5 minutes, and filtered. The filter cake was rinsed with dichloromethane (3 mL), collected, and dried under vacuum to obtain intermediate BB-13-7. MS-ESI m/z: 396.2 $[M+H]^+$. $^1H$ NMR (400 MHz, DMSO_$d_6$) δ: 11.12 (s, 1H), 9.66 (s, 1H), 8.36 (s, 1H), 8.13 (d, J=8.8 Hz, 1H), 8.07 (d, J=8.8 Hz, 1H), 7.85 (d, J=9.2 Hz, 1H), 7.68 (dd, J=2.0 Hz, 8.8 Hz, 1H), 5.00 (dd, J=4.8 Hz, 11.6 Hz, 1H), 2.89-2.76 (m, 1H), 2.68-2.60 (m, 1H), 2.59-2.53 (m, 1H), 2.42-2.30 (m, 1H), 1.52 (s, 9H).

Step 7: Synthesis of Hydrochloride of Intermediate BB-13

Intermediate BB-13-7 (1 g, 2.53 mmol) was dissolved in ethyl acetate (5 mL) at room temperature, then a solution of hydrochloric acid in ethyl acetate (4 M, 20 mL) was added thereto, and the reaction mixture was stirred and reacted at room temperature for 1 hour. After the reaction was completed, the reaction mixture was filtered. The filter cake was rinsed with ethyl acetate (3 mL×3), collected, and dried under vacuum to obtain hydrochloride of intermediate BB-13. MS-ESI m/z: 295.9 $[M+H]^+$.

Reference Example 14

BB-14

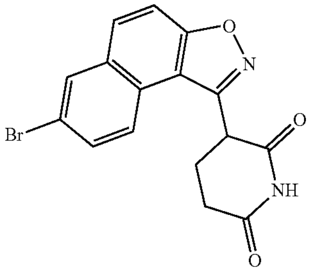

Synthetic Route

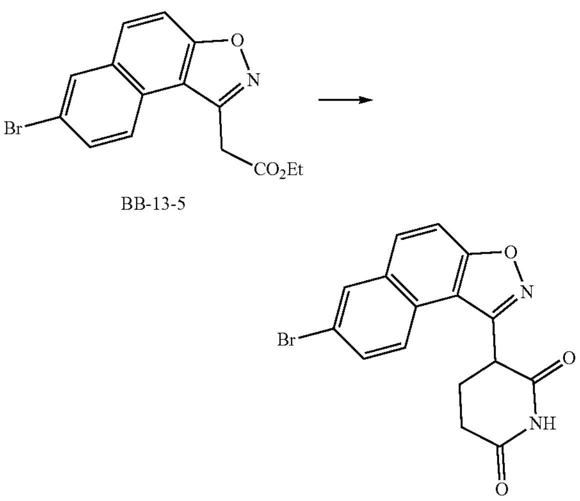

BB-13-5

BB-14

Synthesis of Intermediate BB-14

Intermediate BB-13-5 (3 g, 8.98 mmol) and acrylamide (701.92 mg, 9.88 mmol) were dissolved in tetrahydrofuran (70 mL) at room temperature under nitrogen atmosphere, and the reaction mixture was cooled to 0° C. Potassium tert-butoxide (1.21 g, 10.77 mmol) was added thereto in batches, and the reaction mixture was warmed to room temperature and stirred and reacted for 1 hour. After the reaction was completed, the reaction mixture was poured into 1 M hydrochloric acid (20 mL) and extracted with ethyl acetate (40 mL×3). The organic phases were combined, washed with saturated brine (50 mL), dried over anhydrous sodium sulfate, filtered, and the filtrate was concentrated under reduced pressure to remove the solvent. The resulting residue was added with methyl tert-butyl ether (20 mL), stirred at room temperature for 10 minutes, and filtered. The filter cake was rinsed with methyl tert-butyl ether (5 mL×2), collected, and dried under vacuum to obtain intermediate BB-14. MS-ESI m/z: 359.0 $[M+H]^+$, 361.0 $[M+H+2]^+$. $^1H$ NMR (400 MHz, DMSO_$d_6$) δ: 11.14 (s, 1H), 8.47 (d, J=2.0 Hz, 1H), 8.24-8.17 (m, 2H), 8.01 (d, J=9.2 Hz, 1H), 7.85 (dd, J=2.0 Hz, 8.8 Hz, 1H), 5.06 (dd, J=4.8 Hz, 11.6 Hz, 1H), 2.89-2.78 (m, 1H), 2.70-2.56 (m, 2H), 2.44-2.34 (m, 1H).

Reference Example 15

BB-15

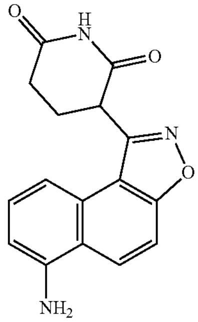

Synthetic Route

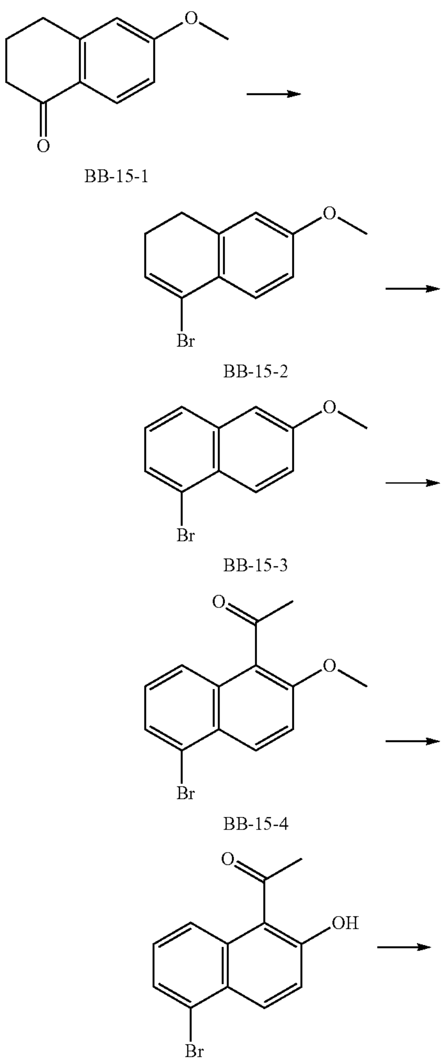

BB-15-1

BB-15-2

BB-15-3

BB-15-4

BB-15-5

-continued

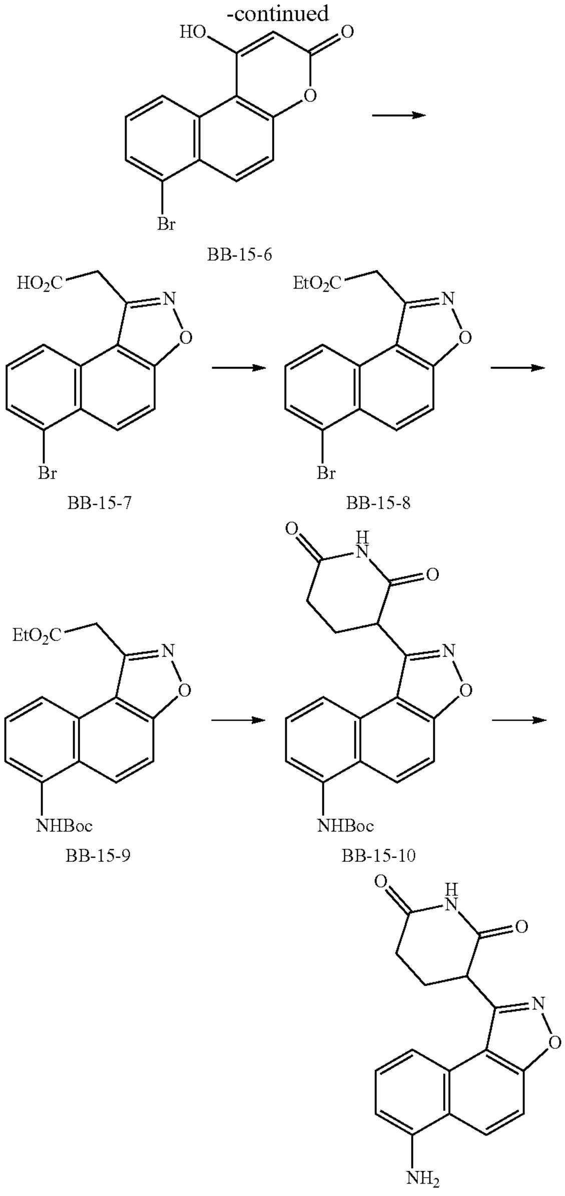

BB-15-6

BB-15-7

BB-15-8

BB-15-9

BB-15-10

BB-15

Step 1: Synthesis of Intermediate BB-15-2

Triphenyl phosphite (193.69 g, 624.25 mmol) was dissolved in dichloromethane (1 L) at room temperature under nitrogen atmosphere, then the reaction mixture was cooled to −70° C., and liquid bromine (108.83 g, 681.00 mmol, 35.11 mL) was added dropwise thereto. After the dropwise addition was completed, triethylamine (74.65 g, 737.75 mmol, 102.69 mL) and compound BB-15-1 (100 g, 567.50 mmol) dissolved in dichloromethane (500 mL) were sequentially added dropwise thereto. After the dropwise addition was completed, the reaction mixture was slowly warmed to room temperature and stirred and reacted for 15 hours. After the reaction was completed, the reaction mixture was poured into saturated sodium sulfite aqueous solution (700 mL), stirred for 10 minutes, and extracted with dichloromethane (800 mL). The organic phase was washed with saturated brine (800 mL), dried over anhydrous sodium sulfate, filtered, and the filtrate was concentrated under reduced pressure to remove the solvent. The resulting residue was separated by column chromatography (eluent: petroleum ether/ethyl acetate=20/1 to 7/1, v/v) to obtain intermediate BB-15-2. $^1$H NMR (400 MHz, DMSO_d$_6$) δ: 7.33 (d, J=8.0 Hz, 1H), 6.84-6.75 (m, 2H), 6.33 (t, J=4.8 Hz, 1H), 3.75 (s, 3H), 2.76 (t, J=8.0 Hz, 2H), 2.32-2.25 (m, 2H).

Step 2: Synthesis of Intermediate BB-15-3

Intermediate BB-15-2 (39.5 g, 165.20 mmol) was dissolved in toluene (500 mL) at room temperature under nitrogen atmosphere, and the reaction mixture was cooled to 0° C. 2,3-Dichloro-5,6-dicyanobenzoquinone (41.25 g, 181.72 mmol) was added thereto in batches, and the reaction mixture was slowly warmed to room temperature and stirred and reacted for 12 hours. After the reaction was completed, the reaction mixture was cooled to 0 to 10° C., added dropwise with saturated sodium sulfite aqueous solution (1 L) and 1 M sodium hydroxide aqueous solution (1 L), and filtered. The filter cake was rinsed with ethyl acetate (300 mL×3) and discarded, and the filtrate was extracted with ethyl acetate (500 mL×3). The organic phases were combined, washed with saturated brine (500 mL×2), dried over anhydrous sodium sulfate, filtered, and the filtrate was concentrated under reduced pressure to remove the solvent. The resulting residue was separated by column chromatography (eluent: petroleum ether) to obtain intermediate BB-15-3. MS-ESI m/z: 237.1 [M+H]$^+$, 239.1 [M+H+2]$^+$. $^1$H NMR (400 MHz, $CDCl_3$) δ: 8.05 (d, J=9.2 Hz, 1H), 7.60 (d, J=8.0 Hz, 1H), 7.53 (d, J=7.2 Hz, 1H), 7.22-7.13 (m, 2H), 7.04 (s, 1H), 3.85 (s, 3H).

Step 3: Synthesis of Intermediate BB-15-4

Acetic anhydride (21.53 g, 210.89 mmol, 19.75 mL) was placed in dichloromethane (400 mL) at room temperature under nitrogen atmosphere, and the reaction mixture was cooled to −60° C. Boron trifluoride diethyl etherate solution (63.68 g, 210.89 mmol, 55.38 mL, purity: 47%) was added dropwise thereto, and the reaction mixture was stirred at −60° C. for 10 minutes. A solution of intermediate BB-15-3 (25 g, 105.44 mmol) dissolved in dichloromethane (250 mL) was added dropwise thereto, and the reaction mixture was slowly warmed to room temperature and stirred and reacted for 12 hours. After the reaction was completed, the reaction mixture was added with ice water (200 mL) and extracted with dichloromethane (100 mL×3). The organic phases were combined, washed with saturated brine (100 mL), dried over anhydrous sodium sulfate, filtered, and the filtrate was concentrated under reduced pressure to remove the solvent. The resulting residue was separated by column chromatography (eluent: petroleum ether/ethyl acetate=100/1 to 20/1) to obtain intermediate BB-15-4. MS-ESI m/z: 279.0 [M+H]$^+$, 281.0 [M+H+2]$^+$. $^1$H NMR (400 MHz, $CDCl_3$) δ: 8.34 (d, J=9.2 Hz, 1H), 7.72 (d, J=8.4 Hz, 1H), 7.67 (dd, J=0.8 Hz, 7.2 Hz, 1H), 7.38 (d, J=9.2 Hz, 1H), 7.31 (dd, J=7.6 Hz, 8.8 Hz, 1H), 4.01 (s, 3H), 2.65 (s, 3H).

Step 4: Synthesis of Intermediate BB-15-5

Intermediate BB-15-4 (18.8 g, 67.35 mmol) was dissolved in dichloromethane (200 mL) at room temperature under nitrogen atmosphere, and the reaction mixture was cooled to 0° C. Boron tribromide (20.25 g, 80.82 mmol, 7.79 mL) was added dropwise thereto, and the reaction mixture was stirred and reacted at 0° C. for 1 hour. After the reaction was completed, the reaction mixture was poured into ice water (300 mL) and extracted with dichloromethane (100 mL×3). The organic phases were combined, washed with saturated brine (100 mL×3), dried over anhydrous sodium sulfate, filtered, and the filtrate was concentrated under reduced pressure to remove the solvent to obtain intermediate BB-15-5. $^1$H NMR (400 MHz, $CDCl_3$) δ: 13.05 (s, 1H), 8.41 (d, J=9.2 Hz, 1H), 8.04 (d, J=8.8 Hz, 1H), 7.70 (dd, J=0.8 Hz, 7.6 Hz, 1H), 7.40 (dd, J=7.6 Hz, 8.4 Hz, 1H), 7.25 (d, J=9.6 Hz, 1H), 2.85 (s, 3H).

Step 5: Synthesis of Intermediate BB-15-6

Intermediate BB-15-5 (13 g, 49.04 mmol) and dimethyl carbonate (17.67 g, 196.15 mmol, 16.51 mL) were dissolved in tetrahydrofuran (130 mL) at room temperature under nitrogen atmosphere, and the reaction mixture was cooled to 0 to 10° C. Potassium tert-butoxide (33.02 g, 294.23 mmol) was added thereto in batches, and the reaction mixture was heated to 70° C. and stirred and reacted for 12 hours. After the reaction was completed, the reaction mixture was cooled to room temperature and concentrated under reduced pressure to remove the solvent. The residue was added with ice water (200 mL) and extracted with methyl tert-butyl ether (70 mL×2). The aqueous phase was added with 6 M hydrochloric acid to adjust the pH to 2 to precipitate a large amount of solid, and filtered. The filter cake was washed with water (30 mL×2), collected, and dried under vacuum to obtain intermediate BB-15-6. MS-ESI m/z: 291.0 $[M+H]^+$, 293.0 $[M+H+2]^+$. $^1$H NMR (400 MHz, DMSO_$d_6$) δ: 13.28 (br s, 1H), 9.38 (t, J=7.2 Hz, 1H), 8.43 (dd, J=6.8 Hz, 9.2 Hz, 1H), 7.96 (t, J=7.2 Hz, 1H), 7.71-7.65 (m, 1H), 7.63-7.56 (m, 1H), 5.92-5.87 (m, 1H).

Step 6: Synthesis of Intermediate BB-15-7

Intermediate BB-15-6 (22 g, 75.58 mmol), sodium acetate (43.40 g, 529.03 mmol), and hydroxylamine hydrochloride (36.76 g, 529.03 mmol) were dissolved in ethanol (400 mL) at room temperature, and the reaction mixture was heated to 80° C. and stirred and reacted for 12 hours. After the reaction was completed, the reaction mixture was cooled to room temperature and concentrated under reduced pressure to remove the solvent. The residue was added with water (100 mL) and methyl tert-butyl ether (50 mL), stirred at room temperature for 0.5 hours, and filtered. The filter cake was rinsed with methyl tert-butyl ether (20 mL×3), collected, and dried under vacuum to obtain intermediate BB-15-7. MS-ESI m/z: 306.0 $[M+H]^+$, 308.0 $[M+H+2]^+$. $^1$H NMR (400 MHz, DMSO_$d_6$) δ: 8.40 (d, J=9.2 Hz, 1H), 8.27 (d, J=8.4 Hz, 1H), 8.05 (d, J=9.2 Hz, 1H), 7.96 (d, J=7.6 Hz, 1H), 7.62 (t, J=8.0 Hz, 1H), 4.25 (s, 2H).

Step 7: Synthesis of Intermediate BB-15-8

Intermediate BB-15-7 (15 g, 49.00 mmol) was dissolved in ethanol (300 mL) at room temperature, then concentrated sulfuric acid (1.29 g, 12.87 mmol, 0.7 mL, purity: 98%) was added thereto, and the reaction mixture was heated to 80° C. and stirred and reacted for 12 hours. The reaction mixture was cooled to room temperature, added with concentrated sulfuric acid (4 mL, purity: 98%), heated to 80° C., and stirred and reacted for 3 hours. After the reaction was completed, the reaction mixture was cooled to room temperature and concentrated under reduced pressure to remove the solvent. The residue was added with saturated sodium bicarbonate solution (100 mL) at 0 to 10° C. and extracted with ethyl acetate (70 mL×3). The organic phases were combined, washed with saturated brine (70 mL×2), dried over anhydrous sodium sulfate, filtered, and the filtrate was concentrated under reduced pressure to remove the solvent to obtain intermediate BB-15-8. MS-ESI m/z: 334.0 $[M+H]^+$, 336.0 $[M+H+2]^+$. $^1$H NMR (400 MHz, $CDCl_3$) δ: 8.50 (d, J=9.6 Hz, 1H), 8.10 (d, J=8.4 Hz, 1H), 7.88 (dd, J=0.8 Hz, 7.6 Hz, 1H), 7.81 (d, J=9.2 Hz, 1H), 7.52 (t, J=8.0 Hz, 1H), 4.34 (s, 2H), 4.22 (q, J=7.2 Hz, 2H), 1.21 (t, J=7.2 Hz, 3H).

Step 8: Synthesis of Intermediate BB-15-9

To a mixed solvent of toluene (90 mL) and water (30 mL) were sequentially added intermediate BB-15-8 (9.5 g, 28.43 mmol), tris(dibenzylideneacetone)dipalladium (1.30 g, 1.42 mmol), 2-di-tert-butylphosphino-2',4',6'-triisopropylbiphenyl (1.21 g, 2.84 mmol), potassium phosphate (24.14 g, 113.72 mmol), and tert-butyl carbamate (3.66 g, 31.27 mmol) at room temperature under nitrogen atmosphere, and the reaction mixture was heated to 100° C. and stirred and reacted for 12 hours. After the reaction was completed, the reaction mixture was cooled to room temperature, added with water (200 mL), and extracted with ethyl acetate (150 mL×3). The organic phases were combined, washed with saturated brine (200 mL×2), dried over anhydrous sodium sulfate, filtered, and the filtrate was concentrated under reduced pressure to remove the solvent. The resulting residue was separated by column chromatography (eluent: petroleum ether/ethyl acetate=6/1 to 2/1, v/v) to obtain intermediate BB-15-9. MS-ESI m/z: 371.2 $[M+H]^+$. $^1$H NMR (400 MHz, DMSO_$d_6$) δ: 8.48 (s, 1H), 8.28 (d, J=9.2 Hz, 1H), 7.95-7.87 (m, 2H), 7.75-7.60 (m, 2H), 4.50 (s, 2H), 4.14 (q, J=7.2 Hz, 2H), 1.50 (s, 9H), 1.16 (t, J=7.2 Hz, 3H).

Step 9: Synthesis of Intermediate BB-15-10

Intermediate BB-15-9 (2.5 g, 6.75 mmol) was dissolved in tetrahydrofuran (35 mL) at room temperature under nitrogen atmosphere, then acrylamide (575.69 mg, 8.10 mmol) and potassium tert-butoxide (1.14 g, 10.12 mmol) were added thereto, and the reaction mixture was stirred and reacted at room temperature for 1 hour. After the reaction was completed, the reaction mixture was poured into 1 M hydrochloric acid (30 mL) and extracted with ethyl acetate (45 mL×3). The organic phases were combined, washed with saturated brine (40 mL×2), dried over anhydrous sodium sulfate, filtered, and the filtrate was concentrated under reduced pressure to remove the solvent. The resulting residue was separated by column chromatography (eluent: petroleum ether/ethyl acetate=5/1 to 1/1, v/v) to obtain intermediate BB-15-10. MS-ESI m/z: 396.2 $[M+H]^+$. $^1$H NMR (400 MHz, DMSO_$d_6$) δ: 11.14 (s, 1H), 9.46 (s, 1H), 8.29 (d, J=9.6 Hz, 1H), 8.04 (br d, J=7.6 Hz, 1H), 7.93 (d, J=9.2 Hz, 1H), 7.75-7.59 (m, 2H), 5.07 (dd, J=4.8 Hz, 11.2 Hz, 1H), 2.97-2.79 (m, 1H), 2.71-2.56 (m, 2H), 2.43-2.31 (m, 1H), 1.50 (s, 9H).

Step 10: Synthesis of Hydrochloride of Intermediate BB-15

To a solution of hydrochloric acid in ethyl acetate (4 M, 15 mL) was added intermediate BB-15-10 (1.5 g, 3.79 mmol) at room temperature, and the reaction mixture was stirred and reacted at room temperature for 12 hours. After the reaction was completed, the reaction mixture was filtered. The filter cake was rinsed with ethyl acetate (30 mL), collected, and dried under vacuum to obtain hydrochloride of intermediate BB-15. MS-ESI m/z: 296.1 $[M+H]^+$. $^1$H NMR (400 MHz, DMSO_$d_6$) δ: 11.14 (s, 1H), 8.34 (d, J=9.6 Hz, 1H), 8.04-7.94 (m, 2H), 7.65 (t, J=8.0 Hz, 1H), 7.46 (d, J=7.6 Hz, 1H), 5.06 (dd, J=4.8 Hz, 11.6 Hz, 1H), 2.95-2.78 (m, 1H), 2.69-2.56 (m, 2H), 2.42-2.31 (m, 1H).

Example 1
WX001
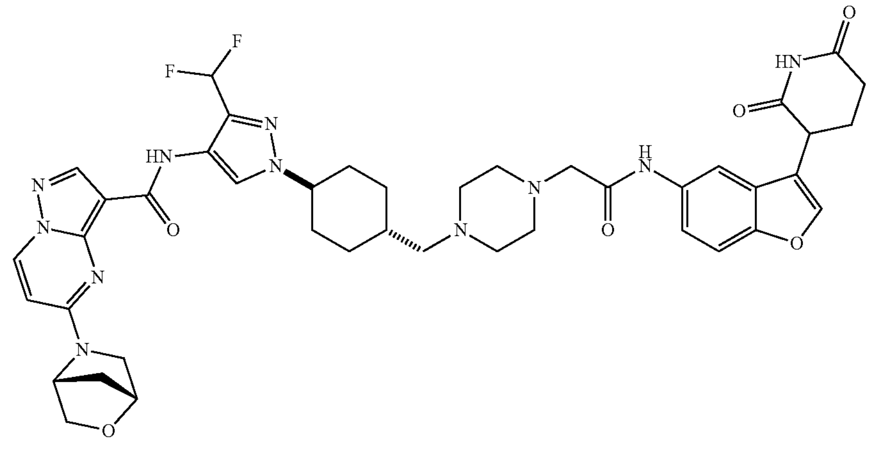
Synthetic Route
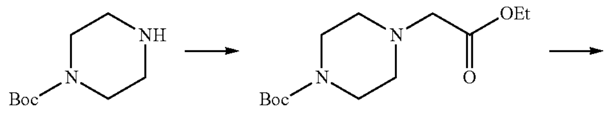
WX001-1 WX001-2
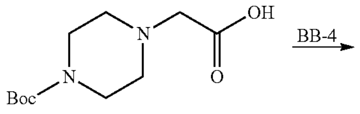
WX001-3
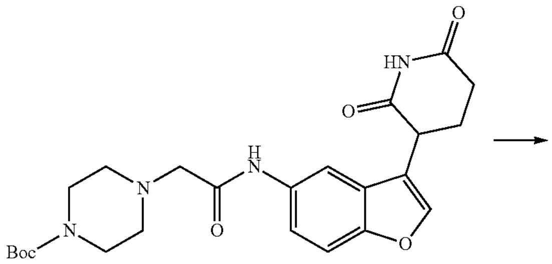
WX001-4
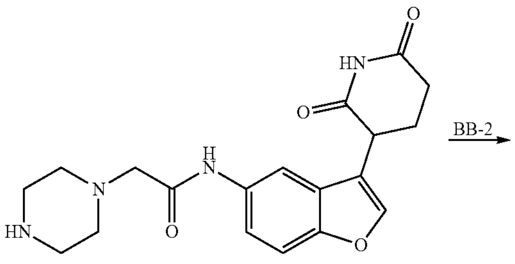
WX001-5

-continued

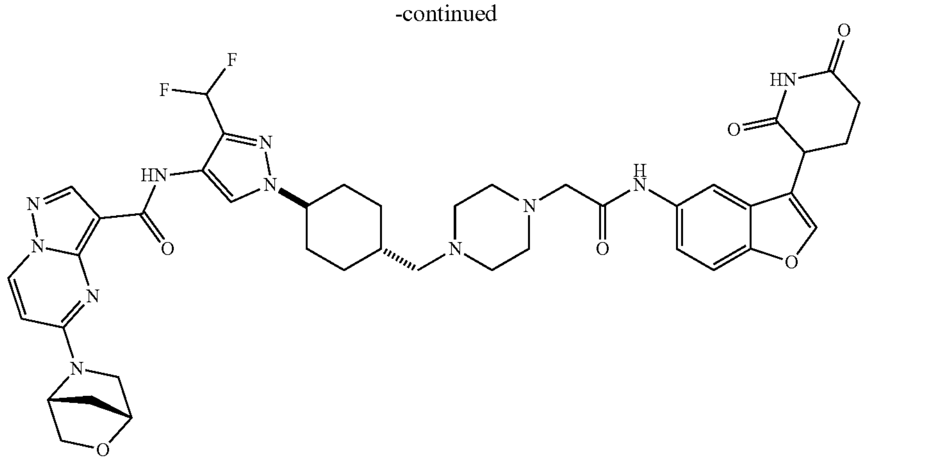

WX001

Step 1: Synthesis of Compound WX001-2

Compound WX001-1 (6 g, 32.21 mmol) was dissolved in tetrahydrofuran (60 mL) at room temperature, then ethyl bromoacetate (6.46 g, 38.66 mmol, 4.28 mL) and triethylamine (3.91 g, 38.66 mmol, 5.38 mL) were sequentially added thereto, and the reaction mixture was stirred and reacted at room temperature for 4 hours. After the reaction was completed, the reaction mixture was added with water (200 mL) and extracted with ethyl acetate (150 mL×2). The organic phases were combined, washed with saturated brine (300 mL), dried over anhydrous sodium sulfate, filtered, and the filtrate was concentrated under reduced pressure to remove the solvent. The resulting residue was added with petroleum ether (50 mL), stirred at room temperature for 5 minutes, and filtered. The filter cake was rinsed with petroleum ether (30 mL), collected, and dried under vacuum to obtain compound WX001-2.

Step 2: Synthesis of Hydrochloride of Compound WX001-3

Compound WX001-2 (5.5 g, 20.20 mmol) was dissolved in methanol (100 mL) at room temperature, then water (20 mL) and lithium hydroxide monohydrate (1.69 g, 40.39 mmol) were sequentially added thereto, and the reaction mixture was stirred and reacted at room temperature for 1 hour. After the reaction was completed, the reaction mixture was directly concentrated under reduced pressure to remove the solvent, then added with 1 M dilute hydrochloric acid to adjust the pH to 5 to 6, and concentrated under reduced pressure to remove the solvent. The resulting residue was separated by reversed-phase column chromatography (chromatographic column: 800 g Agela C18; mobile phase: water (0.04% hydrochloric acid)-methanol; methanol B %: 10% to 40%, 15 minutes) to obtain hydrochloride of compound WX001-3. MS-ESI m/z: 245.2 $[M+H]^+$.

Step 3: Synthesis of Compound WX001-4

Hydrochloride of compound WX001-3 (612.43 mg, 1.85 mmol, purity: 84.92%) and triethylamine (720.96 mg, 7.12 mmol) were dissolved in N,N-dimethylformamide (5 mL) at room temperature, then 2-(7-azabenzotriazol-1-yl)-N,N,N',N'-tetramethyluronium hexafluorophosphate (880.46 mg, 2.32 mmol) was added thereto, and the reaction mixture was stirred and reacted at room temperature for 1 hour. Hydrochloride of compound BB-4 (0.5 g, 1.78 mmol) was then added thereto, and the reaction mixture was stirred and reacted at room temperature for another 4 hours. After the reaction was completed, the reaction mixture was added with methyl tert-butyl ether (20 mL), stirred for 5 minutes, filtered, and the filter cake was rinsed with methyl tert-butyl ether (5 mL). The filtrates were combined, added with water (50 mL) and dichloromethane (100 mL), and the phases were separated. The organic phase was dried over anhydrous sodium sulfate, filtered, and the filtrate was concentrated under reduced pressure to remove the solvent and dried under vacuum to obtain a crude product of compound WX001-4, which was directly used in the next step without further purification. MS-ESI m/z: 471.3 $[M+H]^+$.

Step 4: Synthesis of Hydrochloride of Compound WX001-5

The crude product of compound WX001-4 (0.8 g, 1.70 mmol) was dissolved in dichloromethane (5 mL) at room temperature, then a solution of hydrochloric acid in ethyl acetate (4 M, 20 mL) was added thereto, and the reaction mixture was stirred and reacted at room temperature for 2 hours. After the reaction was completed, the reaction mixture was filtered. The filter cake was rinsed with ethyl acetate (20 mL), collected, and dried under vacuum to obtain hydrochloride of compound WX001-5. $^1H$ NMR (400 MHz, $D_2O$) δ: 7.78 (s, 1H), 7.64 (d, J=2.0 Hz, 1H), 7.57 (d, J=8.8 Hz, 1H), 7.30 (dd, J=2.0 Hz, 8.8 Hz, 1H), 4.21 (dd, J=5.2 Hz, 12.4 Hz, 1H), 4.06 (s, 2H), 3.62-3.50 (m, 8H), 2.90-2.75 (m, 2H), 2.51-2.38 (m, 1H), 2.33-2.24 (m, 1H).

Step 5: Synthesis of Hydrochloride of Compound WX001

Intermediate BB-2 (75 mg, 154.48 mol) was dissolved in N,N-dimethylformamide (2 mL) at room temperature under nitrogen atmosphere, then hydrochloride of compound WX001-5 (62.85 mg, 154.48 mol), potassium acetate (45.48 mg, 463.45 mol), and acetic acid (0.1 mL) were sequentially added thereto, and the reaction mixture was stirred and reacted at room temperature for 2 hours. Sodium triacetoxyborohydride (130.97 mg, 617.94 mol) was then added thereto, and the reaction mixture was stirred and reacted at room temperature for another 16 hours. After the reaction was completed, the reaction mixture was added with water (5 mL) and ethyl acetate (10 mL), and the phases were separated. The aqueous phase was then extracted with ethyl acetate (20 mL×3). The organic phases were combined, washed with saturated brine (20 mL×2), dried over anhydrous sodium sulfate, filtered, and the filtrate was concentrated under reduced pressure to remove the solvent. The resulting residue was separated by preparative HPLC (chromatographic column: Phenomenex Luna C18 80*40 mm*3 μm; mobile phase: water (0.04% hydrochloric acid)-acetonitrile; acetonitrile %: 20% to 38%, 7 minutes) to obtain hydrochloride of target compound WX001. MS-ESI m/z: 840.5 $[M+H]^+$. $^1H$ NMR (400 MHz, DMSO_$d_6$) δ: 10.94 (s, 1H), 10.71 (br s, 1H), 9.51 (d, J=6.4 Hz, 1H), 8.79 (d, J=7.6 Hz, 1H), 8.50-8.37 (m, 1H), 8.26 (d, J=5.2 Hz, 1H), 7.93 (s, 1H), 7.91 (s, 1H), 7.58 (d, J=8.8 Hz, 1H), 7.47 (d, J=8.8 Hz, 1H), 7.28-6.95 (m, 1H), 6.90-6.42 (m, 1H), 5.18 (d, J=79.2 Hz, 1H), 4.77 (d, J=20.0 Hz, 1H), 4.34-4.09 (m, 6H), 3.40-3.20 (m, 4H), 3.06 (s, 2H), 2.85-2.73 (m, 2H), 2.70-2.57 (m, 4H), 2.35-2.19 (m, 2H), 2.17-1.65 (m, 12H), 1.27-1.13 (m, 2H).

Example 2

WX002

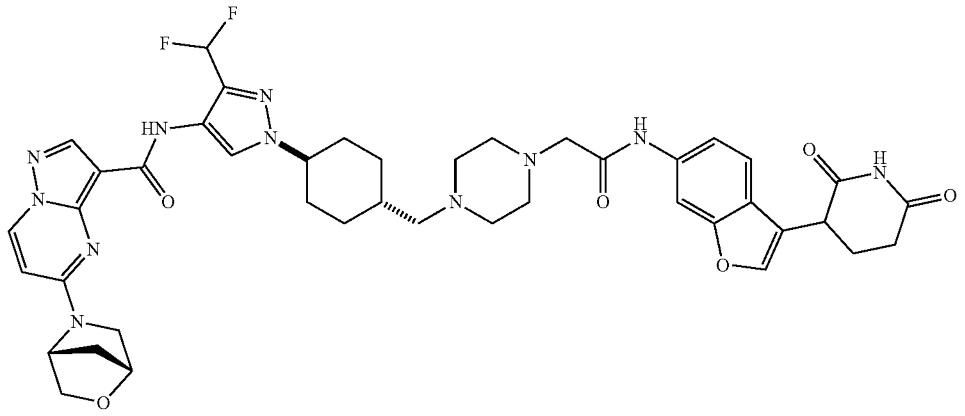

Synthetic Route

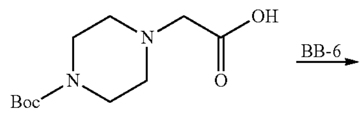

WX001-3

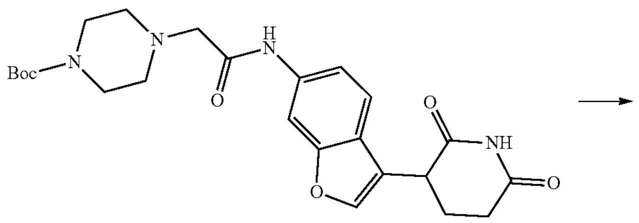

WX002-1

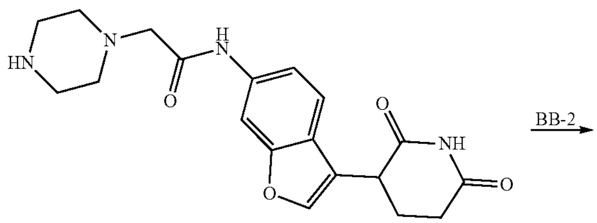

WX002-2

-continued

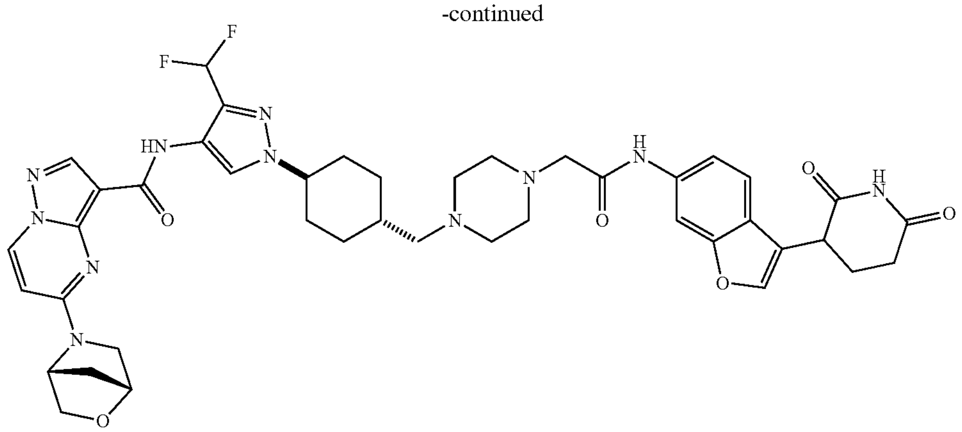

WX002

Step 1: Synthesis of Compound WX002-1

Hydrochloride of compound WX001-3 (0.5 g, 1.78 mmol) and triethylamine (632.58 mg, 6.25 mmol) were dissolved in N,N-dimethylformamide (10 mL) at room temperature, then 2-(7-azabenzotriazol-1-yl)-N,N,N',N'-tetramethyluronium hexafluorophosphate (812.61 mg, 2.14 mmol) was added thereto, and the reaction mixture was stirred and reacted at room temperature for 1 hour. Hydrochloride of intermediate BB-6 (522.08 mg, 1.33 mmol) was then added thereto, and the reaction mixture was stirred and reacted at room temperature for another 16 hours. After the reaction was completed, the reaction mixture was filtered. The filter cake was rinsed with N,N-dimethylformamide (5 mL), then rinsed with methyl tert-butyl ether (20 mL), collected, and dried under vacuum to obtain compound WX002-1. MS-ESI m/z: 471.3 $[M+H]^+$. $^1H$ NMR (400 MHz, DMSO_$d_6$) δ: 10.88 (s, 1H), 9.93 (s, 1H), 8.06 (d, J=1.2 Hz, 1H), 7.83 (s, 1H), 7.50 (d, J=8.4 Hz, 1H), 7.38 (dd, J=1.2 Hz, 8.4 Hz, 1H), 4.10 (dd, J=4.8 Hz, 12.0 Hz, 1H), 3.43-3.36 (m, 4H), 3.35-3.33 (m, 4H), 3.19 (s, 2H), 2.79-2.64 (m, 1H), 2.62-2.54 (m, 1H), 2.37-2.24 (m, 1H), 2.16-2.06 (m, 1H), 1.40 (s, 9H).

Step 2: Synthesis of Hydrochloride of Compound WX002-2

Compound WX002-1 (0.8 g, 1.70 mmol) was dissolved in ethyl acetate (10 mL) at room temperature, then a solution of hydrochloric acid in ethyl acetate (4 M, 40 mL) was added thereto, and the reaction mixture was stirred and reacted at room temperature for 16 hours. After the reaction was completed, the reaction mixture was filtered. The filter cake was rinsed with ethyl acetate (5 mL), collected, and dried under vacuum to obtain hydrochloride of compound WX002-2. MS-ESI m/z: 371.3 $[M+H]^+$. $^1H$ NMR (400 MHz, $D_2O$) δ: 7.75 (d, J=1.6 Hz, 1H), 7.66 (s, 1H), 7.43 (d, J=8.4 Hz, 1H), 7.19 (dd, J=1.2 Hz, 8.4 Hz, 1H), 4.31 (s, 2H), 4.10-4.03 (m, 1H), 3.80-3.72 (m, 4H), 3.71-3.63 (m, 4H), 2.78-2.61 (m, 2H), 2.33-2.20 (m, 1H), 2.18-2.09 (m, 1H).

Step 3: Synthesis of Hydrochloride of Compound WX002

Intermediate BB-2 (75 mg, 154.48 mol) was dissolved in N,N-dimethylformamide (2 mL) at room temperature under nitrogen atmosphere, then hydrochloride of compound WX002-2 (62.85 mg, 154.48 mol), potassium acetate (45.48 mg, 463.45 mol), and acetic acid (0.1 mL) were sequentially added thereto, and the reaction mixture was stirred and reacted at room temperature for 2 hours. Sodium triacetoxyborohydride (172.88 mg, 815.68 mol) was then added thereto, and the reaction mixture was stirred and reacted at room temperature for another 16 hours. After the reaction was completed, the reaction mixture was added with water (5 mL) and ethyl acetate (10 mL), and the phases were separated. The aqueous phase was then extracted with ethyl acetate (20 mL×3). The organic phases were combined, washed with saturated brine (20 mL×2), dried over anhydrous sodium sulfate, filtered, and the filtrate was concentrated under reduced pressure to remove the solvent. The resulting residue was separated by preparative HPLC (chromatographic column: Phenomenex Luna C18 80*40 mm*3 μm; mobile phase: water (0.04% hydrochloric acid)-acetonitrile; acetonitrile %: 15% to 35%, 7 minutes) to obtain hydrochloride of target compound WX002. MS-ESI m/z: 840.3 $[M+H]^+$. $^1H$ NMR (400 MHz, DMSO_$d_6$) δ: 10.96 (s, 1H), 10.90 (s, 1H), 9.51 (d, J=6.0 Hz, 1H), 8.79 (d, J=7.6 Hz, 1H), 8.50-8.37 (m, 1H), 8.26 (d, J=5.6 Hz, 1H), 8.06 (s, 1H), 7.88 (s, 1H), 7.56 (d, J=8.4 Hz, 1H), 7.38 (d, J=8.0 Hz, 1H), 7.28-6.95 (m, 1H), 6.90-6.41 (m, 1H), 5.18 (d, J=78.4 Hz, 1H), 4.77 (d, J=19.6 Hz, 1H), 4.28-4.09 (m, 6H), 3.48-3.32 (m, 4H), 3.28-3.00 (m, 3H), 2.82-2.65 (m, 3H), 2.63-2.57 (m, 2H), 2.38-2.25 (m, 2H), 2.20-1.65 (m, 12H), 1.28-1.11 (m, 2H).

Example 3
WX003
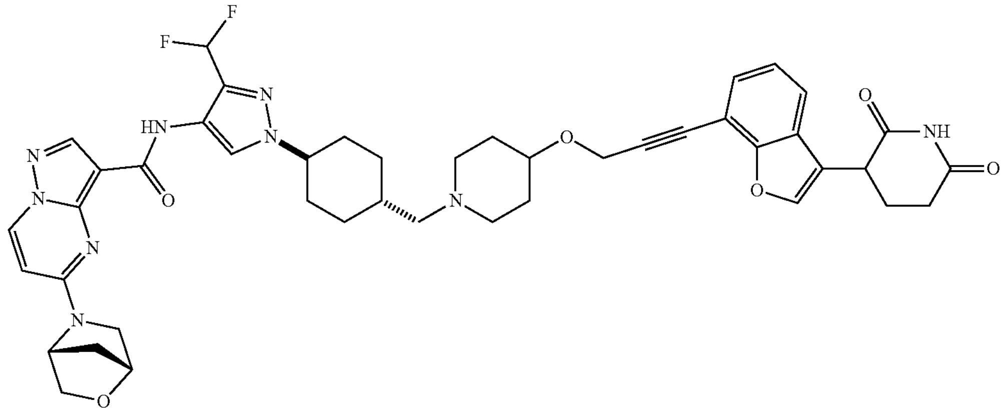
Synthetic Route
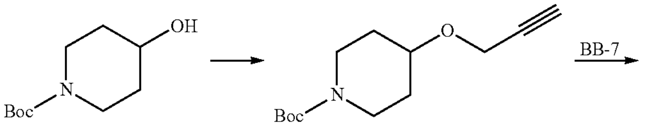
WX003-1
WX003-2
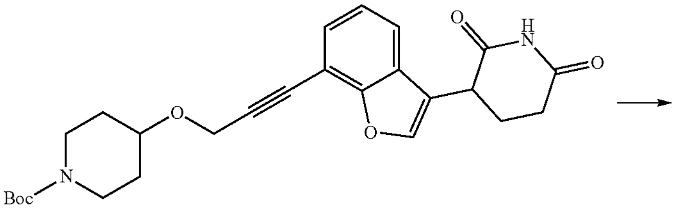
WX003-3
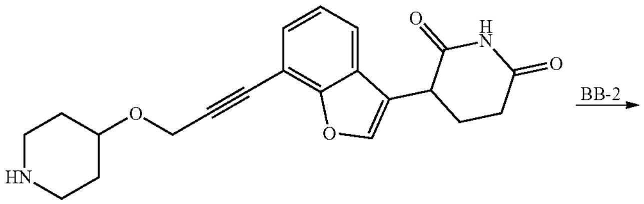
WX003-4

-continued

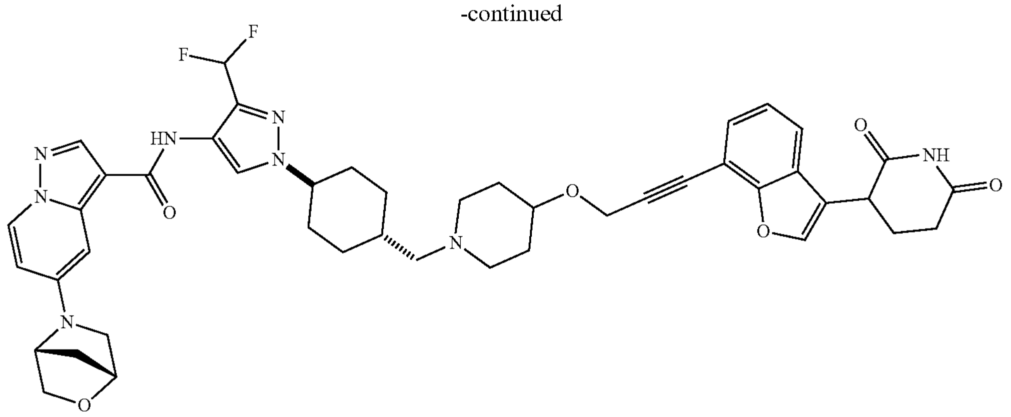

WX003

Step 1: Synthesis of Compound WX003-2

Compound WX003-1 (9 g, 44.72 mmol) was dissolved in tetrahydrofuran (90 mL) at room temperature under nitrogen atmosphere, and the reaction mixture was cooled to 0° C. Sodium hydride (2.15 g, 53.66 mmol, purity: 60%) was slowly added thereto, and the reaction mixture was stirred and reacted at 0° C. for 30 minutes. Propargyl bromide (5.32 g, 44.72 mmol) was then added thereto, and the reaction mixture was slowly warmed to room temperature and stirred and reacted for 16 hours. After the reaction was completed, the reaction mixture was slowly poured into ice water (100 mL) and extracted with ethyl acetate (100 mL×3). The organic phases were combined, washed with saturated brine (100 mL×3), dried over anhydrous sodium sulfate, filtered, and the filtrate was concentrated under reduced pressure to remove the solvent. The resulting residue was separated by column chromatography (eluent: ethyl acetate/petroleum ether=0/1 to 1/1, v/v) to obtain compound WX003-2. $^1$H NMR (400 MHz, $CDCl_3$) δ: 4.20 (d, J=2.4 Hz, 2H), 3.81-3.67 (m, 3H), 3.15-3.06 (m, 2H), 2.42 (t, J=2.4 Hz, 1H), 1.90-1.81 (m, 2H), 1.59-1.49 (m, 2H), 1.46 (s, 9H).

Step 2: Synthesis of Compound WX003-3

Intermediate BB-7 (1 g, 3.25 mmol) was dissolved in N,N-dimethylformamide (20 mL) at room temperature under nitrogen atmosphere, then compound WX003-2 (1.16 g, 4.87 mmol), cesium carbonate (3.17 g, 9.74 mmol), cuprous iodide (124 mg, 694 mol), and bis(triphenylphosphine)palladium(II) chloride (456 mg, 649 mol) were sequentially added thereto, and the reaction mixture was heated to 80° C. and stirred and reacted for 5 hours. After the reaction was completed, the reaction mixture was cooled to room temperature, poured into 1 M hydrochloric acid (80 mL), and extracted with ethyl acetate (10 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=5/1 to 1/1, v/v) to obtain compound WX003-3. $^1$H NMR (400 MHz, $CDCl_3$) δ: 7.98 (s, 1H), 7.64 (s, 1H), 7.49 (dd, J=1.2 Hz, 7.6 Hz, 1H), 7.44 (dd, J=0.8 Hz, 7.6 Hz, 1H), 7.24 (t, J=7.6 Hz, 1H), 4.53 (s, 2H), 4.00 (t, J=7.6 Hz, 1H), 3.88-3.77 (m, 3H), 3.19-3.10 (m, 2H), 2.88-2.69 (m, 2H), 2.43-2.34 (m, 2H), 1.97-1.88 (m, 2H), 1.67-1.59 (m, 2H), 1.47 (s, 9H).

Step 3: Synthesis of Hydrochloride of Compound WX003-4

Compound WX003-3 (990 mg, 2.12 mmol) was dissolved in ethyl acetate (5 mL) at room temperature, then a solution of hydrochloric acid in ethyl acetate (4 M, 33 mL) was added thereto, and the reaction mixture was stirred and reacted at room temperature for 16 hours. After the reaction was completed, the reaction mixture was concentrated under reduced pressure to a volume of 1 to 2 mL, and filtered. The filter cake was washed with ethyl acetate (12 mL×2), collected, and dried under vacuum to obtain hydrochloride of compound WX003-4. $^1$H NMR (400 MHz, DMSO_$d_6$) δ: 10.92 (s, 1H), 8.89-8.80 (m, 2H), 8.00 (s, 1H), 7.65 (dd, J=0.8 Hz, 7.6 Hz, 1H), 7.43 (d, J=7.6 Hz, 1H), 7.26 (t, J=7.6 Hz, 1H), 4.55 (s, 2H), 4.17 (dd, J=4.8 Hz, 12.4 Hz, 1H), 3.90-3.83 (m, 1H), 3.22-3.11 (m, 2H), 3.05-2.94 (m, 2H), 2.81-2.70 (m, 1H), 2.63-2.54 (m, 1H), 2.39-2.27 (m, 1H), 2.17-2.00 (m, 1H), 2.07-2.02 (m, 2H), 1.84-1.73 (m, 2H).

Step 4: Synthesis of Hydrochloride of Compound WX003

To a mixed solvent of tetrahydrofuran (5 mL) and N,N-dimethylformamide (1 mL) were sequentially added intermediate BB-2 (149 mg, 307 mol), hydrochloride of compound WX003-4 (123.6 mg, 307 mol), and potassium acetate (60 mg, 614 mol) at room temperature, and the reaction mixture was stirred and reacted at room temperature for 0.5 hours. Sodium triacetoxyborohydride (130 mg, 614 mol) was then added thereto, and the reaction mixture was stirred and reacted at room temperature for another 16 hours. After the reaction was completed, the reaction mixture was added with water (1 mL) and concentrated under reduced pressure to remove the solvent. The resulting residue was separated by preparative HPLC (chromatographic column: Boston Green ODS 150*30 mm*5 μm; mobile phase: water (0.04% hydrochloric acid)-acetonitrile; acetonitrile %: 22% to 42%, 10 minutes) to obtain hydrochloride of target compound WX003. MS-ESI m/z: 836.3 $[M+H]^+$. $^1$H NMR (400 MHz, DMSO_$d_6$) δ: 10.93 (s, 1H), 9.61-9.45 (m, 2H), 8.80 (d, J=7.6 Hz, 1H), 8.41 (d, J=2.8 Hz, 1H), 8.27 (dd, J=1.6 Hz, 5.6 Hz, 1H), 8.01 (d, J=2.4 Hz, 1H), 7.67 (d, J=7.6 Hz, 1H), 7.44 (d, J=7.2 Hz, 1H), 7.32-6.96 (m, 2H), 6.92-6.43 (m, 1H), 5.18 (d, J=78.4 Hz, 1H), 4.77 (d, J=20.0 Hz, 1H), 4.58 (d, J=2.8 Hz, 2H), 4.29-4.15 (m, 2H), 3.86-3.71 (m, 3H), 3.67-3.59 (m, 2H), 3.42-3.37 (m, 1H), 3.14-2.92 (m, 4H), 2.81-2.71 (m, 1H), 2.69-2.60 (m, 1H), 2.43-2.28 (m, 2H), 2.26-2.18 (m, 1H), 2.17-1.75 (m, 13H), 1.26-1.15 (m, 2H).

Example 4
WX004
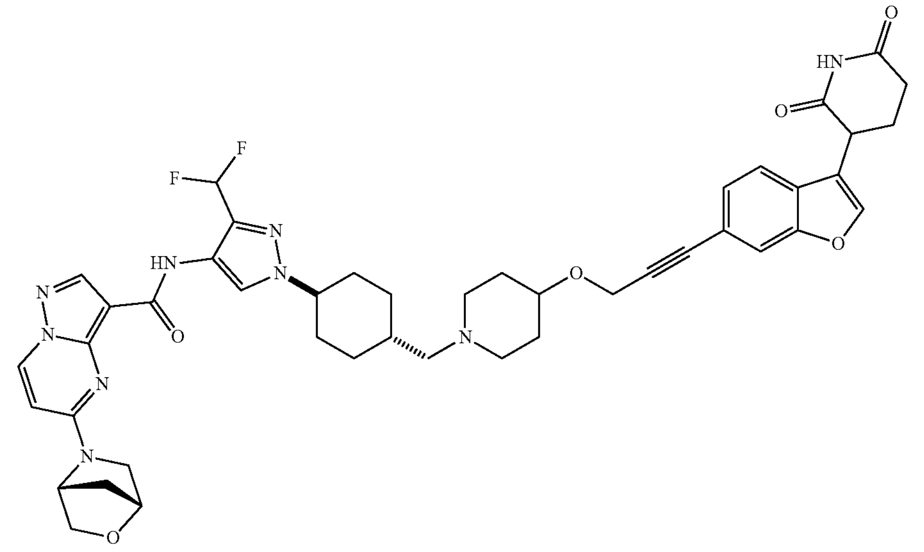
Synthetic Route
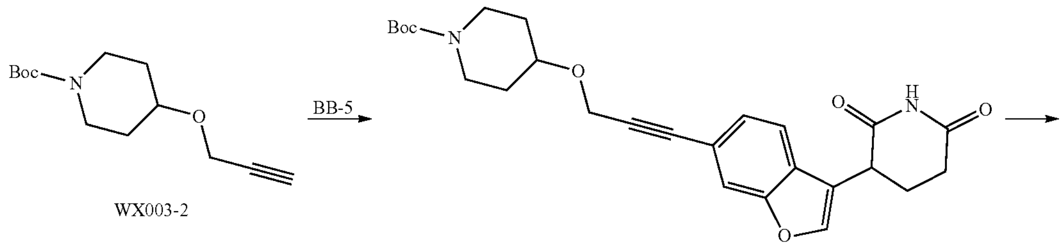
WX003-2
WX004-1
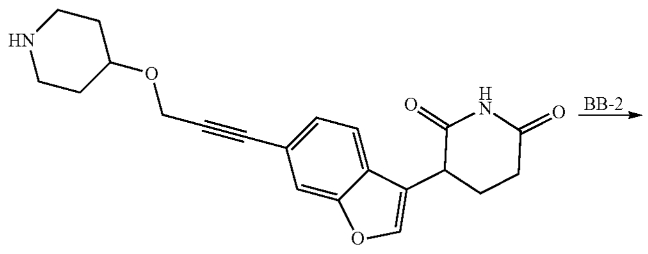
WX004-2

-continued

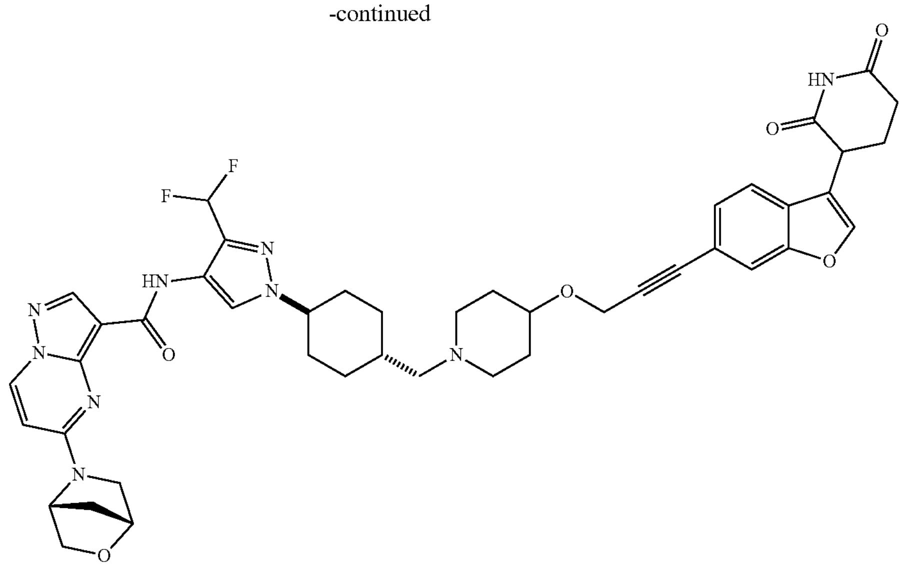

WX004

Step 1: Synthesis of Compound WX004-1

Intermediate BB-5 (0.85 g, 2.76 mmol), compound WX003-2 (990.24 mg, 4.14 mmol), cuprous iodide (105.08 mg, 551.72 mol), bis(triphenylphosphine)palladium(II) chloride (387.25 mg, 551.72 mol), and cesium carbonate (3.60 g, 11.03 mmol) were dissolved in N,N-dimethylformamide (15 mL) at room temperature under nitrogen atmosphere, and the reaction mixture was heated to 80° C. and stirred and reacted for 3 hours. After the reaction was completed, the reaction mixture was cooled to room temperature, poured into water (50 mL), and extracted with ethyl acetate (30 mL×3). The organic phases were combined, washed with saturated brine (30 mL), dried over anhydrous sodium sulfate, filtered, and the filtrate was concentrated under reduced pressure to remove the solvent. The resulting residue was separated by column chromatography (eluent: petroleum ether/ethyl acetate=2/1, v/v) to obtain compound WX004-1. MS-ESI m/z: 367.2 $[M+H-100]^+$. $^1H$ NMR (400 MHz, $CDCl_3$) δ: 7.63 (s, 1H), 7.61 (s, 1H), 7.44 (d, J=8.0 Hz, 1H), 7.35 (dd, J=1.2 Hz, 8.0 Hz, 1H), 4.45 (s, 2H), 3.99 (dd, J=6.8 Hz, 8.8 Hz, 1H), 3.87-3.70 (m, 3H), 3.18-3.09 (m, 2H), 2.87-2.68 (m, 2H), 2.43-2.32 (m, 2H), 1.98-1.86 (m, 2H), 1.67-1.54 (m, 2H), 1.47 (s, 9H).

Step 2: Synthesis of Trifluoroacetate of Compound WX004-2

Compound WX004-1 (0.47 g, 1.01 mmol) was dissolved in dichloromethane (5 mL) at room temperature, then trifluoroacetic acid (1.54 g, 13.51 mmol) was slowly added dropwise thereto, and the reaction mixture was stirred and reacted at room temperature for 1 hour. After the reaction was completed, the reaction mixture was directly concentrated under reduced pressure to remove the solvent. The resulting residue was separated by preparative HPLC (chromatographic column: Phenomenex Luna C18 100*40 mm*5 μm; mobile phase: water (0.05% trifluoroacetic acid)-acetonitrile; acetonitrile %: 1% to 45%, 8 minutes) to obtain trifluoroacetate of compound WX004-2. $^1H$ NMR (400 MHz, DMSO_$d_6$) δ: 10.91 (s, 1H), 8.76-8.44 (m, 2H), 8.00 (s, 1H), 7.71 (s, 1H), 7.59 (d, J=8.0 Hz, 1H), 7.32 (dd, J=1.2 Hz, 8.4 Hz, 1H), 4.47 (s, 2H), 4.16 (dd, J=4.8 Hz, 12.0 Hz, 1H), 3.89-3.79 (m, 1H), 3.25-3.14 (m, 2H), 3.09-2.96 (m, 2H), 2.81-2.70 (m, 1H), 2.58 (dt, J=3.6 Hz, 17.2 Hz, 1H), 2.39-2.25 (m, 1H), 2.16-2.07 (m, 1H), 2.06-1.97 (m, 2H), 1.79-1.68 (m, 2H).

Step 3: Synthesis of Hydrochloride of Compound WX004

Intermediate BB-2 (70 mg, 144.19 mol) and trifluoroacetate of compound WX004-2 (76.20 mg, 158.60 mol) were dissolved in a mixed solvent of N,N-dimethylformamide (2 mL) and glacial acetic acid (0.1 mL) at room temperature, then potassium acetate (42.45 mg, 432.56 mol) was added thereto, and the reaction mixture was stirred and reacted at room temperature for 2 hours. Sodium triacetoxyborohydride (91.68 mg, 432.56 mol) was then added thereto, and the reaction mixture was stirred and reacted at room temperature for another 16 hours. After the reaction was completed, the reaction mixture was filtered, and the filtrate was directly separated by preparative HPLC (chromatographic column: Phenomenex Luna C18 80*40 mm*3 μm; mobile phase: water (0.04% hydrochloric acid)-acetonitrile; acetonitrile %: 28% to 48%, 7 minutes) to obtain hydrochloride of target compound WX004. MS-ESI m/z: 836.3 $[M+H]^+$. $^1H$ NMR (400 MHz, DMSO_$d_6$) δ: 10.92 (s, 1H), 9.73 (br s, 1H), 9.51 (d, J=6.4 Hz, 1H), 8.81-8.77 (m, 1H), 8.40 (d, J=4.0 Hz, 1H), 8.26 (d, J=5.6 Hz, 1H), 8.02 (s, 1H), 7.72 (s, 1H), 7.61 (d, J=8.0 Hz, 1H), 7.33 (d, J=8.4 Hz, 1H), 7.27-6.95 (m 1H), 6.91-6.43 (m, 1H), 5.18 (d, J=78.4 Hz, 1H), 4.76 (d, J=19.6 Hz, 1H), 4.49 (s, 2H), 4.33-4.12 (m, 2H), 3.84-3.71 (m, 3H), 3.66-3.50 (m, 2H), 3.39-3.35 (m, 1H), 3.08-2.94 (m, 4H), 2.80-2.69 (m, 1H), 2.68-2.53 (m, 2H), 2.39-2.26 (m, 2H), 2.22-1.76 (m, 13H), 1.26-1.12 (m, 2H).

Example 5
WX005
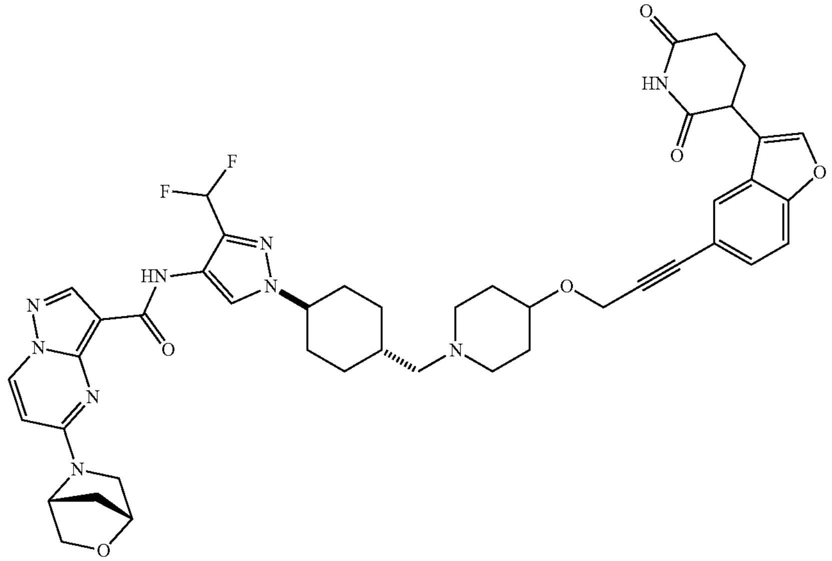
Synthetic Route
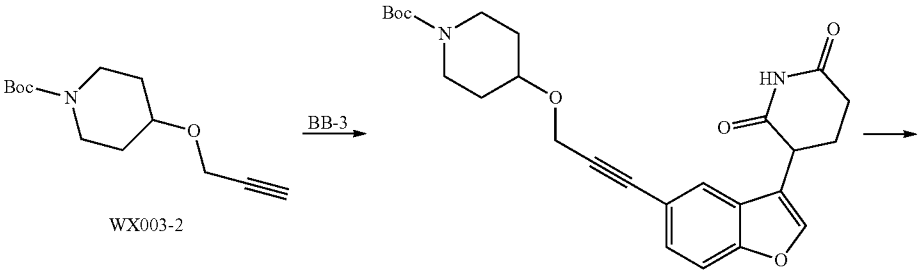
WX003-2
WX005-1
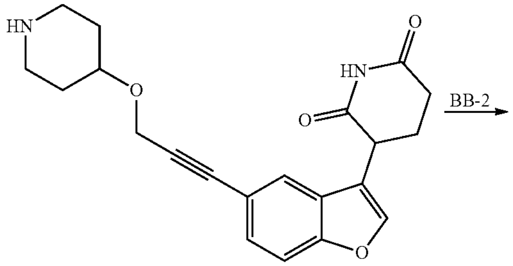
WX005-2

-continued

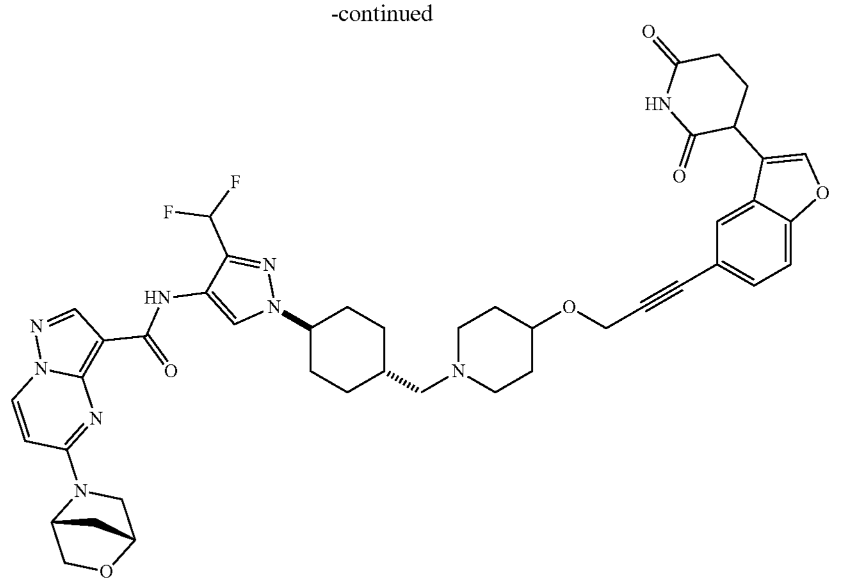

WX005

Step 1: Synthesis of Compound WX005-1

To N,N-dimethylformamide (20 mL) were added intermediate BB-3 (1 g, 2.23 mmol), compound WX003-2 (799.42 mg, 3.34 mmol), cuprous iodide (84.83 mg, 445.40 mol), bis(triphenylphosphine)palladium(II) chloride (312.63 mg, 445.40 mol), and cesium carbonate (2.90 g, 8.91 mmol) at room temperature under nitrogen atmosphere, and the reaction mixture was heated to 80° C. and stirred and reacted for 5 hours. After the reaction was completed, the reaction mixture was cooled to room temperature, poured into water (100 mL), and extracted with ethyl acetate (50 mL×2). The organic phases were combined, washed with saturated brine (100 mL), dried over anhydrous sodium sulfate, filtered, and the filtrate was concentrated under reduced pressure to remove the solvent. The resulting residue was separated by column chromatography (eluent: petroleum ether/ethyl acetate=2/1, v/v) to obtain compound WX005-1. MS-ESI m/z: 367.2 $[M+H-100]^+$.

Step 2: Synthesis of Trifluoroacetate of Compound WX005-2

Compound WX005-1 (360.00 mg, 771.66 mol) was dissolved in dichloromethane (5 mL) at room temperature, then trifluoroacetic acid (1.54 g, 13.51 mmol) was added dropwise thereto, and the reaction mixture was stirred and reacted at room temperature for 2 hours. After the reaction was completed, the reaction mixture was concentrated under reduced pressure to remove the solvent. The resulting residue was separated by preparative HPLC (chromatographic column: Phenomenex Luna C18 100*40 mm*5 μm; mobile phase: water (0.05% trifluoroacetic acid)-acetonitrile; acetonitrile %: 1% to 45%, 8 minutes) to obtain trifluoroacetate of compound WX005-2. $^1$H NMR (400 MHz, DMSO_$d_6$) δ: 10.90 (s, 1H), 8.59-8.20 (m, 2H), 7.98 (s, 1H), 7.73 (d, J=1.2 Hz, 1H), 7.60 (d, J=8.4 Hz, 1H), 7.39 (dd, J=1.6 Hz, 8.4 Hz, 1H), 4.46 (s, 2H), 4.15 (dd, J=4.8 Hz, 12.0 Hz, 1H), 3.88-3.78 (m, 1H), 3.24-3.14 (m, 2H), 3.08-2.96 (m, 2H), 2.80-2.64 (m, 2H), 2.43-2.27 (m, 1H), 2.16-2.06 (m, 1H), 2.05-1.93 (m, 2H), 1.78-1.64 (m, 2H).

Step 3: Synthesis of Hydrochloride of Compound WX005

Intermediate BB-2 (70 mg, 144.19 mol) and trifluoroacetate of compound WX005-2 (76.20 mg, 158.60 mol) were dissolved in a mixed solvent of N,N-dimethylformamide (2 mL) and glacial acetic acid (0.1 mL) at room temperature, then potassium acetate (42.45 mg, 432.56 mol) was added thereto, and the reaction mixture was stirred and reacted at room temperature for 2 hours. Sodium triacetoxyborohydride (91.68 mg, 432.56 mol) was then added thereto, and the reaction mixture was stirred and reacted at room temperature for another 16 hours. After the reaction was completed, the reaction mixture was directly concentrated under reduced pressure to remove the solvent. The resulting residue was separated by preparative HPLC (chromatographic column: Phenomenex Luna 80*30 mm*3 μm; mobile phase: water (0.04% hydrochloric acid)-acetonitrile; acetonitrile %: 20% to 35%, 8 minutes) to obtain hydrochloride of target compound WX005. MS-ESI m/z: 836.3 $[M+H]^+$. $^1$H NMR (400 MHz, DMSO_$d_6$) δ: 10.90 (s, 1H), 9.68 (s, 1H), 9.50 (d, J=6.4 Hz, 1H), 8.78 (d, J=7.6 Hz, 1H), 8.39 (d, J=4.0 Hz, 1H), 8.25 (d, J=5.6 Hz, 1H), 7.98 (s, 1H), 7.76-7.72 (m, 1H), 7.60 (d, J=8.4 Hz, 1H), 7.39 (dd, J=1.6 Hz, 8.8 Hz, 1H), 7.27-6.95 (m, 1H), 6.90-6.43 (m, 1H), 5.17 (d, J=79.6 Hz, 1H), 4.76 (d, J=20.0 Hz, 1H), 4.47 (s, 2H), 4.33-4.12 (m, 2H), 3.98-3.71 (m, 3H), 3.67-3.57 (m, 2H), 3.40-3.33 (m, 1H), 3.16-2.92 (m, 4H), 2.79-2.66 (m, 1H), 2.62-2.55 (m, 1H), 2.38-2.31 (m, 1H), 2.22-1.65 (m, 15H), 1.26-1.10 (m, 2H).

Example 6

WX006

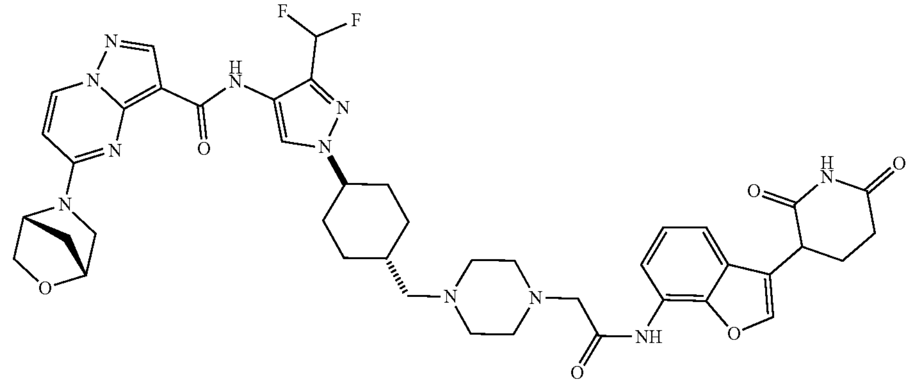

Synthetic Route

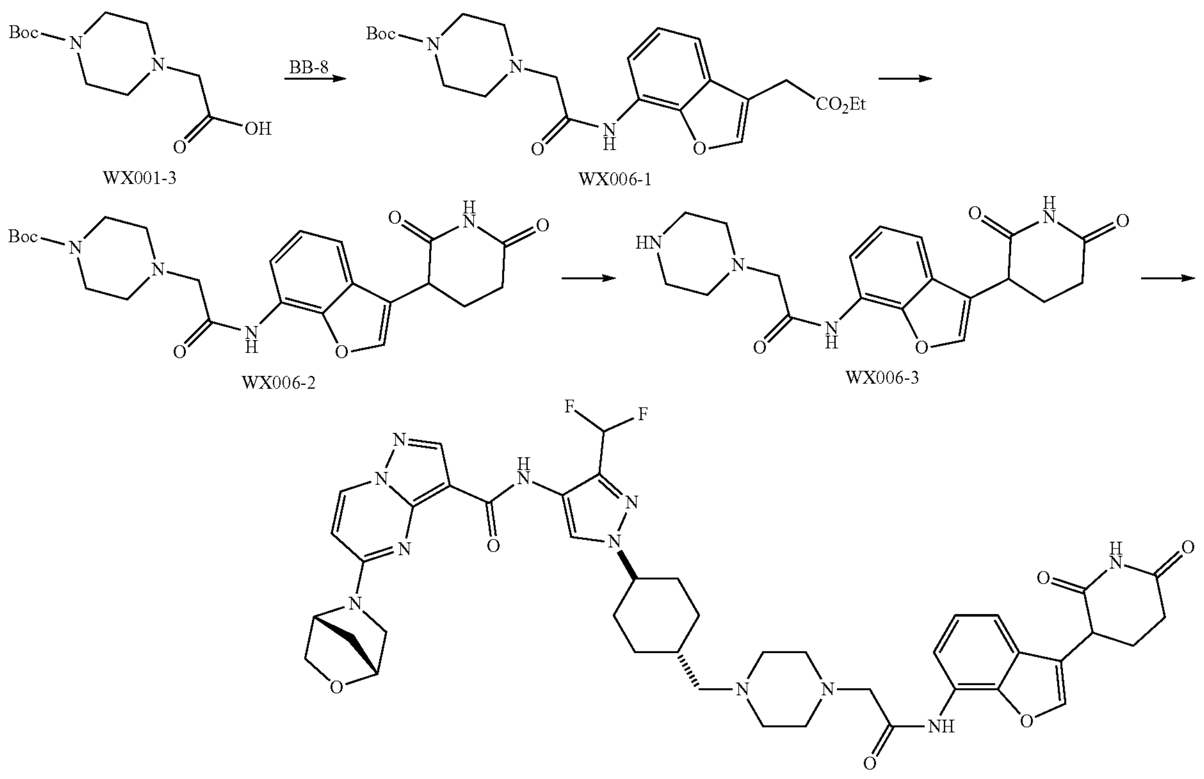

WX001-3

WX006-1

WX006-2

WX006-3

WX006

Step 1: Synthesis of Compound WX006-1

Hydrochloride of compound WX001-3 (1.3 g, 5.31 mmol) was dissolved in N,N-dimethylformamide (15 mL) at room temperature, then 2-(7-azabenzotriazol-1-yl)-N,N,N',N'-tetramethyluronium hexafluorophosphate (1.62 g, 4.25 mmol), N,N-diisopropylethylamine (1.37 g, 10.63 mmol), and hydrochloride of intermediate BB-8 (906 mg, 3.54 mmol) were sequentially added thereto, and the reaction mixture was stirred and reacted at room temperature for 16 hours. After the reaction was completed, the reaction mixture was poured into water (150 mL) and extracted with ethyl acetate (30 mL×3). The organic phases were combined, washed with saturated brine (30 mL), dried over anhydrous sodium sulfate, and filtered. The filtrate was concentrated under reduced pressure to remove the solvent, and the resulting residue was separated by column chromatography (eluent: petroleum ether/ethyl acetate=5/1 to 7/3, v/v) to obtain compound WX006-1. $^1H$ NMR (400 MHz, $CDCl_3$) δ: 9.71 (s, 1H), 8.20 (s, 1H), 7.66 (s, 1H), 7.35-7.29

(m, 1H), 7.26-7.23 (m, 1H), 4.20 (q, J=7.2 Hz, 2H), 3.71 (d, J=1.2 Hz, 2H), 3.59 (m, 4H), 3.26 (m, 2H), 2.65 (m, 4H), 1.49 (s, 9H), 1.28 (t, J=7.2 Hz, 3H).

Step 2: Synthesis of Compound WX006-2

Compound WX006-1 (1.53 g, 3.43 mmol) was dissolved in N,N-dimethylformamide (20 mL) at 0° C. under nitrogen atmosphere, then potassium tert-butoxide (462 mg, 4.12 mmol) and acrylamide (293 mg, 4.12 mmol) were sequentially added thereto, and the reaction mixture was stirred and reacted at room temperature for 1 hour. After the reaction was completed, the reaction mixture was slowly poured into saturated ammonium chloride aqueous solution (30 mL) and extracted with ethyl acetate (15 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=10/1 to 1/1, v/v) to obtain compound WX006-2. $^1$H NMR (400 MHz, $CDCl_3$) δ: 9.74 (s, 1H), 8.27-8.19 (m, 1H), 8.04 (s, 1H), 7.61 (s, 1H), 7.26-7.14 (m, 2H), 4.02 (t, J=7.6 Hz, 1H), 3.58 (s, 4H), 3.26 (s, 2H), 2.86-2.73 (m, 2H), 2.64 (s, 4H), 2.45-2.35 (m, 2H), 1.49 (s, 9H).

Step 3: Synthesis of Hydrochloride of Compound WX006-3

Compound WX006-2 (150 mg, 2.12 mmol) was dissolved in ethyl acetate (3 mL) at room temperature, then a solution of hydrochloric acid in ethyl acetate (4 M, 15 mL) was added thereto, and the reaction mixture was stirred and reacted at room temperature for 2 hours. After the reaction was completed, the reaction mixture was directly concentrated under reduced pressure to remove the solvent to obtain hydrochloride of compound WX006-3, which was directly used in the next step without further purification.

Step 4: Synthesis of Hydrochloride of Compound WX006

Intermediate BB-2 (149 mg, 307 mol) was dissolved in a mixed solvent of tetrahydrofuran (5 mL) and N,N-dimethylformamide (1 mL) at room temperature, then hydrochloride of compound WX006-3 (125 mg, 307 mol) and potassium acetate (60 mg, 614 mol) were sequentially added thereto, and the reaction mixture was stirred and reacted at room temperature for 0.5 hours. Sodium triacetoxyborohydride (130 mg, 614 mol) was then added thereto, and the reaction mixture was stirred and reacted at room temperature for another 16 hours. After the reaction was completed, the reaction mixture was added with water (1 mL) to quench, dried over anhydrous sodium sulfate, filtered, and the filtrate was concentrated under reduced pressure to remove the solvent. The resulting residue was separated by preparative HPLC (chromatographic column: Boston Green ODS 150*30 mm*5 μm; mobile phase: water (0.04% hydrochloric acid)-acetonitrile; acetonitrile %: 15% to 35%, 10 minutes) to obtain hydrochloride of target compound WX006. MS-ESI m/z: 840.4 $[M+H]^+$. $^1$H NMR (400 MHz, DMSO_$d_6$) δ: 10.93 (s, 1H), 10.42 (s, 1H), 9.52 (d, J=7.2 Hz, 1H), 8.78 (d, J=8.0 Hz, 1H), 8.41 (d, J=4.4 Hz, 1H), 8.26 (d, J=5.6 Hz, 1H), 7.97 (s, 1H), 7.73 (d, J=7.6 Hz, 1H), 7.41 (d, J=7.6 Hz, 1H), 7.32-6.96 (m, 3H), 6.90-6.44 (m, 1H), 5.17 (d, J=81.2 Hz, 1H), 4.77 (d, J=20.4 Hz, 1H), 4.29-4.13 (m, 2H), 4.03-3.91 (m, 1H), 3.85-3.79 (m, 2H), 3.77-3.58 (m, 5H), 3.08-2.99 (m, 1H), 2.82-2.71 (m, 2H), 2.70-2.66 (m, 1H), 2.64-2.57 (m, 2H), 2.41-2.27 (m, 2H), 2.17-1.74 (m, 12H), 1.30-1.13 (m, 3H).

Example 7

WX007

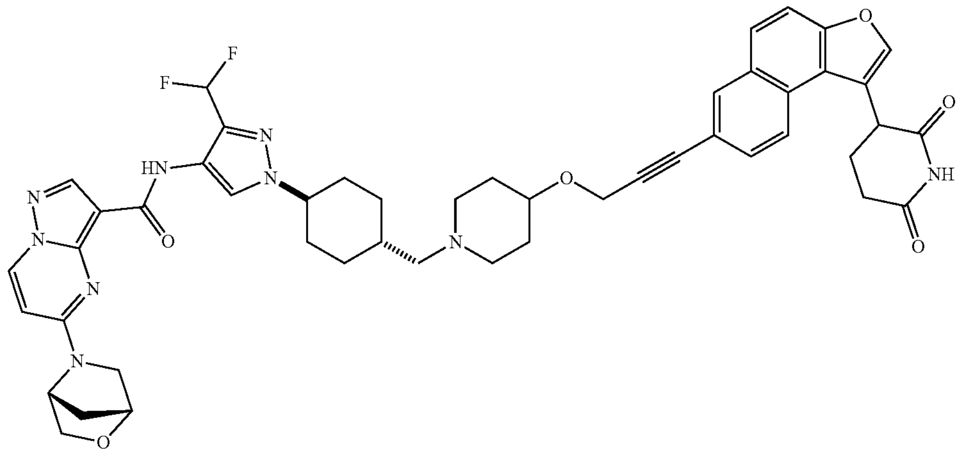

Synthetic Route

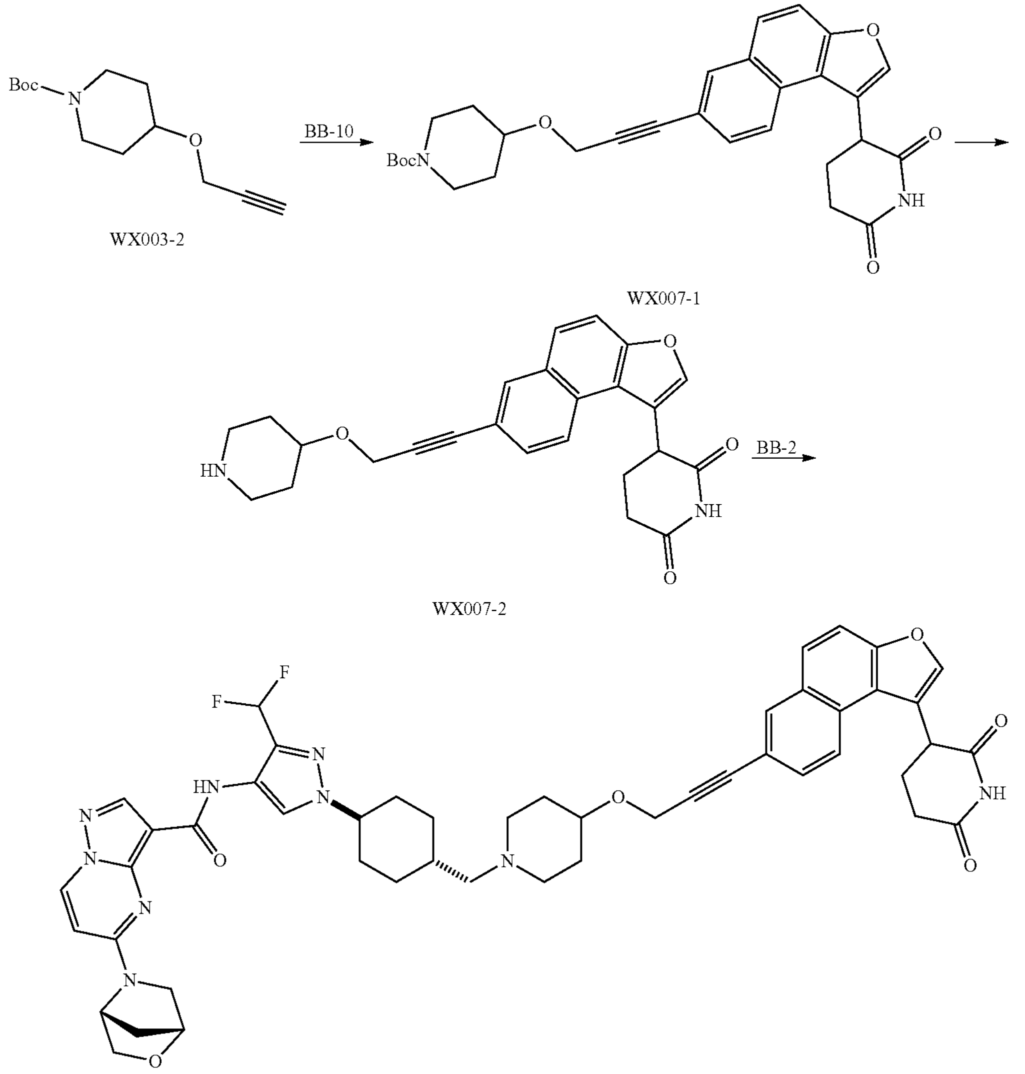

WX003-2

WX007-1

WX007-2

WX007

Step 1: Synthesis of Compound WX007-1

Intermediate BB-10 (300 mg, 838 mol) was dissolved in N,N-dimethylformamide (10 mL) at room temperature under nitrogen atmosphere, then compound WX003-2 (301 mg, 1.26 mmol), cesium carbonate (819 mg, 2.51 mmol), cuprous iodide (32 mg, 168 mol), and bis(triphenylphosphine)palladium(II) chloride (118 mg, 168 mol) were sequentially added thereto, and the reaction mixture was heated to 80° C. and stirred and reacted for 3 hours. After the reaction was completed, the reaction mixture was cooled to room temperature, poured into saturated ammonium chloride solution (100 mL) and extracted with ethyl acetate (10 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=5/1 to 1/1, v/v) to obtain compound WX007-1. MS-ESI m/z: 539.3 $[M+Na]^+$. $^1H$ NMR (400 MHz, $CDCl_3$) δ: 8.11 (d, J=1.2 Hz, 1H), 8.07 (br s, 1H), 7.93 (d, J=8.8 Hz, 1H), 7.76-7.67 (m, 3H), 7.61 (dd, J=1.6 Hz, 8.8 Hz, 1H), 4.53-4.46 (m, 3H), 3.88-3.77 (m, 3H), 3.20-3.10 (m, 2H), 2.89-2.77 (m, 2H), 2.60-2.42 (m, 2H), 1.98-1.88 (m, 2H), 1.68-1.60 (m, 2H), 1.47 (s, 9H).

Step 2: Synthesis of Hydrochloride of Compound WX007-2

Compound WX007-1 (180 mg, 348 mol) was dissolved in ethyl acetate (10 mL) at room temperature, then a solution of hydrochloric acid in ethyl acetate (4 M, 10 mL) was added thereto, and the reaction mixture was stirred and reacted at room temperature for 2 hours. After the reaction was completed, the reaction mixture was concentrated under reduced pressure to remove the solvent. The resulting residue was added with ethyl acetate (10 mL), concentrated again to a volume of 4 to 5 mL, and filtered. The filter cake was rinsed with ethyl acetate (5 mL×2), collected, and dried under vacuum to obtain hydrochloride of compound WX007-2. MS-ESI m/z: 417.0 $[M+H]^+$.

Step 3: Synthesis of Hydrochloride of Compound WX007

Intermediate BB-2 (149 mg, 307 mol) was dissolved in tetrahydrofuran (5 mL) and N,N-dimethylformamide (1 mL) at room temperature under nitrogen atmosphere, then hydrochloride of compound WX007-2 (139 mg, 307 mol) and potassium acetate (90 mg, 921 mol) were added thereto, and the reaction mixture was stirred and reacted at room temperature for 0.5 hours. Sodium triacetoxyborohydride (130 mg, 614 mol) was then added thereto, and the reaction mixture was stirred and reacted at room temperature for 12 hours. After the reaction was completed, the reaction mixture was added with water (1 mL), dried over anhydrous sodium sulfate, filtered, and the filtrate was concentrated under reduced pressure to remove the solvent. The resulting residue was separated by preparative HPLC (chromatographic column: Boston Green ODS 150*30 mm*5 μm; mobile phase: water (0.04% hydrochloric acid)-acetonitrile; acetonitrile %: 27% to 42%, 10 minutes) to obtain hydrochloride of target compound WX007. MS-ESI m/z: 886.4 $[M+H]^+$. $^1H$ NMR (400 MHz, DMSO_$d_6$) δ: 10.95 (s, 1H), 9.51 (d, J=4.4 Hz, 1H), 9.45 (br s, 1H), 8.79 (d, J=7.2 Hz, 1H), 8.40 (d, J=1.6 Hz, 1H), 8.30-8.16 (m, 3H), 8.06 (s, 1H), 7.93-7.85 (m, 2H), 7.58 (d, J=8.0 Hz, 1H), 7.31-6.46 (m, 2H), 5.18 (d, J=79.2 Hz, 1H), 4.83-4.64 (m, 2H), 4.53 (s, 2H), 4.23 (br s, 1H), 4.00-3.72 (m, 3H), 3.67-3.52 (m, 2H), 3.13-2.80 (m, 6H), 2.70-2.59 (m, 1H), 2.30-2.20 (m, 2H), 2.11-1.72 (m, 14H), 1.26-1.15 (m, 2H).

Example 8

WX008

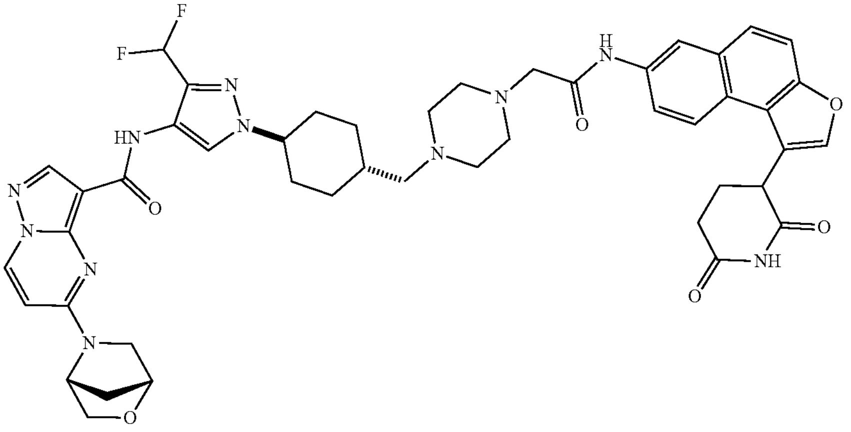

Synthetic Route

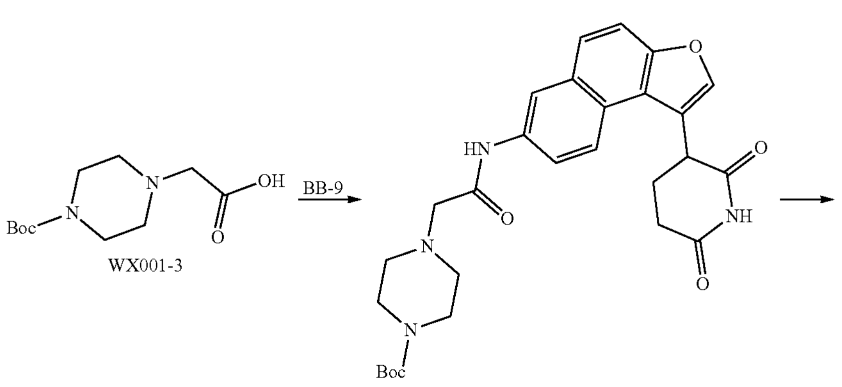

WX001-3

WX008-1

-continued

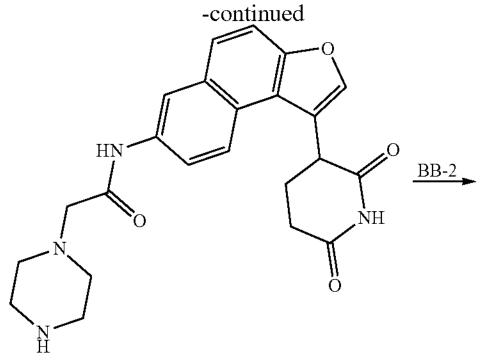

WX008-2

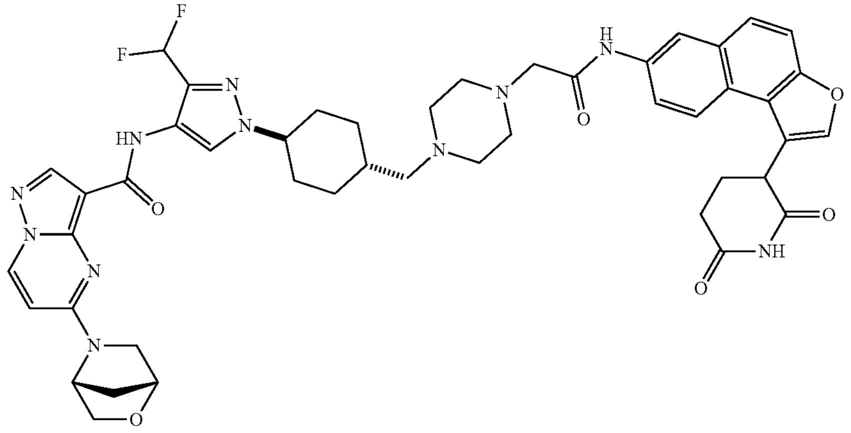

WX008

Step 1: Synthesis of Compound WX008-1

Hydrochloride of compound WX001-3 (387.74 mg, 1.59 mmol) was dissolved in N,N-dimethylformamide (10 mL) at room temperature under nitrogen atmosphere, then 2-(7-azabenzotriazol-1-yl)-N,N,N',N'-tetramethyluronium hexafluorophosphate (482.81 mg, 1.27 mmol), N,N-diisopropylethylamine (410.27 mg, 3.17 mmol), and hydrochloride of intermediate BB-9 (350 mg, 1.06 mmol) were sequentially added thereto, and the reaction mixture was stirred and reacted at room temperature for 12 hours. After the reaction was completed, the reaction mixture was poured into water (50 mL) and extracted with ethyl acetate (10 mL×3). The organic phases were combined, washed with saturated brine (10 mL), dried over anhydrous sodium sulfate, and filtered. The filtrate was concentrated under reduced pressure to remove the solvent, and the resulting residue was separated by column chromatography (eluent: petroleum ether/ethyl acetate=5/1 to 1/1, v/v) to obtain compound WX008-1. MS-ESI m/z: 521.1 $[M+H]^+$. $^{1}$H NMR (400 MHz, $CDCl_3$) δ: 9.25 (s, 1H), 8.28 (s, 1H), 8.10 (br s, 1H), 7.95 (d, J=8.8 Hz, 1H), 7.77-7.71 (m, 2H), 7.69-7.65 (m, 2H), 4.52-4.45 (m, 1H), 3.60-3.51 (m, 4H), 3.24 (s, 2H), 2.84-2.76 (m, 2H), 2.68-2.60 (m, 4H), 2.56-2.46 (m, 2H), 1.49 (s, 9H).

Step 2: Synthesis of Hydrochloride of Compound WX008-2

Compound WX008-1 (160 mg, 288 mol) was dissolved in a solution of hydrochloric acid in 1,4-dioxane (4 M, 12 mL) at room temperature, and the reaction mixture was stirred and reacted at room temperature for 12 hours. After the reaction was completed, the reaction mixture was concentrated under reduced pressure to remove the solvent. The residue was added with ethyl acetate (20 mL) and concentrated under reduced pressure again to remove the solvent to obtain hydrochloride of compound WX008-2. MS-ESI m/z: 421.1 $[M+H]^+$.

Step 3: Synthesis of Hydrochloride of Compound WX008

Intermediate BB-2 (140 mg, 288.37 mol) was dissolved in tetrahydrofuran (5 mL) and N,N-dimethylformamide (1 mL) at room temperature under nitrogen atmosphere, then hydrochloride of compound WX008-2 (124.03 mg, 271.44 mol), potassium acetate (84.90 mg, 865.11 mol), and acetic acid (8.66 mg, 144.19 mol) were added thereto, and the reaction mixture was stirred and reacted at room temperature for 0.5 hours. Sodium triacetoxyborohydride (183 mg, 865 mol) was then added thereto, and the reaction mixture was stirred and reacted at room temperature for 4 hours. After the reaction was completed, the reaction mixture was added with water (20 mL) and extracted with ethyl acetate (15 mL×3) to precipitate a solid. The aqueous phase and organic phase were discarded, and the solid was dissolved in N,N-dimethylformamide (5 mL). The resulting mixture was separated by preparative HPLC (chromatographic column: Boston Green ODS 150*30 mm*5 μm; mobile phase: water (0.04% hydrochloric acid)-acetonitrile; acetonitrile %: 28% to 48%, 10 minutes) to obtain hydrochloride of target compound WX008. MS-ESI m/z: 890.5 $[M+H]^+$. $^{1}$H NMR (400 MHz, DMSO_$d_6$) δ: 10.95 (s, 1H), 10.68 (br s, 1H), 9.51 (d, J=6.8 Hz, 1H), 8.78 (d, J=7.6 Hz, 1H), 8.40 (s, 2H), 8.25 (d, J=5.6 Hz, 1H), 8.17 (d, J=8.8 Hz, 1H), 8.00 (s, 1H), 7.80-7.73 (m, 3H), 7.34-6.95 (m, 1H), 6.90-6.42 (m, 1H), 5.17 (d, J=81.2 Hz, 1H), 4.76 (d, J=20.8 Hz, 1H), 4.66 (dd, J=4.0 Hz, 11.6 Hz, 1H), 4.29-4.19 (m, 1H), 4.02-3.88 (m, 3H), 3.84-3.72 (m, 4H), 3.65-3.59 (m, 4H), 3.10-3.00 (m, 1H), 2.93-2.82 (m, 1H), 2.68-2.59 (m, 1H), 2.43-2.21 (m, 4H), 2.12-1.72 (m, 11H), 1.25-1.16 (m, 3H).
Example 9
WX009
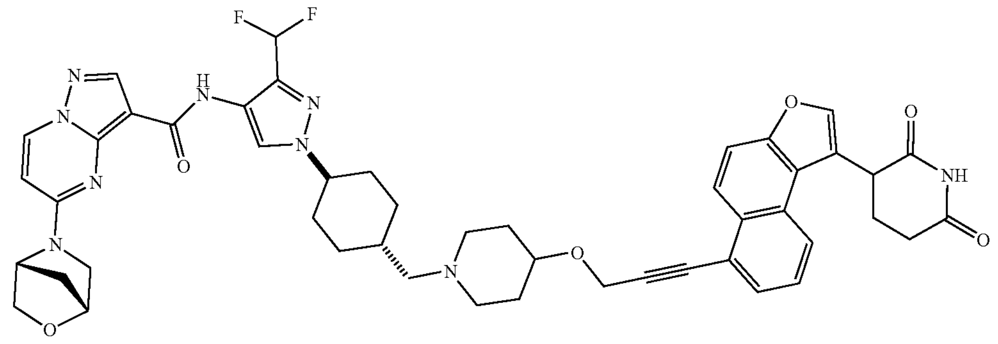
Synthetic Route
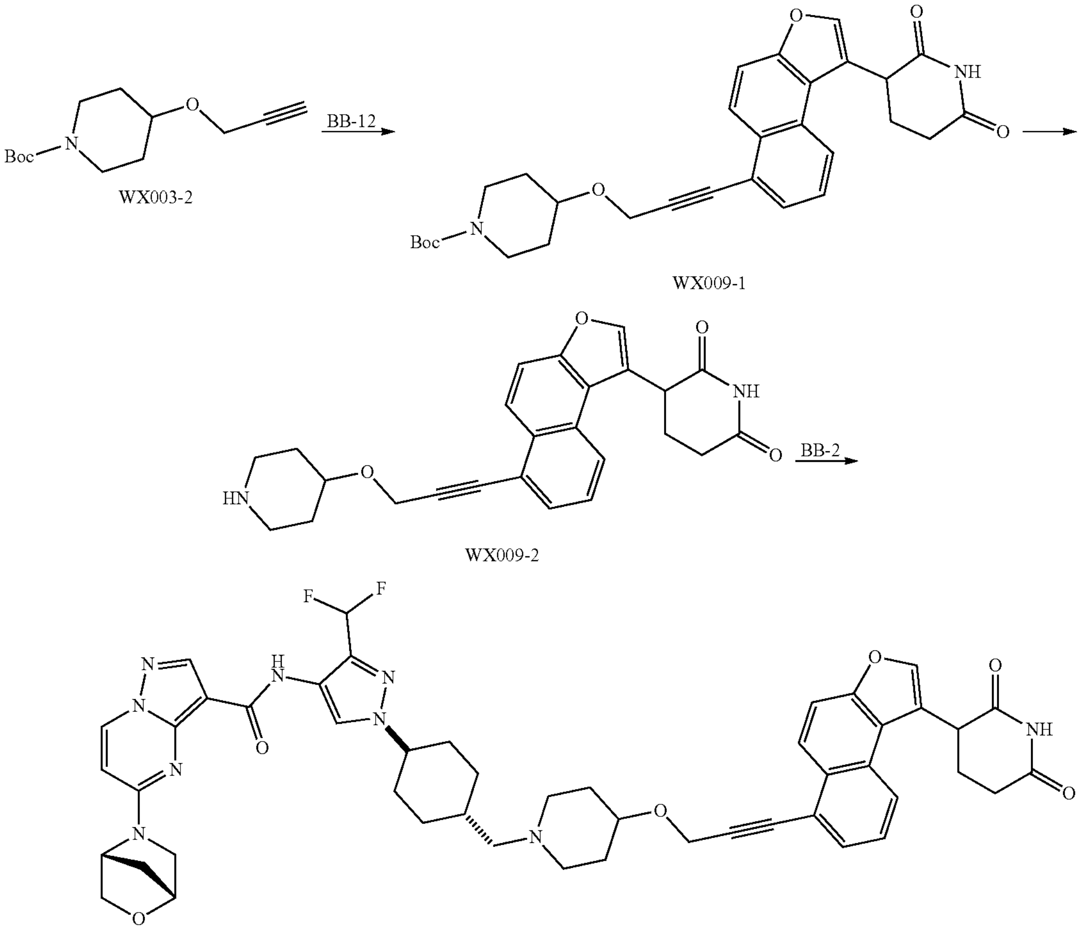
WX003-2
WX009-1
WX009-2
WX009

Step 1: Synthesis of Compound WX009-1

To dimethyl sulfoxide (4 mL) were added compound WX003-2 (400.87 mg, 1.68 mmol), intermediate BB-12 (0.3 g, 837.55 mol), cuprous iodide (31.90 mg, 167.51 mol), bis(triphenylphosphine)palladium(II) chloride (117.58 mg, 167.51 mol), and N,N-diisopropylethylamine (216.50 mg, 1.68 mmol) at room temperature under nitrogen atmosphere, and the reaction mixture was heated to 85° C. and stirred and reacted for 2.5 hours. After the reaction was completed, the reaction mixture was cooled to room temperature, added with water (2 mL), and extracted with ethyl acetate (5 mL×2). The organic phases were combined, washed with saturated brine (5 mL), dried over anhydrous sodium sulfate, filtered, and the filtrate was concentrated under reduced pressure to remove the solvent. The resulting residue was separated by thin-layer chromatography (eluent: petroleum ether/ethyl acetate/dichloromethane=1/1/1, v/v/v) to obtain compound WX009-1. MS-ESI m/z: 417.1 $[M+H-100]^+$. $^1H$ NMR (400 MHz, $CDCl_3$) δ: 8.35 (d, J=8.8 Hz, 1H), 8.06 (s, 1H), 7.99 (d, J=8.4 Hz, 1H), 7.76 (d, J=9.2 Hz, 1H), 7.73-7.68 (m, 2H), 7.54 (dd, J=7.2 Hz, 8.8 Hz, 1H), 4.60 (s, 2H), 4.51 (dd, J=5.2 Hz, 8.8 Hz, 1H), 3.92-3.79 (m, 4H), 3.20-3.12 (m, 2H), 2.87-2.77 (m, 1H), 2.56-2.46 (m, 1H), 2.01-1.92 (m, 2H), 1.91-1.83 (m, 1H), 1.71-1.62 (m, 2H), 1.47 (s, 9H).

Step 2: Synthesis of Trifluoroacetate of Compound WX009-2

Compound WX009-1 (0.1 g, 193.58 mol) was dissolved in dichloromethane (2 mL) at room temperature, then trifluoroacetic acid (617.19 mg, 5.41 mmol) was added thereto, and the reaction mixture was stirred and reacted at room temperature for 2 hours. After the reaction was completed, the reaction mixture was concentrated under reduced pressure to remove the solvent to obtain trifluoroacetate of compound WX009-2. MS-ESI m/z: 417.1 $[M+H]^+$.

Step 3: Synthesis of Hydrochloride of Compound WX009

To a mixed solvent of glacial acetic acid (0.1 mL) and N,N-dimethylformamide (2 mL) were added intermediate BB-2 (90 mg, 185.38 mol), trifluoroacetate of compound WX009-2 (98.34 mg, 185.38 mol), and potassium acetate (54.58 mg, 556.14 mol) at room temperature under nitrogen atmosphere, and the reaction mixture was stirred and reacted at room temperature for 2 hours. Sodium triacetoxyborohydride (117.87 mg, 556.14 mol) was then added thereto, and the reaction mixture was stirred and reacted at room temperature for 15 hours. After the reaction was completed, the reaction mixture was added with saturated ammonium chloride (10 mL) and extracted with ethyl acetate (5 mL×2) to precipitate a large amount of insoluble material, and the organic phase and insoluble material were concentrated under reduced pressure to remove the solvent. The resulting residue was purified by preparative HPLC (chromatographic column: Phenomenex Luna 80*30 mm*3 μm; mobile phase: water (0.04% hydrochloric acid)-acetonitrile; acetonitrile %: 25% to 45%, 8 minutes) to obtain hydrochloride of target compound WX009. MS-ESI m/z: 886.4 $[M+H]^+$. $^1H$ NMR (400 MHz, $CD_3OD$): 8.54-8.48 (m, 1H), 8.38-8.27 (m, 3H), 8.21 (d, J=8.8 Hz, 1H), 7.89 (s, 1H), 7.82-7.77 (m, 1H), 7.69 (d, J=7.2 Hz, 1H), 7.60-7.54 (m, 1H), 7.04-6.71 (m, 2H), 6.46-6.41 (m, 1H), 5.43 (s, 1H), 4.83-4.76 (m, 4H), 4.69-4.62 (m, 3H), 4.26-4.14 (m, 2H), 3.97-3.90 (m, 2H), 3.75-3.63 (m, 2H), 3.54-3.45 (m, 2H), 3.20-3.06 (m, 2H), 2.96-2.4 (m, 1H), 2.81-2.71 (m, 1H), 2.52-2.39 (m, 2H), 2.35-2.15 (m, 4H), 2.13-1.87 (m, 9H), 1.40-1.25 (m, 2H)

Example 10

WX010

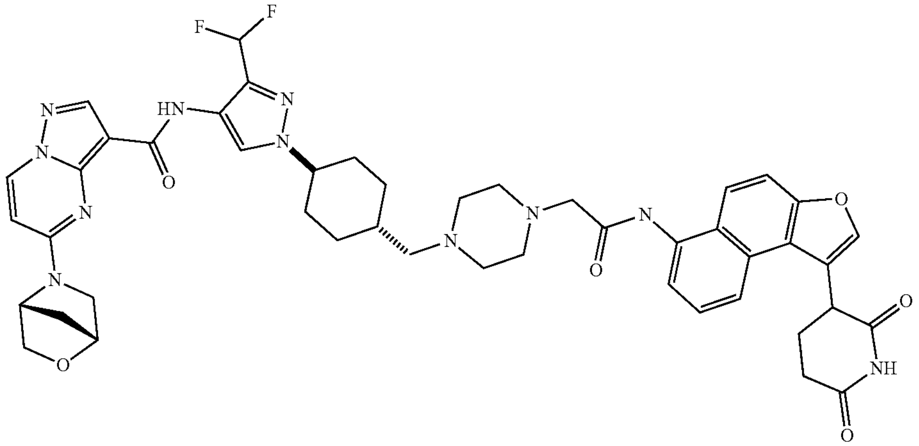

Synthetic Route

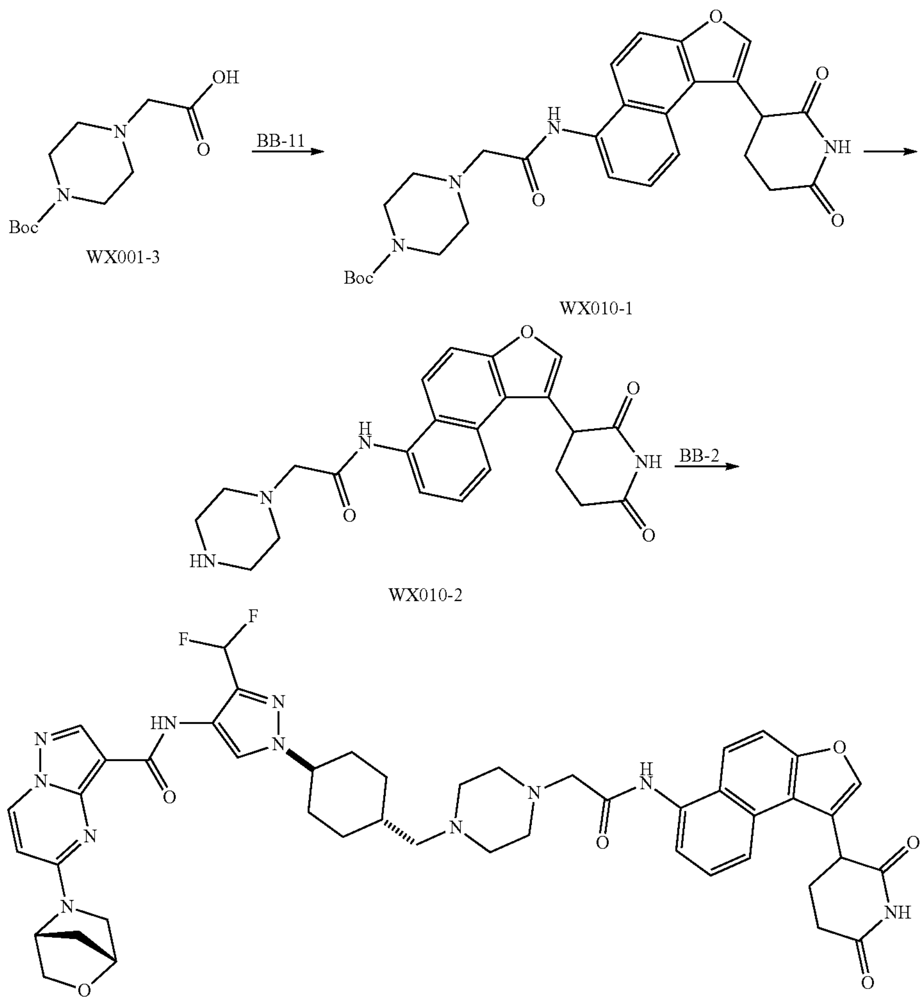

WX001-3
WX010-1
WX010-2
WX010

Step 1: Synthesis of Compound WX010-1

Hydrochloride of compound WX001-3 (186.73 mg, 665.12 mol) was dissolved in N,N-dimethylformamide (5 mL) at room temperature under nitrogen atmosphere, then N,N-diisopropylethylamine (390.73 mg, 3.02 mmol) and 2-(7-azabenzotriazol-1-yl)-N,N,N',N'-tetramethyluronium hexafluorophosphate (344.86 mg, 906.99 mol) were added thereto, and the reaction mixture was stirred and reacted at room temperature for 0.5 hours. Hydrochloride of intermediate BB-11 (0.2 g, 604.66 mol) was added thereto, and the reaction mixture was stirred and reacted at room temperature for another 1.5 hours. After the reaction was completed, the reaction mixture was added with water (30 mL) and extracted with ethyl acetate (20 mL×3). The organic phases were combined, washed with 10% saline (30 mL×2), dried over anhydrous sodium sulfate, filtered, and the filtrate was concentrated under reduced pressure to remove the solvent. The residue was separated by column chromatography (eluent: petroleum ether/ethyl acetate=1/2 to 0/1) to obtain compound WX010-1. MS-ESI m/z: 521.3 $[M+H]^+$.

Step 2: Synthesis of Hydrochloride of Compound WX010-2

Compound WX010-1 (290 mg, 557.08 mol) was dissolved in dichloromethane (2 mL) at room temperature, then a solution of hydrochloric acid in ethyl acetate (4 M, 5 mL) was added thereto, and the reaction mixture was stirred and reacted at room temperature for 12 hours. After the reaction was completed, the reaction mixture was filtered. The filter cake was rinsed with ethyl acetate (10 mL), collected, and dried under vacuum to obtain hydrochloride of compound WX010-2. MS-ESI m/z: 421.2 $[M+H]^+$. $^1H$ NMR (400 MHz, DMSO_$d_4$) δ: 10.96 (s, 1H), 10.77 (s, 1H), 9.85 (s, 2H), 8.16-8.03 (m, 3H), 7.86 (d, J=9.6 Hz, 1H), 7.67-7.57 (m, 2H), 4.71 (dd, J=3.6 Hz, 12.0 Hz, 1H), 4.38 (s, 2H), 3.70-3.55 (m, 4H), 3.52-3.35 (m, 4H), 2.97-2.82 (m, 1H), 2.68-2.59 (m, 1H), 2.48-2.37 (m, 1H), 2.35-2.22 (m, 1H).

Step 3: Synthesis of Hydrochloride of Compound WX010

Intermediate BB-2 (190 mg, 391.36 mol) and hydrochloride of compound WX010-2 (187.76 mg, 410.93 mol) were dissolved in N,N-dimethylformamide (1 mL) at room temperature under nitrogen atmosphere, then potassium acetate (115.22 mg, 1.17 mmol) was added thereto, and the reaction mixture was stirred and reacted at room temperature for 2 hours.

Sodium triacetoxyborohydride (331.78 mg, 1.57 mmol) was then added thereto, and the reaction mixture was stirred and reacted at room temperature for 40 minutes. After the reaction was completed, the reaction mixture was added with 1 M hydrochloric acid (4 mL) and concentrated under reduced pressure to remove the solvent. The resulting residue was purified by preparative HPLC (chromatographic column: Phenomenex Luna 80*30 mm*3 μm; mobile phase: water (0.04% hydrochloric acid)-acetonitrile; acetonitrile %: 10% to 30%, 8 minutes) to obtain hydrochloride of target compound WX010. MS-ESI m/z: 890.2 $[M+H]^+$. $^1H$ NMR (400 MHz, DMSO_$d_6$) δ: 10.96 (s, 1H), 10.59 (s, 1H), 9.51 (d, J=6.4 Hz, 1H), 8.79 (d, J=8.0 Hz, 1H), 8.41 (d, J=4.0 Hz, 1H), 8.26 (d, J=5.6 Hz, 1H), 8.15-8.08 (m, 1H), 8.08-8.00 (m, 2H), 7.87 (d, J=9.2 Hz, 1H), 7.68-7.57 (m, 2H), 7.26-6.96 (m, 1H), 6.90-6.40 (m, 1H), 5.18 (d, J=80.0 Hz, 1H), 4.82-4.65 (m, 2H), 4.34-4.16 (m, 2H), 3.81 (s, 2H), 3.75-3.59 (m, 8H), 3.13-3.01 (m, 2H), 2.95-2.85 (m, 1H), 2.70-2.59 (m, 2H), 2.44-2.38 (m, 1H), 2.36-2.20 (m, 2H), 2.13-1.69 (m, 10H), 1.28-1.12 (m, 2H).

Example 11

WX011

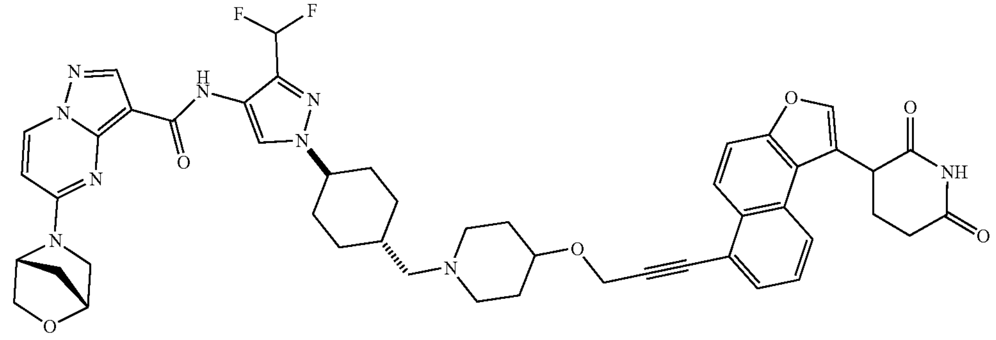

Synthetic Route

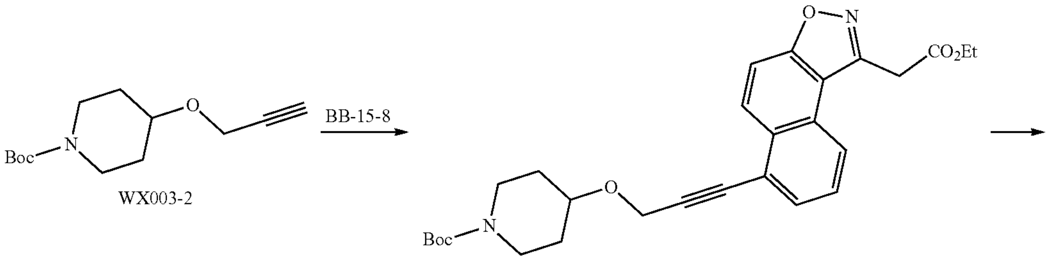

WX003-2

WX011-1

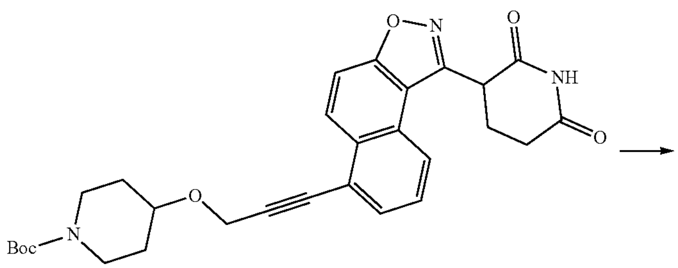

WX011-2

-continued

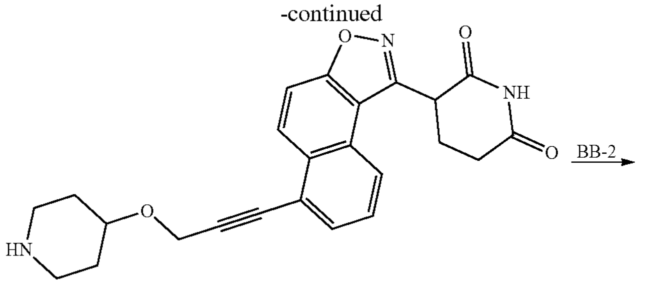

WX011-3

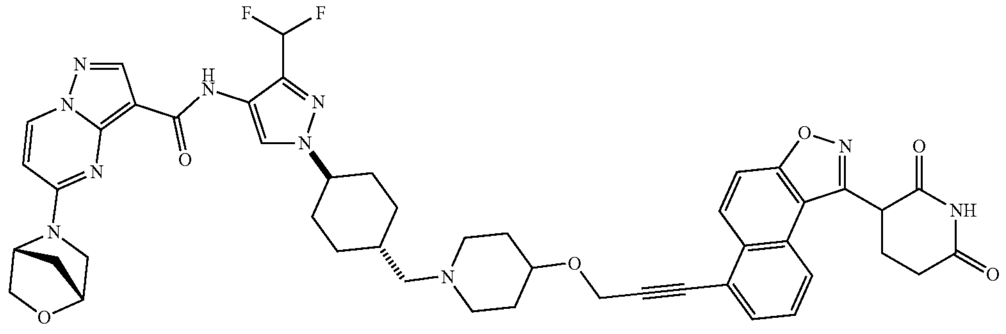

WX011

Step 1: Synthesis of Compound WX011-1

Intermediate BB-15-8 (0.5 g, 1.50 mmol) and compound WX003-2 (716.14 mg, 2.99 mmol) were dissolved in dimethyl sulfoxide (5 mL) at room temperature under nitrogen atmosphere, then bis(triphenylphosphine)palladium(II) chloride (210.05 mg, 299.25 mol), cuprous iodide (56.99 mg, 299.25 mol), and N,N-diisopropylethylamine (386.76 mg, 2.99 mmol) were sequentially added thereto, and the reaction mixture was heated to 85° C. and stirred and reacted for 2 hours. After the reaction was completed, the reaction mixture was cooled to room temperature, added with water (20 mL), and extracted with ethyl acetate (20 mL×3). The organic phases were combined, washed with 10% saline (30 mL×3), dried over anhydrous sodium sulfate, filtered, and the filtrate was concentrated under reduced pressure to remove the solvent. The residue was separated by column chromatography (eluent: petroleum ether/ethyl acetate=1/0 to 6/1) to obtain compound WX011-1. $^1$H NMR (400 MHz, $CDCl_3$) δ: 8.53 (d, J=9.2 Hz, 1H), 8.11 (d, J=8.0 Hz, 1H), 7.78 (d, J=9.2 Hz, 1H), 7.75 (d, J=7.6 Hz, 1H), 7.63 (t, J=8.0 Hz, 1H), 4.59 (s, 2H), 4.34 (s, 2H), 4.22 (q, J=7.0 Hz, 2H), 3.89-3.76 (m, 3H), 3.22-3.12 (m, 2H), 2.00-1.91 (m, 2H), 1.72-1.62 (m, 2H), 1.47 (s, 9H), 1.21 (t, J=7.2 Hz, 3H).

Step 2: Synthesis of Compound WX011-2

Compound WX011-1 (0.3 g, 609.06 mol) was dissolved in tetrahydrofuran (5 mL) at room temperature under nitrogen atmosphere, and the reaction mixture was cooled to 0° C. Acrylamide (47.62 mg, 669.97 mol) and potassium tert-butoxide (82.01 mg, 730.87 mol) were then added thereto, and the reaction mixture was warmed to room temperature and stirred and reacted for 1.5 hours. After the reaction was completed, the reaction mixture was poured into 1 M hydrochloric acid to adjust the pH to 3 to 4, added with water (20 mL), and extracted with ethyl acetate (20 mL×3). The organic phases were combined, washed with saturated brine (30 mL), dried over anhydrous sodium sulfate, filtered, and the filtrate was concentrated under reduced pressure to remove the solvent. The resulting residue was separated by column chromatography (eluent: petroleum ether/ethyl acetate=3/1 to 1/1, v/v) to obtain compound WX011-2. MS-ESI m/z: 418.2 [M+H−100]$^+$. $^1$H NMR (400 MHz, $CDCl_3$) δ: 8.58 (d, J=9.2 Hz, 1H), 8.13 (s, 1H), 8.03 (d, J=8.4 Hz, 1H), 7.81 (d, J=9.6 Hz, 1H), 7.77 (dd, J=0.8 Hz, 7.2 Hz, 1H), 7.65 (t, J=8.0 Hz, 1H), 4.74 (dd, J=4.8 Hz, 8.4 Hz, 1H), 4.60 (s, 2H), 3.90-3.76 (m, 3H), 3.23-3.11 (m, 2H), 3.01-2.87 (m, 1H), 2.85-2.67 (m, 2H), 2.65-2.52 (m, 1H), 2.01-1.89 (m, 2H), 1.70-1.62 (m, 2H), 1.47 (s, 9H).

Step 3: Synthesis of Trifluoroacetate of Compound WX011-3

Compound WX011-2 (0.1 g, 193.21 mol) was dissolved in dichloromethane (2 mL) at room temperature, then trifluoroacetic acid (61.72 mg, 541.29 mol, 40.08 L) was added thereto, and the reaction mixture was stirred and reacted at room temperature for 2 hours. After the reaction was completed, the reaction mixture was concentrated under reduced pressure to remove the solvent to obtain trifluoroacetate of compound WX011-3.

Step 4: Synthesis of Hydrochloride of Compound WX011

To a mixed solvent of glacial acetic acid (0.1 mL) and N,N-dimethylformamide (1 mL) were sequentially added intermediate BB-2 (90 mg, 185.38 mol), trifluoroacetate of compound WX011-3 (98.53 mg, 185.38 mol), and potassium acetate (54.58 mg, 556.14 mol) at room temperature under nitrogen atmosphere, and the reaction mixture was stirred and reacted at room temperature for 2 hours. Sodium triacetoxyborohydride (117.87 mg, 556.14 mol) was then added thereto, and the reaction mixture was stirred and reacted at room temperature for 15 hours. After the reaction was completed, the reaction mixture was added with saturated ammonium chloride (10 mL), extracted with ethyl acetate (5 mL×2) to precipitate a large amount of insoluble material, and the organic phase and insoluble material were concentrated under reduced pressure to remove the solvent. The resulting residue was purified by preparative HPLC (chromatographic column: Phenomenex Luna 80*30 mm*3 μm; mobile phase: water (0.04% hydrochloric acid)-acetonitrile; acetonitrile %: 25% to 45%, 8 minutes) to obtain hydrochloride of target compound WX011. MS-ESI m/z: 887.4 $[M+H]^+$. $^1H$ NMR (400 MHz, MeOD_$d_4$) δ: 8.59 (d, J=9.2 Hz, 1H), 8.51 (t, J=7.6 Hz, 1H), 8.37 (d, J=9.2 Hz, 1H), 8.33-8.26 (m, 2H), 7.91 (d, J=9.2 Hz, 1H), 7.79 (d, J=7.6 Hz, 1H), 7.75-7.68 (m, 1H), 7.06-6.72 (m, 1H), 6.44 (d, J=7.6 Hz, 1H), 5.44 (s, 1H), 5.01 (d, J=4.8 Hz, 10.4 Hz, 1H), 4.96-4.92 (m, 1H), 4.84-4.78 (m, 2H), 4.70 (s, 2H), 4.28-4.15 (m, 2H), 3.98-3.92 (m, 2H), 3.76-3.65 (m, 2H), 3.57-3.46 (m, 2H), 3.24-3.06 (m, 3H), 2.95-2.66 (m, 3H), 2.59-2.50 (m, 1H), 2.47-1.87 (m, 13H), 1.42-1.28 (m, 2H).

Example 12

WX012

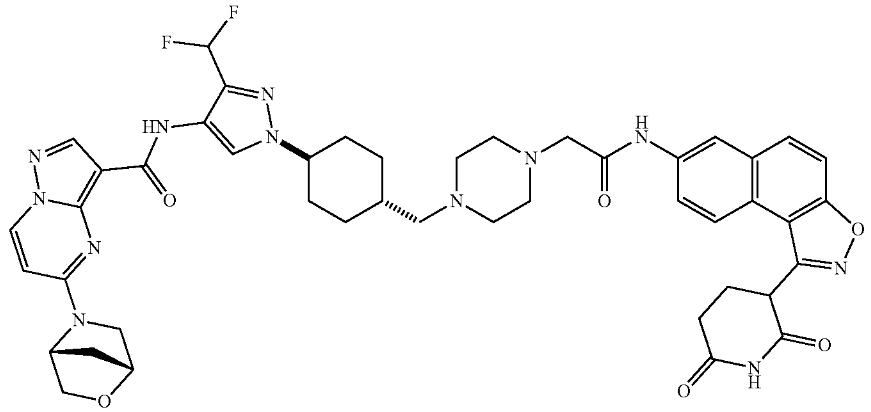

Synthetic Route

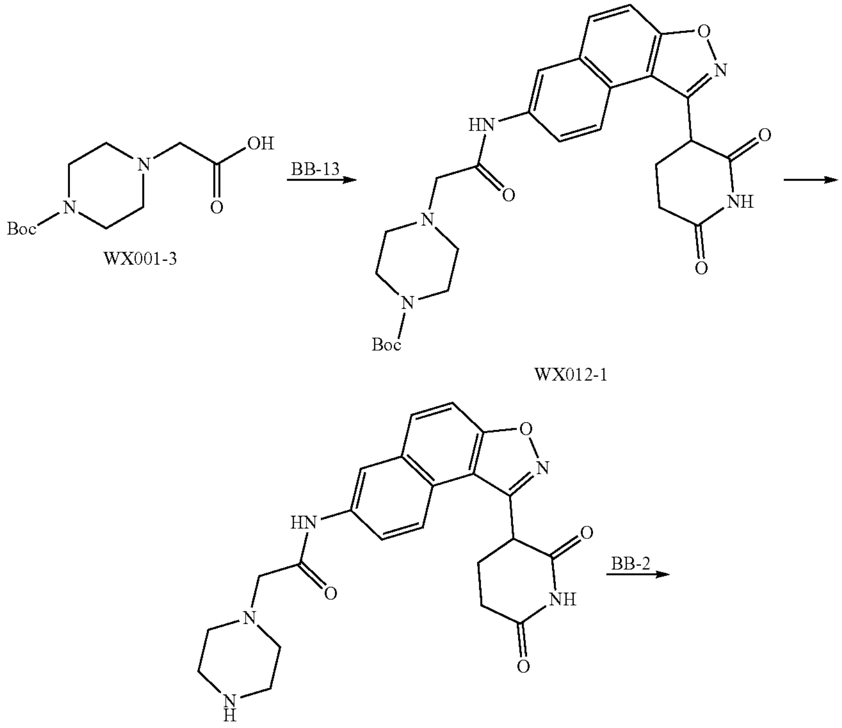

WX001-3

WX012-1

WX012-2

-continued

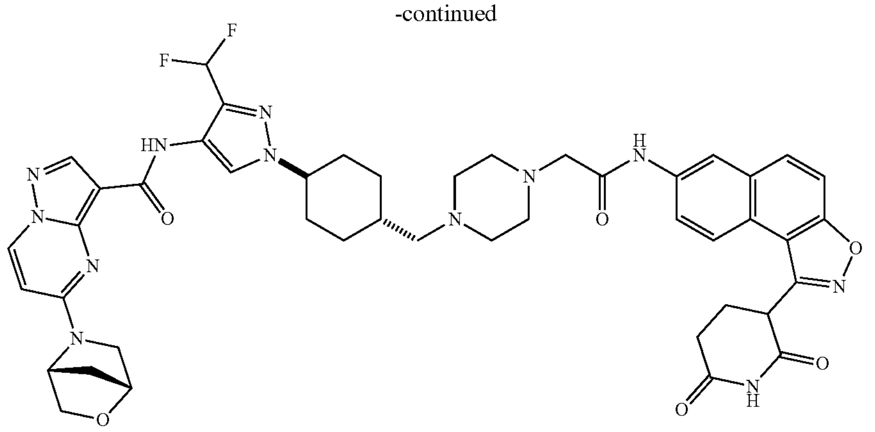

WX012

Step 1: Synthesis of Compound WX012-1

Hydrochloride of compound WX001-3 (93.09 mg, 331.57 mol) was dissolved in N,N-dimethylformamide (2 mL) at room temperature under nitrogen atmosphere, then N,N-diisopropylethylamine (194.78 mg, 1.51 mmol) and 2-(7-azabenzotriazol-1-yl)-N,N,N',N'-tetramethyluronium hexafluorophosphate (171.92 mg, 452.14 mol) were sequentially added thereto, and the reaction mixture was stirred and reacted at room temperature for 0.5 hours. Hydrochloride of intermediate BB-13 (0.1 g, 301.43 mol) was then added thereto, and the reaction mixture was stirred and reacted at room temperature for another 2 hours. After the reaction was completed, the reaction mixture was added with water (20 mL) and extracted with ethyl acetate (20 mL×3). The organic phases were combined, washed with 10% saline (30 mL×3), dried over anhydrous sodium sulfate, filtered, and the filtrate was concentrated under reduced pressure to remove the solvent to obtain compound WX012-1. MS-ESI m/z: 522.3 $[M+H]^+$.

Step 2: Synthesis of Hydrochloride of Compound WX012-2

Compound WX012-1 (150 mg, 287.60 mol) was dissolved in ethyl acetate (1 mL) at room temperature, then a solution of hydrochloric acid in ethyl acetate (4 M, 2 mL) was added thereto, and the reaction mixture was stirred and reacted at room temperature for 16 hours. After the reaction was completed, the reaction mixture was filtered. The filter cake was rinsed with ethyl acetate (10 mL), collected, and dried under vacuum to obtain hydrochloride of compound WX012-2. MS-ESI m/z: 422.2 $[M+H]^+$. $^1H$ NMR (400 MHz, DMSO_$d_6$) δ: 11.25 (s, 1H), 11.14 (s, 1H), 9.85 (s, 2H), 8.52 (d, J=2.0 Hz, 1H), 8.25 (d, J=8.8 Hz, 1H), 8.14 (d, J=9.2 Hz, 1H), 7.96-7.88 (m, 2H), 5.05 (dd, J=4.4 Hz, 11.2 Hz, 1H), 4.29 (s, 2H), 3.60 (s, 4H), 3.45 (s, 4H), 2.90-2.78 (m, 1H), 2.70-2.65 (m, 1H), 2.64-2.56 (m, 1H), 2.45-2.33 (m, 1H).

Step 3: Synthesis of Hydrochloride of Compound WX012

Intermediate BB-2 (95 mg, 195.68 mol) and hydrochloride of compound WX012-2 (98.56 mg, 215.25 mol) were dissolved in N,N-dimethylformamide (2 mL) at room temperature, then potassium acetate (57.61 mg, 587.04 mol) and acetic acid (5.88 mg, 97.84 mol) were sequentially added thereto, and the reaction mixture was stirred and reacted at room temperature for 2 hours. Sodium triacetoxyborohydride (165.89 mg, 782.72 mol) was then added thereto, and the reaction mixture was stirred and reacted at room temperature for another 10 hours. After the reaction was completed, the reaction mixture was added with saturated ammonium chloride solution (20 mL) to precipitate a solid, filtered, and the filter cake was collected. The resulting filter cake was separated by preparative HPLC (chromatographic column: Phenomenex Luna 80*40 mm*3 μm; mobile phase: water (0.04% hydrochloric acid)-acetonitrile; acetonitrile %: 18% to 38%, 7 minutes) to obtain hydrochloride of target compound WX012. MS-ESI m/z: 891.5 $[M+H]^+$. $^1H$ NMR (400 MHz, DMSO_$d_6$) δ: 11.14 (s, 1H), 11.06 (s, 1H), 9.51 (d, J=6.0 Hz, 1H), 8.78 (d, J=7.2 Hz, 1H), 8.51 (d, J=1.6 Hz, 1H), 8.40 (d, J=3.6 Hz, 1H), 8.26 (d, J=5.6 Hz, 2H), 8.14 (d, J=9.2 Hz, 1H), 7.96-7.87 (m, 2H), 7.27-6.96 (m, 1H), 6.90-6.43 (m, 1H), 5.34-4.98 (m, 2H), 4.76 (d, J=20.0 Hz, 1H), 4.36-4.08 (m, 4H), 3.83-3.71 (m, 5H), 3.15-3.00 (m, 2H), 2.91-2.77 (m, 2H), 2.71-2.58 (m, 4H), 2.43-2.31 (m, 2H), 2.14-1.72 (m, 10H), 1.30-1.10 (m, 2H).

Example 13
WX013
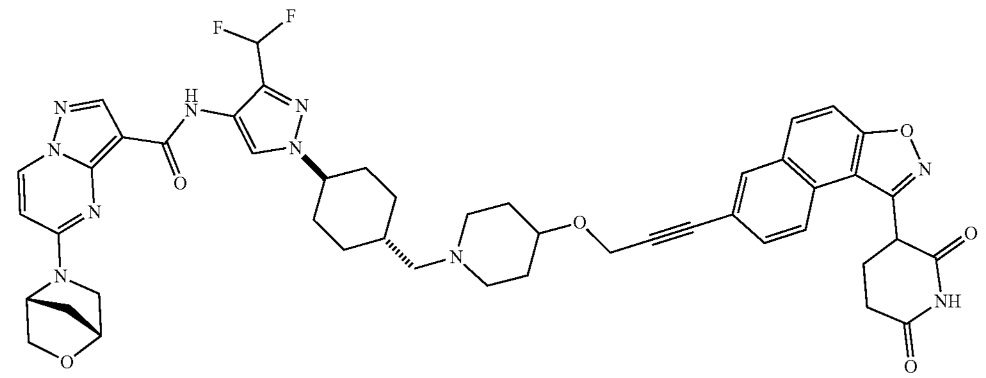
Synthetic Route
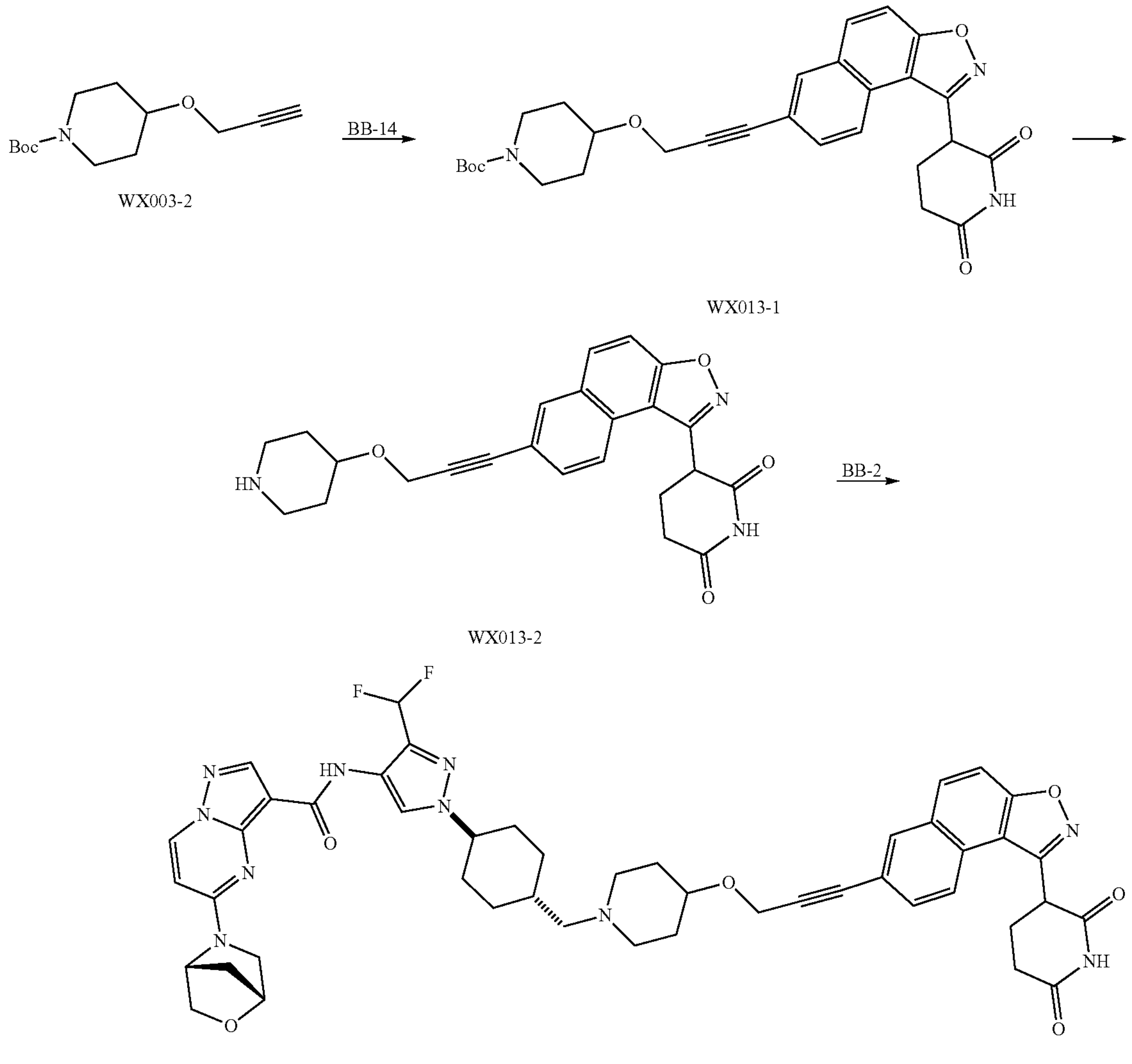
WX003-2
WX013-1
WX013-2
WX013

Step 1: Synthesis of Compound WX013-1

To dimethyl sulfoxide (4 mL) were added compound WX003-2 (399.77 mg, 1.67 mmol), intermediate BB-14 (0.3 g, 835.25 mol), cuprous iodide (31.81 mg, 167.05 mol), bis(triphenylphosphine)palladium(II) chloride (117.25 mg, 167.05 mol), and N,N-diisopropylethylamine (215.90 mg, 1.67 mmol) at room temperature under nitrogen atmosphere, and the reaction mixture was heated to 85° C. and stirred and reacted for 2.5 hours.

After the reaction was completed, the reaction mixture was cooled to room temperature, added with water (2 mL), and extracted with ethyl acetate (5 mL×2). The organic phases were combined, washed with saturated brine (5 mL), dried over anhydrous sodium sulfate, filtered, and the filtrate was concentrated under reduced pressure to remove the solvent. The resulting residue was purified by thin-layer chromatography (eluent: petroleum ether/ethyl acetate/dichloromethane=1/1/1, v/v/v) to obtain compound WX013-1. MS-ESI m/z: 418.2 $[M+H-100]^+$. $^1H$ NMR (400 MHz, $CDCl_3$) δ: 8.13 (br s, 2H), 7.97 (t, J=9.2 Hz, 2H), 7.73 (dd, J=8.8 Hz, 15.2 Hz, 2H), 4.72 (dd, J=4.8 Hz, 8.4 Hz, 1H), 4.49 (s, 2H), 3.91-3.68 (m, 3H), 3.19-3.11 (m, 2H), 3.00-2.89 (m, 1H), 2.85-2.68 (m, 2H), 2.64-2.54 (m, 1H), 1.99-1.88 (m, 2H), 1.68-1.61 (m, 2H), 1.47 (s, 9H).

Step 2: Synthesis of Trifluoroacetate of Compound WX013-2

Compound WX013-1 (0.1 g, 193.21 mol) was dissolved in dichloromethane (2 mL) at room temperature, then trifluoroacetic acid (616.00 mg, 5.40 mmol) was added thereto, and the reaction mixture was stirred and reacted at room temperature for 1 hour. After the reaction was completed, the reaction mixture was concentrated under reduced pressure to remove the solvent to obtain trifluoroacetate of compound WX013-2. MS-ESI m/z: 418.2 $[M+H]^+$.

Step 3: Synthesis of Hydrochloride of Compound WX013

To a mixed solvent of N,N-dimethylformamide (1 mL) and glacial acetic acid (0.1 mL) were added intermediate BB-2 (90 mg, 185.38 mol), trifluoroacetate of compound WX013-2 (98.53 mg, 185.38 mol), and potassium acetate (54.58 mg, 556.14 mol) at room temperature under nitrogen atmosphere, and the reaction mixture was stirred and reacted at room temperature for 2 hours. Sodium triacetoxyborohydride (117.87 mg, 556.14 mol) was then added thereto, and the reaction mixture was stirred and reacted at room temperature for 15 hours. After the reaction was completed, the reaction mixture was added with 1 M hydrochloric acid (1 mL), and the resulting mixture was separated by preparative HPLC (chromatographic column: Phenomenex Luna 80*30 mm*3 μm; mobile phase: water (0.04% hydrochloric acid)-acetonitrile; acetonitrile %: 20% to 40%, 8 minutes) to obtain hydrochloride of target compound WX013. MS-ESI m/z: 887.4 $[M+H]^+$. $^1H$ NMR (400 MHz, $CD_3OD$) δ: 9.74 (s, 1H), 8.55-8.49 (m, 1H), 8.39-8.34 (m, 1H), 8.32-8.28 (m, 1H), 8.24-8.18 (m, 2H), 8.09 (d, J=8.8 Hz, 1H), 7.84 (d, J=9.2 Hz, 1H), 7.75-7.70 (m, 1H), 7.04-6.72 (m, 1H), 6.44 (d, J=7.6 Hz, 1H), 5.44 (s, 1H), 4.96 (dd, J=4.8 Hz, 10.4 Hz, 1H), 4.82-4.78 (m, 2H), 4.58-4.55 (m, 2H), 4.28-4.17 (m, 1H), 4.14-4.09 (m, 1H), 3.99-3.84 (m, 2H), 3.75-3.65 (m, 2H), 3.54-3.46 (m, 2H), 3.36-3.33 (m, 1H), 3.20-3.11 (m, 1H), 3.09 (d, J=6.0 Hz, 2H), 2.94-2.63 (m, 3H), 256-2.47 (m, 1H), 2.43-2.34 (m, 1H), 2.31-2.19 (m, 3H), 2.14-1.82 (m, 9H), 1.41-1.26 (m, 2H).

Example 14

WX014

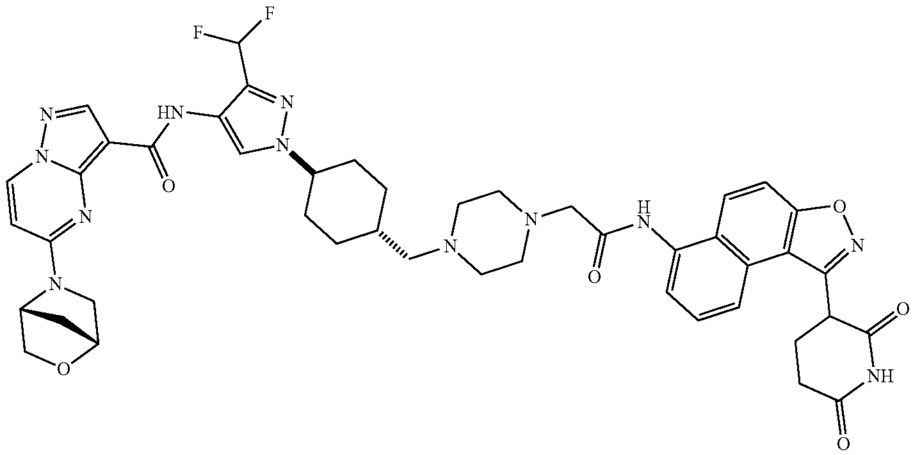

Synthetic Route

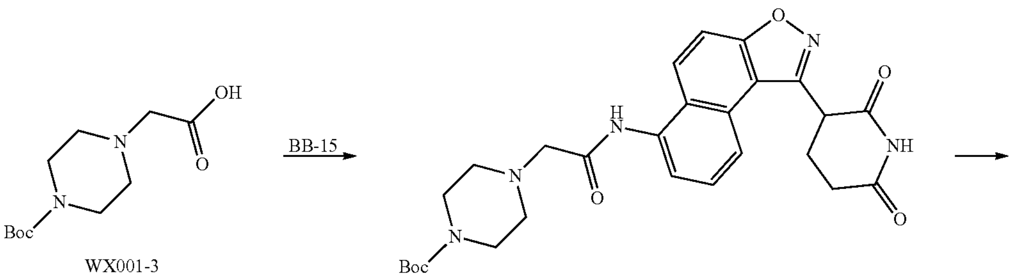

WX001-3

WX014-1

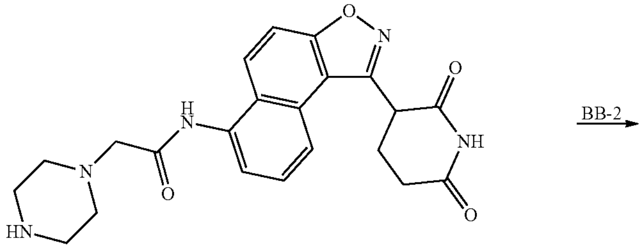

WX014-2

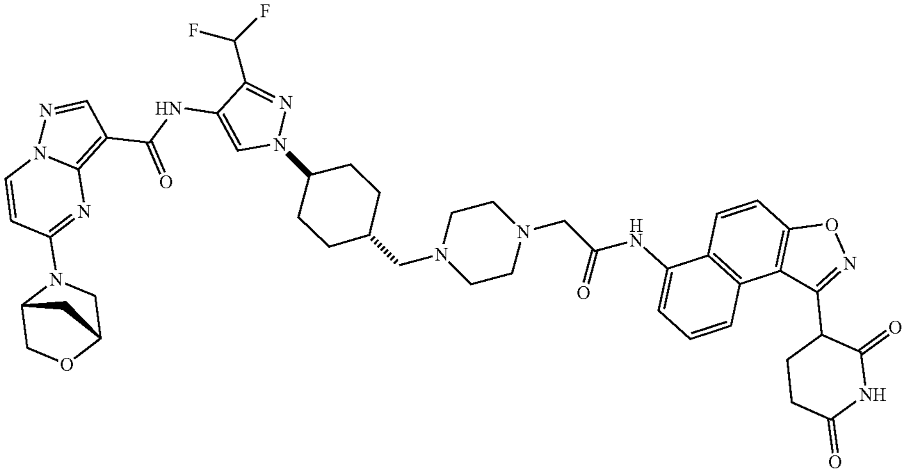

WX014

Step 1: Synthesis of Compound WX014-1

Hydrochloride of compound WX001-3 (465.44 mg, 1.66 mmol) was dissolved in N,N-dimethylformamide (10 mL) at room temperature under nitrogen atmosphere, then N,N-diisopropylethylamine (973.92 mg, 7.54 mmol) and 2-(7-azabenzotriazol-1-yl)-N,N,N',N'-tetramethyluronium hexafluorophosphate (859.59 mg, 2.26 mmol) were sequentially added thereto, and the reaction mixture was stirred and reacted at room temperature for 0.5 hours. Hydrochloride of intermediate BB-15 (0.5 g, 1.51 mmol) was then added thereto, and the reaction mixture was stirred and reacted at room temperature for another 11.5 hours. After the reaction was completed, the reaction mixture was added with water (80 mL) and extracted with ethyl acetate (50 mL×3). The organic phases were combined, washed with 10% saline (60 mL×3), dried over anhydrous sodium sulfate, filtered, and the filtrate was concentrated under reduced pressure to remove the solvent. The resulting residue was separated by column chromatography (eluent: petroleum ether/ethyl acetate=1/2 to 0/1, v/v) to obtain compound WX014-1. MS-ESI m/z: 522.2 $[M+H]^+$.

Step 2: Synthesis of Hydrochloride of Compound WX014-2

Compound WX014-1 (520 mg, 997.00 mol) was dissolved in dichloromethane (5 mL) at room temperature, then a solution of hydrochloric acid in ethyl acetate (4 M, 10 mL) was added thereto, and the reaction mixture was stirred and reacted at room temperature for 12 hours. After the reaction was completed, the reaction mixture was filtered. The filter cake was rinsed with ethyl acetate (15 mL), collected, and dried under vacuum to obtain hydrochloride of compound WX014-2. MS-ESI m/z: 422.2 $[M+H]^+$.

Step 3: Synthesis of Hydrochloride of Compound WX014

Intermediate BB-2 (190 mg, 391.36 mol) and hydrochloride of compound WX014-2 (179.21 mg, 391.36 mol) were dissolved in N,N-dimethylformamide (5 mL) at room temperature under nitrogen atmosphere, then potassium acetate (115.22 mg, 1.17 mmol) was added thereto, and the reaction mixture was stirred and reacted at room temperature for 2 hours. Sodium triacetoxyborohydride (331.78 mg, 1.57 mmol) was then added thereto, and the reaction mixture was stirred and reacted at room temperature for 40 minutes. After the reaction was completed, the reaction mixture was added with 1 M hydrochloric acid solution (4 mL) and concentrated under reduced pressure to remove the solvent. The resulting residue was separated by preparative HPLC (chromatographic column: Phenomenex Luna 80*30 mm*3 μm; mobile phase: water (0.04% hydrochloric acid)-acetonitrile; acetonitrile %: 10% to 30%, 8 minutes) to obtain hydrochloride of target compound WX014. MS-ESI m/z: 891.3 $[M+H]^+$.

$^1H$ NMR (400 MHz, DMSO_$d_6$) δ: 11.15 (s, 1H), 10.71 (s, 1H), 9.51 (d, J=6.4 Hz, 1H), 8.78 (d, J=7.6 Hz, 1H), 8.41 (d, J=3.6 Hz, 1H), 8.36 (d, J=9.2 Hz, 1H), 8.26 (d, J=5.6 Hz, 1H), 8.17 (d, J=5.6 Hz, 1H), 8.00 (d, J=9.2 Hz, 1H), 7.81-7.71 (m, 2H), 7.27-6.96 (m, 1H), 6.90-6.39 (m, 1H), 5.30-5.06 (m, 2H), 4.77 (d, J=19.6 Hz, 1H), 4.39-4.03 (m, 3H), 3.86-3.78 (m, 2H), 3.76-3.57 (m, 8H), 3.14-2.98 (m, 2H), 2.92-2.80 (m, 1H), 2.71-2.53 (m, 3H), 2.46-2.34 (m, 2H), 2.13-2.00 (m, 5H), 1.99-1.73 (m, 5H), 1.29-1.13 (m, 2H).

Example 15

WX015

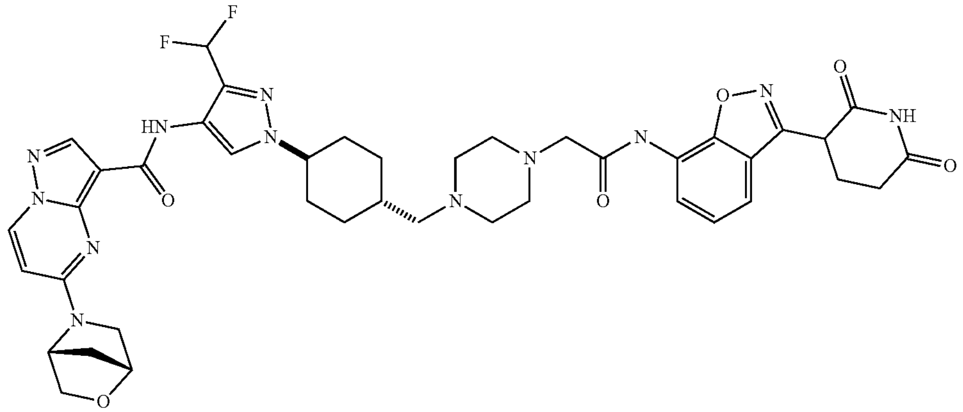

Synthetc Route

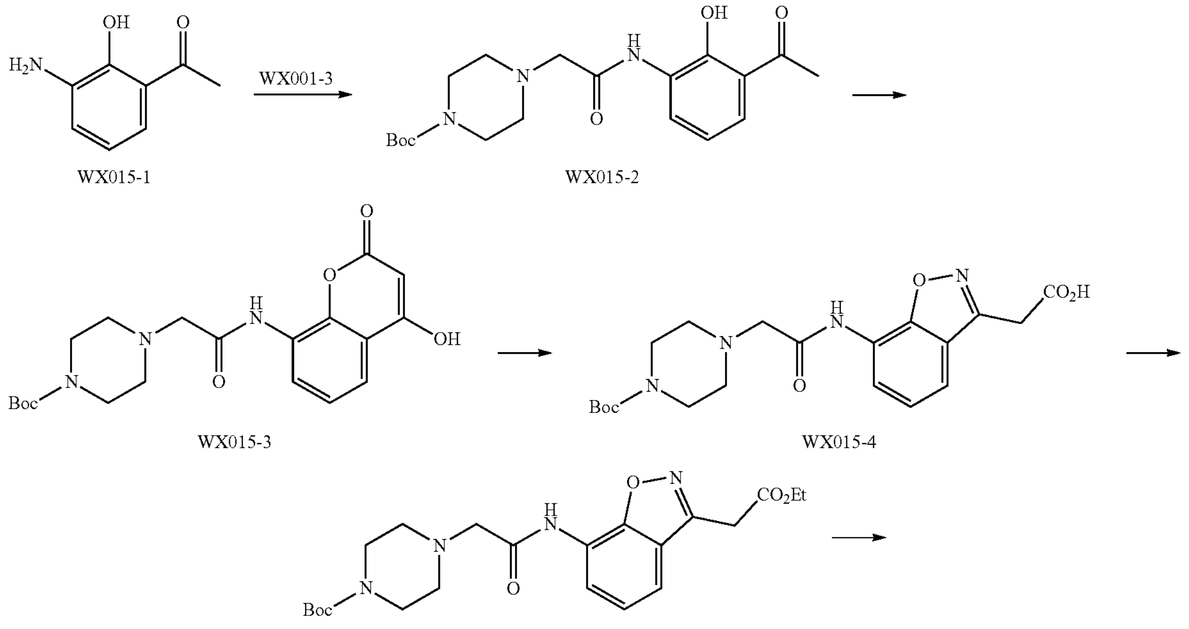

WX015-1

WX015-2

WX015-3

WX015-4

WX015-5

-continued
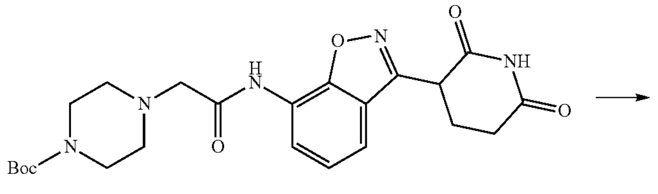
WX015-6
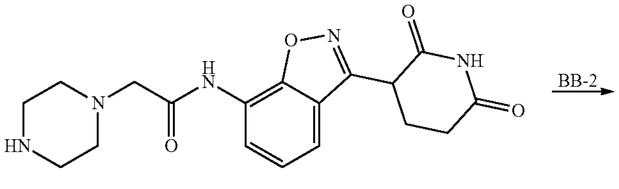
WX015-7
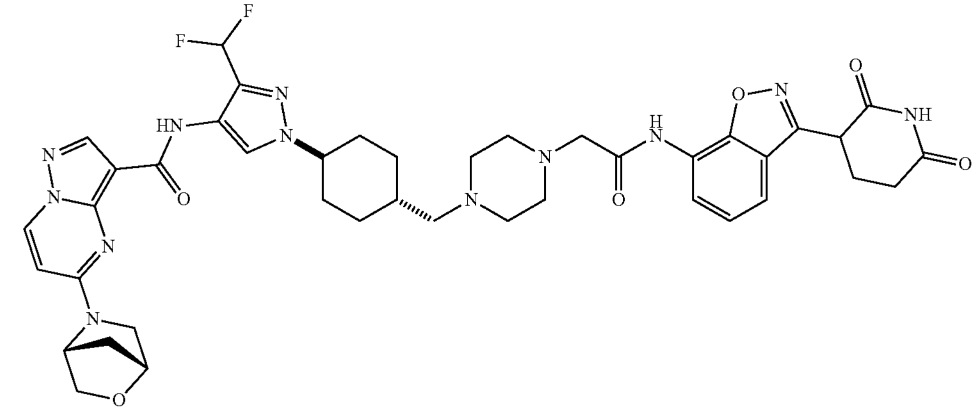
WX015
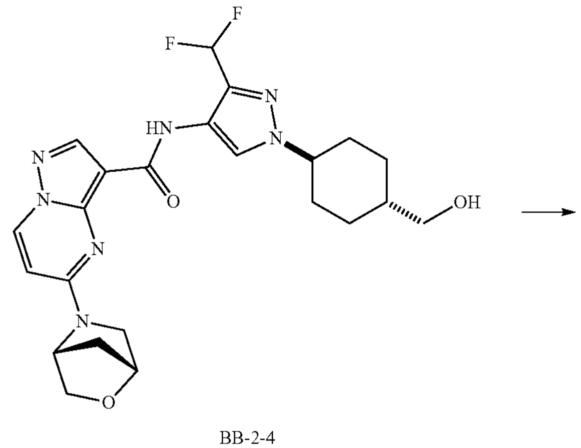
BB-2-4

-continued

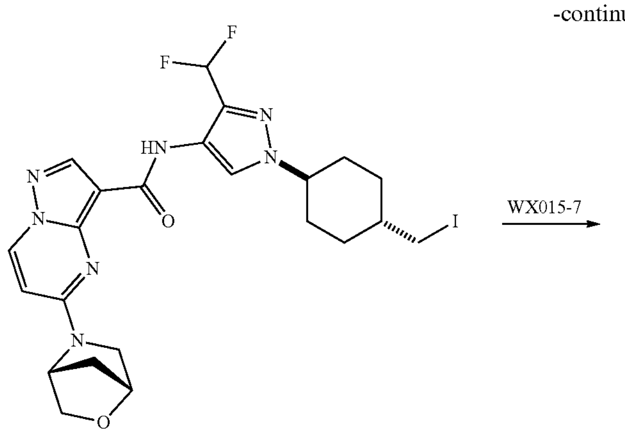

WX015-8

WX015

Step 1: Synthesis of Compound WX015-2

Hydrochloride of compound WX001-3 (9.7 g) was dissolved in N,N-dimethylformamide (50 mL) at room temperature under nitrogen atmosphere, then N,N-diisopropylethylamine (8.55 g, 66.15 mmol) and 2-(7-azabenzotriazol-1-yl)-N,N,N',N'-tetramethyluronium hexafluorophosphate (16.35 g, 43.00 mmol) were sequentially added thereto, and the reaction mixture was stirred and reacted at room temperature for 0.5 hours. Compound WX015-1 (5 g, 33.08 mmol) was then added thereto, and the reaction mixture was stirred and reacted at room temperature for another 2 hours. After the reaction was completed, the reaction mixture was added with water (200 mL) and extracted with ethyl acetate (50 mL×3). The organic phases were combined, washed with saturated brine (100 mL), dried over anhydrous sodium sulfate, filtered, and the filtrate was concentrated under reduced pressure to remove the solvent. The resulting residue was separated by column chromatography (eluent: petroleum ether/ethyl acetate=2/1, v/v) to obtain compound WX015-2. MS-ESI m/z: 378.3 $[M+H]^+$.

Step 2: Synthesis of Compound WX015-3

Compound WX015-2 (4 g, 10.60 mmol) and dimethyl carbonate (3.82 g, 42.39 mmol, 3.57 mL) were dissolved in tetrahydrofuran (50 mL) at room temperature under nitrogen atmosphere, then potassium tert-butoxide (7.14 g, 63.59 mmol) was added thereto, and the reaction mixture was heated to 90° C. and stirred and reacted for 4 hours. After the reaction was completed, the reaction mixture was concentrated under reduced pressure to remove the solvent, dissolved in ice water (50 mL), and extracted with methyl tert-butyl ether (50 mL×2). The aqueous phase was collected, added with 6 M hydrochloric acid to adjust the pH to 7, and concentrated under reduced pressure to obtain compound WX015-3. MS-ESI m/z: 404.2 $[M+H]^+$. $^1H$ NMR (400 MHz, $D_2O$) δ: 7.78 (d, J=7.6 Hz, 1H), 7.60 (d, J=7.6 Hz, 1H), 7.19 (t, J=7.8 Hz, 1H), 5.17 (s, 1H), 3.58-3.45 (m, 4H), 3.27 (s, 2H), 2.62-2.50 (m, 4H), 1.42 (s, 9H).

Step 3: Synthesis of Compound WX015-4

Compound WX015-3 (4.2 g, 10.41 mmol) was dissolved in ethanol (80 mL) at room temperature, then sodium acetate (3.42 g, 41.64 mmol) and hydroxylamine hydrochloride (2.53 g, 36.44 mmol) were added thereto, and the reaction mixture was heated to 80° C. and stirred and reacted for 5 hours. After the reaction was completed, the reaction mixture was cooled to room temperature, filtered, and the filter cake was rinsed with dichloromethane (50 mL×2). The filtrate was concentrated to remove most of the solvent, added with water (100 mL), and extracted with dichloromethane (50 mL×3). The organic phases were combined, washed with saturated brine (100 mL), dried over anhydrous sodium sulfate, filtered, and the filtrate was concentrated under reduced pressure to obtain compound WX015-4. MS-ESI m/z: 419.1 $[M+H]^+$.

Step 4: Synthesis of Compound WX015-5

Compound WX015-4 (2.5 g, 5.97 mmol) was dissolved in dichloromethane (40 mL) at 30° C., then 4-dimethylaminopyridine (1.09 g, 8.96 mmol) and di-tert-butyl carbonate (2 g, 9.16 mmol, 2.11 mL) were added thereto, and the reaction mixture was stirred and reacted at 30° C. for 1.5 hours. Anhydrous ethanol (2.75 g, 59.75 mmol) was then added thereto, and the reaction mixture was stirred and reacted for another 1 hour. After the reaction was completed, the reaction mixture was poured into water (50 mL). The phases were separated, and the aqueous phase was extracted with dichloromethane (30 mL). The organic phases were combined, dried over anhydrous sodium sulfate, filtered, and the filtrate was concentrated under reduced pressure to obtain a crude product. The resulting crude product was purified by column chromatography (eluent: petroleum ether/ethyl acetate=1/5) to obtain compound WX015-5. MS-ESI m/z: 447.3 $[M+H]^+$. $^1H$ NMR (400 MHz, $CDCl_3$) δ: 9.79 (s, 1H), 8.46 (d, J=7.6 Hz, 1H), 7.41 (d, J=7.6 Hz, 1H), 7.32 (t, J=8.0 Hz, 1H), 4.22 (q, J=7.0 Hz, 2H), 4.04 (s, 2H), 3.63-3.54 (m, 4H), 3.26 (s, 2H), 2.69-2.58 (m, 4H), 1.48 (s, 9H), 1.26 (t, J=7.2 Hz, 3H).

Step 5: Synthesis of Compound WX015-6

Compound WX015-5 (0.92 g, 2.06 mmol) and acrylamide (175.75 mg, 2.47 mmol) were dissolved in tetrahydrofuran (20 mL) at room temperature under nitrogen atmosphere, and the reaction mixture was cooled to 0° C. A solution of potassium tert-butoxide in tetrahydrofuran (1 M, 3.09 mL) was added dropwise thereto, and the reaction mixture was stirred and reacted at 0° C. for 1.5 hours. After the reaction was completed, the reaction mixture was added with 0.05 M hydrochloric acid (70 mL) and extracted with ethyl acetate (40 mL×2), and the organic phases were combined. The combined organic phases were washed with saturated brine (40 mL), dried over anhydrous sodium sulfate, filtered, and the filtrate was concentrated under reduced pressure to obtain a crude product. The resulting crude product was purified by column chromatography (eluent: petroleum ether/ethyl acetate=5/1 to 1/1) to obtain compound WX015-6. MS-ESI m/z: 472.2 $[M+H]^+$. $^1H$ NMR (400 MHz, $CDCl_3$) δ: 9.83 (s, 1H), 8.49 (d, J=6.4 Hz, 1H), 8.10 (s, 1H), 7.42 (d, J=7.6 Hz, 1H), 7.35 (t, J=7.8 Hz, 1H), 4.34 (dd, J=5.0 Hz, 9.0 Hz, 1H), 3.66-3.52 (m, 4H), 3.27 (s, 2H), 3.06-2.95 (m, 1H), 2.83-2.73 (m, 1H), 2.71-2.56 (m, 5H), 2.53-2.43 (m, 1H), 1.49 (s, 9H).

Step 6: Synthesis of Hydrochloride of Compound WX015-7

Compound WX015-6 (530 mg, 1.12 mmol) was dissolved in ethyl acetate (1 mL) at room temperature, then a solution of hydrochloric acid in ethyl acetate (4 M, 30 mL) was added thereto, and the reaction mixture was stirred and reacted at room temperature for 3 hours. After the reaction was completed, the reaction mixture was concentrated under reduced pressure to remove the solvent to obtain hydrochloride of compound WX015-7. MS-ESI m/z: 372.1 $[M+H]^+$.

Step 7: Synthesis of Hydrochloride of Compound WX015

Intermediate BB-2 (654.51 mg, 1.35 mmol) and hydrochloride of compound WX015-7 (599 mg) were dissolved in 1,2-dichloroethane (18 mL) and tetrahydrofuran (9 mL) at room temperature under nitrogen atmosphere, then potassium acetate (291.08 mg, 2.97 mmol) and acetic acid (0.5 mL) were added thereto, and the reaction mixture was stirred and reacted at room temperature for 1 hour. Sodium triacetoxyborohydride (857.19 mg, 4.04 mmol) was then added thereto, and the reaction mixture was stirred and reacted at room temperature for 1.5 hours. After the reaction was completed, the reaction mixture was added with 1 M hydrochloric acid solution (10 mL) and concentrated under reduced pressure to remove the solvent. The resulting residue was separated by preparative HPLC (chromatographic column: Phenomenex Luna 80*40 mm*3 μm; mobile phase: water (0.04% hydrochloric acid)-acetonitrile; acetonitrile %: 22% to 37%, 7 minutes) to obtain hydrochloride of target compound WX015. MS-ESI m/z: 841.3 $[M+H]^+$. $^1H$ NMR (400 MHz, DMSO_$d_6$) δ: 11.50 (s, 1H), 11.12 (s, 2H), 9.50 (d, J=6.0 Hz, 1H), 8.78 (d, J=7.6 Hz, 1H), 8.40 (d, J=3.6 Hz, 1H), 8.26 (d, J=5.6 Hz, 1H), 8.02 (d, J=7.6 Hz, 1H), 7.68 (d, J=7.6 Hz, 1H), 7.40 (t, J=7.8 Hz, 1H), 7.27-6.95 (m, 1H), 6.90-6.41 (m, 1H), 5.27 (s, 1H), 5.08 (s, 1H), 4.76 (d, J=18.8 Hz, 1H), 4.65 (dd, J=4.8 Hz, 12.0 Hz, 1H), 4.50-4.15 (m, 3H), 3.90-3.69 (m, 8H), 3.67-3.55 (m, 2H), 3.54-3.37 (m, 2H), 3.19-3.03 (m, 2H), 2.85-2.72 (m, 1H), 2.69-2.53 (m, 2H), 2.28-2.16 (m, 1H), 2.14-2.03 (m, 4H), 2.02-1.87 (m, 2H), 1.85-1.69 (m, 2H), 1.30-1.10 (m, 2H).

Step 8: Synthesis of Compound WX015-8

Intermediate BB-2-4 (80 g, 164.10 mmol) was dissolved in dichloromethane (1.6 L) at room temperature under nitrogen atmosphere, then triphenylphosphine (51.65 g, 196.92 mmol) and imidazole (16.76 g, 246.15 mmol) were added thereto, and the reaction mixture was cooled to 0° C. Elemental iodine (54.15 g, 213.33 mmol) was added thereto, and the reaction mixture was stirred and reacted at room temperature for 14 hours. After the reaction was completed, the reaction mixture was poured into saturated sodium sulfite aqueous solution (600 mL), stirred at room temperature until the mixture was colorless, filtered, and the filter cake was rinsed with dichloromethane (500 mL×3). The mother liquor was separated, and the organic phase was collected. The organic phase was washed with saturated brine (500 mL), dried over anhydrous sodium sulfate, filtered, and the filtrate was concentrated under reduced pressure to remove the solvent. The residue was added with methanol (500 mL), stirred at room temperature for 1 hour, and filtered. The filter cake was rinsed with methanol (500 mL), collected, and dried under vacuum to obtain compound WX015-8. MS-ESI m/z: 598.0 $[M+H]^+$.

Step 9: Synthesis of Compound WX015

Compound WX015-6 (3 g, 6.36 mmol) was dissolved in dichloromethane (30 mL) at room temperature under nitrogen atmosphere, then trifluoroacetic acid (9.24 g, 81.04 mmol, 6 mL) was added thereto, and the reaction mixture was stirred and reacted at room temperature for 4 hours. After the reaction was completed, the reaction mixture was concentrated under reduced pressure to remove the solvent to obtain trifluoroacetate of compound WX015-7. MS-ESI m/z: 372.0 $[M+H]^+$.

Trifluoroacetate of compound WX015-7 (253.65 g, 310.81 mmol) was dissolved in acetonitrile (3.4 L) at room temperature under nitrogen atmosphere, then N,N-diisopropylethylamine (281.19 g, 2.18 mol) and compound WX015-8 (168.8 g, 282.56 mmol) were added thereto, and the reaction mixture was heated to 80° C. and stirred and reacted for 23 hours. After the reaction was completed, the reaction mixture was poured into acetone (4.3 L) and stirred at room temperature for 12 hours. The reaction mixture was filtered, and the filter cake was rinsed with acetone (400 mL×4) and collected. The filter cake was dissolved in dichloromethane (1.5 L), concentrated under reduced pressure to remove the solvent, and the operation of dissolution and concentration was repeated twice to obtain compound WX015. MS-ESI m/z: 841.3 $[M+H]^+$. $^1H$ NMR (400 MHz, DMSO_$d_6$) δ: 11.12 (s, 1H), 10.02 (s, 1H), 9.50 (d, J=6.0 Hz, 1H), 8.77 (d, J=7.6 Hz, 1H), 8.39 (d, J=4.4 Hz, 1H), 8.26 (d, J=5.6 Hz, 1H), 8.10 (d, J=7.6 Hz, 1H), 7.59 (d, J=8.0 Hz, 1H), 7.36 (t, J=8.0 Hz, 1H), 7.27-6.94 (m, 1H), 6.88-6.41 (m, 1H), 5.17 (d, J=84.4 Hz, 1H), 4.76 (d, J=15.6 Hz, 1H), 4.63 (dd, J=4.8 Hz, 12.0 Hz, 1H), 4.24-4.11 (m, 1H), 3.86-3.71 (m, 2H), 3.66-3.40 (m, 2H), 3.36-3.20 (m, 6H), 2.84-2.72 (m, 1H), 2.69-2.53 (m, 5H), 2.48-2.41 (m, 2H), 2.27-2.10 (m, 3H), 2.09-1.85 (m, 6H), 1.82-1.68 (m, 2H), 1.13-0.97 (m, 2H).

Example 16
WX016
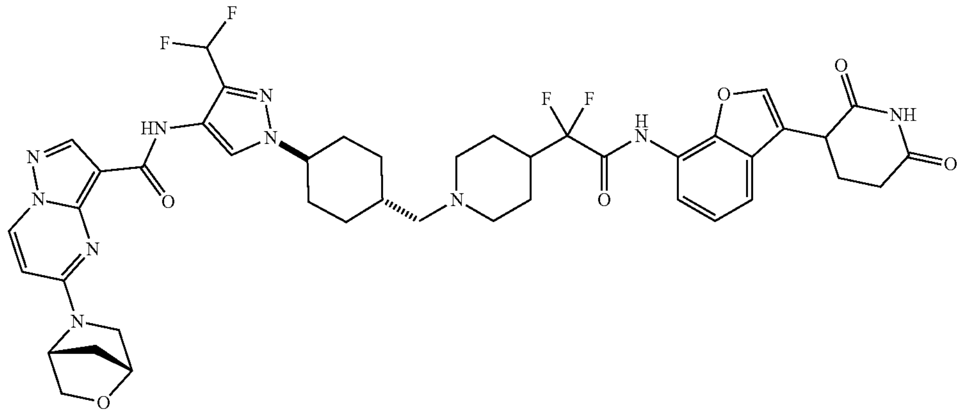
Synthetic Route
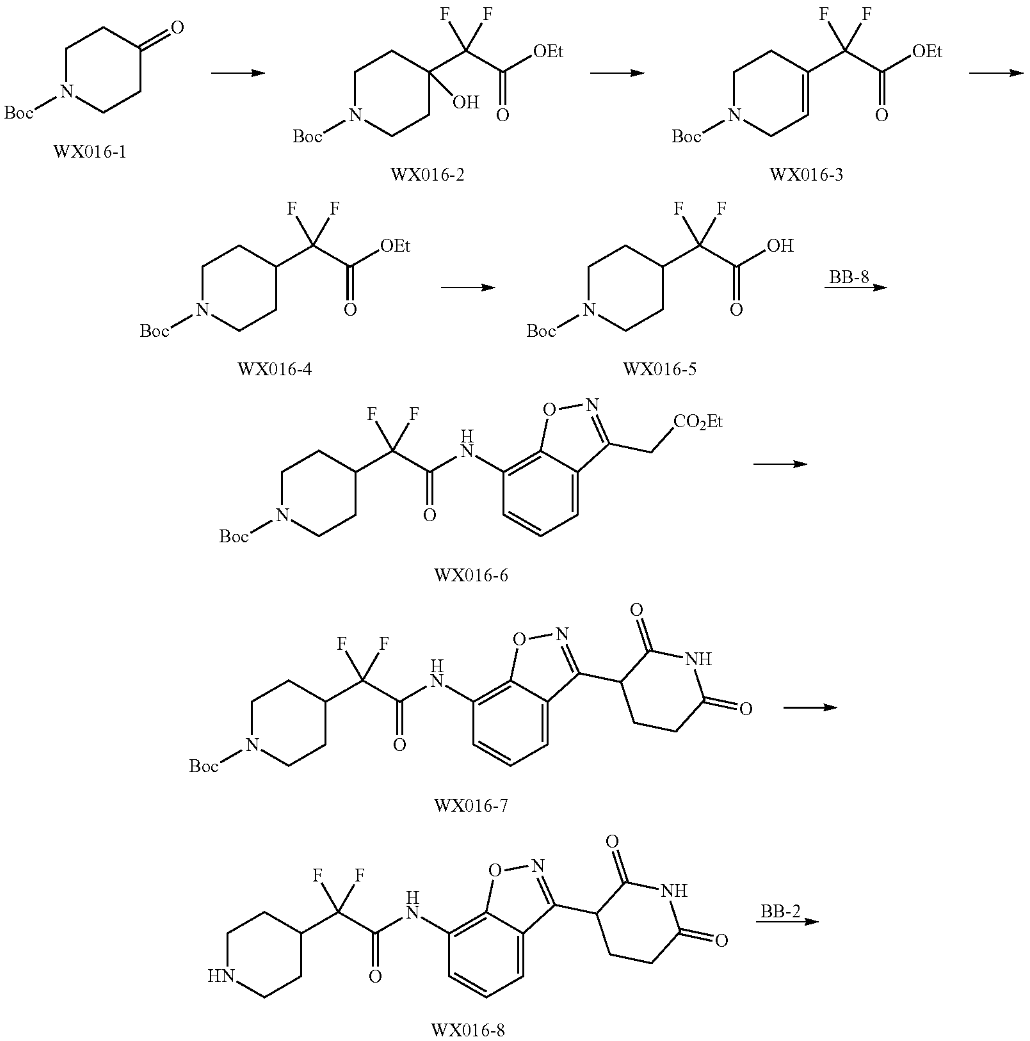
WX016-1
WX016-2
WX016-3
WX016-4
WX016-5
WX016-6
WX016-7
WX016-8

-continued

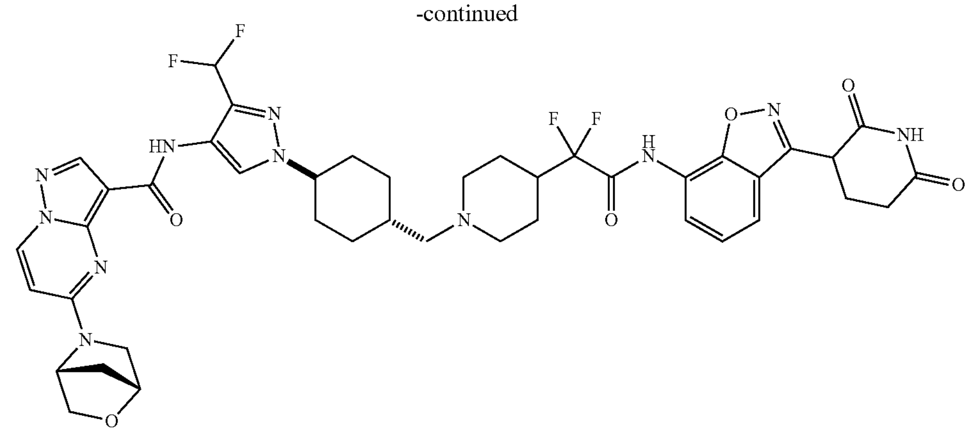

WX016

Step 1: Synthesis of Compound WX016-2

To a dry reaction flask were added titanocene dichloride (1.30 g, 5.02 mmol) and zinc powder (13.31 g, 203.55 mmol) at room temperature under nitrogen atmosphere, then added tetrahydrofuran (100 mL) for dissolution, and added dropwise a solution of ethyl bromodifluoroacetate (20.37 g, 100.38 mmol, 12.90 mL) in tetrahydrofuran (20 mL) (1/10 of the solution was first added dropwise thereto, and the remaining solution was added dropwise thereto after the reaction was initiated (a significant increase in temperature)). After the dropwise addition was completed, the reaction mixture was stirred for 0.5 hours and filtered. To a solution of compound WX016-1 (10 g, 50.19 mmol) in tetrahydrofuran (50 mL) was added the filtrate, and the reaction mixture was stirred and reacted for 12 hours. After the reaction was completed, the reaction mixture was added dropwise with 1 M hydrochloric acid to adjust the pH to 3, diluted with ethyl acetate (100 mL) and water (100 mL), and the phases were separated. The organic phase was collected, and the aqueous phase was extracted with ethyl acetate (50 mL×3). The organic phases were combined, washed with saturated brine (50 mL×3), dried over anhydrous sodium sulfate, filtered, and the filtrate was concentrated under reduced pressure. The resulting residue was separated by column chromatography (eluent: petroleum ether/ethyl acetate=0/1 to 1/1, v/v) to obtain compound WX016-2. MS-ESI m/z: 268.0 $[M+H-56]^+$.

Step 2: Synthesis of Compound WX016-3

To dioxane (15 mL) were added compound WX016-2 (1 g, 3.09 mmol), sulfoxide chloride (2.21 g, 18.56 mmol), and pyridine (1.47 g, 18.56 mmol) at room temperature under nitrogen atmosphere, and the reaction mixture was stirred for 1.5 hours. 4-Dimethylaminopyridine (37.78 mg, 309.28 mol) was then added thereto, and the reaction mixture was stirred and reacted for another 12 hours. After the reaction was completed, the reaction mixture was added with water (20 mL) and extracted with ethyl acetate (30 mL×3). The organic phase was washed with saturated brine (20 mL×3), dried over anhydrous sodium sulfate, filtered, and the filtrate was concentrated under reduced pressure to remove the solvent. The resulting residue was separated by column chromatography (eluent: petroleum ether/ethyl acetate=20/1 to 9/1, v/v) to obtain compound WX016-3. MS-ESI m/z: 206.2 $[M+H-100]^+$. $^1H$ NMR (400 MHz, $CDCl_3$) δ: 6.18 (s, 1H), 4.34 (q, J=7.0 Hz, 2H), 4.02 (d, J=2.0 Hz, 2H), 3.54 (t, J=5.6 Hz, 2H), 2.25 (s, 2H), 1.48 (s, 9H), 1.36 (t, J=7.2 Hz, 3H).

Step 3: Synthesis of Compound WX016-4

To a hydrogenation flask was added wet palladium hydroxide (0.5 g, 712.07 mol, purity: 20%) at room temperature under nitrogen atmosphere, and then methanol (20 mL) and compound WX016-3 (1.5 g, 4.91 mmol) were added thereto. The reaction mixture was replaced with hydrogen three times, and stirred and reacted under 40 psi for 12 hours. After the reaction was completed, the reaction mixture was filtered. The filter cake was rinsed with methanol (50 mL×4), and the filtrate was collected and concentrated under reduced pressure to remove the residual solvent. The resulting residue was separated by column chromatography (eluent: petroleum ether/ethyl acetate=20/1 to 10/1, v/v) to obtain compound WX016-4. MS-ESI m/z: 252.2 $[M+H-56]^+$. $^1H$ NMR (400 MHz, $CDCl_3$) δ: 4.35 (q, J=7.0 Hz, 2H), 4.30-4.15 (m, 2H), 2.68 (t, J=12.8 Hz, 2H), 2.32-2.14 (m, 1H), 1.73 (d, J=12.8 Hz, 2H), 1.49 (d, J=4.8 Hz, 1H), 1.47 (s, 9H), 1.42 (d, J=4.4 Hz, 1H), 1.37 (t, J=7.0 Hz, 3H).

Step 4: Synthesis of Compound WX016-5

Compound WX016-4 (0.26 g, 845.99 mol) was dissolved in a mixed solvent of ethanol (5 mL) and water (2 mL) at room temperature under nitrogen atmosphere, then lithium hydroxide monohydrate (71.00 mg, 1.69 mmol) was added thereto, and the reaction mixture was stirred and reacted at room temperature for 12 hours. After the reaction was completed, the reaction mixture was concentrated under reduced pressure, and the residue was added with 1 M hydrochloric acid to adjust the pH to 2 to 3 to precipitate a solid. The reaction mixture was filtered, and the filter cake was collected and dried under vacuum to obtain compound WX016-5. MS-ESI m/z: 224.0 $[M+H-56]^+$. $^1H$ NMR (400 MHz, DMSO_$d_6$) δ: 4.05-3.94 (m, 2H), 2.80-2.63 (m, 3H), 2.37-2.21 (m, 1H), 1.71-1.61 (m, 2H), 1.39 (s, 9H), 1.27-1.12 (m, 2H).

Step 5: Synthesis of Compound WX016-6

Compound WX016-5 (0.12 g, 429.68 mol) was dissolved in N,N-dimethylformamide (5 mL) at room temperature under nitrogen atmosphere, then 2-(7-azabenzotriazol-1-yl)-N,N,N',N'-tetramethyluronium hexafluorophosphate (272.29 mg, 716.13 mol) and N,N-diisopropylethylamine (277.66 mg, 2.15 mmol, 374.20 L) were added thereto, and the reaction mixture was stirred and reacted for 0.5 hours. Hydrochloride of compound BB-8 (91.56 mg) was then added thereto, and the reaction mixture was stirred and reacted for another 12 hours. After the reaction was completed, the reaction mixture was added with water (20 mL) and extracted with ethyl acetate (30 mL×3). The organic phases were combined, washed with saturated brine (20 mL×3), dried over anhydrous sodium sulfate, filtered, and the filtrate was concentrated under reduced pressure to remove the residual solvent. The resulting residue was separated by column chromatography (eluent: petroleum ether/ethyl acetate=5/1 to 2/1, v/v) to obtain compound WX016-6. MS-ESI m/z: 425.2 [M+H−56]$^+$. $^1$H NMR (400 MHz, $CDCl_3$) δ: 8.45 (s, 1H), 8.16 (d, J=7.6 Hz, 1H), 7.68 (s, 1H), 7.41 (dd, J=1.0, 7.8 Hz, 1H), 4.25-4.17 (m, 3H), 3.71 (d, J=0.8 Hz, 2H), 2.72 (t, J=12.2 Hz, 2H), 2.57-2.42 (m, 1H), 1.84 (d, J=12.8 Hz, 2H), 1.59-1.49 (m, 3H), 1.47 (s, 9H), 1.28 (t, J=7.0 Hz, 3H).

Step 6: Synthesis of Compound WX016-7

Compound WX016-6 (110 mg, 228.93 mol) was dissolved in tetrahydrofuran (3 mL) at room temperature under nitrogen atmosphere, then acrylamide (19.53 mg, 274.71 mol) was added thereto, and the reaction mixture was cooled to 0° C. in an ice bath. A solution of potassium tert-butoxide in tetrahydrofuran (1 M, 503.64 L) was added dropwise thereto, and after the dropwise addition was completed, the reaction mixture was returned to room temperature and stirred for 1 hour. After the reaction was completed, the reaction mixture was poured into 0.1 M hydrochloric acid (10 mL) and extracted with ethyl acetate (20 mL×2). The organic phases were combined, washed with saturated brine (20 mL), dried over anhydrous sodium sulfate, filtered, and the filtrate was concentrated under reduced pressure to remove the solvent. The residue was added with ethyl acetate (2 mL), stirred at room temperature for 5 minutes, and filtered. The filter cake was rinsed with ethyl acetate (2 mL×2), collected, and dried under vacuum to obtain compound WX016-7. MS-ESI m/z: 406.2 [M+H−100]$^+$.

Step 7: Synthesis of Hydrochloride of Compound WX016-8

Compound WX016-7 (70 mg, 138.47 mol) was dissolved in ethyl acetate (1 mL) at room temperature under nitrogen atmosphere, then a solution of hydrochloric acid in ethyl acetate (3 mL, 4 M) was added thereto, and the reaction mixture was stirred and reacted at room temperature for 12 hours. After the reaction was completed, the reaction mixture was filtered. The filter cake was rinsed with ethyl acetate (3 mL×3), collected, and dried under vacuum to obtain hydrochloride of compound WX016-8. MS-ESI m/z: 406.2 [M+H]$^+$. $^1$H NMR (400 MHz, DMSO_$d_6$) δ: 10.92 (s, 1H), 10.80 (s, 1H), 7.94 (s, 1H), 7.53 (dd, J=1.4, 7.0 Hz, 1H), 7.34-7.22 (m, 2H), 4.17 (dd, J=5.0, 12.2 Hz, 1H), 3.38 (d, J=12.8 Hz, 2H), 2.97 (t, J=12.0 Hz, 2H), 2.82-2.70 (m, 1H), 2.69-2.55 (m, 3H), 2.41-2.27 (m, 1H), 2.18-2.07 (m, 1H), 2.03-1.92 (m, 2H), 1.80-1.61 (m, 2H).

Step 8: Synthesis of Hydrochloride of Compound WX016

Hydrochloride of compound WX016-8 (50 mg) was dissolved in 1,2-dichloroethane (3 mL) at room temperature under nitrogen atmosphere, then intermediate BB-2 (54.94 mg, 113.16 mol), potassium acetate (33.32 mg, 339.48 mol), and glacial acetic acid (3.40 mg, 56.58 mol, 3.24 L) were added thereto, and the reaction mixture was stirred at room temperature for 2 hours. Sodium triacetoxyborohydride (95.93 mg, 452.64 mol) was then added thereto, and the reaction mixture was stirred and reacted for another 12 hours. After the reaction was completed, the reaction mixture was added with 1 M hydrochloric acid (2 mL), stirred for 5 minutes, and concentrated under reduced pressure to remove the solvent. The residue was separated by preparative HPLC (chromatographic column: Phenomenex Luna 80*30 mm*3 μm; mobile phase: water (0.04% hydrochloric acid)-acetonitrile; acetonitrile %: 15% to 40%, 8 minutes) to obtain hydrochloride of target compound WX016. MS-ESI m/z: 875.3 [M+H]$^+$. $^1$H NMR (400 MHz, DMSO_$d_6$) δ: 10.92 (s, 1H), 10.84 (s, 1H), 9.50 (d, J=6.4 Hz, 2H), 8.79 (d, J=8.0 Hz, 1H), 8.41 (d, J=3.6 Hz, 1H), 8.26 (d, J=5.6 Hz, 1H), 7.95 (s, 1H), 7.53 (d, J=7.6 Hz, 1H), 7.38-6.94 (m, 3H), 6.91-6.36 (m, 1H), 5.36-5.04 (m, 1H), 4.77 (d, J=20.8 Hz, 1H), 4.25-4.12 (m, 2H), 3.85-3.77 (m, 1H), 3.76-3.42 (m, 4H), 3.12-2.90 (m, 4H), 2.82-2.56 (m, 5H), 2.39-2.27 (m, 1H), 2.18-1.89 (m, 11H), 1.88-1.73 (m, 2H), 1.31-1.11 (m, 2H).

Example 17

WX017

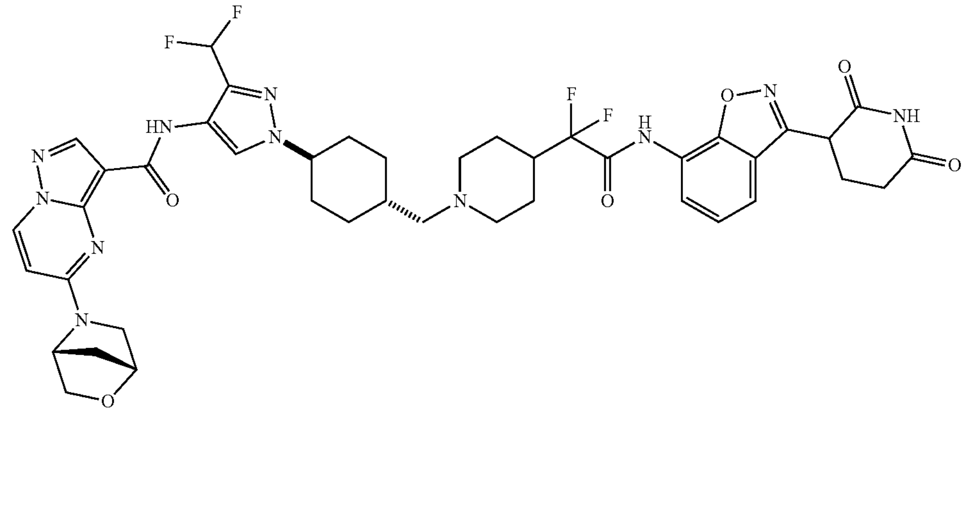

Synthetic Route
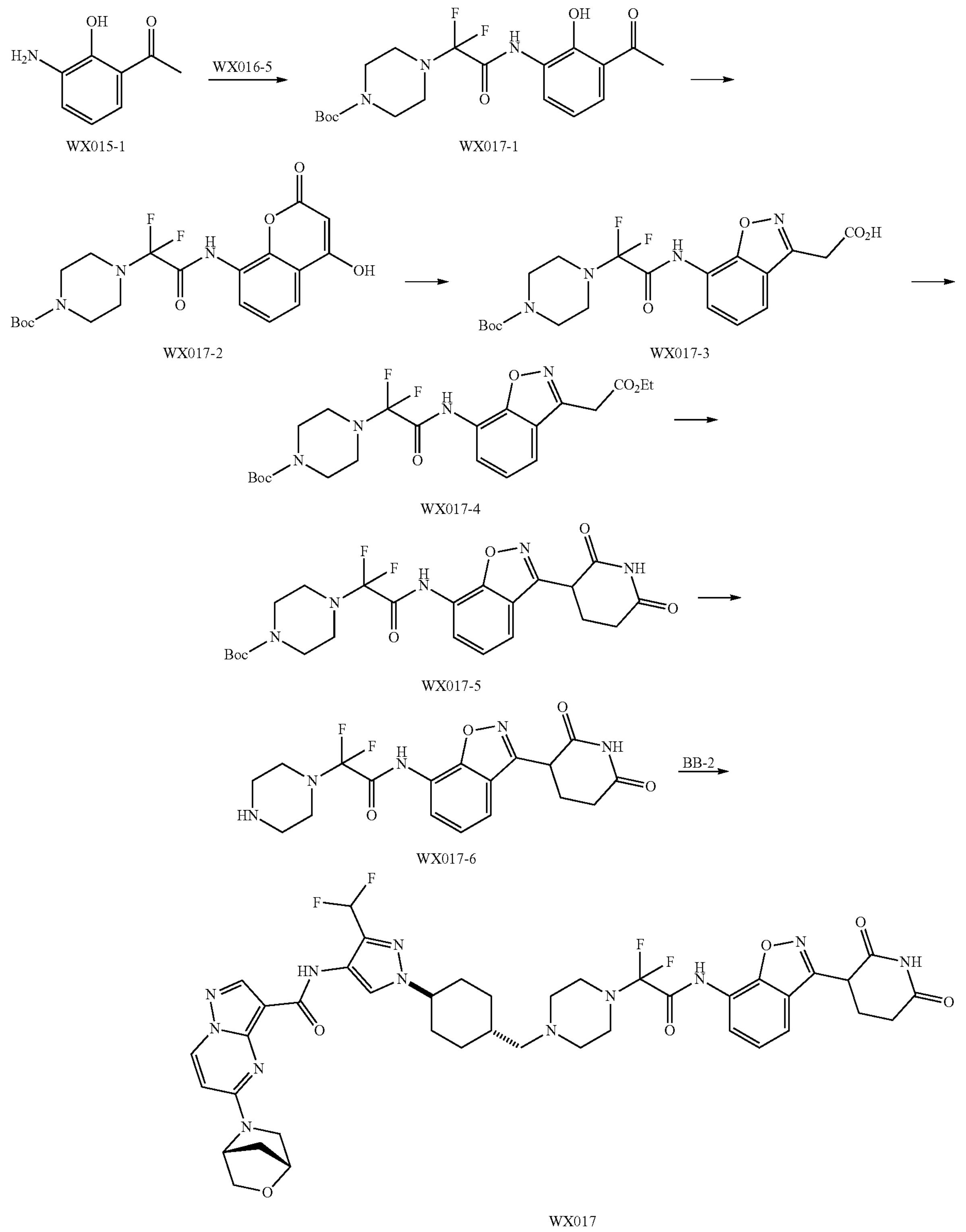
Step 1: Synthesis of Compound WX017-1
Compound WX016-5 (0.7 g, 2.51 mmol) was dissolved in N,N-dimethylformamide (10 mL) at room temperature under nitrogen atmosphere, then 2-(7-azabenzotriazol-1-yl)-N,N,N',N'-tetramethyluronium hexafluorophosphate (1.19 g, 3.13 mmol) and N,N-diisopropylethylamine (809.85 mg, 6.27 mmol, 1.09 mL) were added thereto, and the reaction mixture was stirred at room temperature for 0.5 hours. Compound WX015-1 (315.73 mg, 2.09 mmol) was then added thereto, and the reaction mixture was stirred and reacted for another 12 hours. After the reaction was completed, the reaction mixture was added with water (60 mL) and extracted with ethyl acetate (100 mL×3). The organic phases were combined, washed with saturated brine (100 mL×3), dried over anhydrous sodium sulfate, filtered, and the filtrate was concentrated under reduced pressure to remove the solvent. The resulting residue was separated by column chromatography (eluent: petroleum ether/ethyl acetate=10/1 to 5/1, v/v) to obtain compound WX017-1. MS-ESI m/z: 313.1 $[M+H-100]^+$. $^1H$ NMR (400 MHz, $CDCl_3$) δ: 12.94 (s, 1H), 8.74 (s, 1H), 8.59 (dd, J=0.8, 8.0 Hz, 1H), 7.57 (dd, J=1.4, 8.2 Hz, 1H), 6.98 (t, J=8.0 Hz, 1H), 4.29-4.17 (m, 2H), 2.68 (s, 3H), 2.53-2.40 (m, 1H), 1.81 (d, J=12.4 Hz, 2H), 1.59-1.55 (m, 2H), 1.53-1.48 (m, 2H), 1.46 (s, 9H).

Step 2: Synthesis of Compound WX017-2

Compound WX017-1 (0.67 g, 1.62 mmol) was dissolved in tetrahydrofuran (20 mL) at room temperature under nitrogen atmosphere, then dimethyl carbonate (585.34 mg, 6.50 mmol) was added thereto, and the reaction mixture was cooled to 0° C. in an ice bath. Potassium tert-butoxide (1.09 g, 9.75 mmol) was slowly added thereto, and the reaction mixture was heated to 80° C. and stirred and reacted for 12 hours. After the reaction was completed, the reaction mixture was cooled to room temperature and concentrated under reduced pressure to remove the solvent to obtain compound WX017-2. MS-ESI m/z: 339.2 $[M+H-100]^+$.

Step 3: Synthesis of Compound WX017-3

Compound WX017-2 (0.72 g, 1.64 mmol) was dissolved in ethanol (10 mL) at room temperature under nitrogen atmosphere, then hydroxylamine hydrochloride (399.43 mg, 5.75 mmol) was added thereto, and the reaction mixture was heated to 80° C. and stirred and reacted for 12 hours. After the reaction was completed, the reaction mixture was cooled to room temperature and filtered. The filtrate was concentrated under reduced pressure to remove most of the ethanol, added with water (10 mL), then added with sodium bicarbonate aqueous solution to adjust the pH to 6, and extracted with dichloromethane/ethanol=10/1 (30 mL×5). The organic phase was washed with saturated brine (30 mL), dried over anhydrous sodium sulfate, filtered, and the filtrate was concentrated under reduced pressure to obtain compound WX017-3. MS-ESI m/z: 354.1 $[M+H-100]^+$.

Step 4: Synthesis of Compound WX017-4

Compound WX017-3 (0.78 g, 1.63 mmol) was dissolved in ethanol (10 mL) at room temperature under nitrogen atmosphere, then concentrated sulfuric acid (326.66 mg, 3.26 mmol) was added thereto, and the reaction mixture was heated to 90° C. and stirred and reacted for 12 hours. After the reaction was completed, the reaction mixture was cooled to room temperature, added with water (30 mL), and extracted with ethyl acetate (50 mL×3). The organic phases were combined, washed with saturated brine (50 mL×3), dried over anhydrous sodium sulfate, filtered, and the filtrate was concentrated under reduced pressure to remove the residual solvent. The residue was dissolved in tetrahydrofuran (5 mL) and water (5 mL), then sodium carbonate (344.86 mg, 3.25 mmol) and di-tert-butyl carbonate (355.06 mg, 1.63 mmol) were added thereto, and the reaction mixture was stirred and reacted at room temperature for 2 hours. After the reaction was completed, the reaction mixture was added with water (30 mL) and extracted with ethyl acetate (50 mL×3). The organic phases were combined, washed with saturated brine (50 mL×3), dried over anhydrous sodium sulfate, filtered, and the filtrate was concentrated under reduced pressure to remove the residual solvent. The resulting residue was separated by column chromatography (eluent: petroleum ether/ethyl acetate=3/1 to 2/1, v/v) to obtain compound WX017-4. MS-ESI m/z: 382.1 $[M+H-100]^+$. $^1H$ NMR (400 MHz, $CDCl_3$) δ: 8.47 (s, 1H), 8.42 (d, J=8.0 Hz, 1H), 7.53 (d, J=8.0 Hz, 1H), 7.37 (t, J=7.8 Hz, 1H), 4.27-4.19 (m, 3H), 4.06 (s, 2H), 2.79-2.66 (m, 2H), 2.56-2.46 (m, 1H), 1.83 (d, J=12.4 Hz, 2H), 1.59-1.50 (m, 3H), 1.47 (s, 9H), 1.27 (t, J=7.2 Hz, 3H).

Step 6: Synthesis of Compound WX017-5

Compound WX017-4 (450 mg, 934.60 mol) and acrylamide (79.72 mg, 1.12 mmol) were dissolved in tetrahydrofuran (5 mL) at room temperature under nitrogen atmosphere, and the reaction mixture was cooled to 0° C. in an ice bath. A solution of potassium tert-butoxide in tetrahydrofuran (1 M, 1.87 mL) was added dropwise thereto, and the reaction mixture was stirred and reacted at 0° C. for 1 hour. After the reaction was completed, the reaction mixture was poured into 0.3 M hydrochloric acid (10 mL) and extracted with ethyl acetate (20 mL×3). The organic phase was washed with saturated brine (20 mL×2), dried over anhydrous sodium sulfate, filtered, and the filtrate was concentrated under reduced pressure to remove the solvent. The resulting residue was separated by column chromatography (eluent: petroleum ether/ethyl acetate=5/1 to 1/1, v/v) to obtain compound WX017-5. MS-ESI m/z: 407.1 $[M+H-100]^+$. $^1H$ NMR (400 MHz, DMSO_$d_6$) δ:11.12 (s, 1H), 10.99 (s, 1H), 7.79 (d, J=8.0 Hz, 1H), 7.61 (d, J=7.6 Hz, 1H), 7.41 (t, J=7.6 Hz, 1H), 4.64 (dd, J=4.8, 12.0 Hz, 1H), 4.11-4.06 (m, 1H), 2.86-2.71 (m, 3H), 2.68-2.53 (m, 3H), 2.27-2.15 (m, 1H), 1.81 (d, J=12.4 Hz, 2H), 1.40 (s, 9H), 1.38-1.32 (m, 2H).

Step 7: Synthesis of Hydrochloride of Compound WX017-6

Compound WX017-5 (290 mg, 572.56 mol) was dissolved in ethyl acetate (1 mL) at room temperature under nitrogen atmosphere, then a solution of hydrochloric acid in ethyl acetate (3 mL, 4 M) was added thereto, and the reaction mixture was stirred and reacted at room temperature for 12 hours. After the reaction was completed, the reaction mixture was filtered. The filter cake was rinsed with ethyl acetate (3 mL×3), collected, and dried under vacuum to obtain hydrochloride of compound WX017-6. MS-ESI m/z: 407.1 $[M+H]^+$. $^1H$ NMR (400 MHz, DMSO_$d_6$) δ: 11.13 (s, 1H), 11.09 (s, 1H), 8.74 (s, 2H), 7.80 (d, J=8.0 Hz, 1H), 7.62 (d, J=7.2 Hz, 1H), 7.42 (t, J=7.8 Hz, 1H), 4.65 (dd, J=4.8, 12.0 Hz, 1H), 3.38 (d, J=11.6 Hz, 2H), 2.97 (t, J=12.6 Hz, 2H), 2.85-2.71 (m, 2H), 2.70-2.53 (m, 3H), 2.26-2.16 (m, 1H), 1.96 (d, J=14.0 Hz, 2H), 1.83-1.64 (m, 2H).

Step 8: Synthesis of the Hydrochloride of Compound WX017

Hydrochloride of compound WX017-6 (0.1 g) was dissolved in 1,2-dichloroethane (3 mL) and tetrahydrofuran (2 mL) at room temperature under nitrogen atmosphere, then intermediate BB-2 (101.29 mg, 208.64 mol), potassium acetate (61.43 mg, 625.91 mol), and glacial acetic acid (6.26 mg, 104.32 mol, 5.97 μL) were added thereto, and the reaction mixture was stirred at room temperature for 2 hours. Sodium triacetoxyborohydride (176.87 mg, 834.54 μmol) was then added thereto, and the reaction mixture was stirred for another 1 hour. After the reaction was completed, the reaction mixture was added with 1 M hydrochloric acid (2 mL), stirred for 5 minutes, and concentrated under reduced pressure to remove the solvent. The residue was separated by preparative HPLC (chromatographic column: Phenomenex C18 75*30 mm*3 μm; mobile phase: water (0.04% hydrochloric acid)-acetonitrile; acetonitrile %: 12% to 42%, 8 minutes) to obtain hydrochloride of target compound WX017. MS-ESI m/z: 876.4 $[M+H]^+$. $^1H$ NMR (400 MHz, DMSO_$d_6$) δ: 11.13 (s, 2H), 9.51 (d, J=6.8 Hz, 1H), 9.32 (s, 1H), 8.79 (d, J=7.6 Hz, 1H), 8.43-8.20 (m, 1H), 7.81 (d, J=8.0 Hz, 1H), 7.64 (d, J=7.6 Hz, 1H), 7.43 (t, J=7.8 Hz, 1H), 7.31-6.94 (m, 1H), 6.91-6.41 (m, 1H), 5.30-5.03 (m, 1H), 4.77 (d, J=21.6 Hz, 1H), 4.65 (dd, J=5.0, 12.2 Hz, 1H), 4.32-4.16 (m, 2H), 3.85-3.57 (m, 6H), 3.14-2.94 (m, 4H), 2.84-2.74 (m, 2H), 2.69-2.58 (m, 3H), 2.27-2.17 (m, 1H), 2.14-1.89 (m, 10H), 1.87-1.74 (m, 2H), 1.32-1.08 (m, 2H).

Example 18

WX018

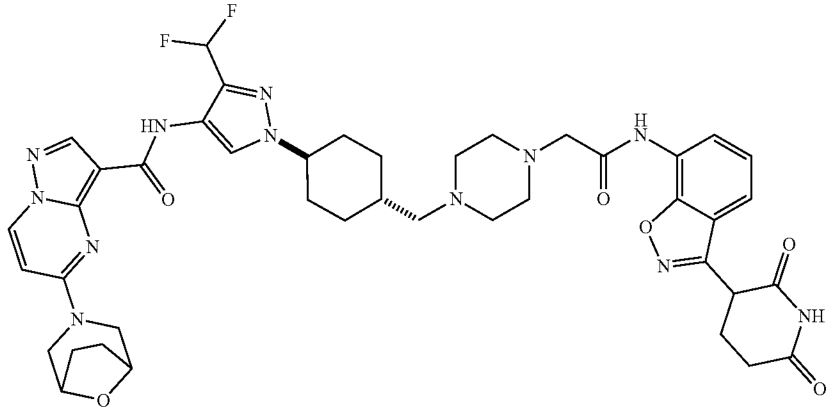

Synthetic Route

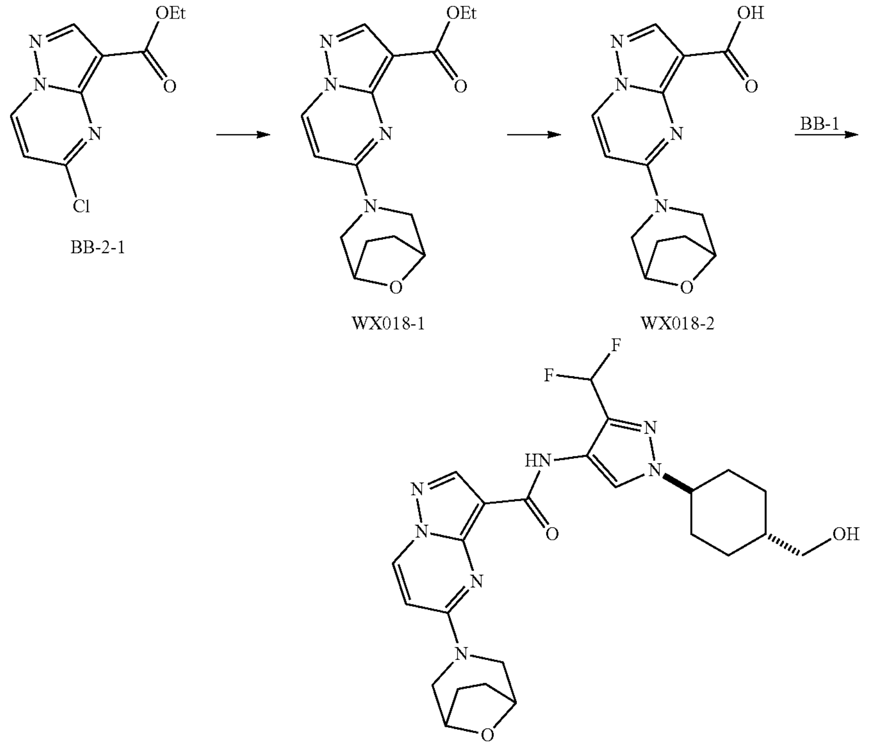

BB-2-1

WX018-1

WX018-2

WX018-3

-continued

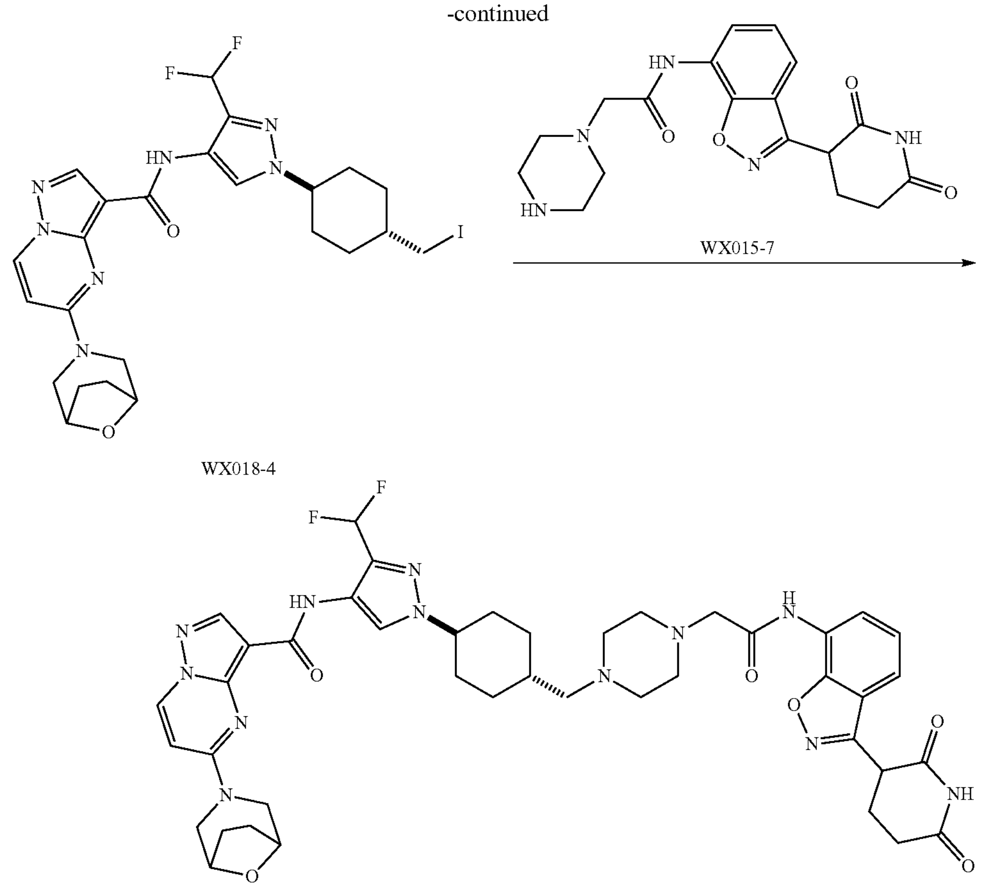

WX018-4

WX018

Step 1: Synthesis of Compound WX018-1

Intermediate BB-2-1 (1.10 g, 4.88 mmol) was dissolved in acetonitrile (10 mL) at room temperature under nitrogen atmosphere, then 8-oxa-3-azabicyclo[3.2.1]octane (0.95 g, 6.35 mmol, hydrochloride) and N,N-diisopropylethylamine (1.89 g, 14.65 mmol, 2.55 mL) were added thereto, and the reaction mixture was heated to 60° C. and stirred and reacted for 2 hours. After the reaction was completed, the reaction mixture was concentrated under reduced pressure to remove the solvent. The resulting residue was added with water (20 mL), and the mixture was stirred at room temperature for 1 hour to precipitate a solid and filtered. The filter cake was washed with water (20 mL×4), collected, and dried under vacuum to obtain compound WX018-1. MS-ESI m/z: 303.2 $[M+H]^+$. $^1H$ NMR (400 MHz, $CDCl_3$) δ: 8.35-8.25 (m, 2H), 6.36 (d, J=8.0 Hz, 1H), 4.53 (s, 2H), 4.35 (q, J=7.4 Hz, 2H), 4.23-3.71 (m, 1H), 3.35 (d, J=12.4 Hz, 2H), 2.00 (t, J=4.6 Hz, 2H), 1.83 (d, J=7.6 Hz, 2H), 1.70 (s, 1H), 1.39 (t, J=7.2 Hz, 3H).

Step 2: Synthesis of Compound WX018-2

Compound WX018-1 (1.4 g, 4.63 mmol) was dissolved in methanol (15 mL) and water (3 mL) at room temperature under nitrogen atmosphere, then lithium hydroxide monohydrate (388.61 mg, 9.26 mmol) was added thereto, and the reaction mixture was heated to 60° C. and stirred and reacted for 12 hours. After the reaction was completed, the reaction mixture was cooled to room temperature, concentrated under reduced pressure to remove methanol, added with 1 M hydrochloric acid to adjust the pH to 3 to 4 to precipitate a large amount of white solid, and filtered. The filter cake was rinsed with water (10 mL×2), collected, and dried under vacuum to obtain compound WX018-2. MS-ESI m/z: 275.2 $[M+H]^+$. $^1H$ NMR (400 MHz, DMSO_$d_6$) δ: 11.70 (s, 1H), 8.73 (d, J=8.0 Hz, 1H), 8.19 (s, 1H), 6.76 (d, J=8.0 Hz, 1H), 4.47 (d, J=2.0 Hz, 2H), 4.30-3.90 (m, 2H), 3.15 (d, J=12.4 Hz, 2H), 1.89-1.80 (m, 2H), 1.73-1.65 (m, 2H).

Step 3: Synthesis of Compound WX018-3

Compound WX018-2 (0.2 g, 729.20 mol) was dissolved in acetonitrile (4 mL) at room temperature under nitrogen atmosphere, then N,N,N',N'-tetramethylchloroformamidinium hexafluorophosphate (245.52 mg, 875.04 mol) and N-methylimidazole (209.54 mg, 2.55 mmol, 203.44 μL) were added thereto, and the reaction mixture was stirred for 0.5 hours. Compound BB-1 (178.85 mg, 729.20 mol) was added thereto, and the reaction mixture was stirred for another 2 hours. After the reaction was completed, the reaction mixture was filtered. The filter cake was rinsed with acetonitrile (3 mL×3), collected, and dried under vacuum to obtain compound WX018-3. MS-ESI m/z: 502.2 $[M+H]^+$. $^1H$ NMR (400 MHz, DMSO_$d_6$) δ: 9.41 (s, 1H), 8.81 (d, J=7.6 Hz, 1H), 8.38 (s, 1H), 8.28 (s, 1H), 7.27-6.95 (m, 1H), 6.82 (d, J=8.0 Hz, 1H), 4.45 (s, 3H), 4.25-4.10 (m, 2H), 3.25

(d, J=6.0 Hz, 2H), 3.23-3.10 (m, 2H), 2.10-1.99 (m, 2H), 1.93-1.81 (m, 4H), 1.80-1.65 (m, 4H), 1.52-1.35 (m, 1H), 1.16-1.10 (m, 2H).

Step 4: Synthesis of Compound WX018-4

Compound WX018-3 (320 mg, 638.05 μmol) was dissolved in dichloromethane (6 mL) at room temperature under nitrogen atmosphere, then triphenylphosphine (200.82 mg, 765.66 mol) and imidazole (65.16 mg, 957.08 μmol) were added thereto, and the reaction mixture was cooled to 0° C. in an ice bath. Elemental iodine (210.52 mg, 829.47 mol) was added thereto, and the reaction mixture was returned to room temperature and stirred for 12 hours. After the reaction was completed, the reaction mixture was poured into saturated sodium sulfite aqueous solution (30 mL) and extracted with dichloromethane (50 mL×3). The organic phases were combined, washed with saturated brine (50 mL×2), dried over anhydrous sodium sulfate, filtered, and the filtrate was concentrated under reduced pressure to remove the solvent. The resulting residue was separated by column chromatography (eluent: petroleum ether/ethyl acetate=3/1 to 0/1, v/v) to obtain compound WX018-4. MS-ESI m/z: 612.1 $[M+H]^+$. $^1H$ NMR (400 MHz, $CDCl_3$) δ: 9.52 (s, 1H), 8.43 (d, J=9.6 Hz, 2H), 8.34 (d, J=8.0 Hz, 1H), 6.77 (t, J=54.2 Hz, 1H), 6.37 (d, J=8.0 Hz, 1H), 4.56 (d, J=2.4 Hz, 2H), 4.11-4.00 (m, 1H), 3.45-3.32 (m, 2H), 3.17 (d, J=6.0 Hz, 2H), 2.27-2.18 (m, 2H), 2.14-2.01 (m, 4H), 1.92-1.79 (m, 4H), 1.67-1.50 (m, 2H), 1.31-1.16 (m, 3H).

Step 5: Synthesis of Formate of Compound WX018

Trifluoroacetate of compound WX015-7 (268.38 mg) was dissolved in acetonitrile (4 mL) at room temperature under nitrogen atmosphere, then N,N-diisopropylethylamine (340.32 mg, 2.63 mmol, 458.66 L) was added thereto, and the reaction mixture was stirred for 5 minutes. Compound WX018-4 (0.23 g, 376.17 mol) was added thereto, and the reaction mixture was heated to 90° C. and stirred and reacted for 12 hours. After the reaction was completed, the reaction mixture was cooled to room temperature, concentrated under reduced pressure to remove acetonitrile, added with water (20 mL), and extracted with ethyl acetate (30 mL×3). The organic phases were combined, washed with saturated brine (30 mL×3), dried over anhydrous sodium sulfate, filtered, and the filtrate was concentrated under reduced pressure to remove the solvent. The resulting residue was separated by preparative HPLC (chromatographic column: Phenomenex Luna 80*30 mm*3 μm; mobile phase: water (0.2% formic acid)-acetonitrile; acetonitrile %: 15% to 40%, 8 minutes) to obtain formate of target compound WX018. MS-ESI m/z: 855.5 $[M+H]^+$. $^1H$ NMR (400 MHz, DMSO_$d_6$) δ: 11.12 (s, 1H), 10.02 (s, 1H), 9.41 (s, 1H), 8.81 (d, J=8.0 Hz, 1H), 8.38 (s, 1H), 8.28 (s, 1H), 8.15 (s, 1H), 8.10 (d, J=7.6 Hz, 1H), 7.59 (dd, J=0.8, 8.0 Hz, 1H), 7.36 (t, J=8.0 Hz, 1H), 7.10 (t, J=53.8 Hz, 1H), 6.82 (d, J=8.0 Hz, 1H), 4.62 (dd, J=4.8, 11.6 Hz, 1H), 4.45 (s, 2H), 4.27-4.10 (m, 2H), 3.45-3.28 (m, 3H), 3.22-3.14 (m, 1H), 2.86-2.72 (m, 2H), 2.69-2.52 (m, 7H), 2.48-2.41 (m, 2H), 2.27-2.13 (m, 3H), 2.11-1.99 (m, 2H), 1.97-1.83 (m, 4H), 1.82-1.68 (m, 4H), 1.66-1.53 (m, 1H), 1.16-0.93 (m, 2H).

Example 19

WX019

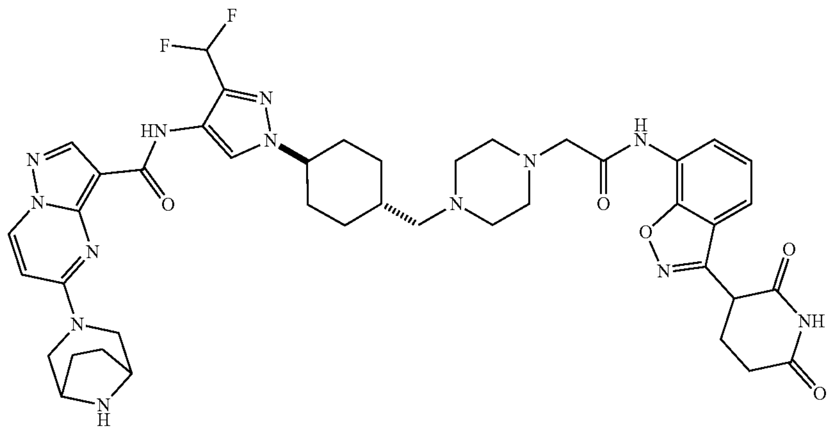

Synthetic Route
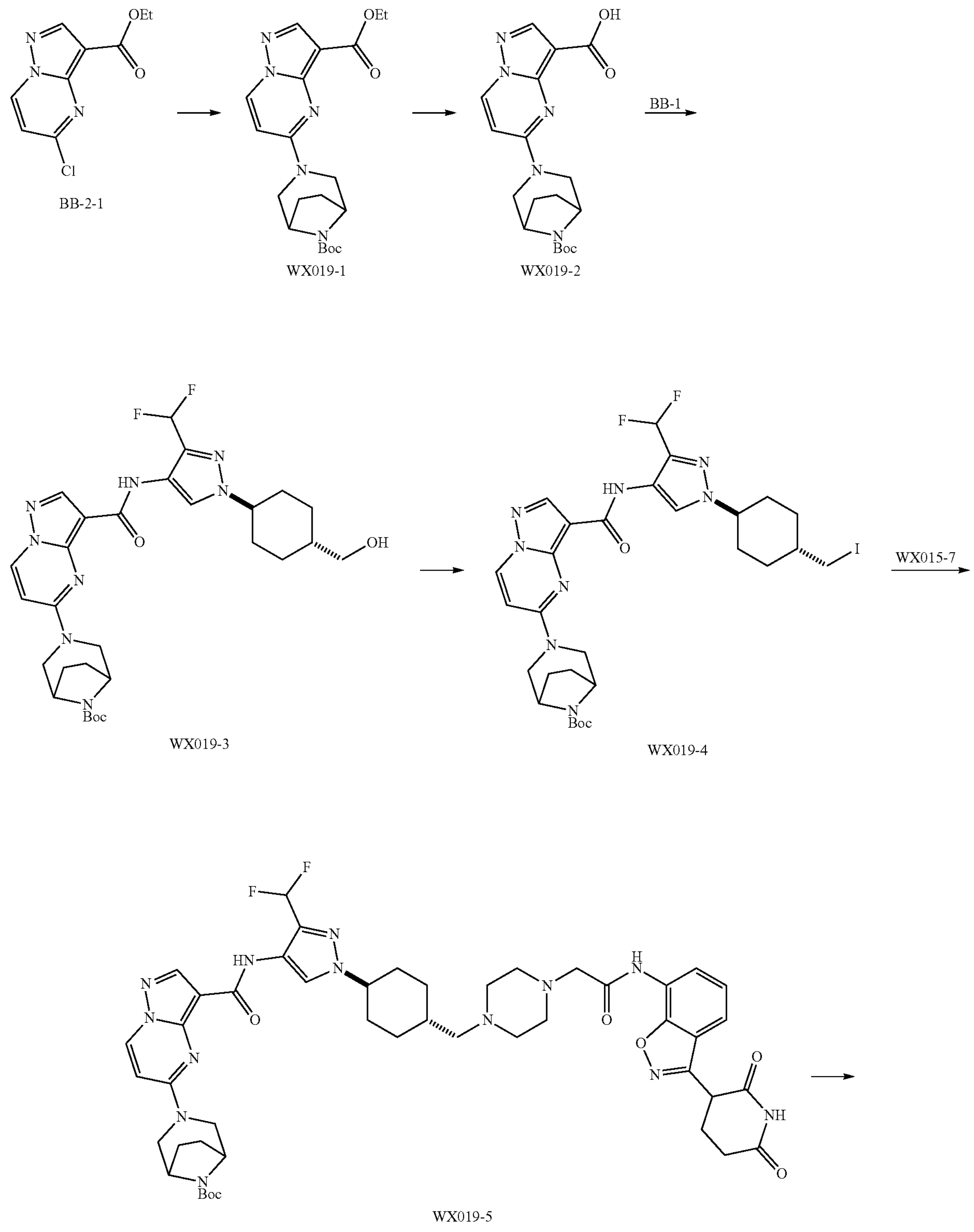

-continued

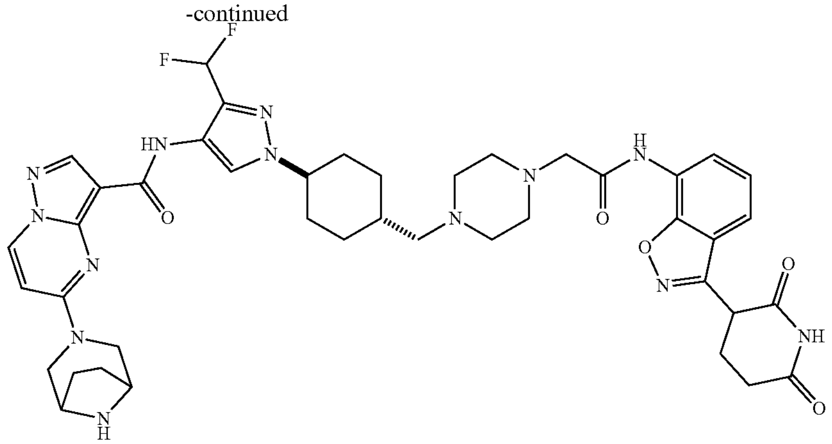

WX019

Step 1: Synthesis of Compound WX019-1

Intermediate BB-2-1 (1.06 g, 4.71 mmol) was dissolved in acetonitrile (10 mL) at room temperature under nitrogen atmosphere, then tert-butyl 3,8-diazabicyclo[3.2.1]octane-8-carboxylate (1 g, 4.71 mmol) and N,N-diisopropylethylamine (1.83 g, 14.13 mmol, 2.46 mL) were added thereto, and the reaction mixture was heated to 60° C. and stirred and reacted for 3 hours. After the reaction was completed, the reaction mixture was cooled to room temperature and concentrated under reduced pressure to remove the solvent. The resulting residue was added with water (20 mL), stirred at room temperature for 1 hour to precipitate a solid, and filtered. The filter cake was washed with water (20 mL×4), collected, and dried under vacuum to obtain compound WX019-1. MS-ESI m/z: 402.3 $[M+H]^+$. $^1H$ NMR (400 MHz, $CDCl_3$) δ: 8.35-8.25 (m, 2H), 6.39 (d, J=8.0 Hz, 1H), 4.55-4.30 (m, 5H), 3.46-3.19 (m, 2H), 2.07-1.93 (m, 2H), 1.83-1.70 (m, 2H), 1.69-1.62 (m, 1H), 1.50 (s, 9H), 1.40 (t, J=7.2 Hz, 3H).

Step 2: Synthesis of Compound WX019-2

Compound WX019-1 (1.35 g, 3.36 mmol) was dissolved in methanol (10 mL) and water (2 mL) at room temperature under nitrogen atmosphere, then lithium hydroxide monohydrate (282.23 mg, 6.73 mmol) was added thereto, and the reaction mixture was heated to 60° C. and stirred and reacted for 2 hours. After the reaction was completed, the reaction mixture was cooled to room temperature, concentrated under reduced pressure to remove methanol, added with 1 M hydrochloric acid to adjust the pH to 3 to 4 to precipitate a large amount of white solid, and filtered. The filter cake was rinsed with water (10 mL×2), collected, and dried under vacuum to obtain compound WX019-2. MS-ESI m/z: 374.2 $[M+H]^+$. $^1H$ NMR (400 MHz, DMSO_$d_6$) δ: 11.72 (s, 1H), 8.74 (d, J=7.6 Hz, 1H), 8.19 (s, 1H), 6.79 (d, J=8.0 Hz, 1H), 4.35-4.18 (m, 3H), 3.41-3.25 (m, 3H), 1.93-1.79 (m, 2H), 1.68-1.57 (m, 2H), 1.43 (s, 9H).

Step 3: Synthesis of Compound WX019-3

Compound WX019-2 (0.4 g, 1.07 mmol) was dissolved in acetonitrile (4 mL) at room temperature under nitrogen atmosphere, then N,N,N',N'-tetramethylchloroformamidinium hexafluorophosphate (360.67 mg, 1.29 mmol) and N-methylimidazole (307.83 mg, 3.75 mmol, 298.86 L) were added thereto, and the reaction mixture was stirred for 0.5 hours. Compound BB-1 (262.74 mg, 1.07 mmol) was added thereto, and the reaction mixture was stirred and reacted for another 1 hour. After the reaction was completed, the reaction mixture was filtered. The filter cake was rinsed with acetonitrile (3 mL×3), collected, and dried under vacuum to obtain compound WX019-3. MS-ESI m/z: 601.4 $[M+H]^+$. $^1H$ NMR (400 MHz, DMSO_$d_6$) δ: 9.41 (s, 1H), 8.83 (d, J=8.0 Hz, 1H), 8.39 (s, 1H), 8.29 (s, 1H), 7.14 (t, J=53.8 Hz, 1H), 6.84 (d, J=8.0 Hz, 1H), 4.64-4.33 (m, 2H), 4.30-4.13 (m, 3H), 3.76 (s, 1H), 3.53-2.96 (m, 5H), 2.10-2.00 (m, 2H), 1.95-1.81 (m, 4H), 1.80-1.62 (m, 4H), 1.44 (s, 9H), 1.18-1.02 (m, 2H).

Step 4: Synthesis of Compound WX019-4

Compound WX019-3 (590 mg, 982.26 mol) was dissolved in dichloromethane (10 mL) at room temperature under nitrogen atmosphere, then triphenylphosphine (309.16 mg, 1.18 mmol) and imidazole (100.31 mg, 1.47 mmol) were added thereto, and the reaction mixture was cooled to 0° C. Elemental iodine (324.10 mg, 1.28 mmol) was added thereto, and the reaction mixture was stirred and reacted at room temperature for 12 hours. After the reaction was completed, the reaction mixture was poured into saturated sodium sulfite aqueous solution (30 mL) and extracted with dichloromethane (50 mL×3). The organic phases were combined, washed with saturated brine (50 mL×2), dried over anhydrous sodium sulfate, filtered, and the filtrate was concentrated under reduced pressure to remove the solvent. The resulting residue was separated by column chromatography (eluent: petroleum ether/ethyl acetate=3/1 to 0/1, v/v) to obtain compound WX019-4. MS-ESI m/z: 711.3 $[M+H]^+$. $^1H$ NMR (400 MHz, $CDCl_3$) δ: 9.52 (s, 1H), 8.44 (s, 1H), 8.41 (s, 1H), 8.35 (d, J=8.0 Hz, 1H), 6.78 (t, J=54.2 Hz, 1H), 6.40 (d, J=7.6 Hz, 1H), 4.53-4.36 (m, 2H), 4.11-4.01 (m, 1H), 3.45-3.23 (m, 2H), 3.17 (d, J=6.0 Hz, 2H), 2.27-2.18 (m, 2H), 2.14-2.06 (m, 2H), 2.05-1.99 (m, 2H), 1.92-1.79 (m, 2H), 1.78-1.71 (m, 2H), 1.63-1.54 (m, 2H), 1.51 (s, 9H), 1.31-1.16 (m, 3H).

Step 5: Synthesis of Compound WX019-5

Trifluoroacetate of compound WX015-7 (291.18 mg) was dissolved in acetonitrile (3 mL) at room temperature under nitrogen atmosphere, then N,N-diisopropylethylamine (369.24 mg, 2.86 mmol) was added thereto, and the reaction mixture was stirred for 5 minutes. Compound WX019-4 (290 mg, 408.13 mol) was added thereto, and the reaction mixture was heated to 90° C. and stirred and reacted for 12 hours. After the reaction was completed, the reaction mixture was cooled to room temperature, concentrated under reduced pressure to remove acetonitrile, added with water (20 mL), and extracted with ethyl acetate (30 mL×3). The organic phases were combined, washed with saturated brine (30 mL×3), dried over anhydrous sodium sulfate, filtered, and the filtrate was concentrated under reduced pressure to remove the solvent. The resulting residue was separated by column chromatography (eluent: dichloromethane/methanol=5/1 to 1/1, v/v) to obtain compound WX019-5. MS-ESI m/z: 954.4 $[M+H]^+$.

Step 6: Synthesis of Hydrochloride of Compound WX019

Compound WX019-5 (0.3 g, 314.45 mol) was dissolved in ethyl acetate (2 mL) at room temperature under nitrogen atmosphere, then a solution of hydrochloric acid in ethyl acetate (8 mL, 4 M) was added thereto, and the reaction mixture was stirred and reacted at room temperature for 2 hours. After the reaction was completed, the reaction mixture was filtered, and the filter cake was rinsed with ethyl acetate (3 mL×3) and collected. The filter cake was separated by preparative HPLC (chromatographic column: Phenomenex Luna 80*30 mm*3 μm; mobile phase: water (0.04% hydrochloric acid)-acetonitrile; acetonitrile %: 1% to 30%, 8 minutes) to obtain hydrochloride of target compound WX019. MS-ESI m/z: 854.4 $[M+H]^+$. $^1H$ NMR (400 MHz, DMSO_$d_6$) δ: 11.12 (s, 1H), 10.69 (s, 1H), 9.83 (d, J=10.0 Hz, 1H), 9.64 (s, 1H), 9.37 (s, 1H), 8.92 (d, J=8.0 Hz, 1H), 8.40 (s, 1H), 8.33 (s, 1H), 8.01 (d, J=7.2 Hz, 1H), 7.66 (d, J=8.0 Hz, 1H), 7.39 (t, J=7.8 Hz, 1H), 7.14 (t, J=53.6 Hz, 1H), 6.91 (d, J=8.0 Hz, 1H), 4.64 (dd, J=4.8, 12.0 Hz, 1H), 4.31-4.20 (m, 2H), 4.14 (s, 2H), 4.03-3.86 (m, 2H), 3.76-3.66 (m, 3H), 3.49-3.19 (m, 8H), 3.13-2.97 (m, 2H), 2.85-2.72 (m, 1H), 2.69-2.63 (m, 1H), 2.62-2.53 (m, 1H), 2.27-2.16 (m, 1H), 2.13-1.73 (m, 11H), 1.32-1.09 (m, 2H).

Example 20

WX020

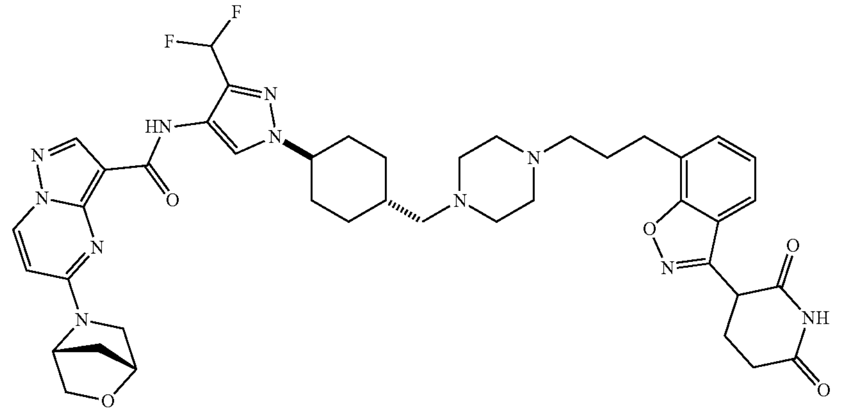

Synthetic Route

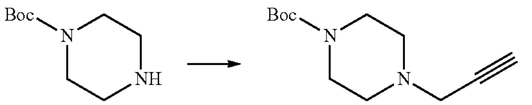

WX020-1 WX020-2

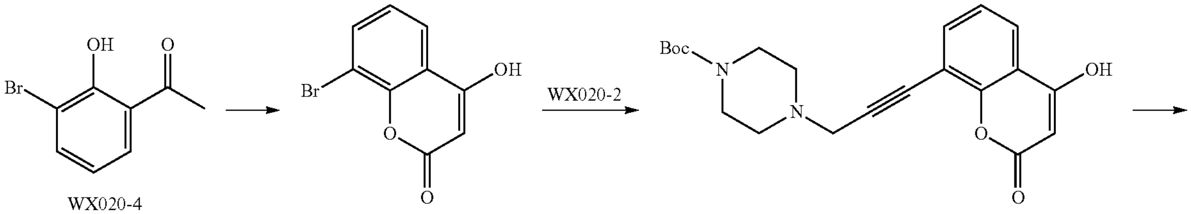

WX020-4 WX020-5 WX020-6

-continued

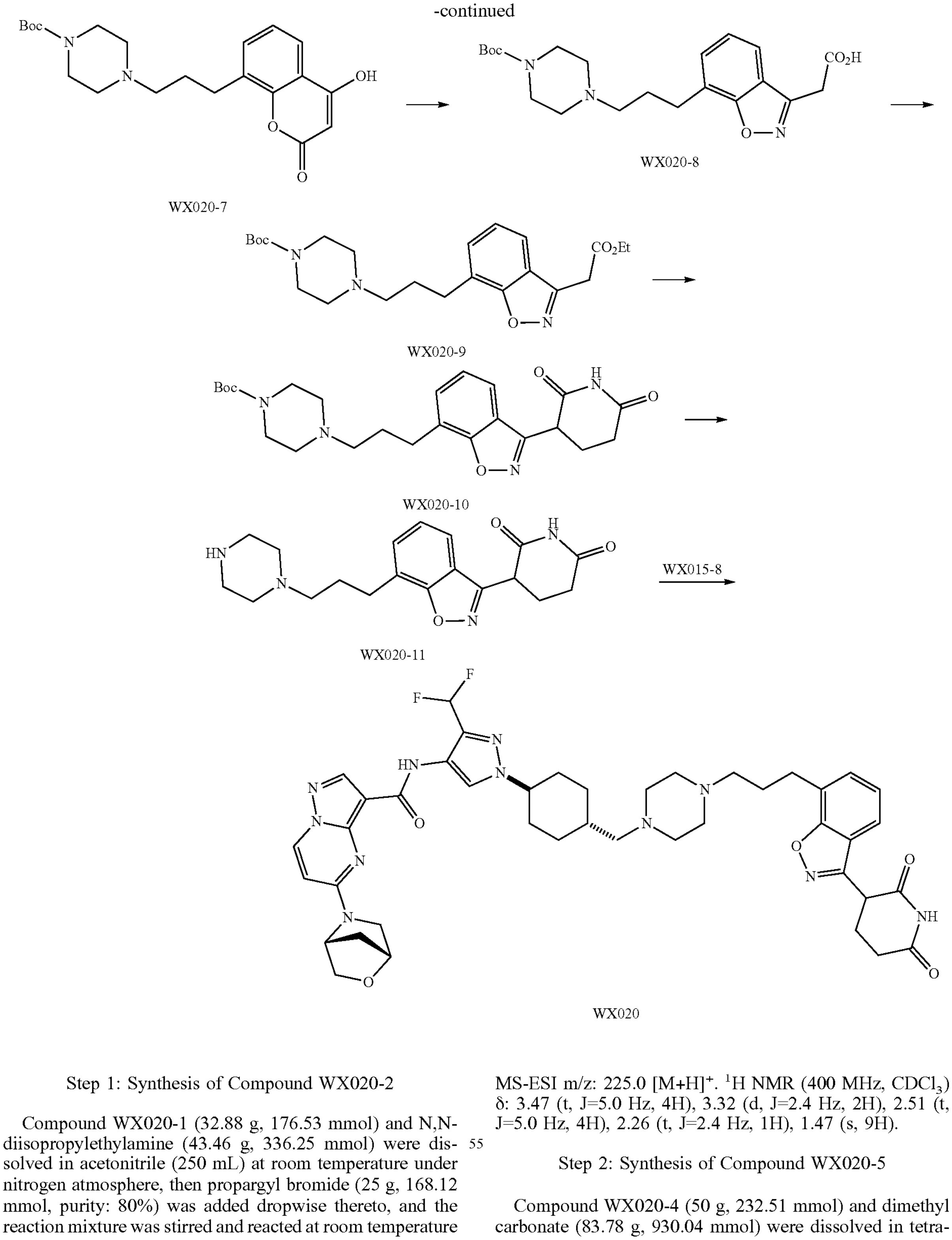

WX020-7 WX020-8 WX020-9 WX020-10 WX020-11 WX020

Step 1: Synthesis of Compound WX020-2

Compound WX020-1 (32.88 g, 176.53 mmol) and N,N-diisopropylethylamine (43.46 g, 336.25 mmol) were dissolved in acetonitrile (250 mL) at room temperature under nitrogen atmosphere, then propargyl bromide (25 g, 168.12 mmol, purity: 80%) was added dropwise thereto, and the reaction mixture was stirred and reacted at room temperature for 12 hours. After the reaction was completed, the reaction mixture was added with saturated ammonium chloride (500 mL) and extracted with ethyl acetate (200 mL×3). The organic phases were combined, sequentially washed with saturated ammonium chloride (200 mL×2) and saturated brine (200 mL), dried over anhydrous sodium sulfate, filtered, and the filtrate was concentrated under reduced pressure to remove the solvent to obtain compound WX020-2. MS-ESI m/z: 225.0 $[M+H]^+$. $^1H$ NMR (400 MHz, $CDCl_3$) δ: 3.47 (t, J=5.0 Hz, 4H), 3.32 (d, J=2.4 Hz, 2H), 2.51 (t, J=5.0 Hz, 4H), 2.26 (t, J=2.4 Hz, 1H), 1.47 (s, 9H).

Step 2: Synthesis of Compound WX020-5

Compound WX020-4 (50 g, 232.51 mmol) and dimethyl carbonate (83.78 g, 930.04 mmol) were dissolved in tetrahydrofuran (1.5 L) at room temperature under nitrogen atmosphere, then potassium tert-butoxide (156.54 g, 1.40 mol) was added thereto, and the reaction mixture was heated to 70° C. and stirred and reacted for 12 hours. After the reaction was completed, the reaction mixture was cooled to room temperature, concentrated under reduced pressure to remove the solvent, added with ice water (1000 mL), then added with 6 M hydrochloric acid to adjust the pH to 2 to 3 to precipitate a white solid, and filtered. The filter cake was rinsed with water (100 mL×2), collected, and dried under vacuum to obtain compound WX020-5. MS-ESI m/z: 240.9 $[M+H]^+$, 243.7 $[M+H+2]^+$. $^1$H NMR (400 MHz, DMSO_$d_6$) δ: 12.80 (s, 1H), 7.92 (dd, J=1.4, 7.8 Hz, 1H), 7.81 (dd, J=1.4, 7.8 Hz, 1H), 7.27 (t, J=8.0 Hz, 1H), 5.65 (s, 1H).

Step 3: Synthesis of Compound WX020-6

Compound WX020-5 (15 g, 62.23 mmol), compound WX020-2 (27.92 g, 124.46 mmol), cuprous iodide (1.19 g, 6.22 mmol), bis(triphenylphosphine)palladium(II) chloride (4.37 g, 6.22 mmol), and triethylamine (25.19 g, 248.92 mmol) were dissolved in N,N-dimethylformamide (300 mL) at room temperature under nitrogen atmosphere, and the reaction mixture was heated to 80° C. and stirred and reacted for 3 hours. After the reaction was completed, the reaction mixture was cooled to 0 to 10° C., poured into ice water (1.2 L), added with 1 M hydrochloric acid to adjust the pH to 5 to 6, and extracted with ethyl acetate (300 mL×3). The aqueous phase was collected and concentrated under reduced pressure to obtain compound WX020-6. MS-ESI m/z: 385.1 $[M+H]^+$.

Step 4: Synthesis of Compound WX020-7

Pd/C hydroxide (7 g, 24.92 mmol, purity: 20%) and Pd/C (7 g, 13.01 mmol, purity: 10%) were suspended in methanol (700 mL) at room temperature under argon atmosphere, and compound WX020-6 (35 g, 91.05 mmol) was added thereto. The reaction mixture was replaced with hydrogen three times, and stirred and reacted at room temperature under a controlled hydrogen pressure of 30 psi for 16 hours. After the reaction was completed, the reaction mixture was filtered. The filter cake was rinsed with methanol (200 mL×5), and the filtrate was concentrated under reduced pressure to remove the solvent. The resulting crude product was added with dichloromethane (50 mL) and water (300 mL) to precipitate a solid, and filtered. The filter cake was rinsed with water (30 mL×3), collected, and dried under vacuum to obtain compound WX020-7. MS-ESI m/z: 389.1 $[M+H]^+$. $^1$H NMR (400 MHz, DMSO_$d_6$) δ: 10.21 (s, 1H), 7.71 (d, J=8.0 Hz, 1H), 7.56 (d, J=7.2 Hz, 1H), 7.29 (t, J=7.6 Hz, 1H), 5.71 (s, 1H), 4.10-3.65 (m, 2H), 3.50-3.20 (m, 6H), 3.16-3.10 (m, 2H), 2.82 (t, J=7.6 Hz, 2H), 2.13-1.99 (m, 2H), 1.40 (s, 9H).

Step 5: Synthesis of Compound WX020-8

Compound WX020-7 (4.40 g, 11.33 mmol) was dissolved in ethanol (50 mL) at room temperature under argon atmosphere, then hydroxylamine hydrochloride (2.75 g, 39.64 mmol) and sodium acetate (3.25 g, 39.64 mmol) were added thereto, and the reaction mixture was heated to 80° C. and stirred and reacted for 12 hours. After the reaction was completed, the reaction mixture was cooled to room temperature, added with water (350 mL), extracted with methyl tert-butyl ether (100 mL×4), and the aqueous phase was collected. The organic phase was washed with 5% sodium bicarbonate aqueous solution (50 mL×3), discarded, and the aqueous phase was collected. The two aqueous phases were combined, added with 1 M hydrochloric acid to adjust the pH to 6 to 7, and extracted with a mixed solvent of dichloromethane and methanol (v/v: 10:1, 100 mL×4). The organic phase was washed with saturated brine (50 mL), dried over anhydrous sodium sulfate, filtered, and the filtrate was concentrated under reduced pressure to obtain compound WX020-8. MS-ESI m/z: 404.2 $[M+H]^+$. $^1$H NMR (400 MHz, DMSO_$d_6$) δ: 7.66 (d, J=7.6 Hz, 1H), 7.47 (d, J=6.8 Hz, 1H), 7.31 (t, J=7.6 Hz, 1H), 4.07 (s, 2H), 3.49-3.39 (m, 4H), 2.91 (t, J=7.6 Hz, 2H), 2.42-2.26 (m, 6H), 1.95-1.79 (m, 2H), 1.39 (s, 9H).

Step 6: Synthesis of Compound WX020-9

Compound WX020-8 (1.3 g, 3.22 mmol) was dissolved in anhydrous ethanol (20 mL) at room temperature, then concentrated sulfuric acid (632.03 mg, 6.44 mmol) was added thereto, and the reaction mixture was heated to 80° C. and stirred and reacted for 12 hours. After the reaction was completed, the reaction mixture was cooled to room temperature and concentrated under reduced pressure to remove the solvent. The residue was dissolved in tetrahydrofuran (17 mL) and water (8 mL). Sodium bicarbonate (1.08 g, 12.89 mmol) was added thereto in batches, then di-tert-butyl dicarbonate (773.60 mg, 3.54 mmol) was added thereto, and the reaction mixture was stirred and reacted at room temperature for 2 hours. After the reaction was completed, the reaction mixture was added with water (70 mL) and extracted with ethyl acetate (30 mL×3). The organic phases were combined, washed with saturated brine (30 mL×2), dried over anhydrous sodium sulfate, filtered, and the filtrate was concentrated under reduced pressure to obtain a residue. The resulting residue was separated by column chromatography (eluent: petroleum ether/ethyl acetate=2/1 to 0/1 v/v) to obtain compound WX020-9. MS-ESI m/z: 432.2 $[M+H]^+$. $^1$H NMR (400 MHz, $CDCl_3$) δ: 7.54 (d, J=7.6 Hz, 1H), 7.35 (d, J=6.8 Hz, 1H), 7.24 (d, J=7.6 Hz, 1H), 4.22 (q, J=7.2 Hz, 2H), 4.04 (s, 2H), 3.51-3.35 (m, 4H), 2.99 (t, J=7.6 Hz, 2H), 2.52-2.30 (m, 6H), 2.03-1.91 (m, 2H), 1.46 (s, 9H), 1.27 (t, J=7.0 Hz, 3H).

Step 7: Synthesis of Compound WX020-10

Acrylamide (59.30 mg, 834.25 mol) and compound WX020-9 (0.3 g, 695.21 mol) were dissolved in anhydrous tetrahydrofuran (6 mL) at room temperature under argon atmosphere, and the reaction mixture was cooled to 0 to 5° C. in an ice bath. A solution of potassium tert-butoxide in tetrahydrofuran (1 M, 1.04 mL) was added dropwise thereto, and after the dropwise addition was completed, the reaction mixture was stirred and reacted at the same temperature for 1 hour. After the reaction was completed, the reaction mixture was poured into 0.1 M hydrochloric acid (10.43 mL) and extracted with ethyl acetate (3 mL×3). The organic phases were combined, washed with saturated brine (3 mL×2), dried over anhydrous sodium sulfate, filtered, and the filtrate was concentrated under reduced pressure to remove the solvent. The resulting residue was separated by column chromatography (eluent: petroleum ether/ethyl acetate/tetrahydrofuran=1/1/0 to 0/1/0 to 0/1/1, v/v/v) to obtain compound WX020-10. MS-ESI m/z: 457.2 $[M+H]^+$. $^1$H NMR (400 MHz, $CDCl_3$) δ: 8.00 (s, 1H), 7.54 (d, J=8.0 Hz, 1H), 7.38 (d, J=7.2 Hz, 1H), 7.30-7.25 (m, 1H), 4.34 (dd, J=5.2, 8.8 Hz, 1H), 3.52-3.35 (m, 4H), 3.10-2.95 (m, 3H), 2.83-2.71 (m, 1H), 2.69-2.56 (m, 1H), 2.53-2.30 (m, 7H), 2.04-1.90 (m, 2H), 1.47 (s, 9H).

Step 8: Synthesis of Trifluoroacetate of Compound WX020-11

Compound WX020-10 (107 mg, 234.37 mol) was dissolved in dichloromethane (3 mL) at room temperature, then trifluoroacetic acid (924.00 mg, 8.10 mmol) was added thereto, and the reaction mixture was stirred and reacted at room temperature for 1 hour. After the reaction was completed, the reaction mixture was concentrated under reduced pressure to remove the solvent to obtain trifluoroacetate of compound WX020-11. MS-ESI m/z: 357.1 $[M+H]^+$.

Step 9: Synthesis of Hydrochloride of Compound WX020

Trifluoroacetate of compound WX020-11 (143.24 mg) was dissolved in acetonitrile (2 mL) at room temperature, then N,N-diisopropylethylamine (199.04 mg, 1.54 mmol) was added thereto, and the reaction mixture was stirred for 5 minutes. Compound WX015-8 (115 mg, 192.50 mol) was added thereto, and the reaction mixture was heated to 80° C. and stirred and reacted for 16 hours. After the reaction was completed, the reaction mixture was cooled to room temperature and concentrated under reduced pressure to remove the solvent. The resulting residue was separated by preparative HPLC (chromatographic column: Phenomenex Luna 80*30 mm*3 μm; mobile phase: water (0.04% hydrochloric acid)-acetonitrile; acetonitrile %: 1% to 35%, 8 minutes) to obtain hydrochloride of target compound WX020. MS-ESI m/z: 826.6 $[M+H]^+$. $^1H$ NMR (400 MHz, DMSO_$d_6$) δ: 12.24-11.82 (m, 1H), 11.76-11.36 (m, 1H), 11.10 (s, 1H), 9.50 (d, J=6.4 Hz, 1H), 8.78 (d, J=7.6 Hz, 1H), 8.39 (d, J=4.0 Hz, 1H), 8.25 (d, J=5.6 Hz, 1H), 7.73 (d, J=8.0 Hz, 1H), 7.55 (d, J=7.2 Hz, 1H), 7.35 (t, J=7.6 Hz, 1H), 7.27-6.94 (m, 1H), 6.91-6.40 (m, 1H), 5.17 (d, J=78.8 Hz, 1H), 4.76 (d, J=17.6 Hz, 1H), 4.62 (dd, J=4.8, 12.0 Hz, 1H), 4.43-4.05 (m, 6H), 3.91-3.40 (m, 8H), 3.32-3.15 (m, 2H), 3.11-2.94 (m, 3H), 2.86-2.72 (m, 1H), 2.68-2.58 (m, 1H), 2.57-2.44 (m, 1H), 2.27-2.15 (m, 3H), 2.13-1.87 (m, 6H), 1.68-1.85 (m, 2H), 1.85-1.67 (m, 2H).

Example 21

WX021

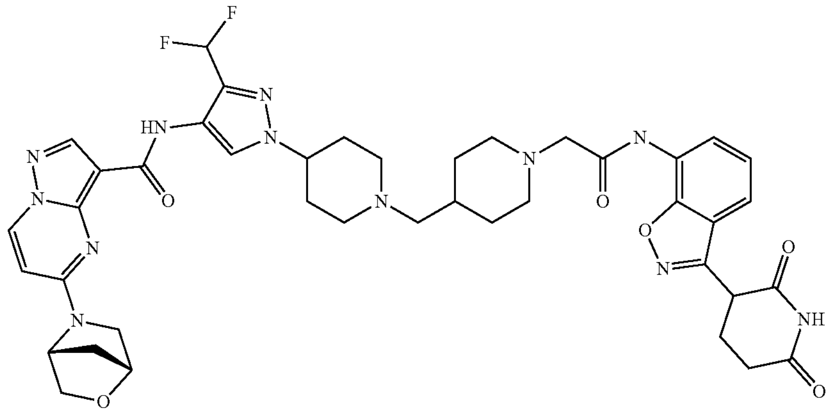

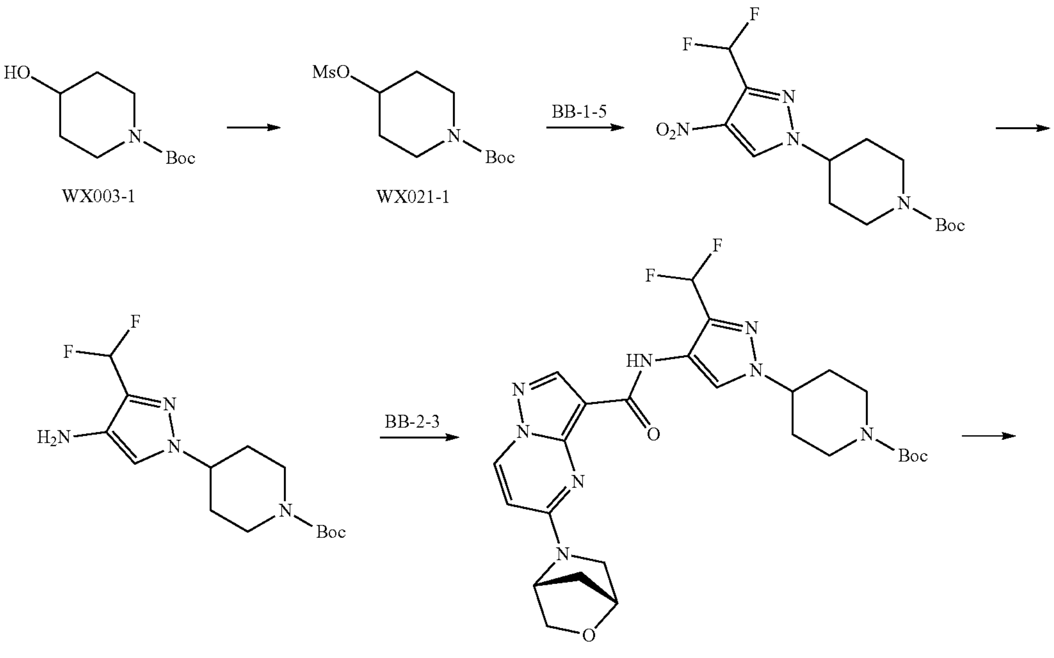

WX003-1

WX021-1

WX021-4

-continued
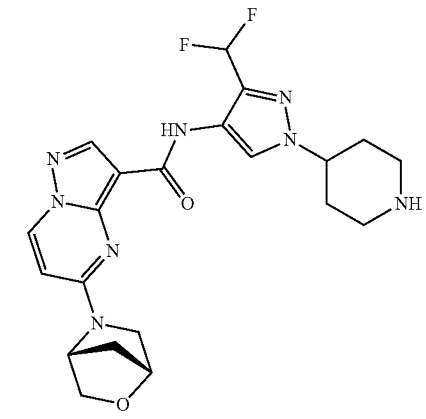
WX021-5
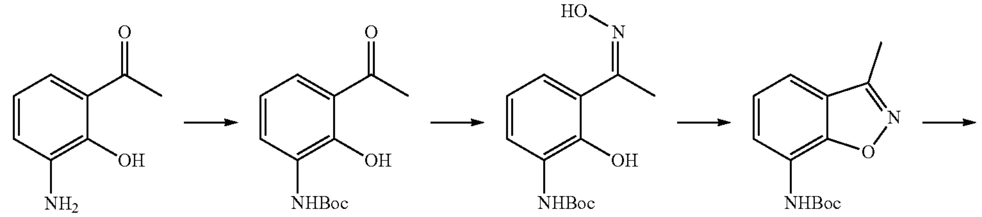
WX021-6 WX021-7 WX021-8 WX021-9
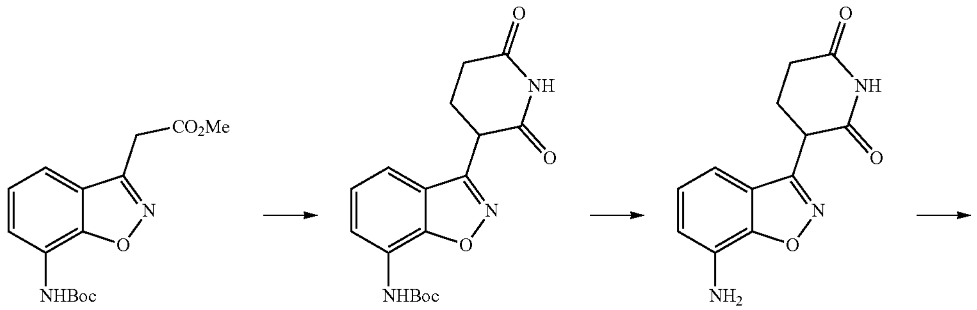
WX021-10 WX021-11 WX021-12
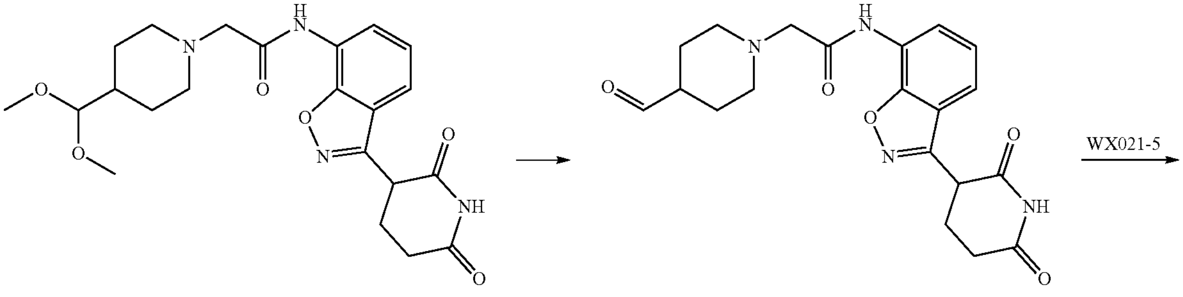
WX021-13 WX021-14

-continued

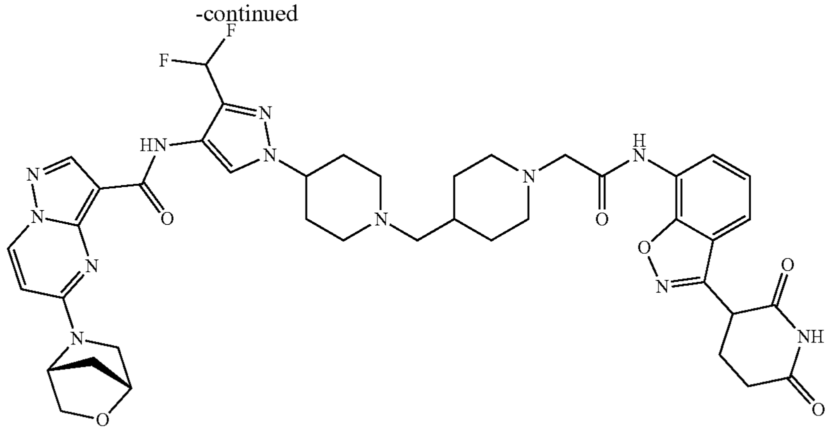

WX021

Step 1: Synthesis of Compound WX021-1

Compound WX003-1 (10 g, 49.69 mmol) was dissolved in dichloromethane (100 mL) at room temperature under nitrogen atmosphere, then triethylamine (10.06 g, 99.37 mmol, 13.83 mL) was added thereto, and the reaction mixture was cooled to 0° C. in an ice bath. Methanesulfonyl chloride (7.25 g, 63.29 mmol) was added dropwise thereto, and the reaction mixture was stirred and reacted for 2 hours. After the reaction was completed, the reaction mixture was added with water (100 mL) and extracted with dichloromethane (100 mL×2). The organic phases were combined, washed with saturated brine (100 mL), dried over anhydrous sodium sulfate, filtered, and the filtrate was concentrated under reduced pressure to obtain compound WX021-1.

Step 2: Synthesis of Compound WX021-2

Compound BB-1-5 (6.2 g, 38.02 mmol) and potassium carbonate (10.51 g, 76.04 mmol) were dissolved in N,N-dimethylformamide (120 mL) at room temperature under nitrogen atmosphere, then compound WX021-1 (14.87 g, 53.22 mmol) was added thereto, and the reaction mixture was heated to 80° C. and stirred and reacted for 15 hours. After the reaction was completed, the reaction mixture was cooled to room temperature, added with water (700 mL), and extracted with ethyl acetate (300 mL×2). The organic phases were combined, washed with saturated brine (500 mL), dried over anhydrous sodium sulfate, filtered, and the filtrate was concentrated under reduced pressure. The resulting residue was separated by column chromatography (eluent: ethyl acetate/petroleum ether=1/5 to 1/3, v/v) to obtain compound WX021-2. MS-ESI m/z: 247.1 $[M+H-100]^+$. $^1H$ NMR (400 MHz, $CDCl_3$) δ: 8.23 (s, 1H), 7.12 (t, J=53.4 Hz, 1H), 4.42-4.22 (m, 3H), 2.99-2.80 (m, 2H), 2.26-2.14 (m, 2H), 2.00-1.86 (m, 2H), 1.49 (s, 9H).

Step 3: Synthesis of Compound WX021-3

Compound WX021-2 (3.58 g, 10.34 mmol) was dissolved in tetrahydrofuran (90 mL) at room temperature under argon atmosphere, and Pd/C (1 g, purity: 10%) was added thereto. The reaction mixture was replaced with hydrogen three times, and stirred and reacted under a maintained pressure of 15 psi for 15 hours. After the reaction was completed, the reaction mixture was filtered. The filter cake was rinsed with methanol (50 mL×4), and the filtrate was concentrated under reduced pressure to obtain compound WX021-3. MS-ESI m/z: 261.0 $[M+H-56]^+$.

Step 4: Synthesis of Compound WX021-4

Intermediate BB-2-3 (0.97 g, 3.73 mmol) was dissolved in acetonitrile (20 mL) at room temperature under nitrogen atmosphere, then tetramethylchlorourea hexafluorophosphate (1.25 g, 4.47 mmol) and N-methylimidazole (1.07 g, 13.05 mmol) were added thereto, and the reaction mixture was stirred for 10 minutes. Compound WX021-3 (1.30 g, 4.10 mmol) was added thereto, and the reaction mixture was stirred and reacted at room temperature for 15 hours. After the reaction was completed, the reaction mixture was concentrated under reduced pressure to remove the solvent, added with saturated brine (50 mL), and extracted with dichloromethane (20 mL×3). The organic phases were combined, dried over anhydrous sodium sulfate, filtered, and the filtrate was concentrated under reduced pressure. The resulting residue was separated by column chromatography (eluent: petroleum ether/ethyl acetate=1/1 to 0/1, v/v) to obtain compound WX021-4. MS-ESI m/z: 559.3 $[M+H]^+$. $^1H$ NMR (400 MHz, $CDCl_3$) δ: 9.61 (s, 1H), 8.43 (d, J=10.0 Hz, 2H), 8.31 (d, J=7.6 Hz, 1H), 6.77 (t, J=54.4 Hz, 1H), 6.12 (d, J=8.0 Hz, 1H), 5.45 (s, 1H), 4.80 (s, 1H), 4.33-4.17 (m, 3H), 4.03-3.94 (m, 2H), 3.62-3.46 (m, 2H), 2.98-2.83 (m, 2H), 2.17-2.07 (m, 3H), 2.03-1.90 (m, 3H), 1.49 (s, 9H).

Step 5: Synthesis of Hydrochloride of Compound WX021-5

Compound WX021-4 (0.51 g, 913.03 mol) was dissolved in ethyl acetate (2 mL) at room temperature under nitrogen atmosphere, then a solution of hydrochloric acid in ethyl acetate (4 M, 20.40 mL) was added thereto, and the reaction mixture was stirred and reacted at room temperature for 15 hours. After the reaction was completed, the reaction mixture was concentrated under reduced pressure to obtain hydrochloride of compound WX021-5. MS-ESI m/z: 459.1 $[M+H]^+$.

Step 6: Synthesis of Compound WX021-7

Compound WX021-6 (200 g, 1.32 mol) was dissolved in ethanol (1.5 L) at room temperature under nitrogen atmosphere, then di-tert-butyl dicarbonate (346.51 g, 1.59 mol)

was added thereto in batches, and the reaction mixture was heated to 60° C. and stirred and reacted for 16 hours. After the reaction was completed, the reaction mixture was cooled to room temperature and concentrated under reduced pressure to remove the solvent. The residue was added with isopropanol (500 mL), cooled to 0° C., stirred for 1 hour, and filtered. The filter cake was rinsed with isopropanol (200 mL), and the filtrate collected. The filtrate was concentrated under reduced pressure to obtain compound WX021-7. MS-ESI m/z: 196.1 $[M+H-56]^+$. $^1H$ NMR (400 MHz, DMSO_$d_6$) δ: 12.60 (s, 1H), 8.12 (s, 1H), 7.90 (d, J=7.6 Hz, 1H), 7.66 (d, J=8.0 Hz, 1H), 6.94 (d, J=8.0 Hz, 1H), 2.66 (s, 3H), 1.46 (s, 9H).

Step 7: Synthesis of Compound WX021-8

Compound WX021-7 (200 g, 795.93 mmol), sodium acetate (97.94 g, 1.19 mol), and hydroxylamine hydrochloride (60.84 g, 875.53 mmol) were dissolved in methanol (1.2 L) at room temperature under nitrogen atmosphere, and the reaction mixture was stirred and reacted at room temperature for 16 hours. The reaction mixture was then heated to 50° C. and reacted for 1 hour. Additional hydroxylamine hydrochloride (11.06 g, 159.19 mmol) was added thereto, and the reaction mixture was stirred and reacted for another 1 hour. After the reaction was completed, the reaction mixture was cooled to room temperature, added with water (1.5 L) and methyl tert-butyl ether (1.5 L), stirred for 5 minutes, and the phases were separated. The aqueous phase was then extracted with methyl tert-butyl ether (500 mL×2). The organic phases were combined, washed with 10% saline (500 mL×2), dried over anhydrous sodium sulfate, filtered, and the filtrate was concentrated under reduced pressure to remove the solvent to obtain compound WX021-8. MS-ESI m/z: 211.1 $[M+H-56]^+$. $^1H$ NMR (400 MHz, DMSO_$d_6$) δ: 12.27 (s, 1H), 11.67 (s, 1H), 7.82 (s, 1H), 7.69 (d, J=7.2 Hz, 1H), 7.23 (d, J=8.0 Hz, 1H), 6.86 (t, J=8.0 Hz, 1H), 2.27 (s, 3H), 1.46 (s, 9H).

Step 8: Synthesis of Compound WX021-9

Compound WX021-8 (100 g, 375.53 mmol) and triethylamine (49.40 g, 488.19 mmol) were dissolved in tetrahydrofuran (1 L) at room temperature under nitrogen atmosphere, then N,N'-carbonyldiimidazole (66.98 g, 413.08 mmol) was slowly added thereto, and the reaction mixture was heated to 70° C. and stirred and reacted for 1 hour. After the reaction was completed, the reaction mixture was cooled to room temperature, added with water (1 L), and extracted with a mixed solvent of methyl tert-butyl ether and petroleum ether (v/v: 1/1, 500 mL×2). The organic phase was washed with 10% saline (500 mL×2), dried over anhydrous sodium sulfate, filtered, and the filtrate was concentrated under reduced pressure to remove the solvent to obtain compound WX021-9. MS-ESI m/z: 249.1 $[M+H]^+$. $^1H$ NMR (400 MHz, $CDCl_3$) δ: 8.16 (s, 1H), 7.30 (s, 1H), 7.00 (s, 1H), 2.59 (s, 3H), 1.57 (s, 9H).

Step 9: Synthesis of Compound WX021-10

A solution of lithium diisopropylamide in tetrahydrofuran (2 M, 741.11 mL) was cooled to −68° C. at room temperature under nitrogen atmosphere, and dimethyl carbonate (36.72 g, 407.61 mmol, 34.31 mL) and a solution of compound WX021-9 (92 g, 370.55 mmol) in tetrahydrofuran (920 mL) were added dropwise thereto in about 30 minutes. After the dropwise addition was completed, the reaction mixture was stirred and reacted at a controlled temperature of −50° C. to −68° C. for 30 minutes. After the reaction was completed, the reaction mixture was slowly poured into saturated ammonium chloride (1.5 L) and extracted with ethyl acetate (500 mL×3). The organic phase was washed with saturated brine (500 mL), dried over anhydrous sodium sulfate, filtered, and the filtrate was concentrated under reduced pressure to remove the solvent to obtain compound WX021-10. MS-ESI m/z: 307.1 $[M+H]^+$.

Step 10: Synthesis of Compound WX021-11

Compound WX021-10 (10 g, 32.65 mmol) and acrylamide (2.78 g, 39.18 mmol) were dissolved in tetrahydrofuran (100 mL) at room temperature under nitrogen atmosphere, and the reaction mixture was cooled to 0 to 5° C. in an ice bath. A solution of potassium tert-butoxide in tetrahydrofuran (1 M, 48.97 mL) was added dropwise thereto, and after the dropwise addition was completed, the reaction mixture was stirred at the same temperature for 2 hours. After the reaction was completed, the reaction mixture was poured into 1 M hydrochloric acid (150 mL) and extracted with ethyl acetate (150 mL×2). The organic phases were combined, washed with saturated brine (150 mL), dried over anhydrous sodium sulfate, filtered, and the filtrate was concentrated under reduced pressure to obtain a crude product. The crude product was added with methyl tert-butyl ether (150 mL), and the mixture was stirred at room temperature for 30 minutes and filtered. The filter cake was rinsed with methyl tert-butyl ether (50 mL), collected, and dried under vacuum to obtain compound WX021-11. $^1H$ NMR (400 MHz, DMSO_$d_6$) δ: 11.10 (s, 1H), 9.55 (s, 1H), 7.69 (d, J=7.6 Hz, 1H), 7.54 (d, J=7.6 Hz, 1H), 7.30 (t, J=8.0 Hz, 1H), 4.60 (dd, J=5.0, 11.8 Hz, 1H), 2.84-2.72 (m, 1H), 2.66-2.57 (m, 1H), 2.57-2.43 (m, 1H), 2.25-2.15 (m, 1H), 1.49 (s, 9H).

Step 11: Synthesis of Hydrochloride of Compound WX021-12

Compound WX021-11 (9.4 g, 27.22 mmol) was dissolved in ethyl acetate (50 mL) at room temperature, then a solution of hydrochloric acid in ethyl acetate (4 M, 150 mL) was added thereto, and the reaction mixture was stirred and reacted at room temperature for 12 hours. After the reaction was completed, the reaction mixture was filtered. The filter cake was rinsed with ethyl acetate (20 mL) and collected to obtain hydrochloride of compound WX021-12. $^1H$ NMR (400 MHz, DMSO_$d_6$) δ: 11.09 (s, 1H), 8.32 (s, 2H), 7.31 (d, J=7.6 Hz, 1H), 7.26-7.16 (m, 2H), 4.59 (dd, J=4.8, 12.0 Hz, 1H), 2.83-2.71 (m, 1H), 2.65-2.56 (m, 1H), 2.55-2.42 (m, 1H), 2.25-2.15 (m, 1H).

Step 12: Synthesis of Compound WX021-13

Hydrochloride of compound WX021-12 (300 mg) was dissolved in anhydrous dichloromethane (6 mL) at room temperature under nitrogen atmosphere, then the reaction mixture was cooled to 0 to 5° C. in an ice bath, and triethylamine (323.30 mg, 3.19 mmol) and chloroacetyl chloride (144.34 mg, 1.28 mmol) were sequentially added dropwise thereto. The reaction mixture was stirred at the same temperature for 2 hours, then slowly returned to room temperature, and stirred and reacted for 2 hours. After the reaction was completed, the reaction mixture was added with water (20 mL) and extracted with dichloromethane (7 mL×3). The organic phases were combined, washed with saturated brine (10 mL), dried over anhydrous sodium sulfate, filtered, and the filtrate was concentrated under reduced pressure to obtain a residue. The resulting residue and 4-(dimethoxymethyl)piperidine (185.60 mg, 1.17 mmol) were dissolved in acetonitrile (6 mL), then sodium iodide (139.78 mg, 932.50 mol) and N,N-diisopropylethylamine (301.30 mg, 2.33 mmol) were added thereto, and the reaction mixture was heated to 80° C. and stirred for 2 hours. After the reaction was completed, the reaction mixture was cooled to room temperature, added with water (30 mL), and extracted with ethyl acetate (10 mL×3). The organic phases were combined, washed with saturated brine (10 mL×2), dried over anhydrous sodium sulfate, filtered, and the filtrate was concentrated under reduced pressure. The resulting residue was separated by column chromatography (eluent: ethyl acetate/dichloromethane/methanol=1/0/0 to 0/20/1, v/v/v) to obtain compound WX021-13. MS-ESI m/z: 445.1 $[M+H]^+$.

Step 13: Synthesis of Compound WX021-14

Compound WX021-13 (247 mg, 555.71 mol) was dissolved in tetrahydrofuran (4 mL) at room temperature under nitrogen atmosphere, then sulfuric acid (2 M, 1 mL) was added thereto, and the reaction mixture was heated to 70° C. and stirred and reacted for 12 hours. After the reaction was completed, the reaction mixture was cooled to room temperature, added with water (20 mL), extracted with ethyl acetate (7 mL×2), and the organic phase was discarded. The aqueous phase was added with saturated sodium bicarbonate aqueous solution to adjust the pH to 7 to 8, and extracted with ethyl acetate (15 mL×5). The organic phases were combined, washed with saturated brine (10 mL), dried over anhydrous sodium sulfate, filtered, and the filtrate was concentrated under reduced pressure to obtain compound WX021-14. MS-ESI m/z: 399.1 $[M+H]^+$.

Step 14: Synthesis of Hydrochloride of Compound WX021

Hydrochloride of compound WX021-5 (80 mg) and compound WX021-14 (64.40 mg, 161.64 mol) were dissolved in a mixed solvent of 1,2-dichloroethane (3 mL) and tetrahydrofuran (1 mL) at room temperature under nitrogen atmosphere, then potassium acetate (47.59 mg, 484.92 mol) and glacial acetic acid (0.1 mL) were added thereto, and the reaction mixture was stirred and reacted at room temperature for 2 hours. Sodium triacetoxyborohydride (102.77 mg, 484.92 mol) was then added thereto, and the reaction mixture was stirred and reacted for another 15 hours. After the reaction was completed, the reaction mixture was added with 1 M hydrochloric acid (1 mL) and concentrated under reduced pressure to remove the organic solvent. The resulting residue was separated by preparative HPLC (chromatographic column: Phenomenex Luna 80*30 mm*3 μm; mobile phase: water (0.04% hydrochloric acid)-acetonitrile; acetonitrile %: 1% to 30%, 8 minutes) to obtain hydrochloride of target compound WX021. MS-ESI m/z: 841.6 $[M+H]^+$. $^1H$ NMR (400 MHz, DMSO_$d_6$) δ: 11.13 (s, 2H), 10.44 (s, 1H), 10.12 (s, 1H), 9.54 (d, J=6.4 Hz, 1H), 8.80 (d, J=7.6 Hz, 1H), 8.46 (d, J=3.2 Hz, 1H), 8.27 (d, J=5.6 Hz, 1H), 8.01 (d, J=7.6 Hz, 1H), 7.69 (d, J=8.0 Hz, 1H), 7.41 (t, J=8.0 Hz, 1H), 7.32-7.00 (m, 1H), 6.91-6.41 (m, 1H), 5.31-5.02 (m, 1H), 4.77 (d, J=20.8 Hz, 1H), 4.65 (dd, J=5.0, 12.2 Hz, 1H), 4.60-4.52 (m, 1H), 4.41-4.23 (m, 2H), 3.83-3.80 (m, 1H), 3.76-3.62 (m, 4H), 3.48-3.36 (m, 2H), 3.29-2.98 (m, 6H), 2.85-2.73 (m, 1H), 2.68-2.52 (m, 2H), 2.48-2.32 (m, 3H), 2.31-1.77 (m, 7H), 1.70-1.54 (m, 2H).

Example 22

WX022

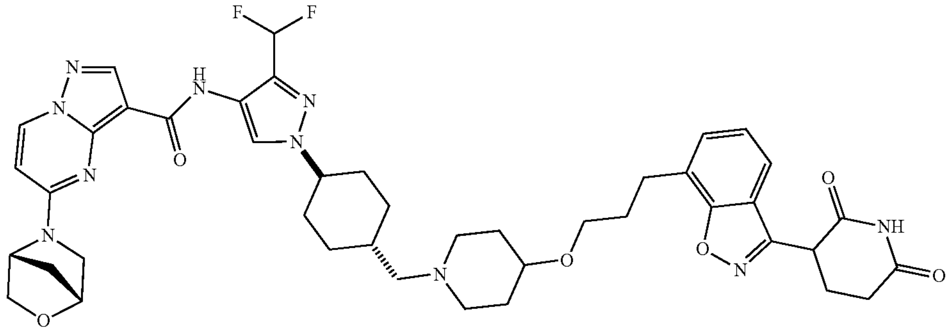

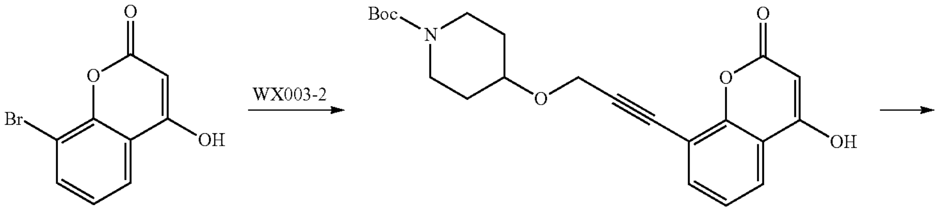

WX020-5

WX022-1

-continued

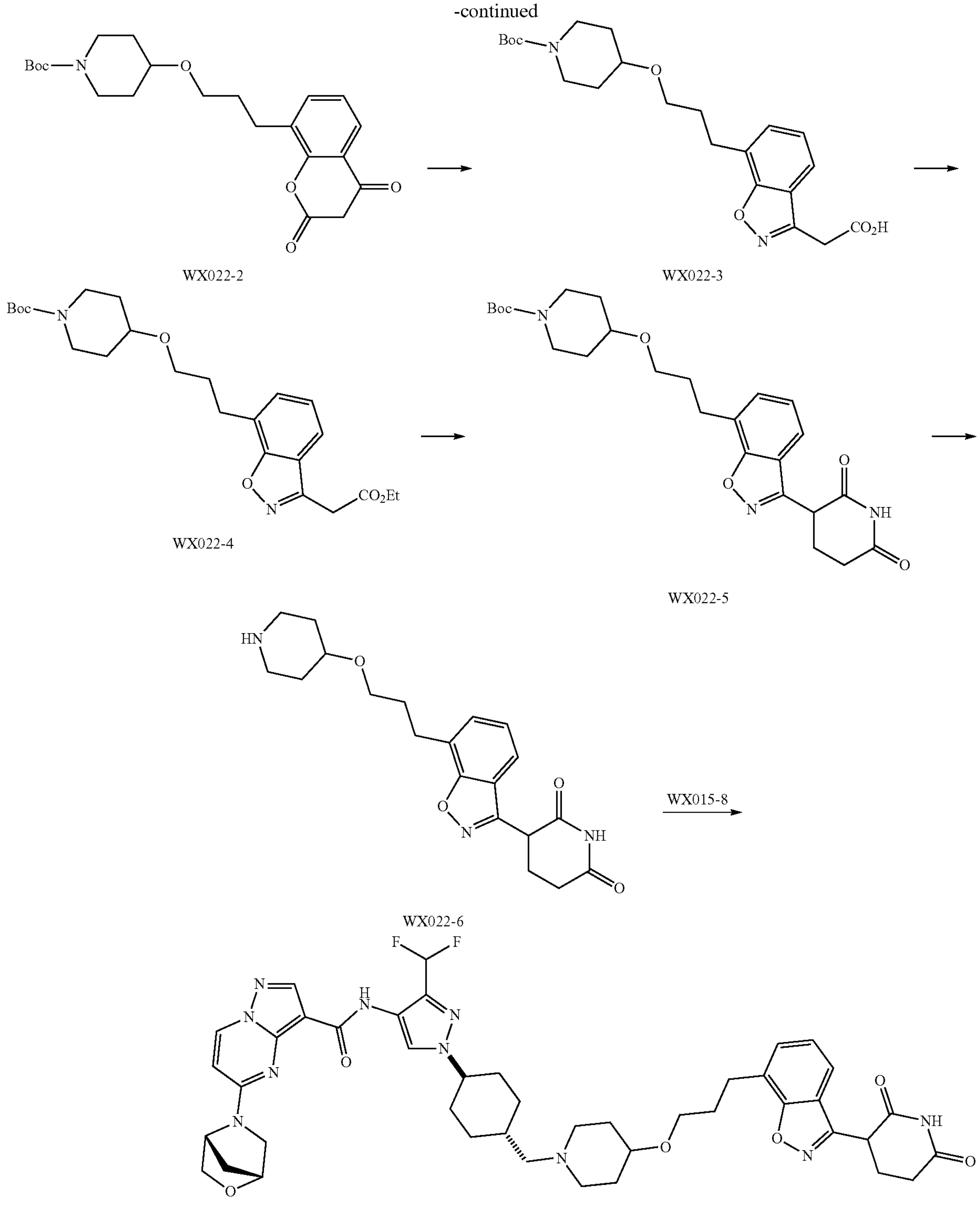

WX022-2

WX022-3

WX022-4

WX022-5

WX022-6

WX022

Step 1: Synthesis of Compound WX022-1

Compound WX020-5 (15 g, 62.23 mmol) was dissolved in N,N-dimethylformamide (250 mL) under nitrogen atmosphere, then cuprous iodide (1.19 g, 6.22 mmol), bis(triphenylphosphine)palladium(II) chloride (4.37 g, 6.22 mmol), and N,N-diisopropylethylamine (32.17 g, 248.92 mmol) were added thereto, and the reaction mixture was heated to 85° C. A solution of compound WX003-2 (59.57 g, 248.92 mmol) in N,N-dimethylformamide (50 mL) was added dropwise thereto for 2 hours, and after the dropwise addition was completed, the reaction mixture was stirred and reacted for another 1 hour. After the reaction was completed, the reaction mixture was cooled to room temperature, poured into water (1000 mL), extracted with ethyl acetate (300 mL×3), and the organic phase was discarded. The aqueous phase was collected, added with 1 M hydrochloric acid to adjust the pH to 5 to 6, and extracted with ethyl acetate (300 mL×2). The organic phases were combined, washed with saturated brine (500 mL×2), dried over anhydrous sodium sulfate, filtered, and the filtrate was concentrated under reduced pressure to obtain compound WX022-1. MS-ESI m/z: 300.0 $[M+H-100]^+$.

Step 2: Synthesis of Compound WX022-2

To methanol (400 mL) were added Pd/C (5 g, purity: 10%) and Pd/C hydroxide (5 g, purity: 20%) at room temperature under argon atmosphere, and compound WX022-1 (30 g, 75.11 mmol) was added thereto. The reaction mixture was replaced with hydrogen (balloon) three times, and stirred and reacted at room temperature for 24 hours. The reaction system was filtered, then the filtrate was added with Pd/C (5 g, purity: 10%) and Pd/C hydroxide (5 g, purity: 20%), and the reaction mixture was stirred and reacted at room temperature under a hydrogen pressure of 30 psi for another 24 hours. After the reaction was completed, the reaction mixture was filtered. The filter cake was rinsed with methanol (50 mL×3), and the filtrate was concentrated under reduced pressure. The residue was purified by reversed-phase column chromatography (column: DAC-150 Luna, flow rate: 650 mL/minute, mobile phase: purified water). The fraction was added with saturated sodium bicarbonate aqueous solution to adjust the pH to 7 to 8, concentrated under reduced pressure to remove most of the organic solvent, extracted with dichloromethane (100 mL), and the organic phase was discarded. The aqueous phase was added with 1 M hydrochloric acid to adjust the pH to 5 to 6, and extracted with dichloromethane (100 mL×2). The organic phase was washed with saturated brine (100 mL), dried over anhydrous sodium sulfate, filtered, and the filtrate was concentrated under reduced pressure to obtain compound WX022-2. MS-ESI m/z: 304.1 $[M+H-100]^+$. $^1H$ NMR (400 MHz, $CDCl_3$) δ: 11.06 (s, 1H), 7.78 (dd, J=1.4, 7.8 Hz, 1H), 7.44 (dd, J=1.2, 7.6 Hz, 1H), 7.22 (t, J=7.6 Hz, 1H), 5.88 (s, 1H), 3.72-3.62 (m, 2H), 3.47 (t, J=6.2 Hz, 2H), 3.44-3.36 (m, 1H), 3.18-3.03 (m, 2H), 2.94 (t, J=7.4 Hz, 2H), 2.03-1.91 (m, 2H), 1.82-1.71 (m, 2H), 1.54-1.41 (m, 11H).

Step 3: Synthesis of Compound WX022-3

Compound WX022-2 (1.90 g, 4.71 mmol) was dissolved in ethanol (20 mL) at room temperature under nitrogen atmosphere, then hydroxylamine hydrochloride (1.15 g, 16.48 mmol) and sodium acetate (1.35 g, 16.48 mmol) were added thereto, and the reaction mixture was heated to 85° C. and stirred and reacted for 15 hours. Additional hydroxylamine hydrochloride (0.383 g, 5.5 mmol) and sodium acetate (0.45 g, 5.5 mmol) were added thereto, and the reaction mixture was stirred and reacted for another 15 hours. After the reaction was completed, the reaction mixture was concentrated under reduced pressure to remove most of the organic solvent, added with sodium bicarbonate aqueous solution to adjust the pH to 7 to 8, extracted with methyl tert-butyl ether (50 mL×2), and the organic phase was discarded. The aqueous phase was added with 1 N hydrochloric acid to adjust the pH to 5 to 6, and extracted with dichloromethane (50 mL×2). The organic phase was dried over anhydrous sodium sulfate, filtered, and the filtrate was concentrated under reduced pressure to obtain compound WX022-3. MS-ESI m/z: 319.1 $[M+H-100]^+$.

Step 4: Synthesis of Compound WX022-4

Compound WX022-3 (0.87 g, 2.08 mmol) was dissolved in ethanol (10 mL) at room temperature under nitrogen atmosphere, then concentrated sulfuric acid (407.80 mg, 4.16 mmol, purity: 98%) was added dropwise thereto, and the reaction mixture was heated to 85° C. and stirred and reacted for 15 hours. After the reaction was completed, the reaction mixture was concentrated under reduced pressure to obtain a crude product. The crude product was dissolved in a mixed solvent of tetrahydrofuran (10 mL) and water (5 mL), then sodium bicarbonate (523.89 mg, 6.24 mmol) and di-tert-butyl dicarbonate (453.96 mg, 2.08 mmol) were added thereto, and the reaction mixture was stirred and reacted for 3 hours. After the reaction was completed, the reaction mixture was extracted with ethyl acetate (10 mL×2).

The organic phases were combined, washed with saturated brine (20 mL), dried over anhydrous sodium sulfate, filtered, and the filtrate was concentrated under reduced pressure. The resulting residue was separated by column chromatography (eluent: petroleum ether/ethyl acetate=4/1, v/v) to obtain compound WX022-4. MS-ESI m/z: 347.1 $[M+H-100]^+$. $^1H$ NMR (400 MHz, $CDCl_3$) δ: 7.54 (dd, J=0.8, 8.0 Hz, 1H), 7.36 (d, J=6.8 Hz, 1H), 7.24 (d, J=7.6 Hz, 1H), 4.22 (q, J=7.2 Hz, 2H), 4.04 (s, 2H), 3.81-3.71 (m, 2H), 3.50 (t, J=6.2 Hz, 2H), 3.46-3.37 (m, 1H), 3.15-2.98 (m, 4H), 2.13-1.99 (m, 2H), 1.87-1.74 (m, 2H), 1.57-1.39 (m, 11H), 1.27 (t, J=7.2 Hz, 3H).

Step 5: Synthesis of Compound WX022-5

Compound WX022-4 (310 mg, 694.23 mol) was dissolved in anhydrous tetrahydrofuran (6 mL) at room temperature under nitrogen atmosphere, and the reaction mixture was cooled to 0° C. in an ice bath. A solution of lithium diisopropylamide in tetrahydrofuran (2 M, 520.68 L) was added dropwise thereto, and the reaction mixture was stirred at the same temperature for 15 minutes. A solution of acrylamide (59.21 mg, 833.08 mol) in anhydrous tetrahydrofuran (2 mL) was added dropwise thereto, and the reaction mixture was stirred and reacted at room temperature for 12 hours. After the reaction was completed, the reaction mixture was poured into 1 M hydrochloric acid (10 mL) and extracted with ethyl acetate (5 mL×3). The organic phases were combined, washed with saturated brine (5 mL), dried over anhydrous sodium sulfate, filtered, and the filtrate was concentrated under reduced pressure. The resulting residue was separated by thin-layer chromatography (developing solvent: petroleum ether/ethyl acetate=1/2, v/v) to obtain compound WX022-5. $^1H$ NMR (400 MHz, $CDCl_3$) δ: 8.19 (s, 1H), 7.53 (d, J=8.0 Hz, 1H), 7.38 (d, J=7.2 Hz, 1H), 7.31-7.23 (m, 1H), 4.34 (dd, J=5.4, 8.6 Hz, 1H), 3.85-3.65 (m, 2H), 3.50 (t, J=6.2 Hz, 2H), 3.46-3.38 (m, 1H), 3.15-2.97 (m, 5H), 2.83-2.72 (m, 1H), 2.68-2.56 (m, 1H), 2.52-2.40 (m, 1H), 2.13-2.00 (m, 2H), 1.87-1.74 (m, 2H), 1.57-1.41 (m, 11H).

Step 6: Synthesis of Trifluoroacetate of Compound WX022-6

Compound WX022-5 (92 mg, 195.10 mol) was dissolved in anhydrous dichloromethane (2 mL) at room temperature under nitrogen atmosphere, then trifluoroacetic acid (616.00 mg, 5.40 mmol, 0.4 mL) was added thereto, and the reaction mixture was stirred and reacted at room temperature for 12 hours. After the reaction was completed, the reaction mixture was concentrated under reduced pressure to obtain trifluoroacetate of compound WX022-6. MS-ESI m/z: 372.0 $[M+H]^+$.

Step 7: Synthesis of Hydrochloride of Compound WX022

Trifluoroacetate of compound WX022-6 (139.2 mg) was dissolved in acetonitrile (2 mL) at room temperature under nitrogen atmosphere, then N,N-diisopropylethylamine (201.72 mg, 1.56 mmol) was added thereto, and the reaction mixture was stirred for 10 minutes. Compound WX015-8 (139.86 mg, 234.11 mol) was added thereto, and the reaction mixture was heated to 80° C. and stirred and reacted for 12 hours. After the reaction was completed, the reaction mixture was concentrated under reduced pressure to remove acetonitrile. The resulting residue was separated by preparative HPLC (chromatographic column: Phenomenex Luna 80*30 mm*3 μm; mobile phase: water (0.04% hydrochloric acid)-acetonitrile; acetonitrile %: 25% to 55%, 8 minutes) to obtain hydrochloride of target compound WX022. MS-ESI m/z: 841.5 $[M+H]^+$. $^1H$ NMR (400 MHz, DMSO_$d_6$) δ: 11.10 (s, 1H), 9.51 (br d, J=6.4 Hz, 2H), 8.78 (d, J=7.6 Hz, 1H), 8.40 (d, J=4.0 Hz, 1H), 8.25 (d, J=5.6 Hz, 1H), 7.69 (d, J=8.0 Hz, 1H), 7.49 (t, J=7.2 Hz, 1H), 7.36-7.28 (m, 1H), 7.27-6.95 (m, 1H), 6.91-6.42 (m, 1H), 5.34-5.03 (m, 1H), 4.83-4.71 (m, 1H), 4.60 (dd, J=4.8, 12.0 Hz, 1H), 4.32-4.15 (m, 1H), 3.94-3.57 (m, 3H), 3.55-3.25 (m, 5H), 3.07-2.85 (m, 6H), 2.84-2.71 (m, 1H), 2.70-2.55 (m, 2H), 2.25-2.14 (m, 1H), 2.13-1.65 (m, 16H), 1.27-1.07 (m, 2H).

Example 23

WX023

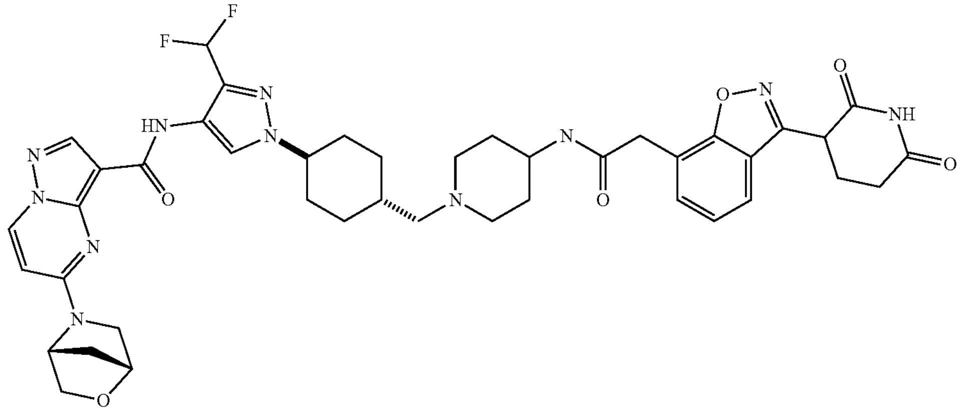

Synthetic Route

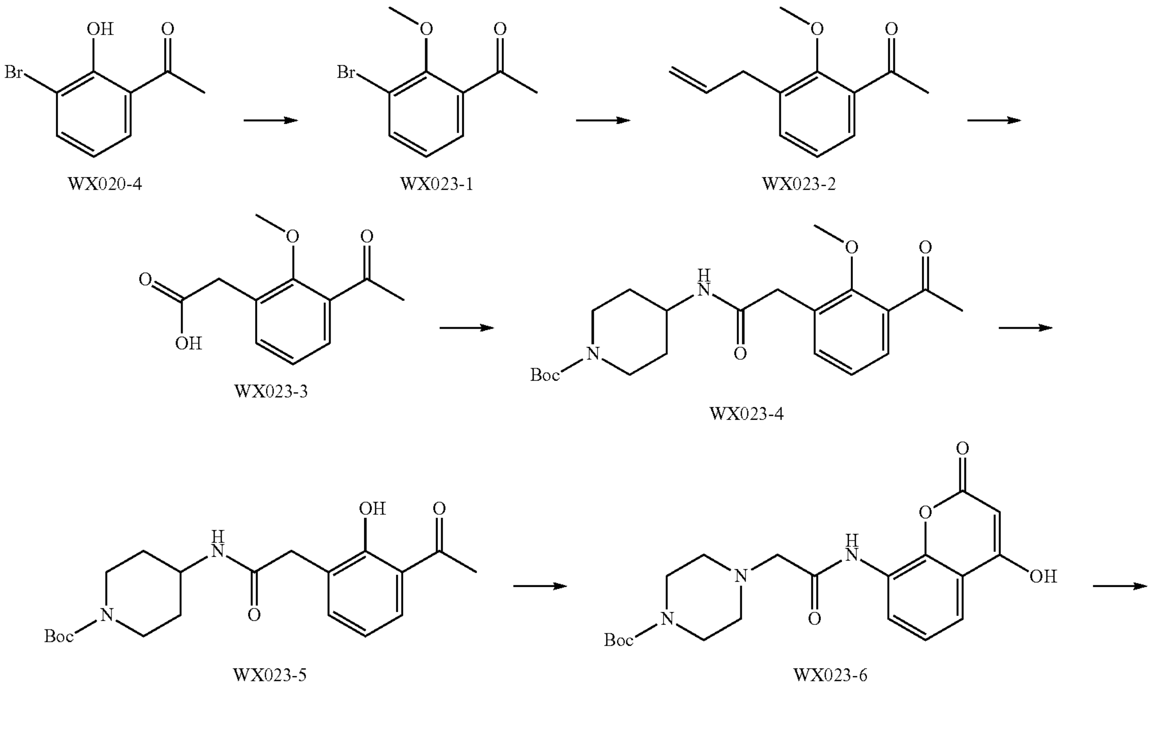

WX020-4

WX023-1

WX023-2

WX023-3

WX023-4

WX023-5

WX023-6

-continued

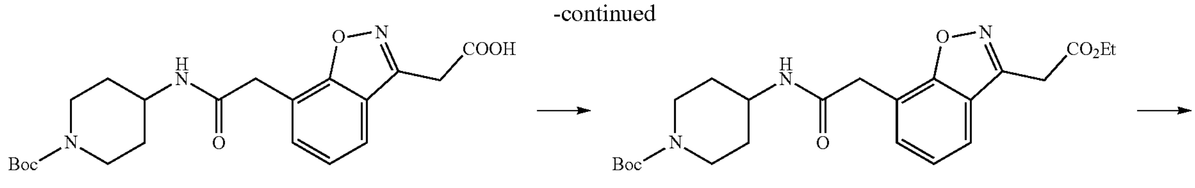

WX023-7 WX023-8

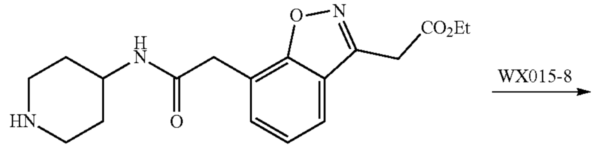

WX023-9

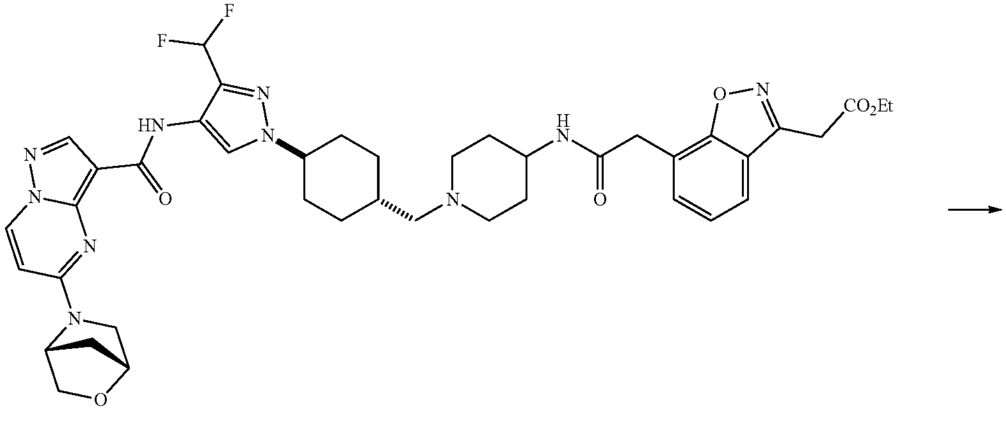

WX023-10

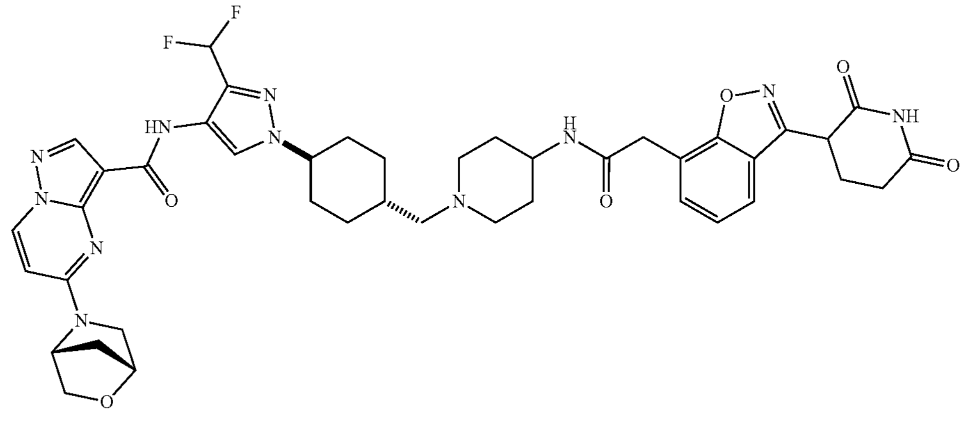

WX023

Step 1: Synthesis of Compound WX023-1

Compound WX020-4 (10 g, 46.50 mmol) was dissolved in N,N-dimethylformamide (100 mL) at room temperature under nitrogen atmosphere, then potassium carbonate (12.85 g, 93.00 mmol) was added thereto, and the reaction mixture was cooled to 0° C. in an ice bath. Iodomethane (19.80 g, 139.50 mmol) was slowly added thereto, and after the dropwise addition was completed, the reaction mixture was slowly returned to room temperature and stirred and reacted for 3 hours. After the reaction was completed, the reaction mixture was cooled to 0° C., slowly added with ammonia water (10 mL), stirred for 15 minutes, then added with water (100 mL), and extracted with ethyl acetate (100 mL×3). The organic phases were combined, washed with saturated brine (200 mL), dried over anhydrous sodium sulfate, filtered, and the filtrate was concentrated under reduced pressure to obtain compound WX023-1. MS-ESI m/z: 229.1 $[M+H]^+$, 231.1 $[M+H+2]^+$. $^1H$ NMR (400 MHz, DMSO_$d_6$) δ: 7.83 (dd, J=1.6, 8.0 Hz, 1H), 7.61 (dd, J=1.6, 7.6 Hz, 1H), 7.18 (t, J=7.8 Hz, 1H), 3.80 (s, 3H), 2.58 (s, 3H).

Step 2: Synthesis of Compound WX023-2

Compound WX023-1 (10 g, 43.65 mmol) and allylboronic acid pinacol ester (14.67 g, 87.31 mmol) were dissolved in 1,4-dioxane (100 mL) and water (10 mL) at room temperature under nitrogen atmosphere, then potassium carbonate (12.07 g, 87.31 mmol) and [1,1'-bis(diphenylphosphino)ferrocene]dichloropalladium(II) dichloromethane (3.57 g, 4.37 mmol) were added thereto, and the reaction mixture was heated to 100° C. and stirred and reacted for 12 hours. After the reaction was completed, the reaction mixture was cooled to room temperature, added with water (100 mL), and extracted with ethyl acetate (100 mL×3). The organic phases were combined, washed with saturated brine (100 mL), dried over anhydrous sodium sulfate, filtered, and the filtrate was concentrated under reduced pressure to obtain a crude product. The crude product was separated by column chromatography (eluent: petroleum ether/ethyl acetate=1/0 to 0/1, v/v) to obtain compound WX023-2. MS-ESI m/z: 191.2 $[M+H]^+$. $^1H$ NMR (400 MHz, DMSO_$d_6$) δ: 7.44 (dd, J=1.6, 7.6 Hz, 1H), 7.38 (dd, J=1.6, 7.6 Hz, 1H), 7.16 (t, J=7.6 Hz, 1H), 6.04-5.88 (m, 1H), 5.11-5.09 (m, 1H), 5.08-5.05 (m, 1H), 3.69 (s, 3H), 3.42 (d, J=6.4 Hz, 2H), 2.56 (s, 3H).

Step 3: Synthesis of Compound WX023-3

Compound WX023-2 (7.4 g, 38.90 mmol) was dissolved in a mixture of ethyl acetate (150 mL), acetonitrile (150 mL), and water (225 mL) at room temperature under nitrogen atmosphere, and the reaction mixture was cooled to 0° C. Sodium periodate (54.08 g, 252.84 mmol) and ruthenium (III) chloride (161.38 mg, 777.97 mol) were added thereto in batches, and the reaction mixture was slowly returned to room temperature and stirred and reacted for 12 hours. After the reaction was completed, the reaction mixture was cooled to 0° C., slowly added with saturated sodium sulfite aqueous solution (100 mL), stirred at room temperature for 20 minutes, then added with 2 M hydrochloric acid to adjust the pH to 5 to 6, and extracted with ethyl acetate (500 mL×3). The organic phases were combined, washed with saturated brine (500 mL), dried over anhydrous sodium sulfate, filtered, and the filtrate was concentrated under reduced pressure to obtain compound WX023-3. MS-ESI m/z: 207.1 $[M-H]^-$. $^1H$ NMR (400 MHz, $CDCl_3$) δ: 10.04 (s, 1H), 7.55 (dd, J=1.6, 7.6 Hz, 1H), 7.43 (dd, J=1.2, 7.6 Hz, 1H), 7.16 (t, J=7.6 Hz, 1H), 3.94 (s, 2H), 3.78 (s, 3H), 2.64 (s, 3H).

Step 4: Synthesis of Compound WX023-4

Compound WX023-3 (4.8 g, 23.05 mmol) was dissolved in N,N-dimethylformamide (50 mL) at room temperature under nitrogen atmosphere, then N,N-diisopropylethylamine (8.94 g, 69.16 mmol) and 2-(7-azabenzotriazol-1-yl)-N,N,N',N'-tetramethyluronium hexafluorophosphate (9.64 g, 25.36 mmol) were added thereto, and the reaction mixture was stirred for 15 minutes. 1-tert-Butoxycarbonyl-4-aminopiperidine (4.62 g, 23.05 mmol) was added thereto, and the reaction mixture was stirred and reacted at room temperature for 8 hours. After the reaction was completed, the reaction mixture was poured into water (50 mL) and extracted with ethyl acetate (50 mL×3). The organic phases were combined, washed with 15% saline (100 mL), then washed with saturated brine (100 mL), dried over anhydrous sodium sulfate, filtered, and the filtrate was concentrated under reduced pressure to obtain a crude product. The crude product was separated by column chromatography (eluent: petroleum ether/ethyl acetate=1/0 to 0/1, v/v) to obtain compound WX023-4. MS-ESI m/z: 389.3 $[M-H]^-$. $^1H$ NMR (400 MHz, $CDCl_3$) δ: 7.52 (dd, J=1.6, 7.6 Hz, 1H), 7.42 (dd, J=1.6, 7.6 Hz, 1H), 7.15 (t, J=7.6 Hz, 1H), 5.78 (d, J=7.6 Hz, 1H), 4.05-3.88 (m, 3H), 3.77 (s, 3H), 3.58 (s, 2H), 2.62 (s, 3H), 1.86-1.82 (m, 2H), 1.50-1.38 (m, 11H), 1.30-1.24 (m, 2H).

Step 5: Synthesis of Compound WX023-5

Compound WX023-4 (2.1 g, 5.38 mmol) was dissolved in dichloromethane (42 mL) at room temperature under nitrogen atmosphere, and the reaction mixture was cooled to 0 to 5° C. Boron tribromide (1.62 g, 6.45 mmol) was added dropwise thereto, and the reaction mixture was stirred and reacted at 0 to 5° C. for 2 hours. After the reaction was completed, the reaction mixture was added dropwise with saturated sodium carbonate aqueous solution to adjust the pH to 7 to 8, then added with di-tert-butyl dicarbonate (1.41 g, 6.47 mmol), and stirred and reacted at room temperature for 2 hours. After the reaction was completed, the reaction mixture was added with 1 M hydrochloric acid to adjust the pH to 7, then added with water (70 mL) and dichloromethane (20 mL), and the aqueous phase was extracted with dichloromethane (50 mL×2). The organic phases were combined, washed with saturated brine (30 mL×2), dried over anhydrous sodium sulfate, filtered, and the filtrate was concentrated under reduced pressure to obtain compound WX023-5. MS-ESI m/z: 321.2 $[M+H-56]^+$.

Step 6: Synthesis of Compound WX023-6

Compound WX023-5 (2 g, 5.31 mmol) was dissolved in tetrahydrofuran (40 mL) at room temperature under nitrogen atmosphere, then dimethyl carbonate (1.91 g, 21.25 mmol) and potassium tert-butoxide (3.58 g, 31.88 mmol) were added thereto, and the reaction mixture was heated to 75° C. and stirred and reacted for 2 hours. After the reaction was completed, the reaction mixture was concentrated under reduced pressure to obtain compound WX023-6. MS-ESI m/z: 303.3 $[M+H-100]^+$.

Step 7: Synthesis of Compound WX023-7

Compound WX023-6 (2 g, 4.97 mmol) was dissolved in ethanol (60 mL) at room temperature under nitrogen atmosphere, and the reaction mixture was added with glacial acetic acid (1.79 g, 29.82 mmol) to adjust the pH to 6 to 7. Hydroxylamine hydrochloride (2.59 g, 37.27 mmol) was added thereto, and the reaction mixture was heated to 80° C. and stirred and reacted for 8 hours. After the reaction was completed, the reaction mixture was cooled to room temperature, filtered, and the filter cake was rinsed with ethanol (10 mL×2). The filtrate was added with water (15 mL), concentrated under reduced pressure to remove most of the solvent, and then extracted with dichloromethane (30 mL×3). The organic phases were combined, washed with saturated brine (30 mL), dried over anhydrous sodium sulfate, filtered, and the filtrate was concentrated under reduced pressure to obtain compound WX023-7. MS-ESI m/z: 318.2 $[M+H-100]^+$.

Step 8: Synthesis of Compound WX023-8

Compound WX023-7 (1.2 g, 2.87 mmol) was dissolved in ethanol (10 mL) at room temperature under nitrogen atmosphere, then concentrated sulfuric acid (563.87 mg, 5.75 mmol, 306.45 L) was added thereto, and the reaction mixture was heated to 70° C. and stirred and reacted for 6 hours. After the reaction was completed, the reaction mixture was concentrated under reduced pressure to remove the solvent, added with tetrahydrofuran (5 mL), added with saturated sodium carbonate aqueous solution to adjust the pH to 7, then added with di-tert-butyl dicarbonate (750.68 mg, 3.44 mmol), and stirred and reacted at room temperature for 2 hours. After the reaction was completed, the reaction mixture was added with 1 M hydrochloric acid to adjust the pH to 7, and extracted with dichloromethane (20 mL×3). The organic phases were combined, washed with saturated brine (30 mL), dried over anhydrous sodium sulfate, filtered, and concentrated under reduced pressure to obtain a crude product. The crude product was separated by column chromatography (eluent: petroleum ether/ethyl acetate=1/0 to 0/1, v/v) to obtain compound WX023-8. MS-ESI m/z: 346.2 $[M+H-100]^+$. $^1$H NMR (400 MHz, $CDCl_3$) δ: 7.65 (d, J=8.0 Hz, 1H), 7.52 (d, J=6.8 Hz, 1H), 7.33 (t, J=7.6 Hz, 1H), 5.64 (d, J=7.6 Hz, 1H), 4.23 (q, J=7.12 Hz, 2H), 4.05 (s, 2H), 4.01-3.90 (m, 2H), 3.84 (s, 2H), 2.90-2.82 (m, 2H), 1.92-1.80 (m, 3H), 1.45 (s, 9H), 1.30-1.26 (m, 4H).

Step 9: Synthesis of Trifluoroacetate of Compound WX023-9

Compound WX023-8 (390 mg, 875.41 mol) was dissolved in dichloromethane (4 mL) at room temperature under nitrogen atmosphere, then trifluoroacetic acid (2.46 g, 21.61 mmol, 1.6 mL) was added thereto, and the reaction mixture was stirred and reacted at room temperature for 1 hour. After the reaction was completed, the reaction mixture was concentrated under reduced pressure to obtain trifluoroacetate of compound WX023-9. MS-ESI m/z: 346.2 $[M+H]^+$.

Step 10: Synthesis of Compound WX023-10

Trifluoroacetate of compound WX023-9 (450 mg) was dissolved in acetonitrile (5 mL) at room temperature under nitrogen atmosphere, then N,N-diisopropylethylamine (619.39 mg, 4.79 mmol) was added thereto, and the reaction mixture was stirred and reacted for 10 minutes. Compound WX015-8 (520.56 mg, 871.37 mol) was added thereto, and the reaction mixture was heated to 80° C. and reacted for another 8 hours. After the reaction was completed, the reaction mixture was cooled to room temperature, poured into saturated ammonium chloride aqueous solution (10 mL), and extracted with a mixed solvent of dichloromethane and ethanol (v/v: 10:1, 10 mL×3). The organic phases were combined, washed with saturated brine (15 mL), dried over anhydrous sodium sulfate, filtered, and the filtrate was concentrated under reduced pressure to obtain a crude product. The crude product was separated on a silica gel plate (developing solvent: dichloromethane/methanol=8/1, v/v) to obtain compound WX023-10. MS-ESI m/z: 815.2 $[M+H]^+$. $^1$H NMR (400 MHz, DMSO_$d_6$) δ: 9.50 (d, J=5.6 Hz, 1H), 8.78 (d, J=8.0 Hz, 1H), 8.39 (d, J=4.4 Hz, 1H), 8.26 (d, J=5.6 Hz, 1H), 8.19 (d, J=6.8 Hz, 1H), 7.69 (d, J=8.0 Hz, 1H), 7.51 (d, J=7.4 Hz, 1H), 7.34 (t, J=7.6 Hz, 1H), 7.27-6.95 (m, 1H), 6.88-6.40 (m, 1H), 5.17 (d, J=82.8 Hz, 1H), 4.77 (d, J=16.8 Hz, 1H), 4.19 (s, 2H), 3.81 (s, 2H), 3.75 (s, 2H), 3.68-3.50 (m, 3H), 3.44 (d, J=9.6 Hz, 1H), 2.90-2.75 (m, 2H), 2.25-2.08 (m, 2H), 2.07-1.85 (m, 8H), 1.83-1.67 (m, 4H), 1.65-1.37 (m, 3H), 1.27-1.16 (m, 4H), 1.12-0.97 (m, 2H).

Step 11: Synthesis of Formate of Compound WX023

Compound WX023-10 (200 mg, 245.44 mol) was dissolved in tetrahydrofuran (5 mL) at room temperature under nitrogen atmosphere, then the reaction mixture was cooled to 0° C., and acrylamide (19.19 mg, 269.98 mol) and a solution of potassium tert-butoxide in tetrahydrofuran (1 M, 368.15 L) were sequentially added thereto. The reaction mixture was stirred and reacted for 4 hours, then returned to room temperature, and stirred and reacted for 4 hours. After the reaction was completed, the reaction mixture was poured into formic acid aqueous solution (0.1%, 5 mL), stirred for 2 minutes, and concentrated under reduced pressure to obtain a crude product. The crude product was first separated by preparative HPLC (chromatographic column: Phenomenex C18 75*30 mm*3 μm; mobile phase: water (0.2% formic acid)-acetonitrile; acetonitrile %: 1% to 35%, 8 minutes), and then separated by preparative HPLC (chromatographic column: Phenomenex Luna 80*30 mm*3 μm; mobile phase: water (0.2% formic acid)-acetonitrile; acetonitrile %: 10% to 30%, 8 minutes) to obtain formate of target compound WX023. MS-ESI m/z: 840.3 $[M+H]^+$. $^1$H NMR (400 MHz, DMSO_$d_6$) δ: 11.09 (s, 1H), 9.50 (d, J=6.4 Hz, 1H), 8.78 (d, J=7.6 Hz, 1H), 8.38 (d, J=4.4 Hz, 1H), 8.26 (d, J=6.0 Hz, 1H), 8.21-8.12 (m, 2H), 7.74-7.65 (m, 1H), 7.55-7.46 (m, 1H), 7.37-7.29 (m, 1H), 7.26-6.94 (m, 1H), 6.90-6.40 (m, 1H), 5.18 (d, J=82.8 Hz, 1H), 4.77 (d, J=18.4 Hz, 1H), 4.60 (dd, J=5.2, 12.0 Hz, 1H), 4.23-4.11 (m, 1H), 3.85-3.78 (m, 2H), 3.77-3.71 (m, 2H), 3.66-3.58 (m, 1H), 3.57-3.50 (m, 1H), 3.48-3.42 (m, 1H), 2.82-2.73 (m, 3H), 2.66-2.58 (m, 1H), 2.57-2.51 (m, 1H), 2.24-2.15 (m, 1H), 2.11 (d, J=6.8 Hz, 2H), 2.07-2.00 (m, 3H), 1.99-1.93 (m, 3H), 1.92-1.83 (m, 2H), 1.79-1.69 (m, 4H), 1.62-1.50 (m, 1H), 1.48-1.38 (m, 2H), 1.10-0.97 (m, 2H).

Example 24

WX024

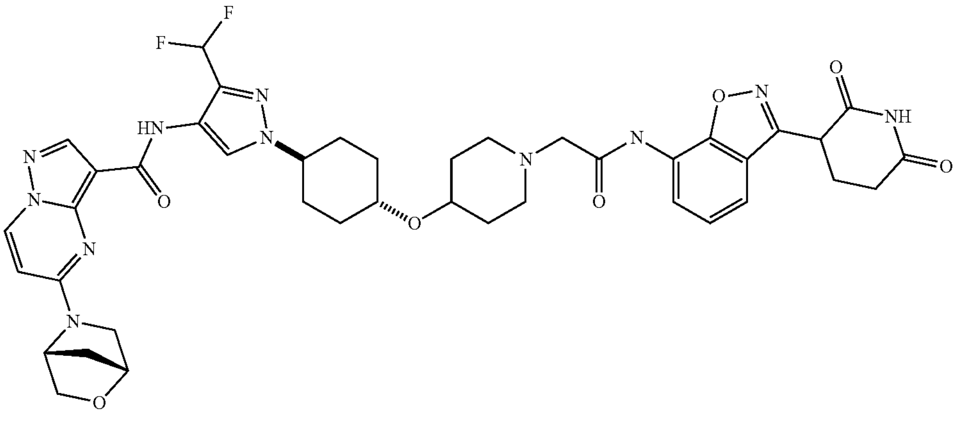

Synthetic Route
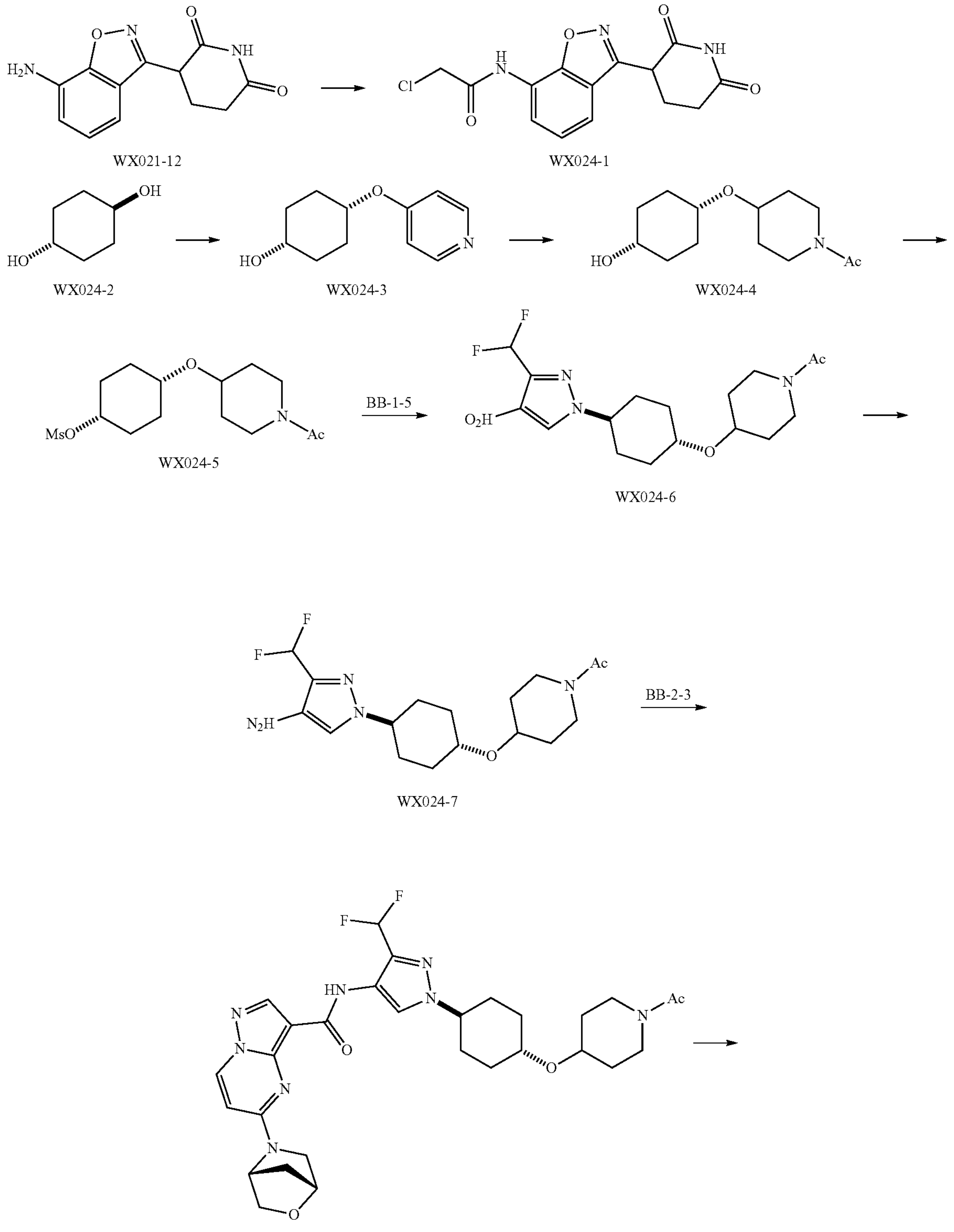
WX021-12
WX024-1
WX024-2
WX024-3
WX024-4
WX024-5
WX024-6
WX024-7
WX024-8

-continued

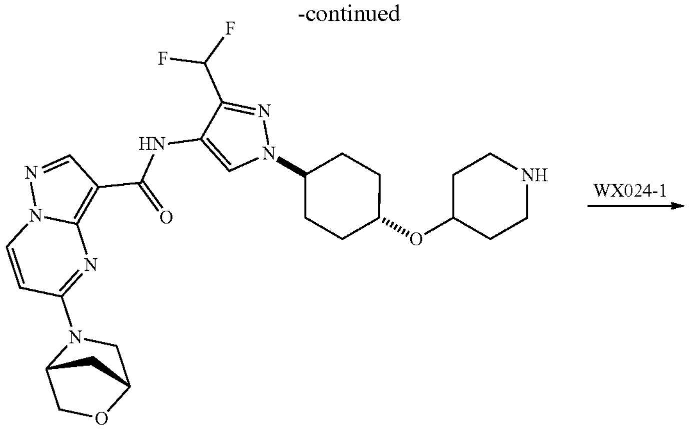

WX024-9

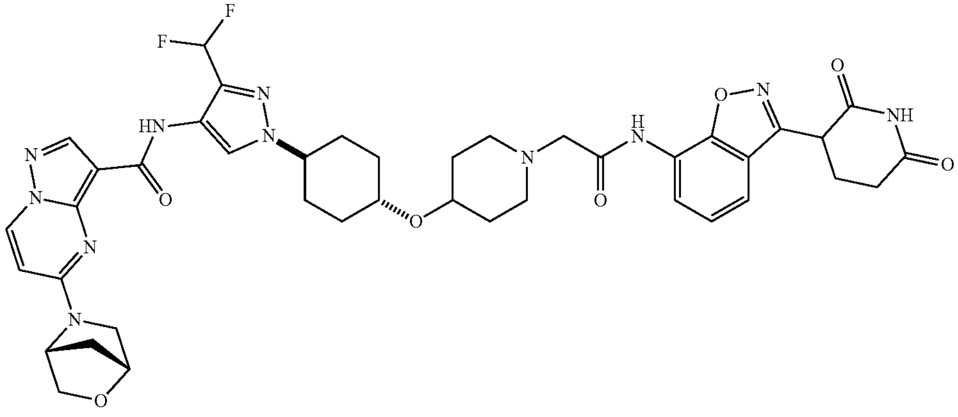

WX024

Step 1: Synthesis of Compound WX024-1

Hydrochloride of compound WX021-12 (300 mg) was dissolved in dichloromethane (6 mL) at room temperature under nitrogen atmosphere, then the reaction mixture was cooled to 0 to 5° C., and triethylamine (323.30 mg, 3.19 mmol) and chloroacetyl chloride (144.34 mg, 1.28 mmol) were sequentially added dropwise thereto. The reaction mixture was stirred and reacted at the same temperature for 2 hours, then slowly returned to room temperature, and stirred and reacted for 2 hours. After the reaction was completed, the reaction mixture was added with water (20 mL) and extracted with dichloromethane (7 mL×3). The organic phases were combined, washed with saturated brine (10 mL), dried over anhydrous sodium sulfate, filtered, and the filtrate was concentrated under reduced pressure to obtain compound WX024-1, which was directly used in the next step.

Step 2: Synthesis of Compound WX024-3

4-Hydroxypyridine (9 g, 94.64 mmol), compound WX024-2 (21.99 g, 189.28 mmol), and triphenylphosphine (24.82 g, 94.64 mmol) were dissolved in anhydrous tetrahydrofuran (200 mL) at room temperature under nitrogen atmosphere, and the reaction mixture was cooled to 0 to 5° C. Diisopropyl azodicarboxylate (19.14 g, 94.64 mmol, 18.40 mL) was added dropwise thereto, and after the dropwise addition was completed, the reaction mixture was slowly returned to room temperature and stirred and reacted for 12 hours. After the reaction was completed, the reaction mixture was added with water (500 mL) and extracted with ethyl acetate (200 mL×3). The organic phases were combined, washed with saturated brine (200 mL×2), dried over anhydrous sodium sulfate, filtered, and the filtrate was concentrated under reduced pressure to remove the solvent. The resulting residue was separated by column chromatography (eluent: dichloromethane/methanol=50/1 to 30/1, v/v) to obtain compound WX024-3. MS-ESI m/z: 194.1 $[M+H]^+$. $^1H$ NMR (400 MHz, $CDCl_3$) δ: 8.41 (d, J=6.0 Hz, 2H), 6.86-6.74 (m, 2H), 4.52-4.45 (m, 1H), 3.91-3.79 (m, 1H), 2.09-1.99 (m, 2H), 1.91-1.64 (m, 6H).

Step 3: Synthesis of Compound WX024-4

Platinum dioxide (660 mg, 2.91 mmol) was suspended in ice acetic acid (33 mL) at room temperature under argon atmosphere, and compound WX024-3 (3.3 g, 17.08 mmol) and acetic anhydride (5.45 g, 53.38 mmol) were added thereto. The reaction mixture was replaced with hydrogen three times with the hydrogen pressure maintained at 50 psi, heated to 50° C., and stirred and reacted for 96 hours. After the reaction was completed, the reaction mixture was filtered. The filter cake was rinsed with methanol (200 mL×7), and the mother liquor was collected and concentrated under reduced pressure to remove the solvent. The resulting residue was separated by column chromatography (eluent: dichloromethane/methanol=100/1 to 30/1, v/v) to obtain compound WX024-4. MS-ESI m/z: 242.1 $[M+H]^+$. $^1H$ NMR (400 MHz, $CDCl_3$) δ: 3.95-3.83 (m, 1H), 3.80-3.70

(m, 1H), 3.69-3.58 (m, 2H), 3.56-3.46 (m, 1H), 3.42-3.31 (m, 1H), 3.30-3.18 (m, 1H), 2.09 (s, 3H), 1.85-1.74 (m, 4H), 1.73-1.62 (m, 4H), 1.61-1.48 (m, 4H).

Step 4: Synthesis of Compound WX024-5

Compound WX024-4 (1.25 g, 5.18 mmol) and triethylamine (1.05 g, 10.36 mmol, 1.44 mL) were dissolved in dichloromethane (12.5 mL) at room temperature under nitrogen atmosphere, and the reaction mixture was cooled to 0 to 5° C. Methanesulfonyl chloride (1.04 g, 9.08 mmol) was added dropwise thereto, and after the dropwise addition was completed, the reaction mixture was stirred and reacted at the same temperature for 2 hours. After the reaction was completed, the reaction mixture was added with water (70 mL) and extracted with dichloromethane (20 mL×3). The organic phases were combined, washed with saturated brine (20 mL×3), dried over anhydrous sodium sulfate, filtered, and the filtrate was concentrated under reduced pressure to obtain compound WX024-5, which was directly used in the next step.

Step 5: Synthesis of Compound WX024-6

Compound BB-1-5 (0.7 g, 4.29 mmol) was dissolved in N,N-dimethylformamide (14 mL) at room temperature under nitrogen atmosphere, then potassium carbonate (1.19 g, 8.58 mmol) and compound WX024-5 (1.65 g, 5.15 mmol) were sequentially added thereto, and the reaction mixture was heated to 80° C. and stirred and reacted for 12 hours. After the reaction was completed, the reaction mixture was cooled to room temperature, added with water (50 mL), and extracted with ethyl acetate (20 mL×3). The organic phases were combined, washed with saturated brine (20 mL×3), dried over anhydrous sodium sulfate, filtered, and the filtrate was concentrated under reduced pressure to remove the solvent. The resulting residue was separated by column chromatography (eluent: petroleum ether/ethyl acetate=1/1 to 0/1, v/v) to obtain compound WX024-6. MS-ESI m/z: 387.1 $[M+H]^+$. $^1$H NMR (400 MHz, $CDCl_3$) δ: 8.22 (s, 1H), 7.10 (t, J=53.6 Hz, 1H), 4.26-4.16 (m, 1H), 3.99-3.89 (m, 1H), 3.72-3.63 (m, 2H), 3.54-3.42 (m, 1H), 3.34-3.21 (m, 2H), 2.31-2.22 (m, 2H), 2.19-2.11 (m, 2H), 2.09 (s, 3H), 1.89-1.74 (m, 4H), 1.68-1.46 (m, 4H).

Step 6: Synthesis of Compound WX024-7

Pd/C (0.1 g, purity: 10%) was suspended in tetrahydrofuran (10 mL) at room temperature under nitrogen atmosphere, and compound WX024-6 (478 mg, 1.24 mmol) was added thereto. The reaction mixture was replaced with hydrogen (balloon) three times, and stirred and reacted at room temperature for 2 hours. After the reaction was completed, the reaction mixture was filtered. The filter cake was rinsed with methanol (50 mL×5), and the filtrate was collected and concentrated under reduced pressure to remove the solvent. The resulting residue was separated by column chromatography (eluent: petroleum ether/ethyl acetate/ethanol=1/1/0 to 0/1/0 to 0/10/1, v/v/v) to obtain compound WX024-7. MS-ESI m/z: 357.1 $[M+H]^+$.

Step 7: Synthesis of Compound WX024-8

Intermediate BB-2-3 (143.70 mg, 552.17 mol) was dissolved in acetonitrile (3 mL) at room temperature under nitrogen atmosphere, then N,N,N',N'-tetramethylchloroformamidinium hexafluorophosphate (154.93 mg, 552.17 mol) and N-methylimidazole (132.23 mg, 1.61 mmol) were added thereto, and the reaction mixture was stirred for 10 minutes. Compound WX024-7 (164 mg, 460.14 mol) was added thereto, and the reaction mixture was stirred and reacted for another 16 hours. After the reaction was completed, the reaction mixture was poured into ice water (30 mL) and extracted with ethyl acetate (10 mL×3). The organic phases were combined, washed with saturated brine (10 mL×3), dried over anhydrous sodium sulfate, filtered, and the filtrate was concentrated under reduced pressure. The resulting residue was separated on a silica gel plate (eluent: dichloromethane/methanol=10/1, v/v) to obtain compound WX024-8. MS-ESI m/z: 599.4 $[M+H]^+$.

Step 8: Synthesis of Compound WX024-9

Compound WX024-8 (181.5 mg, 303.19 mol) was dissolved in ethanol (7 mL) at room temperature under nitrogen atmosphere, then sodium hydroxide solution (1 M, 7 mL) was added thereto, and the reaction mixture was heated to 80° C. and stirred and reacted for 16 hours. After the reaction was completed, the reaction mixture was cooled to room temperature, added with 1 M hydrochloric acid to adjust the pH to 7, and concentrated under reduced pressure to remove the solvent to obtain compound WX024-9. MS-ESI m/z: 557.3 $[M+H]^+$.

Step 9: Synthesis of Compound WX024

Compound WX024-9 (168.76 mg, 303.19 mol), compound WX024-1 (126.81 mg, 394.15 mol), and sodium iodide (59.08 mg, 394.15 mol) were dissolved in acetonitrile (3 mL) at room temperature under nitrogen atmosphere, then N,N-diisopropylethylamine (156.74 mg, 1.21 mmol, 211.24 L) was added thereto, and the reaction mixture was heated to 80° C. and stirred and reacted for 2 hours. After the reaction was completed, the reaction mixture was concentrated under reduced pressure to remove the solvent. The resulting residue was first separated by preparative HPLC (chromatographic column: Phenomenex Luna C18 80*40 mm*3 μm; mobile phase: water (0.04% hydrochloric acid)-acetonitrile; acetonitrile %: 25% to 50%, 7 minutes), and then separated by preparative HPLC (chromatographic column: Phenomenex C18 75*30 mm*3 μm; mobile phase: water (10 mM ammonium bicarbonate)-acetonitrile; acetonitrile %: 35% to 55%, 8 minutes) to obtain compound WX024. MS-ESI m/z: 842.5 $[M+H]^+$. $^1$H NMR (400 MHz, DMSO_$d_6$) δ: 11.12 (s, 1H), 11.08 (d, J=6.4 Hz, 1H), 10.02 (s, 1H), 9.50 (d, J=6.4 Hz, 1H), 8.78 (d, J=7.6 Hz, 1H), 8.39 (d, J=3.2 Hz, 1H), 8.25 (d, J=5.6 Hz, 1H), 8.02 (dd, J=2.8, 7.2 Hz, 1H), 7.69 (d, J=7.6 Hz, 1H), 7.41 (t, J=7.8 Hz, 1H), 7.27-6.95 (m, 1H), 6.90-6.40 (m, 1H), 5.17 (d, J=78.4 Hz, 1H), 4.70 (d, J=21.2 Hz, 1H), 4.64 (dd, J=5.0, J=12.2 Hz, 1H), 4.41-4.18 (m, 3H), 3.92-3.78 (m, 2H), 3.76-3.49 (m, 6H), 3.36-3.11 (m, 2H), 2.88-2.72 (m, 1H), 2.68-2.53 (m, 2H), 2.29-2.17 (m, 1H), 2.14-1.67 (m, 12H), 1.49-1.27 (m, 2H).

Example 25 and Example 26
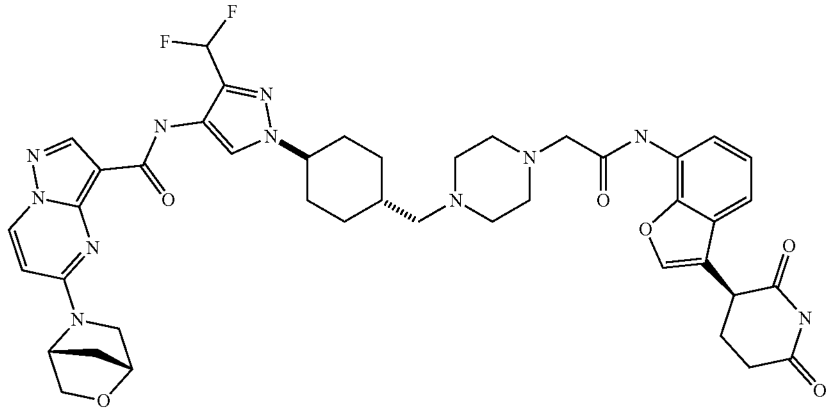
WX025 or WX026
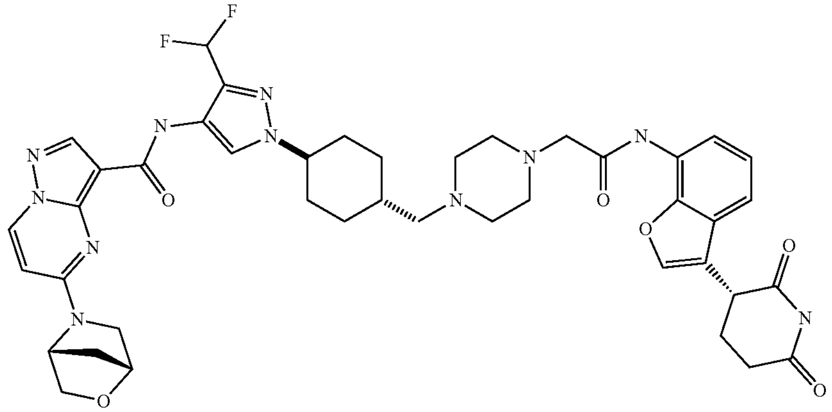
WX025 or WX026
Synthetic Route
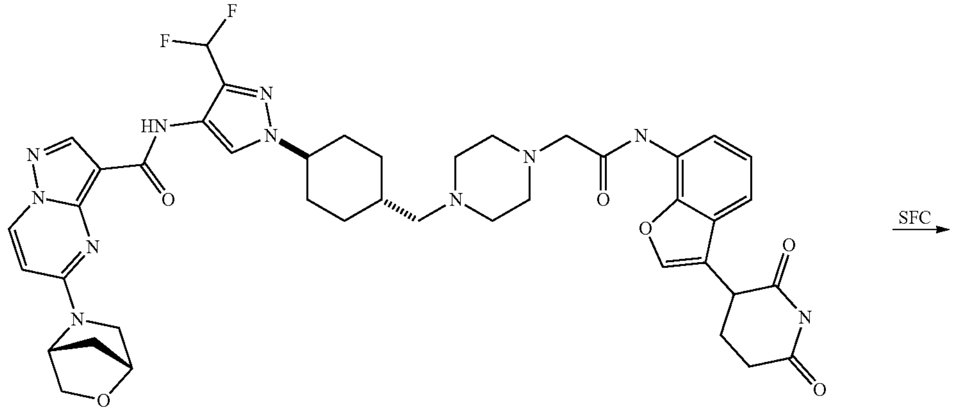
WX006

-continued

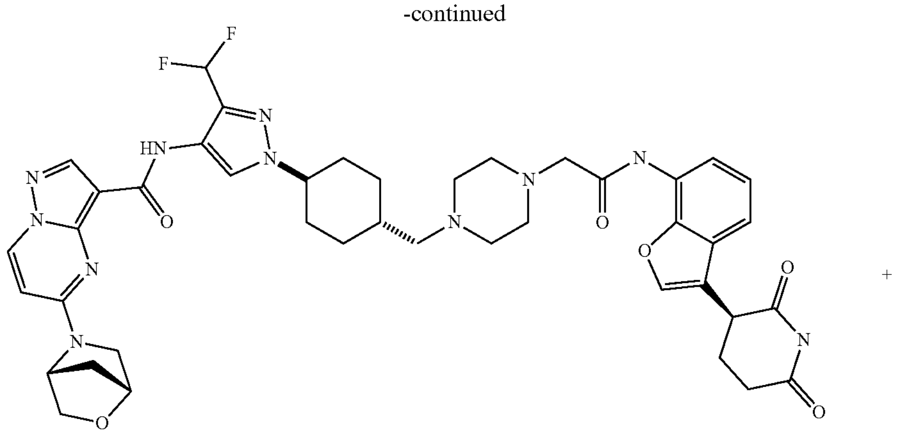

WX025 or WX026

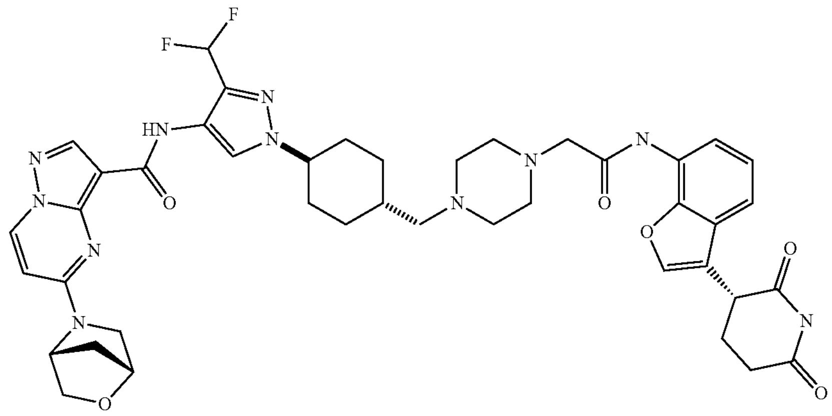

WX026 or WX025

Synthesis of Hydrochloride of Compound WX025 and Hydrochloride of Compound WX026

Hydrochloride of compound WX006 (500 mg) was separated by supercritical fluid chromatography (separation conditions: chromatographic column: REGIS (S,S) WHELK-01 (250 mm*25 mm, 10 μm); mobile phase: A: $CO_2$; B: EtOH/ACN; B %: 70% to 70%, 25 minutes. Analysis method: chromatographic column: (S,S)-WHELK-01, 50×4.6 mm I.D., 3.5 μm; mobile phase: A: $CO_2$, B: EtOH: ACN=1:1 (0.1% IPAm, v/v), 4 minutes). The sample with a retention time of 2.631 minutes was collected and then separated by preparative HPLC (chromatographic column: Phenomenex Luna 80*40 mm*3 μm; mobile phase: water (0.04% hydrochloric acid)-acetonitrile; acetonitrile %: 5% to 35%, 7 minutes) to obtain hydrochloride of compound WX025 (ee %: 99.10%). The sample with a retention time of 5.384 minutes was collected and then separated by preparative HPLC (chromatographic column: Phenomenex Luna 80*40 mm*3 μm; mobile phase: water (0.04% hydrochloric acid)-acetonitrile; acetonitrile %: 5% to 35%, 7 minutes) to obtain hydrochloride of compound WX026 (ee %: 98.94%).

Hydrochloride of compound WX025: $^1$H NMR (400 MHz, DMSO_$d_6$) δ: 11.18 (s, 1H), 10.92 (s, 1H), 10.58 (s, 1H), 9.50 (d, J=6.4 Hz, 1H), 8.78 (d, J=7.6 Hz, 1H), 8.40 (d, J=3.6 Hz, 1H), 8.26 (d, J=5.6 Hz, 1H), 7.98 (s, 1H), 7.73 (d, J=7.6 Hz, 1H), 7.41 (d, J=7.6 Hz, 1H), 7.27-6.96 (m, 2H), 6.90-6.41 (m, 1H), 5.18 (d, J=79.2 Hz, 1H), 4.76 (d, J=18.8 Hz, 1H), 4.33-4.21 (m, 1H), 4.17 (dd, J=4.8 Hz, 12.0 Hz, 1H), 3.85-3.55 (m, 13H), 3.13-2.95 (m, 2H), 2.82-2.72 (m, 1H), 2.64-2.54 (m, 1H), 2.41-2.26 (m, 1H), 2.18-1.65 (m, 11H), 1.32-1.08 (m, 2H).

Hydrochloride of compound WX026: $^1$H NMR (400 MHz, DMSO_$d_6$) δ: 10.92 (s, 1H), 10.44 (s, 1H), 9.51 (d, J=6.0 Hz, 1H), 8.78 (d, J=7.6 Hz, 1H), 8.40 (d, J=4.0 Hz, 1H), 8.25 (d, J=5.6 Hz, 1H), 7.97 (s, 1H), 7.73 (d, J=7.6 Hz, 1H), 7.41 (d, J=8.0 Hz, 1H), 7.24 (d, J=7.6 Hz, 1H), 7.22-6.95 (m, 1H), 6.90-6.43 (m, 1H), 5.17 (d, J=79.2 Hz, 1H), 4.77 (d, J=19.6 Hz, 1H), 4.32-4.20 (m, 1H), 4.17 (dd, J=4.8 Hz, 12.0 Hz, 1H), 3.85-3.54 (m, 13H), 3.14-2.95 (m, 2H), 2.82-2.69 (m, 1H), 2.64-2.55 (m, 1H), 2.41-2.27 (m, 1H), 2.19-1.65 (m, 11H), 1.28-1.11 (m, 2H).

Example 27 and Example 28
WX027 or WX028
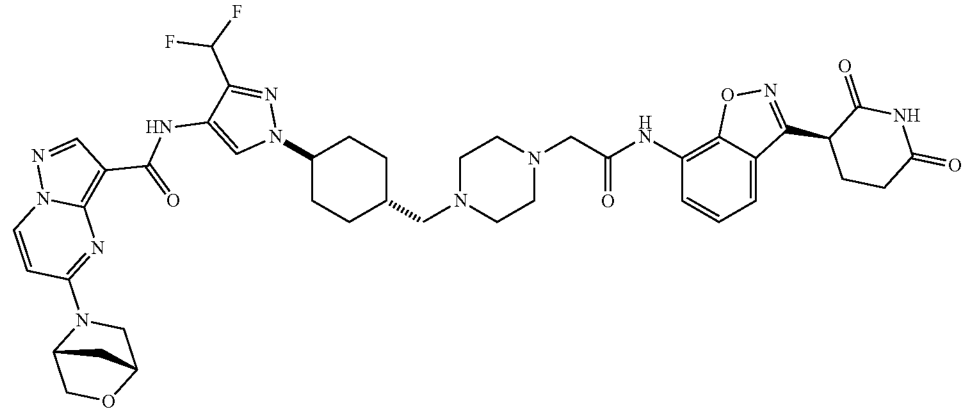
WX028 or WX027
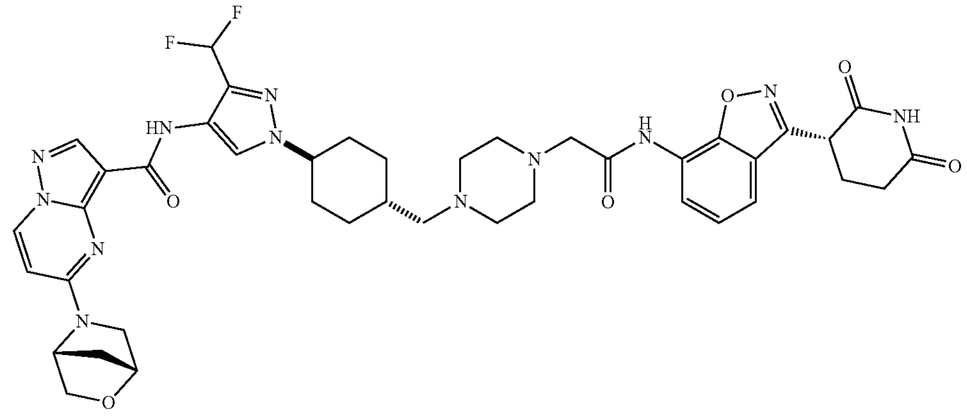
Synthetic Route
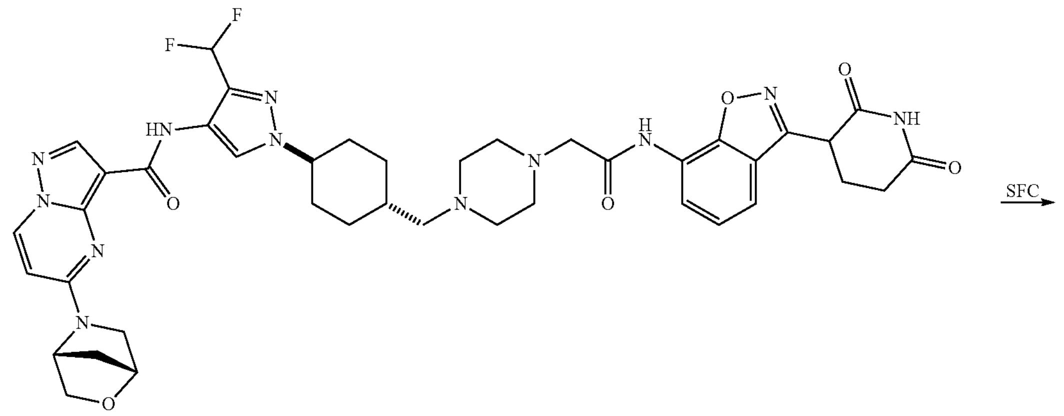
WX015

-continued

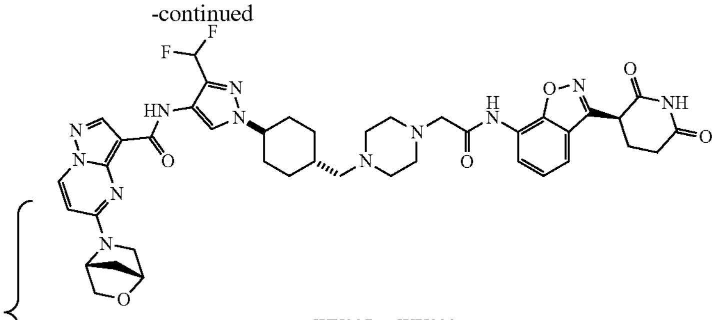

WX027 or WX028

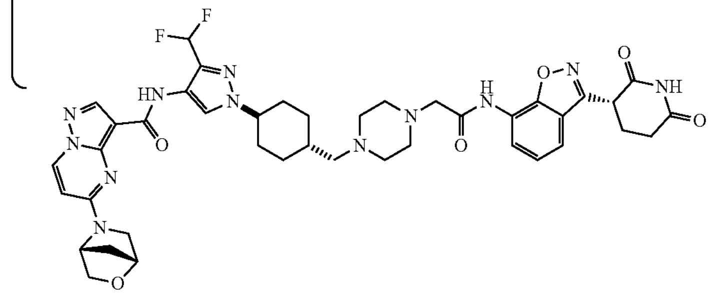

WX028 or WX027

Synthesis of Hydrochloride of Compound WX027 and Hydrochloride of Compound WX028

Hydrochloride of compound WX015 (500 mg) was separated by supercritical fluid chromatography (separation conditions: chromatographic column: REGIS (S,S) WHIELK-01 (250 mm*25 mm, 10 μm); mobile phase: A: $CO_2$; B: EtOH/ACN (0.100 IPAm, v/v); B: 65% to 65%, 6 minutes. Analysis method: chromatographic column: (S,S)-WHELK-01, 50×4.6 mm I.D., 3.5 μm; mobile phase: A: $CO_2$; B: EtOH:ACN=1:1 (0.1% IPAm, v/v), 4 minutes). The sample with a retention time of 1.678 minutes was collected and then separated by preparative HPLC (chromatographic column: Phenomenex Luna C18 80*40 mm*3 μm; mobile phase: water (0.04% hydrochloric acid)-acetonitrile; acetonitrile %: 23% to 4300, 7 minutes) to obtain hydrochloride of compound WX027 (ee %: 96.68%). The sample with a retention time of 2.265 minutes was collected and then separated by preparative HPLC (chromatographic column: Phenomenex Luna 80*30 mm*3 μm; mobile phase: water (0.04% hydrochloric acid)-acetonitrile; acetonitrile %: 1% to 30%, 8 minutes) to obtain hydrochloride of compound WX028 (ee %: 95.18%).

Hydrochloride of compound WX027: $^1H$ NMR (400 MHz, DMSO_$d_6$) δ: 11.12 (s, 1H), 10.49 (s, 1H), 9.51 (d, J=6.0 Hz, 1H), 8.79 (d, J=8.0 Hz, 1H), 8.41 (d, J=4.4 Hz, 1H), 8.26 (d, J=5.6 Hz, 1H), 8.01 (d, J=7.6 Hz, 1H), 7.65 (d, J=8.0 Hz, 1H), 7.38 (t, J=8.0 Hz, 1H), 7.27-6.95 (m, 1H), 6.90-6.44 (m, 1H), 5.18 (d, J=78.0 Hz, 1H), 4.76 (d, J=20.4 Hz, 1H), 4.64 (dd, J=4.8 Hz, 12.0 Hz, 1H), 4.29-4.18 (m, 1H), 3.85-3.58 (m, 14H), 3.47-3.42 (m, 1H), 3.10-2.96 (m, 2H), 2.84-2.73 (m, 1H), 2.68-2.53 (m, 2H), 2.26-2.16 (m, 1H), 2.12-1.73 (m, 8H), 1.28-1.11 (m, 2H).

Hydrochloride of compound WX028: $^1H$ NMR (400 MHz, DMSO_$d_6$) δ: 11.12 (s, 1H), 10.47 (s, 1H), 9.51 (d, J=6.0 Hz, 1H), 8.79 (d, J=7.6 Hz, 1H), 8.40 (d, J=4.0 Hz, 1H), 8.26 (d, J=5.6 Hz, 1H), 8.01 (d, J=7.6 Hz, 1H), 7.65 (d, J=8.0 Hz, 1H), 7.38 (t, J=8.0 Hz, 1H), 7.28-6.95 (m, 1H), 6.90-6.43 (m, 1H), 5.18 (d, J=79.2 Hz, 1H), 4.76 (d, J=20.8 Hz, 1H), 4.64 (dd, J=4.8 Hz, 12.0 Hz, 1H), 4.29-4.18 (m, 1H), 3.87-3.41 (m, 14H), 3.10-2.94 (m, 2H), 2.84-2.73 (m, 1H), 2.67-2.53 (m, 2H), 2.25-2.17 (m, 1H), 2.13-1.69 (m, 9H), 1.28-1.11 (m, 2H).

Bioassay

Experimental Example 1: Evaluation of Target Protein Degradation Effect in K562 IRAK4-HiBiT Cells Experimental purpose: In this experiment, the degradation effect of the test compound on the target protein IRAK4 in K562 IRAK4-HiBiT cells was detected.

Experimental Materials

1. Cells and Culture Media

Cells: K562 IRAK4-HiBiT cells

Culture media: RPMI 1640+10% FBS+2 mM GlutaMax+1 mM sodium pyruvate+penicillin/streptomycin Positive control: 1000 nM; negative control: 0.1% DMSO 2. Reagents and Consumables

| Reagents and consumables | Manufacturers | Cat. No. |
|---|---|---|
| RPMI 1640 | Gibco | Cat# 31800 |
| Serum (FBS) | Biosera | #FB-1058/500 |
| P/S double antibody | Biosera | #LM-A4118 |
| DPBS | Invitrogen | #14190 |
| 0.25% Trypsin-EDTA | Invitrogen | #25200 |
| Glutamine | Invitrogen | Cat# 35050061 |
| Sodium pyruvate | Invitrogen | Cat# 11360070 |
| Nano-Glo ® HiBiT Assay Kit | Promega | Promega# N3040 |
| 384-well white plate, flat bottom | Corning | Cat# 3570 |
| 384_LDV compound plate | Labcyte | Cat# LP-0200 |

3. Instruments

| Instrument name | Manufacturers | Instrument model |
|---|---|---|
| ECHO pipette | Labcyte | Echo 550 |
| Bravo automatic liquid handling platform | Agilent | 16050-101 |
| Envision plate reader | PerkinElmer | 2104 |
| Autosampler | Thermo Fisher | Multidrop Combi |
| Cell counter | Thermo | Countess II FL |

Experimental Scheme

Day 1

1. Compound Preparation (1). The compound to be tested in powder form was dissolved in DMSO to 10 mM as a storage concentration, and 9 μL of the 10 mM compound to be tested was manually pipetted to column 1 and column 13 of an LDV plate using a pipette;

(2). 6 μL of DMSO was added to columns 2 to 12 and 14 to 24 using Multidrop Combi;

(3). the compound to be tested was 3-fold diluted (3 μL+6 μL) from columns 1 to 11 and 13 to 23 using Bravo;

(4). 25 nL of compound solution (columns 1 to 24 of the LDV plate) was transferred to an assay plate using Echo according to the plate layout;

(5). 25 nL of 1 mM positive control solution was transferred to the assay plate as a 100% degradation control (i.e., LC, HPE) and 25 nL of DMSO was transferred to the assay plate as a 0% control (i.e., HC, ZPE) using Echo.

2. Cell Plating (1). The cell culture medium was discarded, and the cells were washed once with DPBS, digested with trypsin, and counted to prepare a cell suspension of $2\times10^{-5}$ cells/mL;

(2). 25 L/well of cell suspension was added to the assay plate containing the compound to be tested using Multidrop Combi at medium speed;

(3). the assay plate containing cells was returned to an incubator with 5% $CO_2$ at 37° C. and incubated for 16 to 18 hours.

Day 2

(1). 25 L/well of assay reagent (NanoGlo lysis buffer+substrate+LgBit protein) was added to the assay plate using Multidrop Combi at high speed, and the plate was shaken for 10 minutes;

(2). the plate was centrifuged at 2000 rpm for 1 minute to remove air bubbles;

(3). the plate was read on Envision using US Luminescence detection method.

3. Data Analysis

The inhibition rate (IR) of the test compound was calculated using the following formula: IR (%)=(RLU vehicle control−RLU compound)/(RLU vehicle control−RLU positive control)×100%, and the vehicle control is the blank control. The inhibition rates of compounds at different concentrations were calculated in Excel, and then XLFit software was used to plot inhibition curves and calculate relevant parameters, including minimum inhibition rate, maximum inhibition rate, and $DC_{50}$.

The test results are shown in Table 1.

TABLE 1

Target protein degradation effect of compounds of the present disclosure in K562 IRAK4-HiBiT cells

| Compound | $DC_{50}$ (nM) | Maximum inhibition rate (%) |
|---|---|---|
| Hydrochloride of WX002 | 24.27 | 56.72 |
| Hydrochloride of WX003 | 25.48 | 100.06 |
| Hydrochloride of WX006 | 12.86 | 97.11 |
| Hydrochloride of WX010 | 6.54 | 74.90 |
| Hydrochloride of WX014 | 4.29 | 85.62 |
| Hydrochloride of WX015 | 4.12 | 106.70 |
| Hydrochloride of WX016 | 34.23 | 112.11 |
| Hydrochloride of WX017 | 7.02 | 115.78 |
| Formate of WX018 | 9.11 | 97.79 |
| Hydrochloride of WX020 | 5.43 | 100.80 |
| Hydrochloride of WX021 | 2.59 | 102.77 |
| Hydrochloride of WX022 | 7.14 | 103.04 |
| Formate of WX023 | 2.55 | 103.01 |
| WX024 | 1.37 | 109.35 |
| Hydrochloride of WX027 | 8.86 | 107.58 |
| Hydrochloride of WX028 | 10.46 | 106.67 |

Conclusion

The compound of the present disclosure exhibits excellent degradation effect on the target protein TRAK4 in K562 TRAK4-HiBiT cells.

Experimental Example 2: Pharmacokinetic Evaluation of Compounds in Mice

Experimental Purpose

In this study, CD-1 or C57BL/6N male mice were selected as test animals, and LC/MS/MS method was used to quantify plasma concentrations of the test compound intravenously injected or intragastrically administered to mice at different time points, so as to evaluate the pharmacokinetic profile of the test drug in mice.

Experimental Materials

CD-1 mice (male, 20 to 35 g, 7 to 10 weeks old, Beijing Vital River) or C57BL/6N mice (male, 20 to 30 g, 7 to 10 weeks old, Beijing Vital River)

Experimental Operation A

A clarified solution or suspension of the test compound was injected into CD-1 mice (overnight fasting) via the tail vein (vehicle: 10% DMSO/10% Solutol/80% $H_2O$), or intragastrically administered into CD-1 mice (overnight fasting). For intravenous injection, blood was collected from the saphenous vein at 0 h (pre-administration) and 0.083 h, 0.25 h, 0.5 h, 1 h, 2 h, 4 h, 8 h, and 24 h after administration, and placed in an anticoagulant tube added with EDTA-K2. The mixture was thoroughly vortexed and mixed, and centrifuged at 3200 g for 10 minutes at 4° C. to obtain plasma. For oral administration, blood was collected from the saphenous vein at 0.25 h, 0.5 h, 1 h, 2 h, 4 h, 8 h, and 24 h after administration, and placed in an anticoagulant tube added with EDTA-K2 (Jiangsu Kangjian Medical Apparatus Co., Ltd.). The mixture was thoroughly vortexed and mixed, and centrifuged at 3200 g for 10 minutes at 4° C. to obtain plasma. Plasma concentrations were determined by LC-MS/MS method, and relevant pharmacokinetic parameters were calculated using Phoenix WinNonlin™ Version 6.3 (Pharsight, Mountain View, CA) pharmacokinetic software with non-compartmental model linear-log trapezoidal method.

Experimental Operation B

A clarified solution or suspension of the test compound was injected into C57BL/6N mice (overnight fasting) via the tail vein (vehicle: 5% DMSO/10% Solutol/85% $H_2O$), or intragastrically administered into C57BL/6N mice (overnight fasting). For intravenous injection, 50 L of blood was collected via the cheek puncture at 0 h (pre-administration) and 0.083 h, 0.25 h, 0.5 h, 1 h, 2 h, 4 h, 6 h, 8 h, and 24 h after administration, and placed in an anticoagulant tube added with heparin sodium. The mixture was thoroughly vortexed and mixed, and centrifuged at 6000 g for 3 minutes at 2 to 8° C. For oral administration, blood was collected via the cheek puncture at 0 h (pre-administration) and 0.083 h, 0.25 h, 1 h, 2 h, 4 h, 6 h, 8 h, and 24 h after administration, and placed in an anticoagulant tube added with heparin sodium. The mixture was thoroughly vortexed and mixed, and centrifuged at 6000 g for 3 minutes at 2 to 8° C. Plasma concentrations were determined by LC-MS/MS method, and relevant pharmacokinetic parameters were calculated using Phoenix WinNonlin 8.2.0 pharmacokinetic software with non-compartmental model linear-log trapezoidal method.

The test results are shown in Table 2.

Conclusion: The compound of the present disclosure has high oral systemic plasma exposure ($AUC_{0-inf}$). It has superior pharmacokinetic properties in rodents such as mice.

Experimental Example 3: Pharmacokinetic Evaluation of Compounds in Beagles

Experimental Purpose

In this study, male Beagles were selected as test animals, and LC/MS/MS method was used to quantify plasma concentrations of the test compound intravenously injected or intragastrically administered to Beagles at different time points, so as to evaluate the pharmacokinetic profile of the test drug in Beagles.

Experimental Materials

Beagles (male, 9 to 11 kg, Jiangsu Yadong Institute of Experimental Animals Co., Ltd.).

Experimental Operation

A clarified solution or suspension of the test compound was injected into Beagles (feeding) via the tail vein (vehicle: 5% DMSO/10% Solutol/85% $H_2O$), or intragastrically administered into Beagles (feeding). For intravenous injection, 1 mL of blood was collected from the forelimb vein at 0 h (pre-administration) and 0.083 h, 0.25 h, 0.5 h, 1 h, 2 h, 4 h, 6 h, 8 h, and 24 h after administration, and anticoagulated with EDTA-2K. The mixture was thoroughly vortexed and mixed, and centrifuged at 6000 g for 3 minutes at 2 to 8° C. For oral administration, 1 mL of blood was collected from the forelimb vein at 0 h (pre-administration) and 0.083 h, 0.25 h, 0.5 h, 1 h, 2 h, 4 h, 6 h, 8 h, and 24 h after administration, and anticoagulated with EDTA-2K. The mixture was thoroughly vortexed and mixed, and centrifuged at 6000 g for 3 minutes at 2 to 8° C. Plasma concentrations were determined by LC-MS/MS method, and relevant pharmacokinetic parameters were calculated using Phoenix WinNonlin 8.2.0 pharmacokinetic software with non-compartmental model linear-log trapezoidal method.

TABLE 2

Pharmacokinetic parameters of compounds of the present disclosure in mice

| | | Pharmacokinetic parameters in mice | | | | | | | |
|---|---|---|---|---|---|---|---|---|---|
| | | Intravenous injection | | | | Intragastric administration | | | |
| Compound No. | Experimental operation | Plasma clearance (mL/min/kg) | Elimination half-life (h) | Apparent volume of distribution (L/kg) | Area under the drug-time curve (0-inf, μM · h) | Peak concentration (μM) | Time to peak concentration (h) | Area under the drug-time curve (0-inf, μM · h) | Bio-availability F (%) |
| Hydrochloride of WX003 (IV_1 mg/kg; PO_10 mg/kg) | A | 11.7 | 1.74 | 1.71 | 1.72 | 0.61 | 4.0 | 4.83 | 28.2 |
| Hydrochloride of WX006 (IV_1 mg/kg; PO_10 mg/kg) | A | 16.8 | 1.03 | 1.47 | 1.18 | 1.73 | 1.0 | 7.73 | 65.6 |
| Hydrochloride of WX015 (IV_2 mg/kg; PO_10 mg/kg) | B | 27.6 | 4.25 | 4.82 | 1.45 | 0.4 | 1.33 | 2.51 | 34.6 |

The test results are shown in Table 3.

TABLE 3

| Pharmacokinetic parameters of compounds of the present disclosure in Beagles | | | | | | | | |
|---|---|---|---|---|---|---|---|---|
| | Pharmacokinetic parameters in Beagles | | | | | | | |
| | Intravenous injection (0.5 mg/kg) | | | | Intragastric administration (3 mg/kg) | | | |
| Compound No. | Plasma clearance (mL/min/kg) | Elimination half-life (h) | Apparent volume of distribution (L/kg) | Area under the drug-time curve (0-inf, μM · h) | Peak concentration (μM) | Time to peak concentration (h) | Area under the drug-time curve (0-inf, μM · h) | Bio-availability F (%) |
| Hydrochloride of WX015 | 37.5 | 2.93 | 8.44 | 0.27 | 0.12 | 4.67 | 1.13 | 70.3 |

Conclusion: The compound of the present disclosure has high oral systemic plasma exposure ($AUC_{0\text{-}inf}$). It has superior pharmacokinetic properties in non-rodent animals such as Beagles.

Experimental Example 4: Pharmacokinetic Evaluation of Compounds in Cynomolgus Monkeys

Experimental Purpose

In this study, male cynomolgus monkeys were selected as test animals, and LC/MS/MS method was used to quantify plasma concentrations of the test compound intravenously injected or intragastrically administered to cynomolgus monkeys at different time points, so as to evaluate the pharmacokinetic profile of the test drug in cynomolgus monkeys.

Experimental Materials

Cynomolgus monkeys (male, 2 to 5 kg, Hainan Jingang Biotech Co., Ltd.).

Experimental Operation

A clarified solution of the test compound was slowly injected into cynomolgus monkeys (feeding) via the peripheral vein (vehicle: 5% DMSO/10% Solutol/85% $H_2O$), or intragastrically administered into cynomolgus monkeys (feeding). For intravenous injection, 0.5 mL of blood was collected from the peripheral vein at 0 h (pre-administration) and 0.083 h, 0.25 h, 0.5 h, 1 h, 2 h, 4 h, 6 h, 8 h, and 24 h after administration, placed in an anticoagulant tube added with EDTA-2K, and centrifuged at 3200 g for 10 minutes at 2 to 8° C. to separate the supernatant. For oral administration, 0.5 mL of blood was collected from the peripheral vein at 0 h (pre-administration) and 0.083 h, 0.25 h, 0.5 h, 1 h, 2 h, 4 h, 6 h, 8 h, and 24 h after administration, placed in an anticoagulant tube added with EDTA-2K, and centrifuged at 3200 g for 10 minutes at 2 to 8° C. to separate the supernatant. Plasma concentrations were determined by LC-MS/MS method, and relevant pharmacokinetic parameters were calculated using Phoenix WinNonlin 6.3 pharmacokinetic software with non-compartmental model linear-log trapezoidal method.

The test results are shown in Table 4.

TABLE 4

| Pharmacokinetic parameters of compounds of the present disclosure in cynomolgus monkeys | | | | | | | | |
|---|---|---|---|---|---|---|---|---|
| | Pharmacokinetic parameters in cynomolgus monkeys | | | | | | | |
| | Intravenous injection (0.5 mg/kg) | | | | Intragastric administration (5 mg/kg) | | | |
| Compound No. | Plasma clearance (mL/min/kg) | Elimination half-life (h) | Apparent volume of distribution (L/kg) | Area under the drug-time curve (0-inf, μM · h) | Peak concentration (μM) | Time to peak concentration (h) | Area under the drug-time curve (0-inf, μM · h) | Bio-availability F (%) |
| Hydrochloride of WX015 | 48.5 | 2.33 | 8.83 | 0.21 | 0.14 | 4.0 | 1.14 | 55.5 |

Conclusion: The compound of the present disclosure has high oral systemic plasma exposure ($AUC_{0\text{-}inf}$). It has superior pharmacokinetic properties in non-rodent animals such as cynomolgus monkeys.

Experimental Example 5: Study on the Preventive and Therapeutic Effect of Compounds on Sodium Urate-Induced Acute Gouty Arthritis in Rats

Experimental Purpose

It is to evaluate the preventive and therapeutic effect of compounds on sodium urate-induced acute gouty arthritis in rats.

Experimental Materials

Animals: 5-week-old male SD rats; source: Zhejiang Vital River Laboratory Animal Technology Co., Ltd.

Experimental Reagents

Sodium urate: Sigma; Cat. No.: BCCB4889;
DMSO: GENERAL-REAGENT, Cat. No.: P1908824;
sterile water for injection: Guangdong Aixida Pharmaceutical Co., Ltd., Cat. No.: 200913203;
Solutol: BASF SE; Cat. No.: 35907288Q0;
vehicle: 10% DMSO+10% Solutol+80% $H_2O$.

Experimental Instruments

Toe swelling tester: YLS-7B, Jinan Yiyan Technology Development Co., Ltd.
Bipedal balance pain tester: Incapacitance Testers, Linton Experimental Operation Experimental grouping: After 3 days of acclimatization, all animals were measured for basal hindfoot volume, arthritis index score, and bilateral hindfoot pain threshold. 50 animals were selected and divided equally into 5 groups with 10 animals each based on body weight, hindfoot volume, arthritis index, and bilateral hindfoot pain threshold.

TABLE 5

Experimental grouping

| Group | Drug | Number of animals | Administration dose (mg/kg) | Administration volume (mL/kg) | Administration concentration (mg/mL) | Route and cycle of administration |
|---|---|---|---|---|---|---|
| 1 | Normal group | 10 | NA | 10 | NA | Intragastric administration, twice a day for 6 consecutive days |
| 2 | Model group | 10 | NA | 10 | NA | Intragastric administration, twice a day for 6 consecutive days |
| 3 | Test compound | 10 | 30 | 10 | 3 | Intragastric administration, twice a day for 6 consecutive days |
| 4 | Test compound | 10 | 100 | 10 | 10 | Intragastric administration, twice a day for 6 consecutive days |
| 5 | Test compound | 10 | 200 | 10 | 20 | Intragastric administration, twice a day for 6 consecutive days |

The day of initiation of administration was recorded as D-1, and intragastric administration was performed twice a day for 6 consecutive days (D-1 to D34). 1 hour after the first administration at D0 (1 day after administration), except for the blank control group, the other rats were anesthetized with isoflurane, and 50 μL (50 mg/mL) of sodium urate solution was injected into the joint cavity for modeling at the lateral posterior side of the right ankle joint, which was used as a puncture point. Joint swelling would peak after 8 to 12 hours (lasting about 72 hours). Foot volumes of the animals were measured and arthritis index (AI) scoring was performed before and 2, 5, 8, 11, 24, 48, 72, and 96 hours after the onset of inflammation; pain thresholds were measured using a bipedal balance pain tester before and 2, 24, 48, 72, and 96 hours after the onset of inflammation. Photographs of critical swelling were taken at the peak of joint swelling (8 to 12 hours) in each group of animals and retained.

Clinical observation: The clinical symptoms of experimental animals were observed once a day to record any abnormalities.

Foot volume measurement: Before measurement, a line was drawn at the ankle joint of a rat with a marker to mark the position, and the instrument was added with clean water and zeroed to be ready for measurement. The hind limbs of the rat were placed in the water so that the marked line at the ankle joint was on the surface of the liquid, at which time the foot pedal was pressed to read the foot volume of the rat. At the end of the measurement, the foot pedal was pressed again for zeroing to be ready for the measurement of the next rat.

Arthritis index (AI): The foot volume was measured while the swelling of the modeled foot was scored. Arthritis index scoring criteria:

TABLE 6

Clinical scoring criteria for arthritis

| Score | Degree |
|---|---|
| 0 | No swelling with normal appearance |
| 1 | Slight swelling of the ankle joint with visible bony landmarks |
| 2 | Obvious redness and swelling of the ankle joint with loss of bony landmarks, but the swelling is confined to the joint area |
| 3 | Swelling of toes beyond the ankle joint |

Data Statistics:

Experimental data were expressed as Mean±SD; data were statistically analyzed using IBM SPSS Statistics 21, and $p<0.05$ was considered a significant difference between the two groups.

The test results of foot volume, arthritis index, and hindfoot weight-bearing difference are shown in Table 7, Table 8, and Table 9.

TABLE 7

Effect of test substances on hindfoot volume of sodium urate-induced acute gouty arthritis in rats (n = 10, $\bar{x} \pm s$)

| Group | Foot volume (mL)/time (h) 0 | 2 | 5 | 8 | 11 | 24 | 48 | 72 | 96 |
|---|---|---|---|---|---|---|---|---|---|
| Normal group | 3.62 ± 0.2 | 3.77 ± 0.2** | 3.79 ± 0.2** | 3.8 ± 0.2*** | 3.82 ± 0.2** | 3.87 ± 0.2 | 3.92 ± 0.2 | 3.95 ± 0.2 | 3.99 ± 0.2 |
| Model group | 3.63 ± 0.1 | 3.97 ± 0.1 | 4.05 ± 0.1 | 4.15 ± 0.2 | 4.12 ± 0.2 | 3.99 ± 0.2 | 3.98 ± 0.2 | 4.02 ± 0.2 | 4.02 ± 0.2 |
| Hydrochloride of WX015 (30 mg/kg) | 3.63 ± 0.1 | 3.88 ± 0.2 | 3.9 ± 0.1* | 3.9 ± 0.1** | 3.92 ± 0.2* | 3.9 ± 0.2 | 3.91 ± 0.2 | 3.94 ± 0.1 | 3.96 ± 0.2 |
| Hydrochloride of WX015 (100 mg/kg) | 3.63 ± 0.1 | 3.85 ± 0.2 | 3.88 ± 0.2* | 3.9 ± 0.1** | 3.91 ± 0.2** | 3.88 ± 0.2 | 3.9 ± 0.2 | 3.93 ± 0.2 | 3.95 ± 0.2 |
| Hydrochloride of WX015 (200 mg/kg) | 3.62 ± 0.1 | 3.84 ± 0.1* | 3.88 ± 0.1* | 3.89 ± 0.1** | 3.88 ± 0.1** | 3.87 ± 0.1 | 3.89 ± 0.2 | 3.91 ± 0.1 | 3.93 ± 0.3 |

*p < 0.05,
**p < 0.01,
***p < 0.001 comparison model group

TABLE 8

Effect of test substances on hindfoot arthritis index of sodium urate-induced acute gouty arthritis in rats (n = 10, $\bar{x} \pm s$)

| Group | Arthritis index/time (h) 0 | 2 | 5 | 8 | 11 | 24 | 48 | 72 | 96 |
|---|---|---|---|---|---|---|---|---|---|
| Normal group | 0 ± 0 | 0 ± 0*** | 0 ± 0*** | 0 ± 0*** | 0 ± 0*** | 0 ± 0*** | 0 ± 0*** | 0 ± 0** | 0 ± 0 |
| Model group | 0 ± 0 | 1.1 ± 0.3 | 1.3 ± 0.5 | 2 ± 0.8 | 1.7 ± 0.7 | 1.1 ± 0.3 | 0.8 ± 0.4 | 0.5 ± 0.5 | 0.2 ± 0.4 |
| Hydrochloride of WX015 (30 mg/kg) | 0 ± 0 | 1 ± 0 | 1 ± 0 | 1 ± 0** | 1 ± 0** | 0.9 ± 0.3 | 0.5 ± 0.5 | 0.3 ± 0.5 | 0.1 ± 0.3 |
| Hydrochloride of WX015 (100 mg/kg) | 0 ± 0 | 1 ± 0 | 1 ± 0 | 1 ± 0** | 1 ± 0** | 0.6 ± 0.5* | 0.3 ± 0.5* | 0.2 ± 0.4 | 0 ± 0 |
| Hydrochloride of WX015 (200 mg/kg) | 0 ± 0 | 1 ± 0 | 1 ± 0 | 1 ± 0** | 1 ± 0** | 0.5 ± 0.5** | 0.2 ± 0.4** | 0 ± 0** | 0 ± 0 |

*p < 0.05,
**p < 0.01,
***p < 0.001 comparison model group

TABLE 9

Effect of test substances on hindfoot weight-bearing difference of sodium urate-induced acute gouty arthritis in rats (n = 10, $\bar{x} \pm s$)

| Group | Hindfoot weight-bearing difference (g)/time (h) 0 | 2 | 24 | 48 | 72 | 96 |
|---|---|---|---|---|---|---|
| Normal group | 0.22 ± 0.7 | 0.49 ± 0.3*** | −0.61 ± 0.9*** | −0.2 ± 0.6*** | −0.36 ± 0.7*** | 0.07 ± 0.4*** |
| Model group | 0.13 ± 0.9 | 28.12 ± 0.7 | 20.32 ± 1.1 | 11.99 ± 0.6 | 5.12 ± 0.3 | 2.64 ± 0.1 |
| Hydrochloride of WX015 (30 mg/kg) | 0.69 ± 0.9 | 19.09 ± 0.6*** | 13.22 ± 0.8*** | 6.6 ± 0.4*** | 4.3 ± 0.3* | 2.1 ± 0.2* |
| Hydrochloride of WX015 (100 mg/kg) | 0.12 ± 0.6 | 16.38 ± 0.6*** | 12.2 ± 1*** | 5.72 ± 0.6*** | 3 ± 0.2*** | 2.01 ± 0.1** |

TABLE 9-continued

Effect of test substances on hindfoot weight-bearing difference of sodium urate-induced acute gouty arthritis in rats (n = 10, $\bar{x} \pm s$)

| Group | Hindfoot weight-bearing difference (g)/time (h) 0 | 2 | 24 | 48 | 72 | 96 |
|---|---|---|---|---|---|---|
| Hydrochloride of WX015 (200 mg/kg) | −0.23 ± 1 | 14.81 ± 1*** | 11.32 ± 0.9*** | 3.91 ± 0.5*** | 2.1 ± 0.2*** | 1.94 ± 0.1* |

*p < 0.05,
**p < 0.01,
***p < 0.001 comparison model group

Experimental Conclusion

The compound of the present disclosure has a therapeutic effect on hindfoot volume, hindfoot arthritis index score, and hindfoot weight-bearing difference in sodium urate-induced acute gouty arthritis in rats in a dose-dependent manner.

Experimental Example 6: Evaluation of Efficacy of Compounds on Imiquimod-Induced Psoriasis Model in Mice

Experimental Purpose

It is to evaluate the efficacy of compounds on imiquimod-induced psoriasis model in BALB/c mice.

Experimental Materials

Animals: BALB/c mice, male, 18 to 20 g; source: Zhejiang Vital River Laboratory Animal Technology Co., Ltd.

Experimental Reagents

Imiquimod: 3M Health Care Limited, Drug Registration No. H20160079;
DMSO: Anergy Chemical, Cat. No.: E081359;
Solutol: Sigma-Aldrich, Cat. No.: 42966;
MC: Sigma-Aldrich, Cat. No.: M0202;
Tween 20: Sigma-Aldrich, Cat. No.: 9005-64-5;
vehicle: 10% DMSO+10% Solutol+80% $H_2O$.

Experimental Instruments

Electronic balance: Sartorius, Cat. No.: QUINTIX124-1CN;
Electronic scale: Shanghai Yueping Scientific Instrument, Cat. No.: YP10001;
Ultrasonic cleaner: Kunshang, Cat. No.: KQ3200E;
Electronic oscillator: Scientific Industries, Cat. No.: SI-0256;
Anesthesia machine: Yuyan Instruments, Cat. No.: ABS-4.

Experimental Operation

Experimental grouping and administration: After acclimatization, 50 male BALB/c mice were randomly divided into 5 groups (n=6 or 9) according to body weight: normal (control, G1) group, vehicle (model, G2) group, test compound low-dose (30 mg/kg, BID, G3) group, test compound medium-dose (100 mg/kg, BID, G4) group, and test compound high-dose (300 mg/kg, BID, G5) group.

Model induction: the dorsal skin of the experimental animals was shaved (surface area=2×3 cm) before the application of imiquimod. In addition to the normal group, imiquimod cream was topically applied to the shaved back (47 mg) and left ear (15 mg) at 62 mg/mouse per day for 8 consecutive days (from D0 to D7). For administration groups (G2 to G5), the vehicle or test compound was intragastrically administered twice a day from D-1 to D6 and only once on D7. The administration volume was 10 mL/kg in each group. (Note: It is specified that the first application of imiquimod is D0; since it is administered one day earlier, the first administration is D-1).

TABLE 10

Experimental grouping

| Group | Model induction | Drug | Number of animals | Administration dose (mg/kg) | Administration volume (mL/kg) | Route of administration | Route and cycle of administration |
|---|---|---|---|---|---|---|---|
| 1 | — | Normal group | 6 | — | — | — | — |
| 2 | Imiquimod | Model group | 9 | — | 10 | Intragastric administration | Twice a day from D-1 to D 6; once on D 7 |
| 3 | Imiquimod | Test compound | 9 | 30 | 10 | Intragastric administration | Twice a day from D-1 to D 6; once on D 7 |
| 4 | Imiquimod | Test compound | 9 | 100 | 10 | Intragastric administration | Twice a day from D-1 to D 6; once on D 7 |
| 5 | Imiquimod | Test compound | 9 | 300 | 10 | Intragastric administration | Twice a day from D-1 to D 6; once on D 7 |

Data Collection and Analysis:

Clinical score: Clinical disease scores for erythema, scale, and thickness were measured daily according to a grading system, and cumulative scores were calculated.

TABLE 11

Scoring system: erythema, scale, and thickness

| Score | Clinical symptom |
|---|---|
| 0 | Normal |
| 1 | Slight |
| 2 | Mild |
| 3 | Moderate |
| 4 | Significant |

Ear thickness: The left ear thickness was measured on D0, D3, D5, and D7 for a total of 4 times, and the increased ear thickness on D7 relative to D0 was calculated.

Spleen weight: The spleen weight was measured after the animals were sacrificed on D7.

Inflammatory factors: The skin was taken from the lesion site after the animals were sacrificed on D7, and the relative levels of interleukin 17, interleukin 6, and tumor necrosis factor α were detected using fluorescence quantitative PCR.

Experimental Results:

Experimental data were expressed as Mean±SEM; data were statistically analyzed using one-way ANOVA in GraphPad Prism software, and $p<0.05$ was considered a significant difference between the two groups.

The test results of pathological scores, increased ear thickness, spleen weight, and inflammatory factors in mice are shown in Table 12 and Table 13.

TABLE 12

Effect of test substances on pathological scores, increased ear thickness, and spleen weight of imiquimod-induced psoriasis model in mice (n = 6 or 9)

| Group | Normal group | Model group | WX015 (30 mg/kg) | WX015 (100 mg/kg) | WX015 (300 mg/kg) |
|---|---|---|---|---|---|
| Pathological score | 0 ± 0*** | 22.2 ± 0.38 | 20.2 ± 0.89 | 20.5 ± 1.18 | 19.0 ± 0.55 |
| Increased ear thickness (μM) | 4.3 ± 1.02*** | 228.8 ± 4.62 | 208.4 ± 6.00* | 217.1 ± 5.67 | 185.1 ± 2.68*** |
| Spleen weight (mg) | 76.17 ± 4.82*** | 188.89 ± 13.83 | 175.78 ± 13.01** | 153.78 ± 11.67** | 132.78 ± 3.94** |

*p < 0.05,
**p < 0.01,
***p < 0.001 comparison model group

TABLE 13

Effect of test substances on relative levels of skin inflammatory factors of imiquimod-induced psoriasis model in mice (n = 3 or 9)

| Group | Normal group | Model group | WX015 (30 mg/kg) | WX015 (100 mg/kg) | WX015 (300 mg/kg) |
|---|---|---|---|---|---|
| Interleukin 17 | 1.00 ± 0.98* | 142.4 ± 55.7 | 102.4 ± 36.9 | 113.1 ± 49.4 | 97.3 ± 35.3 |
| Interleukin 6 | 1.00 ± 0.52* | 19.9 ± 7.1 | 8.0 ± 3.3* | 13.8 ± 2.3* | 4.7 ± 2.0* |
| Tumor necrosis factor α | 1.00 ± 0.33*** | 6.7 ± 0.6 | 5.2 ± 0.7** | 5.2 ± 0.8** | 3.7 ± 0.6** |

*p < 0.05,
**p < 0.01,
***p < 0.001 comparison model group

Experimental Conclusion

The compound of the present disclosure has an ameliorating effect on pathological scores, increased ear thickness, and spleen weight of imiquimod-induced psoriasis model in mice, as well as an inhibitory effect on inflammatory factors in the skin at the lesion site, suggesting that it has a therapeutic effect in the psoriasis model in animals, and that the therapeutic effect of high dose (300 mpk) is superior to that of medium and low doses (100 mpk and 30 mpk).

The invention claimed is:

1. A compound of formula (VII-0) or a pharmaceutically acceptable salt thereof, (VII-0)

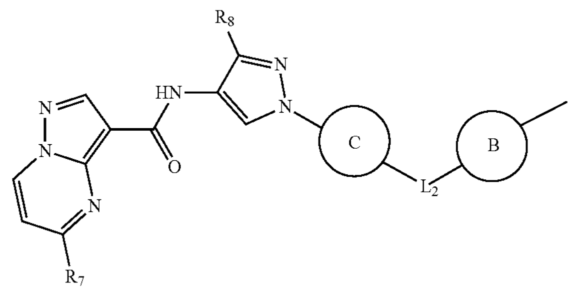

-continued

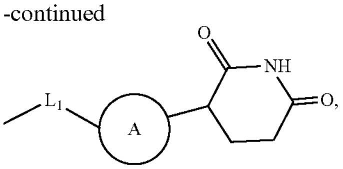

wherein $L_1$ is selected from

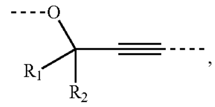

,

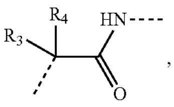

, $—(CH_2)_3—$, and $—O(CH_2)_3—$;

$L_2$ is selected from $—CR_5R_6—$ and O;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$R_7$ is selected from

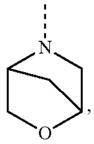, 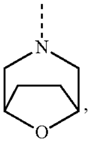, and 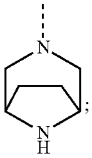;

$R_8$ is selected from $C_{1-4}$ alkyl, $C_{1-4}$ haloalkyl, cyclopropyl, and halocyclopropyl;

ring A is selected from

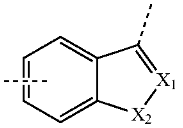 or 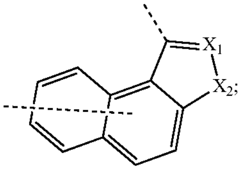;

$X_1$ is selected from CH and N;

$X_2$ is selected from NH, O, S, and Se;

ring B is selected from $C_{5-8}$ cycloalkyl and 5- to 8-membered heterocycloalkyl, and the $C_{5-8}$ cycloalkyl and 5- to 8-membered heterocycloalkyl are each independently and optionally substituted by 1, 2, 3, or 4 $R_a$;

$R_a$ is selected from halogen, OH, $NH_2$, $C_{1-3}$ alkyl, $C_{1-3}$ alkoxy, $C_{1-3}$ haloalkyl, and $C_{1-3}$ haloalkoxy;

ring C is selected from $C_{5-8}$ cycloalkyl and 5- to 8-membered heterocycloalkyl, and the $C_{5-8}$ cycloalkyl and 5- to 8-membered heterocycloalkyl are each independently and optionally substituted by 1, 2, 3, or 4 $R_b$;

$R_b$ is selected from halogen, OH, $NH_2$, $C_{1-3}$ alkyl, $C_{1-3}$ alkoxy, $C_{1-3}$ haloalkyl, and $C_{1-3}$ haloalkoxy;

the 5- to 8-membered heterocycloalkyl refers to a saturated cyclic group consisting of 5 to 8 ring atoms, wherein 1, 2, 3, or 4 ring atoms are heteroatoms independently selected from O, S, N, Si, or Se, and the rest are carbon atoms.

2. The compound or the pharmaceutically acceptable salt thereof according to claim 1, wherein the compound is selected form a compound of formula (VII), (VII)

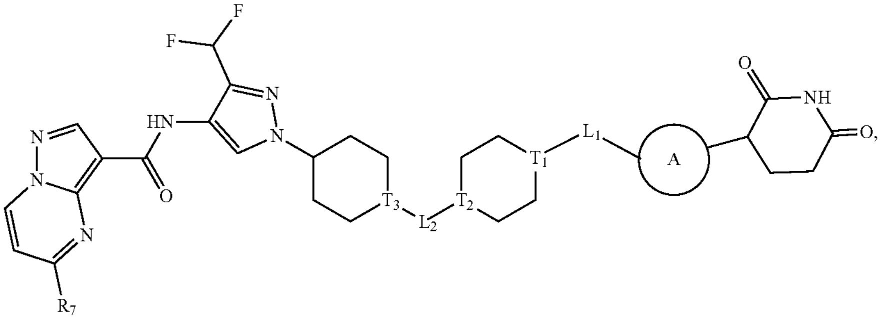

wherein $L_1$ is selected from

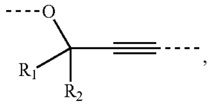, 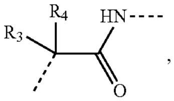, $-(CH_2)_3-$, and $-O(CH_2)_3-$;

$L_2$ is selected from $-CR_5R_6-$ and O;

$R_1$, $R_2$, $R_3$, $R_4$, $R_5$, and $R_6$ are each independently selected from H and halogen;

or, $R_1$ and $R_2$, $R_3$ and $R_4$, $R_5$ and $R_6$, optionally together with the carbon atom to which they are attached form a cyclopropyl ring;

$R_7$ is selected from

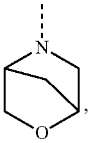, 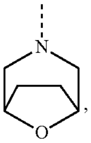, and 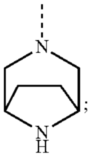;

$T_1$ is selected from CH and N;

$T_2$ is selected from CH and N;

$T_3$ is selected from CH and N;

ring A is selected from

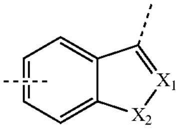 or 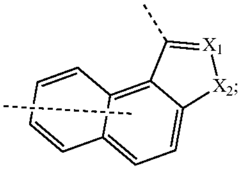;

$X_1$ is selected from CH and N;

$X_2$ is selected from NH, O, S, and Se.

3. The compound or the pharmaceutically acceptable salt thereof according to claim 1, wherein $R_1$, $R_2$, $R_3$, $R_4$, $R_5$, and $R_6$ are each independently selected from H and F.

4. The compound or the pharmaceutically acceptable salt thereof according to claim 1, wherein $L_1$ is selected from

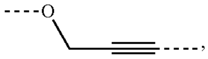,
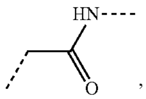,
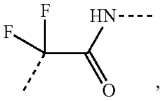,
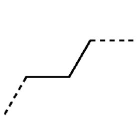, and
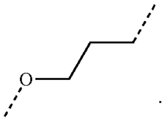.

5. The compound or the pharmaceutically acceptable salt thereof according to claim 1, wherein $L_2$ is selected from —$CH_2$— and O.

6. The compound or the pharmaceutically acceptable salt thereof according to claim 2, wherein the structural moiety

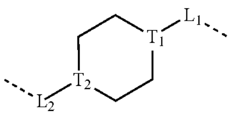

is selected from

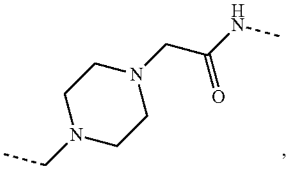,

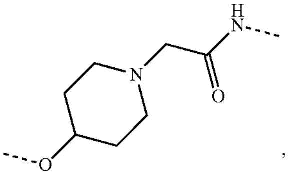,

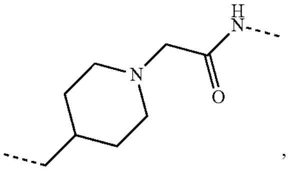,

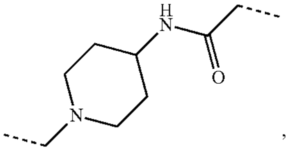,

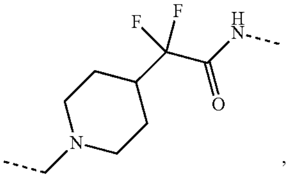,

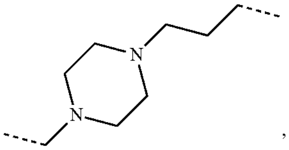,

-continued

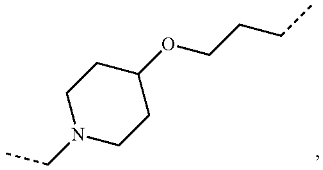, and

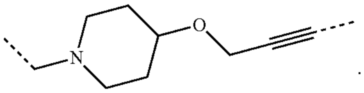.

7. The compound or the pharmaceutically acceptable salt thereof according to claim 2, wherein the structural moiety

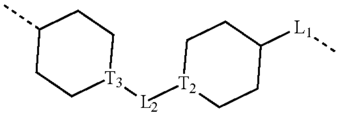

is selected from

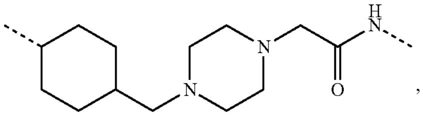,

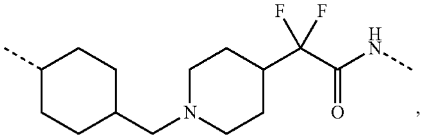,

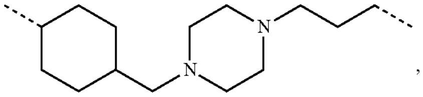,

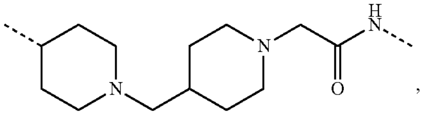,

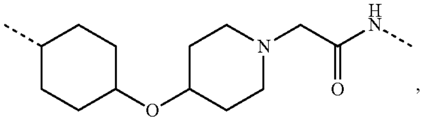,

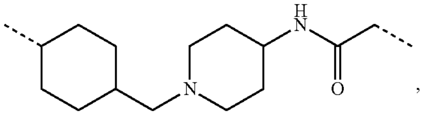,

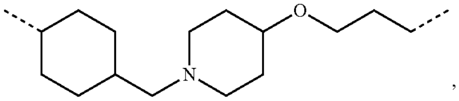, and

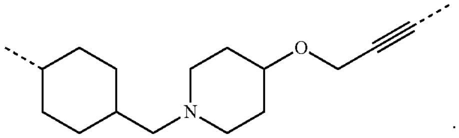.

8. The compound or the pharmaceutically acceptable salt thereof according to claim 1, wherein ring A is selected from

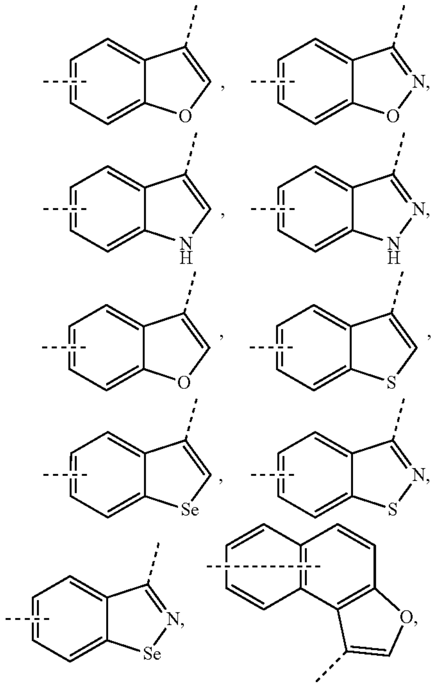
and
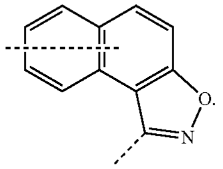
9. The compound or the pharmaceutically acceptable salt thereof according to claim 8, wherein ring A is selected from
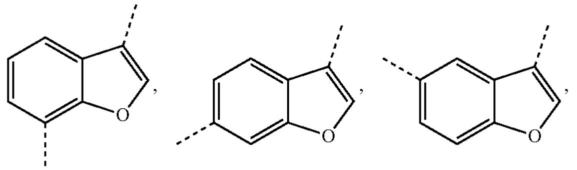
-continued
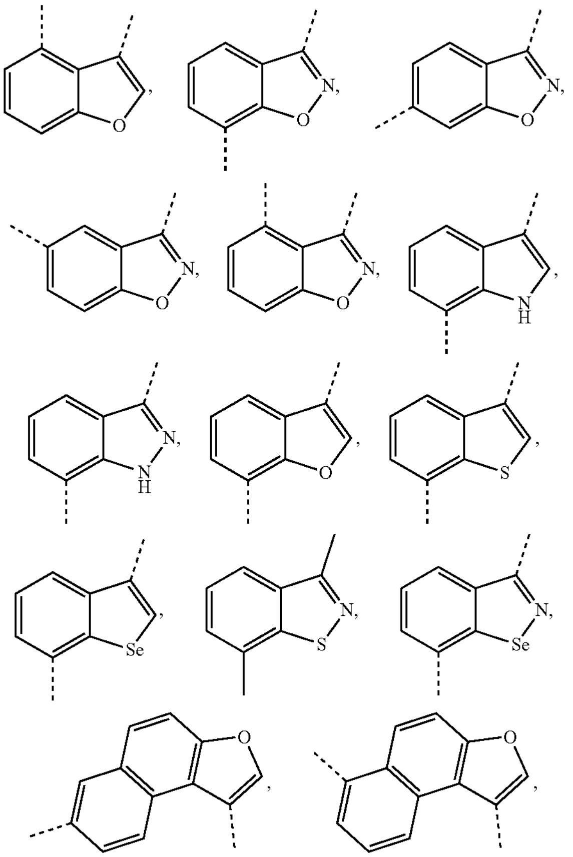
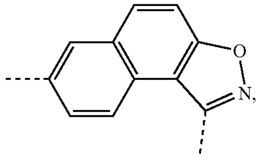
and
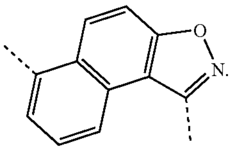
10. The compound or the pharmaceutically acceptable salt thereof according to claim 1, wherein the compound is selected from structures of formulas (VII-1), (VII-2), (VII-3), (VII-4), (VII-5), and (VII-6),
(VII-1)
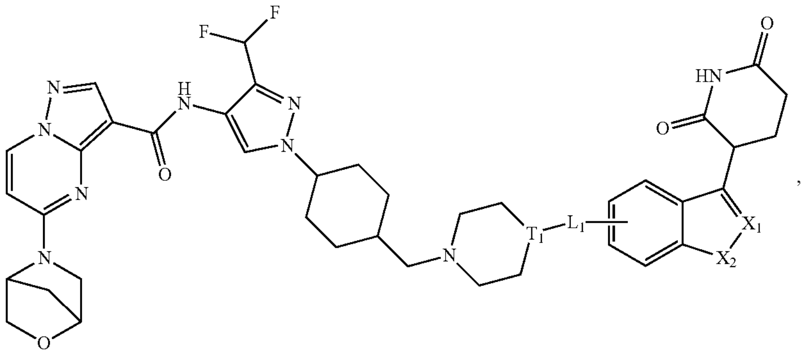
, -continued
(VII-2)
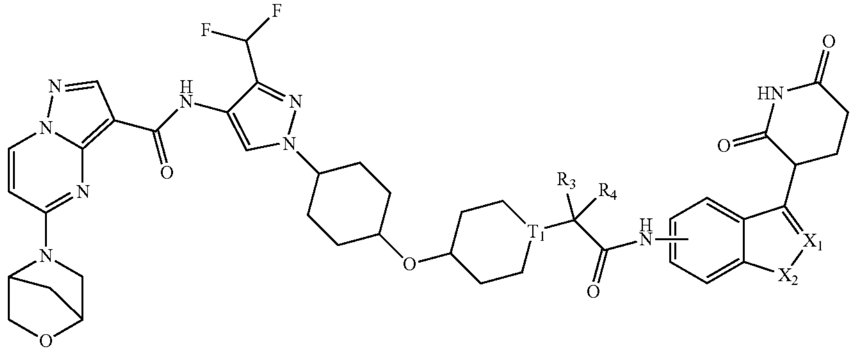
,
(VII-3)
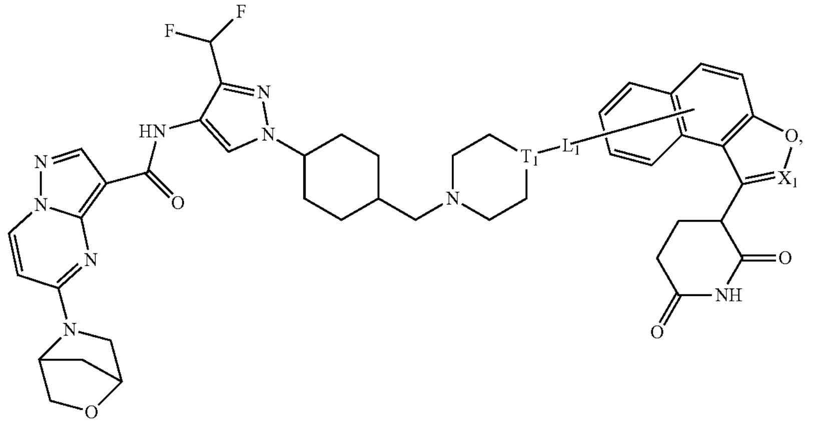
(VII-4)
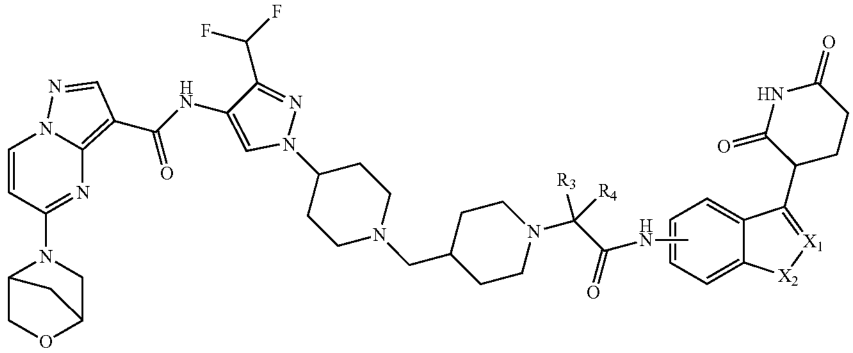
,
(VII-5)
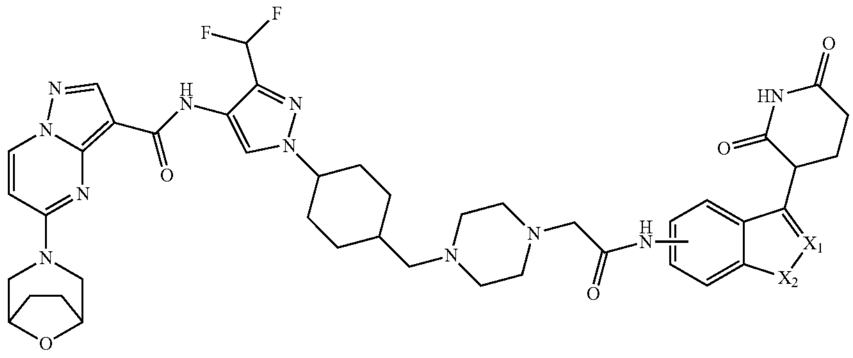
, and -continued
(VII-6)
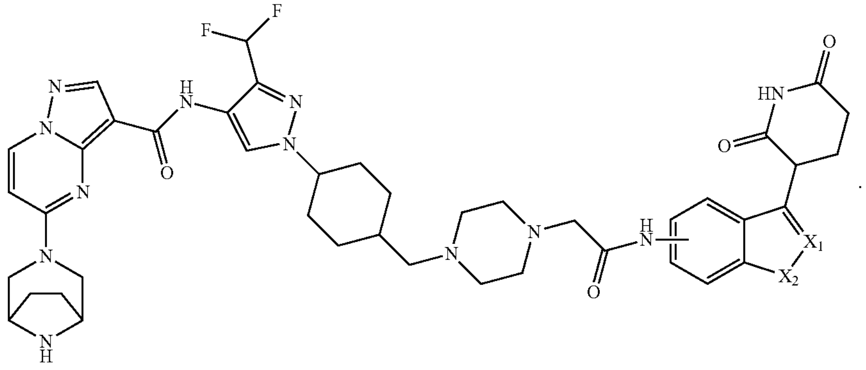
11. The compound or the pharmaceutically acceptable salt thereof according to claim 1, wherein the compound is selected from structures of formulas (VII-1R), (VII-1S), (VII-2R), (VII-2S), (VII-3R), (VII-3S), (VII-4R), and (VII-4S),
(VII-1R)
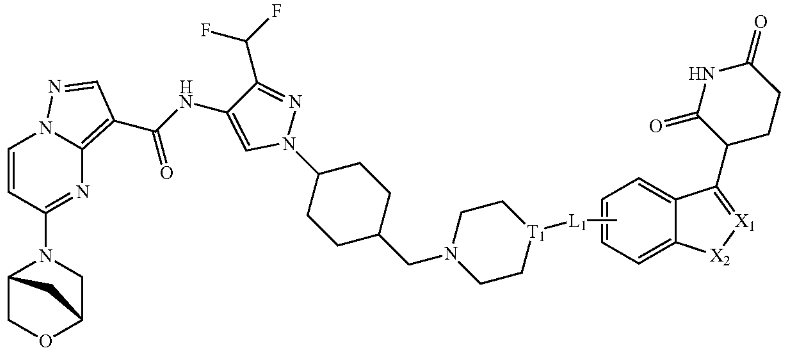
,
(VII-1S)
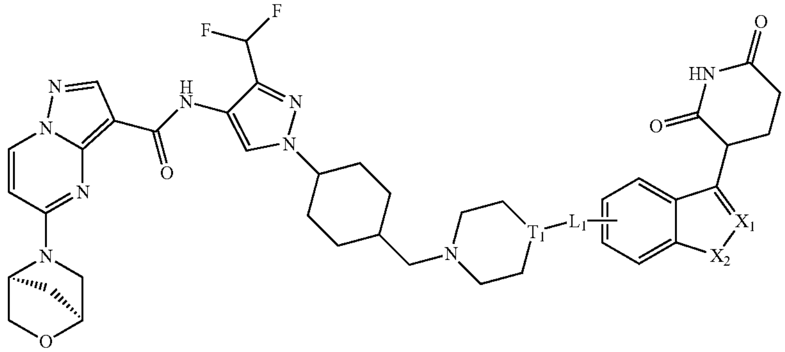
, -continued
(VII-2R)
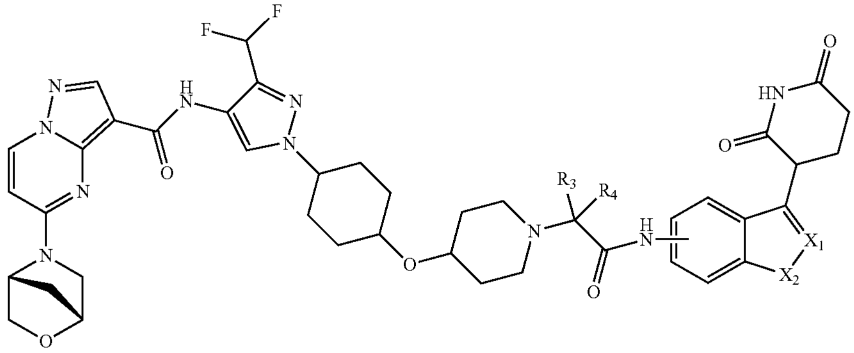
,
(VII-2S)
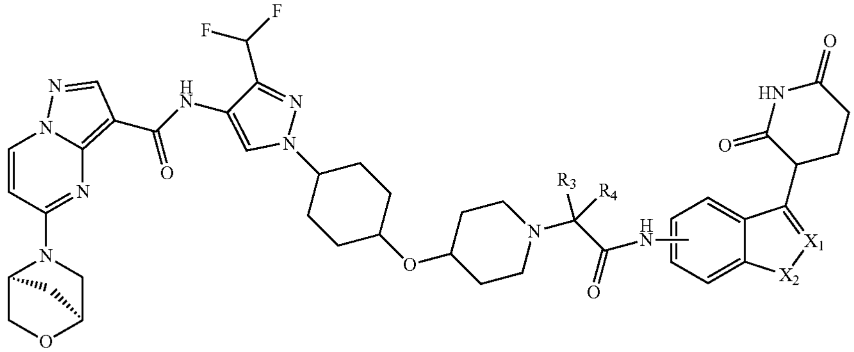
,
(VII-3R)
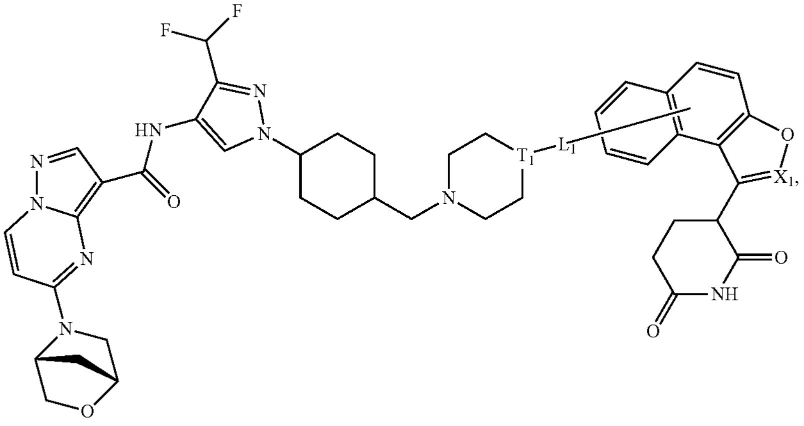
, -continued
(VII-3S)
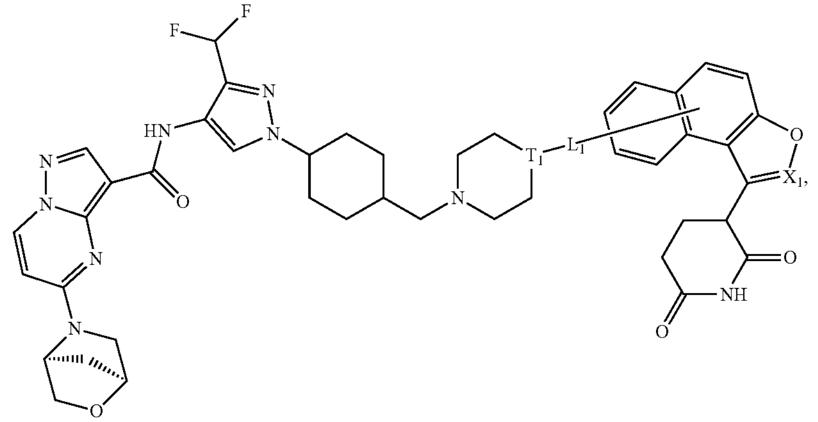
(VII-4R)
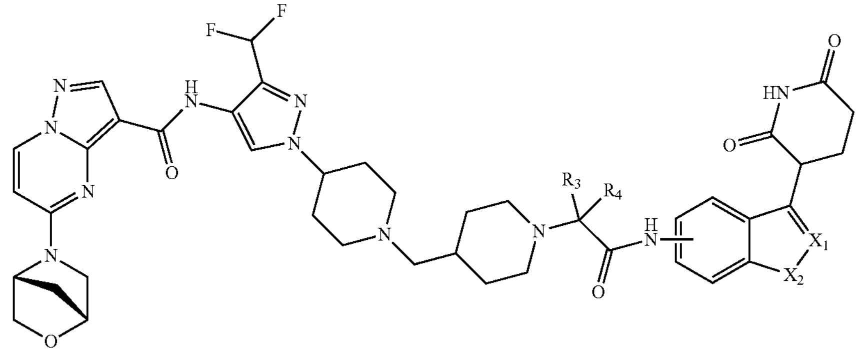
, and
(VII-4S)
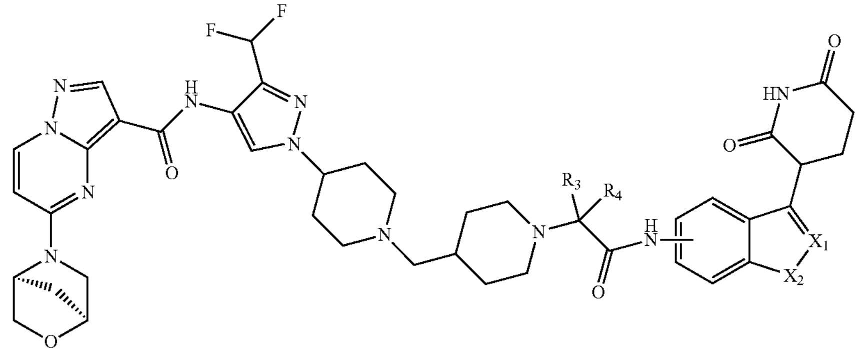
.
12. The compound or the pharmaceutically acceptable salt thereof according to claim 1, wherein the compound is selected from structures of formulas (VII-1RT), (VII-1ST), (VII-2RT), (VII-2ST), (VII-3RT), (VII-3ST), (VII-5T), and (VII-6T), (VII-1RT)
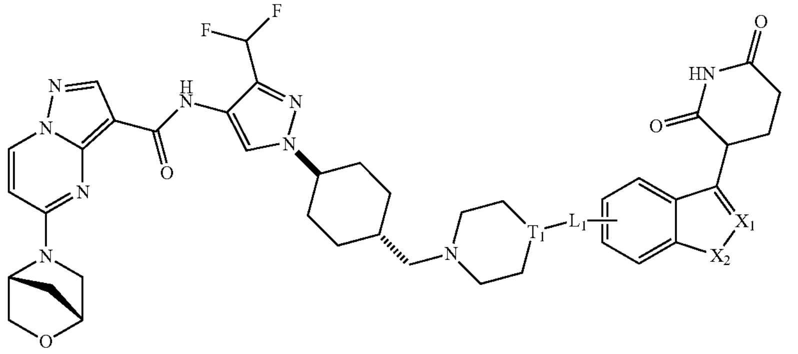
(VII-1ST)
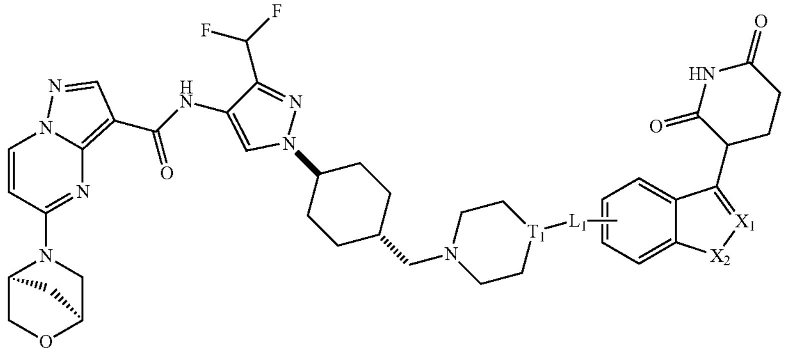
(VII-2RT)
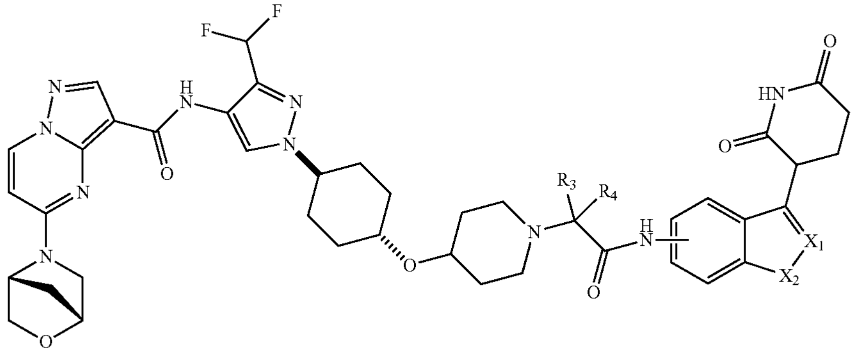
(VII-2ST)
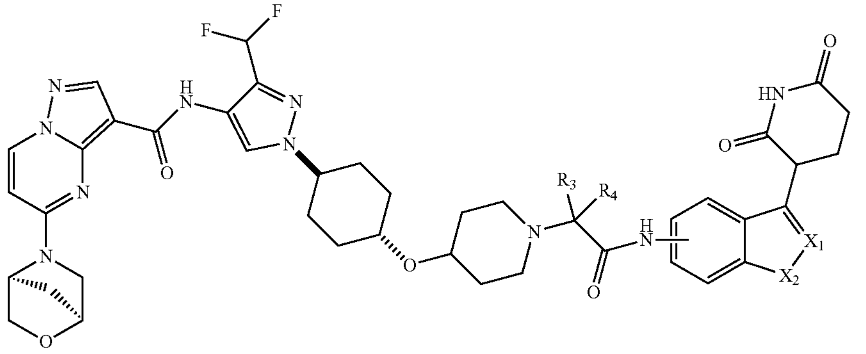

-continued
(VII-3RT)
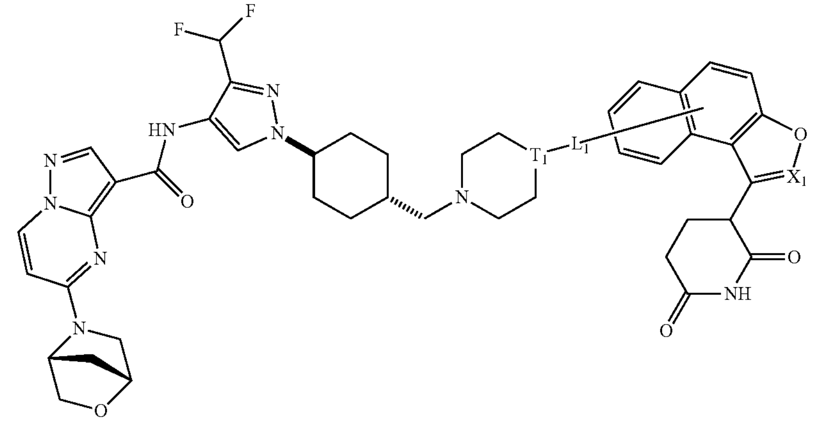
(VII-3ST)
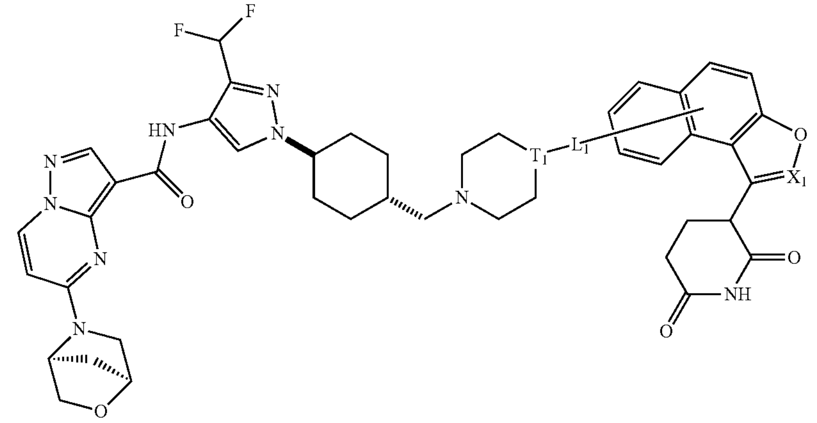
(VII-5T)
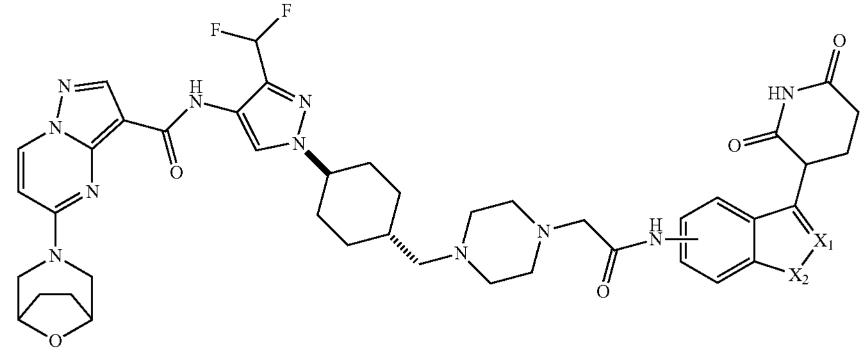
and
(VII-6T)
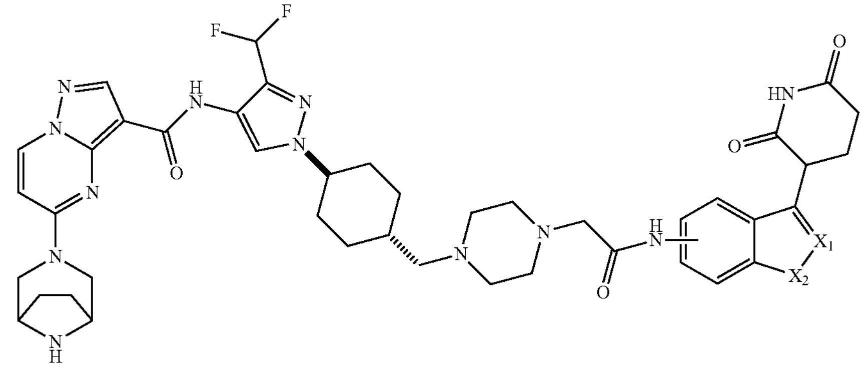
.

13. The compound or the pharmaceutically acceptable salt thereof according to claim 1, wherein the compound is selected from structures of the following formulas,
(VII-1RTS)
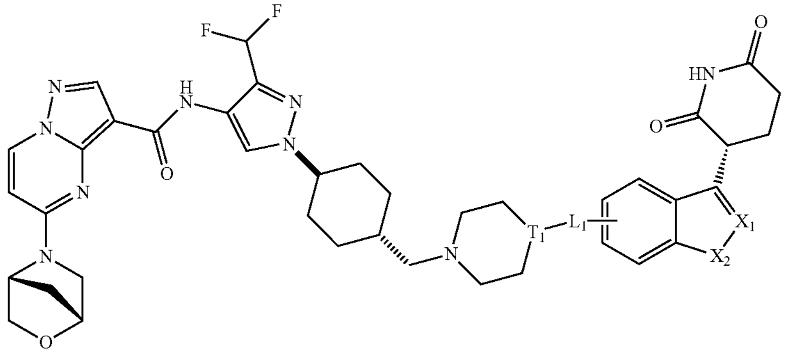
(VII-1RTT)
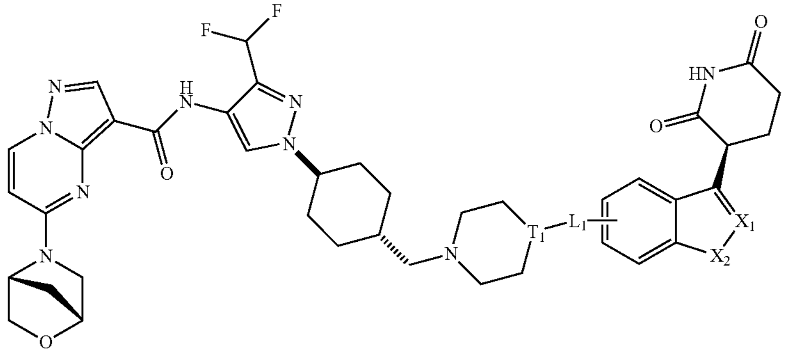
(VII-1STS)
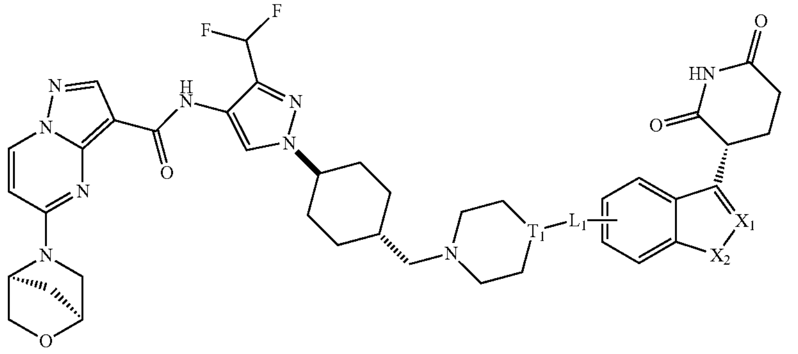
(VII-1STT)
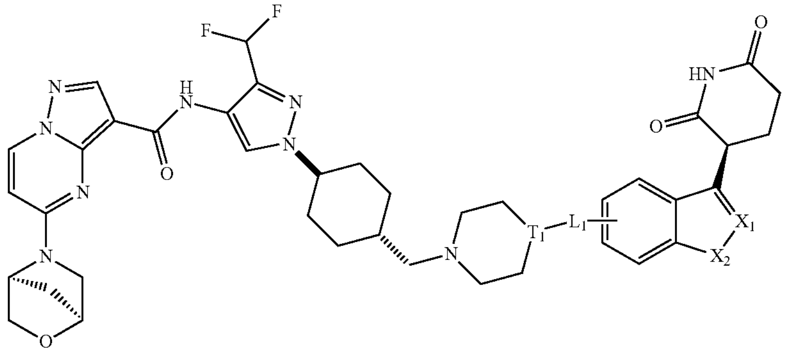

-continued
(VII-2RTS)
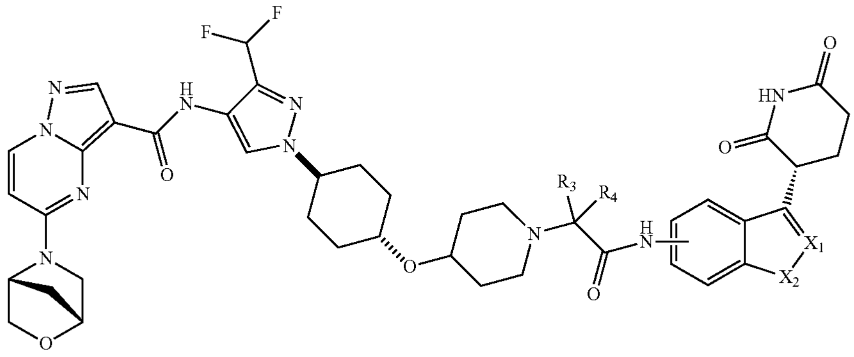
(VII-2RTT)
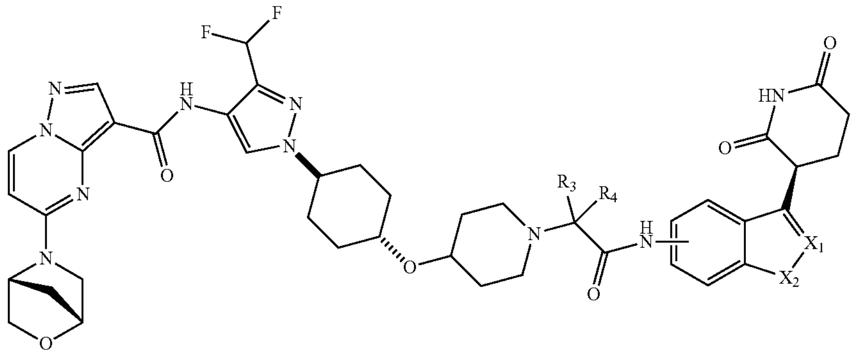
(VII-2STS)
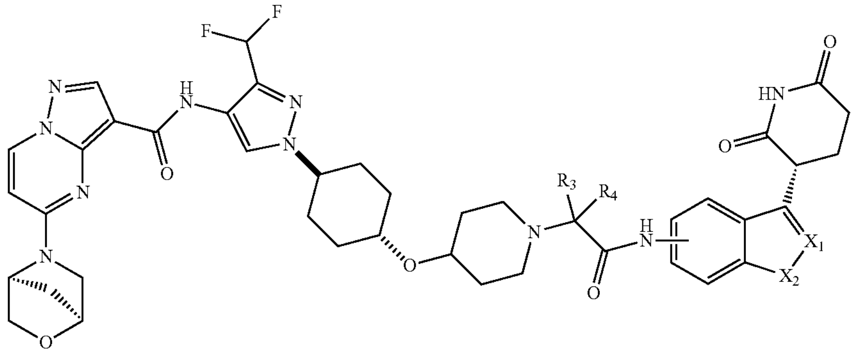
(VII-2STT)
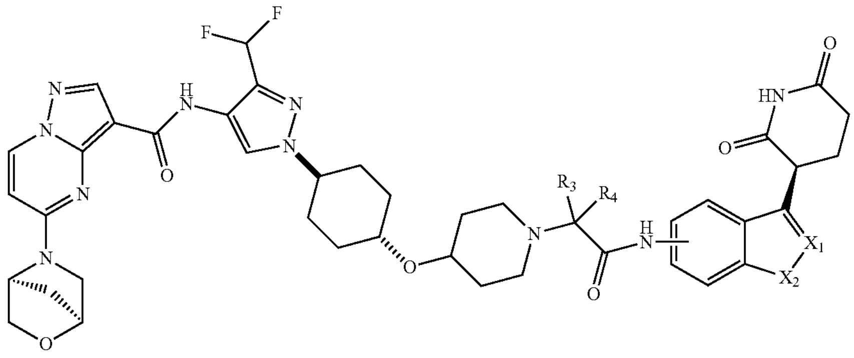

-continued
(VII-3RTS)
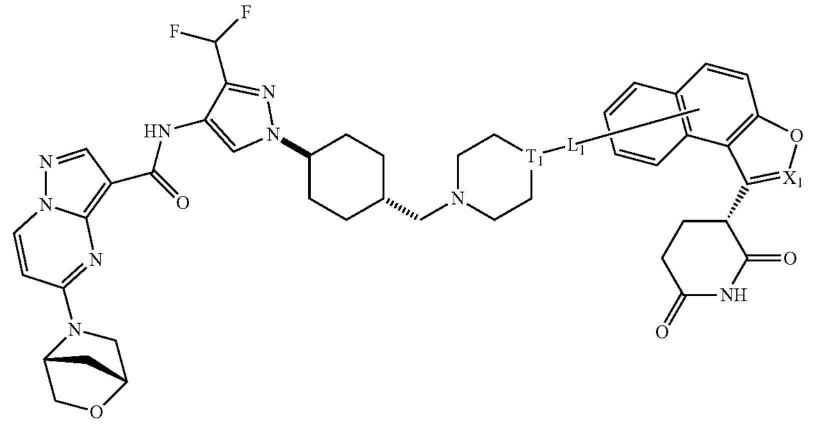
(VII-3RTT)
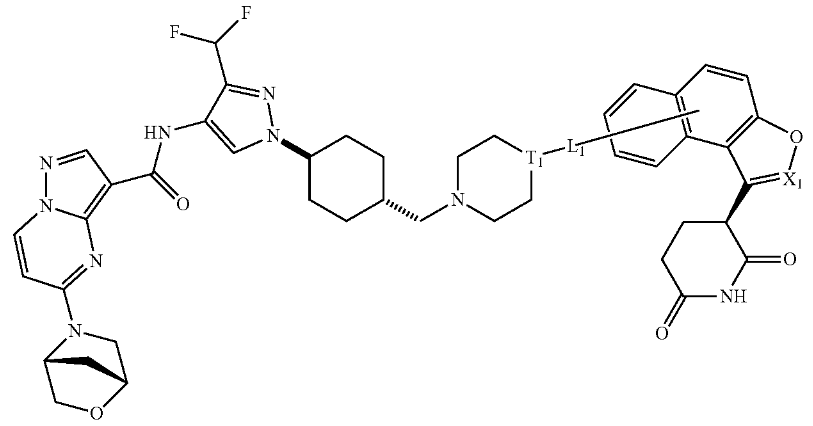
(VII-3STS)
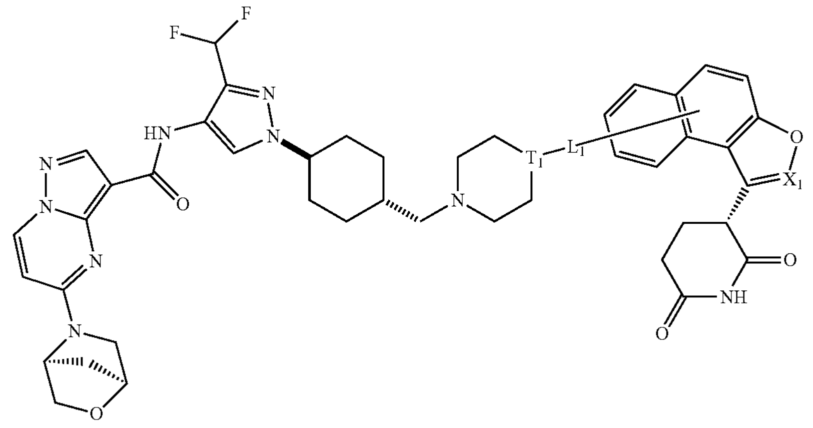

-continued
(VII-3STT)
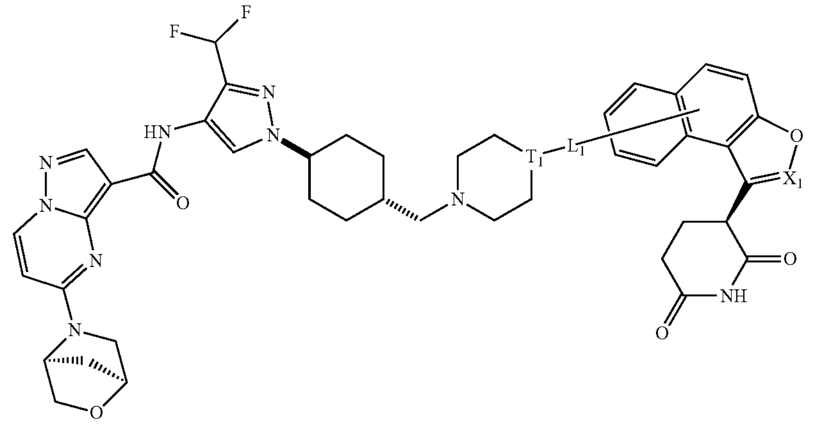
(VII-4RS)
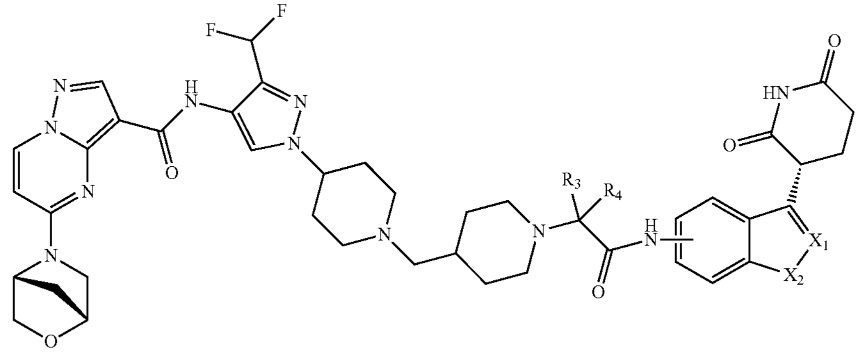
(VII-4RT)
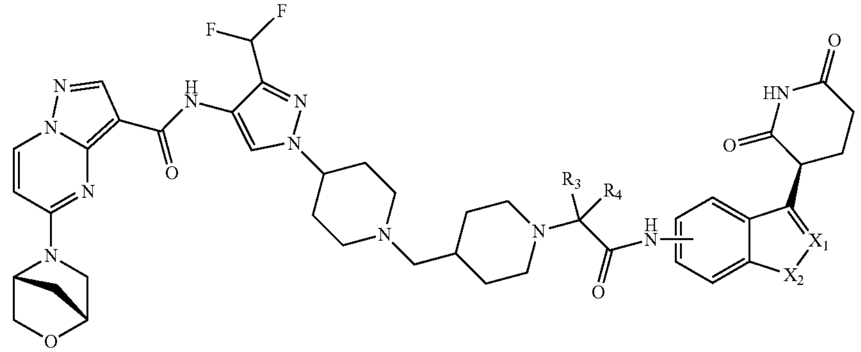
(VII-5TS)
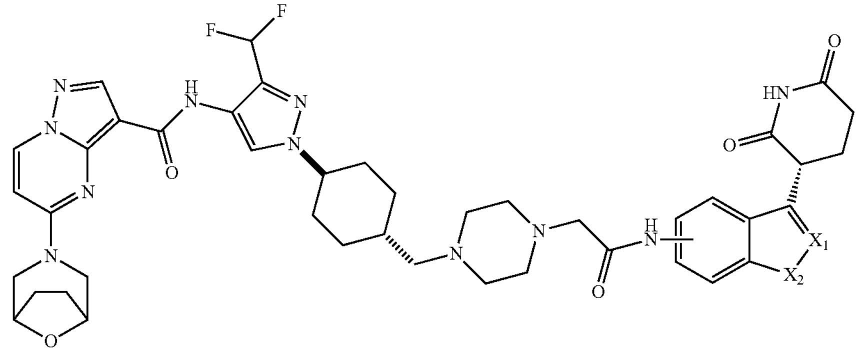

-continued
(VII-5TT)
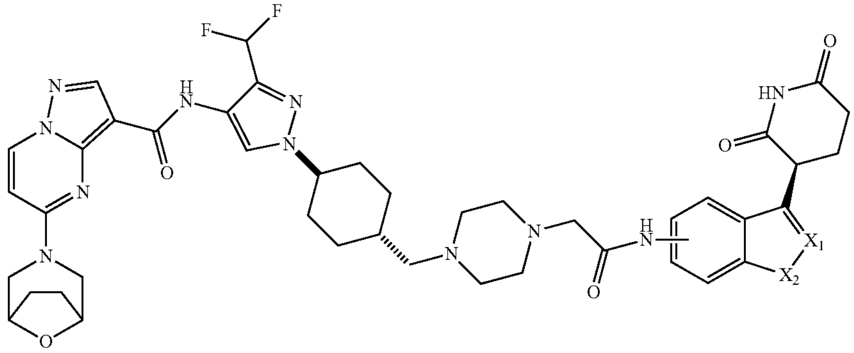
(VII-6TS)
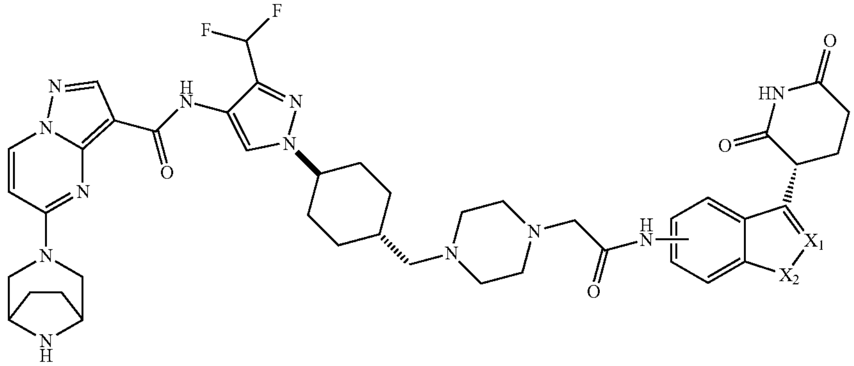
, and
(VII-6TT)
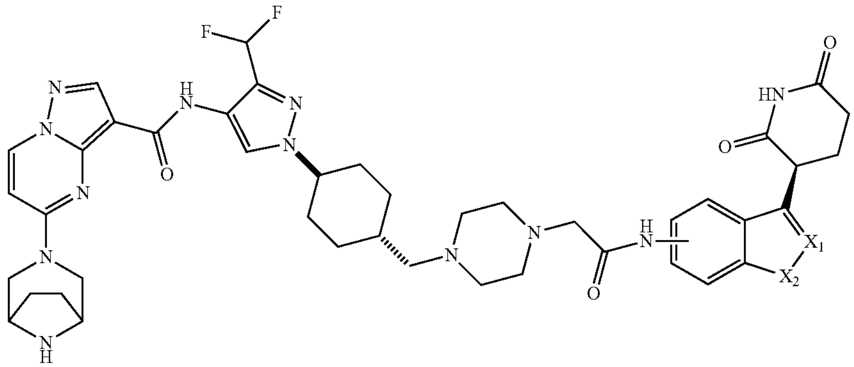
.
14. A compound of the following formulas or a pharmaceutically acceptable salt thereof,
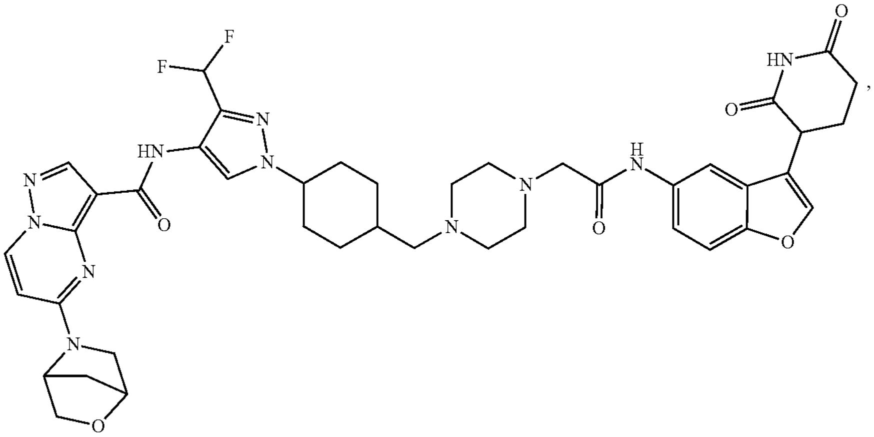
, -continued
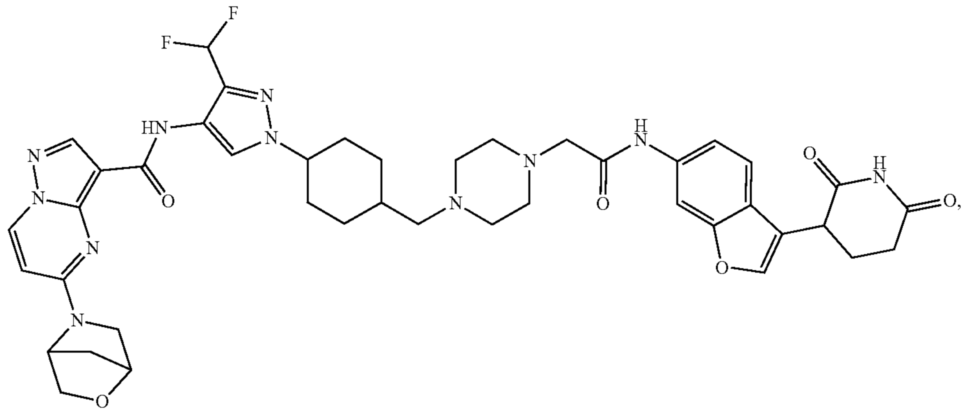
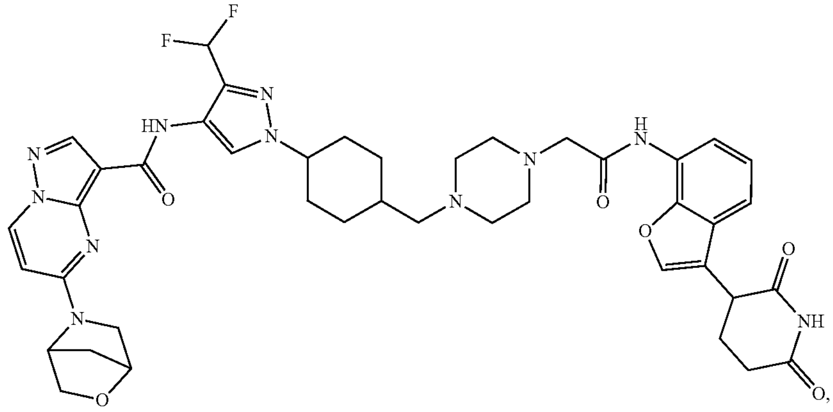
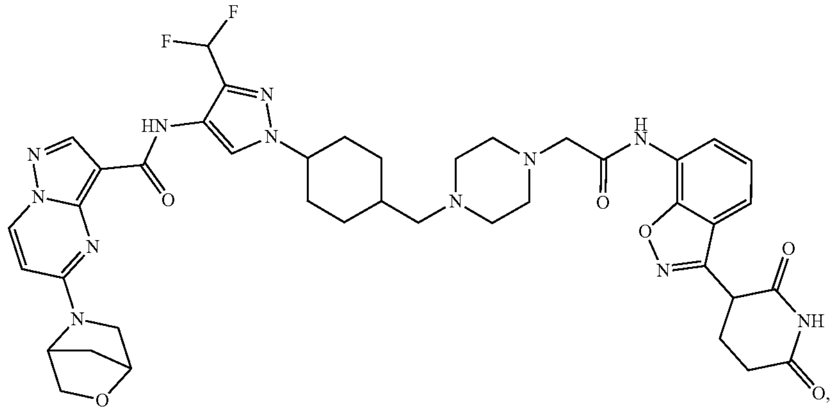
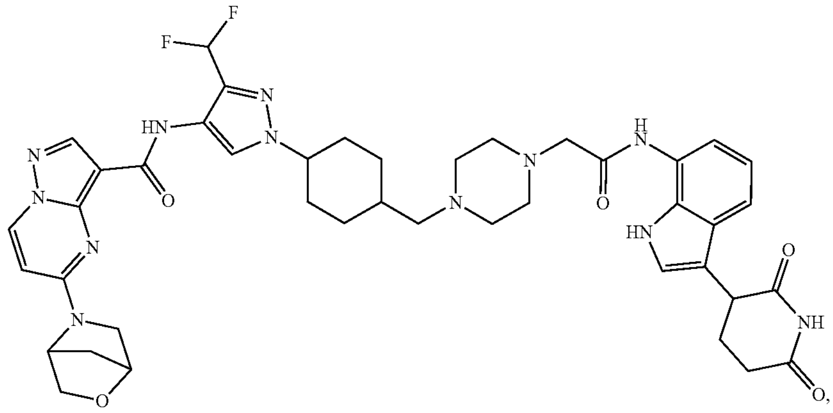

-continued
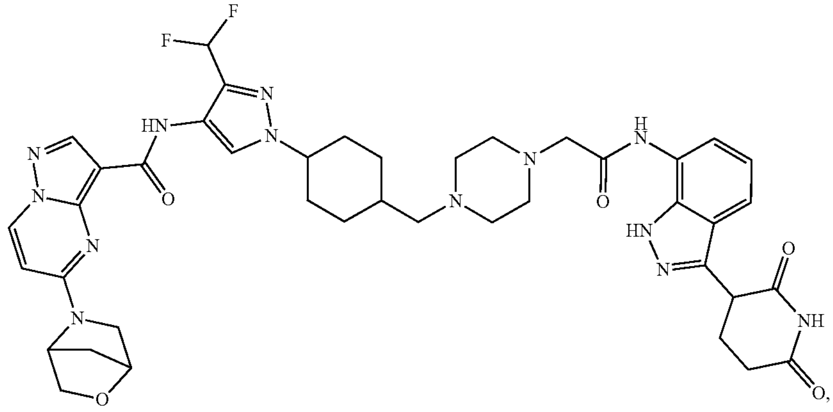
,
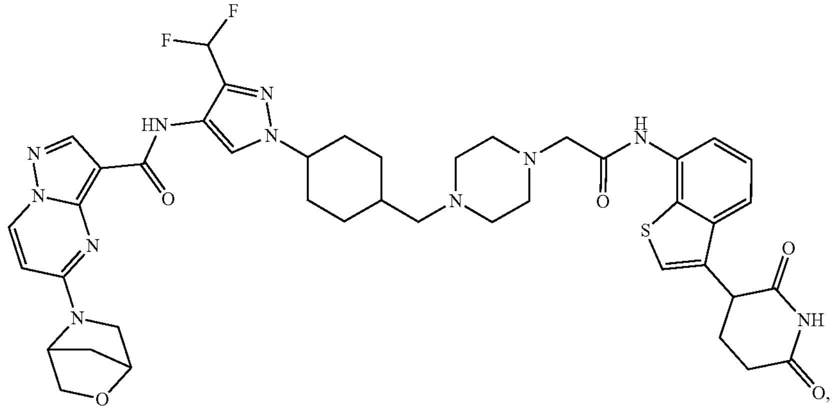
,
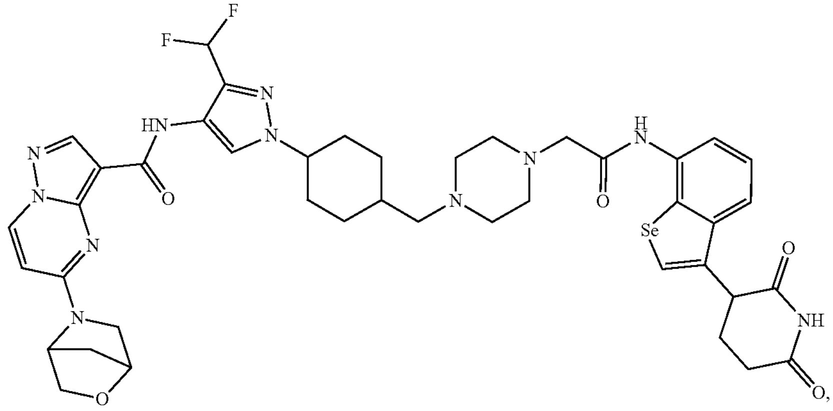
,
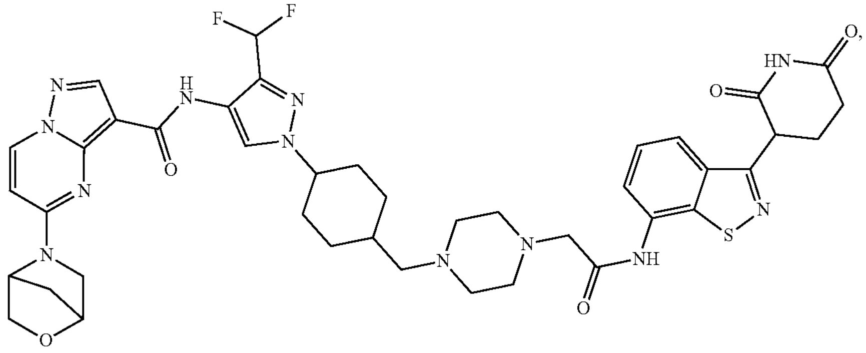
,

-continued
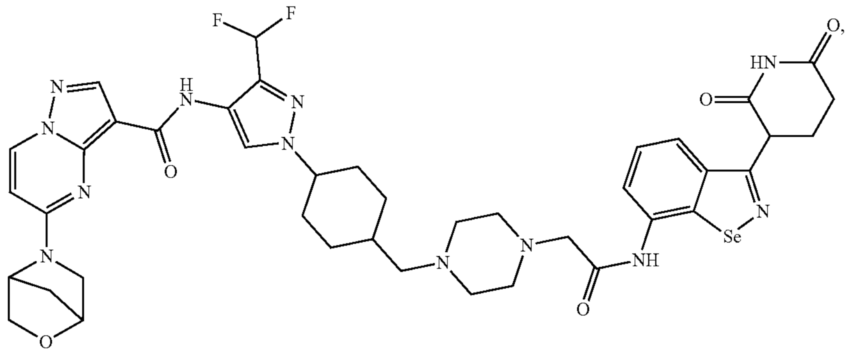
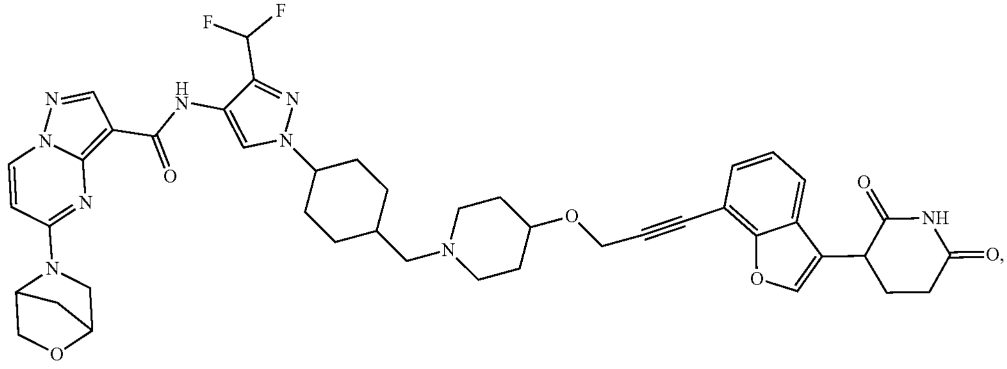
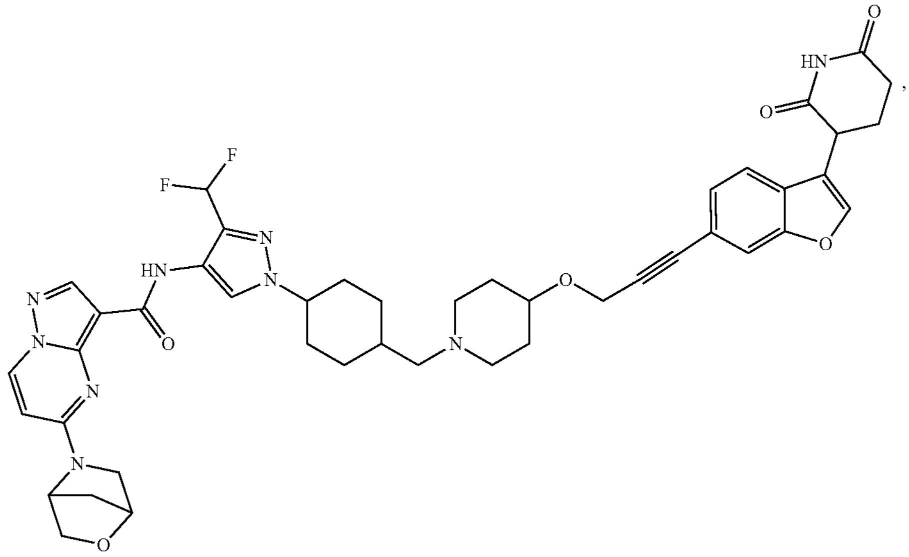
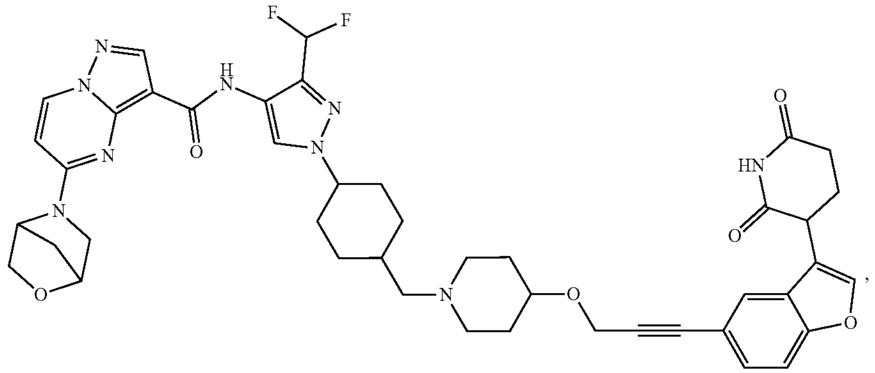

-continued
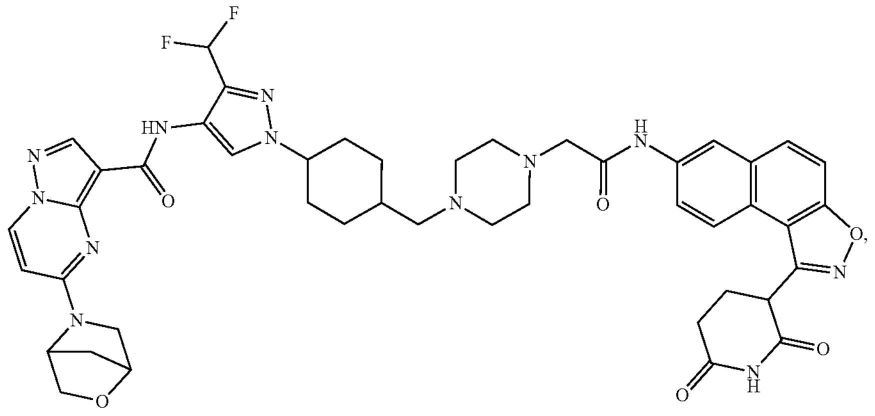
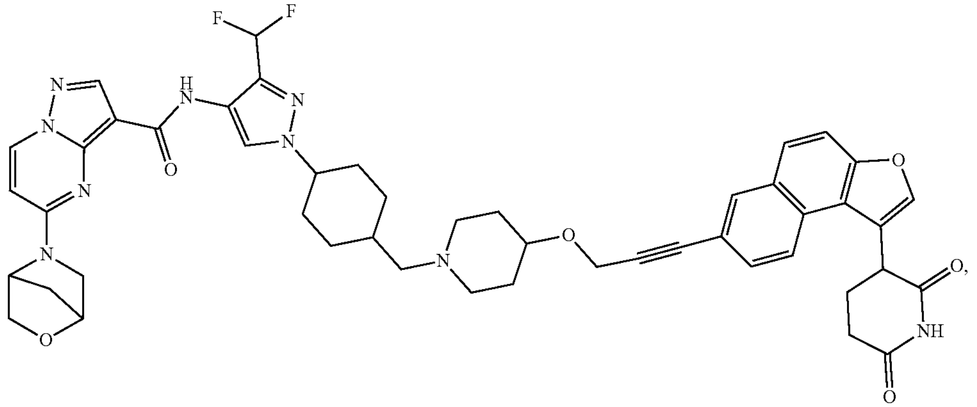
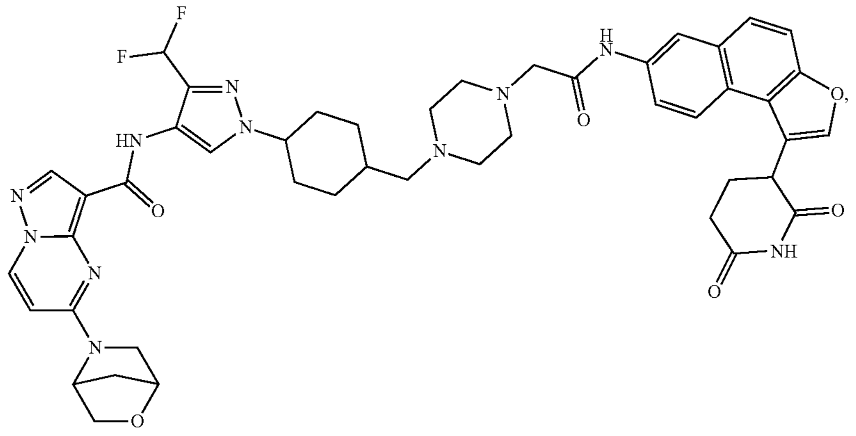
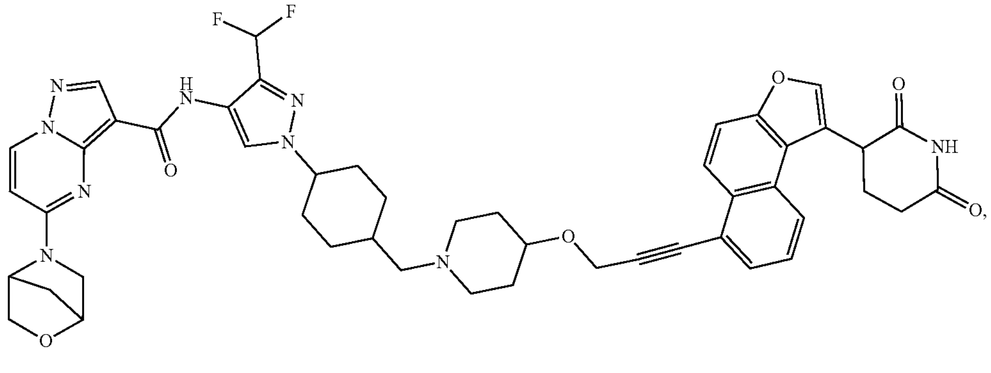

-continued
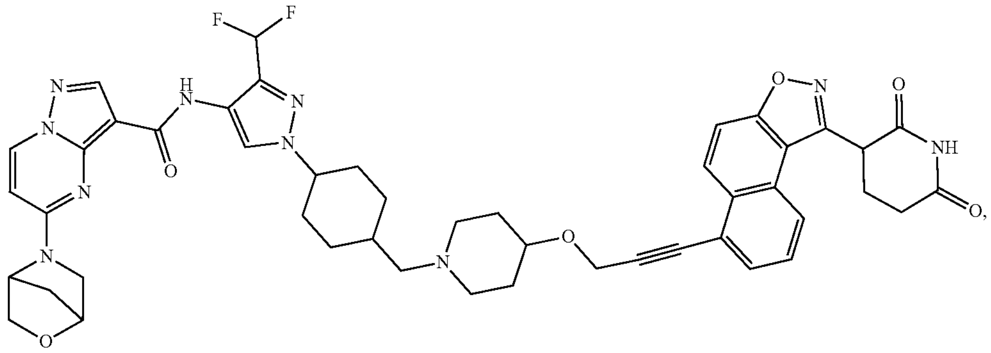
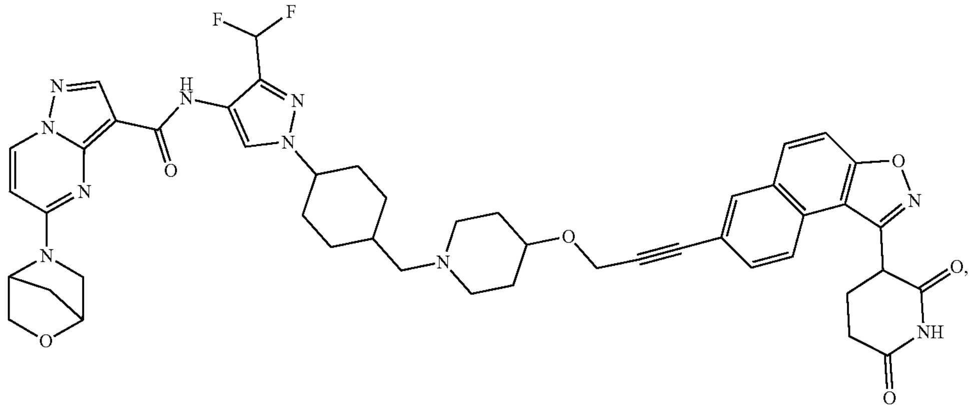
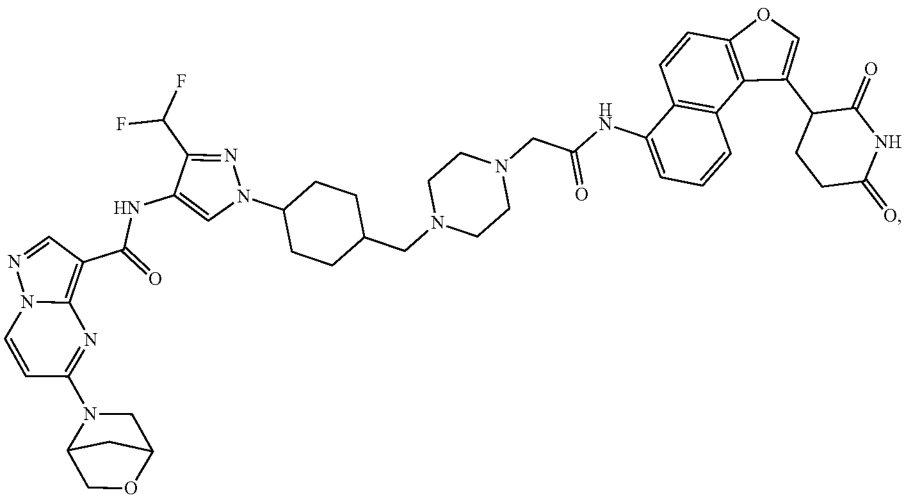

-continued
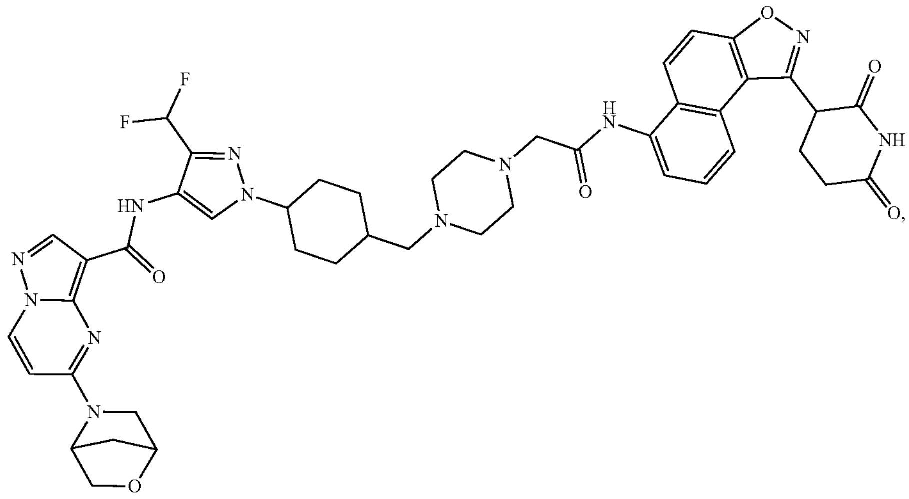
,
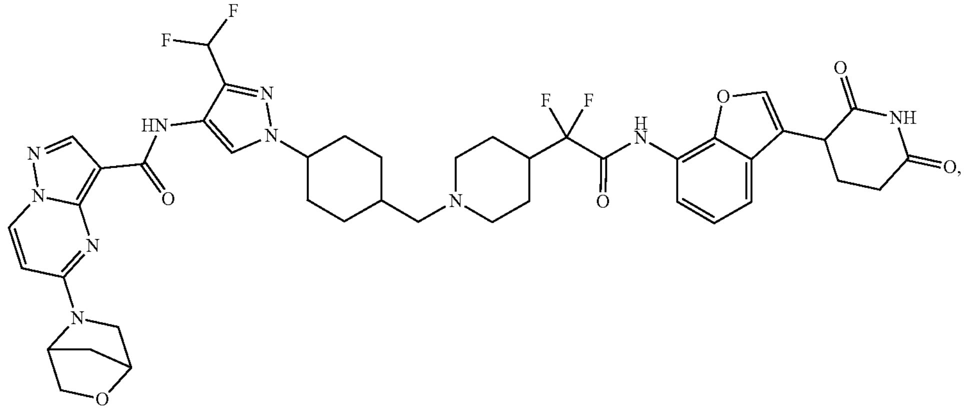
,
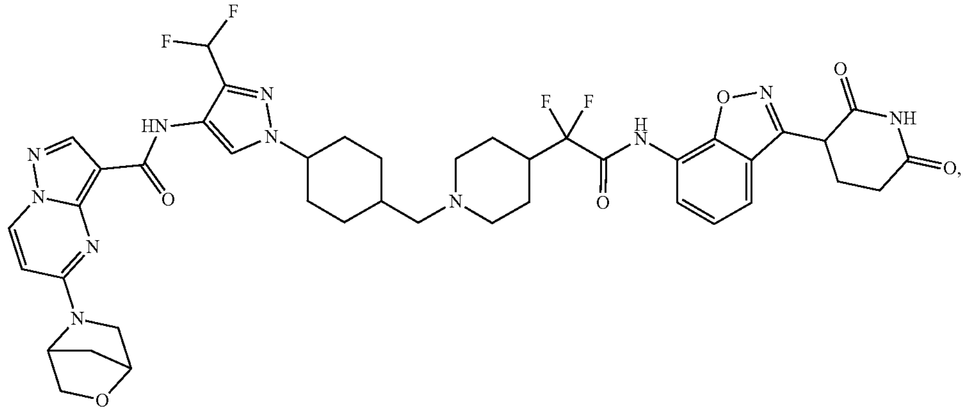
,

-continued
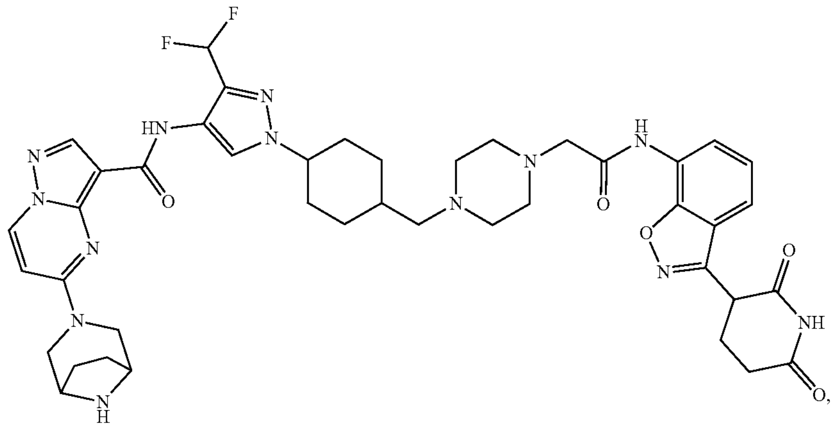
,
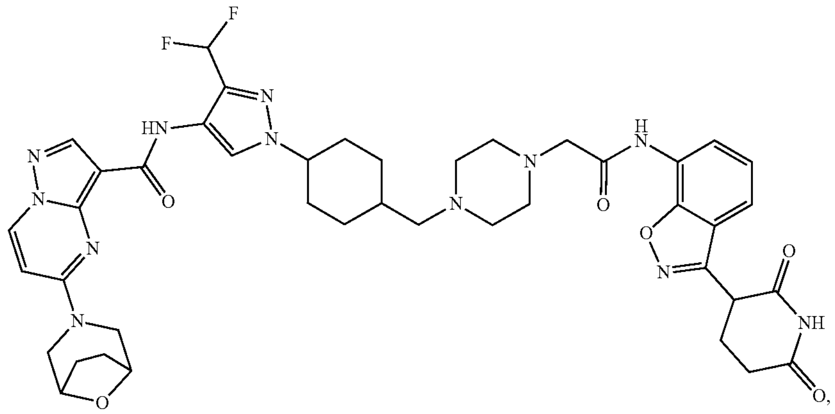
,
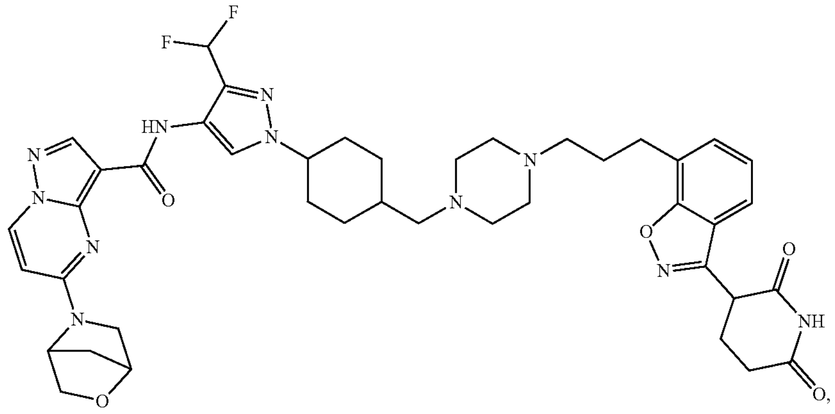
,
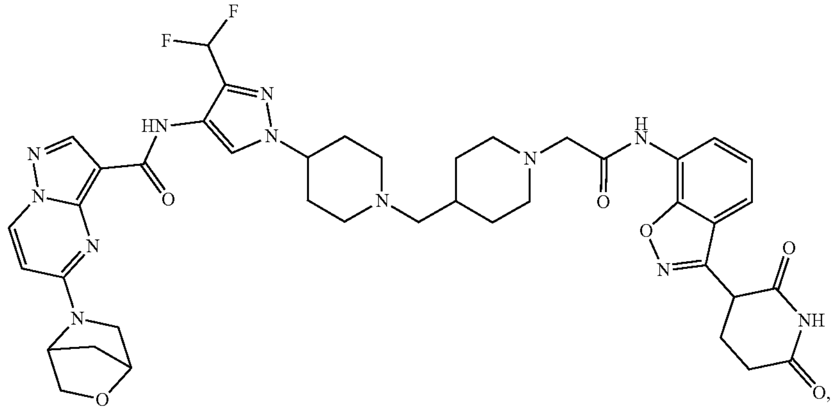
,

-continued
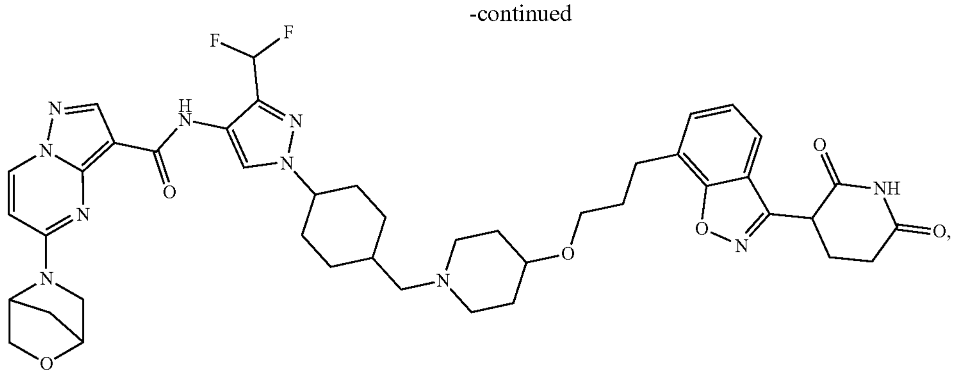
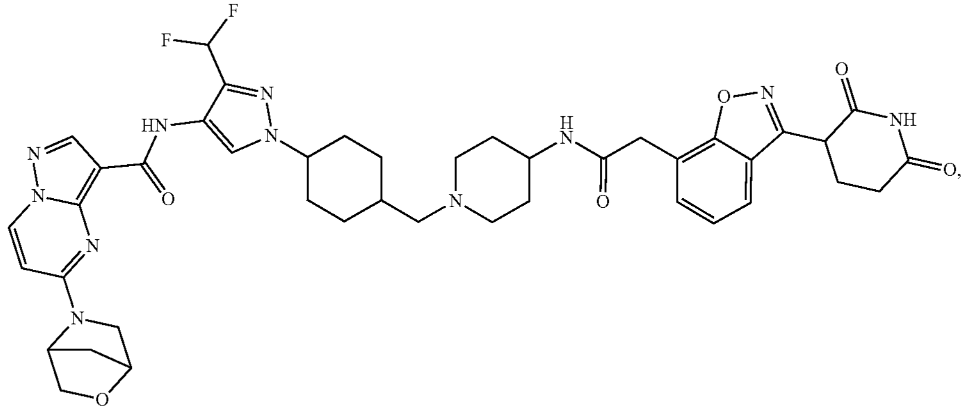
and
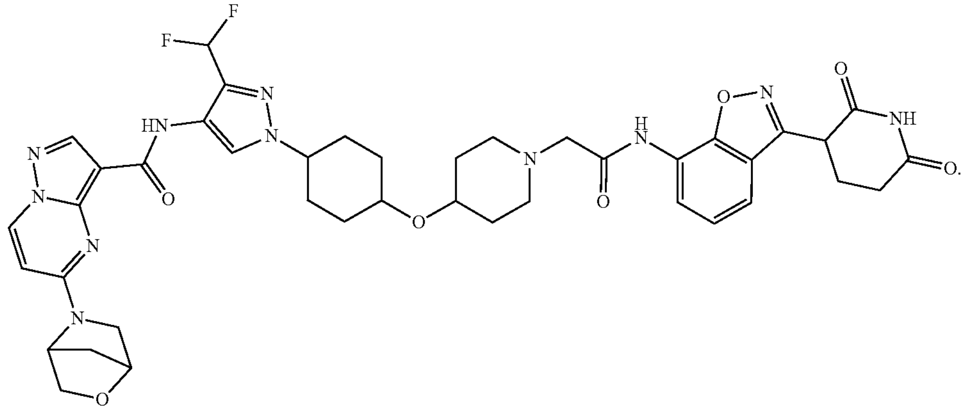
15. The compound or the pharmaceutically acceptable salt thereof according to claim 14, wherein the compound is selected from:

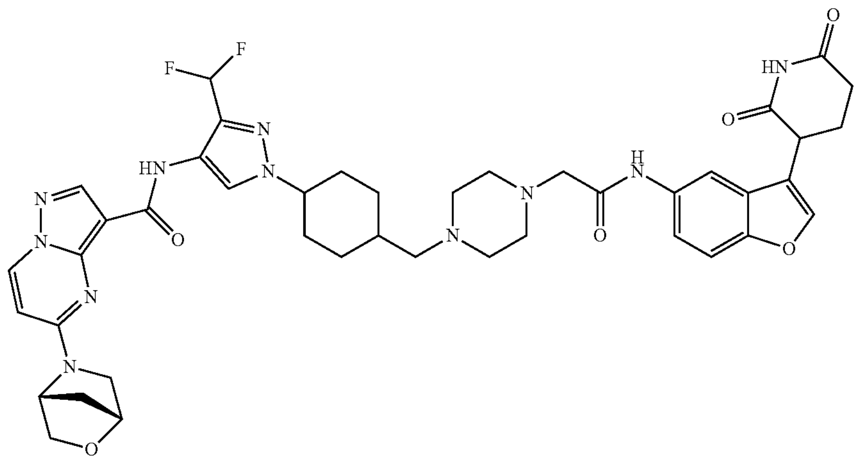
,
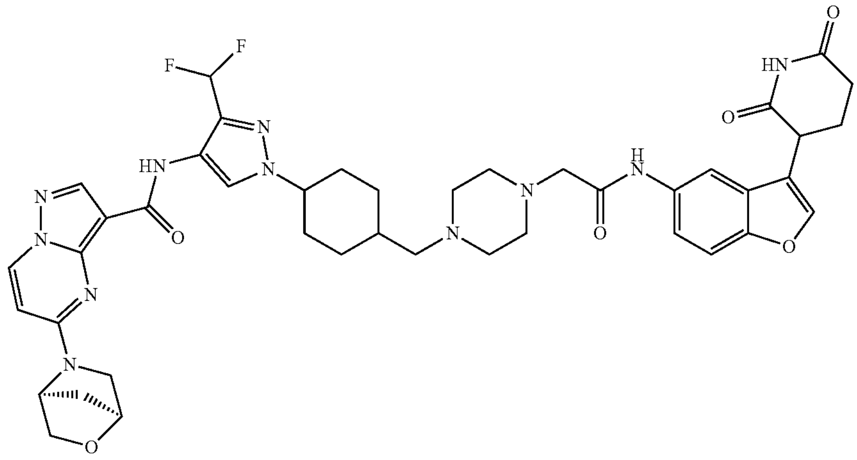
,
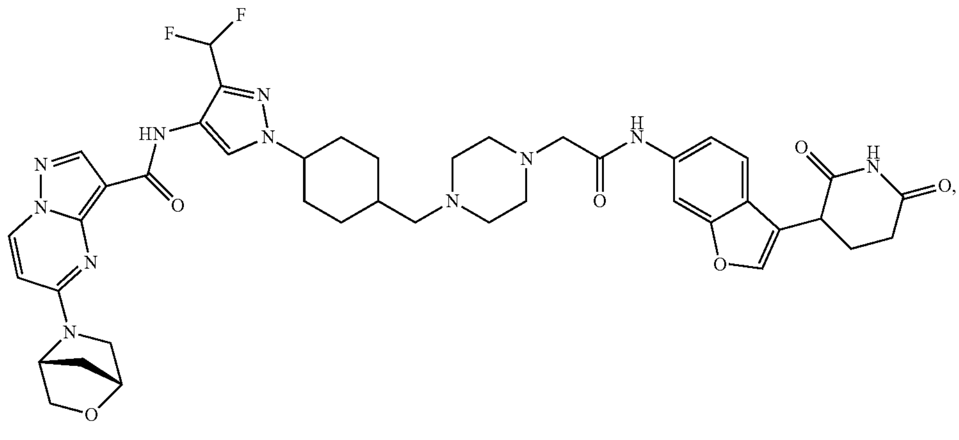
,

-continued
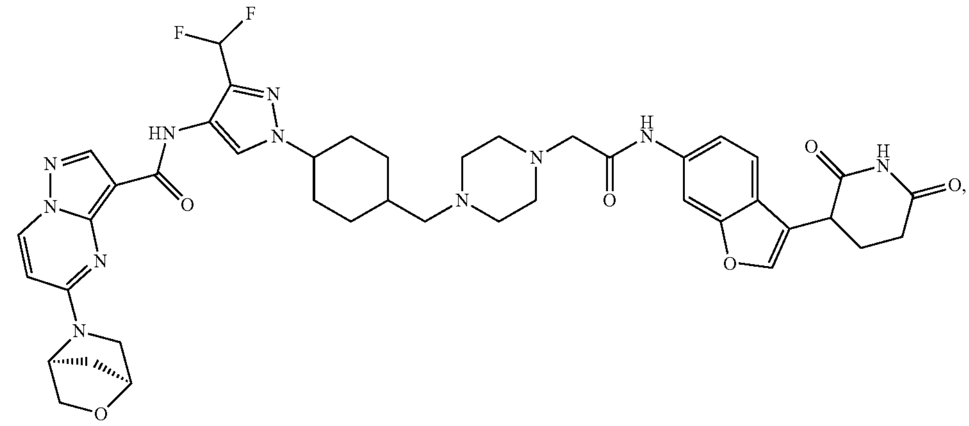
,
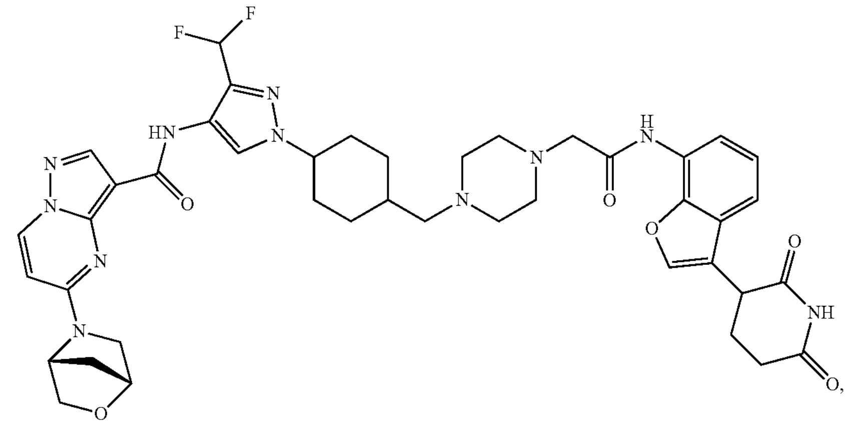
,
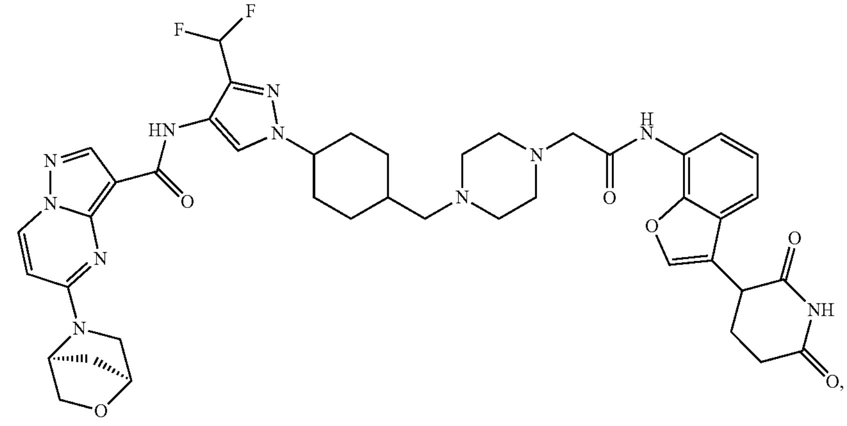
,
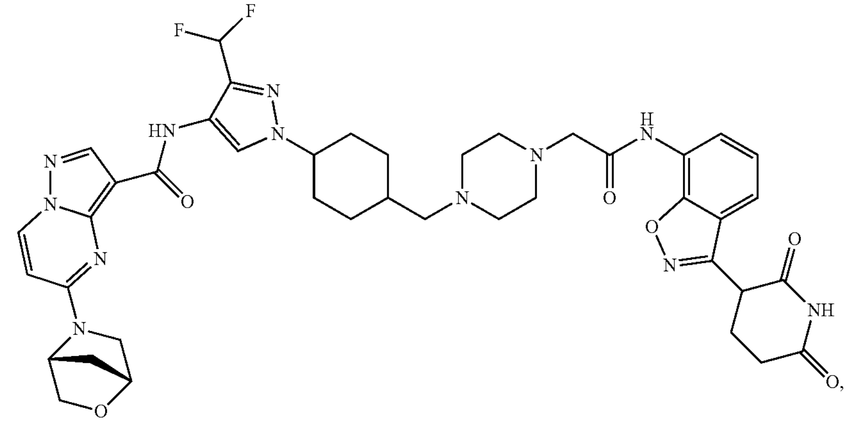
,

-continued
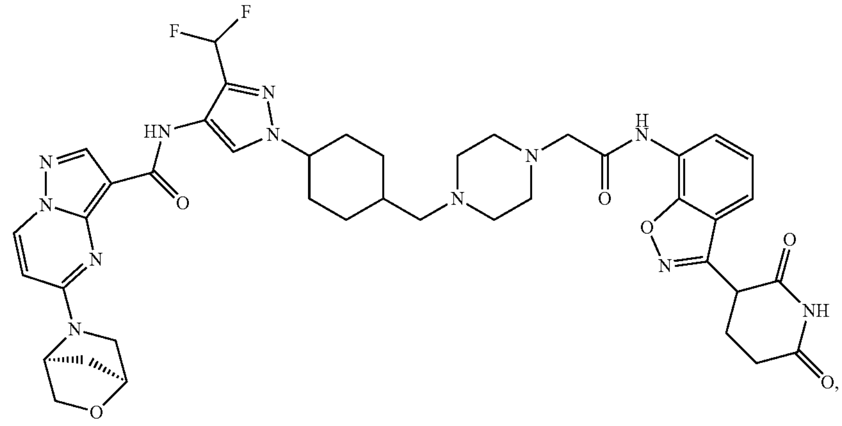
,
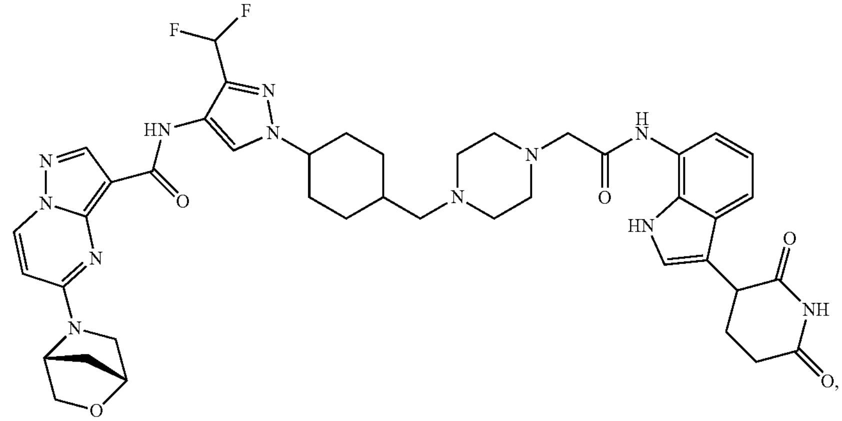
,
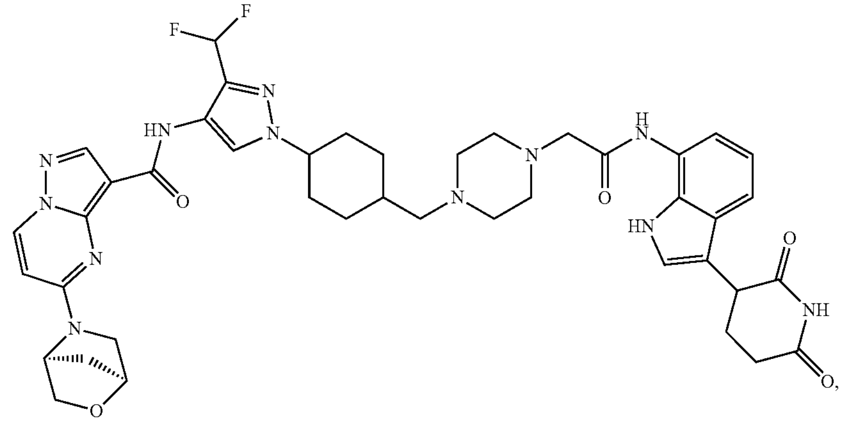
,
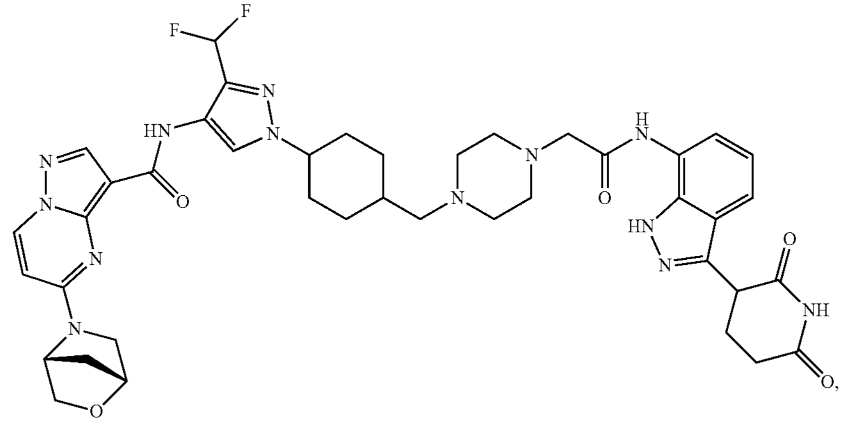
,

-continued
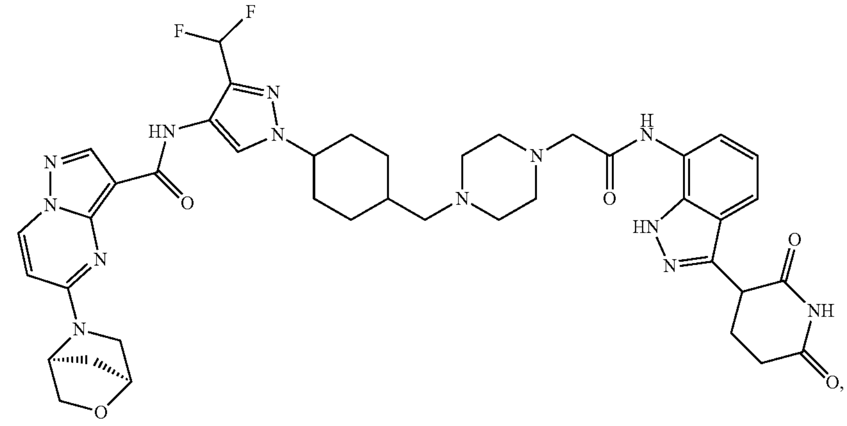
,
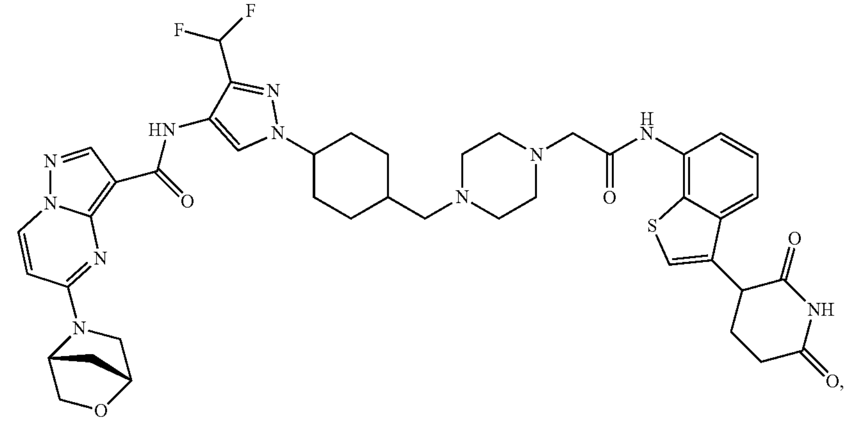
,
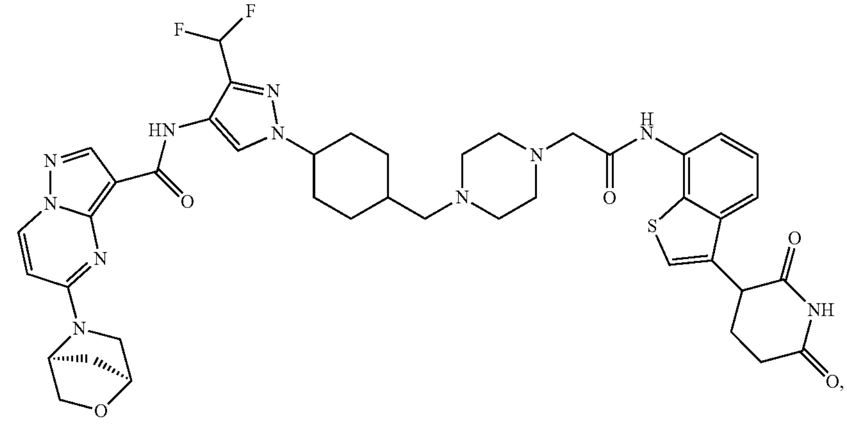
,
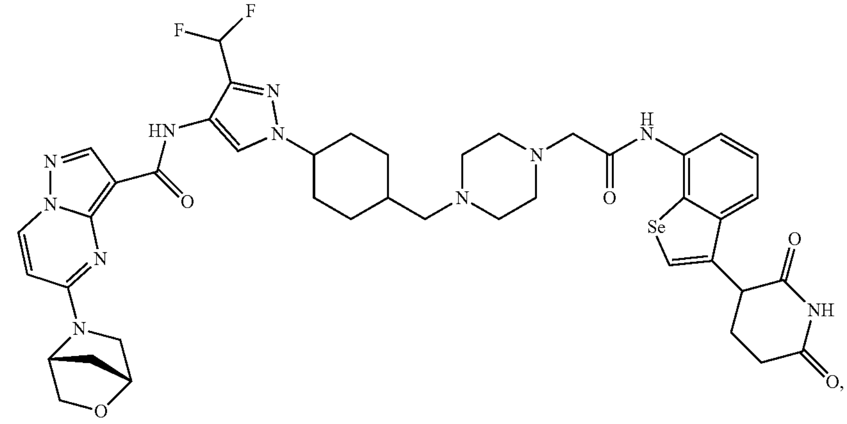
,

-continued
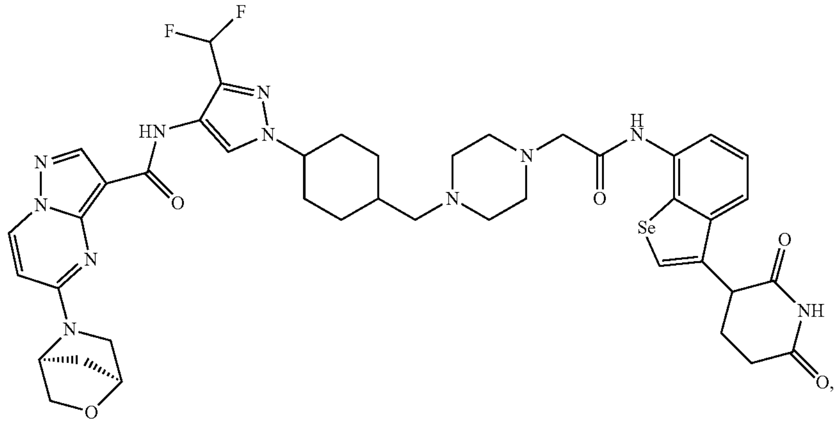
,
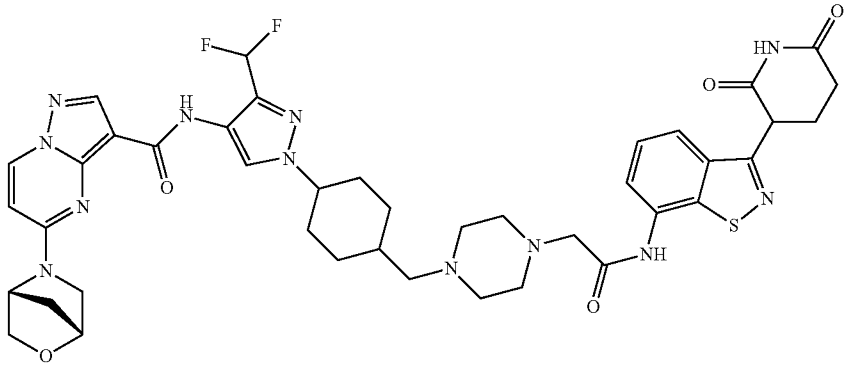
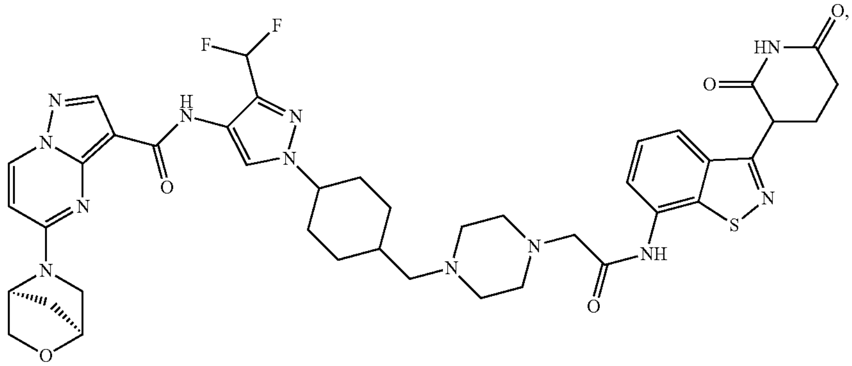
,
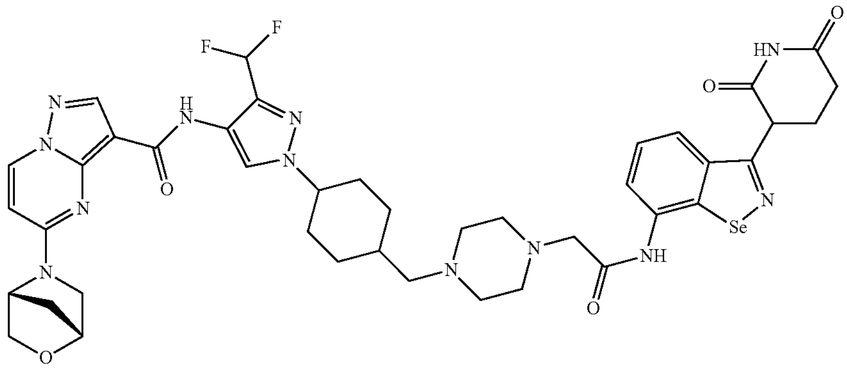

-continued
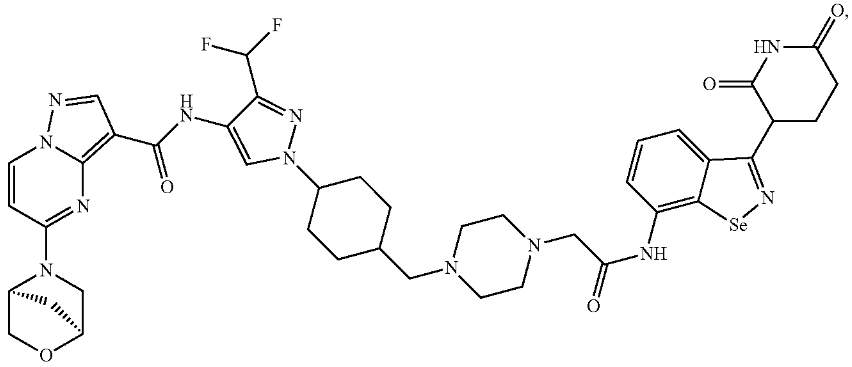
O,
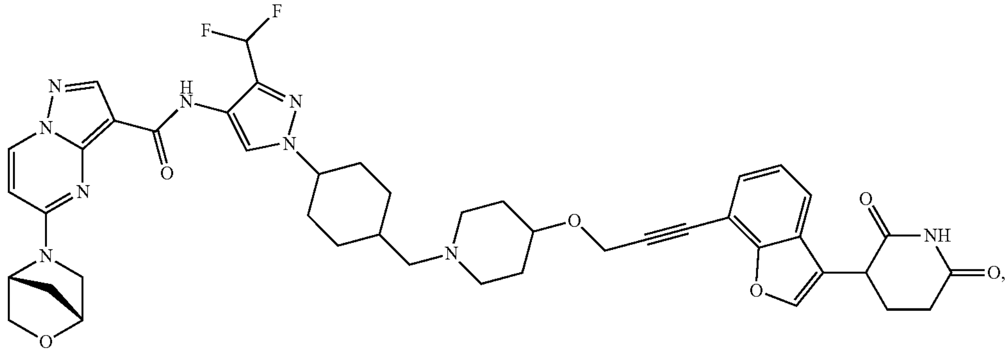
O,
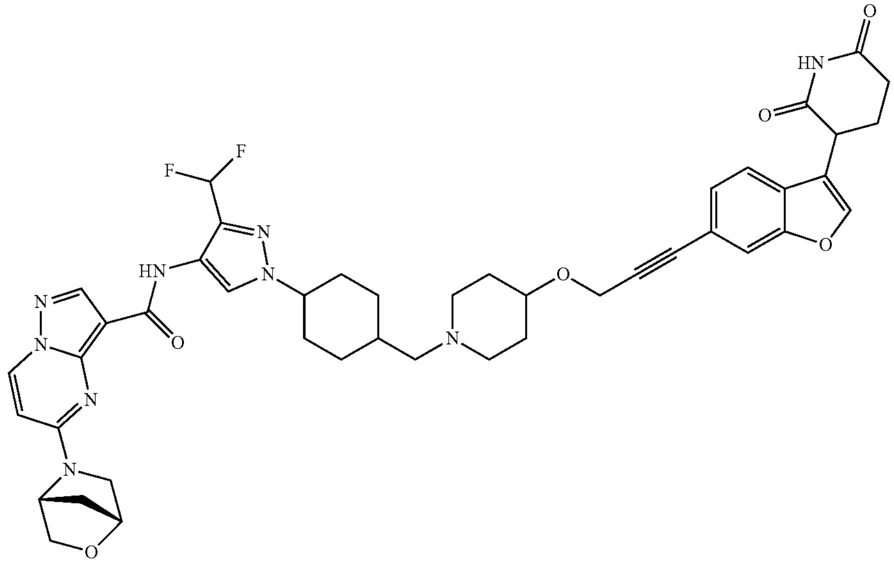
,
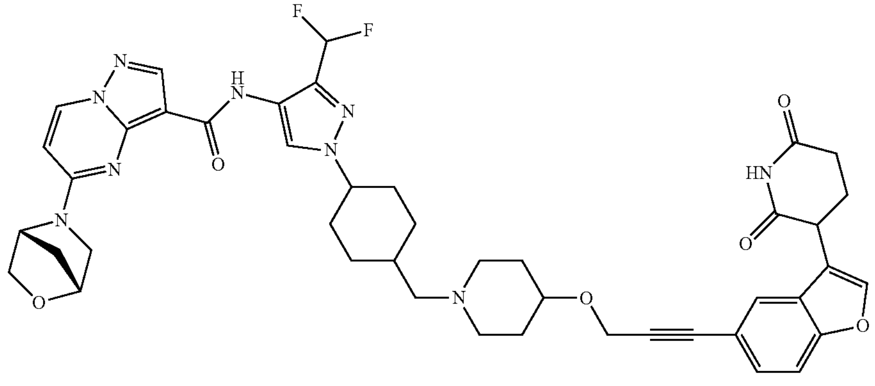
,

-continued
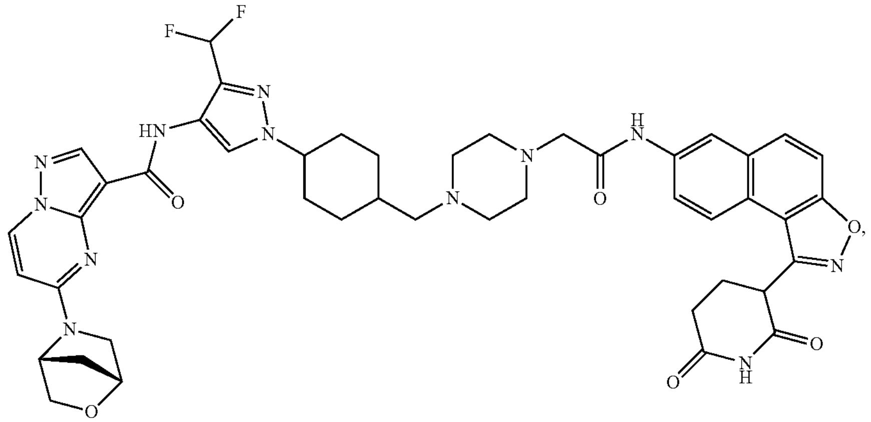
,
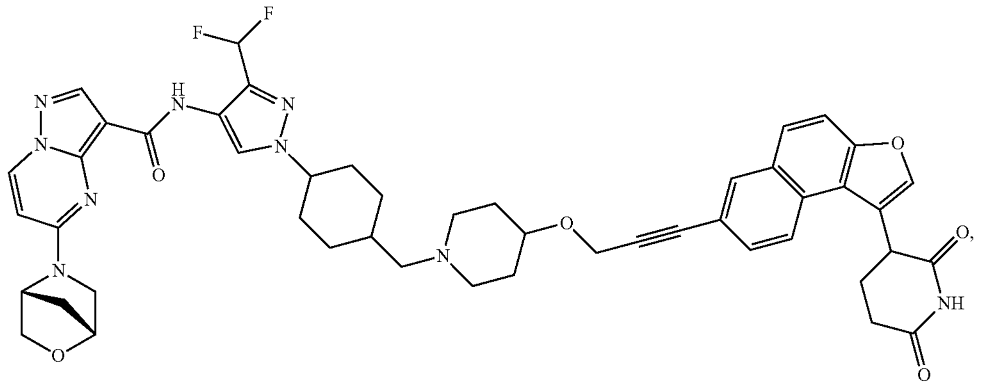
,
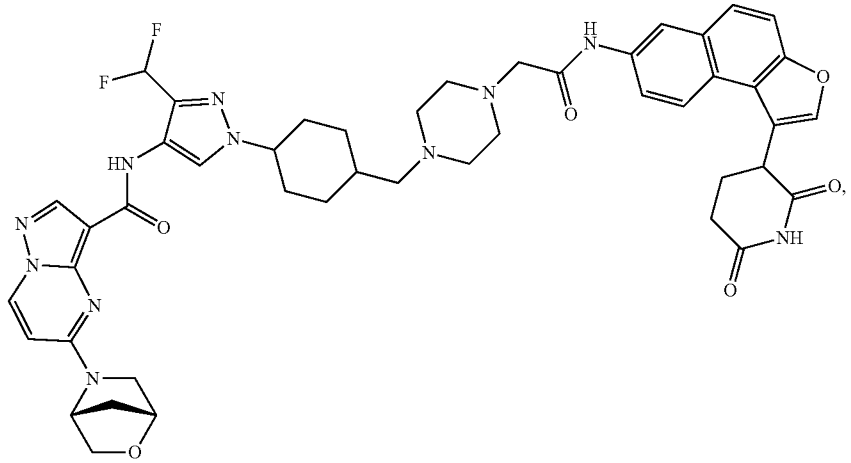
,
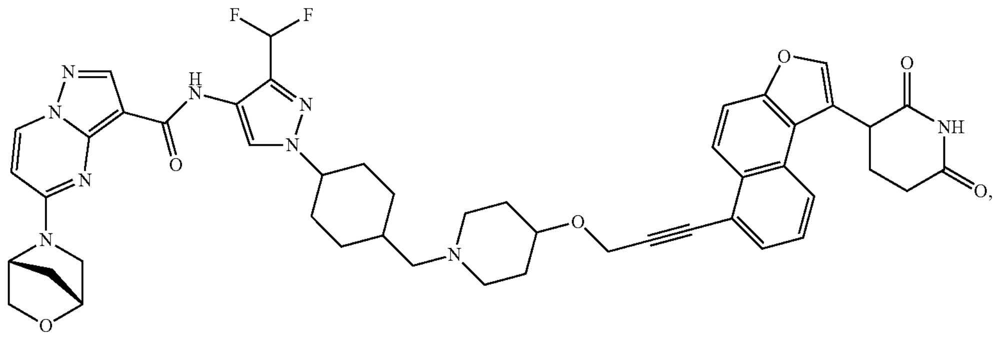
,

-continued
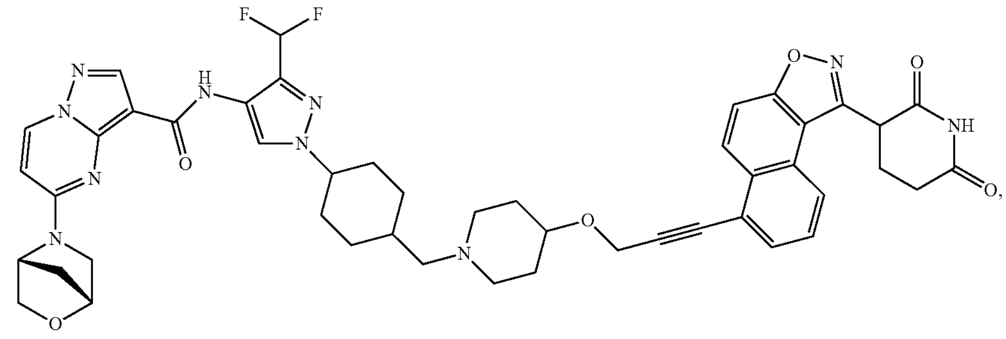
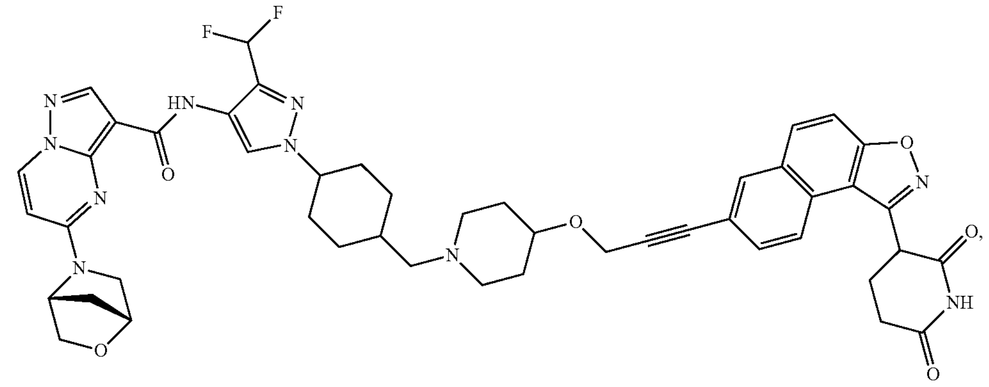
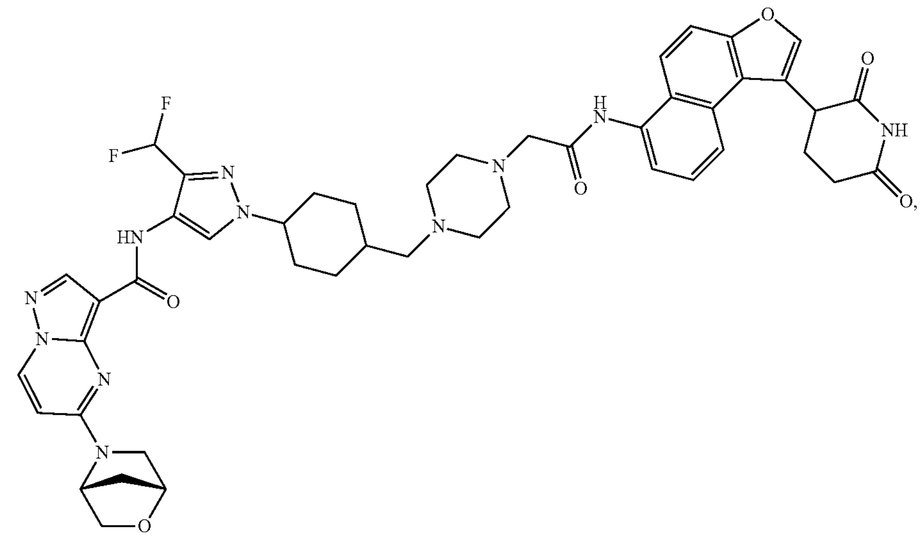

-continued
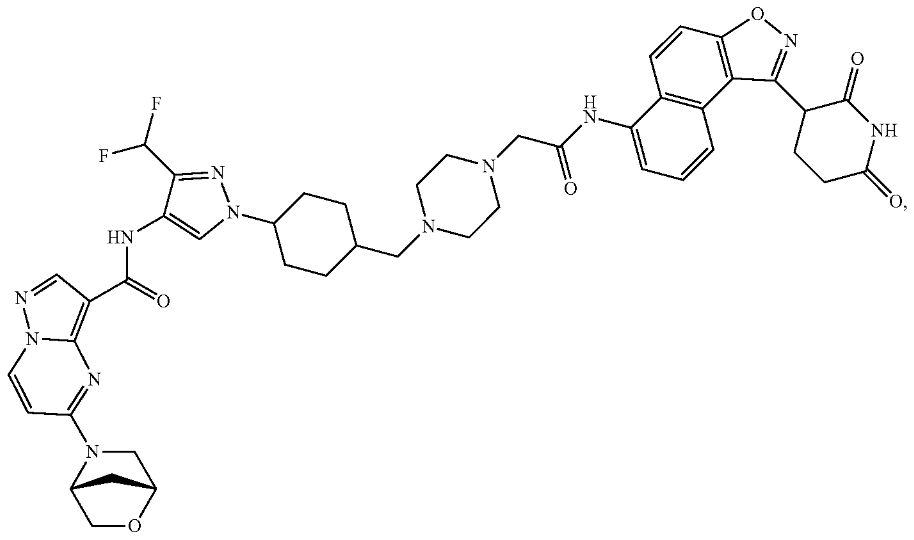
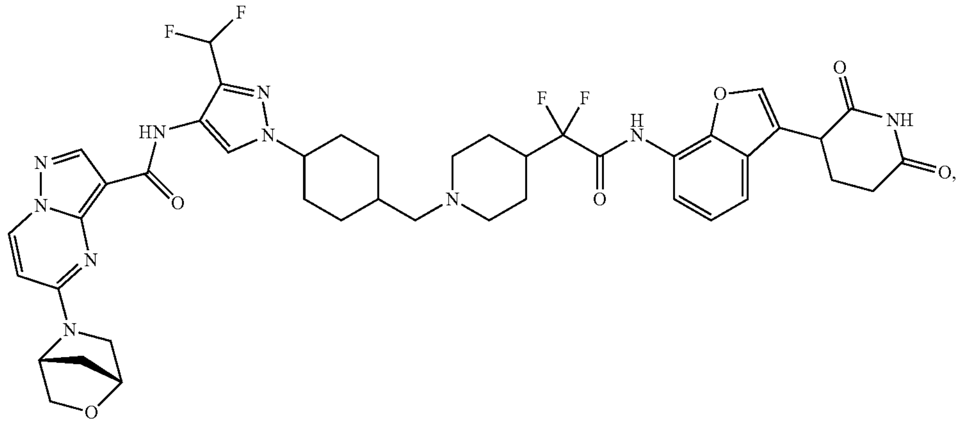
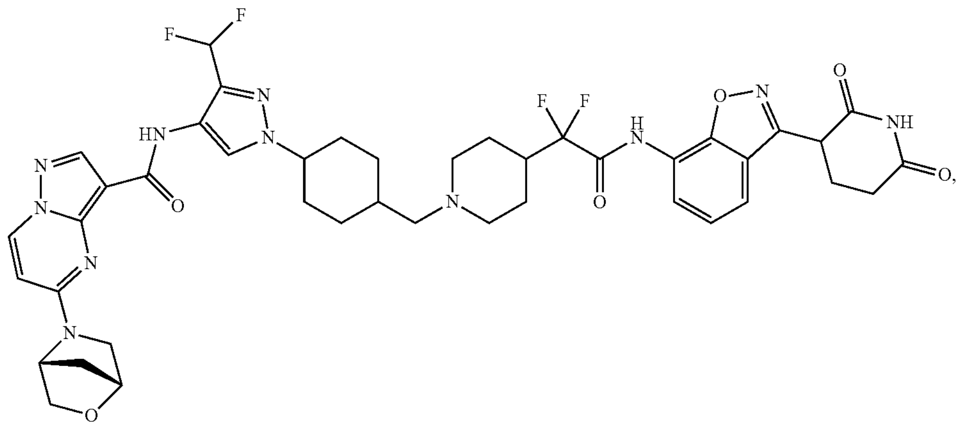

-continued
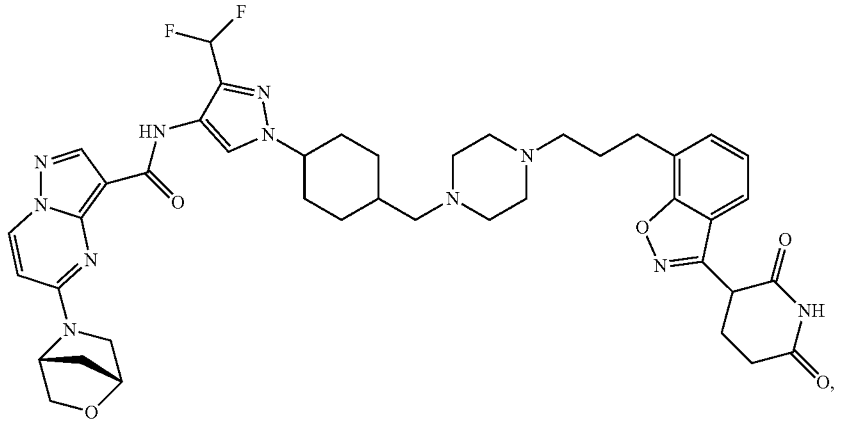
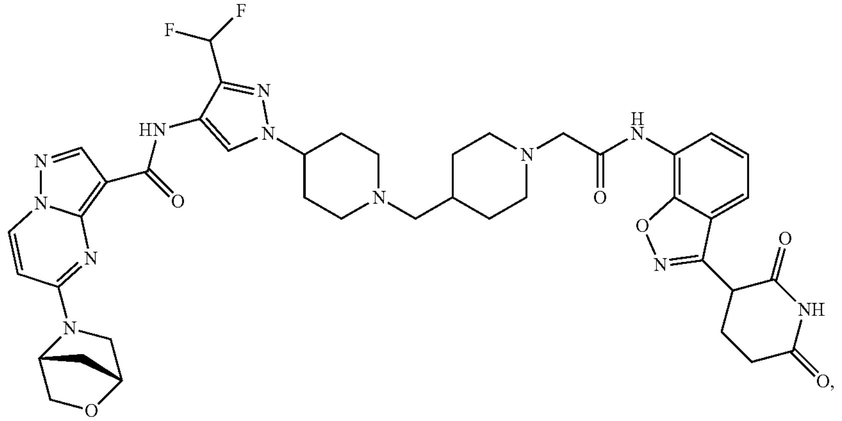
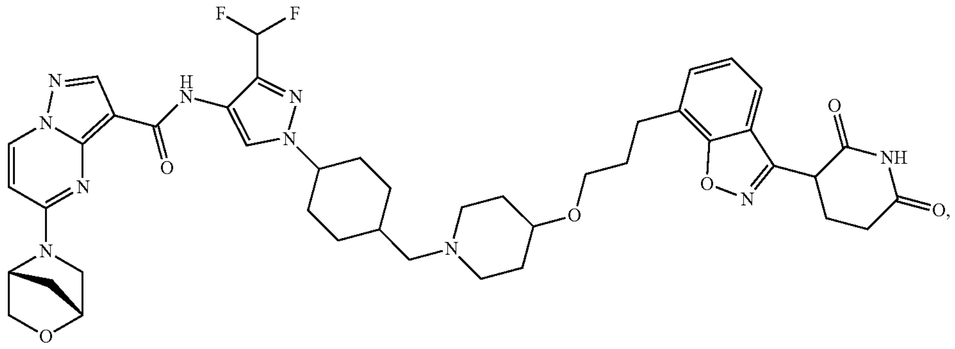
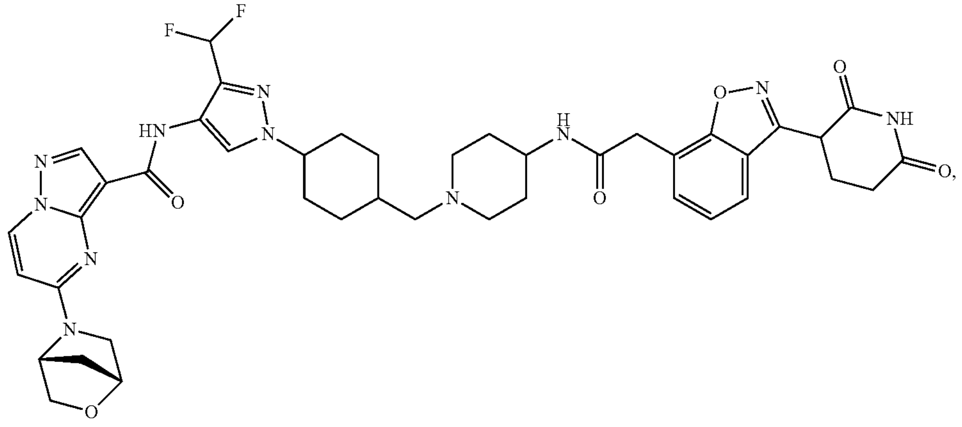
and

-continued
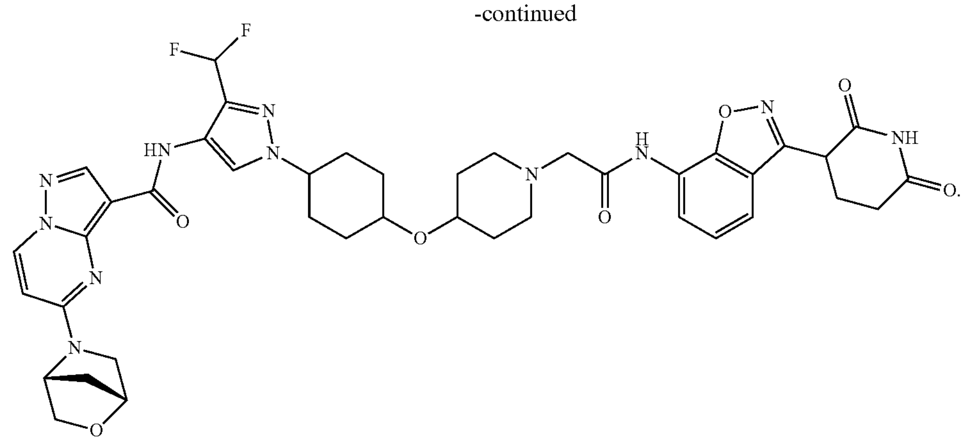
16. The compound or the pharmaceutically acceptable salt thereof according to claim 14, wherein the compound is selected from:
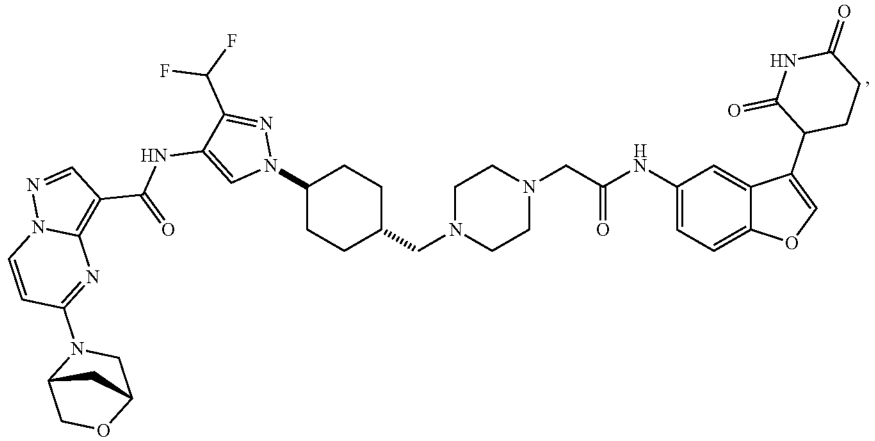
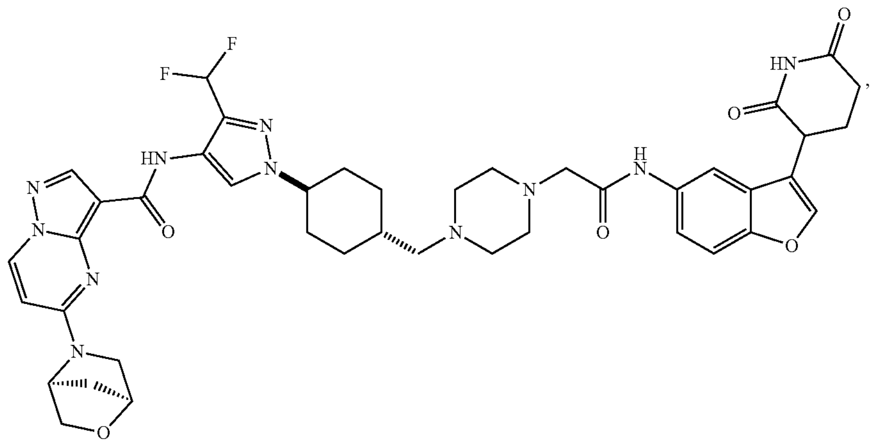

-continued
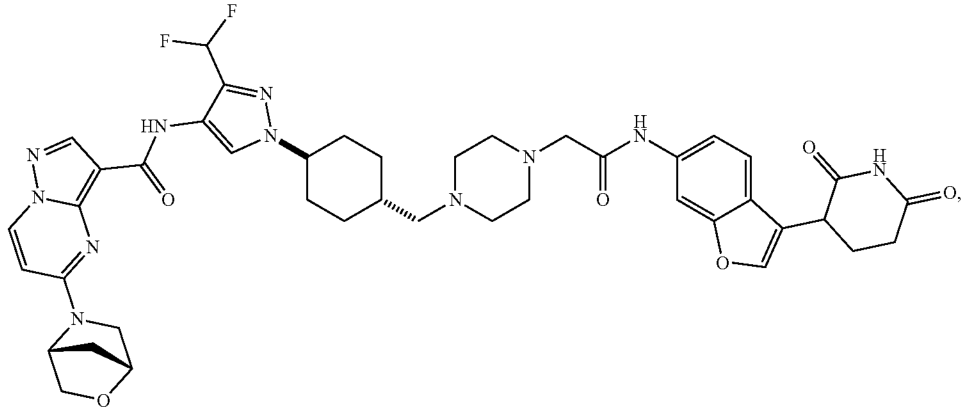
,
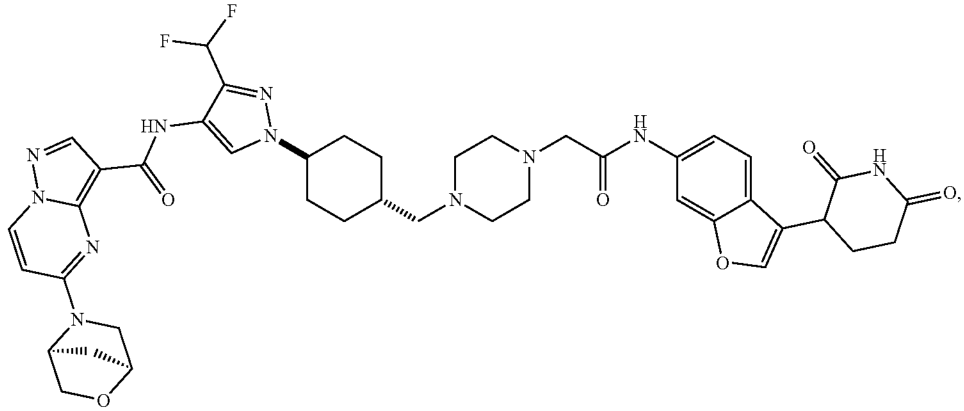
,
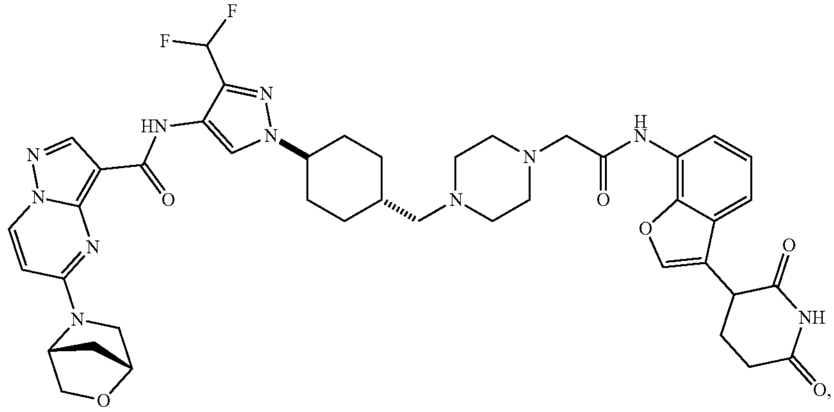
,
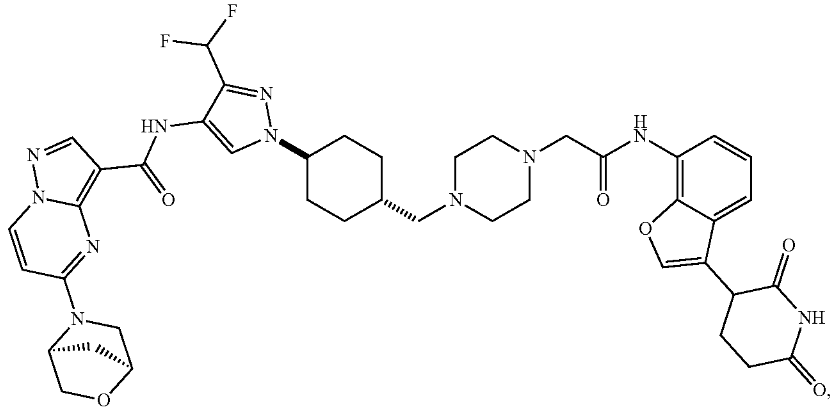
,

-continued
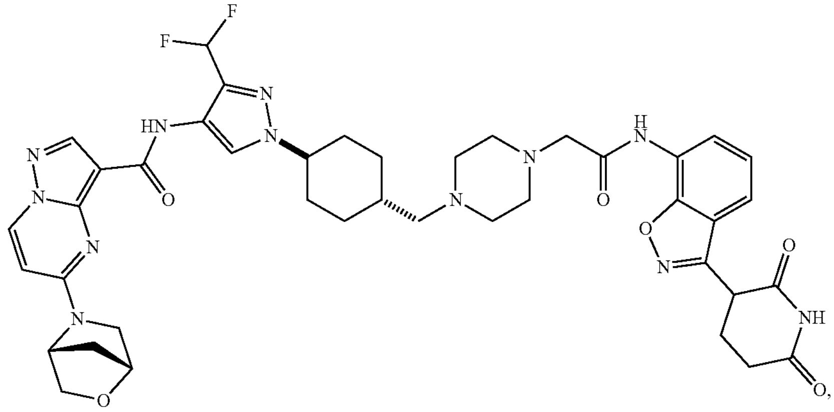
,
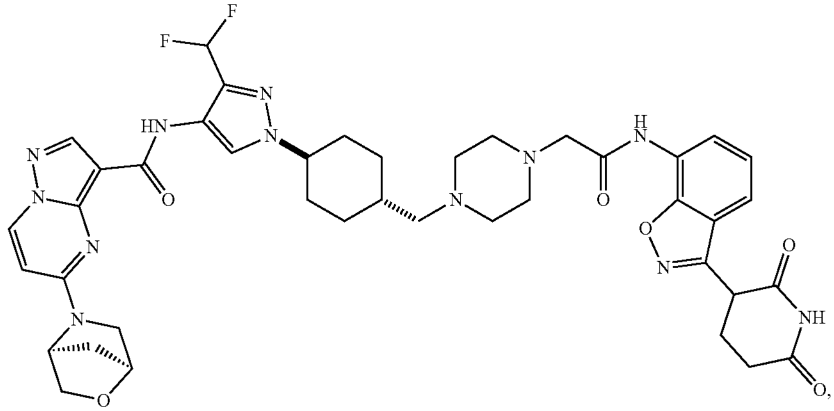
,
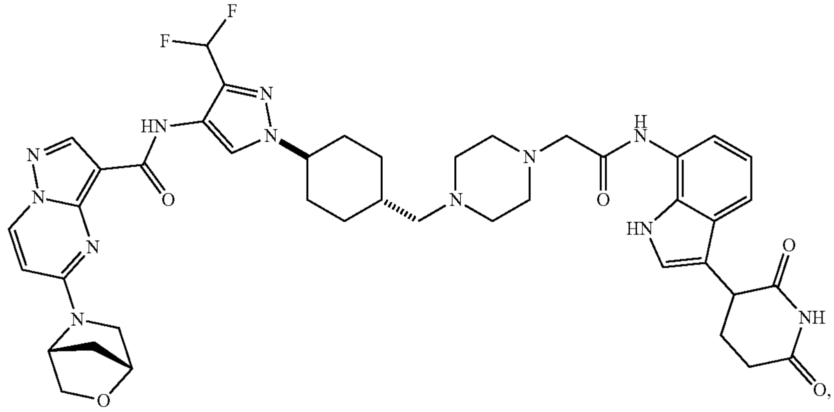
,
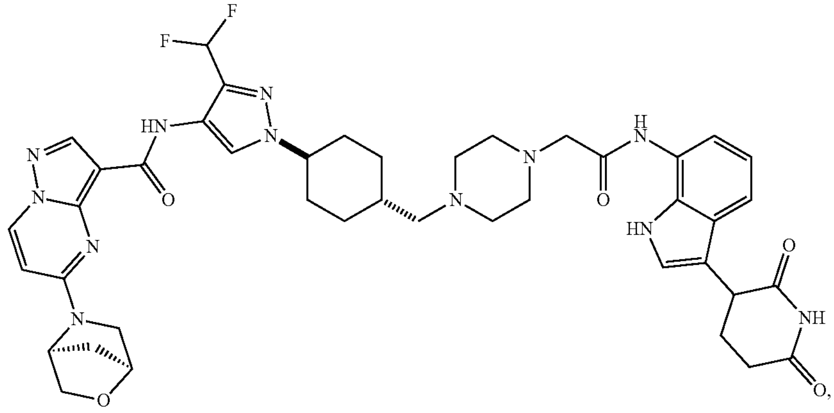
,

-continued
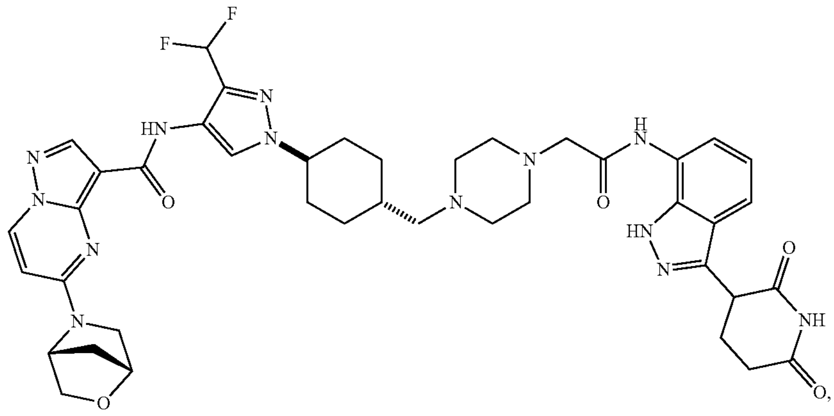
,
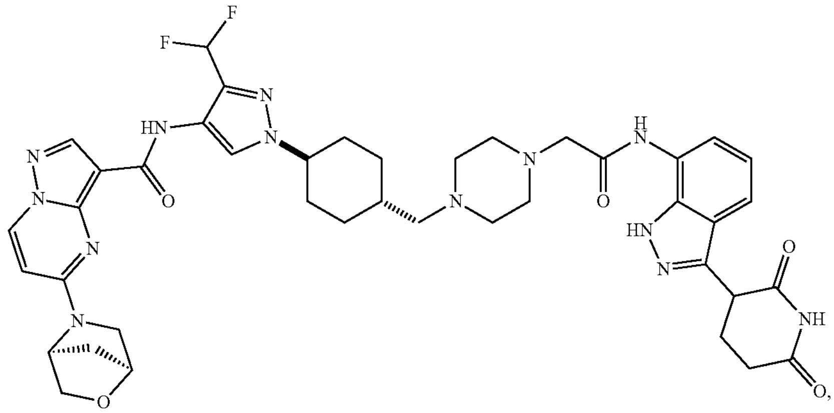
,
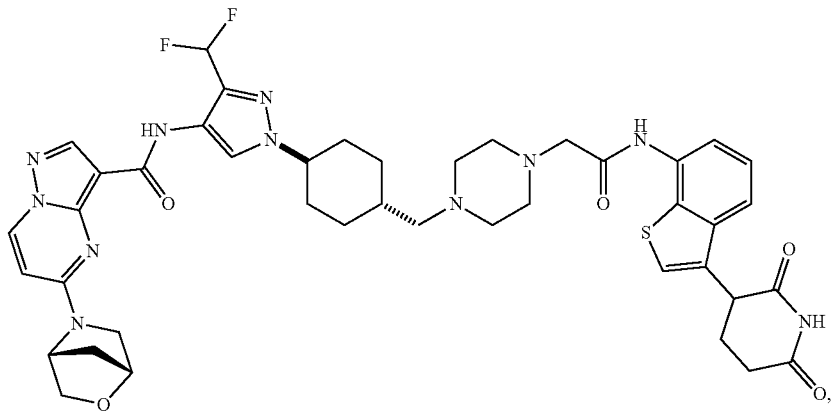
,
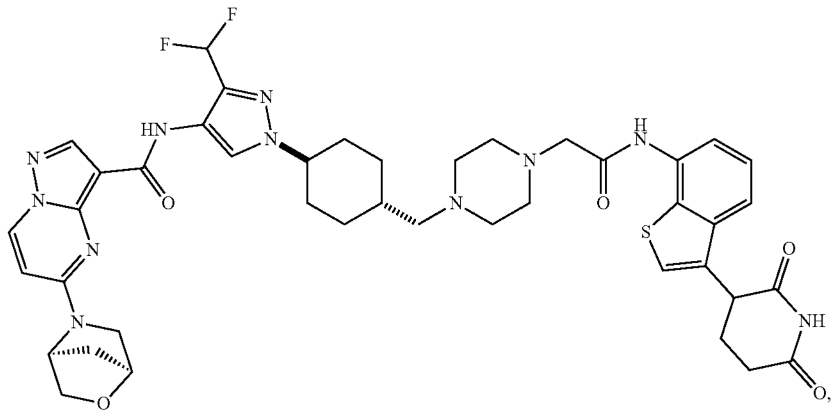
,

-continued
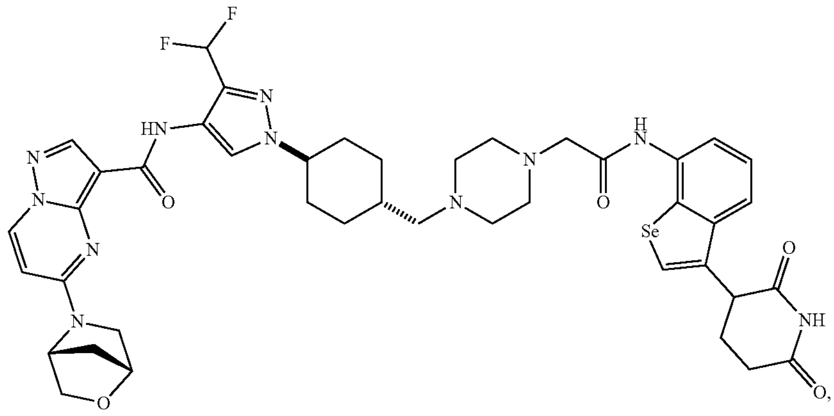
,
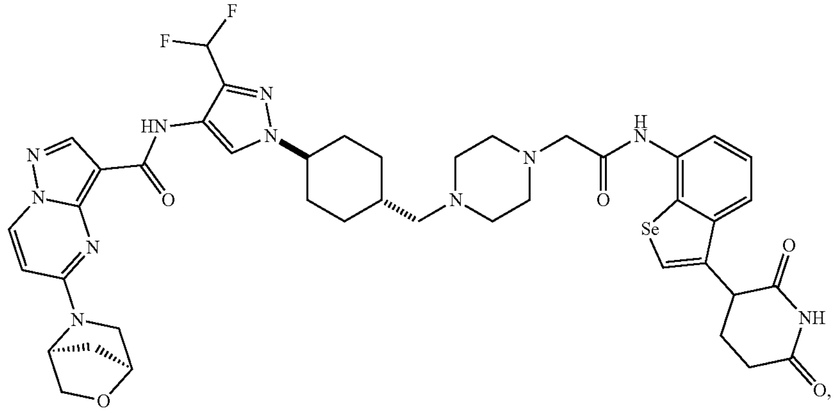
,
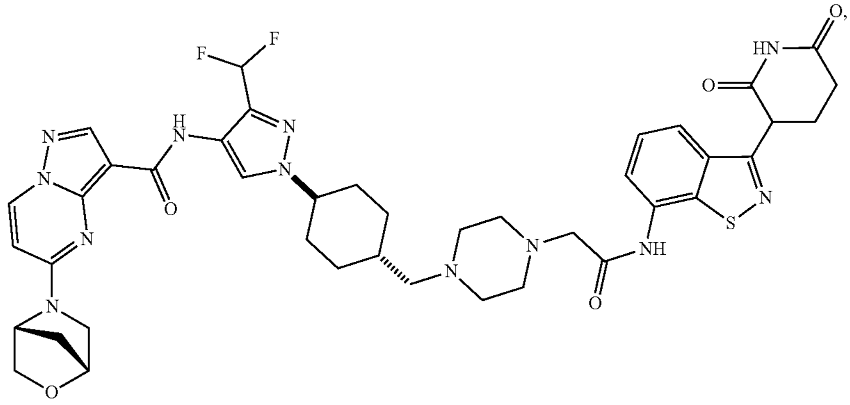
,
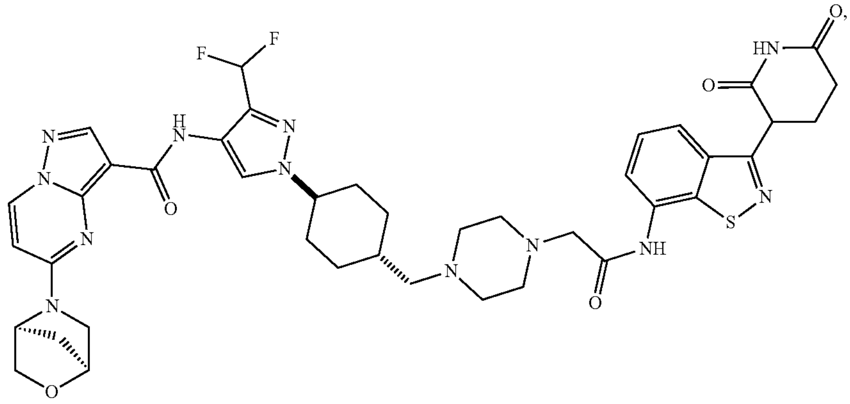
,

-continued
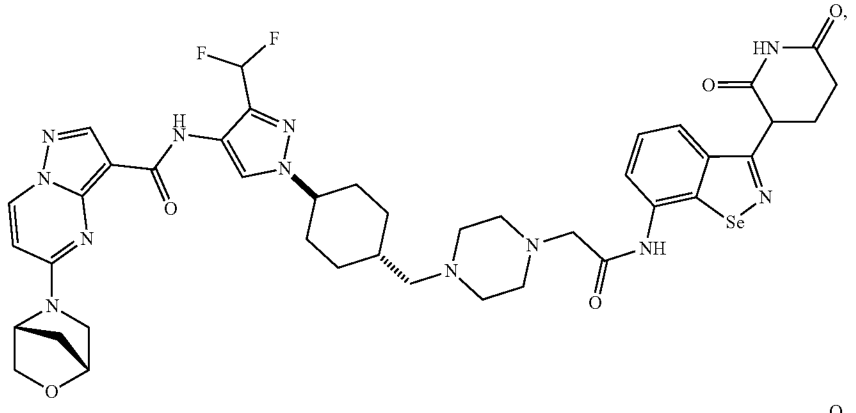
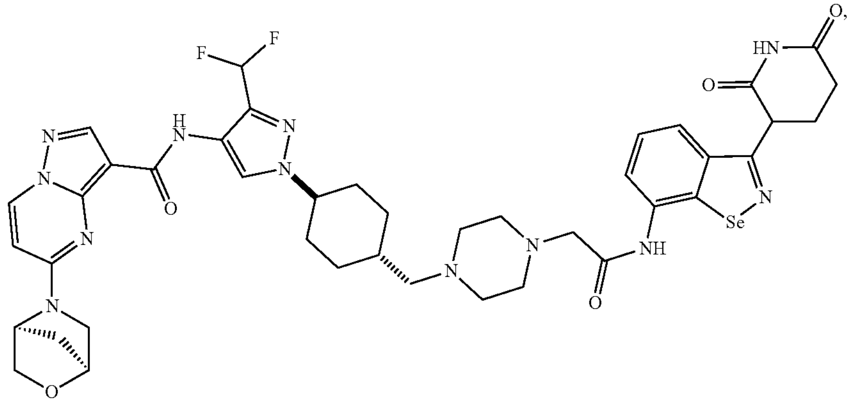
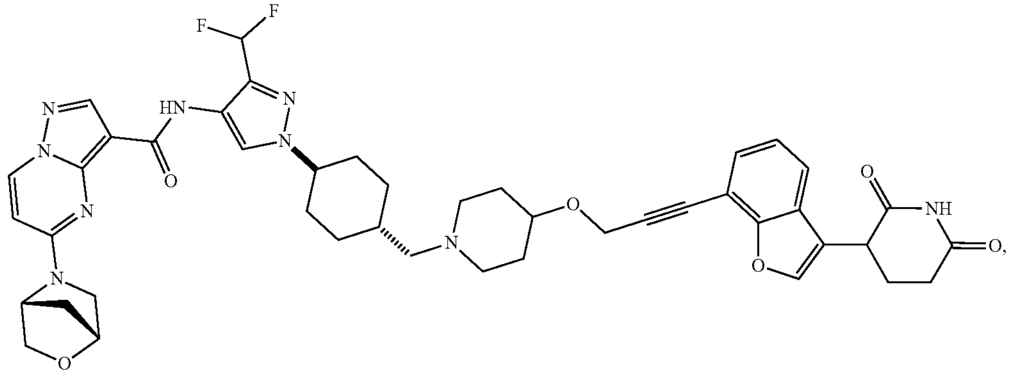
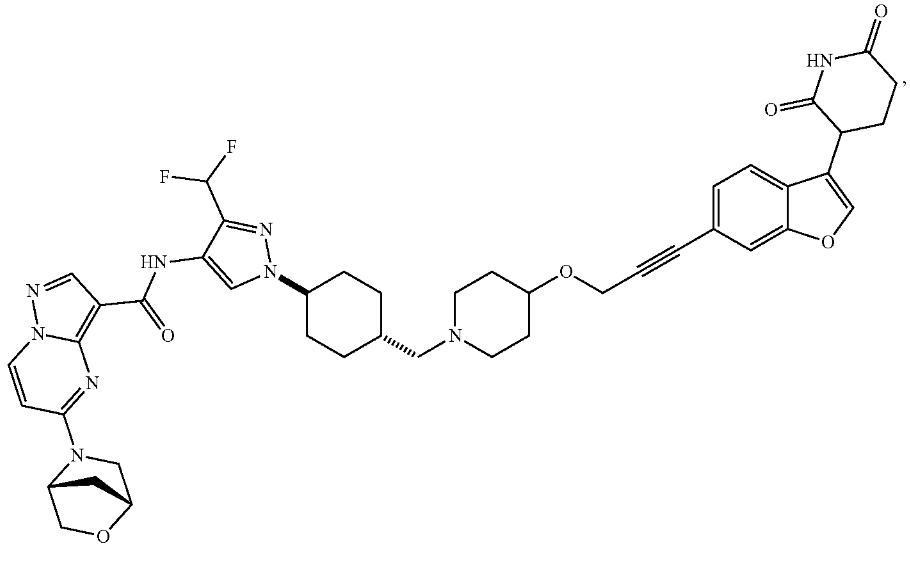

-continued
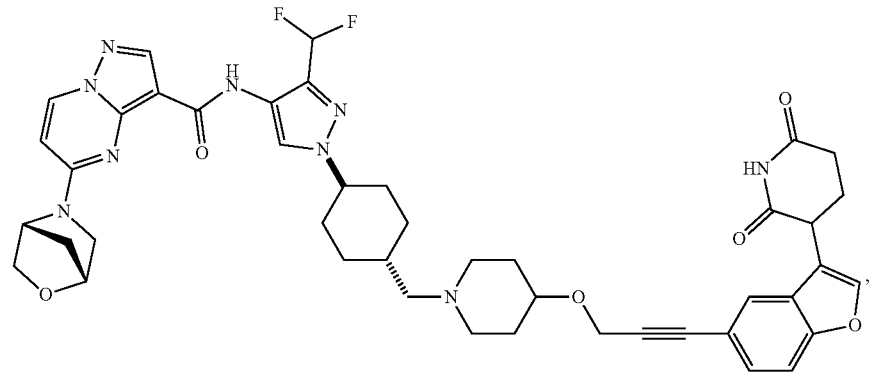
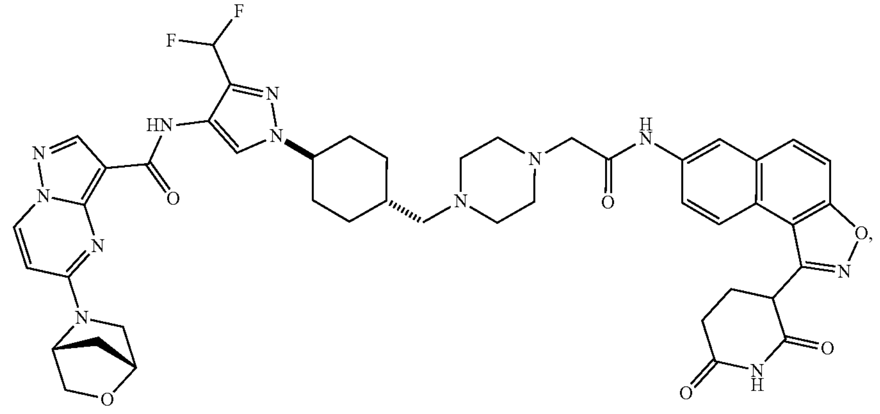
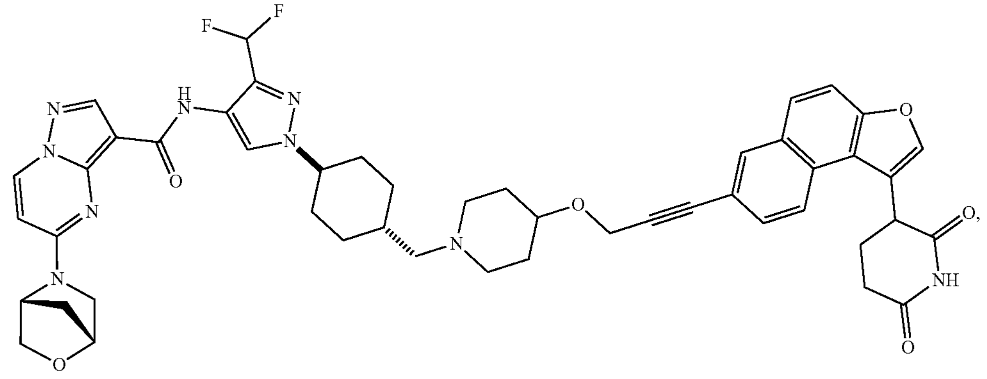
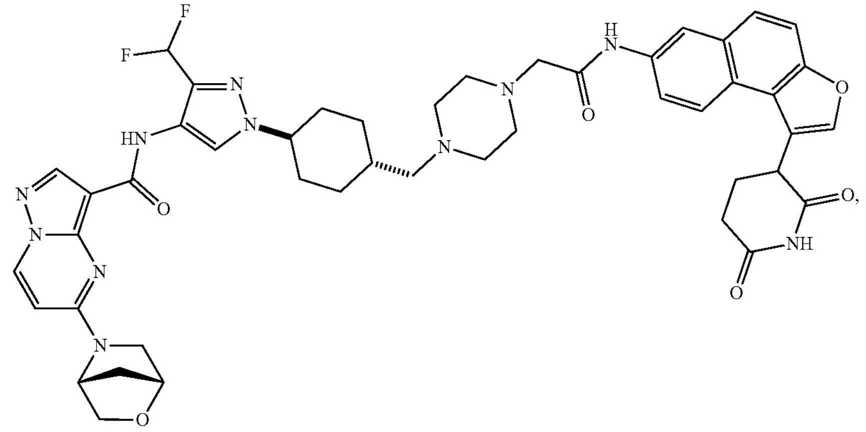

-continued
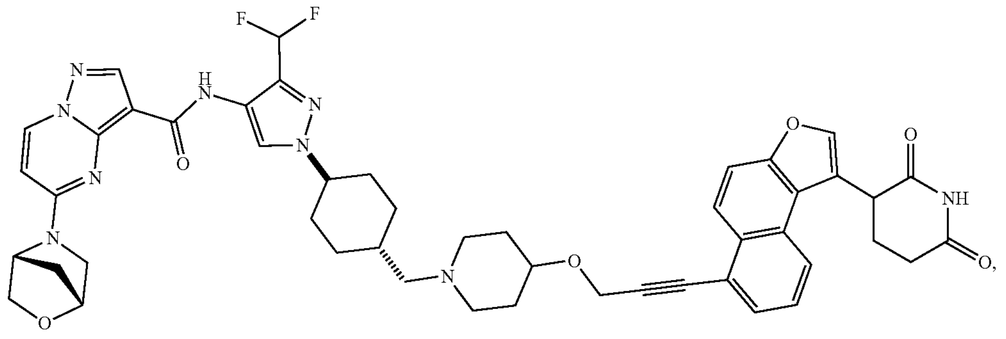
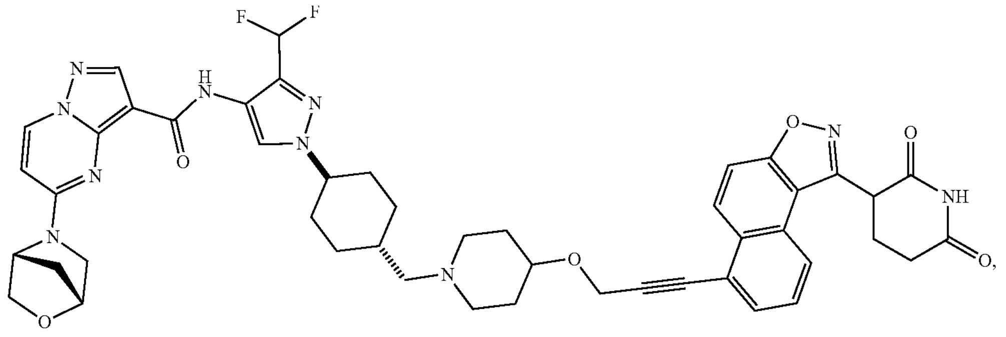
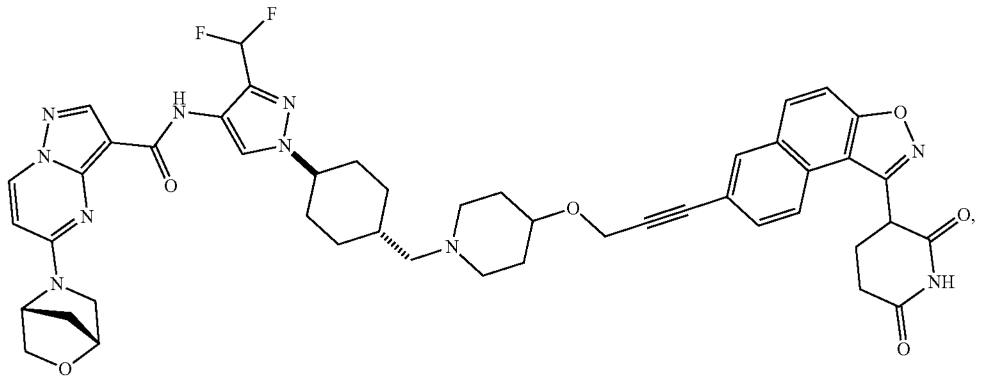
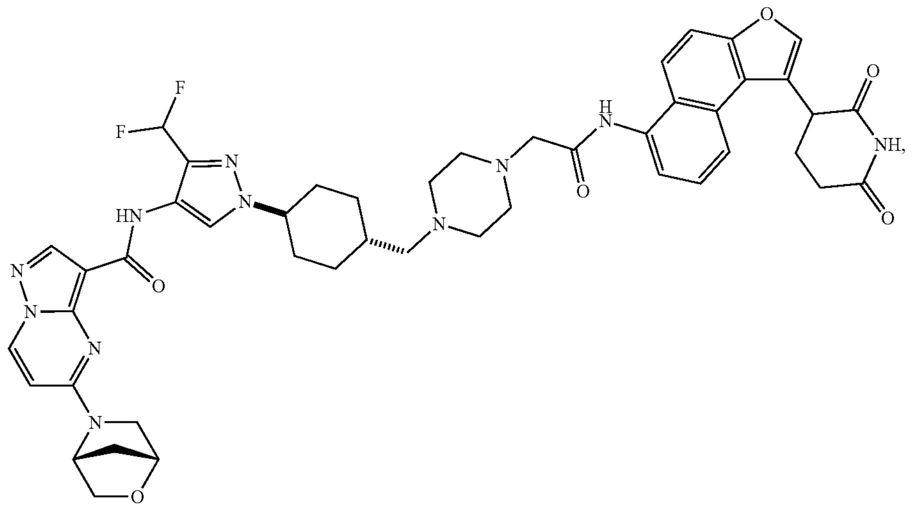

-continued
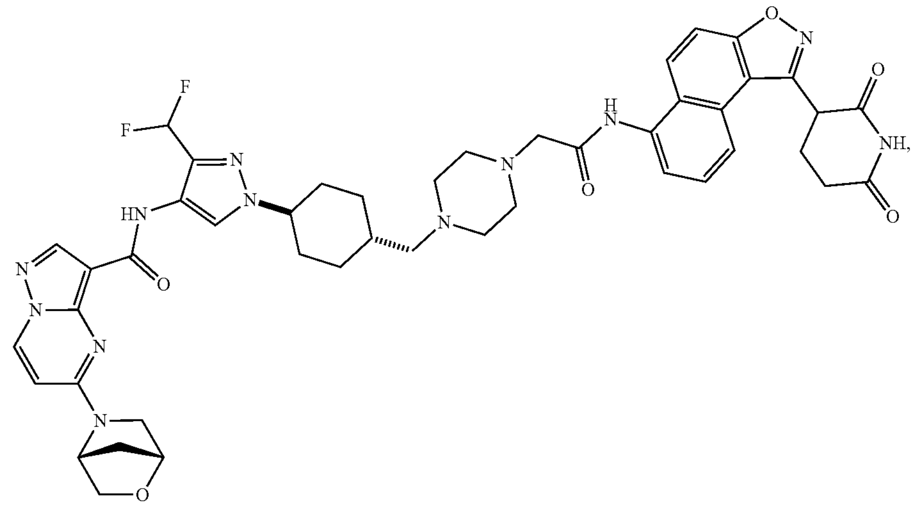
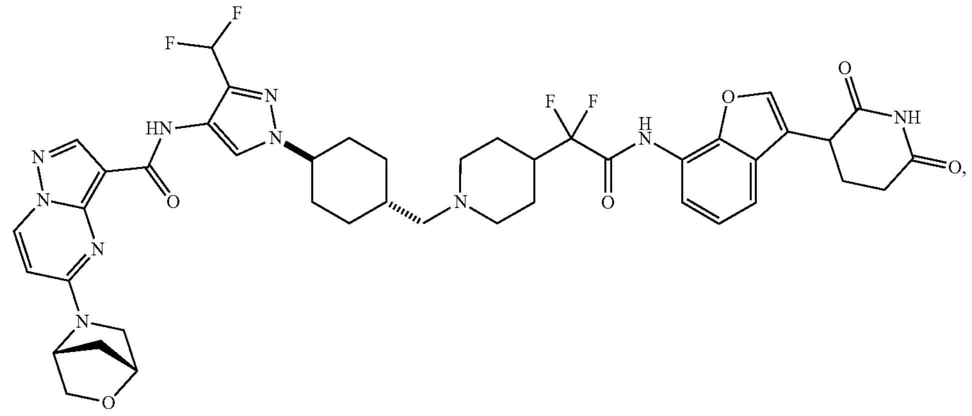
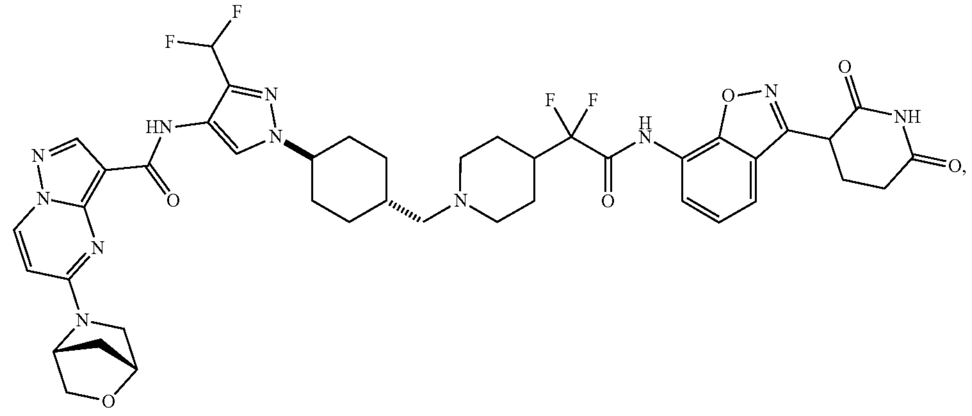

-continued
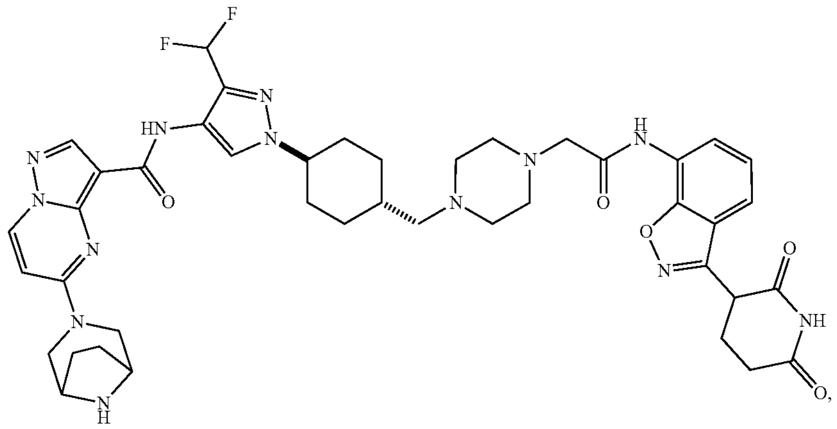
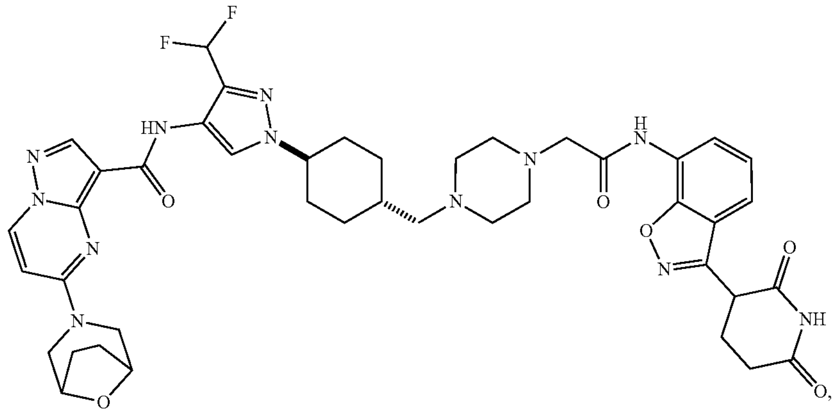
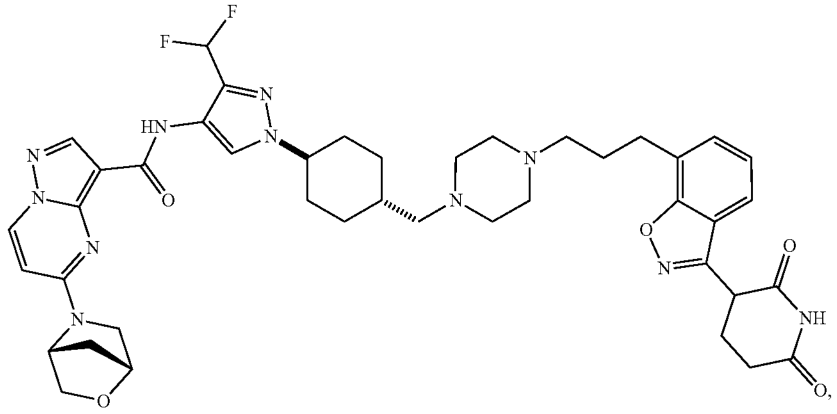
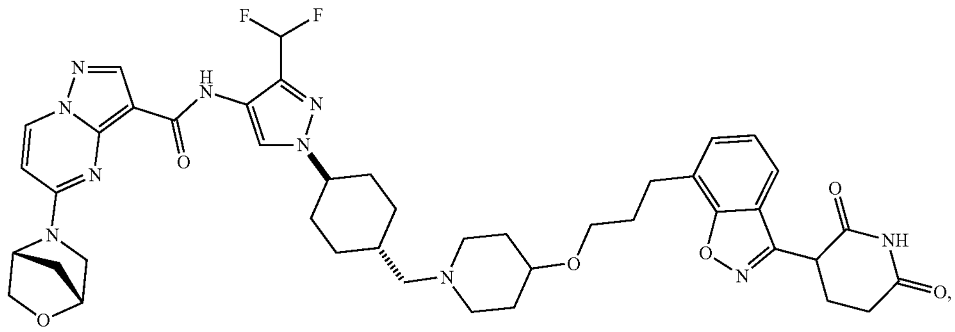

-continued
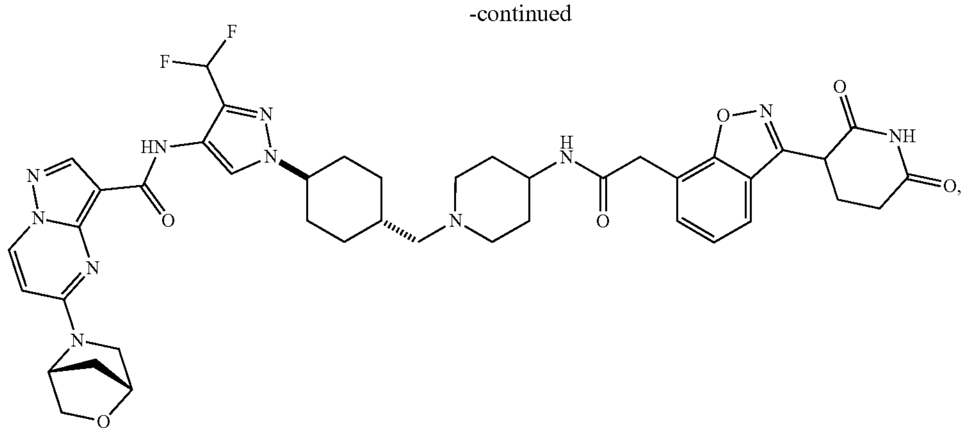
and
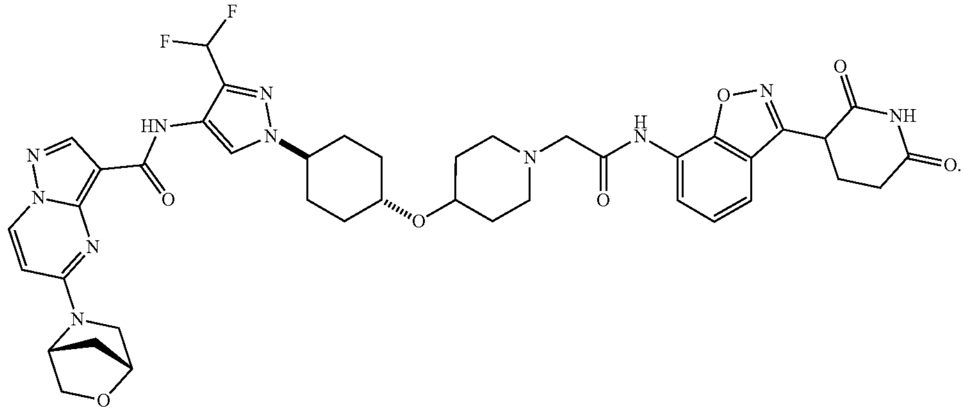
.
17. The compound or the pharmaceutically acceptable salt thereof according to claim 14, wherein the compound is selected from:
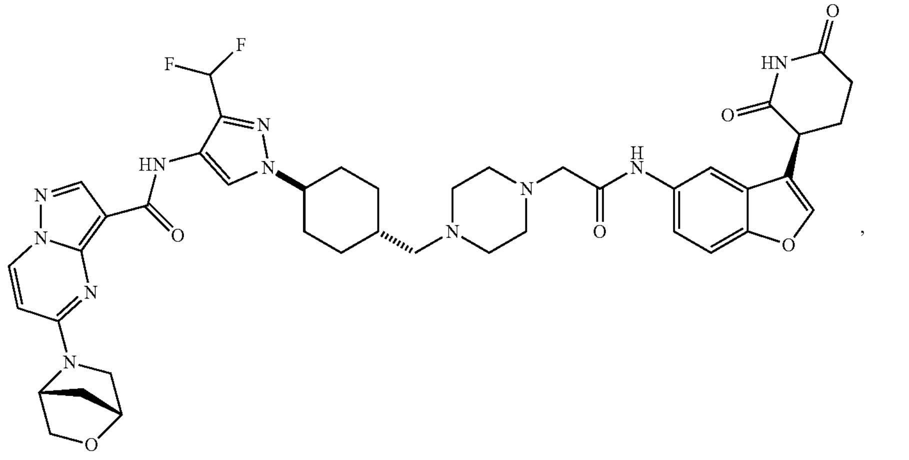
, -continued
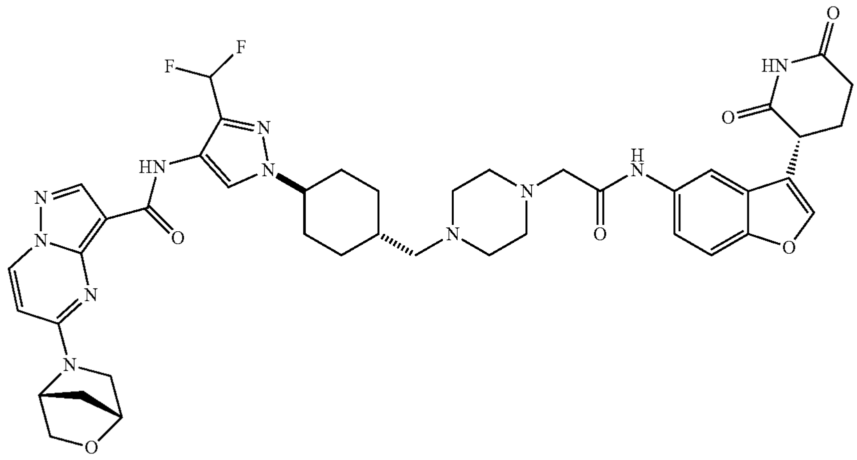
,
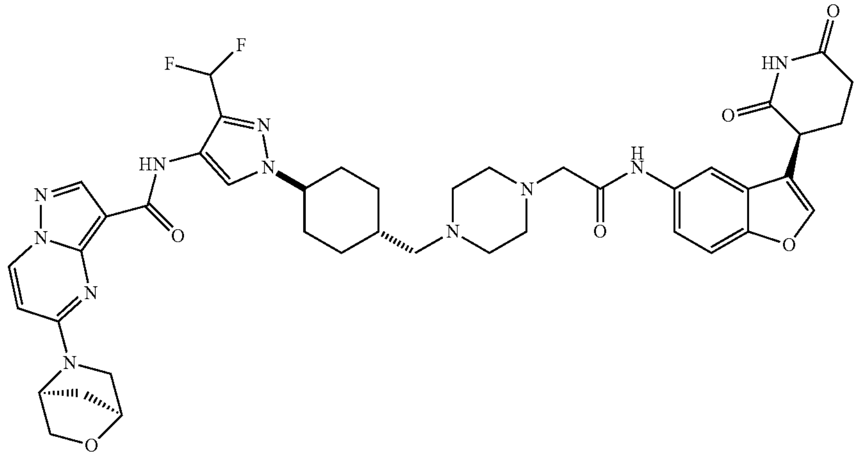
,
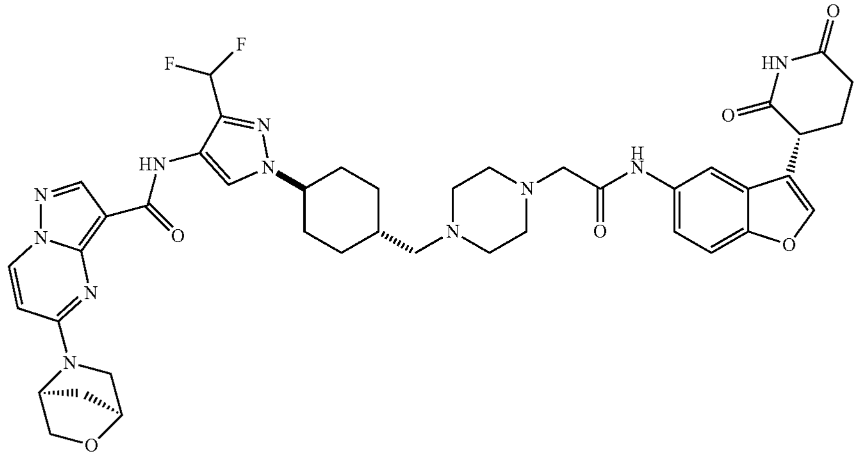
, -continued
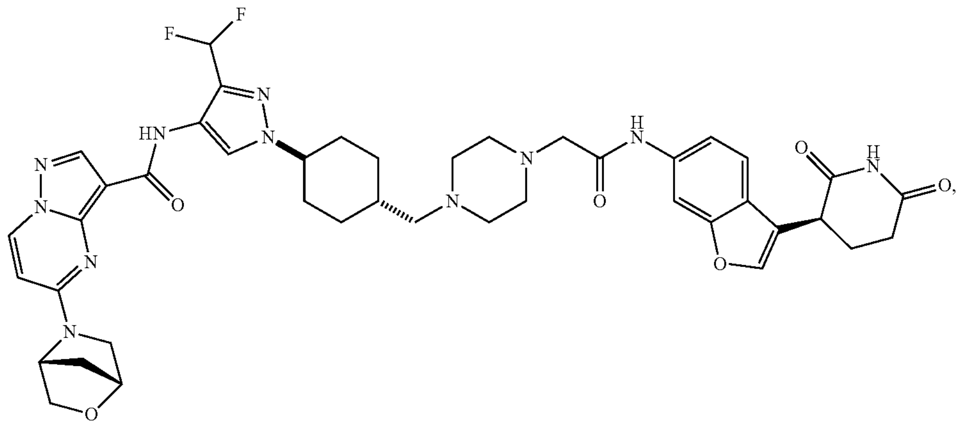
,
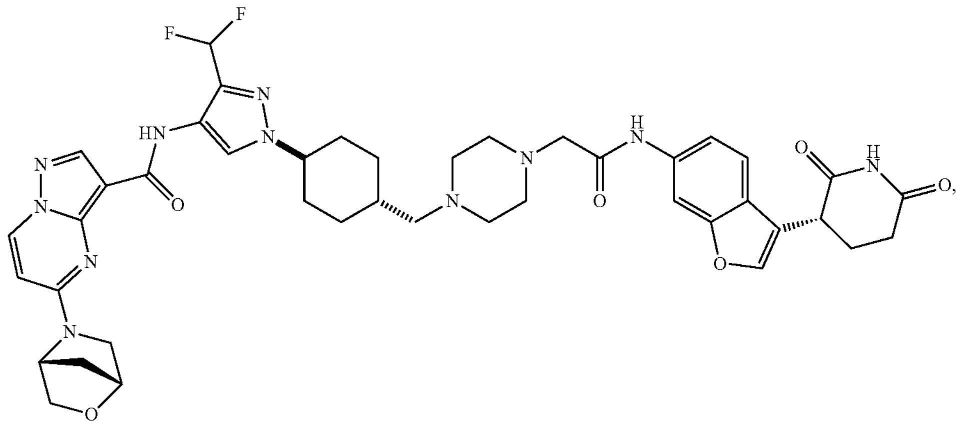
,
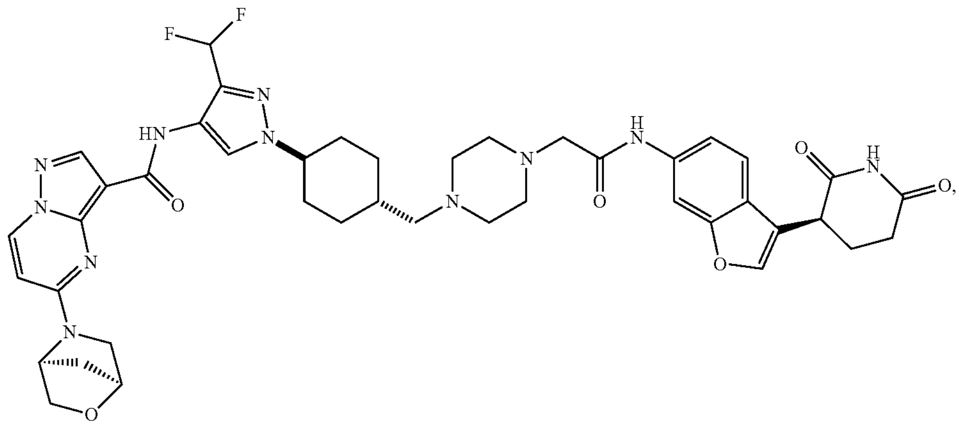
,
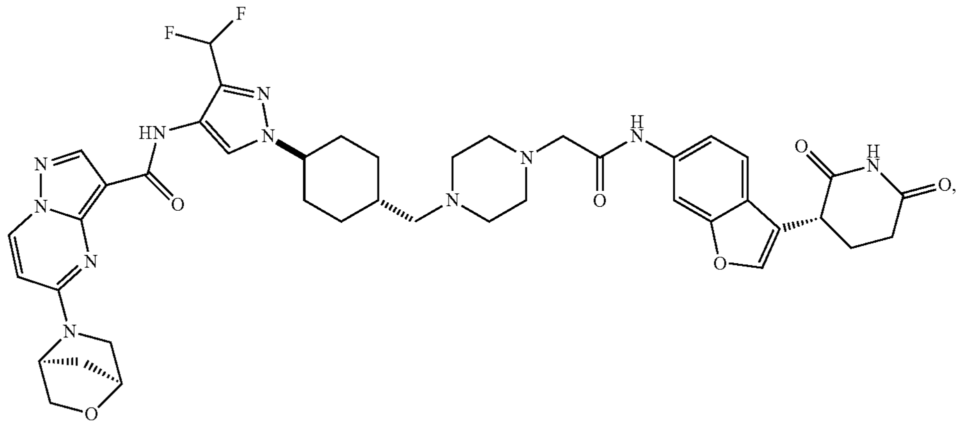
, -continued
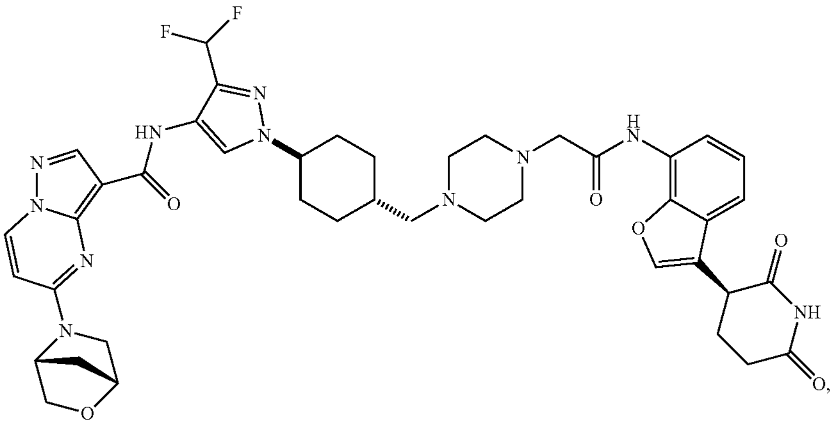
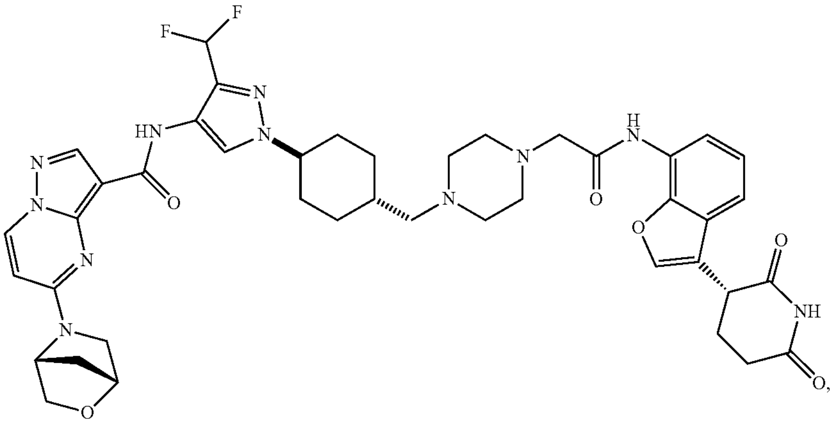
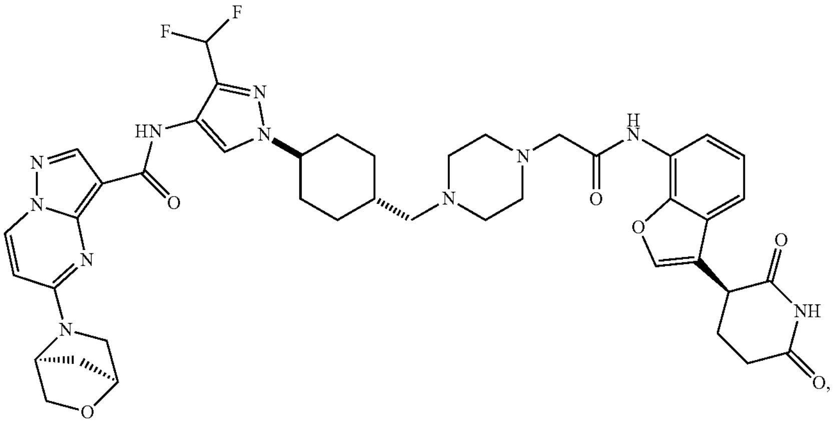
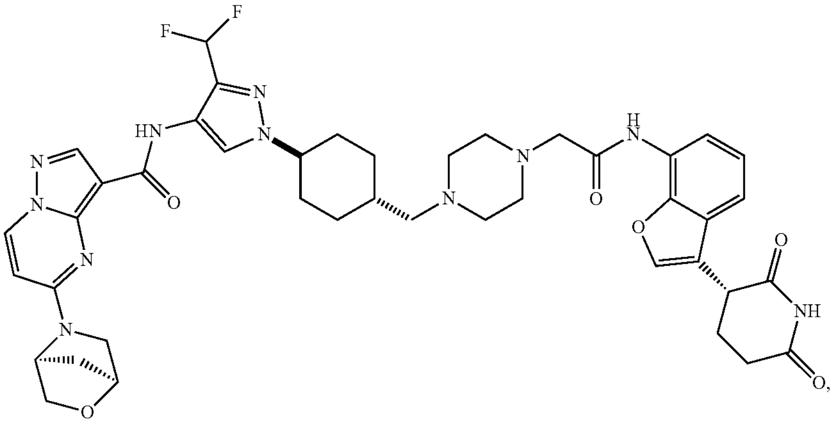

-continued
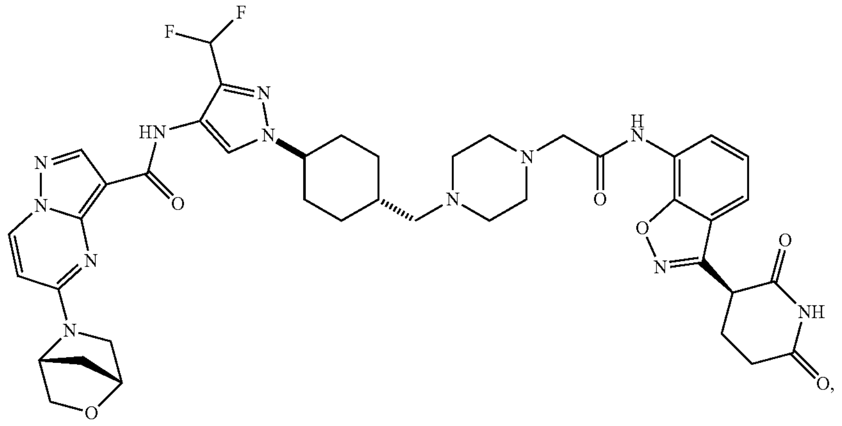
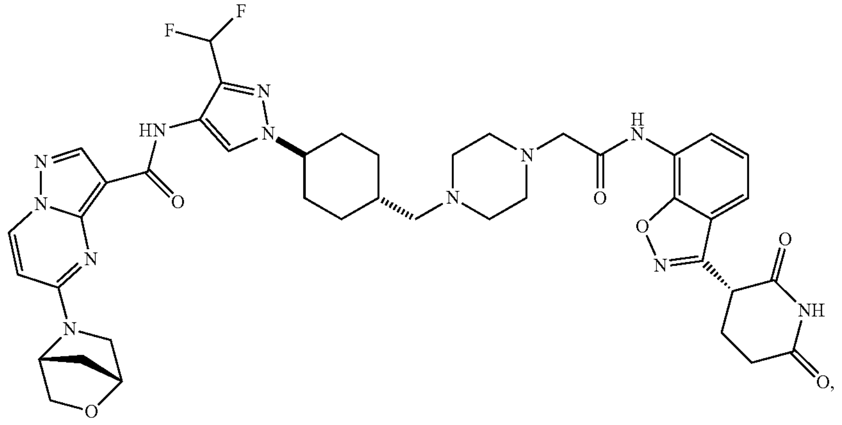
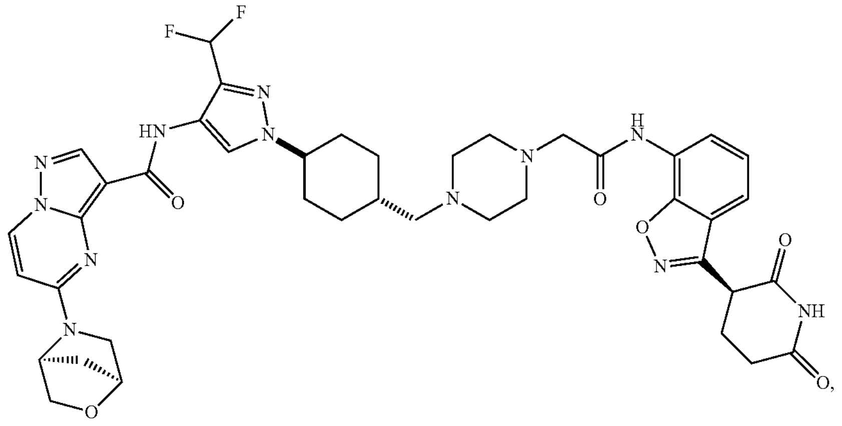
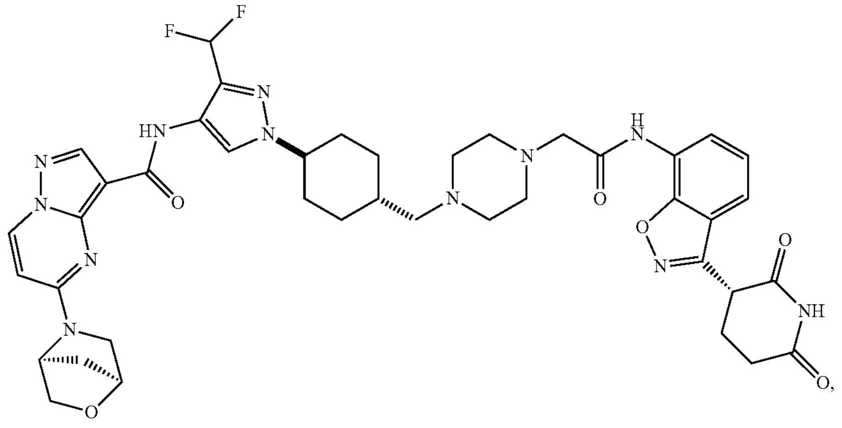

-continued
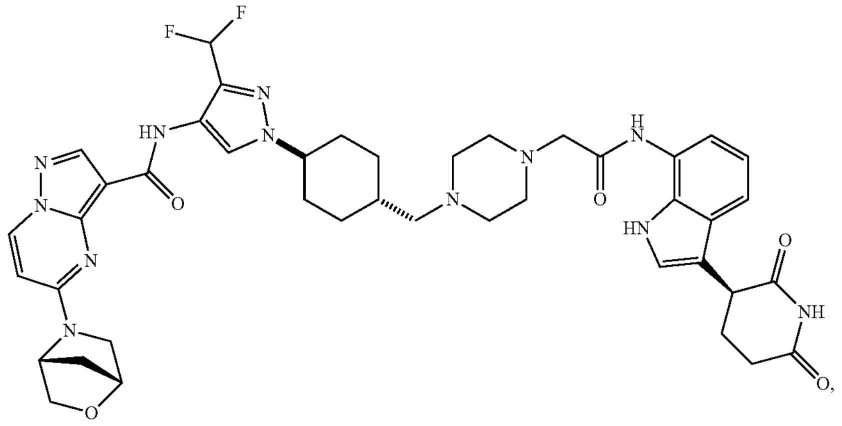
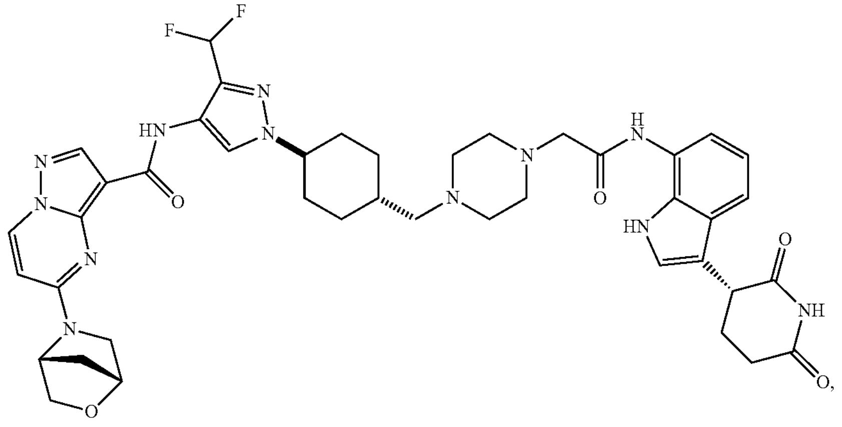
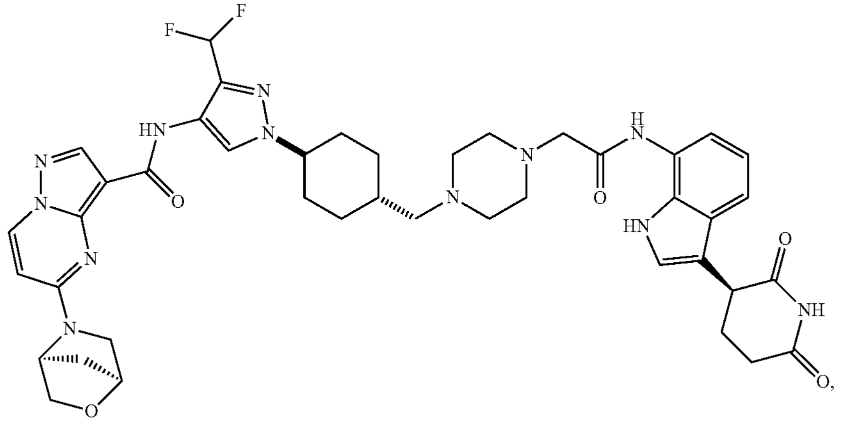
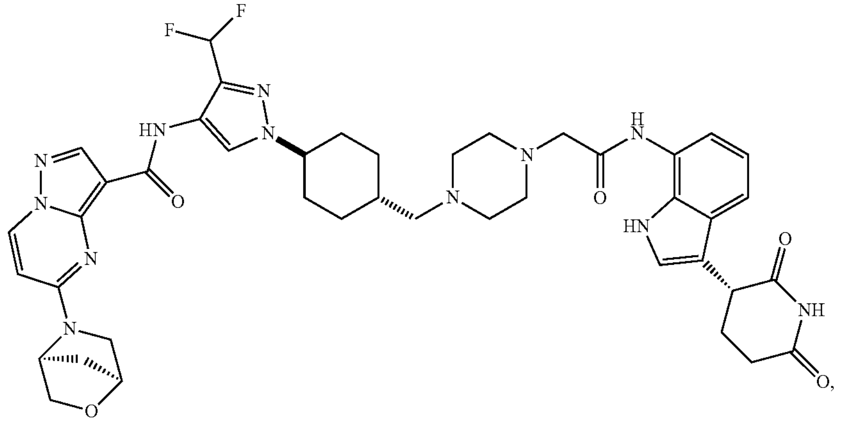

-continued
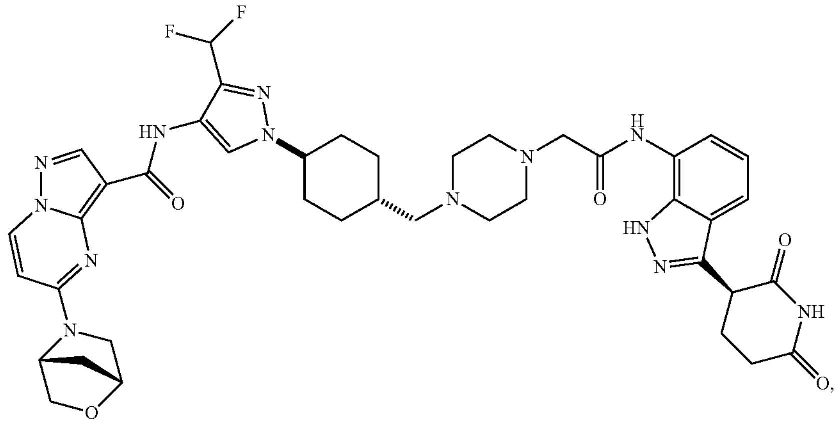
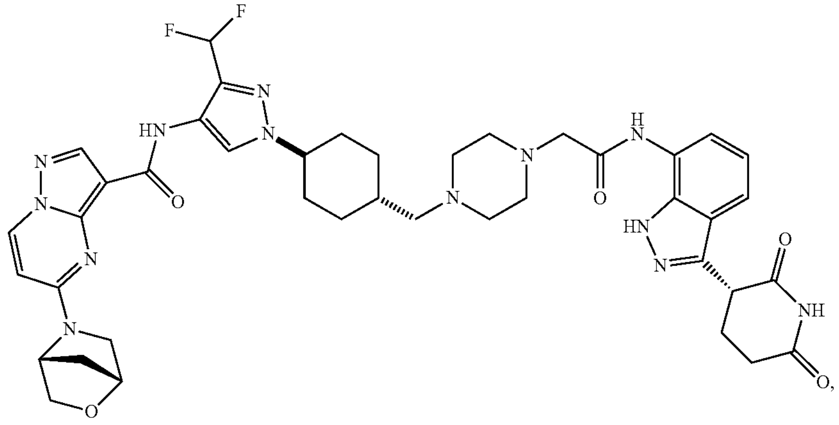
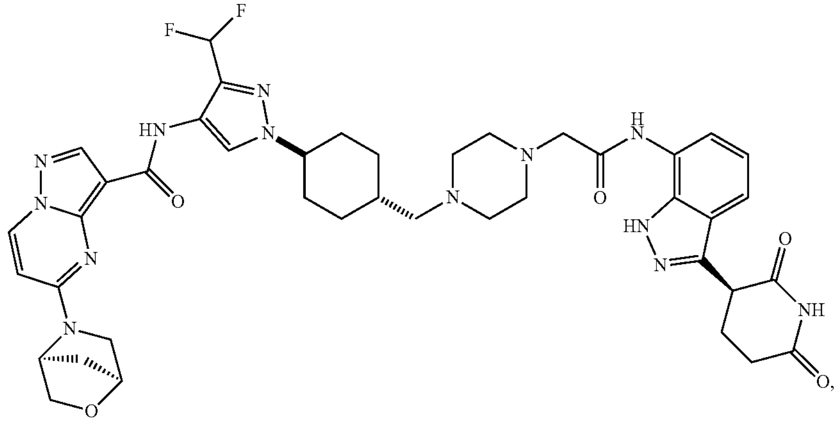
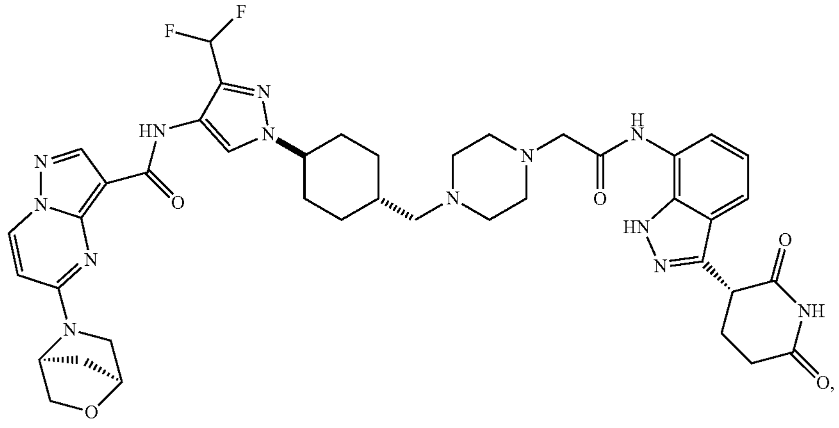

-continued
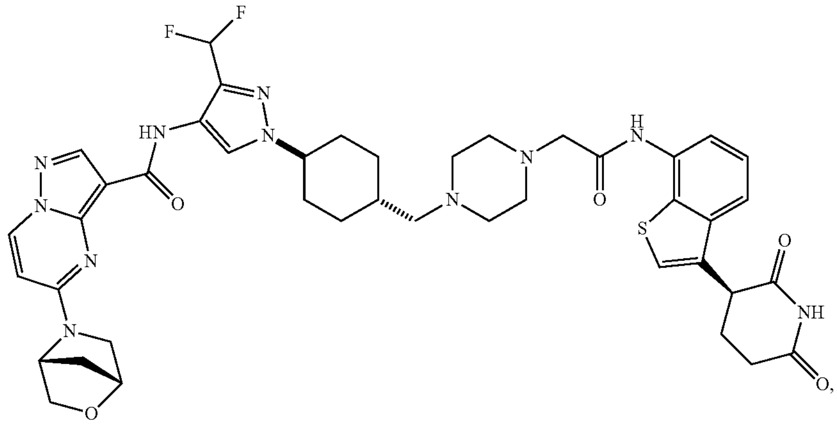
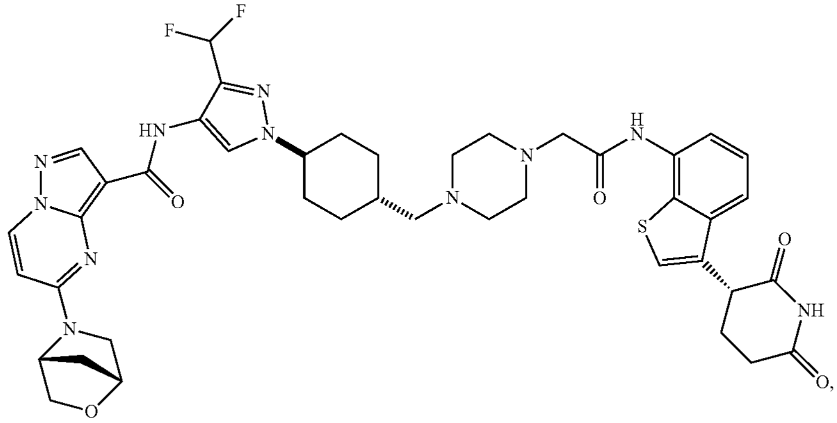
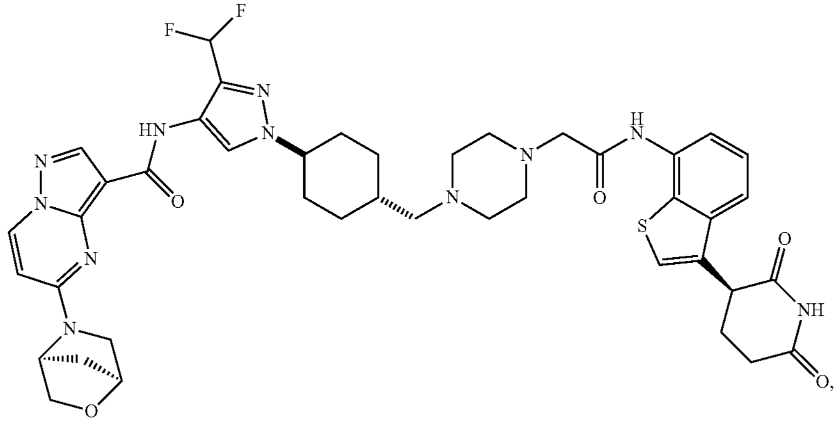
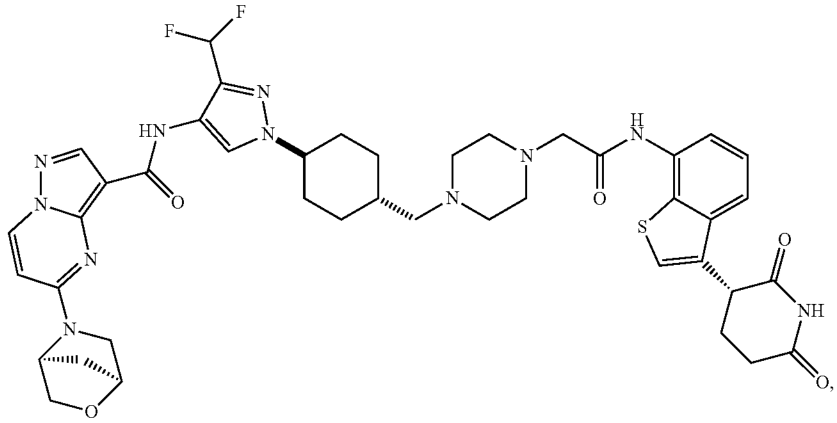

-continued
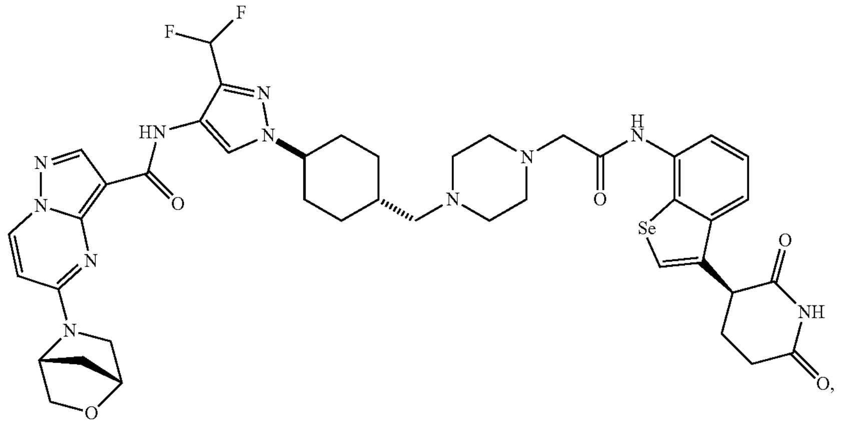
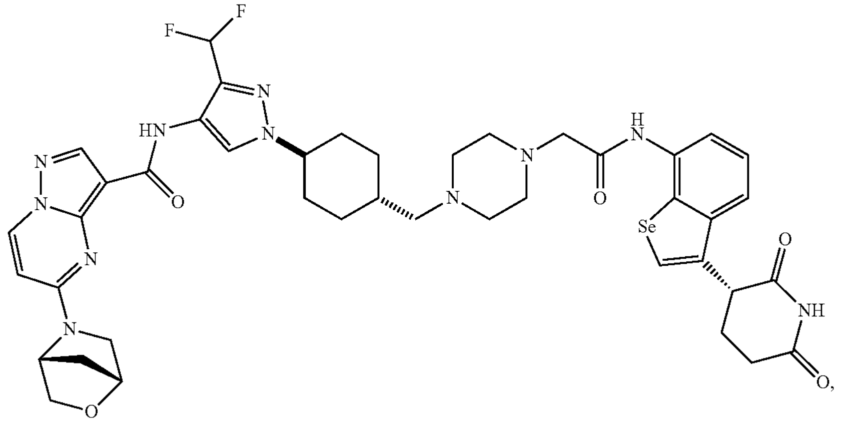
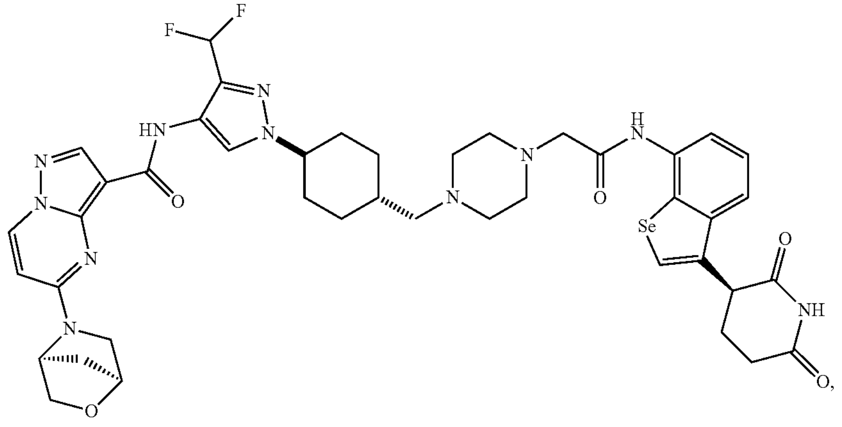
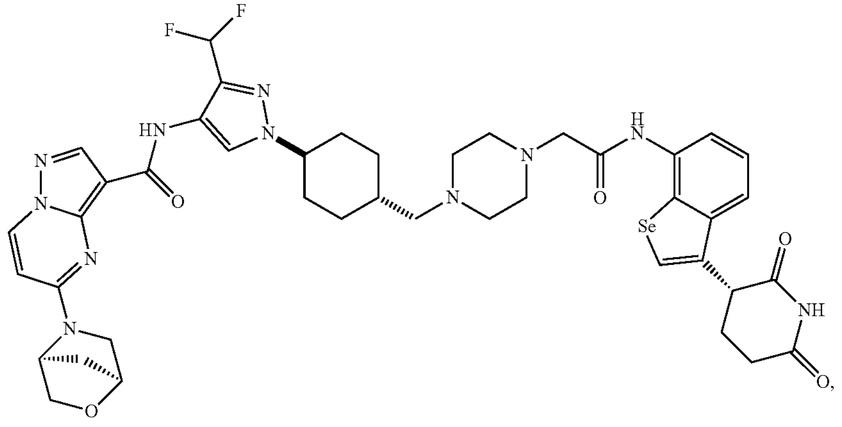

-continued
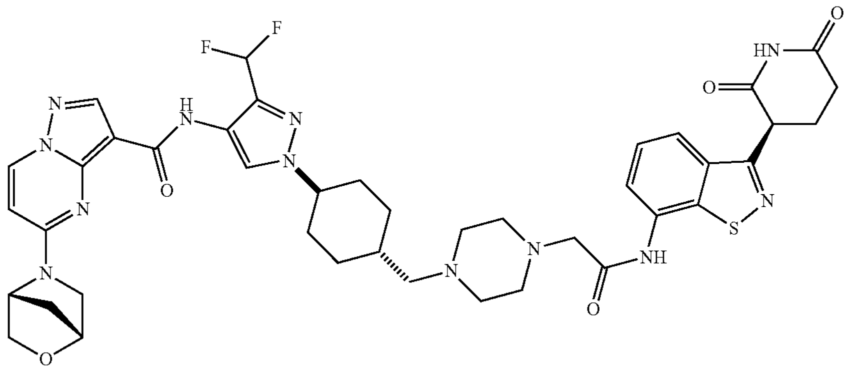
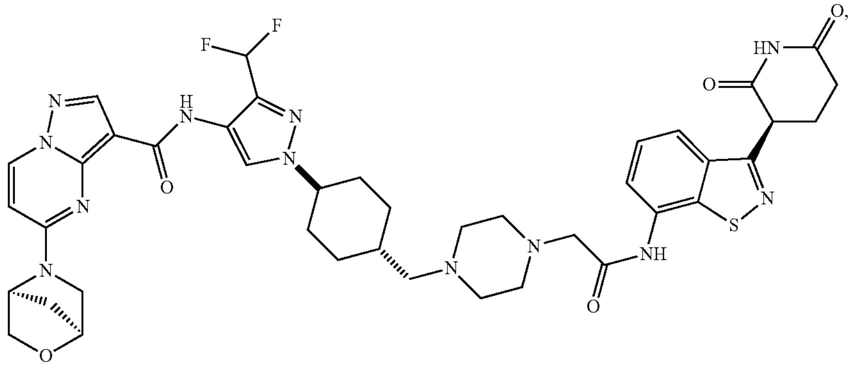
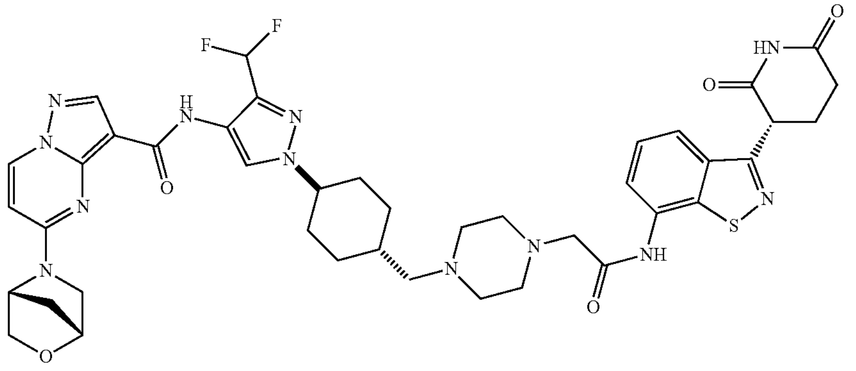
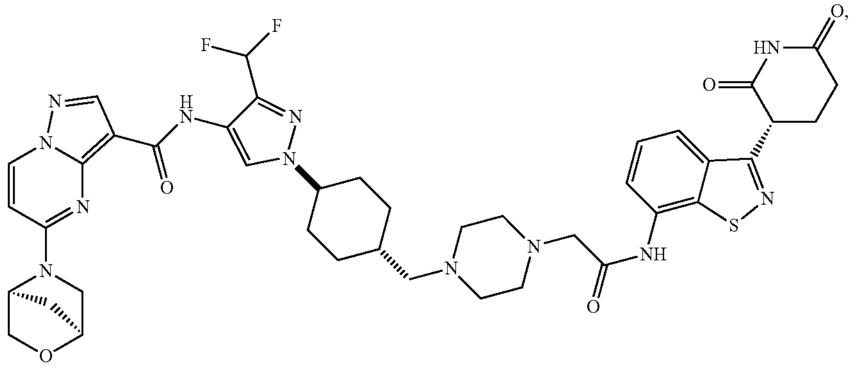

-continued
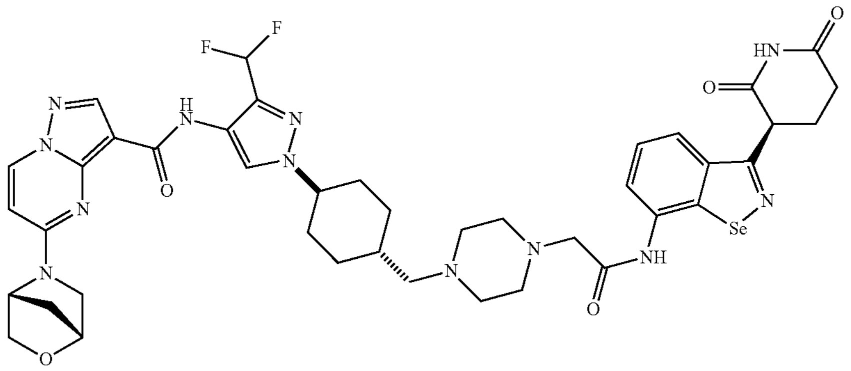
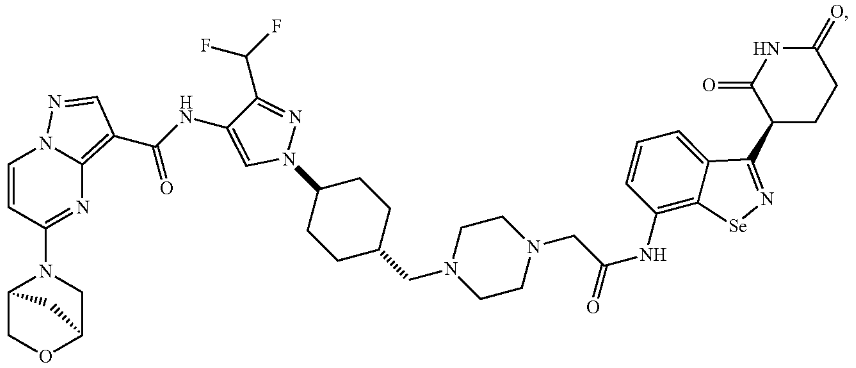
,
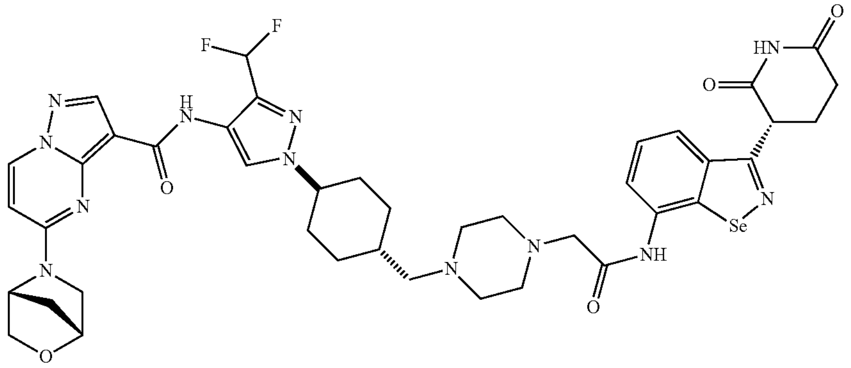
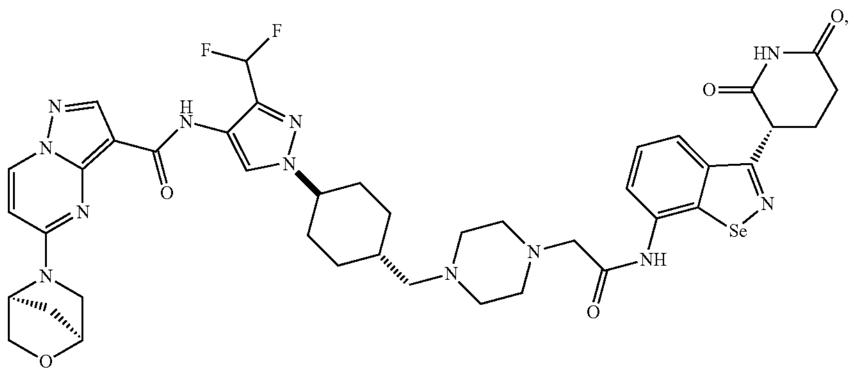
,

-continued
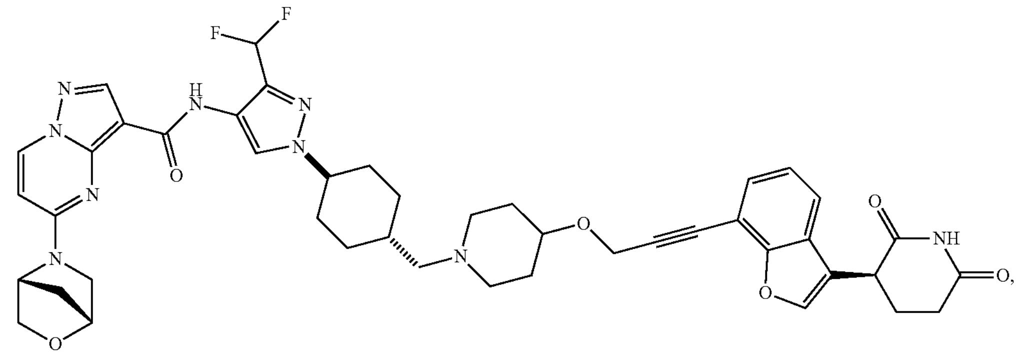
,
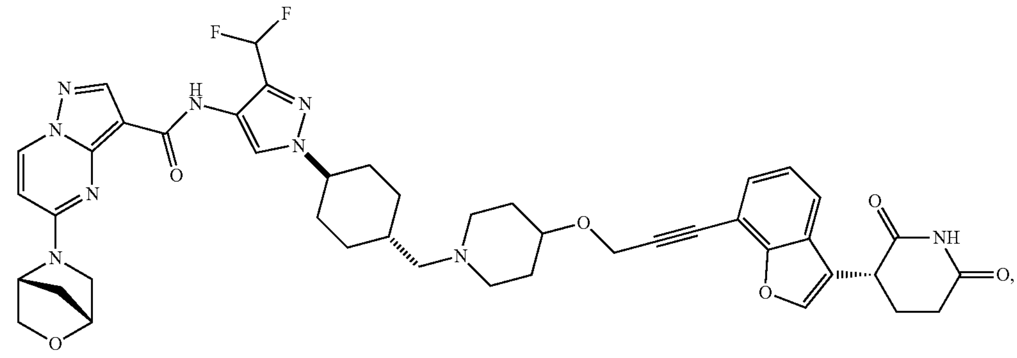
,
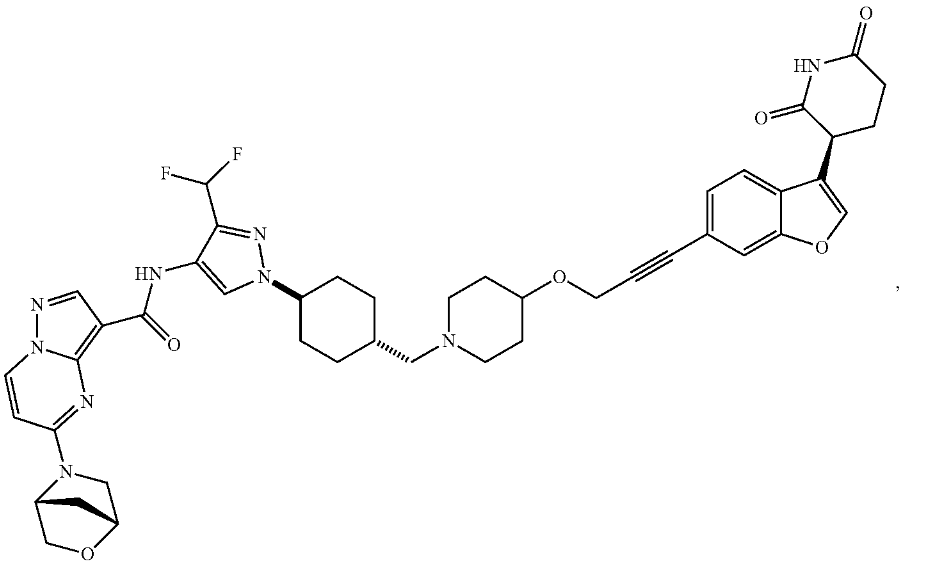 [SMILES: O=C1CC[C@H](c2coc3cc(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)ccc23)C(=O)N1]
,

-continued
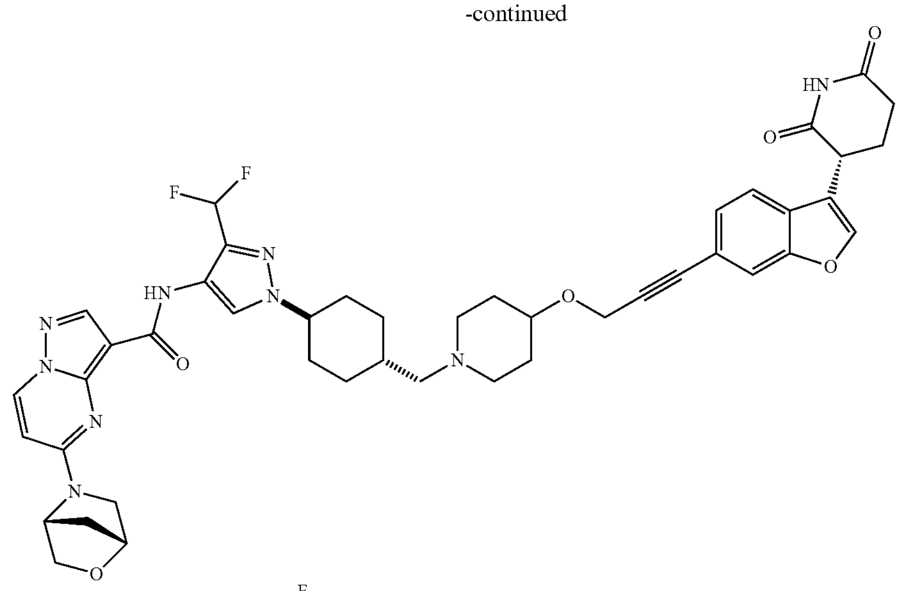
,
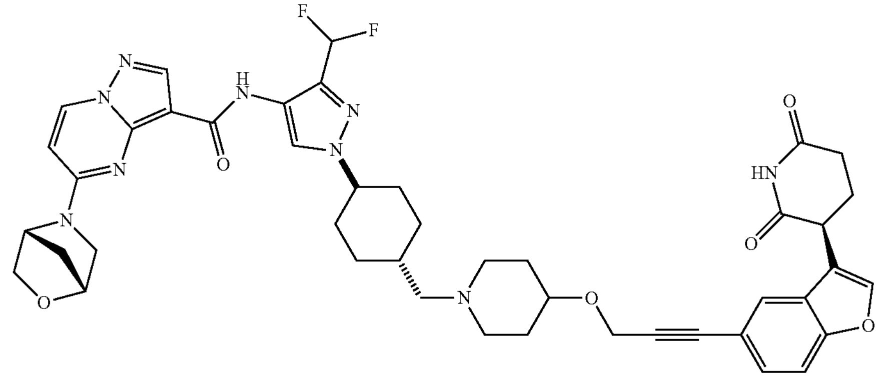
,
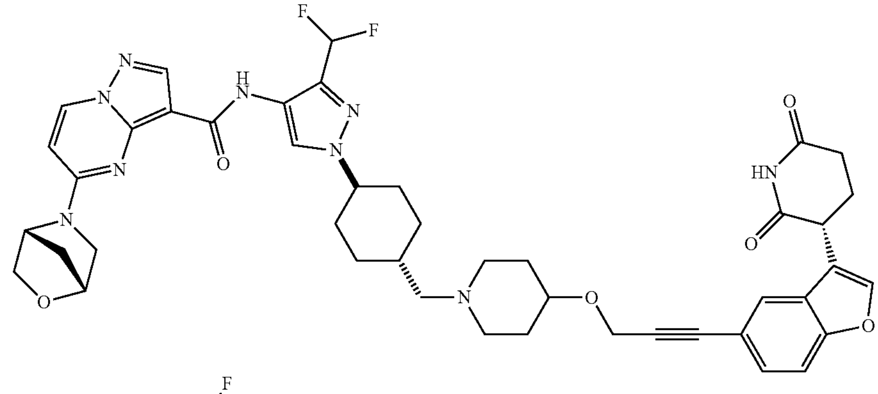
,
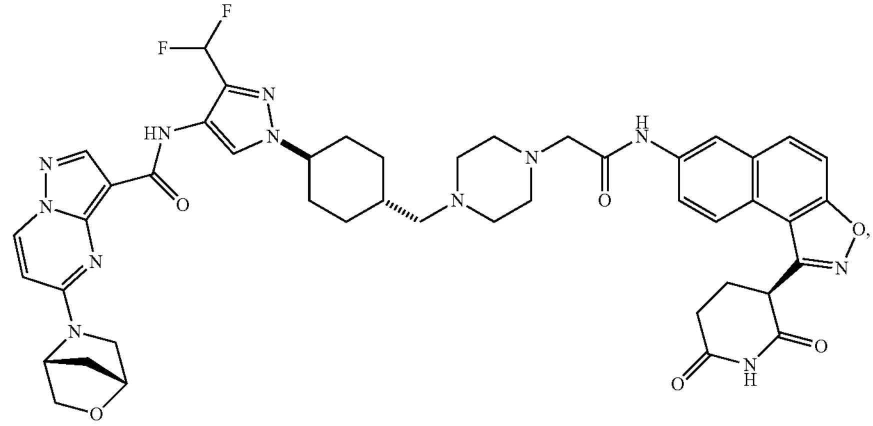
,

-continued
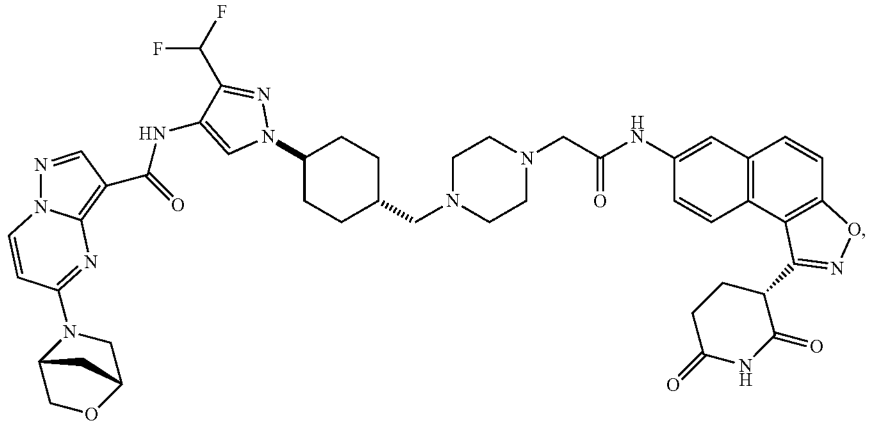
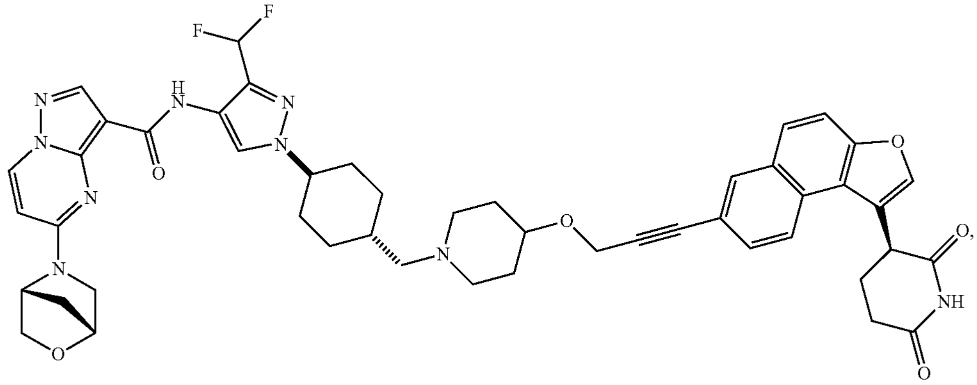
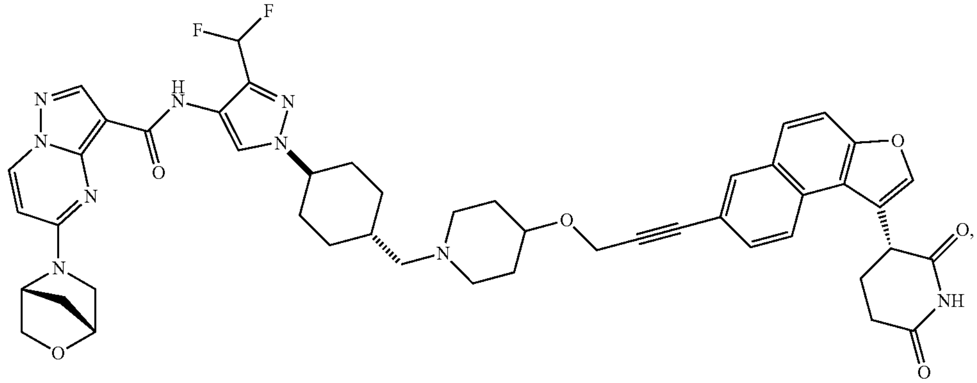
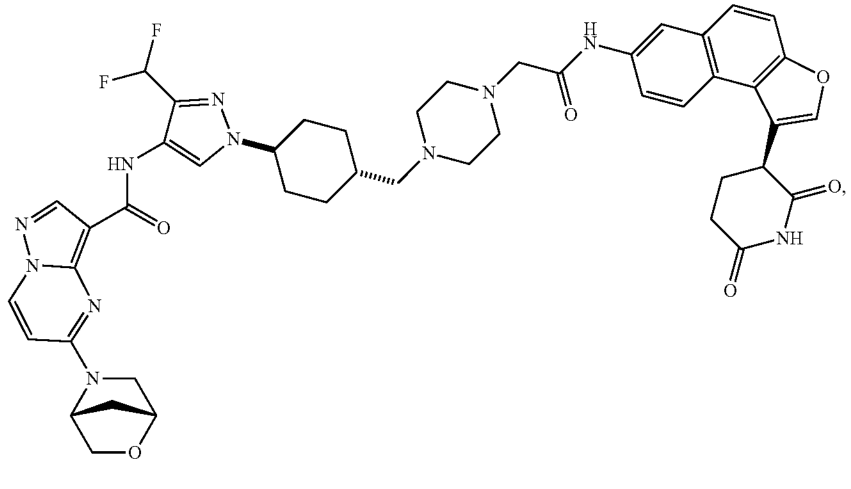

-continued
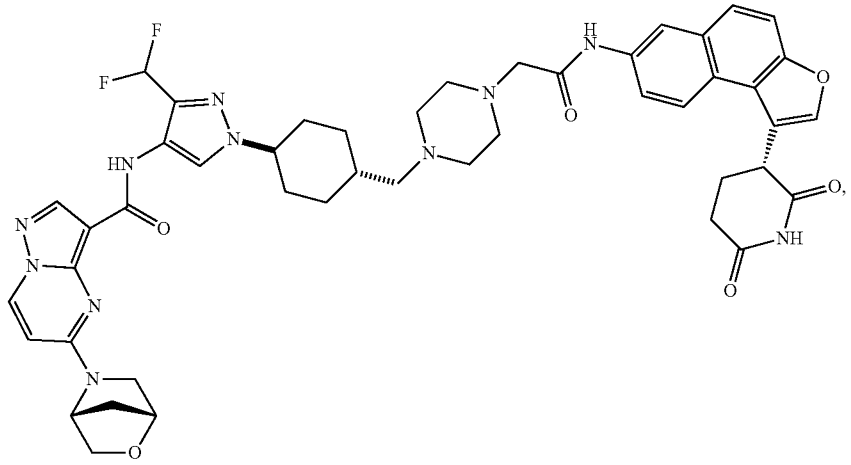
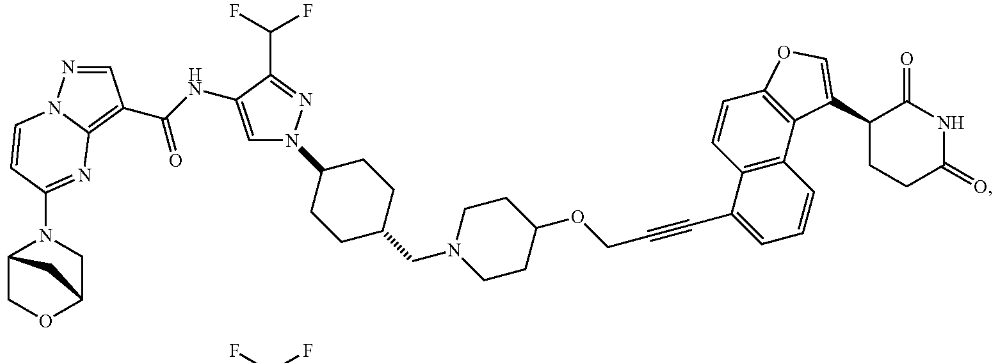
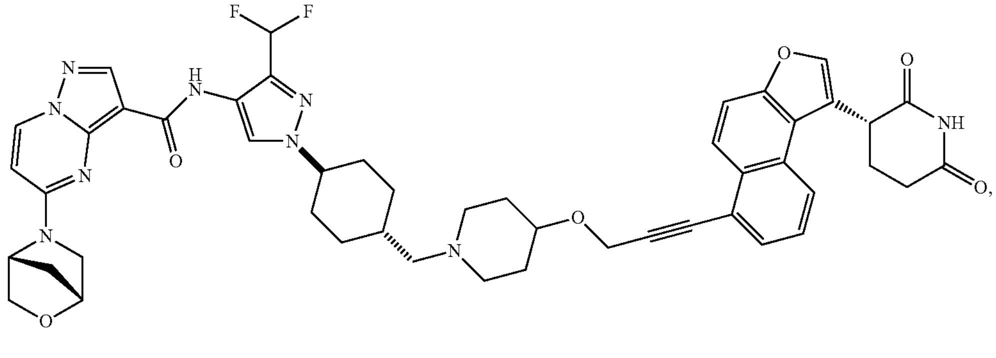
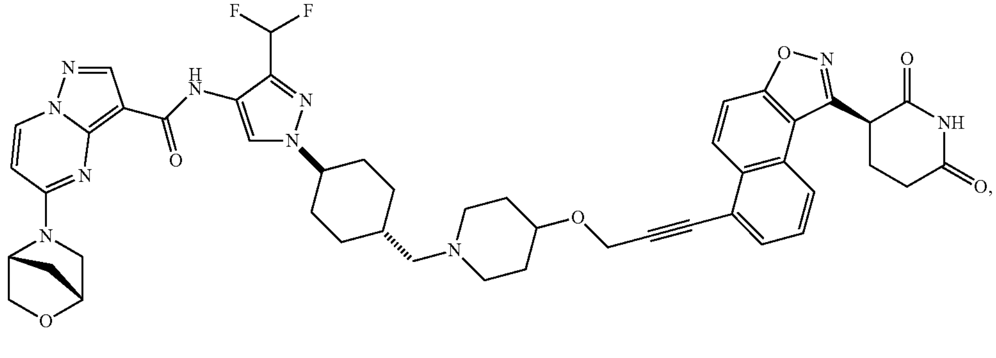

-continued
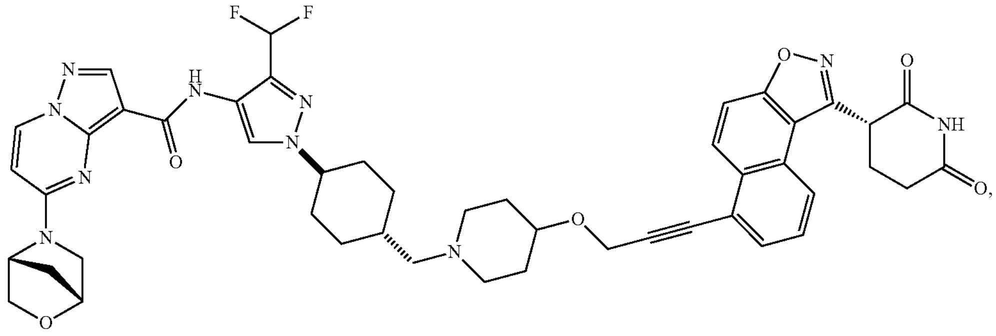
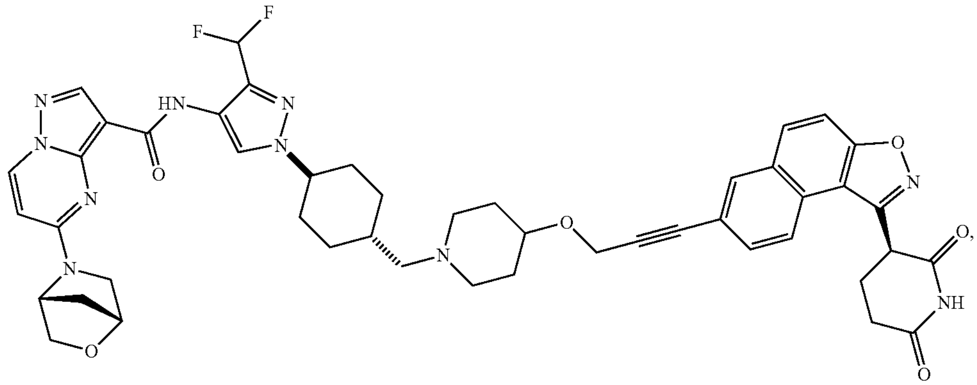
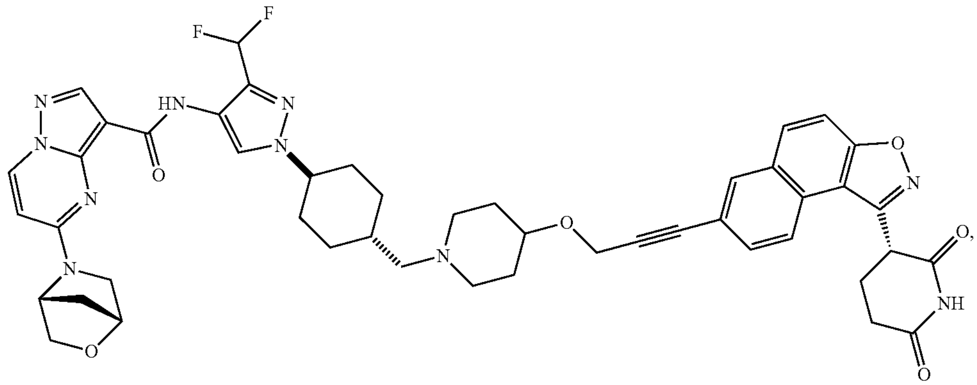
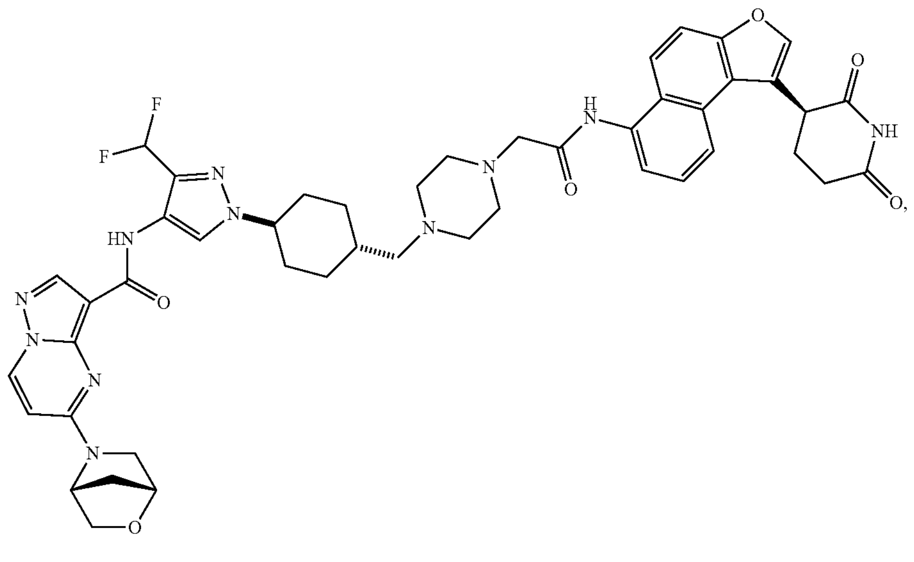

-continued
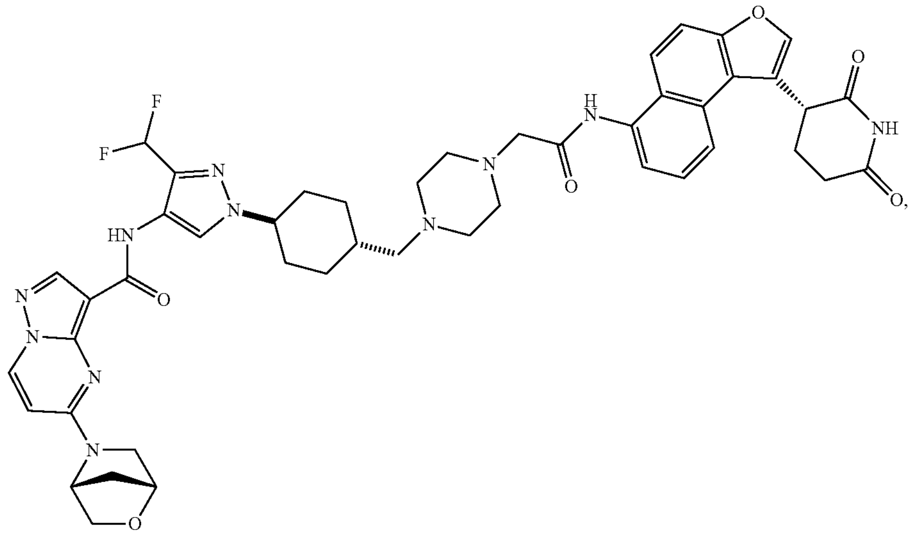
,
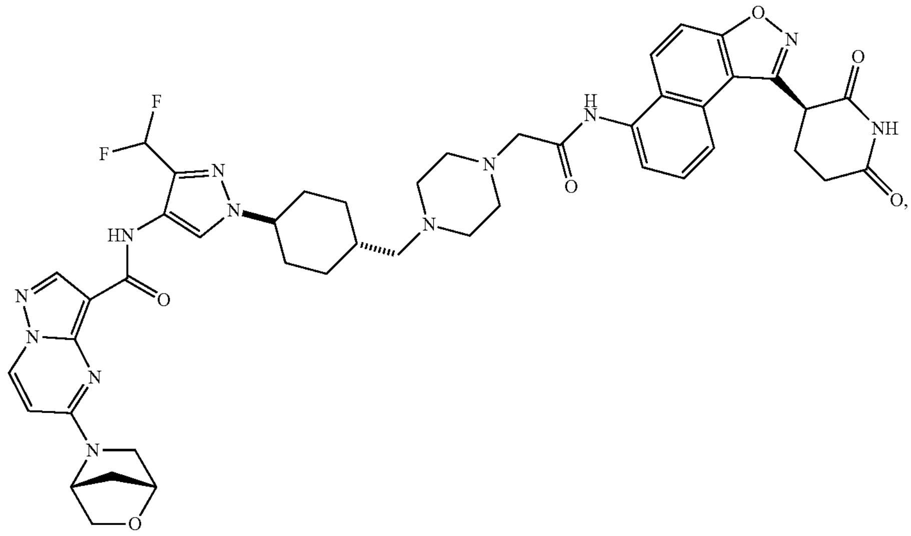
,
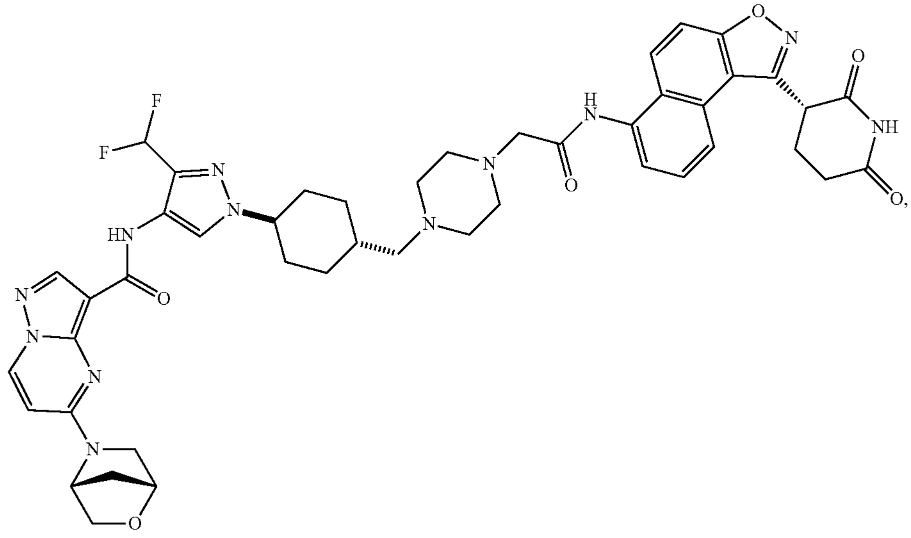
,

-continued
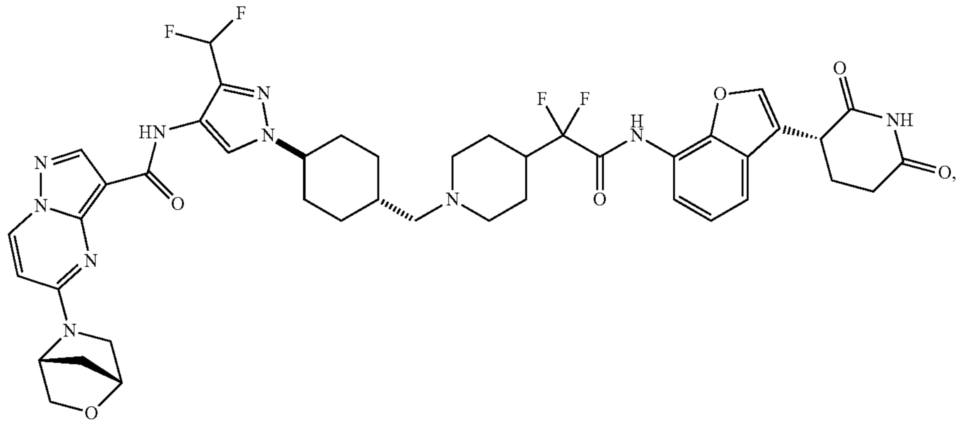
,
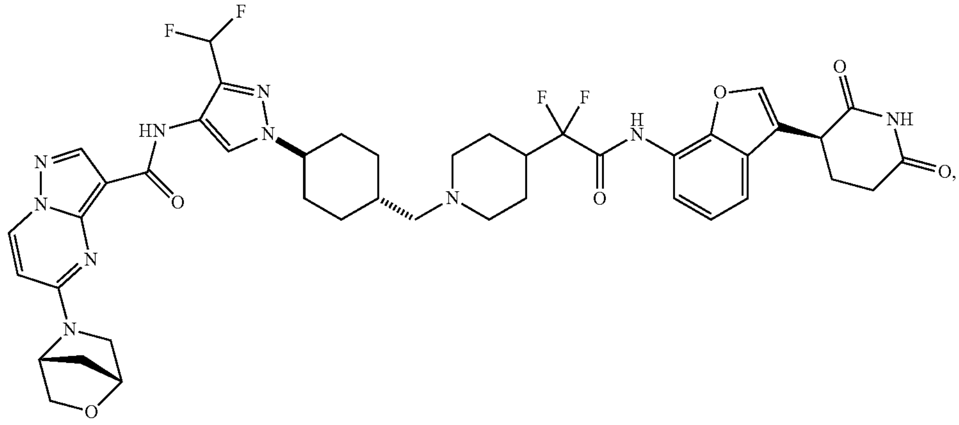
,
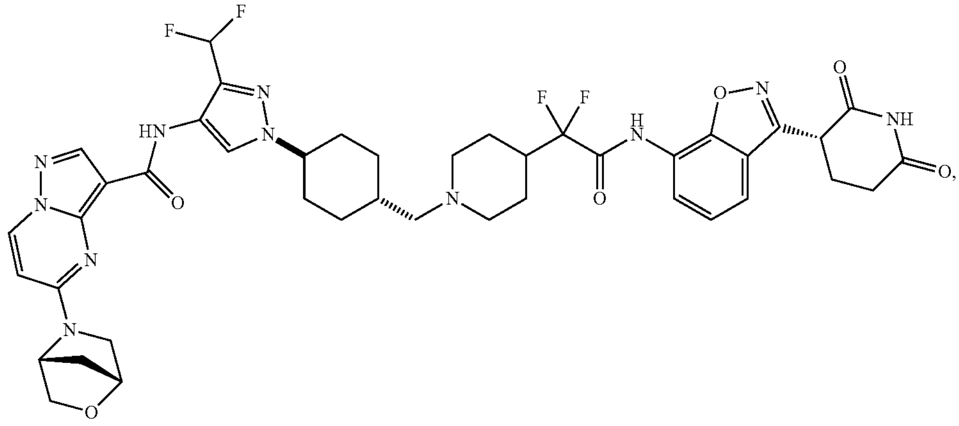
,
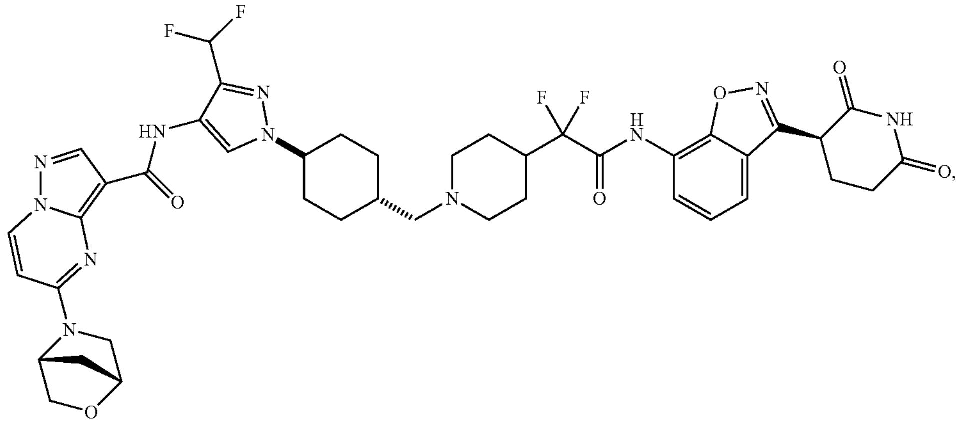
,

-continued
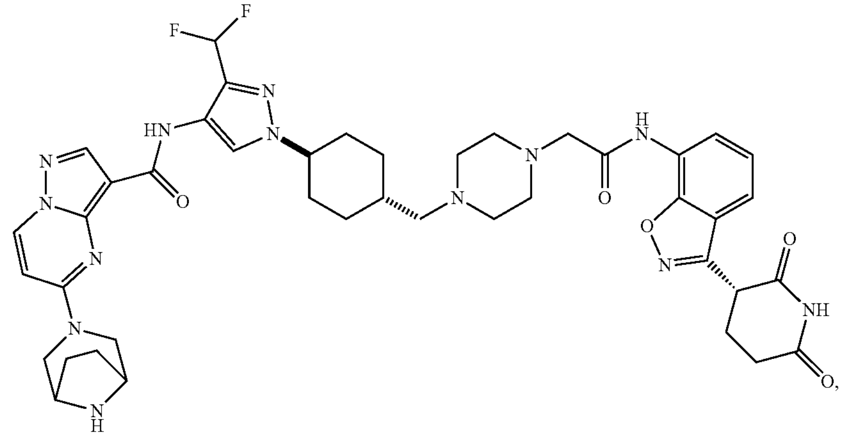
,
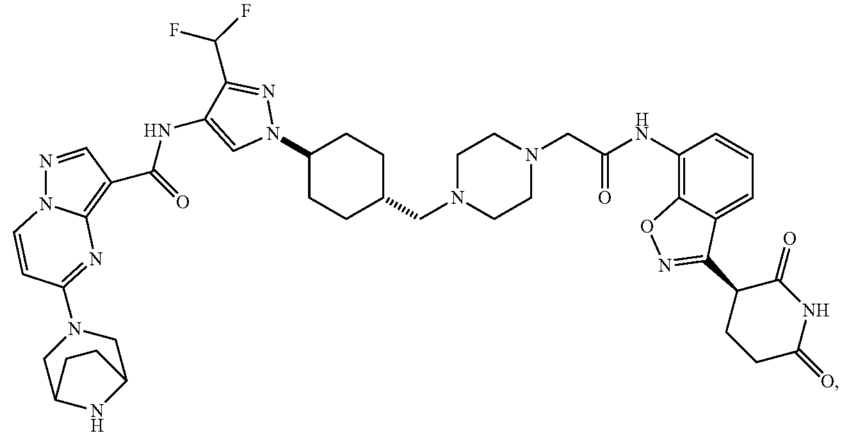
,
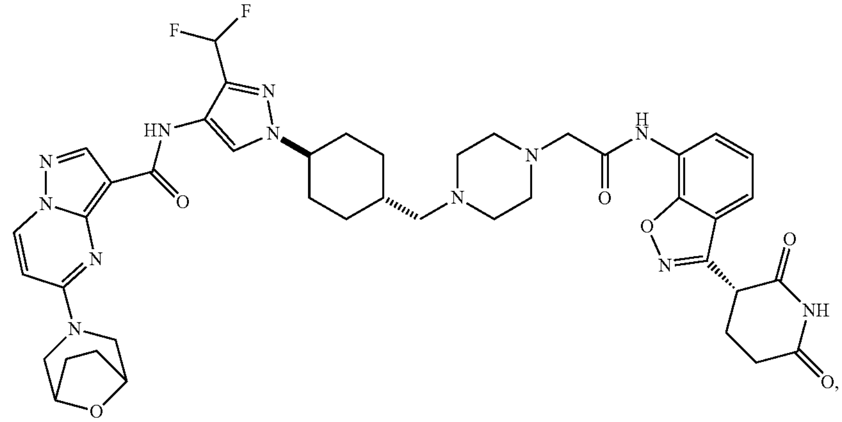
,
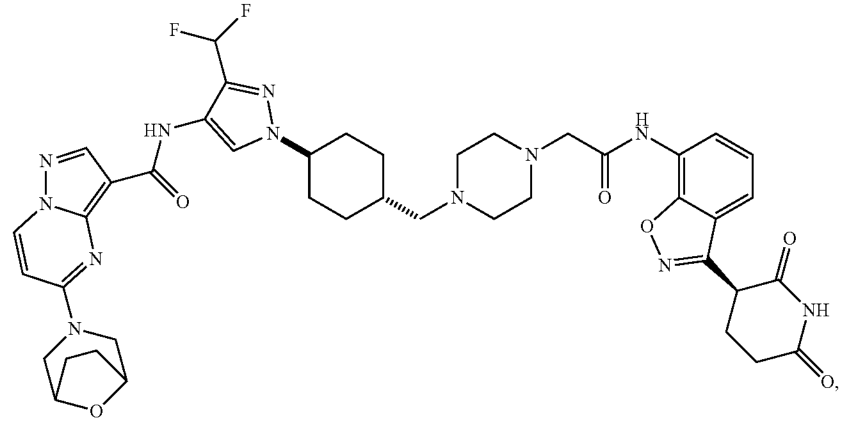
,

-continued
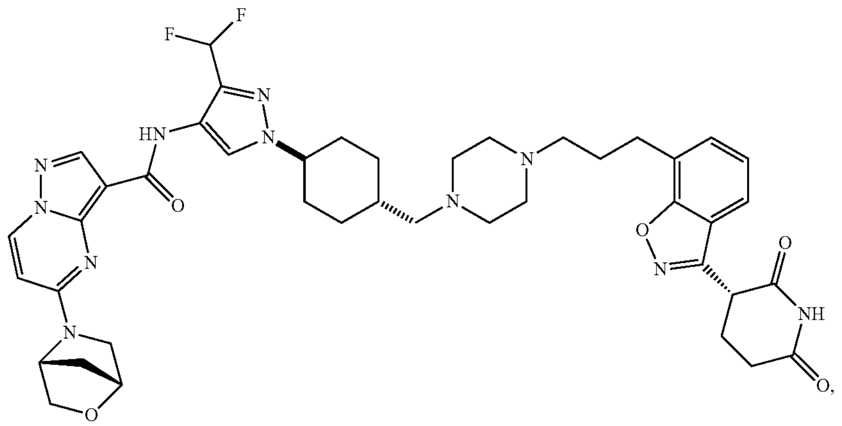
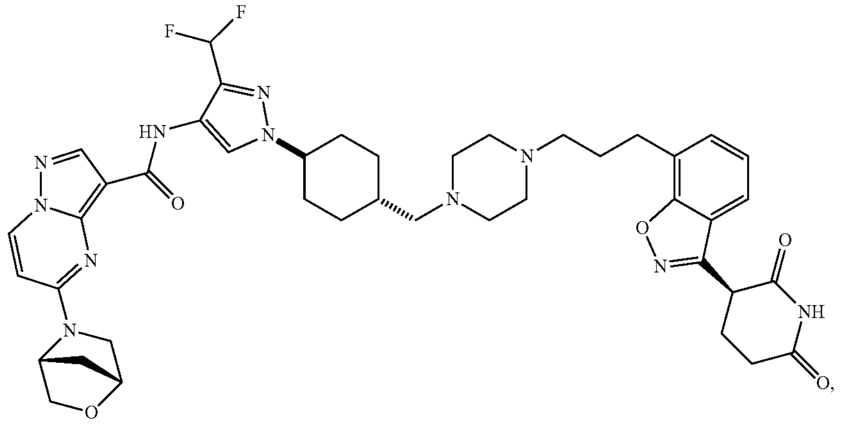
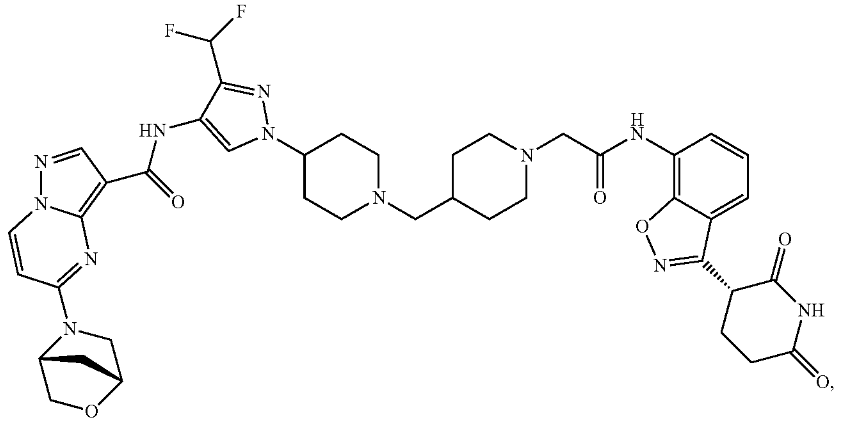
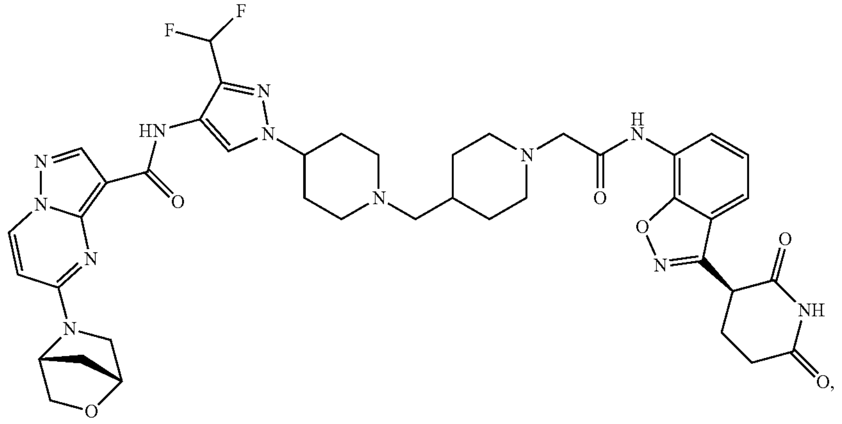

-continued
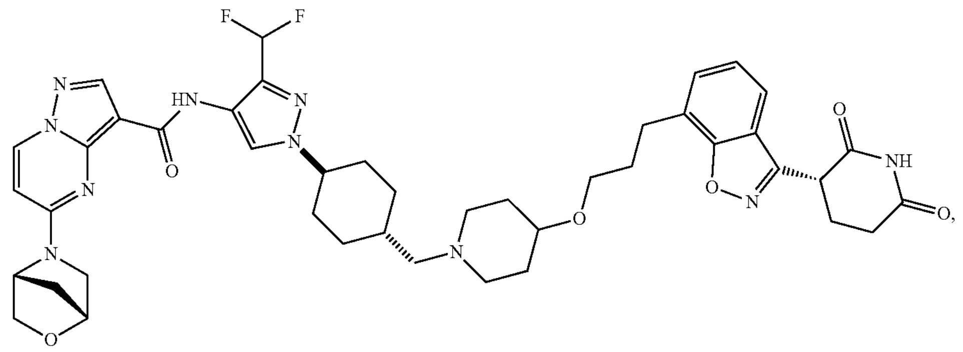
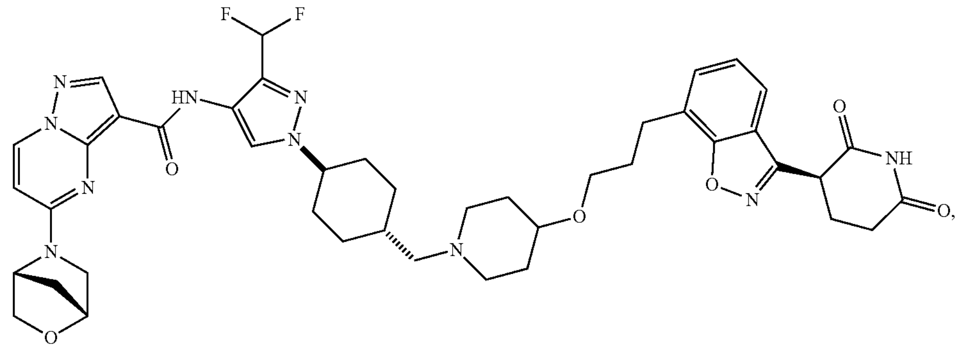
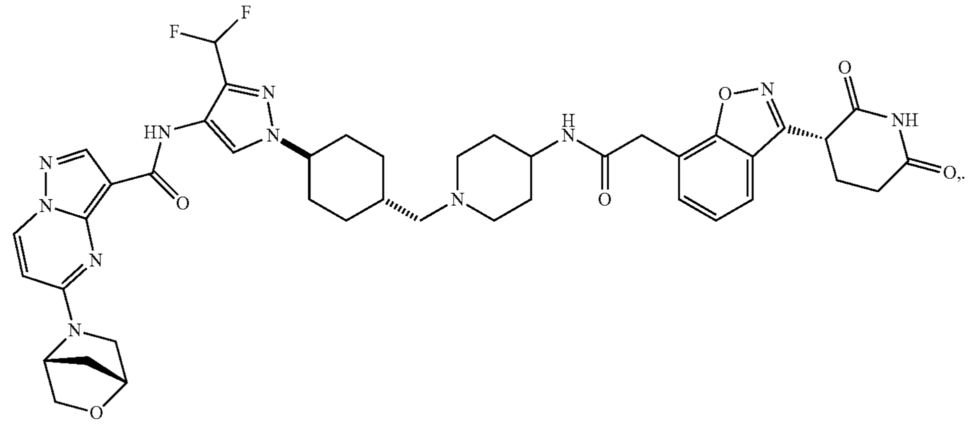
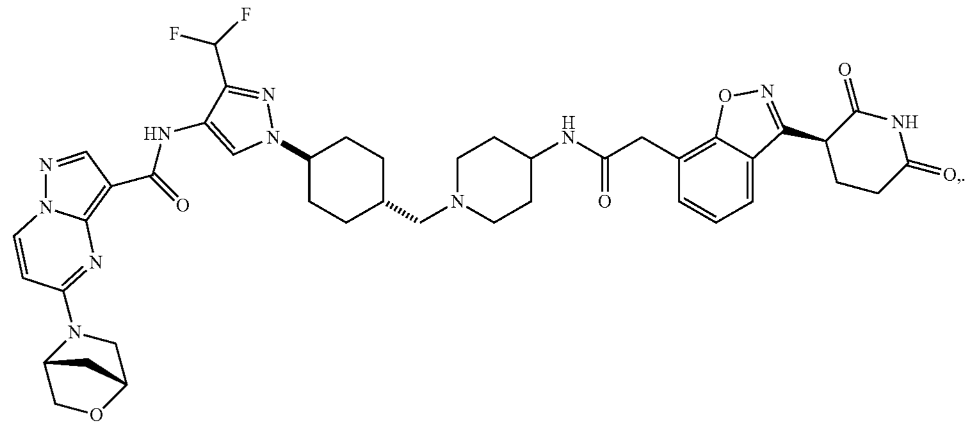

-continued

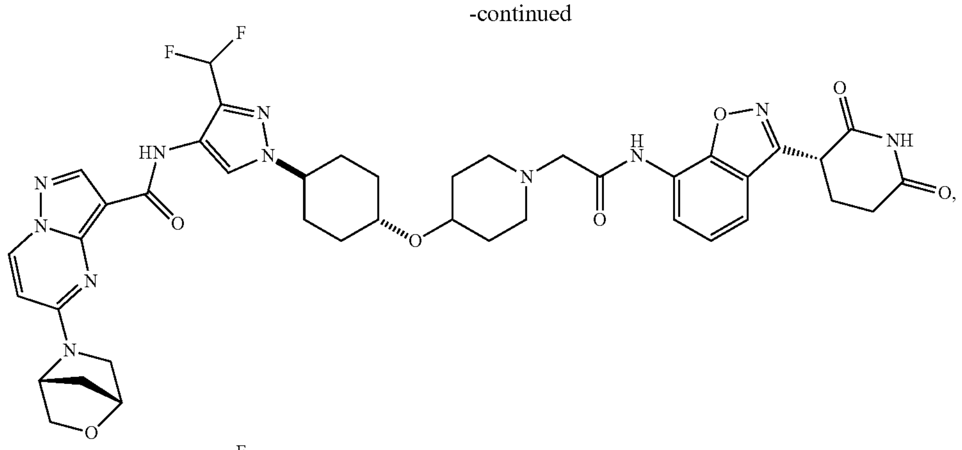

and

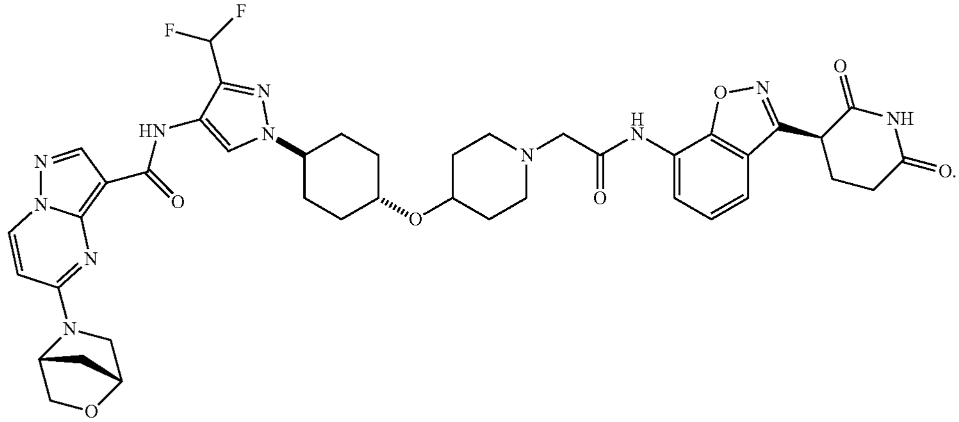

.

18. A method for treating a disease related to interleukin-1 receptor-associated kinase 4 proteolysis targeting chimera in a subject in need thereof, comprising administering: the compound or the pharmaceutically acceptable salt thereof according to claim 1.

19. The method according to claim 18, wherein the disease related to interleukin-1 receptor-associated kinase 4 proteolysis targeting chimera is inflammatory or immune disease.

* * * * *